(12) United States Patent
Banno et al.

(10) Patent No.: US 9,090,601 B2
(45) Date of Patent: Jul. 28, 2015

(54) THIAZOLE DERIVATIVES

(75) Inventors: Hiroshi Banno, Osaka (JP); Masaaki Hirose, Cambridge, MA (US); Osamu Kurasawa, Osaka (JP)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/657,854

(22) Filed: Jan. 28, 2010

(65) Prior Publication Data

US 2011/0003807 A1 Jan. 6, 2011

Related U.S. Application Data

(60) Provisional application No. 61/148,533, filed on Jan. 30, 2009, provisional application No. 61/229,399, filed on Jul. 29, 2009.

(51) Int. Cl.
| | | |
|---|---|---|
| C07D 417/14 | (2006.01) | |
| C07D 487/04 | (2006.01) | |
| C07D 513/04 | (2006.01) | |
| C07D 495/04 | (2006.01) | |
| A61K 9/20 | (2006.01) | |
| C07D 417/04 | (2006.01) | |
| C07D 471/04 | (2006.01) | |

(52) U.S. Cl.
CPC ........... *C07D 417/14* (2013.01); *A61K 9/2059* (2013.01); *C07D 417/04* (2013.01); *C07D 471/04* (2013.01); *C07D 487/04* (2013.01); *C07D 495/04* (2013.01); *C07D 513/04* (2013.01)

(58) Field of Classification Search
USPC ........... 514/383, 394; 548/262.2, 304.4, 202, 548/154; 546/121, 270.4
See application file for complete search history.

(56) References Cited

U.S. PATENT DOCUMENTS

| | | | |
|---|---|---|---|
| 3,257,203 A | 6/1966 | Sus et al. | |
| 3,821,384 A | 6/1974 | Ariyan et al. | |
| 3,852,293 A | 12/1974 | Ariyan et al. | |
| 4,371,607 A | 2/1983 | Donges | |
| 5,134,142 A | 7/1992 | Matsuo et al. | |
| 6,015,826 A | 1/2000 | Pechacek et al. | |
| 6,555,501 B1 | 4/2003 | Bastiaans et al. | |
| 6,608,087 B1* | 8/2003 | Charifson et al. ............ | 514/318 |
| 6,984,652 B2 | 1/2006 | Yager et al. | |
| 7,074,801 B1 | 7/2006 | Yoshida et al. | |
| 7,405,235 B2* | 7/2008 | Levy et al. ..................... | 514/394 |
| 7,504,513 B2* | 3/2009 | Boylan et al. ................. | 548/181 |
| 7,511,041 B2 | 3/2009 | Shimada et al. | |
| 7,560,568 B2 | 7/2009 | Emmitte | |
| 7,741,348 B2 | 6/2010 | Nan et al. | |
| 8,183,240 B2 | 5/2012 | Cardin et al. | |
| 8,440,664 B2 | 5/2013 | Cardin et al. | |
| 8,586,582 B2 | 11/2013 | Liang et al. | |
| 8,765,746 B2 | 7/2014 | Freeze et al. | |
| 8,796,268 B2 | 8/2014 | Freeze et al. | |
| 8,796,271 B2 | 8/2014 | Hirose et al. | |
| 2002/0022729 A1 | 2/2002 | Kawai et al. | |
| 2003/0096816 A1 | 5/2003 | Cao et al. | |
| 2004/0116425 A1 | 6/2004 | Li et al. | |
| 2004/0198773 A1 | 10/2004 | Hart et al. | |
| 2004/0248896 A1 | 12/2004 | Dean et al. | |
| 2004/0266751 A1 | 12/2004 | King | |
| 2005/0004122 A1 | 1/2005 | Brown et al. | |
| 2005/0054697 A1 | 3/2005 | Yager et al. | |
| 2005/0124678 A1* | 6/2005 | Levy et al. ..................... | 514/394 |
| 2006/0041006 A1 | 2/2006 | Ibrahim et al. | |
| 2006/0074119 A1 | 4/2006 | Andrews et al. | |
| 2006/0128732 A1 | 6/2006 | Shimada et al. | |
| 2006/0199804 A1 | 9/2006 | Hummersone et al. | |
| 2007/0066666 A1 | 3/2007 | Emmitte | |

(Continued)

FOREIGN PATENT DOCUMENTS

| | | |
|---|---|---|
| CN | 1816549 A | 8/2006 |
| DE | 275870 A1 | 2/1990 |

(Continued)

OTHER PUBLICATIONS

Al-Azawe et al., Journal of the Iraqi Chemical Society, (1988), 13(1), pp. 1-13.*
Nagasaki et al., CA 139:52925, 2003.*
Nagasaki et al., Heterocycles, 2003, vol. 60, No. 2, pp. 321-335.*
Golub et al., Science, vol. 286, Oct. 15, 1999, pp. 531-537.*
International Search Report and Written Opinion dated Jan. 6, 2010 from International Application No. PCT/US2010/000234, which relates to U.S. Appl. No. 12/657,853.
Non-final rejection, U.S. Appl. No. 12/657,853, dated Apr. 13, 2012.
Non-final rejection, U.S. Appl. No. 12/657,801, dated Jul. 2, 2012.
Final rejection, U.S. Appl. No. 12/657,853, dated Feb. 15, 2013.

(Continued)

*Primary Examiner* — Laura L. Stockton
(74) *Attorney, Agent, or Firm* — Choate, Hall & Stewart LLP; Andrea L.C. Reid

(57) ABSTRACT

The present invention relates to a compound represented by the formula (I) or (I'):

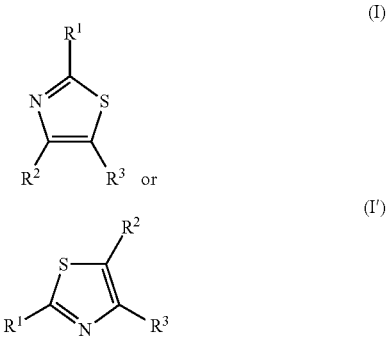

wherein each symbol is as defined in the specification, or a salt thereof, and a PI3K and(or) mTOR inhibitor containing the compound or a prodrug thereof.

10 Claims, No Drawings

(56) References Cited

U.S. PATENT DOCUMENTS

| | | | |
|---|---|---|---|
| 2007/0142415 A1 | 6/2007 | Vanotti et al. | |
| 2007/0203210 A1* | 8/2007 | Boylan et al. | 514/370 |
| 2008/0021217 A1 | 1/2008 | Borchardt et al. | |
| 2008/0045570 A1 | 2/2008 | Brenchley et al. | |
| 2008/0132546 A1* | 6/2008 | Basarab et al. | 514/338 |
| 2008/0255120 A1 | 10/2008 | Lin et al. | |
| 2008/0293716 A1 | 11/2008 | Drewry et al. | |
| 2008/0306060 A1 | 12/2008 | Alexander et al. | |
| 2008/0306121 A1 | 12/2008 | Nan et al. | |
| 2009/0012031 A1 | 1/2009 | Chinnaiyan et al. | |
| 2009/0030016 A1 | 1/2009 | Gandhi et al. | |
| 2009/0036435 A1 | 2/2009 | Curry et al. | |
| 2009/0247567 A1 | 10/2009 | Do et al. | |
| 2009/0325925 A1 | 12/2009 | Renou et al. | |
| 2010/0075951 A1 | 3/2010 | Cardin et al. | |
| 2010/0130473 A1 | 5/2010 | Hummersone et al. | |
| 2010/0256172 A1 | 10/2010 | Shi et al. | |
| 2010/0267759 A1 | 10/2010 | Seefeld et al. | |
| 2011/0003806 A1 | 1/2011 | Hirose et al. | |
| 2011/0021531 A1 | 1/2011 | Chobanian et al. | |
| 2012/0142732 A1 | 6/2012 | Cullis et al. | |
| 2012/0172345 A1 | 7/2012 | Freeze et al. | |
| 2012/0178723 A1 | 7/2012 | Hirose et al. | |
| 2012/0214794 A1 | 8/2012 | Freeze et al. | |
| 2013/0165464 A1 | 6/2013 | Chau et al. | |
| 2013/0165472 A1 | 6/2013 | Chau et al. | |
| 2013/0165483 A1 | 6/2013 | Chau et al. | |
| 2013/0217689 A1 | 8/2013 | Cardin et al. | |
| 2013/0267563 A1 | 10/2013 | Hirose et al. | |

FOREIGN PATENT DOCUMENTS

| | | |
|---|---|---|
| EP | 0853083 A1 | 7/1998 |
| EP | 2313399 B1 | 5/2014 |
| GB | 874634 A | 8/1961 |
| JP | 10087490 A | 4/1998 |
| JP | 2006-508063 A | 3/2006 |
| JP | 2006-525266 A | 11/2006 |
| JP | 2007-519720 A | 7/2007 |
| JP | 2007-197324 A | 8/2007 |
| JP | 2008-531537 A | 8/2008 |
| WO | WO-97/12615 A1 | 4/1997 |
| WO | WO-98/08845 A1 | 3/1998 |
| WO | WO-98/47894 A1 | 10/1998 |
| WO | WO-00/02871 A1 | 1/2000 |
| WO | WO-00/35912 A1 | 6/2000 |
| WO | WO-00/63204 A2 | 10/2000 |
| WO | WO-02/088107 A1 | 11/2002 |
| WO | WO-03/015776 A1 * | 2/2003 |
| WO | WO-03/027085 A2 | 4/2003 |
| WO | WO-03/027107 A1 | 4/2003 |
| WO | WO-03/040096 A2 | 5/2003 |
| WO | WO-2004/016592 A1 | 2/2004 |
| WO | WO-2004/016741 A2 | 2/2004 |
| WO | WO 2004/096797 A1 | 11/2004 |
| WO | WO-2006/046031 A1 | 5/2006 |
| WO | WO-2006/051270 A1 | 5/2006 |
| WO | WO-2006/068933 A2 | 6/2006 |
| WO | WO-2006/069063 A1 | 6/2006 |
| WO | WO-2006/078287 A2 | 7/2006 |
| WO | WO-2006/097030 A1 | 9/2006 |
| WO | WO-2006/102194 A1 | 9/2006 |
| WO | WO-2006/114313 A1 | 11/2006 |
| WO | WO-2007/002559 A1 | 1/2007 |
| WO | WO-2007/043400 A1 | 4/2007 |
| WO | WO-2007/087488 A2 | 8/2007 |
| WO | WO-2007/096315 A1 | 8/2007 |
| WO | WO-2007/110344 A1 | 10/2007 |
| WO | WO 2007/129044 A1 | 11/2007 |
| WO | WO-2007/129161 A2 | 11/2007 |
| WO | WO-2007/138110 A2 | 12/2007 |
| WO | WO-2008/014238 A2 | 1/2008 |
| WO | WO-2008/021235 A2 | 2/2008 |
| WO | WO-2008/023159 A1 | 2/2008 |
| WO | WO-2008/024980 A2 | 2/2008 |
| WO | WO-2008/036541 A1 | 3/2008 |
| WO | WO-2008/047109 A1 | 4/2008 |
| WO | WO-2008/070740 A1 | 6/2008 |
| WO | WO-2008/073785 A2 | 6/2008 |
| WO | WO-2008/083070 A1 | 7/2008 |
| WO | WO-2008/090382 A1 | 7/2008 |
| WO | WO-2008/097835 A2 | 8/2008 |
| WO | WO-2008/098105 A1 | 8/2008 |
| WO | WO-2008/134679 A1 | 11/2008 |
| WO | WO-2008/139161 A1 | 11/2008 |
| WO | WO-2008/157273 A1 * | 12/2008 |
| WO | WO-2009/040730 A2 | 4/2009 |
| WO | WO-2009/042607 A1 | 4/2009 |
| WO | WO-2009/049028 A1 | 4/2009 |
| WO | WO-2009/094224 A1 | 7/2009 |
| WO | WO-2009/106885 A1 * | 9/2009 |
| WO | WO-2009/122148 A1 | 10/2009 |
| WO | WO-2009/153592 A1 | 12/2009 |
| WO | WO-2009/154300 A2 | 12/2009 |
| WO | WO-2009/154741 A1 | 12/2009 |
| WO | WO-2009/158374 A2 | 12/2009 |
| WO | WO-2010/001126 A1 | 1/2010 |
| WO | WO-2010/005841 A1 | 1/2010 |
| WO | WO-2010/017079 A1 | 2/2010 |
| WO | WO-2010/055304 A2 | 5/2010 |
| WO | WO-2010/071741 A1 * | 6/2010 |
| WO | WO-2010/080873 A1 | 7/2010 |
| WO | WO-2010/090716 A1 | 8/2010 |
| WO | WO-2010/121675 A2 | 10/2010 |
| WO | WO-2010/132598 A1 | 11/2010 |
| WO | WO-2011/043371 A1 | 4/2011 |

OTHER PUBLICATIONS

Non-final rejection, U.S. Appl. No. 12/657,801, dated Apr. 15, 2013.
Lucchesini, "A Simple Way to Sequentially Connected Polycycles Containing Terminal Pyrrole Rings: Synthesis of Possible Precursors of Materials for Nonlinear Optics" *Tetrahedron* 48(45):9951-9966 (1992).
U.S. Appl. No. 14/318,223, Jun. 27, 2014, Freeze et al.
U.S. Appl. No. 14/445,373, Jul. 29, 2014, Hirose et al.
U.S. Appl. No. 14/445,376, Jul. 29, 2014, Freeze et al.
1,2,4-Oxadiazole, 5-[5-(1H-imidazol-2-yl)-2-thienyl]-3-(methoxymethyl)-(CA Index Name), CAS Registry No. 1069660-66-7, entered Nov. 2, 2008.
1,2,4-Oxadiazole-3-ethanamine, 5-[5-(1H-imidazol-2-yl)-2-thienyl]-N,N-dimethyl- (CA Index Name), CAS Registry No. 1066888-52-5, entered Oct. 27, 2008.
1H-Pyrazole-1-carboxylic acid, 5-[2,2'-bithiophen]-5-yl-, ethyl ester (CA Index Name), CAS Registry No. 957595-63-0, entered Dec. 12, 2007.
2,7-Naphthyridine, 1,2,3,4-tetrahydro-5-[5-[5-(1H-imidazol-2-yl)-2-thienyl]-1,2,4-oxadiazol-3-yl]- 6-methyl- (CA Index Name), CAS Registry No. 1069717-72-1, entered Nov. 2, 2008.
2-Thiazolamine, 4-[5-(2H-tetrazol-5-yl)-2-thienyl]- (CA Index Name), CAS Registry No. 937625-84-8, entered Jun. 17, 2007.
2-Thiophenecarboxylic acid, 3-(4-chlorophenyl)-4-cyano-5-(4-morpholinyl)-(CA Index Name), CAS Registry No. 883097-33-4, entered May 5, 2006.
2-Thiophenecarboxylic acid, 3-(4-chlorophenyl)-4-cyano-5-(4-morpholinyl)-, methyl ester (CA Index Name), CAS Registry No. 882283-38-7, entered Apr. 30, 2006.
3H-1,2,4-Triazole-3-thione, 2,4-dihydro-4-methyl-5-[4-methyl-2-(5-methyl-3-isoxazolyl)-5-thiazolyl]-(CA Index Name), CAS Registry No. 264616-86-6, entered May 12, 2000.
4-Oxazolecarboxylic acid, 5-[(ethoxymethylene)amino]-2-(4-pyridinyl)-, ethyl ester- (CA Index Name), CAS Registry No. 885901-22-4, entered May 29, 2006.
4-Thiazolecarboxamide, 2-(4-acetyl-5-methyl-1H-1,2,3-triazol-1-yl)-N,N-diethyl-5-phenyl- (CA Index Name), CAS Registry No. 709639-21-4, entered Jul. 14, 2004.
5-Thiazolecarboxamide, N-[2'-(aminosulfonyl)[1,1'-biphenyl]-2-yl]-4-(4-methoxyphenyl)-2-(1H-pyrrol-1-yl)- (CA Index Name), CAS Registry No. 1027033-64-2, entered Jun. 10, 2008.

(56) References Cited

OTHER PUBLICATIONS

Abdelrazek et al., Heterocyclic Synthesis with Nitriles: Synthesis of Some Novel Thiophene and Thieno[2,3-d]Pyrimidine Derivatives, Phosphorus, Sulfur, and Silicons, 71:93-97 (1992).
Acetamide, N-(3,5-dichlorophenyl)-2[[4-methyl-5[4-methyl-2-(5-methyl-3-isoxazolyl)-5-thiazolyl]-4H-1,2,4-triazol-3-yl]thio]- (CA Index Name), CAS Registry No. 264626-19-9, entered May 12, 2000.
Acetamide, N-(4-chlorophenyl)-2[[4-methyl-5[4-methyl-2-(5-methyl-3-isoxazolyl)-5-thiazolyl]-4H-1,2,4-triazol-3-yl]thio]-(CA Index Name), CAS Registry No. 264626-21-3, entered May 12, 2000.
Adib, M. et al., Facile One-Pot Three-Component Synthesis of Functionalized Pyridylfuran-2-amines, Helvetica Chimica Acta, 89(2):299-303 (2006).
Amer, A. et al, Ring Closure Reactions involving 1-Hydrazinophthalazine [1]. Reactions with 1,2,4-Tricarbonyl and 1,3-Dicarbonyl Compounds, Journal of Heterocyclic Chemistry, 20: 1231-1238 (1983).
Amer, A., et al., Factors Influencing the Pathway of Reactions of 1-Hydra-Zinophthalazine With Di- and Tricarbonyl Compounds, Hetercycles, 26(7): 1853-1862 (1987).
Annis, D. A., et al., Inhibitors of the Lipid Phosphatase SHIP2 Discovered by High Throughput Affinity Selection-Mass Spectrometry Screening of Combinatorial Libraries, Combinatorial Chemistry & High Throughput Screening, 12:760-771 (2009).
Batista et al., Synthesis and characterization of new thienylpyrrolyl-benzothiazoles as efficient and thermally stable nonlinear optical chromophores, Tetrahedron, 63(20):4258-4265 (2007).
Batista et al., Synthesis and Second-Order Nonlinear Optical Properties of New Chromophores Containing Benzimidazole, Thiophene, and Pyrrole Heterocycles, Tetrahedron, 63(39): 9842-9849 (2007).
Benzamide, N,N'-(4,4'-di-2-thienyl[2,2'-bithiazole]-5,5'-diyl)bis-(CA Index Name) CAS Registry No. 691381-57-4, entered Jun. 10, 2004.
Benzamide, N,N'-[4,4'-bis(4-fluorophenyl)[2,2'-bithiazole]-5,5'-diyl]bis[4-methyl- (CA Index Name) CAS Registry No. 691381-60-9, entered Jun. 10, 2004.
Benzamide, N-(4'-amino-2',3'-dihydro-3',4-diphenyl-2'-thioxo[2,5'-bithiazol]-5-yl)- (CA Index Name)CAS Registry No. 879910-33-5, entered Apr. 10, 2006.
Benzamide, N-[2-(5-amino-1-phenyl-1H-pyrazol-4-yl)-4-phenyl-5-thiazolyl]-4-methyl- (CA Index Name), CAS Registry No. 1017527-68-2, entered Apr. 27, 2008.
Berndt, A. et al., The p110α crystal structure uncovers mechanisms for selectivity and potency of novel PI3K inhibitors, Nature Chemical Biology, 6(2):117-124 (2010).
Boppana, K. et al., Knowledge based identification of MAO-B selective inhibitors using pharmacophore and structure based virtual screening models, European Journal of Medicinal Chemistry, 44:3584-3590 (2009).
Caballero, J., et al., Investigation of the Differences in Activity between Hydroxycycloalkyl N1 Substituted Pyrazole Derivatives as Inhibitors of B-Raf Kinase by Using Docking, Molecular Dynamics, QM/MM, and Fragment-Based De Novo Design: Study of Binding Mode of Diastereomer Compounds, Journal of Chemical Information and Modeling, 51: 2920-2931 (2011).
Carbamic acid, N,N'-(4,4'-di-2-thienyl[2,2'-bithiazole]-5,5'-diyl)bis-,C,C'-dimethyl ester (CA Index Name) CAS Registry No. 691381-58-5, entered Jun. 10, 2004.
Carbamic acid,4,4'-diphenyl[2,2'-bithiazole]-5,5'-diyl)bis-, dimethyl ester (9CI)(CA Index Name), CAS Registry No. 505060-78-6, entered Apr. 25, 2003.
Chattopadhyay, S. K. et al., Efficient Construction of the Carbon Skeleton of the Novel Polyoxazole-Based Cyclopeptide IB-01211 via a Biomimetic Macrocyclisation, SYNLETT, 4:555-558 (2010).
Choi, W. et al., Synthesis and Antiproliferative Activities of 1-Substituted-3-(3-chloro-5-methoxyphenyl)-4-pyridinylpyrazole Derivatives Against Melanoma Cell Line, Bulletin of the Korean Chemical Society, 30(9):2027-2031 (2009).
Cudworth et al., Structure- Activity Relationship Development of Dihaloaryl Triazole Compounds as Insecticides and Acaricides. 1. Phenyl Thiophen-2-yl Triazoles, Journal of Agricultural and Food Chemistry, 55(18): 7517-7526 (2007).
Database CAS Registry (Columbus, Ohio), RN 893689-50-4 (Entered Jul. 17, 2006).
Database CAS Registry (Columbus, Ohio), RN 893692-42-7 (Entered Jul. 17, 2006).
Database CAS Registry (Columbus, Ohio), RN 893704-20-6 (Entered Jul. 17, 2006).
Database CAS Registry (Columbus, Ohio), RN 893705-40-3 (Entered Jul. 17, 2006).
Database CAS Registry (Columbus, Ohio), RN 898517-78-7 (Entered Aug. 3, 2006).
Database CHEMCATS, Chemical Abstracts Service, Columbus, Ohio, US, XP002545555, order No. T5337328 (Jan. 25, 2008).
Datta et al., A Novel Route to Methyl 3-3(3,4-Disubstituted 5-alkylthio/amino-2-thienyl) propenoates, Synthesis, 7:556-567 (1988).
Di Fabio, R. et al., Dihydropyrrole[2,3-d]Pyridine Derivatives as Novel Corticotropin-Releasing Factor-1 Antagonists: Mapping of the Receptor Binding Pocket by in Silico Docking Studies, Journal of Medicinal Chemistry, 51(22): 7273-7286 (2008).
Dzvinchuk, I.B. et al., Selective Recyclization of 2-Aroylmethyl-1H-Benzimidazole Hydrazones by Condensation With Dimethylformamide, Chemistry of Heterocyclic Compounds, 37(9): 1096-1101 (2001).
Dzvinchuk, I.B. et al., Synthesis and Tautomerism of 2-[3(5)-Aryl(Methyl)Pyrazol-4-yl]-1-Benzimidazoles, Chemistry of Heterocyclic Compounds, 42(9): 1190-1196 (2006).
Emmitte et al., Discovery of Thiophene Inhibitors of Polo-like Kinase, Bioorganic & Medicinal Chemistry Letters, 19(3): 1018-1021 (2009).
Fletcher, A. N. et al., Laser Dye Stability, Part 12. The Pyridinium Salts, Applied Physics, B43:155-160 (1987).
Fridman et al., Spectroscopy, Photophysical and Photochemical Properties of Bisimidazole, Derivatives, Journal of Photochemistry and Photobiology, A: Chemistry, 188(1): 25-33 (2007).
Ge, M. et al., A General Method for the Preparation of 3-Acyl-4-Cyano-5-Amino-Pyrazoles, Tetrahedron Letters, 47: 5797-5799 (2006).
Green et al., Parallel Synthesis of 2-aryl-4-aminobenzimidazoles and their Evaluation as Gonadotropin Releasing Hormone Antagonists, Journal of Combinatorial Chemistry, 11(1): 117-125 (2009).
Hernandez, D. et al., Synthesis and Antitumor Activity of Mechercharmycin A Analogues, Journal of Medicinal Chemistry, 51: 5722-5730 (2008).
Hernandez, D. et al., Synthesis of Natural Product Derivatives Containing 2,4- Concatenated Oxazoles, European Journal of Organic Chemistry, (19): 3389-3396 (2008).
Heyde et al., A Simple Route to N,N-Dialkyl Derivatives of 2-Amino-5-thiophenecarboxylates, Eur. J. Org. Chem.: 3273-3278 (2000).
Hirai et al., Heterocyclic Cation Systems. 14. Synthesis of Thieno[3,2-e][1,4]diazepine, Thiazolo[4,5-e][1,4]diazepine, and s-Triazolo[3,4-c]thiazolo[4,5-e][1,4]diazepine Derivatives, Journal of Organic Chemistry, 45:253-260 (1980).
Hirai et al., Novel Synthesis of Thiophene Derivatives from 1,3-Oxathiol-2-ylideneimmonium Salt, Chemical & Pharmaceutical Bulletin, 19(10): 2194-2197 (1971).
Imidazo[1,2-a]pyridine, 6-[3-[5-(2H-tetrazol-5-yl)-2-thienyl]-1H-pyrazol-4-yl]-3-(2-thiazolyl)-(CA Index Name) CAS Registry No. 732241-18-8, entered Aug. 25, 2004).
International Search Report for PCT/US09/00513, 3 pages (Jun. 10, 2009).
International Search Report for PCT/US09/03607, 4 pages (Sep. 23, 2009).
International Search Report for PCT/US11/47245, 2 pages (Dec. 22, 2011).
International Search Report for PCT/US11/47407, 2 pages (Dec. 22, 2011).
International Search Report for PCT/US11/56135, 4 pages (May 31, 2012).

(56) References Cited

OTHER PUBLICATIONS

International Search Report for PCT/US2011/047241, 3 pages (Jan. 6, 2012).
Laszlo et al., Pyrroles and Other Heterocycles as Inhibitors of P38 Kinase, Bioorganic and Medical Chemistry Letters, 8: 2689-2694 (1998).
Lethu et al., Discovery of a New Class of Protein Farnesyltransferase Inhibitors in the Arylthiophene Series, J. Med. Chem., 52: 6205-6208 (2009).
Liang, J. et al., Crystal Structure of Pl3K [sic] SH3 Domain at 2.0 A Resolution, Journal of Molecular Biology, 257:632-643 (1996).
Lima, L. and Barreiro, E., Bioisosterism: A Useful Strategy for Molecular Modification and Drug Design, Current Medicinal Chemistry, 12: 23-49 (2005).
Liu et al., Highly Selective and Potent Thiophenes as PI3K Inhibitors with Oral Antitumor Activity, Med. Chem. Lett., 2:809-813 (2011).
Mamedov et al., Synthesis and Some Properties of the Methyl Ester and N,N-diethylamide of 2-Azido-5-Phenyl-4-Thiazolecarboxylic Acid, Chemistry of Heterocyclic Compounds, 29(5): 607-611 (1993).
Matschke et al., Quinomethides Versus Unsymmetric Hybrids: Two Variations of Non-Radicaloid SEM-States in Four-Electron Redox Systems of bis-4H-imidazoles, Structural Chemistry, 19(3):399-405 (2008).
Men Ear, K. A. et al., Identification and optimisation of novel and selective small molecular weight kinase inhibitors of mTOR, Bioorg. Med. Chem. Lett., 19:5898-5901 (2009).
Moorthy et al., In Silico-Based Structural Analysis of Arylthiophene Derivatives for Ftase Inhibitory Activity, hERG, and Other Toxic Effects, Journal of Biomolecular Screening, 16(9):1037-1046 (2011).
Morpholine, 4-(5-(4,5-diphenyl-1H-imidazol-2-yl)-2-thienyl]-, Ryan Scientific Screening Library, Publication date: Jan. 25, 2008, CAS Registry No. 851954-74-0.
Pinto et al., The Synthesis of 5-Alkoxy and 5-Amino Substituted Thiophenes, Tetrahedron Letters, 41(10): 1597-1600 (2000).
Pyrazolo[1,5-a]pyrimidin-7(4H)-one,3-ethyl-5-[5-(1H-imidazol-2-yl)-2-thienyl]- (CA Index Name), CAS Registry No. 1087437-07-7, entered Dec. 21, 2008.
RAAP, Some Synthesis with Dimethyl Monothionemalonate, Canadian Journal of Chemistry, 46:13, 2255-2261 (1968).
Rehwald et al., New Synthesis of 2,4-Diaminothiophenes- Use of (1,3-oxathiol-2-ylidene)Malononitrile, Heterocycles, 45(3): 493-500 (1997).
Revesz, L. et al., SAR of 2,6-Diamino-3,5-difluoropyridinyl Substituted Heterocycles as Novel p38 MAP Kinase Inhibitors, Bioorg. Med. Chem. Lett., 12(16):2109-2112 (2002).
Sheridan, The Most Common Chemical Replacements in Drug-Like Compounds, J. Chem. Inf. Comput. Sci., 42:103-108 (2002).
Thompson, M. J. et al., Development of a Diversity-Oriented Approach to Oxazole-5-amide Libraries, Journal of Organic Chemistry, 74(10):3856-3865 (2009).
Tsuge, O., and Torii, A., Compounds Related to Acridine. VIII.[1)] Reaction of 9-Vinylacridine with p-Substituted Nitrosobenzenes, Bull. Chem. Soc. Japan, 45: 3187-3191 (1972).
Wang, Q. et al., Copper-Mediated Amidation of Heterocyclic and Aromatic C-H Bonds, Organic Letters, 11(22): 5178-5180 (2009).
Welker et al., Recent Syntheses of PI3K/Akt/mTOR signaling pathway inhibitors, Bioorganic & Medicinal Chemistry, 21(14): 4063-4091 (2013).
Written Opinion for PCT/US09/00513, 5 pages (Jun. 10, 2009).
Written Opinion for PCT/US09/03607, 5 pages (Sep. 23, 2009).
Written Opinion for PCT/US11/47245, 5 pages (Dec. 22, 2011).
Written Opinion for PCT/US11/47407, 7 pages (Jun. 10, 2009).
Written Opinion for PCT/US11/56135, 13 pages (May 31, 2012).
Written Opinion for PCT/US2011/047241, 9 pages (Jan. 6, 2012).
Ye, L., et al., Pyrazolylthiazole as ΔF508-Cystic Fibrosis Transmembrane Conductance Regulator Correctors with Improved Hydrophilicity Compared to Bithiazoles, Journal of Medicinal Chemistry, 53:3772-3781 (2010).
Zhang, F. et al., Decarboxylative C-H Cross-Coupling of Azoles, Angew. Chem. Int. Ed., 49(15): 2768-2771 (2010).
Zhou et al., Selenium-Containing Heterocycles from Isoselenocyanates: Synthesis of 1,3- Selenazoles from N-Phenylimidoyl Isoselenocyanates, Helvetica Chimica Acta, 83: 1576-1598 (2000).

* cited by examiner

THIAZOLE DERIVATIVES

The present application claims the benefit of U.S. Provisional Application Ser. No. 61/148,533, filed Jan. 30, 2009 (pending) and U.S. Provisional Application Ser. No. 61/229,399, filed Jul. 29, 2009 (pending). The entire contents of each of the above-referenced patent applications are incorporated herein by this reference.

TECHNICAL FIELD

The present invention relates to a thiazole derivative having a PI3K inhibitory activity and(or) an mTOR inhibitory activity, and useful for the prophylaxis or treatment of cancer, and use thereof.

BACKGROUND

PI3-Kinase (Phosphoinositide 3-Kinase, PI3K) is an enzyme responsible for the phosphorylation of hydroxyl group at the 3-position of the inositol ring of inositol phospholipid. Inositol triphosphate (PIP3) converted by PI3-Kinase activates AKT and the like and plays an important role in the growth, survival, motility and the like of a cell in response to extracellular signals (non-patent document 1).

PI3-Kinase is largely divided into Classes I, II and III based on its protein primary structure, of which Class I PI3-Kinase alone catalyzes a reaction from PIP2 as a substrate to PIP3. ClassI PI3-Kinase is further divided into Class IA (PIK3CA, PIK3CB, PIK3CD), and Class IB (PIK3CG). Among these, Class IA PI3-Kinase transmits growth or motility signals from a tyrosine kinase receptor to the downstream thereof, and Class IB PI3-Kinase is responsible for signal transduction from a G protein-conjugated receptor such as cytokine receptor and the like (non-patent document 2).

In addition, an enzyme (PTEN) responsible for a dephosphorylation reaction from inositol triphosphate (PIP3) to inositol diphosphate (PIP2) is defective due to various cancers (non-patent document 3), and PI3KCA is also reported to show active mutation in various cancers (non-patent documents 4, 5 and 6). Furthermore, an active mutant of PIK3CA can cancerate cells (non-patent documents 7 and 8).

Therefore, PI3-Kinase pathway is presumed to be highly frequently activated in cancer cells, and inhibition of PI3-Kinase is expected to lead a negative action on the growth, survival or motility of cancer. Accordingly, a PI3-Kinase inhibitor is expected to be a therapeutic drug for cancer.

On the other hand, signals of activated PI3-Kinase are transmitted to mTOR (mammalian Target of Rapamycin) molecule at the downstream via several molecules. This molecule forms two kinds of complexes (TORC1 and TORC2) having different functions depending on the two kinds of molecules (Raptor and Rictor) to be bonded (non-patent document 9). Rapamycin and analogs thereof suppress the activity of TORC1, but do not inhibit the activity of TORC2 (non-patent documents 9 and 10). Rapamycin analogs show a strong antitumor action clinically as well (non-patent documents 11 and 12), and inhibition of mTOR is also confirmed to be a promising target in cancer treatments. However, Rapamycin analogs are known to activate Akt molecule according to the status of IRS-1, since they inhibit TORC1 alone (non-patent document 13), and inhibition of not only PI3-Kinase but also mTOR is expected to show a strong antitumor action.

Non-Patent Document 1
Cantley, L. C., The Phosphoinositide 3-Kinase Pathway. Science. 296, 1655-1657 (2002)

Non-Patent Document 2
Wymann, M. P., and Pirola, L., Structure and function of phosphoinositide 3-Kinases. Biochim. Biophys. Acta 1436. 127-150 (1998)

Non-Patent Document 3
Li, J., et al., PTEN, a Putative Protein Tyrosine Phosphatase Gene Mutated in Human Brain, Breast, and Prostate Cancer. Science 275, 1943-1947 (1997)

Non-Patent Document 4
Lee, J. W., et al., PIK3CA gene is frequently mutated in breast carcinomas and hepatocellular carcinomas. Oncogene, 24, 1477-1480 (2005)

Non-Patent Document 5
Karakas, B., Bechman, K. E., and Park, B. H., Mutation of the PIK3CA oncogene in human cancers. British J. Cancer, 94, 455-459 (2006)

Non-Patent Document 6
Whyte, D. B., and Holbeck, S. L., Correlation of PIK3Ca mutations with gene expression and drug sensitivity in NCI-60 cell lines. Biochem, Biophys. Res. Comm. 340, 469-475 (2006)

Non-Patent Document 7
Zhao, J. J., et al., The oncogenic properties of mutant p110a and p110b phosphatidilinositol 3-kinases in human mammary epithelial cells. Proc. Natl. Acad. Sci. USA, 102, 18443-18448 (2005)

Non-Patent Document 8
Bader, A. G., Kang, S., and Vogt, K., Cancer-specific mutations in PIK3CA are oncogenic in vivo. Proc. Natl. Acad. Sci. USA, 103, 1475-1479 (2006)

Non-Patent Document 9
Bhaskar P T, Hay N., The two TORCs and Akt. Dev. Cell. 12, 487-502 (2007)

Non-Patent Document 10
Wullschleger S, Loewith R, Hall M N., TOR signaling in growth and metabolism. Cell. 124, 471-84. (2006) Review.

Non-Patent Document 11
Garcia J A, Danielpour D., Mammalian target of rapamycin inhibition as a therapeutic strategy in the management of urologic malignancies. Mol Cancer Ther. 7, 1347-1354 (2008)

Non-Patent Document 12
Johnson B E, Jackman D, Jänne P A., Rationale for a phase I trial of erlotinib and the mammalian target of rapamycin inhibitor everolimus (RAD001) for patients with relapsed non small cell lung cancer. Clin Cancer Res. 13 (15 Pt 2): s4628-4631 (2007)

Non-Patent Document 13
Easton J B, Kurmasheva R T, Houghton P J., IRS-1: auditing the effectiveness of mTOR inhibitors. Cancer Cell. 9, 153-155. (2006)

Many thiazole derivatives useful as pharmaceutical agents and the like have been reported (patent documents 1-26, non-patent documents 14-32).
patent document 1: US2007/0203210
patent document 2: WO2005/075470
patent document 3: EP1813613
patent document 4: US2008/0132546
patent document 5: U.S. Pat. No. 4,528,291
patent document 6: WO2005/103043
patent document 7: U.S. Pat. No. 4,080,457
patent document 8: U.S. Pat. No. 4,571,402
patent document 9: US2006/0160799
patent document 10: US2005/0124678
patent document 11: US2003/0229065
patent document 12: U.S. Pat. No. 5,939,462
patent document 13: U.S. Pat. No. 6,245,817
patent document 14: WO98/35944 patent document 15: U.S. Pat. No. 7,138,403
patent document 16: U.S. Pat. No. 6,608,087
patent document 17: US2004-0024030
patent document 18: U.S. Pat. No. 6,930,116
patent document 19: US2003-0170858
patent document 20: W2004-0024030
patent document 21: U.S. Pat. No. 6,930,116
patent document 22: U.S. Pat. No. 3,882,138
patent document 23: U.S. Pat. No. 3,964,896
patent document 24: WO2006-122011
patent document 25: WO2006-020767
patent document 26: WO2005-070994
non-patent document 14: Bioorganic & Medical Chemistry Letters (2002), 12(16), 2109-2112
non-patent document 15: Zeitschrift fuer chemie (1970), 10(12), 460-2
non-patent document 16: Farmacia (Bucharest) (2000), 48(3), 65-73
non-patent document 17: Journal of the American Chemical Society (2007), 129(48), 15072-15084
non-patent document 18: PPMSE Preprints (2007), 96, 885-886
non-patent document 19: Chemistry—A European Journal (2005), 11(10), 2914-2922
non-patent document 20: Synthetic Metals (2005), 148(3), 219-226
non-patent document 21: Synlett (2004), (15), 2681-2684
non-patent document 22: Journal of the American Chemical Society (2004), 126(13), 4318-4328
non-patent document 23: Journal of the American Chemical Society(2003), 125(17), 5040-5050
non-patent document 24: Angewandte Chemie, International Edition (2002), 41(19), 3598-3601
non-patent document 25: American Chemical Society, Division of Polymer Chemistry (2002), 42(2), 540-541
non-patent document 26: Materials Research Society Symposium Proceedings (2000), 598
non-patent document 27: Chemistry of Materials (2000), 12(6), 1519-1522
non-patent document 28: American Chemical Society, Division of Polymer Chemistry (1999), 40(2), 1235-1236
non-patent document 29: Chemistry Letters (1998), (3), 235-236
non-patent document 30: Helvetica Chimica Acta (1945), 28, 824-28
non-patent document 31: Helvetica Chimica Acta (1953), 36, 354-7
non-patent document 32: Chemische Berichte (1951), 84, 518-24

DISCLOSURE OF THE INVENTION

The present invention aims to provide a compound having a superior PI3K inhibitory activity and(or) a superior mTOR inhibitory activity, which is low toxic and sufficiently satisfactory as a pharmaceutical product.

The present inventors have conducted intensive studies and found that a compound represented by the following formula (I) or a salt thereof (sometimes to be referred to as compound (I) in the present specification) has a superior PI3K inhibitory activity and(or) a superior mTOR inhibitory activity, and conducted further intensive studies, which resulted in the completion of the present invention.

Accordingly, the present invention provides
[1] A compound represented by the formula (I):

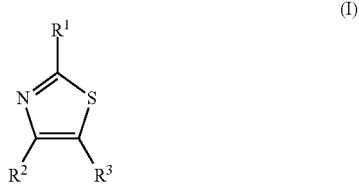

or a pharmaceutically acceptable salt thereof, wherein
$R^1$ is an optionally substituted nitrogen-containing aromatic heterocyclic group (excluding 3-isoxazolyl group, 2-pyridyl group, 3-pyridyl group, 5-pyrimidyl group, 2-pyrimidyl group and pyrazinyl group),
$R^2$ is a halogen atom, or an optionally substituted group bonded via a carbon atom, a nitrogen atom, an oxygen atom or a sulfur atom,
$R^3$ is (1) —CON($R^4$)$R^{4'}$, wherein $R^4$ and $R^{4'}$ are representively hydrogen, —$Z_1$—$R^5$, optionally substituted $C_{1-6}$ aliphatic, or optionally substituted 3-10-membered cycloaliphatic, wherein $Z_1$ is selected from an optionally substituted $C_{1-3}$ alkylene chain, —S(O)—, —S(O)$_2$—, —C(O)—, —CO$_2$—, —C(O)NR$^{4a}$—, or —S(O)$_2$NR$^{4a}$—, wherein $R^{4a}$ is hydrogen or an optionally substituted $C_{1-4}$ aliphatic, and $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
(2) an optionally substituted 5-membered aromatic heterocyclic group containing 2 to 4 nitrogen atoms besides carbon atom, which is bonded via a carbon atom, or
(3) an optionally substituted 5-membered aromatic heterocyclic group containing 1 to 3 nitrogen atoms besides carbon atom and further containing one oxygen atom or sulfur atom, which is bonded via a carbon atom,
provided that when $R^3$ is an optionally substituted thiazolyl group and $R^1$ is an optionally substituted thiazolyl group, then the optionally substituted thiazolyl group for $R^1$ is a group represented by

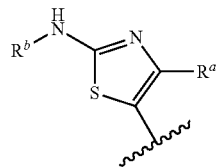

wherein $R^a$ is a hydrogen atom, an alkyl group or a halogen atom,
$R^b$ is (i) a hydrogen atom, (ii) an optionally substituted hydrocarbon-carbonyl group, (iii) an optionally substituted heterocyclyl-carbonyl group, (iv) an optionally substituted carbamoyl group, (v) an optionally substituted alkoxycarbonyl group, (vi) an optionally substituted hydrocarbon-sulfonyl group, (vii) an optionally substituted heterocyclyl-sulfonyl group, (viii) an optionally substituted sulfamoyl group, (ix) an optionally substituted hydrocarbon group or (x) an optionally substituted heterocyclic group, or a salt thereof, (excluding

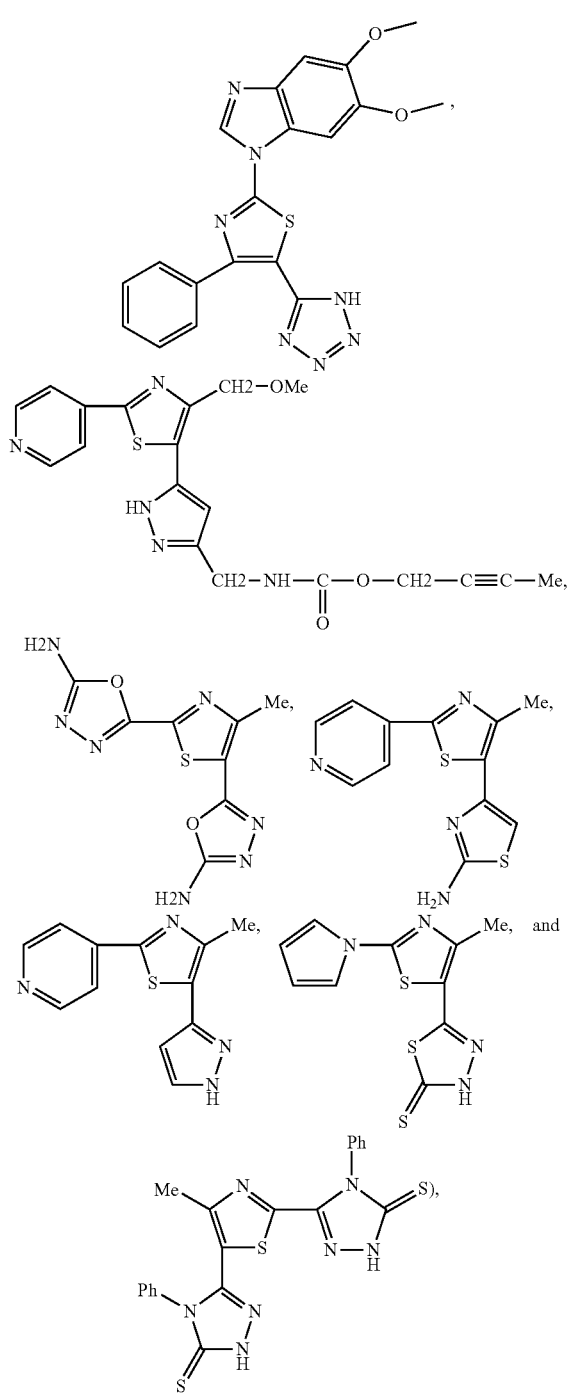

and further provided that the compound is other than: 5-Thiazolecarboxamide, N-[2'-(aminosulfonyl)[1,1'-biphenyl]-2-yl]-4-(4-methoxyphenyl)-2-(1H-pyrrol-1-yl)-; 5-Thiazolecarboxamide, 4-(4-nitrophenyl)-2-(4-pyridinyl)-N-[3-(trifluoromethyl)phenyl]-; 5-Thiazolecarboxamide, 4-(4-bromophenyl)-N-(1-methylethyl)-2-(2-propyl-4-pyridinyl)-; 5-Thiazolecarboxamide, 4-phenyl-N-[(1S,2S)-2-(phenylmethoxy)cyclopentyl]-2-(1H-pyrazol-1-yl)-; 5-Thiazolecarboxamide, 4-phenyl-N-(phenylmethyl)-2-(1H-pyrazol-1-yl)-; 5-Thiazolecarboxamide, N-[(4-chlorophenyl)methyl]-2-(3-methoxy-1H-pyrazol-1-yl)-4-phenyl-; 5-Thiazolecarboxamide, 4-phenyl-N-[1-(phenylmethyl)-3-pyrrolidinyl]-2-(1H-pyrazol-1-yl)-; 5-Thiazolecarboxamide, N-[(1S,2R)-1-[(3,5-difluorophenyl)methyl]-3-[[1-(3-ethynylphenyl)cyclopropyl]amino]-2-hydroxypropyl]-4-phenyl-2-(1H-pyrrol-1-yl)-; 5-Thiazolecarboxamide, 2-(1H-benzimidazol-1-yl)-4-phenyl-; 5-Thiazolecarboxamide, 2-(5,6-dimethoxy-1H-benzimidazol-1-yl)-4-phenyl-; 5-Thiazolecarboxamide, 2-(5,6-dimethoxy-1H-benzimidazol-1-yl)-N,N-dimethyl-4-phenyl-; 5-Thiazolecarboxamide, 2-(5,6-dimethoxy-1H-benzimidazol-1-yl)-N-ethyl-4-phenyl-; 5-Thiazolecarboxamide, N-cyclopropyl-2-(5,6-dimethoxy-1H-benzimidazol-1-yl)-4-phenyl-; 5-Thiazolecarboxamide, 4-(3-chlorophenyl)-2-(5,6-dimethoxy-1H-benzimidazol-1-yl)-; 5-Thiazolecarboxamide, 2-(5,6-dimethoxy-1H-benzimidazol-1-yl)-N,4-diphenyl-; 5-Thiazolecarboxylic acid, 4-(3-chlorophenyl)-2-(5,6-dimethoxy-1H-benzimidazol-1-yl)-, 2-(2-thienylcarbonyl)hydrazide; 5-Thiazolecarboxamide, 4-(3-chlorophenyl)-2-(5,6-dimethoxy-1H-benzimidazol-1-yl)-N-4-pyrimidinyl-; 5-Thiazolecarboxamide, 4-(3-chlorophenyl)-2-(5,6-dimethoxy-1H-benzimidazol-1-yl)-N-(3-methoxyphenyl)-; 5-Thiazolecarboxamide, 4-(3-chlorophenyl)-2-(5,6-dimethoxy-1H-benzimidazol-1-yl)-N-2-thiazolyl-; 5-Thiazolecarboxamide, 4-(3-chlorophenyl)-2-(5,6-dimethoxy-1H-benzimidazol-1-yl)-N-4H-1,2,4-triazol-4-yl-; 5-Thiazolecarboxylic acid, 4-(3-chlorophenyl)-2-(5,6-dimethoxy-1H-benzimidazol-1-yl)-, 2-(3-methylbenzoyl)hydrazide; 5-Thiazolecarboxamide, 4-(3-chlorophenyl)-N-(2,3-dihydro-2-oxo-4-pyrimidinyl)-2-(5,6-dimethoxy-1H-benzimidazol-1-yl)-.

The present invention also provides [2], compounds of formula (I) when $R^3$ is —CON($R^4$)$R^{4a}$, $R^4$ and $R^{4a}$ are hydrogen.

The present invention also provides [3]: a compound represented by the formula Ia

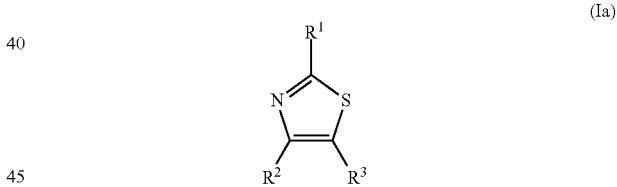

or a pharmaceutically acceptable salt, wherein $R^1$ is an optionally substituted nitrogen-containing aromatic heterocyclic group (excluding 3-isoxazolyl group, 2-pyridyl group, 3-pyridyl group, 5-pyrimidyl group, 2-pyrimidyl group and pyrazinyl group), $R^2$ is a halogen atom, or an optionally substituted group bonded via a carbon atom, a nitrogen atom, an oxygen atom or a sulfur atom, and $R^3$ is (1) an optionally substituted 5-membered aromatic heterocyclic group containing 2 to 4 nitrogen atoms besides carbon atom, which is bonded via a carbon atom, or (2) an optionally substituted 5-membered aromatic heterocyclic group containing 1 to 3 nitrogen atoms besides carbon atom and further containing one oxygen atom or sulfur atom, which is bonded via a carbon atom, provided that when $R^3$ is an optionally substituted thiazolyl group and $R^1$ is an optionally substituted thiazolyl group, then the optionally substituted thiazolyl group for $R^1$ is a group represented by

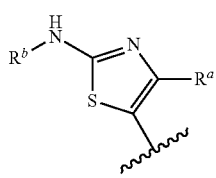

wherein R<sup>a</sup> is a hydrogen atom, an alkyl group or a halogen atom,

R<sup>b</sup> is (i) a hydrogen atom, (ii) an optionally substituted hydrocarbon-carbonyl group, (iii) an optionally substituted heterocyclyl-carbonyl group, (iv) an optionally substituted carbamoyl group, (v) an optionally substituted alkoxycarbonyl group, (vi) an optionally substituted hydrocarbon-sulfonyl group, (vii) an optionally substituted heterocyclyl-sulfonyl group, (viii) an optionally substituted sulfamoyl group, (ix) an optionally substituted hydrocarbon group or (x) an optionally substituted heterocyclic group

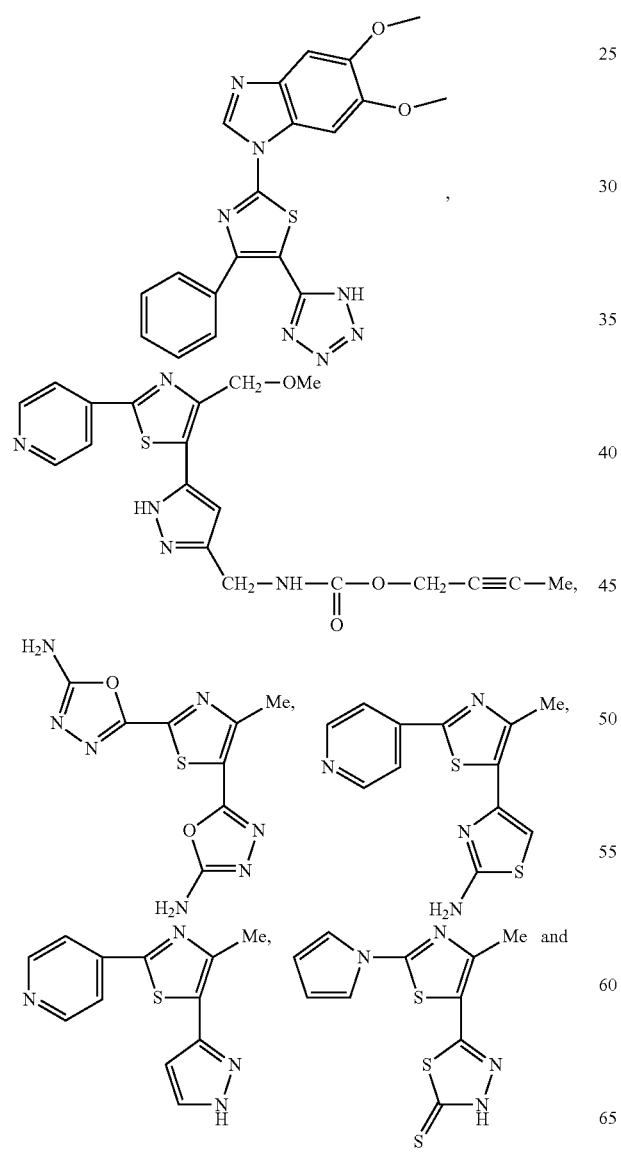

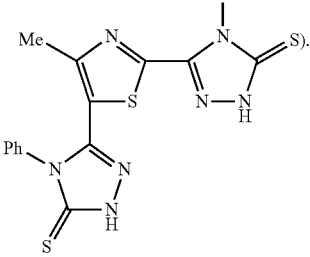

The present invention also provides [4] the compound of [1], [2], or [3] wherein;

a) the optionally substituted group bonded via a carbon atom is selected from cyano, an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, or an optionally substituted carbamoyl group;

b) the optionally substituted group bonded via a nitrogen atom is selected from
  i) amino;
  ii) mono- or di-substituted amino, wherein the amino is substituted by an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, or an optionally substituted carbamoyl group, and
  iii) an optionally substituted heterocyclic group bonded via a nitrogen atom;

c) the optionally substituted group bonded via an oxygen atom is selected from hydroxy optionally substituted by an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, or an optionally substituted carbamoyl group, and d) the optionally substituted group bonded via a sulfur atom is selected from mercapto optionally substituted by: an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, or an optionally substituted carbamoyl group.

The present invention also provides [5] the compound of [1], [2], [3] or [4] wherein $R^1$ is (i) an optionally substituted group represented by

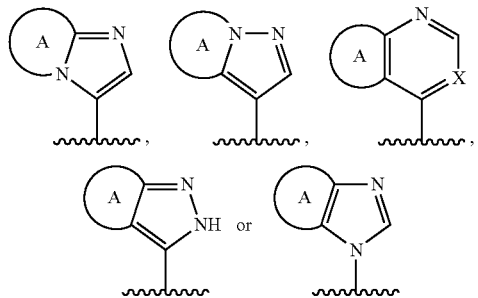

wherein A is a cyclic group and X is CH or N, or (ii) a pyridyl group, a pyrimidinyl group, a pyrazolyl group, a thiazolyl group, an oxazolyl group, an imidazolyl group, a triazolyl group, an isothiazolyl group or a pyridazinyl group, each of which is optionally substituted;

The present invention also provides [6] the compound of [1], [2], [3], [4] or [5] wherein $R^1$ is (i) an optionally substituted group represented by

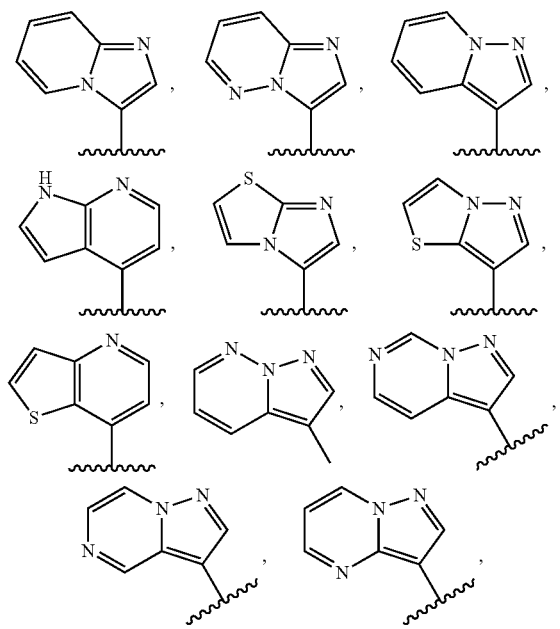

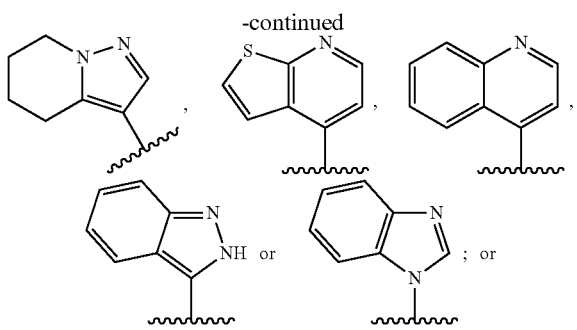

(ii) a group represented by

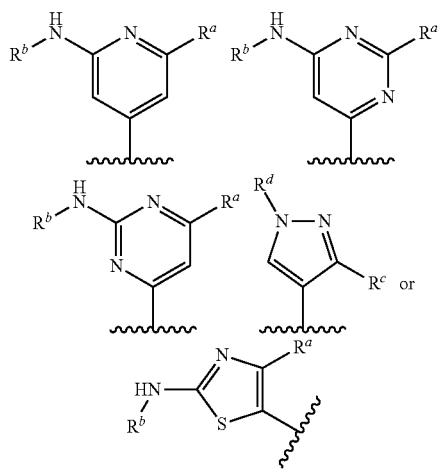

wherein $R^a$ and $R^c$ are each a hydrogen atom, an alkyl group or a halogen atom, $R^b$ is (i) a hydrogen atom, (ii) an optionally substituted hydrocarbon-carbonyl group, (iii) an optionally substituted heterocyclyl-carbonyl group, (iv) an optionally substituted carbamoyl group, (v) an optionally substituted alkoxycarbonyl group, (vi) an optionally substituted hydrocarbon-sulfonyl group, (vii) an optionally substituted heterocyclyl-sulfonyl group, (viii) an optionally substituted sulfamoyl group, (ix) an optionally substituted hydrocarbon group or (x) an optionally substituted heterocyclic group, and $R^d$ is (i) a hydrogen atom, (ii) an optionally substituted hydrocarbon group or (iii) an optionally substituted heterocyclic group;

The present invention also provides [7] the compound of [1], [2], [3], [4], [5] or [6] wherein $R^2$ is (i) a halogen atom, (ii) an optionally substituted hydroxy group, (iii) an optionally substituted hydrocarbon group, (iv) an optionally substituted heterocyclic group, (v) an optionally substituted amino group, (vi) an optionally substituted thiol group or (vii) an acyl group;

The present invention also provides [8] the compound of [1], [3], [4], [5] or [6] wherein $R^3$ is an optionally substituted triazolyl group;

The present invention also provides [9] the compound of [1], [3], [6], [7] or [8] wherein:

$R^1$ is selected from:

(i) an 8- to 10-membered nitrogen-containing aromatic fused heterocyclic group optionally containing, besides carbon atom and nitrogen atom, 1 to 4 heteroatoms selected from an oxygen atom and a sulfur atoms, which is optionally substituted by substituent(s) selected from (1) hydroxy, (2)

$C_{1-6}$alkyl, (3) $C_{1-6}$ alkoxy optionally substituted by hydroxy, (4) $C_{6-18}$ aryl-$C_{1-4}$alkyl-oxy, (5) 4- to 7-membered monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom and (6) 4- to 7-membered monocyclic non-aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom, or (ii) a 4-pyridyl group or a pyrazolyl group optionally substituted by substituent(s) selected from (1) a halogen atom, (2) $C_{1-6}$ alkyl, (3) $C_{1-8}$ alkyl-carbonylamino optionally substituted by substituent(s) selected from $C_{6-18}$ arylthio, and 4- to 7-membered monocyclic aromatic heterocyclic group or monocyclic non-aromatic heterocyclic group containing, as a ring constituting atom besides carbon atom, 1 to 4 heteroatoms selected from an oxygen atom, a sulfur atom and a nitrogen atom, (4) $C_{3-8}$ cycloalkyl-carbonylamino, (5) $C_{6-18}$ aryl-carbonylamino optionally substituted by substituent(s) selected from a halogen atom, $C_{1-6}$ alkyl, $C_{1-6}$ alkoxy, amino and mono- or di-$C_{1-6}$ alkylamino, (6) $C_{6-18}$ aryl-$C_{1-4}$ alkyl-carbonylamino and (7) 4- to 7-membered monocyclic heterocyclyl-carbonylamino, said monocyclic heterocyclyl contains, as a ring constituting atom besides carbon atom, 1 to 4 heteroatoms selected from an oxygen atom, a sulfur atom and a nitrogen atom and is optionally substituted by $C_{1-6}$ alkyl;

wherein $R^2$ is selected from:
(i) a $C_{1-8}$ alkyl group,
(ii) a $C_{2-8}$ alkenyl group,
(iii) a $C_{3-8}$ cycloalkyl group,
(iv) a hydroxyl group optionally substituted by a $C_{1-8}$ alkyl, $C_{2-8}$ alkenyl or $C_{6-18}$ aryl-$C_{1-4}$ alkyl,
(v) a $C_{6-18}$ aryl group optionally substituted by a halogen atom, optionally halogenated $C_{1-8}$ alkyl or $C_{1-8}$ alkoxy,
(vi) a $C_{6-18}$ aryl-$C_{1-4}$ alkyl group,
(vii) a 4- to 7-membered aromatic monocyclic heterocyclic group containing, besides carbon atom, 1 to 3 heteroatoms selected from a nitrogen atom, an oxygen atom and a sulfur atom, or
(viii) a 4- to 7-membered non-aromatic heterocyclic group containing, besides carbon atom, 1 to 3 heteroatoms selected from a nitrogen atom, an oxygen atom and a sulfur atom; and wherein $R^3$ is a 5-membered aromatic heterocyclic group containing 2 to 4 nitrogen atoms, which is bonded via a carbon atom and optionally substituted by $C_{1-8}$ alkyl;

The present invention also provides [10] a compound having formula Ib:

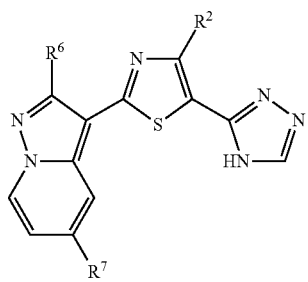

or a pharmaceutically salt, wherein
$R^2$ is (i) a halogen atom, (ii) an optionally substituted hydroxy group, (iii) an optionally substituted hydrocarbon group, (iv) an optionally substituted heterocyclic group, (v) an optionally substituted amino group, (vi) an optionally substituted thiol group or (vii) an acyl group $R^6$ is hydrogen or optionally substituted $C_{1-4}$alkyl, and $R^7$ is H, hydroxyl optionally substituted by optionally halogenated $C_{1-6}$ alkyl, $C_{1-6}$ alkoxy optionally substituted by a group selected from hydroxy, $C_{1-6}$ alkyl-carbonylamino and amino-$C_{1-6}$ alkyl-carbonylamino, $C_{6-18}$ aryl-$C_{1-4}$alkyl-oxy, 4- to 7-membered monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by $C_{1-6}$ alkyl optionally substituted by halogen and 4- to 7-membered monocyclic non-aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by a group selected from halogen, $C_{1-6}$ alkyl, $C_{1-6}$ alkylsulfonyloxy and $C_{1-6}$ alkyl-carbonyl optionally substituted by hydroxy.

The present invention also provides [11] the compound of [10], wherein $R^2$ is an optionally substituted phenyl group.

The present invention also provides [12] a compound having formula I':

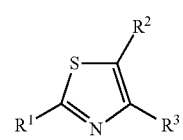

or a pharmaceutically acceptable salt thereof, wherein
$R^1$ is an optionally substituted nitrogen-containing aromatic heterocyclic group (excluding 3-isoxazolyl group, 2-pyridyl group, 3-pyridyl group, 5-pyrimidyl group, 2-pyrimidyl group and pyrazinyl group), $R^2$ is a halogen atom, or an optionally substituted group bonded via a carbon atom, a nitrogen atom, an oxygen atom or a sulfur atom, and $R^3$ is (1) CON($R^4$)$R^{4'}$, wherein $R^4$ and $R^{4'}$ are hydrogen or optionally substituted $C_1$-$C_6$ aliphatic, or (2) an optionally substituted 5-membered aromatic heterocyclic group containing 2 to 4 nitrogen atoms besides carbon atom, which is bonded via a carbon atom; (2) an optionally substituted 5-membered aromatic heterocyclic group containing 2 to 4 nitrogen atoms besides carbon atom, which is bonded via a carbon atom; or (3) an optionally substituted 5-membered aromatic heterocyclic group containing 1 to 3 nitrogen atoms besides carbon atom and further containing one oxygen atom or sulfur atom, which is bonded via a carbon atom, provided that the compound of formula I' is other than: 4-Thiazolecarboxamide, 2-(4-acetyl-5-methyl-1H-1,2,3-triazol-1-yl)-N,N-diethyl-5-phenyl-; 1H-1,2,3-Triazole-4-acetic acid, 1-[4-[(diethylamino)carbonyl]-5-phenyl-2-thiazolyl]-5-methyl-a-oxo-, ethyl ester; 4-Thiazolecarboxamide, 2-[4-(1,2-dioxopropyl)-5-methyl-1H-1,2,3-triazol-1-yl]-N, N-diethyl-5-phenyl; and further provided that when $R^1$ is optionally substituted 1H-indazol-3-yl and $R^3$ is CON($R^4$)$R^{4'}$, then $R^2$ is a group other than unsubstituted phenyl or 3-pyridyl.

The present invention also provides [13] the compound [12] wherein when $R^3$ is —CON($R^4$)$R^{4'}$, and $R^4$ and $R^{4'}$ are hydrogen.

The present invention also provides [14] the compound [12] or [13], wherein:

a) the optionally substituted group bonded via a carbon atom is selected from cyano, an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, or an optionally substituted carbamoyl group;

b) the optionally substituted group bonded via a nitrogen atom is selected from
  i) amino;
  ii) mono- or di-substituted amino, wherein the amino is substituted by an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, or an optionally substituted carbamoyl group, and
  iii) an optionally substituted heterocyclic group bonded via a nitrogen atom;

c) the optionally substituted group bonded via an oxygen atom is selected from hydroxy optionally substituted by an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, or an optionally substituted carbamoyl group, and d) the optionally substituted group bonded via a sulfur atom is selected from mercapto optionally substituted by: an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, or an optionally substituted carbamoyl group.

The present invention also provides [15] the compound [12] or [13], wherein $R^1$ is:

(i) an optionally substituted group represented by

wherein A is a cyclic group and X is CH or N, or (ii) a pyridyl group, a pyrimidinyl group, a pyrazolyl group, a thiazolyl group, an oxazolyl group, an imidazolyl group, a triazolyl group, an isothiazolyl group or a pyridazinyl group, each of which is optionally substituted.

The present invention also provides [16] the compound [12] or [13], wherein $R^1$ is an optionally substituted group represented by

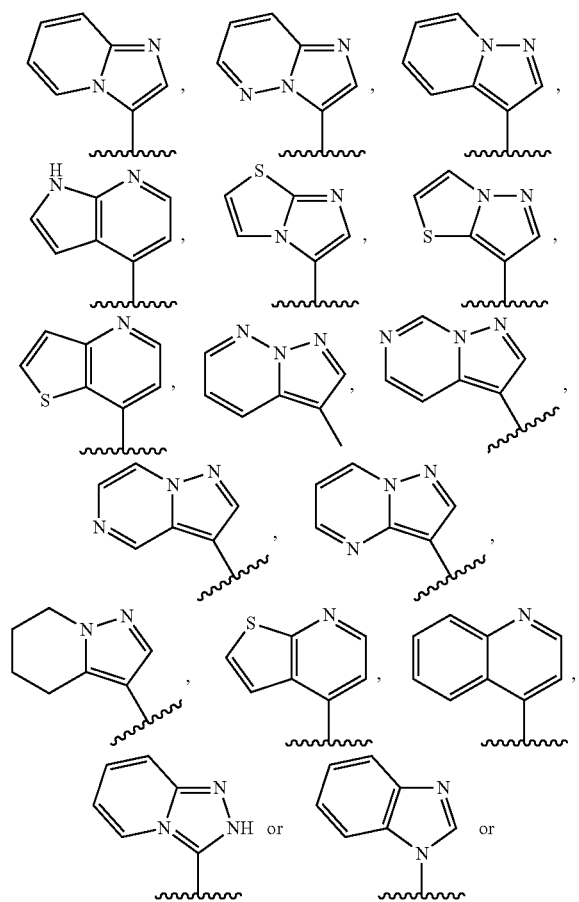

a group represented by:

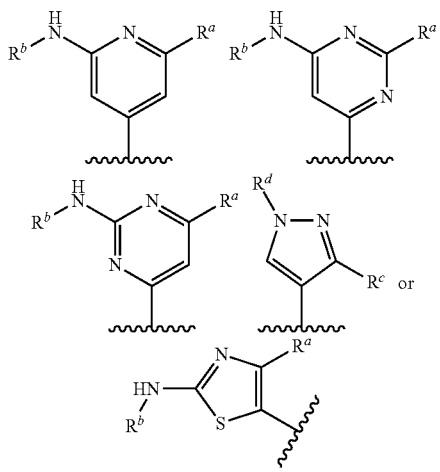

wherein $R^a$ and $R^c$ are each a hydrogen atom, an alkyl group or a halogen atom, $R^b$ is (i) a hydrogen atom, (ii) an optionally substituted hydrocarbon-carbonyl group, (iii) an optionally substituted heterocyclyl-carbonyl group, (iv) an optionally substituted carbamoyl group, (v) an optionally substituted alkoxycarbonyl group, (vi) an optionally substituted hydrocarbonsulfonyl group, (vii) an optionally substituted heterocyclyl-sulfonyl group, (viii) an optionally substituted sulfamoyl group, (ix) an optionally substituted hydrocarbon group or (x) an optionally substituted heterocyclic group, and $R^d$ is (i) a hydrogen atom, (ii) an optionally substituted hydrocarbon group or (iii) an optionally substituted heterocyclic group.

The present invention also provides [17] the compound [12], [13], [14], [15] or [16] wherein $R^2$ is (i) a halogen atom, (ii) an optionally substituted hydroxy group, (iii) an optionally substituted hydrocarbon group, (iv) an optionally substituted heterocyclic group, (v) an optionally substituted amino group, (vi) an optionally substituted thiol group or (vii) an acyl group.

The present invention also provides [18] the compound [12], [13], [14], [15] or [16] wherein $R^3$ is an optionally substituted triazolyl group.

The present invention also provides [19] the compound [12] wherein:

$R^1$ is selected from:
(i) an 8- to 10-membered nitrogen-containing aromatic fused heterocyclic group optionally containing, besides carbon atom and nitrogen atom, 1 to 4 heteroatoms selected from an oxygen atom and a sulfur atoms, which is optionally substituted by substituent(s) selected from (1) hydroxy, (2) $C_{1-6}$alkyl, (3) $C_{1-6}$ alkoxy optionally substituted by hydroxy, (4) $C_{6-18}$ aryl-$C_{1-4}$alkyl-oxy, (5) 4- to 7-membered monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom and (6) 4- to 7-membered monocyclic non-aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom, or (ii) a 4-pyridyl group or a pyrazolyl group optionally substituted by substituent(s) selected from (1) a halogen atom, (2) $C_{1-6}$ alkyl, (3) $C_{1-8}$ alkyl-carbonylamino optionally substituted by substituent(s) selected from $C_{6-18}$ arylthio, and 4- to 7-membered monocyclic aromatic heterocyclic group or monocyclic non-aromatic heterocyclic group containing, as a ring constituting atom besides carbon atom, 1 to 4 heteroatoms selected from an oxygen atom, a sulfur atom and a nitrogen atom, (4) $C_{3-8}$ cycloalkyl-carbonylamino, (5) $C_{6-18}$ aryl-carbonylamino optionally substituted by substituent(s) selected from a halogen atom, $C_{1-6}$ alkyl, $C_{1-6}$ alkoxy, amino and mono- or di-$C_{1-6}$ alkylamino, (6) $C_{6-18}$ aryl-$C_{1-4}$ alkyl-carbonylamino and (7) 4- to 7-membered monocyclic heterocyclyl-carbonylamino, said monocyclic heterocyclyl contains, as a ring constituting atom besides carbon atom, 1 to 4 heteroatoms selected from an oxygen atom, a sulfur atom and a nitrogen atom and is optionally substituted by $C_{1-6}$ alkyl;

wherein $R^2$ is selected from:
(i) a $C_{1-8}$ alkyl group,
(ii) a $C_{2-8}$ alkenyl group,
(iii) a $C_{3-8}$ cycloalkyl group,
(iv) a hydroxyl group optionally substituted by a $C_{1-8}$ alkyl, $C_{2-8}$ alkenyl or $C_{6-18}$ aryl-$C_{1-4}$ alkyl,
(v) a $C_{6-18}$ aryl group optionally substituted by a halogen atom, optionally halogenated $C_{1-8}$ alkyl or $C_{1-8}$ alkoxy,
(vi) a $C_{6-18}$ aryl-$C_{1-4}$ alkyl group,
(vii) a 4- to 7-membered aromatic monocyclic heterocyclic group containing, besides carbon atom, 1- to 3 heteroatoms selected from a nitrogen atom, an oxygen atom and a sulfur atom, or
(viii) a 4- to 7-membered non-aromatic heterocyclic group containing, besides carbon atom, 1 to 3 heteroatoms selected from a nitrogen atom, an oxygen atom and a sulfur atom; and wherein $R^3$ is a 5-membered aromatic heterocyclic group containing 2 to 4 nitrogen atoms, which is bonded via a carbon atom and optionally substituted by $C_{1-8}$ alkyl.

The present invention also provides:
[20] a prodrug of the compound of [1], [2], [3], [10], [12], or [13];
[21] a pharmaceutical composition comprising the compound of [1], [2], [3], [10], [12], or [13] or a prodrug thereof;
[22] a pharmaceutical composition comprising the compound of [1], [2], [3], [10], [12], or [13];
[23] the pharmaceutical composition of [21], which is a kinase inhibitor;
[24] the pharmaceutical composition of [22], which is a kinase inhibitor;
[25] the pharmaceutical composition of [21], which is a PI3K inhibitor and(or) an mTOR inhibitor;
[26] the pharmaceutical composition of [22], which is a PI3K inhibitor and(or) an mTOR inhibitor;
[27] the pharmaceutical composition of [21], which is an agent for the prophylaxis or treatment of cancer;
[28] the pharmaceutical composition of [22], which is an agent for the prophylaxis or treatment of cancer;
[29] a method of treating cancer, comprising administering an effective amount of the compound of [1], [2], [3], [10], [12], or [13] or a salt thereof, or a prodrug thereof to a mammal;
[30] a method of treating cancer, comprising administering an effective amount of the compound of [1], [2], [3], [10], [12], or [13] or a salt thereof, to a mammal;

[31] a composition comprising a compound of [1], [2], [3], [10], [12], or [13] and a pharmaceutically acceptable carrier;

[32] a method of treating a proliferative disorder in a patient comprising administering to said patient a therapeutically effective amount of a compound of [1], [2], [3], [10], [12], or [13],

[33] The method of [32], wherein the proliferative disorder is breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer,

[34] a method of treating an inflammatory or cardiovascular disorder in a patient comprising administering to said patient a therapeutically effective amount of a compound of [1], [2], [3], [10], [12], or [13],

[35] The method of [34], wherein the inflammatory or cardiovascular disorder is selected from allergies/anaphylaxis, acute and chronic inflammation, rheumatoid arthritis; autoimmunity disorders, thrombosis, hypertension, cardiac hypertrophy, and heart failure.

Furthermore, the present invention provides [36] the compound of [1], [2], [3], or [12], wherein $R^3$ is a 5-membered aromatic heterocyclic group (particularly, triazolyl group) containing 2 to 4 nitrogen atoms, which is bonded via a carbon atom and optionally substituted by $C_{1-8}$ alkyl.

According to the present invention, a thiazole derivative having a superior PI3K inhibitory activity and(or) a superior mTOR inhibitory activity, which is low toxic and sufficiently satisfactory as a pharmaceutical product, and use thereof are provided.

As the "optionally substituted group bonded via a carbon atom" in the present specification, cyano, an optionally substituted alkyl group (preferably $C_{1-20}$ alkyl group, particularly preferably $C_{1-8}$ alkyl group), an optionally substituted alkenyl group (preferably $C_{2-8}$ alkenyl group), an optionally substituted alkynyl group (preferably $C_{2-8}$ alkynyl group), an optionally substituted $C_{1-8}$ alkyl-carbonyl group, an optionally substituted $C_{3-8}$ cycloalkyl group, an optionally substituted aryl group (preferably $C_{6-18}$ aryl group), an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group (heterocyclic group bonded via a carbon atom), an optionally substituted heterocyclyl-$C_{1-4}$ alkyl group, an optionally substituted heterocyclyl-carbonyl group, an optionally substituted heterocyclyl-$C_{1-4}$alkyl-carbonyl group, an optionally substituted carbamoyl group and the like can be used.

Examples of the "$C_{1-20}$ alkyl group" of the above-mentioned "optionally substituted $C_{1-20}$ alkyl group" include $C_{1-8}$ alkyl such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl etc., and the like.

The "alkyl group" of the above-mentioned "optionally substituted alkyl group" may have not less than 1 (preferably 1 to 5, more preferably 1 to 3) substituents at substitutable position(s). Such substituent(s) may be one to an acceptable maximum number of substituents at any substitutable position(s), which is/are selected from a substituent group consisting of (1) a halogen atom (e.g., fluorine, chlorine, bromine, iodine);
(2) cyano;
(3) nitro;
(4) hydroxy;
(5) $C_{1-6}$alkoxy (e.g., methoxy, ethoxy, propoxy, isopropoxy, butoxy, isobutoxy, tort-butoxy etc.) optionally having 1 to 3 substituents selected from a halogen atom (e.g., fluorine, chlorine, bromine, iodine) and $C_{1-6}$ alkoxy (e.g., methoxy, ethoxy, propoxy, isopropoxy, butoxy, isobutoxy, tert-butoxy etc.);
(6) $C_{2-6}$alkenyloxy (e.g., ethenyloxy, propenyloxy, butenyloxy, pentenyloxy, hexenyloxy etc.) optionally having 1 to 3 halogen atoms (e.g., fluorine, chlorine, bromine, iodine);
(7) $C_{2-6}$alkynyloxy (e.g., ethynyloxy, propynyloxy, butynyloxy, pentynyloxy, hexynyloxy etc.) optionally having 1 to 3 halogen atoms (e.g., fluorine, chlorine, bromine, iodine);
(8) $C_{3-8}$ cycloalkyloxy (e.g., cyclopropyloxy, cyclobutyloxy, cyclopentyloxy, cyclohexyloxy) optionally having 1 to 3 halogen atoms (e.g., fluorine, chlorine, bromine, iodine);
(9) $C_{3-8}$ cycloalkenyloxy (e.g., cyclopropenyloxy, cyclobutenyloxy, cyclopentenyloxy, cyclohexenyloxy etc.) optionally having 1 to 3 halogen atoms (e.g., fluorine, chlorine, bromine, iodine);
(10) $C_{6-14}$aryloxy (e.g., phenyloxy, 1-naphthyloxy, 2-naphthyloxy etc.) optionally having 1 to 3 halogen atoms (e.g., fluorine, chlorine, bromine, iodine);
(11) $C_{3-8}$ cycloalkyl-C1-6 alkoxy (e.g., cyclopropylmethyloxy, cyclopropylethyloxy, cyclobutylmethyloxy, cyclopentylmethyloxy, cyclohexylmethyloxy, cyclohexylethyloxy etc.) optionally having 1 to 3 halogen atoms (e.g., fluorine, chlorine, bromine, iodine);
(12) $C_{3-8}$ cycloalkenyl-$C_{1-6}$ alkoxy (e.g., cyclopentenylmethyloxy, cyclohexenylmethyloxy, cyclohexenylethyloxy, cyclohexenylpropyloxy etc.) optionally having 1 to 3 halogen atoms (e.g., fluorine, chlorine, bromine, iodine);
(13) $C_{6-14}$ aryl-$C_{1-6}$ alkoxy (e.g., phenylmethyloxy, phenylethyloxy etc.) optionally having 1 to 3 halogen atoms (e.g., fluorine, chlorine, bromine, iodine);
(14) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom;
(15) 4- to 7-membered (preferably 5- or 6-membered) monocyclic non-aromatic heterocyclyl-$C_{1-4}$ alkyl-oxy (e.g., morpholinylethyloxy, piperidinylethyloxy etc.) containing, as a ring constituting atom besides carbon atom, 1 to 4 heteroatoms selected from an oxygen atom, a sulfur atom and a nitrogen atom;
(16) $C_{1-6}$ alkyl-aminosulfonyl (e.g., methylaminosulfonyl, ethylaminosulfonyl, propylaminosulfonyl etc.);
(17) di-$C_{1-6}$ alkyl-aminosulfonyl (e.g., dimethylaminosulfonyl, diethylaminosulfonyl, dipropylaminosulfonyl etc.);
(18) $C_{1-6}$ alkyl-aminocarbonyl (e.g., methylaminocarbonyl, ethylaminocarbonyl, propylaminocarbonyl etc.);
(19) di-$C_{1-6}$ alkyl-aminocarbonyl (e.g., dimethylaminocarbonyl, diethylaminocarbonyl, dipropylaminocarbonyl etc.);
(20) formyl;
(21) $C_{1-6}$ alkyl-carbonyl (e.g., acetyl, ethylcarbonyl, propylcarbonyl, isopropylcarbonyl etc.);
(22) $C_{2-6}$ alkenyl-carbonyl (e.g., ethenylcarbonyl, propenylcarbonyl, butenylcarbonyl, pentenylcarbonyl, hexenylcarbonyl etc.);
(23) $C_{2-6}$ alkynyl-carbonyl (e.g., ethynylcarbonyl, propynylcarbonyl, butynylcarbonyl, pentynylcarbonyl, hexynylcarbonyl etc.);
(24) $C_{3-8}$ cycloalkyl-carbonyl (e.g., cyclopropylcarbonyl, cyclobutylcarbonyl, cyclopentylcarbonyl, cyclohexylcarbonyl etc.);

(25) $C_{3-6}$ cycloalkenyl-carbonyl (e.g., cyclopropenylcarbonyl, cyclobutenylcarbonyl, cyclopentenylcarbonyl, cyclohexenylcarbonyl etc.);

(26) $C_{6-14}$ aryl-carbonyl (e.g., benzoyl, 1-naphthylcarbonyl, 2-naphthylcarbonyl etc.);

(27) $C_{3-8}$ cycloalkyl-$C_{1-6}$alkyl-carbonyl (e.g., cyclopropylmethylcarbonyl, cyclopropylethylcarbonyl, cyclobutylmethylcarbonyl, cyclopentylmethylcarbonyl, cyclohexylmethylcarbonyl, cyclohexylethylcarbonyl etc.);

(28) $C_{3-6}$ cycloalkenyl-$C_{1-6}$ alkyl-carbonyl (e.g., cyclopentenylmethylcarbonyl, cyclohexenylmethylcarbonyl, cyclohexenylethylcarbonyl, cyclohexenylpropylcarbonyl etc.);

(29) $C_{6-14}$ aryl-$C_{1-6}$alkyl-carbonyl (e.g., benzylcarbonyl, phenylethylcarbonyl etc.);

(30) 4- to 7-membered (preferably 5- or 6-membered) monocyclic aromatic heterocyclyl-carbonyl (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl etc.) containing, as a ring constituting atom besides carbon atom, 1 to 4 heteroatoms selected from a nitrogen atom, an oxygen atom and a sulfur atom;

(31) 8- to 12-membered fused aromatic heterocyclyl-carbonyl (e.g., benzofurylcarbonyl, isobenzofurylcarbonyl, benzothienylcarbonyl, isobenzothienylcarbonyl, indolylcarbonyl, isoindolylcarbonyl, 1H-indazolylcarbonyl, benzimidazolylcarbonyl, benzoxazolylcarbonyl etc.) containing, as a ring constituting atom besides carbon atom, 1 to 4 heteroatoms selected from a nitrogen atom, an oxygen atom and a sulfur atom;

(32) 4- to 7-membered (preferably 5- or 6-membered) non-aromatic heterocyclyl-carbonyl (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidinylcarbonyl etc.) containing, as a ring constituting atom besides carbon atom, 1 to 4 heteroatoms selected from a nitrogen atom, an oxygen atom and a sulfur atom;

(33) $C_{1-6}$ alkylsulfonyl (e.g., methylsulfonyl, ethylsulfonyl etc.);

(34) $C_{2-6}$ alkenylsulfonyl (e.g., ethenylsulfonyl, propenylsulfonyl etc.);

(35) $C_{2-6}$ alkynylsulfonyl (e.g., ethynylsulfonyl, propynylsulfonyl, butynylsulfonyl, pentynylsulfonyl, hexynylsulfonyl etc.);

(36) $C_{3-8}$ cycloalkylsulfonyl (e.g., cyclopropylsulfonyl, cyclobutylsulfonyl etc.);

(37) $C_{3-6}$ cycloalkenylsulfonyl (e.g., cyclopropenylsulfonyl, cyclobutenylsulfonyl etc.);

(38) $C_{6-10}$ arylsulfonyl (e.g., phenylsulfonyl etc.);

(39) $C_{3-8}$ cycloalkyl-$C_{1-6}$alkyl-sulfonyl (e.g., cyclopropylmethylsulfonyl etc.);

(40) $C_{3-6}$ cycloalkenyl-$C_{1-6}$alkyl-sulfonyl (e.g., cyclopentenylmethylsulfonyl etc.);

(41) $C_{6-14}$ aryl-$C_{1-6}$ alkyl-sulfonyl (e.g., benzylsulfonyl etc.);

(42) 4- to 7-membered (preferably 5- or 6-membered) monocyclic aromatic heterocyclyl-sulfonyl (e.g., furylsulfonyl, thienylsulfonyl, pyridylsulfonyl etc.) containing, as a ring constituting atom besides carbon atom, 1 to 4 heteroatoms selected from a nitrogen atom, an oxygen atom and a sulfur atom;

(43) 8- to 12-membered fused aromatic heterocyclyl-sulfonyl (e.g., benzofurylsulfonyl, isobenzofurylsulfonyl etc.) containing, as a ring constituting atom besides carbon atom, 1 to 4 heteroatoms selected from a nitrogen atom, an oxygen atom and a sulfur atom;

(44) 4- to 7-membered (preferably 5- or 6-membered) non-aromatic heterocyclyl-sulfonyl (e.g., oxiranylsulfonyl, azetidinylsulfonyl etc.) containing, as a ring constituting atom besides carbon atom, 1 to 4 heteroatoms selected from a nitrogen atom, an oxygen atom and a sulfur atom;

(45) amino;

(46) mono-$C_{1-6}$ alkylamino (e.g., methylamino, ethylamino, propylamino, isopropylamino, butylamino, isobutylamino, tert-butylamino etc.);

(47) di-$C_{1-6}$ alkylamino (e.g., dimethylamino, diethylamino, dipropylamino, diisopropylamino, dibutylamino, diisobutylamino, di-tert-butylamino etc.);

(48) mono($C_{1-6}$alkyl-carbonyl)amino (e.g., acetylamino, ethylcarbonylamino, propylcarbonylamino, tert-butylcarbonylamino etc.) optionally having 1 to 3 halogen atoms (e.g., fluorine, chlorine, bromine, iodine);

(49) mono($C_{6-14}$arylthio (e.g., phenylthio)-$C_{1-8}$ alkyl-carbonyl)amino (e.g., $C_{1-6}$ alkyl-carbonylamino group such as acetylamino, ethylcarbonylamino etc.; phenylthioethylcarbonylamino etc.);

(50) mono(heterocyclyl-$C_{1-8}$ alkyl-carbonyl)amino (the heterocyclyl is 4- to 7-membered (preferably 5- or 6-membered) monocyclic aromatic heterocycle or monocyclic non-aromatic heterocycle (e.g., morpholinyl) containing, as a ring constituting atom besides carbon atom, 1 to 4 heteroatoms selected from an oxygen atom, a sulfur atom and a nitrogen atom) (e.g., morpholinylethylcarbonylamino etc.);

(51) mono($C_{3-6}$ cycloalkyl-carbonyl)amino (e.g., cyclopropylcarbonylamino, cyclobutylcarbonylamino, cyclopentylcarbonylamino, cyclohexylcarbonylamino etc.);

(52) mono($C_{6-14}$aryl-carbonyl)amino (e.g., benzoylamino etc.) optionally having 1 to 3 halogen atoms (e.g., fluorine, chlorine, bromine, iodine);

(53) mono(5- to 7-membered monocyclic aromatic heterocyclyl-carbonyl)amino (which 5- to 7-membered monocyclic aromatic heterocyclyl contains, as a ring constituting atom besides carbon atom, 1 to 4 heteroatoms selected from a nitrogen atom, an oxygen atom and a sulfur atom) (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, pyridylcarbonylamino, pyrazolylcarbonylamino etc.);

(54) mono(8- to 12-membered fused aromatic heterocyclyl-carbonyl)amino (which 8- to 12-membered fused aromatic heterocyclyl contains, as a ring constituting atom besides carbon atom, 1 to 4 heteroatoms selected from a nitrogen atom, an oxygen atom and a sulfur atom) (e.g., benzofurylcarbonylamino, isobenzofurylcarbonylamino, benzothienylcarbonylamino, isobenzothienylcarbonylamino etc.);

(55) mono(non-aromatic heterocyclyl-carbonyl)amino (which non-aromatic heterocyclyl is 4- to 7-membered (preferably 5- or 6-membered) non-aromatic heterocycle containing, as a ring constituting, atom besides carbon atom, 1 to 4 heteroatoms selected from a nitrogen atom, an oxygen atom and a sulfur atom) (e.g., oxiranylcarbonylamino, azetidinylcarbonylamino, oxetanylcarbonylamino etc.);

(56) thiol;

(57) $C_{1-6}$ alkylsulfanyl (e.g., methylsulfanyl, ethylsulfanyl etc.);

(58) $C_{2-6}$ alkenylsulfanyl (e.g., ethenylsulfanyl, propenylsulfanyl etc.);

(59) $C_{2-6}$ alkynylsulfanyl (e.g., ethynylsulfanyl, propynylsulfanyl, butynylsulfanyl, pentynylsulfanyl, hexynylsulfanyl etc.);
(60) $C_{3-8}$ cycloalkylsulfanyl (e.g., cyclopropylsulfanyl, cyclobutylsulfanyl etc.);
(61) $C_{3-6}$ cycloalkenylsulfanyl (e.g., cyclopropenylsulfanyl, cyclobutenylsulfanyl etc.);
(62) $C_{6-14}$ arylsulfanyl (e.g., phenylsulfanyl etc.);
(63) $C_{3-8}$ cycloalkyl-$C_{1-6}$ alkyl-sulfanyl (e.g., cyclopropylmethylsulfanyl etc.);
(64) $C_{3-6}$ cycloalkenyl-$C_{1-6}$ alkyl-sulfanyl (e.g., cyclopentenylmethylsulfanyl etc.);
(65) a 4- to 7-membered (preferably 5- or 6-membered) monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.) optionally having 1 to 3 C1-4 alkyl (e.g., methyl, ethyl etc.), containing, as a ring constituting atom besides carbon atom, 1 to 4 heteroatoms selected from a nitrogen atom, an oxygen atom and a sulfur atom;
(66) an 8- to 12-membered fused aromatic heterocyclic group (e.g., benzofuryl, isobenzofuryl, benzothienyl, isobenzothienyl, indolyl, isoindolyl, 1H-indazolyl, benzimidazolyl, benzoxazolyl etc.) containing, as a ring constituting atom besides carbon atom, 1 to 4 heteroatoms selected from a nitrogen atom, an oxygen atom and a sulfur atom;
(67) a 4- to 7-membered (preferably 5- or 6-membered) non-aromatic heterocyclic group (e.g., oxiranyl, azetidinyl, oxetanyl, thietanyl, pyrrolidinyl, tetrahydrofuryl, thiolanyl, piperidinyl etc.) containing, as a ring constituting atom besides carbon atom, 1 to 4 heteroatoms selected from a nitrogen atom, an oxygen atom and a sulfur atom;
(68) 4- to 7-membered (preferably 5- or 6-membered) monocyclic aromatic heterocyclyl-oxy (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy etc.) containing, as a ring constituting atom besides carbon atom, 1 to 4 heteroatoms selected from a nitrogen atom, an oxygen atom and a sulfur atom;
(69) 8- to 12-membered fused aromatic heterocyclyl-oxy (e.g., benzofuryloxy, isobenzofuryloxy, benzothienyloxy, isobenzothienyloxy, indolyloxy, isoindolyloxy, 1H-indazolyloxy, benzimidazolyloxy, benzoxazolyloxy etc.) containing, as a ring constituting atom besides carbon atom, 1 to 4 heteroatoms selected from a nitrogen atom, an oxygen atom and a sulfur atom;
(70) 5 or 7-membered non-aromatic heterocyclyl-oxy (e.g., oxiranyloxy, azetidinyloxy, oxetanyloxy, thietanyloxy, pyrrolidinyloxy, tetrahydrofuryloxy, thiolanyloxy, piperidinyloxy etc.) containing, as a ring constituting atom besides carbon atom, 1 to 4 heteroatoms selected from a nitrogen atom, an oxygen atom and a sulfur atom;
(71) oxo;
(72) C1-6 alkylsulfinyl (e.g., methylsulfinyl, ethylsulfinyl etc.);
(73) $C_{2-6}$ alkenylsulfinyl (e.g., ethenylsulfinyl, propenylsulfinyl etc.);
(74) $C_{2-6}$ alkynylsulfinyl (e.g., ethynylsulfinyl, propynylsulfinyl, butynylsulfinyl, pentynylsulfinyl, hexynylsulfinyl etc.);
(75) $C_{3-8}$ cycloalkylsulfinyl (e.g., cyclopropylsulfinyl, cyclobutylsulfinyl etc.);
(76) $C_{3-6}$ cycloalkenylsulfinyl (e.g., cyclopropenylsulfinyl, cyclobutenylsulfinyl etc.);
(77) $C_{6-14}$ arylsulfinyl (e.g., phenylsulfinyl etc.);
(78) $C_{3-8}$ cycloalkyl-$C_{1-6}$ alkyl-sulfinyl (e.g., cyclopropylmethylsulfinyl etc.);
(79) $C_{3-6}$ cycloalkenyl-$C_{1-6}$ alkyl-sulfinyl (e.g., cyclopentenylmethylsulfinyl etc.);
(80) aminothiocarbonyl substituted by $C_{1-6}$ alkyl or $C_{6-14}$ aryl-$C_{1-4}$ alkyl-carbonyl (e.g., methylaminothiocarbonyl, ethylaminothiocarbonyl, propylaminothiocarbonyl, benzylcarbonylaminothiocarbonyl etc.);
(81) di-$C_{1-6}$ alkyl-aminothiocarbonyl (e.g., dimethylaminothiocarbonyl, diethylaminothiocarbonyl, dipropylaminothiocarbonyl etc.);
(82) carboxy;
(83) $C_{1-6}$ alkoxycarbonyl (e.g., methoxycarbonyl, ethoxycarbonyl, propoxycarbonyl, isopropoxycarbonyl, butoxycarbonyl, isobutoxycarbonyl, tert-butoxycarbonyl etc.);
(84) $C_{2-6}$ alkenyloxy-carbonyl (e.g., ethenyloxycarbonyl, propenyloxycarbonyl, butenyloxycarbonyl, pentenyloxycarbonyl, hexenyloxycarbonyl etc.);
(85) $C_{2-6}$ alkynyloxy-carbonyl (e.g., ethynyloxycarbonyl, propynyloxycarbonyl, butynyloxycarbonyl, pentynyloxycarbonyl, hexynyloxycarbonyl etc.);
(86) $C_{3-8}$ cycloalkyl-oxy-carbonyl (e.g., cyclopropyloxycarbonyl, cyclobutyloxycarbonyl, cyclopentyloxycarbonyl, cyclohexyloxycarbonyl etc.);
(87) $C_{3-6}$ cycloalkenyloxy-carbonyl (e.g., cyclopropenyloxycarbonyl, cyclobutenyloxycarbonyl, cyclopentenyloxycarbonyl, cyclohexenyloxycarbonyl etc.);
(88) $C_{6-14}$ aryloxy-carbonyl (e.g., phenyloxycarbonyl, 1-naphthyloxycarbonyl, 2-naphthyloxycarbonyl etc.);
(89) $C_{3-8}$ cycloalkyl-$C_{1-6}$alkoxy-carbonyl (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl etc.);
(90) $C_{3-6}$ cycloalkenyl-$C_{1-6}$ alkoxy-carbonyl (e.g., cyclopentenylmethyloxycarbonyl, cyclohexenylmethyloxycarbonyl, cyclohexenylethyloxycarbonyl, cyclohexenylpropyloxycarbonyl etc.); and
(91) $C_{6-14}$ aryl-$C_{1-6}$alkoxy-carbonyl (e.g., phenylmethyloxycarbonyl, phenylethyloxycarbonyl etc.) (hereinafter to be abbreviated as substituent group X). When two or more substituents are present, they may be the same or different, and preferable number of substituents is 1 to 5, more preferably 1 to 3.

Examples of the "$C_{2-8}$ alkenyl group" of the above-mentioned "optionally substituted $C_{2-8}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

Examples of the "alkenyl group" of the above-mentioned "optionally substituted alkenyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{2-8}$ alkynyl group" of the above-mentioned "optionally substituted $C_{2-8}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like.

The "alkynyl group" of the above-mentioned "optionally substituted alkynyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{1-8}$ alkyl-carbonyl group" of the above-mentioned "optionally substituted C1-8 alkyl-carbonyl group" include acetyl, ethylcarbonyl, propylcarbonyl, isopropylcarbonyl, butylcarbonyl, isobutylcarbonyl, sec-butylcarbonyl, tert-butylcarbonyl, pentylcarbonyl, isopentylcarbonyl, neopentylcarbonyl, 1-ethylpropylcarbonyl, hexylcarbonyl, isohexylcarbonyl, 1,1-dimethylbutylcarbonyl, 2,2-dimethylbutylcarbonyl, 3,3-dimethylbutylcarbonyl, 2-ethylbutylcarbonyl, heptylcarbonyl, octylcarbonyl and the like.

The "$C_{1-8}$ alkyl-carbonyl group" of the above-mentioned "optionally substituted $C_{1-8}$ alkyl-carbonyl group" may have one or more (preferably 1 to 5, more preferably 1 to 3) substituents at substitutable position(s). Examples Of such substituent include substituents selected from substituent group X. When the number of the substituents is two or more, the respective substituents may be the same or different.

Examples of the "$C_{3-8}$ cycloalkyl group" of the above-mentioned "optionally substituted C3-8 cycloalkyl group" include cyclopropyl, cyclobutyl, cyclopentyl, cyclohexyl, cycloheptyl, cyclooctyl and the like.

The "$C_{3-8}$ cycloalkyl group" of the above-mentioned "optionally substituted $C_{3-8}$ cycloalkyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{6-18}$ aryl group" of the above-mentioned "optionally substituted $C_{6-18}$ aryl group" include phenyl, naphthyl, anthryl, phenanthryl, acenaphthylenyl, biphenylyl and the like, and phenyl is preferable.

The "aryl group" of the above-mentioned "optionally substituted aryl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{6-18}$ aryl-$C_{1-4}$ alkyl group" of the above-mentioned "optionally substituted $C_{6-18}$ aryl-$C_{1-4}$alkyl group" include benzyl, phenethyl, phenylpropyl, naphthylmethyl, biphenylylmethyl and the like.

The "$C_{6-18}$ aryl-$C_{1-4}$ alkyl group" of the above-mentioned "optionally substituted $C_{6-18}$ aryl-$C_{1-4}$ alkyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{6-18}$ aryl-carbonyl group" of the above-mentioned "optionally substituted $C_{6-18}$ aryl-carbonyl group" include phenylcarbonyl, naphthylcarbonyl, anthrylcarbonyl, phenanthrylcarbonyl, acenaphthylenylcarbonyl, biphenylylcarbonyl and the like.

The "$C_{6-18}$ aryl-carbonyl group" of the above-mentioned "optionally substituted $C_{6-18}$ aryl-carbonyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{6-18}$aryl-$C_{1-4}$alkyl-carbonyl group" of the above-mentioned "optionally substituted $C_{6-18}$ aryl-$C_{1-4}$ alkyl-carbonyl group" include benzylcarbonyl, phenethylcarbonyl, phenylpropylcarbonyl, naphthylmethylcarbonyl, biphenylylmethylcarbonyl and the like.

The "$C_{6-18}$ aryl-$C_{1-4}$ alkyl-carbonyl group" of the above-mentioned "optionally substituted $C_{6-18}$ aryl-$C_{1-4}$ alkyl-carbonyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "heterocyclic group" of the above-mentioned "optionally substituted heterocyclic group" include an aromatic heterocyclic group and a non-aromatic heterocyclic group.

Examples of the aromatic heterocyclic group include a 4- to 7-membered (preferably 5- or 6-membered) monocyclic aromatic heterocyclic group containing, as a ring constituting atom besides carbon atom, 1 to 4 heteroatoms selected from an oxygen atom, a sulfur atom and a nitrogen atom, and a 8- to 12-membered fused aromatic heterocyclic group. Examples of the fused aromatic heterocyclic group include a group derived from a fused ring wherein a ring corresponding to such 4- to 7-membered monocyclic aromatic heterocyclic group, and 1 or 2 rings selected from a 5- or 6-membered aromatic heterocycle containing 1 or 2 nitrogen atoms, a 5-membered aromatic heterocycle containing one sulfur atom and a benzene ring are condensed, and the like.

Preferable examples of the aromatic heterocyclic group include a monocyclic aromatic heterocyclic group such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; a fused aromatic heterocyclic group such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl3-benzofuryl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), pyrrolopyrimidinyl (e.g., 1H-pyrrolo[2,3-d]pyrimidin-2-yl, 1H-pyrrolo[2,3-d]pyrimidin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]

pyridin-3-yl), pyrazolothienyl (e.g., 2H-pyrazolo[3,4-b] thiophen-2-yl), pyrazolotriazinyl (e.g., pyrazolo[5,1-c][1,2, 4]triazin-3-yl) and the like.

Examples of the non-aromatic heterocyclic group include a 4- to 7-membered (preferably 5- or 6-membered) monocyclic non-aromatic heterocyclic group containing, as a ring constituting atom besides carbon atom, 1 to 4 heteroatoms selected from an oxygen atom, a sulfur atom and a nitrogen atom, and a 8- to 12-membered fused non-aromatic heterocyclic group. Examples of the fused non-aromatic heterocyclic group include a group derived from a fused ring wherein a ring corresponding to such 4- to 7-membered monocyclic non-aromatic heterocyclic group, and 1 or 2 rings selected from a 5- or 6-membered heterocycle containing 1 or 2 nitrogen atoms, a 5-membered heterocycle containing one sulfur atom and a benzene ring are condensed, and the like.

Preferable examples of the non-aromatic heterocyclic group include a monocyclic non-aromatic heterocyclic group such as oxetanyl (e.g., 2-oxetanyl, 3-oxetanyl), pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), 2-thioxo-1,3-oxazolidin-5-yl, pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1, 2,3-triazol-1-yl) and the like; a fused non-aromatic heterocyclic group such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like.

The "heterocyclic group" of the above-mentioned "optionally substituted heterocyclic group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the above-mentioned "optionally substituted heterocyclyl-$C_{1-4}$alkyl group" include a group wherein $C_{1-4}$ alkyl (e.g., methyl, ethyl, propyl, isopropyl, butyl, isobutyl, sec-butyl, tert-butyl) is substituted by the above-mentioned "optionally substituted heterocyclic group".

Examples of the above-mentioned "optionally substituted heterocyclyl-carbonyl group" include a group wherein carbonyl is bonded to the above-mentioned "optionally substituted heterocyclic group".

Examples of the above-mentioned "optionally substituted heterocyclyl-$C_{1-4}$alkyl-carbonyl group" include a group wherein carbonyl is bonded to the above-mentioned "optionally substituted heterocyclyl-$C_{1-4}$alkyl group".

The "carbamoyl group" of the above-mentioned "optionally substituted carbamoyl group" may have 1 or 2 substituents. Examples of such substituent include the aforementioned optionally substituted $C_{1-8}$ alkyl group, optionally substituted $C_{2-8}$alkenyl group, optionally substituted $C_{2-8}$alkynyl group, optionally substituted $C_{1-8}$ alkyl-carbonyl group, optionally substituted $C_{3-8}$cycloalkyl group, optionally substituted $C_{6-18}$ aryl group, optionally substituted $C_{6-18}$aryl-$C_{1-4}$alkyl group, optionally substituted $C_{6-18}$ arylcarbonyl group, optionally substituted $C_{6-18}$aryl-$C_{1-4}$alkyl-carbonyl group, optionally substituted heterocyclic group (heterocyclic group bonded via a carbon atom), optionally substituted heterocyclyl-$C_{1-4}$ alkyl group, optionally substituted heterocyclyl-carbonyl group and optionally substituted heterocyclyl-$C_{1-4}$alkyl-carbonyl group. When the number of the substituents is two or more, the respective substituents may be the same or different.

Examples of the "optionally substituted group bonded via a nitrogen atom" include
(i) amino,
(ii) amino monosubstituted by the above-mentioned "optionally substituted group bonded via a carbon atom",
(iii) amino disubstituted by the above-mentioned "optionally substituted group bonded via a carbon atom", preferably $C_{1-6}$ alkyl (e.g., methyl, ethyl, propyl, isopropyl, butyl, isobutyl, sec-butyl, tert-butyl, pentyl, hexyl etc.), and
(iv) the above-mentioned optionally substituted heterocyclic group (heterocyclic group bonded via a nitrogen atom) and the like.

Examples of the "optionally substituted group bonded via an oxygen atom" include hydroxy optionally substituted by the above-mentioned "optionally substituted group bonded via a carbon atom".

Examples of the "optionally substituted group bonded via a sulfur atom" include mercapto optionally substituted by the above-mentioned "optionally substituted group bonded via a carbon atom". The sulfur atom may be oxidized.

$R^1$ is an optionally substituted nitrogen-containing aromatic heterocyclic group (excluding 3-isoxazolyl group, 2-pyridyl group, 3-pyridyl group, 5-pyrimidyl group, 2-pyrimidyl group and pyrazinyl group).

Examples of the "nitrogen-containing aromatic heterocyclic group" include a 4- to 7-membered (preferably 5- or 6-membered) monocyclic nitrogen-containing aromatic heterocyclic group containing, as a ring constituting atom, carbon atom and 1 to 4 nitrogen atoms, and further, optionally containing 1 or 2 heteroatoms selected from an oxygen atom and a sulfur atom, and a 8- to 12-membered fused nitrogen-containing aromatic heterocyclic group. Examples of the fused nitrogen-containing aromatic heterocyclic group include a group derived from a fused ring wherein a ring corresponding to such 4- to 7-membered monocyclic nitrogen-containing aromatic heterocyclic group, and 1 or 2 rings selected from a 5- or 6-membered aromatic heterocycle containing 1 or 2 nitrogen atoms, a 5-membered aromatic heterocycle containing one sulfur atom and a benzene ring are fused, and the like.

Preferable examples of the nitrogen-containing aromatic heterocyclic group include a monocyclic nitrogen-containing aromatic heterocyclic group such as pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; a fused nitrogen-containing aromatic heterocyclic group such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), pyrrolopyrimidinyl (e.g., 1H-pyrrolo[2,3-d]pyrimidin-2-yl, 1H-pyrrolo[2,3-d]pyrimidin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), tetrahydropyrazolopyridyl, pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

As preferable examples of the substituent of the "nitrogen-containing aromatic heterocyclic group", a group selected from a substituent group consisting of (1) a halogen atom (e.g., fluorine, chlorine, bromine, iodine);
(2) cyano;
(3) nitro;
(4) an optionally substituted hydrocarbon group;
(5) an optionally substituted heterocyclic group;
(6) a formyl group;
(7) an optionally substituted hydrocarbon-carbonyl group;
(8) an optionally substituted heterocyclyl-carbonyl group;
(9) an optionally substituted hydroxy group, specifically a hydroxy group optionally substituted by a group selected from an optionally substituted hydrocarbon group and an optionally substituted heterocyclic group;
(10) an optionally substituted amino group, specifically an amino group optionally substituted by 1 or 2 groups selected from an optionally substituted hydrocarbon group, an optionally substituted heterocyclic group, an optionally substituted hydrocarbon-carbonyl group and an optionally substituted heterocyclyl-carbonyl group;
(11) an optionally substituted carbamoyl group, specifically a carbamoyl group optionally substituted by 1 or 2 groups selected from an optionally substituted hydrocarbon group, an optionally substituted heterocyclic group, an optionally substituted hydrocarbon-carbonyl group and an optionally substituted heterocyclyl-carbonyl group;
(12) an optionally substituted sulfonyl group, specifically a sulfonyl group optionally substituted by a group selected from an optionally substituted hydrocarbon group and an optionally substituted heterocyclic group;
(13) an optionally substituted sulfamoyl group, specifically a sulfamoyl group optionally substituted by a group selected from an optionally substituted hydrocarbon group and an optionally substituted heterocyclic group; and
(14) an optionally esterified carboxyl group, specifically a carboxyl group optionally esterified by a group selected from an optionally substituted hydrocarbon group and an optionally substituted heterocyclic group, preferably an optionally substituted alkoxycarbonyl group, particularly preferably a carboxyl group optionally esterified by $C_{1-8}$ alkyl (e.g., $C_{1-6}$ alkyl such as methyl, ethyl and the like) (hereinafter to be abbreviated as substituent group Y) can be used. Particularly, a group selected from the above-mentioned substituent group X can be used.

As the "optionally substituted hydrocarbon group" in the explanation of substituent group Y, an optionally substituted alkyl group (preferably $C_{1-20}$ alkyl group, particularly preferably $C_{1-8}$ alkyl group), an optionally substituted alkenyl group (preferably $C_{2-8}$ alkenyl group), an optionally substituted alkynyl group (preferably $C_{2-8}$ alkynyl group), an optionally substituted $C_{3-8}$ cycloalkyl group, an optionally substituted aryl group (preferably $C_{6-18}$ aryl group), an optionally substituted $C_{6-18}$ aryl-$C_{1-4}$ alkyl group and the like, which are exemplified as "optionally substituted group bonded via a carbon atom", can be used.

As the "optionally substituted heterocyclic group" in the explanation of substituent group Y, a group similar to the optionally substituted heterocyclic group exemplified as the "optionally substituted group bonded via a carbon atom" can be used.

As the "optionally substituted hydrocarbon" of the "optionally substituted hydrocarbon-carbonyl group" in the explanation of substituent group Y, a group similar to the above-mentioned "optionally substituted hydrocarbon group" can be used.

As the "optionally substituted heterocyclyl" of the "optionally substituted heterocyclyl-carbonyl group" in the explanation of substituent group Y, a group similar to the optionally substituted heterocyclic group exemplified as the "optionally substituted group bonded via a carbon atom" can be used.

As the "optionally substituted carbamoyl group" in the explanation of substituent group Y, a group similar to the optionally substituted carbamoyl group exemplified as the "optionally substituted group bonded via a carbon atom" can be used.

Among these, as the substituent of the "nitrogen-containing aromatic heterocyclic group", a halogen atom, an optionally substituted hydrocarbon group, an optionally substituted heterocyclic group, an optionally substituted hydroxy group, an optionally substituted amino group and the like are preferable. As the substituent of the monocyclic nitrogen-containing aromatic heterocyclic group (e.g., 4-pyridyl, pyrimidyl, pyrazolyl, particularly 4-pyridyl), particularly preferred are an optionally substituted amino group, particularly (1) C1-8 alkyl-carbonylamino (e.g., C1-6 alkyl-carbonylamino such as acetylamino, phenoxyacetylamino, ethylcarbonylamino, propylcarbonylamino, isopropylcarbonylamino, tert-butylcarbonylamino and the like; phenylthioethylcarbonylamino; thienylmethylcarbonyl, morpholinylethylcarbonylamino and the like) optionally substituted by substituent(s) selected from $C_{6-18}$ arylthio (e.g., phenylthio), $C_{6-18}$ aryloxy (e.g., phenoxy), a 4- to 7-membered (preferably 5- or 6-membered) monocyclic aromatic heterocyclic group (e.g., thienyl) containing, as a ring constituting atom besides carbon atom, 1 to 4 heteroatoms selected from an oxygen atom, a sulfur atom and a nitrogen atom and a monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, (2) $C_{3-4}$ cycloalkyl-carbonylamino (e.g., cyclopropylcarbonylamino, cyclopentyl, cyclohexylcarbonylamino), (3) $C_{6-18}$ aryl-carbonylamino (e.g., fluorophenylcarbonyl, chlorophenylcarbonyl, difluorophenylcarbonyl, methoxyphenylcarbonyl, dimethylaminophenylcarbonylamino) optionally substituted by a substituent(s) selected from a halogen atom, $C_{1-6}$alkoxy, amino and mono- or di-$C_{1-6}$ alkylamino, (4) $C_{6-18}$ aryl-$C_{1-4}$ alkyl-carbonylamino (e.g., benzylcarbonylamino), (5) 4- to 7-membered (preferably 5- or 6-membered) monocyclic heterocyclyl (e.g., furyl, thienyl, isoxazolyl, pyridyl)-carbonylamino (e.g., furylcarbonylamino, methylisoxazolyl), said monocyclic heterocyclyl contains, as a ring constituting atom besides carbon atom, 1 to 4 heteroatoms selected from an oxygen atom, a sulfur atom and a nitrogen atom and is optionally substituted by $C_{1-6}$ alkyl.

More specifically, preferable examples of $R^1$ include
(i) a group represented by

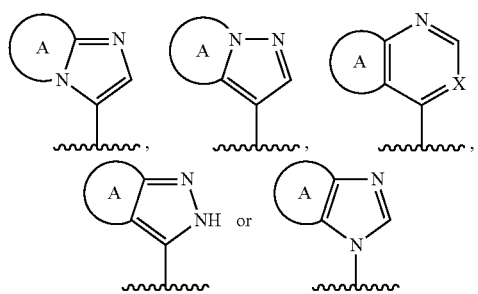

wherein A is a cyclic group and X is CH or N, optionally substituted by the above-mentioned substituent(s), particularly, (1) hydroxy, (2) $C_{1-6}$alkyl such as methyl, ethyl and the like, (3) $C_{1-6}$alkoxy optionally substituted by hydroxy, (4) $C_{6-18}$ aryl-$C_{1-4}$alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom, (6) 4- to 7-membered (preferably 5- or 6-membered) monocyclic non-aromatic heterocyclyl-$C_{1-4}$alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom, and the like, or
(ii) a 4-pyridyl group, a pyrimidinyl group, a pyrazolyl group, a thiazolyl group, an oxazolyl group, an imidazolyl group, a triazolyl group, an isothiazolyl group or a pyridazinyl group, particularly a 4-pyridyl group and the like, which are optionally substituted by the above-mentioned substituent(s), particularly, (1) a halogen atom (e.g., chlorine atom), (2) $C_{1-6}$ alkyl (e.g., methyl, ethyl, propyl), (3) $C_{1-8}$ alkyl-carbonylamino (e.g., $C_{1-6}$alkyl-carbonylamino such as acetylamino, phenoxyacetylamino, ethylcarbonylamino, propylcarbonylamino, isopropylcarbonylamino, tert-butylcarbonylamino and the like; phenylthioethylcarbonylamino; thienyl methylcarbonyl, morpholinylethyl-carbonylamino and the like) optionally substituted by substituent(s) selected from $C_{6-18}$ arylthio (e.g., phenylthio), $C_{6-18}$ aryloxy (e.g., phenoxy), and 4- to 7-membered (preferably 5- or 6-membered) monocyclic aromatic heterocyclic group (e.g., thienyl) or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, (4) $C_{3-8}$cycloalkyl-carbonylamino (e.g., cyclopropylcarbonylamino, cyclopentylcarbonylamino, cyclohexylcarbonylamino), (5) $C_{6-18}$aryl-carbonylamino (e.g., fluorophenylcarbonylamino, chlorophenylcarbonylamino, difluorophenylcarbonylamino, methylphenylcarbonylamino, methoxyphenylcarbonylamino, dimethylaminophenylcarbonylamino) optionally substituted by a substituent(s) selected from a halogen atom, $C_{1-6}$ alkyl, $C_{1-6}$alkoxy, amino and mono- or di-$C_{1-6}$ alkylamino, (6) $C_{6-18}$ aryl-$C_{1-4}$ alkyl-carbonylamino (e.g., benzylcarbonylamino) and (7) 4- to 7-membered (preferably 5- or 6-membered) monocyclic heterocyclyl (e.g., furyl, thienyl, isoxazolyl, pyridyl)-carbonylamino (e.g., furylcarbonylamino, methylisoxazolylcarbonylamino), said monocyclic heterocyclyl contains, as a ring constituting atom besides carbon atom, 1 to 4 heteroatoms selected from an oxygen atom, a sulfur atom and a nitrogen atom and is optionally substituted by $C_{1-6}$ alkyl.

As the cyclic group for A, cyclic hydrocarbon or heterocycle can be used.

As the cyclic hydrocarbon, $C_{6-18}$ cyclic hydrocarbon such as benzene, naphthalene and the like, $C_{3-8}$ cycloalkane such as cyclopentane, cyclohexane, cycloheptane, cyclooctane, etc. and the like are used.

As the heterocycle, a ring corresponding to the heterocyclic group exemplified as the group bonded via a carbon atom can be used.

As $R^1$, a 4-pyridyl group, a 4-pyrimidyl group, a pyrazolyl group or a thiazolyl group, particularly a 4-pyridyl group, optionally substituted by substituent(s) selected from (1) $C_{1-8}$ alkyl-carbonylamino (e.g., $C_{1-6}$ alkyl-carbonylamino such as acetylamino, phenoxyacetylamino, ethylcarbonylamino, propylcarbonylamino, isopropylcarbonylamino, tert-butylcarbonylamino and the like; phenylthioethylcarbonylamino; thienylmethylcarbonyl, morpholinylethylcarbonylamino and the like) optionally substituted by substituent(s) selected from $C_{6-18}$ arylthio (e.g., phenylthio), $C_{6-18}$ aryloxy (e.g., phenoxy), and 4- to 7-membered (preferably 5- or 6-membered) monocyclic aromatic heterocyclic group (e.g., thienyl) or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, (2) $C_{3-8}$ cycloalkyl-carbonylamino (e.g., cyclopropylcarbonylamino, cyclopentylcarbonylamino, cyclohexylcarbonylamino), (3) $C_{6-18}$ aryl-carbonylamino (e.g., fluorophenylcarbonylamino, chlorophenylcarbonylamino, difluorophenylcarbonylamino, methylphenylcarbonylamino, methoxyphenylcarbonylamino, dimethylaminophenylcarbonylamino) optionally substituted by substituent(s) selected from a halogen atom, $C_{1-6}$ alkyl, $C_{1-6}$alkoxy, amino and mono- or di-$C_{1-6}$ alkylamino, (4) $C_{6-18}$ aryl-$C_{1-4}$ alkyl-carbonylamino (e.g., benzylcarbonylamino) and (5) 4- to 7-membered (preferably 5- or 6-membered) monocyclic heterocyclyl (e.g., furyl, thienyl, isoxazolyl, pyridyl)-carbonylamino (e.g., furylcarbonylamino, methyl isoxazolylcarbonylamino), said monocyclic heterocyclyl contains, as a ring constituting atom besides carbon atom, 1 to 4 heteroatoms selected from an oxygen atom, a sulfur atom and a nitrogen atom and is optionally substituted by $C_{1-6}$ alkyl, is preferable.

Particularly, as $R^1$,
(i) a group represented by

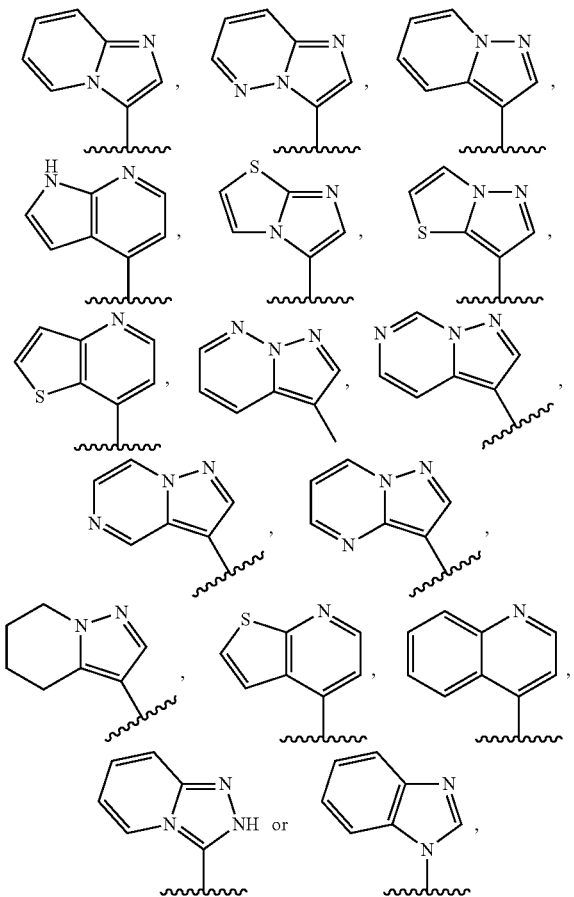

particularly, a group represented by

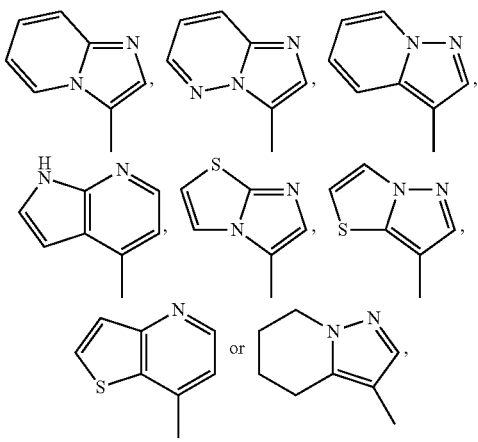

optionally substituted by the above-mentioned substituent(s), particularly, (1) hydroxy, (2) $C_{1-6}$ alkyl such as methyl and the like which is optionally substituted by 4- to 7-membered (preferably 5- or 6-membered) monocyclic aromatic heterocyclyl-carbonyl-amino or $C_{1-6}$ alkylcarbonylamino optionally substituted by amino containing, as a ring constituting atom besides carbon atom, 1 to 4 heteroatoms selected from an oxygen atom, a sulfur atom and a nitrogen atom, (3) $C_{1-6}$ alkoxy optionally substituted by hydroxy, (4) $C_{6-18}$ aryl-$C_{1-4}$ alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom which is optionally substituted by $C_{1-6}$ alkyl optionally substituted by halogen, (6) 4- to 7-membered (preferably 5- or 6-membered) monocyclic non-aromatic heterocyclyl-$C_{1-4}$ alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom and the like (e.g., hydroxy, $C_{1-6}$ alkyl such as methyl and the like) as well as (7) halogen, (8) $C_{2-6}$ alkenyl, (9) $C_{3-8}$ cycloalkyl, (10) $C_{6-18}$ aryl optionally substituted by $C_{1-6}$ alkoxy or halogen, (11) 4- to 7-membered (preferably 5- or 6-membered) monocyclic aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (12) 4- to 7-membered (preferably 5- or 6-membered) monocyclic non-aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl,
(ii) a group represented by

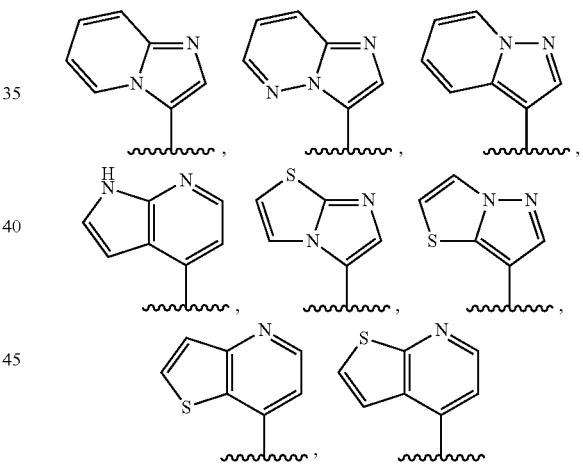

optionally substituted by the above-mentioned substituent(s), particularly, (1) hydroxy, (2) $C_{1-6}$ alkyl such as methyl and the like which is optionally substituted by 4- to 7-membered (preferably 5- or 6-membered) monocyclic aromatic heterocyclyl-carbonyl-amino or C1-6 alkylcarbonylamino optionally substituted by amino containing, as a ring constituting atom besides carbon atom, 1 to 4 heteroatoms selected from an oxygen atom, a sulfur atom and a nitrogen atom, (3) $C_{1-6}$ alkoxy optionally substituted by hydroxy, (4) $C_{6-18}$ aryl-$C_{1-4}$ alkyl-oxy (e.g., benzyloxy), (5) 4- to 7-membered (preferably 5- or 6-membered) monocyclic aromatic heterocyclyl-C1-4 alkyl-oxy containing, as a ring constituting atom besides carbon atom, 1 to 4 heteroatoms selected from an oxygen atom, a sulfur atom and a nitrogen atom, which is optionally substituted by $C_{1-6}$ alkyl optionally substituted by halogen (6) 4- to 7-membered (preferably 5- or 6-membered) monocyclic non-aromatic heterocyclyl-$C_{1-4}$ alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom and the like (e.g., hydroxy, $C_{1-6}$ alkyl such as methyl and the like) as well as (7) halogen, (8) $C_{2-6}$ alkenyl, (9) $C_{3-8}$ cycloalkyl, (10) $C_{6-18}$ aryl optionally substituted by $C_{1-6}$ alkoxy or halogen, (11) 4- to 7-membered (preferably 5- or 6-membered) monocyclic aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (12) 4- to 7-membered (preferably 5- or 6-membered) monocyclic non-aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, or (iii) a group represented by

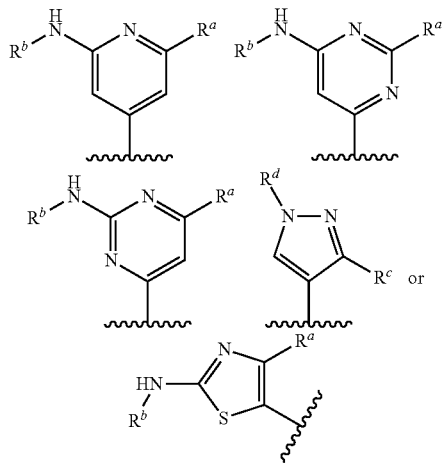

wherein Ra and Rc are each a hydrogen atom, an alkyl group (for example, the aforementioned $C_{1-20}$ alkyl group, preferably the aforementioned $C_{1-6}$ alkyl group) or a halogen atom, $R_b$ is (i) a hydrogen atom, (ii) an optionally substituted hydrocarbon-carbonyl group, (iii) an optionally substituted heterocyclyl-carbonyl group, (iv) an optionally substituted carbamoyl group, (v) an optionally substituted alkoxycarbonyl group, (vi) an optionally substituted hydrocarbon-sulfonyl group, (vii) an optionally substituted heterocyclyl-sulfonyl group, (viii) an optionally substituted sulfamoyl group, (ix) an optionally substituted hydrocarbon group or (x) an optionally substituted heterocyclic group, and Rd is (i) a hydrogen atom, (ii) an optionally substituted hydrocarbon group or (iii) an optionally substituted heterocyclic group, particularly a group represented by

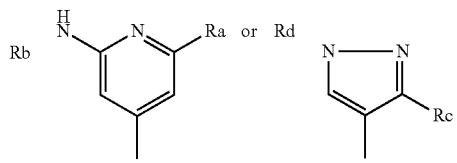

and the like, is preferable.

As the alkyl group for $R^a$ or $R^c$, a $C_{1-20}$ alkyl group, preferably a $C_{1-8}$ alkyl group such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl and the like can be used. Of these, a $C_{1-6}$ alkyl group such as methyl, ethyl, propyl and the like are preferable.

As the halogen atom for $R^a$ or $R^c$, a fluorine atom, a chlorine atom, a bromine atom and an iodine atom can be used. Of these, a chlorine atom is preferable.

As the "optionally substituted hydrocarbon-carbonyl group" for $R^b$, a group similar to the "optionally substituted hydrocarbon-carbonyl group" of the aforementioned substituent group Y can be used.

As the "optionally substituted heterocyclyl-carbonyl group" for $R^b$, a group similar to the "optionally substituted heterocyclyl-carbonyl group" of the aforementioned substituent group Y can be used.

As the "optionally substituted carbamoyl group" for $R^b$, those similar to the "optionally substituted carbamoyl group" exemplified as the "optionally substituted group bonded via a carbon atom" can be used.

As the "optionally substituted alkoxycarbonyl group" for $R^b$, a $C_{1-8}$ alkoxycarbonyl group (e.g., methoxycarbonyl, ethoxycarbonyl, propoxycarbonyl and the like) optionally substituted by substituent(s) selected from the aforementioned substituent group X and the like can be used.

As the "optionally substituted hydrocarbon" of the "optionally substituted hydrocarbon-sulfonyl group" for $R^b$, a group similar to the "optionally substituted hydrocarbon group" of the aforementioned substituent group Y can be used.

As the "optionally substituted heterocyclyl" of the "optionally substituted heterocyclyl-sulfonyl group" for $R^b$, a group similar to the "optionally substituted heterocyclic group" of the aforementioned substituent group Y can be used.

As the "optionally substituted sulfamoyl group" for $R^b$, a group similar to the "optionally substituted sulfamoyl group" of the aforementioned substituent group Y can be used.

As the "optionally substituted hydrocarbon group" for $R^b$, a group similar to the "optionally substituted hydrocarbon group" of the aforementioned substituent group Y can be used.

As the "optionally substituted heterocyclic group" for $R^b$, a group similar to the "optionally substituted heterocyclic group" of the aforementioned substituent group Y can be used.

As the "optionally substituted hydrocarbon group" for $R^d$, a group similar to the "optionally substituted hydrocarbon group" of the aforementioned substituent group Y can be used.

As the "optionally substituted heterocyclic group" for $R^d$, a group similar to the "optionally substituted heterocyclic group" of the aforementioned substituent group Y can be used.

As $R^a$, a hydrogen atom, a halogen atom (e.g., chlorine atom), a $C_{1-6}$ alkyl group such as methyl, ethyl, propyl and the like are preferable.

As $R^b$, (1) a hydrogen atom, (2) a $C_{1-8}$ alkyl-carbonyl group (e.g., $C_{1-6}$ alkyl-carbonyl group such as acetyl, ethylcarbonyl and the like) optionally substituted by a substituent(s) selected from $C_{6-18}$ arylthio (e.g., phenylthio), 4- to 7-membered (preferably 5- or 6-membered) monocyclic aromatic heterocyclic group or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, and the like, (3) a $C_{3-8}$ cycloalkyl-carbonyl group (e.g., cyclopropylcarbonyl) and the like are preferable.

As $R^c$ or $R^d$, a hydrogen atom, a $C_{1-6}$ alkyl group such as methyl, ethyl, propyl and the like, and the like are preferable.

In addition, preferable examples of $R^1$ include (i) a 8- to 10-membered nitrogen-containing aromatic fused heterocyclic group containing, besides carbon atom and nitrogen atom, 1 to 4 heteroatoms selected from an oxygen atom and a sulfur atom, which is optionally substituted by substituent(s) selected from (1) hydroxy, (2) $C_{1-6}$ alkyl such as methyl and the like, (3) $C_{1-6}$ alkoxy optionally substituted by hydroxy, (4) $C_{6-18}$ aryl-$C_{1-4}$ alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom and (6) 4- to 7-membered (preferably 5- or 6-membered) monocyclic non-aromatic heterocyclyl-$C_{1-4}$ alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom, (ii) a 4-pyridyl group or a pyrazolyl group, particularly a 4-pyridyl group, optionally substituted by substituent(s) selected from (1) a halogen atom (e.g., a chlorine atom), (2) C1-6 alkyl (e.g., methyl, ethyl, propyl), (3) $C_{1-8}$alkyl-carbonylamino (e.g., $C_{1-6}$alkyl-carbonylamino such as acetylamino, phenoxyacetylamino, ethylcarbonylamino, propylcarbonylamino, isopropylcarbonylamino, tert-butylcarbonylamino and the like; phenylthioethylcarbonylamino; thienylmethylcarbonyl, morpholinylethylcarbonylamino and the like) optionally substituted by substituent(s) selected from $C_{6-18}$ arylthio (e.g., phenylthio), $C_{6-18}$ aryloxy (e.g., phenoxy), and 4- to 7-membered (preferably 5- or 6-membered) monocyclic aromatic heterocyclic group (e.g., thienyl) or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, (4) $C_{3-8}$ cycloalkyl-carbonylamino (e.g., cyclopropylcarbonylamino, cyclopentylcarbonylamino, cyclohexylcarbonylamino), (5) $C_{6-18}$ arylcarbonylamino (e.g., fluorophenylcarbonylamino, chlorophenylcarbonylamino, difluorophenylcarbonylamino, methylphenylcarbonylamino, methoxyphenylcarbonylamino, dimethylaminophenylcarbonylamino) optionally substituted by substituent(s) selected from a halogen atom, $C_{1-6}$ alkyl, $C_{1-6}$ alkoxy, amino and mono- or di-$C_{1-6}$ alkylamino, (6) $C_{6-18}$ aryl-$C_{1-4}$ alkyl-carbonylamino (e.g., benzylcarbonylamino) and (7) 4- to 7-membered (preferably 5- or 6-membered) monocyclic heterocyclyl (e.g., furyl, thienyl, isoxazolyl, pyridyl)-carbonylamino (e.g., furylcarbonylamino, methylisoxazolylcarbonylamino), said monocyclic heterocyclyl contains, as a ring constituting atom besides carbon atom, 1 to 4 heteroatoms selected from an oxygen atom, a sulfur atom and a nitrogen atom and is optionally substituted by $C_{1-6}$ alkyl, and the like.

$R^2$ is a halogen atom, or the aforementioned optionally substituted group bonded via a carbon atom, a nitrogen atom, an oxygen atom or a sulfur atom. Particularly, (i) a halogen atom, (ii) an optionally substituted hydroxy group, (iii) an optionally substituted hydrocarbon group, (iv) an optionally substituted heterocyclic group, (v) an optionally substituted amino group, (vi) an optionally substituted thiol group or (vii) an acyl group is preferable.

As the halogen atom, a fluorine atom, a chlorine atom, a bromine atom or an iodine atom is used.

As the "optionally substituted hydroxy group", a group similar to the "optionally substituted hydroxy group" for the aforementioned substituent group Y is used.

As the "optionally substituted hydrocarbon group", a group similar to the "optionally substituted hydrocarbon group" for the aforementioned substituent group Y is used.

As the "optionally substituted heterocyclic group", a group similar to the "optionally substituted heterocyclic group" for the aforementioned substituent group Y is used.

As the "optionally substituted amino group", a group similar to the "optionally substituted amino group" for the aforementioned substituent group Y is used.

As the "optionally substituted thiol group", a thiol group optionally substituted by the "optionally substituted hydrocarbon group" for the aforementioned substituent group Y or the "optionally substituted heterocyclic group" for the aforementioned substituent group Y is used.

As the "acyl group", a "formyl group", an "optionally substituted hydrocarbon-carbonyl group", an "optionally substituted heterocyclyl-carbonyl group", an "optionally substituted carbamoyl group", an "optionally substituted sulfonyl group"; an "optionally substituted sulfamoyl group", an "optionally esterified carboxyl group" and the like for the aforementioned substituent group Y are used.

As $R^2$, an optionally substituted hydrocarbon group, an optionally substituted heterocyclic group and the like are preferable. For example, (i) a $C_{1-8}$ alkyl group (preferably a $C_{1-6}$ alkyl group) (e.g., a tert-butyl group), (ii) a $C_{2-8}$ alkenyl group (e.g., a $C_{2-6}$ alkenyl group such as a propenyl group and the like), (iii) a $C_{3-8}$ cycloalkyl group (e.g., a cyclohexyl group), (iv) a hydroxy group (e.g., an ethyloxy group, a propyloxy group, a propenyloxy group, a benzyloxy group) optionally substituted by $C_{1-8}$ alkyl (preferably $C_{1-6}$ alkyl), $C_{2-8}$ alkenyl (preferably $C_{2-6}$ alkenyl) or $C_{6-18}$ aryl-$C_{1-4}$ alkyl (preferably phenyl-$C_{1-4}$ alkyl), (v) a $C_{6-18}$ aryl group (preferably a phenyl group) optionally substituted by a halogen atom, an optionally halogenated $C_{1-8}$ alkyl (preferably optionally halogenated $C_{1-6}$ alkyl) or $C_{1-8}$ alkoxy (preferably $C_{1-6}$ alkoxy) (e.g., a phenyl group, a trifluoromethylphenyl group, a fluorophenyl group, a difluorophenyl group, a methoxyphenyl group, a chlorophenyl group), (vi) a $C_{6-18}$ aryl-$C_{1-4}$ alkyl group (preferably a phenyl-$C_{1-4}$alkyl group) (e.g., a benzyl group), (vii) a 4- to 7-membered (preferably 5- or 6-membered) aromatic monocyclic heterocyclic group (e.g., a thienyl group, a furyl group) containing, besides carbon atom, 1 to 3 heteroatoms selected from a nitrogen atom, an oxygen atom and a sulfur atom, (vii) a 4- to 7-membered (preferably 5- or 6-membered) non-aromatic heterocyclic group (e.g., a tetrahydropyranyl group) containing, besides carbon atom, 1 to 3 heteroatoms selected from a nitrogen atom, an oxygen atom and a sulfur atom and the like are preferably used. Among these, a $C_{6-18}$ aryl group (e.g., phenyl group, trifluoromethylphenyl group, fluorophenyl group, difluorophenyl group, methoxyphenyl group, chlorophenyl group) optionally substituted by a halogen atom, an optionally halogenated $C_{1-8}$ alkyl or $C_{1-8}$ alkoxy, and the like are preferable.

$R^3$ is (1) CON($R^4$)$R^{4\prime}$, wherein $R^4$ and $R^{4\prime}$ are hydrogen or optionally substituted $C_1$-$C_6$ aliphatic, or (2) an optionally substituted 5-membered aromatic heterocyclic group containing 2 to 4 nitrogen atoms besides carbon atom, which is bonded via a carbon atom; (2) an optionally substituted 5-membered aromatic heterocyclic group containing 2 to 4 nitrogen atoms besides carbon atom, which is bonded via a carbon atom or (3) an optionally substituted 5-membered aromatic heterocyclic group containing 1 to 3 nitrogen atoms besides carbon atom and further containing one oxygen atom or sulfur atom, which is bonded via a carbon atom.

As $R^3$, (1) an optionally substituted 5-membered aromatic heterocyclic group containing 2 to 4 nitrogen atoms besides carbon atom, which is bonded via a carbon atom or (2) an optionally substituted 5-membered aromatic heterocyclic group containing 1 to 3 nitrogen atoms besides carbon atom and further containing one oxygen atom or sulfur atom, which is bonded via a carbon atom is preferable.

However, when $R^3$ is an optionally substituted thiazolyl group and $R^1$ is an optionally substituted thiazolyl group, the optionally substituted thiazolyl group for $R^1$ is a group represented by

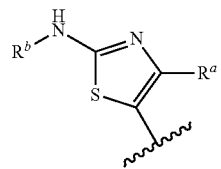

wherein $R^a$ is a hydrogen atom, an alkyl group or a halogen atom, $R^b$ is (i) a hydrogen atom, (ii) an optionally substituted hydrocarbon-carbonyl group, (iii) an optionally substituted heterocyclyl-carbonyl group, (iv) an optionally substituted carbamoyl group, (v) an optionally substituted alkoxycarbonyl group, (vi) an optionally substituted hydrocarbonsulfonyl group, (vii) an optionally substituted heterocyclyl-sulfonyl group, (viii) an optionally substituted sulfamoyl group, (ix) an optionally substituted hydrocarbon group or (x) an optionally substituted heterocyclic group.

Examples of the "5-membered aromatic heterocyclic group containing 2 to 4 nitrogen atoms besides carbon atom, which is bonded via a carbon atom" include imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl) and the like. Particularly, triazolyl (e.g., 1,2,4-triazol-1-yl, 1,2,4-triazol-3-yl, 1,2,3-triazol-1-yl, 1,2,3-triazol-2-yl, 1,2,3-triazol-4-yl) is preferable.

As the substituent of the "5-membered aromatic heterocyclic group containing 2 to 4 nitrogen atoms besides carbon atom, which is bonded via a carbon atom", a group selected from the aforementioned substituent group X is used. Particularly, $C_{1-8}$ alkyl (preferably, $C_{1-6}$ alkyl such as methyl and the like) and the like are preferable.

As the "5-membered aromatic heterocyclic group containing 1 to 3 nitrogen atoms besides carbon atom and further containing one oxygen atom or sulfur atom, which is bonded via a carbon atom", thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl) and the like are used.

As the substituent of the "5-membered aromatic heterocyclic group containing 1 to 3 nitrogen atoms besides carbon atom and further containing one oxygen atom or sulfur atom, which is bonded via a carbon atom", a group selected from the aforementioned substituent group X is used. Particularly, $C_{1-8}$ alkyl (preferably, $C_{1-6}$ alkyl such as methyl and the like) and the like are preferable.

As $R^3$, triazolyl (e.g., 1,2,4-triazol-1-yl, 1,2,4-triazol-3-yl, 1,2,3-triazol-1-yl, 1,2,3-triazol-2-yl, 1,2,3-triazol-4-yl) optionally substituted by $C_{1-8}$ alkyl (preferably, $C_{1-6}$ alkyl such as methyl and the like) and the like are preferable.

$R^4$ and $R^{4'}$ are respectively hydrogen, $—Z_1—R^5$, optionally substituted $C_{1-6}$ aliphatic, or optionally substituted 3-10-membered cycloaliphatic, wherein $Z_1$ is selected from an optionally substituted $C_{1-3}$ alkylene chain, $—S(O)—$, $—S(O)_2—$, $—C(O)—$, $—CO_2—$, $—C(O)NR^{4a}—$, or $—S(O)_2NR^{4a}—$, wherein $R^{4a}$ is hydrogen or an optionally substituted $C_{1-4}$ aliphatic, and $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Examples of "optionally substituted $C_{1-6}$ aliphatic group" include $C_{1-6}$ alkyl (e.g. methyl, ethyl, propyl, isopropyl, butyl, isobutyl, sec-butyl, tert-butyl, pentyl, isopentyl), $C_{2-6}$ alkenyl group (e.g. ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl) or $C_{2-6}$ alkynyl group (e.g. ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl) each of which is optionally substituted by a group selected from the aforementioned substituent group X.

Examples of "optionally substituted 3-10-membered cycloaliphatic group" includes $C_{3-10}$ cycloalkyl group (e.g. cyclopropyl, cyclobutyl, cyclopentyl, cyclohexyl, cycloheptyl, cyclooctyl) optionally substituted by a group selected from the aforementioned substituent group X.

Examples of "optionally substituted $C_{1-3}$ alkylene chain" include methylene, ethylene or propylene each of which is optionally substituted by a group selected from the aforementioned substituent group X.

Examples of "optionally substituted $C_{1-4}$ aliphatic group" include $C_{1-4}$ alkyl (e.g. methyl, ethyl, propyl, isopropyl, butyl, isobutyl, sec-butyl, tert-butyl), $C_{2-4}$ alkenyl group (e.g. ethenyl, 1-propenyl, 2-propenyl, 2-methyl-1-propenyl, 1-butenyl, 2-butenyl, 3-butenyl, 3-methyl-2-butenyl) or $C_{2-4}$ alkynyl group (e.g. ethynyl, 1-propynyl, 2-propynyl, 1-butynyl, 2-butynyl, 3-butynyl) each of which is optionally substituted by a group selected from the aforementioned substituent group X.

Examples of "optionally substituted 4-10-membered heterocyclyl group having 1-5 heteroatoms independently selected from nitrogen, oxygen, or sulfur" include the 4- to 7-membered (preferably 5- or 6-membered) monocyclic non-aromatic heterocyclic group containing, as a ring constituting atom besides carbon atom, 1 to 4 heteroatoms selected from an oxygen atom, a sulfur atom and a nitrogen atom mentioned above or the fused non-aromatic heterocyclic group derived from a fused ring wherein a ring corresponding to such 4- to 7-membered monocyclic non-aromatic heterocyclic group, and 1 or 2 rings selected from a 5- or 6-membered heterocycle containing 1 or 2 nitrogen atoms, a 5-membered heterocycle containing one sulfur atom and a benzene ring are condensed each of which is optionally substituted by a group selected from the aforementioned substituent group X.

Examples of "optionally substituted 6-10-membered aryl group" include phenyl, naphthyl, anthryl, phenanthryl, acenaphthylenyl, biphenylyl and the like, especially phenyl, each of which is optionally substituted by a group selected from the aforementioned substituent group X.

Examples of "optionally substituted 5-10-membered heteroaryl group having 1-5 heteroatoms independently selected from nitrogen, oxygen, or sulfur" include the 4- to 7-membered (preferably 5- or 6-membered) monocyclic aromatic heterocyclic group containing, as a ring constituting atom besides carbon atom, 1 to 4 heteroatoms selected from an oxygen atom, a sulfur atom and a nitrogen atom mentioned above or the fused aromatic heterocyclic group derived from a fused ring wherein a ring corresponding to such 4- to 7-membered monocyclic aromatic heterocyclic group, and 1 or 2 rings selected from a 5- or 6-membered aromatic heterocycle containing 1 or 2 nitrogen atoms, a 5-membered aromatic heterocycle containing one sulfur atom and a benzene ring are condensed mentioned above each of which is optionally substituted by a group selected from the aforementioned substituent group X.

As $R^4$ and $R^{4a}$, hydrogen is preferable.

As $R^{4a}$, hydrogen or $C_{1-4}$alkyl is preferable.

$R^6$ is hydrogen or optionally substituted $C_{1-4}$alkyl.

As the substituent of the "$C_{1-4}$ alkyl", a group selected from the aforementioned substituent group X is used.

As $R^6$, hydrogen or $C_{1-6}$ alkyl such as methyl and the like are preferable.

$R^7$ is H, hydroxy, $C_{1-6}$alkyl, $C_{1-6}$ alkoxy optionally substituted by a group selected from hydroxy, $C_{1-6}$ alkyl-carbonylamino and amino-$C_{1-6}$ alkyl-carbonylamino, $C_{6-18}$ aryl-$C_{1-4}$alkyl-oxy, 4- to 7-membered monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by $C_{1-6}$ alkyl optionally substituted by halogen and 4- to 7-membered monocyclic non-aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by a group selected from halogen, $C_{1-6}$ alkyl, $C_{1-6}$ alkylsulfonyloxy and $C_{1-6}$ alkyl-carbonyl optionally substituted by hydroxyl.

For the compound (I), (Ia), (Ib) or (I'), any combinations of preferable groups for each symbol mentioned above are preferably used.

As the compound (I), (Ia) or (I'), the following compound is preferable.

(i) The compound (I), (Ia) or (I'), especially (I) or (Ia) wherein, $R^1$ is (i) an optionally substituted group represented by

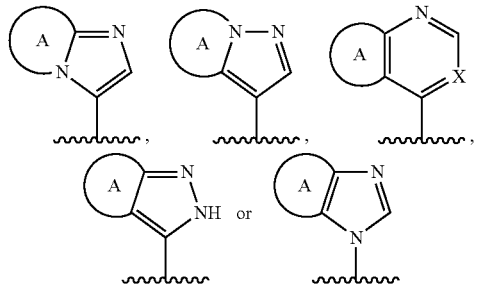

wherein A is a cyclic group and X is CH or N, or (ii) a pyridyl group, a pyrimidinyl group, a pyrazolyl group, a thiazolyl group, an oxazolyl group, an imidazolyl group, a triazolyl group, an isothiazolyl group or a pyridazinyl group, each of which is optionally substituted;

$R^2$ is an optionally substituted aryl group optionally substituted by substituents selected from substituent group X, a $C_{6-18}$ aryl-$C_{1-4}$ alkyl group optionally substituted by substituents selected from substituent group X, a 4- to 7-membered (preferably 5- or 6-membered) monocyclic aromatic heterocyclic group containing, as a ring constituting atom besides carbon atom, 1 to 4 heteroatoms selected from an oxygen atom, a sulfur atom and a nitrogen atom, or a group derived from a fused ring wherein a ring corresponding to such 4- to 7-membered monocyclic aromatic heterocyclic group, and 1 or 2 rings selected from a 5- or 6-membered aromatic heterocycle containing 1 or 2 nitrogen atoms, a 5-membered aromatic heterocycle containing one sulfur atom and a benzene ring are condensed, $R^3$ is (1) an optionally substituted 5-membered aromatic heterocyclic group containing 2 to 4 nitrogen atoms besides carbon atom, which is bonded via a carbon atom or (2) an optionally substituted 5-membered aromatic heterocyclic group containing 1 to 3 nitrogen atoms besides carbon atom and further containing one oxygen atom or sulfur atom.

(ii) The compound (1), (Ia) or (I'), especially (I) or (Ia) wherein, $R^1$ is (i) a group represented by

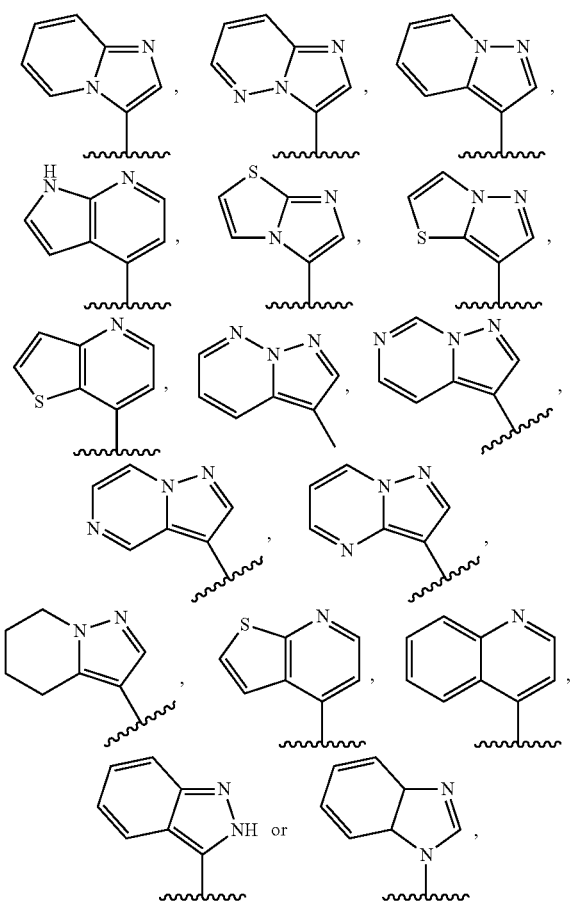

particularly, a group represented by

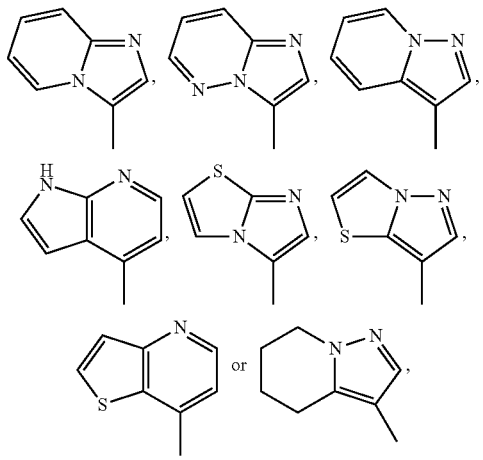

optionally substituted by the above-mentioned substituent(s), particularly, (1) hydroxy, (2) $C_{1-6}$ alkyl such as methyl and the like which is optionally substituted by 4- to 7-membered (preferably 5- or 6-membered) monocyclic aromatic heterocyclyl-carbonyl-amino or $C_{1-6}$ alkylcarbonylamino optionally substituted by amino containing, as a ring constituting atom besides carbon atom, 1 to 4 heteroatoms selected from an oxygen atom, a sulfur atom and a nitrogen atom, (3) $C_{1-6}$ alkoxy optionally substituted by hydroxy, (4) $C_{6-18}$ aryl-$C_{1-4}$ alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom which is optionally substituted by $C_{1-6}$ alkyl optionally substituted by halogen, (6) 4- to 7-membered (preferably 5- or 6-membered) monocyclic non-aromatic heterocyclyl-$C_{1-4}$alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom and the like (e.g., hydroxy, $C_{1-6}$alkyl such as methyl and the like) as well as (7) halogen, (8) $C_{2-6}$ alkenyl, (9) $C_{3-8}$ cycloalkyl, (10) $C_{6-18}$ aryl optionally substituted by $C_{1-6}$alkoxy or halogen, (11) 4- to 7-membered (preferably 5- or 6-membered) monocyclic aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (12) 4- to 7-membered (preferably 5- or 6-membered) monocyclic non-aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (ii) a group represented by

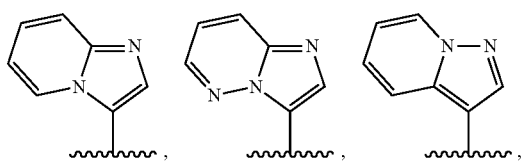

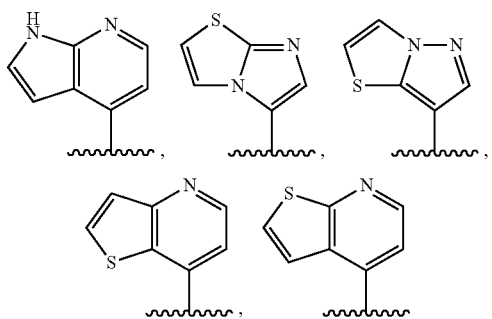

optionally substituted by the above-mentioned substituent(s), particularly, (1) hydroxy, (2) $C_{1-6}$ alkyl such as methyl and the like which is optionally substituted by 4- to 7-membered (preferably 5- or 6-membered) monocyclic aromatic heterocyclyl-carbonyl-amino or C1-6 alkylcarbonylamino optionally substituted by amino containing, as a ring constituting atom besides carbon atom, 1 to 4 heteroatoms selected from an oxygen atom, a sulfur atom and a nitrogen atom, (3) $C_{1-6}$ alkoxy optionally substituted by hydroxy, (4) $C_{6-18}$ aryl-$C_{1-4}$ alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom, which is optionally substituted by $C_{1-6}$ alkyl optionally substituted by halogen (6) 4- to 7-membered (preferably 5- or 6-membered) monocyclic non-aromatic heterocyclyl-$C_{1-4}$ alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom and the like (e.g., hydroxy, $C_{1-6}$ alkyl such as methyl and the like) as well as (7) halogen, (8) $C_{2-6}$ alkenyl, (9)$C_{3-8}$ cycloalkyl, (10) $C_{6-18}$ aryl optionally substituted by $C_{1-6}$ alkoxy or halogen, (11) 4- to 7-membered (preferably 5- or 6-membered) monocyclic aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (12) 4- to 7-membered (preferably 5- or 6-membered) monocyclic non-aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, or (iii) a group represented by

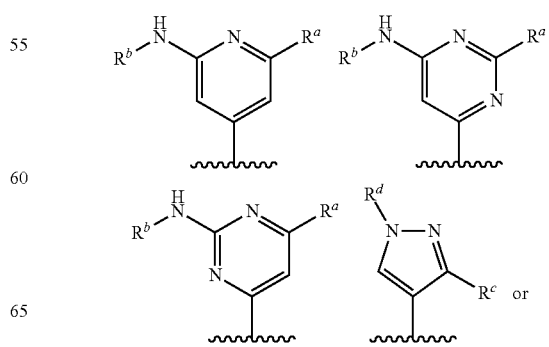

-continued

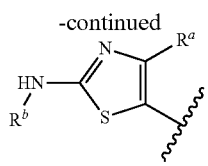

wherein $R^a$ is a hydrogen atom, a halogen atom (e.g., chlorine atom), a $C_{1-6}$ alkyl group such as methyl, ethyl, propyl and the like, $R^b$ is (1) a hydrogen atom, (2) a $C_{1-8}$ alkyl-carbonyl group (e.g., $C_{1-6}$ alkyl-carbonyl group such as acetyl, ethylcarbonyl and the like) optionally substituted by a substituent(s) selected from $C_{6-18}$ arylthio (e.g., phenylthio), 4- to 7-membered (preferably 5- or 6-membered) monocyclic aromatic heterocyclic group or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, and the like, (3) a $C_{3-8}$ cycloalkyl-carbonyl group (e.g., cyclopropylcarbonyl) and the like, $R^c$ is a hydrogen atom, a $C_{1-6}$ alkyl group such as methyl, ethyl, propyl and the like, and Rd is (i) a hydrogen atom, (ii) a $C_{1-6}$ alkyl group such as methyl, ethyl, propyl and the like, or (iii) an optionally substituted heterocyclic group represented by

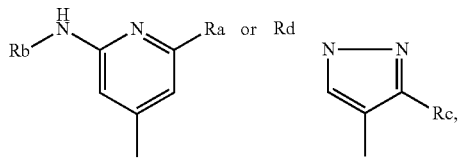

especially,
wherein $R^a$, $R^b$ and $R^c$ are as defined above, and $R^d$ is hydrogen atom, a $C_{1-6}$ alkyl group such as methyl, ethyl, propyl and the like, especially $R^1$ is
(i) a group represented by

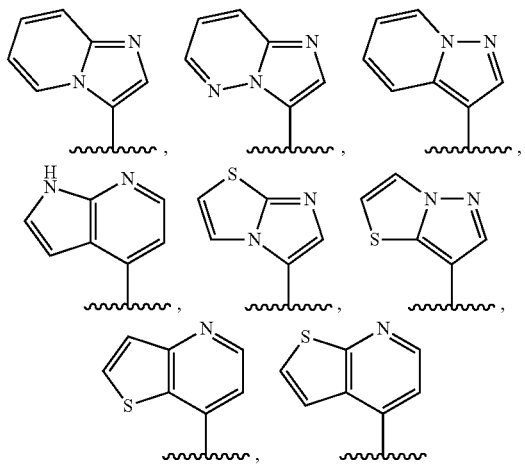

optionally substituted by the above-mentioned substituent(s), particularly, (1) hydroxy, (2) $C_{1-6}$ alkyl such as methyl and the like which is optionally substituted by 4- to 7-membered (preferably 5- or 6-membered) monocyclic aromatic heterocyclyl-carbonyl-amino or C1-6 alkylcarbonylamino optionally substituted by amino containing, as a ring constituting atom besides carbon atom, 1 to 4 heteroatoms selected from an oxygen atom, a sulfur atom and a nitrogen atom, (3) $C_{1-6}$ alkoxy optionally substituted by hydroxy, (4) $C_{6-18}$ aryl-$C_{1-4}$ alkyl-oxy (e.g., benzyloxy), (5) 4- to 7-membered (preferably 5- or 6-membered) monocyclic aromatic heterocyclyl-C1-4 alkyl-oxy containing, as a ring constituting atom besides carbon atom, 1 to 4 heteroatoms selected from an oxygen atom, a sulfur atom and a nitrogen atom, which is optionally substituted by $C_{1-6}$ alkyl optionally substituted by halogen (6) 4- to 7-membered (preferably 5- or 6-membered) monocyclic non-aromatic heterocyclyl-$C_{1-4}$alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom and the like (e.g., hydroxy, $C_{1-6}$ alkyl such as methyl and the like) as well as (7) halogen, (8) $C_{2-6}$ alkenyl, (9) $C_{3-8}$ cycloalkyl, (10) $C_{6-18}$ aryl optionally substituted by $C_{1-6}$ alkoxy or halogen, (11) 4- to 7-membered (preferably 5- or 6-membered) monocyclic aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (12) 4- to 7-membered (preferably 5- or 6-membered) monocyclic non-aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, or
(iii) a group represented by

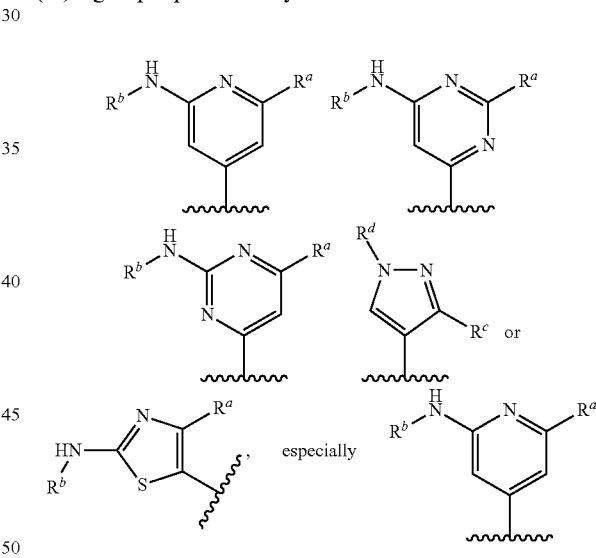

wherein $R^a$ is a hydrogen atom, a halogen atom (e.g., chlorine atom), a $C_{1-6}$ alkyl group such as methyl, ethyl, propyl and the like, $R^b$ is (1) a hydrogen atom, (2) a $C_{1-8}$ alkyl-carbonyl group (e.g., $C_{1-6}$ alkyl-carbonyl group such as acetyl, ethylcarbonyl and the like) optionally substituted by a substituent(s) selected from $C_{6-18}$ arylthio (e.g., phenylthio), 4- to 7-membered (preferably 5- or 6-membered) monocyclic aromatic heterocyclic group or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, and the like, (3) a $C_{3-8}$ cycloalkyl-carbonyl group (e.g., cyclopropylcarbonyl) and the like, especially a $C_{1-8}$ alkyl-carbonyl group (e.g., $C_{1-6}$ alkyl-carbonyl group such as acetyl, ethylcarbonyl and the like) optionally substituted by a substituent(s)

selected from $C_{6-18}$ arylthio (e.g., phenylthio), 4- to 7-membered (preferably 5- or 6-membered) monocyclic aromatic heterocyclic group or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, and the like.

$R^c$ is a hydrogen atom, a $C_{1-6}$ alkyl group such as methyl, ethyl, propyl and the like, and $R^d$ is (i) a hydrogen atom, (ii) a $C_{1-6}$ alkyl group such as methyl, ethyl, propyl and the like, or (iii) an optionally substituted heterocyclic group represented by

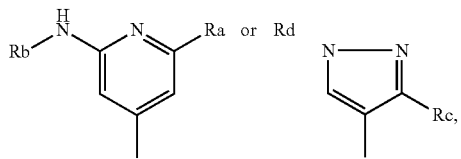

especially, wherein $R^a$, $R^b$ and $R^c$ are as defined above, and $R^d$ is hydrogen atom, a $C_{1-6}$ alkyl group such as methyl, ethyl, propyl and the like, $R^2$ is (i) a $C_{1-8}$ alkyl group (preferably a $C_{1-6}$ alkyl group) (e.g., a tert-butyl group), (ii) a $C_{2-8}$ alkenyl group (e.g., a $C_{2-6}$ alkenyl group such as a propenyl group and the like), (iii) a $C_{3-8}$ cycloalkyl group (e.g., a cyclohexyl group), (iv) a hydroxy group (e.g., an ethyloxy group, a propyloxy group, a propenyloxy group, a benzyloxy group) optionally substituted by $C_{1-8}$ alkyl (preferably $C_{1-6}$ alkyl), alkenyl (preferably $C_{2-6}$ alkenyl) or $C_{6-18}$ aryl-$C_{1-4}$ alkyl (preferably phenyl-$C_{1-4}$ alkyl), (v) a $C_{6-18}$ aryl group (preferably a phenyl group) optionally substituted by a halogen atom, an optionally halogenated $C_{1-8}$ alkyl (preferably optionally halogenated $C_{1-6}$ alkyl) or $C_{1-8}$ alkoxy (preferably $C_{1-6}$ alkoxy) (e.g., a phenyl group, a trifluoromethylphenyl group, a fluorophenyl group, a difluorophenyl group, a methoxyphenyl group, a chlorophenyl group), (vi) a $C_{6-18}$ aryl-$C_{1-4}$ alkyl group (preferably a phenyl-$C_{1-4}$ alkyl group) (e.g., a benzyl group), (vii) a 4- to 7-membered (preferably 5- or 6-membered) aromatic monocyclic heterocyclic group (e.g., a thienyl group, a furyl group) containing, besides carbon atom, 1 to 3 heteroatoms selected from a nitrogen atom, an oxygen atom and a sulfur atom, or (vii) a 4- to 7-membered (preferably 5- or 6-membered) non-aromatic heterocyclic group (e.g., a tetrahydropyranyl group) containing, besides carbon atom, 1 to 3 heteroatoms selected from a nitrogen atom, an oxygen atom and a sulfur atom and the like are preferably used. Among these, a $C_{6-18}$ aryl group (e.g., phenyl group, trifluoromethylphenyl group, fluorophenyl group, difluorophenyl group, methoxyphenyl group, chlorophenyl group) optionally substituted by a halogen atom, an optionally halogenated $C_{1-8}$ alkyl or $C_{1-8}$ alkoxy, especially, (i) a $C_{6-18}$ aryl group (preferably a phenyl group) optionally substituted by a halogen atom, an optionally halogenated $C_{1-8}$ alkyl (preferably optionally halogenated $C_{1-6}$ alkyl) or $C_{1-8}$ alkoxy (preferably $C_{1-6}$ alkoxy) (e.g., a phenyl group, a trifluoromethylphenyl group, a fluorophenyl group, a difluorophenyl group, a methoxyphenyl group, a chlorophenyl group), or (ii) a 4- to 7-membered (preferably 5- or 6-membered) aromatic monocyclic heterocyclic group (e.g., a thienyl group, a furyl group) containing, besides carbon atom, 1 to 3 heteroatoms selected from a nitrogen atom, an oxygen atom and a sulfur atom, $R^3$ is triazolyl (e.g., 1,2,4-triazol-1-yl, 1,2,4-triazol-3-yl, 1,2,3-triazol-1-yl, 1,2,3-triazol-2-yl, 1,2,3-triazol-4-yl) optionally substituted by $C_{1-8}$ alkyl (preferably, $C_{1-6}$ alkyl such as methyl and the like). The compound (Ia) is preferable among compounds (I), (Ia), (Ib) and (I').

As a salt of compound represented by the formula (I), (Ia), (Ib) or (I'), for example, metal salts, ammonium salts, salts with organic bases, salts with inorganic acids, salts with organic acids, salts with basic or acidic amino acids and the like can be mentioned. As preferable examples of the metal salt, alkali metal salts such as sodium salt, potassium salt and the like; alkaline earth metal salts such as calcium salt, magnesium salt, barium salt and the like; aluminum salt and the like can be mentioned. As preferable examples of the salts with organic bases, salts with trimethylamine, triethylamine, pyridine, picoline, 2,6-lutidine, ethanolamine, diethanolamine, triethanolamine, tromethamine[tris(hydroxymethyl)methylamine], t-butylamine, cyclohexylamine, dicyclohexylamine, N,N'-dibenzylethylenediamine and the like can be mentioned. As preferable examples of the salts with inorganic acids, salts with hydrochloric acid, hydrobromic acid, nitric acid, sulfuric acid, phosphoric acid and the like can be mentioned. As preferable examples of the salts with organic acids, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like can be mentioned. As preferable examples of the salts with basic amino acids, salts with arginine, lysine, ornithine and the like can be mentioned. As preferable examples of the salts with acidic amino acids, salts with aspartic acid, glutamic acid and the like can be mentioned.

Of those, pharmaceutically acceptable salts are preferable. For example, when a compound has an acidic functional group therein, salts with inorganic bases such as alkali metal salts (e.g., sodium salt, potassium salt and the like), alkaline earth metal salts (e.g., calcium salt, magnesium salt, barium salt and the like) and the like, ammonium salt and the like can be mentioned. When a compound has a basic functional group therein, salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like can be mentioned.

Production Methods

The production methods of the compounds (I) and (I'), and subsets thereof, of the present invention are described in the following. Each symbol in the compound in the schemes is as defined above.

One of ordinary skill in the art will recognise that numerous variations in reaction conditions including variations in solvent, reagents, catalysts, reaction temperatures and times are possible for each of the reactions described. Variation of order of synthetic steps and alternative synthetic routes are also possible according to the well known organic synthetic procedure.

Usually, we can start the synthesis from commercially available thiazole analogs to prepare target compounds. In some cases, we can prepare specially functionalized thiazole analogs for our special purpose by the procedure describing in scheme 1.

Compound (I) of the present invention can be generally produced by, for example, subjecting thioamide derivative (II) shown below wherein P is $R^1$ itself or a substituent convertible to $R^1$ by applying a generally known method and α-halocarbonyl compound (III) wherein X is Br, I or Cl, W is $R^2$ itself or a substituent convertible to $R^2$ by applying a generally known method and Q is $R^3$ itself or a substituent convertible to $R^3$ by applying a generally known method to a condensation reaction to give intermediate (A) [each symbol is as defined above] and subjecting the intermediate to a generally known functional group conversion reaction (formula 1).

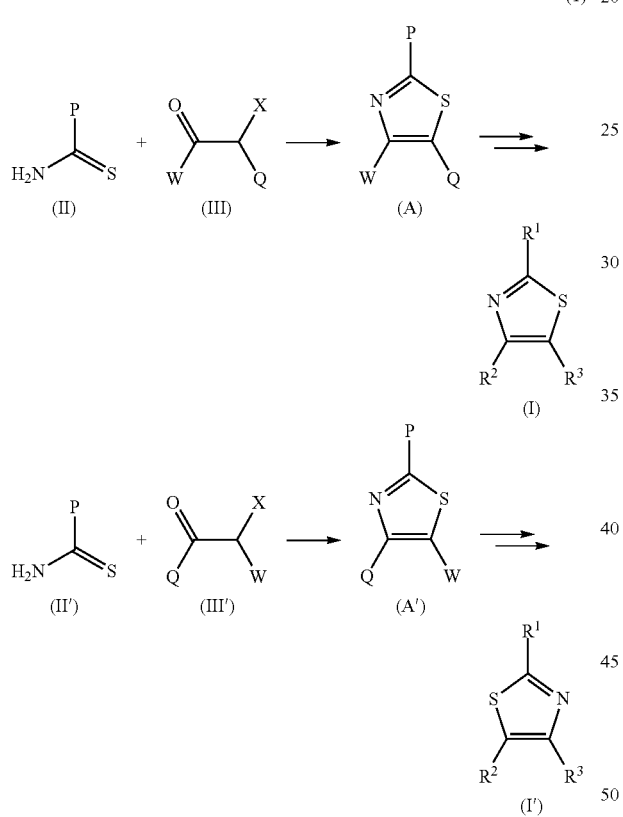

If α-halocarbonyl compound (III'), wherein X is Br, I or Cl, W is $R^2$ itself or a substituent convertible to $R^2$ by applying a generally known method and Q is $R^3$ itself or a substituent convertible to $R^3$ by applying a generally known method, is suitably selected, reverse type of thiazole intermediates (A') can be obtained by the same manner as described above.

Functional group transformation methods described below for P, W, or Q are also applicable to intermediate (A') to afford reverse type of thiazole analogs (I').

A condensation reaction to give (A) [each symbol is as defined above] is preferably performed in a solvent using 0.2 to 10 equivalents, preferably 0.5 to 5 equivalents, of (III) [Q and W are as defined above] relative to (II) [P is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, acetic acid or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. Where necessary, a base may be added. As the base, an inorganic base, an organic base and the like are used, and specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium tert-butoxide, sodium hydride, sodium amide, diazabicycloundecene (DBU) and the like are used.

A conversion reaction from (A) [each symbol is as defined above] to compound (I) can be performed, for example, by a combination of generally known functional group conversion reactions shown below.

From (formula 2) to (formula 11) shown below is one example of a method of introducing $R^2$ into compound (I).

For example, (A-2) [W=X, other symbols are each as defined above] can be obtained by reacting (A-1) [W=H, each symbol is as defined above] with a generally known halogenating reagent such as bromine, N-bromosuccinimide, N-iodosuccinimide, N-chlorosuccinimide or sulfuryl chloride and the like (formula 2).

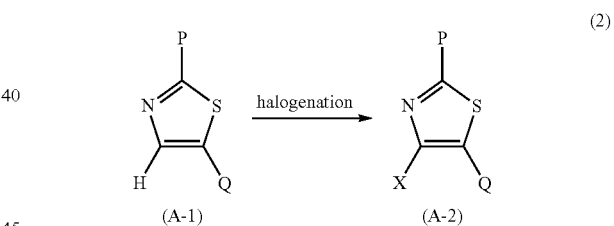

The reaction here is preferably performed in a solvent using 1 to 10 equivalents, preferably 1 to 5 equivalents, of a halogenating reagent such as bromine, N-bromosuccinimide, N-iodosuccinimide, N-chlorosuccinimide or sulfuryl chloride and the like relative to (A-1) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like. Preferably, halogenated hydrocarbons such as dichloromethane, chloroform, carbon tetrachloride, 1,2-dichloroethane and the like, ethers such as diethyl ether, tetrahydrofuran, dioxane and the like, acetone or acetonitrile is used. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr.

In addition, the obtained (A-2) [each symbol is as defined above] can be subjected to a generally known reaction to further convert X to various functional groups.

For example, (A-2) [each symbol is as defined above] can be converted to (A-3) [W=NR4R5, other symbols are each as defined above] by reaction with amine ($R^4R^{4'}NH$) wherein $R^4$ and $R^5$ are hydrogen atoms, or each is an alkyl group, an aryl group or a heterocyclic group, each of which is optionally substituted, or $R^4$ and $R^{4'}$ may be bonded to form, together with the nitrogen atom, cyclic amine such as piperidine or morpholine, which is commercially available or can be produced by a generally known method (formula 3).

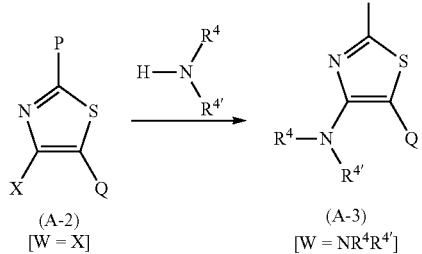

(3)

(A-2)
[W = X]

(A-3)
[W = $NR^4R^{4'}$]

The reaction here is preferably performed in a solvent and using 1 to 10 equivalents, preferably 1 to 5 equivalents, of amine ($R^4R^{4'}NH$) [$R^4$ and $R^{4'}$ are as defined above] relative to (A-2) [each symbol is as defined above]. In addition, 0 to 10 equivalents, preferably 0 to 2 equivalents, of a base may be used. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. Preferably, tetrahydrofuran, acetonitrile, N,N-dimethylformamide, N,N-dimethylacetamide or 1-methyl-2-pyrrolidone is used. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. As the base for the aforementioned reaction, an inorganic base, an organic base and the like are used, and specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium tert-butoxide, sodium hydride, sodium amide, diazabicycloundecene (DEW) and the like are used.

In addition, (A-4) [W=$R^{6a}$, other symbols are each as defined above] can be obtained by reacting, for example, (A-2) [each symbol is as defined above] with an organic boronic acid reagent (IV) [$R^{6a}$—$B(OR^{7a})_2$: wherein $R^{6a}$ is an alkyl group, an aryl group or a heterocyclic group, each of which is optionally substituted, $R^{7a}$ is a hydrogen atom or an alkyl group, and $R^{7a}R^{7a}$ may be bonded to form a cyclic boric acid ester], which is commercially available or can be produced by a generally known method, or an organic tin reagent (V) [$R^{6a}$—$SnR^8_3$: wherein $R^8$ is a $C_{1-6}$ alkyl group such as methyl, ethyl, propyl, butyl and the like and other symbols are each as defined above], which is commercially available or can be produced by a generally known method, in the presence of a palladium catalyst (formula 4).

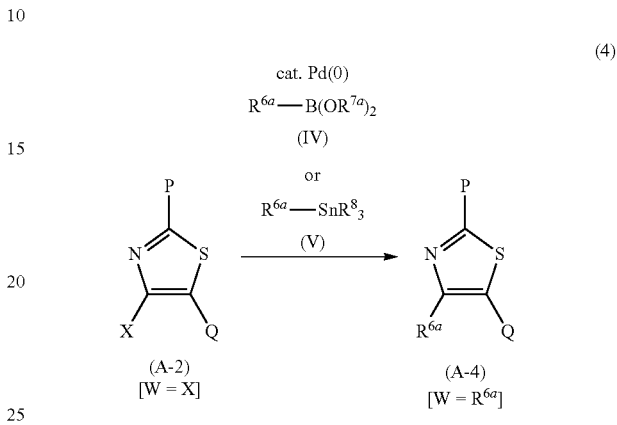

(4)

(A-2)
[W = X]

(A-4)
[W = $R^{6a}$]

The reaction here is preferably performed in a solvent and using 1 to 10 equivalents, preferably 1 to 5 equivalents, of an organic boronic acid reagent (IV) [each symbol is as defined above] or an organic tin reagent (V) [each symbol is as defined above] relative to (A-2) [each symbol is as defined above]. In addition, 0 equivalent to a large excess, preferably 0 to 10 equivalents, of a base may be used as necessary. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction is performed at room temperature or under beating (about 40 to 200° C., preferably about 40 to 160° C.), and the reaction time is generally about 1 to 30 hr, preferably about 1 to 20 hr, more preferably about 1 to 10 hr. As the base for the aforementioned reaction, an inorganic base, an organic base and the like are used, and specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium tert-butoxide, sodium hydride, sodium amide, diazabicycloundecene (DBU) and the like are used. As the palladium complex to be used as a catalyst, palladium acetate, palladium chloride, tris(dibenzylideneacetone)dipalladium(0) or [1,1'-bis(diphenylphosphino)ferrocene]dichloropalladium(II), dichlorobis(triphenylphosphine)palladium, tetrakis(triphenylphosphine)palladium and the like can be used, and a phosphine ligand such as triphenylphosphine, 2,2'-bis(diphenylphosphino)-1,1'-binaphthyl (BINAP), dicyclohexyl(2',4',6'-triisopropylbiphenyl-2-yl)phosphine (X-Phos), 1,1'-bis(diphenylphosphino)ferrocene (DPPF) and the like is added as necessary. As X in this case, Br or I is preferable.

Moreover, for example, (A-5) [W=SR$^9$, other symbols are each as defined above] can be obtained by reacting (A-2) [each symbol is as defined above] with thiol (R$^9$SH) wherein R$^9$ is an alkyl group, an aryl group or a heterocyclic group, each of which is optionally substituted, and other symbols are each as defined above, which is commercially available or can be produced by a generally known method, in the presence of a base (formula 5).

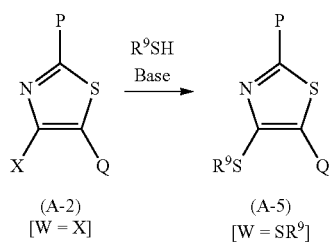

(A-2) [W = X]  (A-5) [W = SR$^9$]  (5)

The reaction here is preferably performed in a solvent and using 1 to 10 equivalents, preferably 1 to 5 equivalents, of thiol (R$^9$SH) [R$^9$ is as defined above] and 1 equivalent to 20 equivalents, preferably 1 to 10 equivalents, of a base, relative to (A-2) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. As the base for the aforementioned reaction, an inorganic base, an organic base and the like are used, and specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium tert-butoxide, sodium hydride, sodium amide, diazabicycloundecene (DBU) and the like are used.

When α-halocarbonyl compound is (III-A) [W=OR$^{10}$ wherein R$^{10}$ is an alkyl group or an aryl group, each of which is optionally substituted, and other symbols are each as defined above], (A-6) [W=OH, and other symbols are each as defined above] can be obtained by condensation with (II) [each symbol is as defined above] (formula 6).

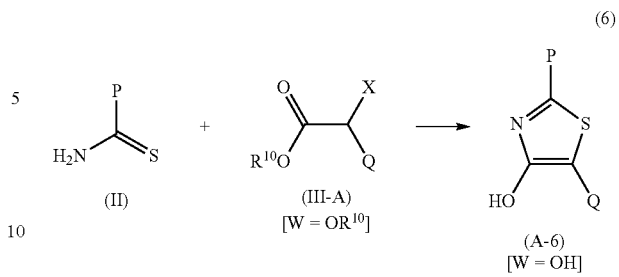

(II)  (III-A) [W = OR$^{10}$]  (A-6) [W = OH]  (6)

The reaction here can be performed under the conditions described for the formula 1. (A-6) [each symbol is as defined above] can be lead to (A-7) [W=OR$^{11}$ wherein R$^{11}$ is an optionally substituted alkyl group, and other symbols are each as defined above] by a reaction with R$^{11}$—X wherein X is as defined above, which is commercially available or can be produced by a generally known method, in the presence of a base (formula 7).

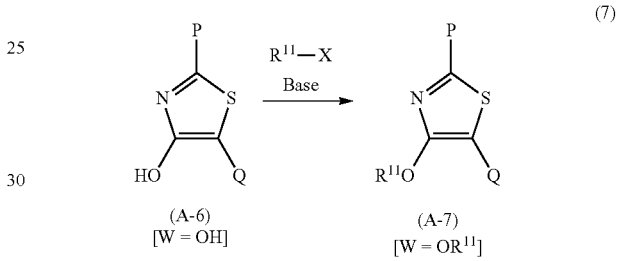

(A-6) [W = OH]  (A-7) [W = OR$^{11}$]  (7)

The reaction here is preferably performed in a solvent and using 1 to 10 equivalents, preferably 1 to 5 equivalents, of R$^{11}$—X [each symbol is as defined above] and 1 equivalent to 20 equivalents, preferably 1 to 10 equivalents, of a base, relative to (A-6) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. As the base for the aforementioned reaction, an inorganic base, an organic base and the like are used, and specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium tert-butoxide, sodium hydride, sodium amide, diazabicycloundecene (DBU) and the like are used.

(A-6) [each symbol is as defined above] can be converted to (A-8) [W=OTf, and other symbols are each as defined above] by reacting trifluoromethanesulfonic anhydride (Tf$_2$O) in the presence of a base (formula 8).

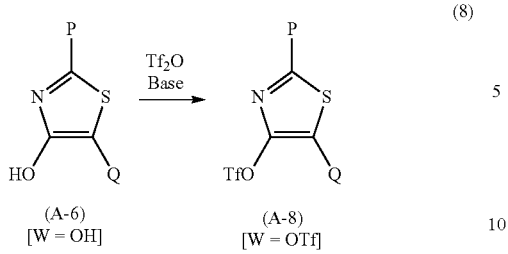

(A-6)  (A-8)
[W = OH]  [W = OTf]

The reaction here is preferably performed in a solvent and using 1 to 10 equivalents, preferably 1 to 5 equivalents, of trifluoromethanesulfonic anhydride ($Tf_2O$) and 1 equivalent to a solvent amount, preferably 1 to 10 equivalents, of a base as necessary, relative to (A-6) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. As the base for the aforementioned reaction, an organic base is generally used, and specifically, for example, triethylamine, N-ethyldiisopropylamine, pyridine, N,N-dimethylaminopyridine, diazabicycloundecene (DBU) and the like are used.

In addition, the obtained (A-8) [each symbol is as defined above] can be subjected to a generally known reaction to further convert a trifluoromethanesulfonyloxy group (OTf) to various functional groups.

For example, (A-3) [each symbol is as defined above] can be obtained by reacting (A-8) [each symbol is as defined above] with amine ($R^4R^{4'}NH$) [$R^4$ and $R^{4'}$ is as defined above], which is commercially available or can be produced by a generally known method (formula 9).

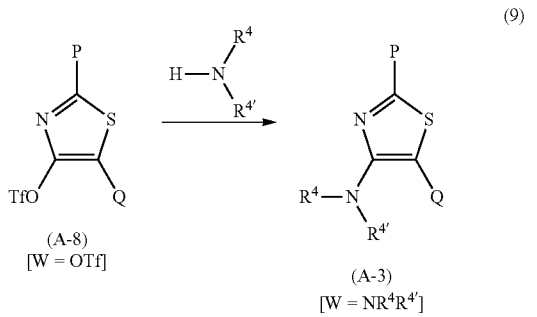

(A-8)  (A-3)
[W = OTf]  [W = $NR^4R^{4'}$]

The reaction here can be performed under the conditions described for the formula 3.

In addition, (A-4) [each symbol is as defined above] can be obtained by, for example, by reacting (A-8) [each symbol is as defined above] with an organic boronic acid reagent (IV) [$R^{6a}$—$B(OR^{7a})_2$: each symbol is as defined above], which is commercially available or can be produced by a generally known method, or an organic tin reagent (V) [$R^{6a}$—$SnR^8_3$: each symbol is as defined above], which is commercially available or can be produced by a generally known method, in the presence of a palladium catalyst (formula 10).

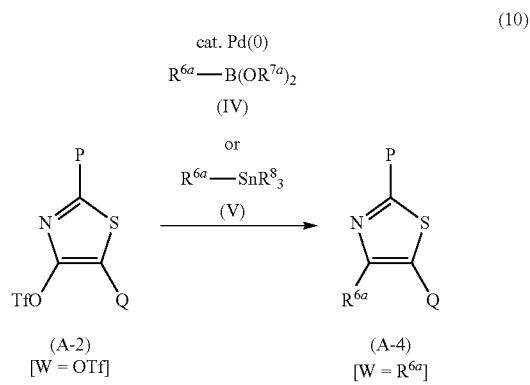

(A-2)  (A-4)
[W = OTf]  [W = $R^{6a}$]

The reaction here can be performed under the conditions described for the formula 4.

Moreover, (A-5) [each symbol is as defined above] can be obtained by reacting, for example, (A-8) [each symbol is as defined above] with thiol ($R^9SH$) [$R^9$ is as defined above], which is commercially available or can be produced by a generally known method, in the presence of a base (formula 11).

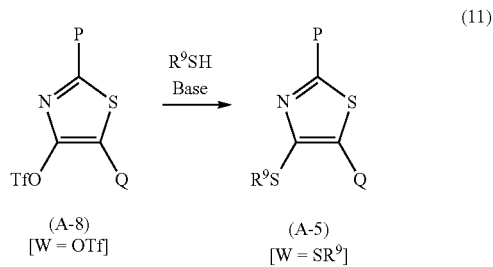

(A-8)  (A-5)
[W = OTf]  [W = $SR^9$]

The reaction here can be performed under the conditions described for the formula 5.

From (formula 12) to (formula 25) shown below is one example of a method of introducing $R^3$ into (I).

A compound wherein $R^3$ is a 4-pyrazolyl group can be produced by the method shown in (formula 12) and subsequent (formula 13).

That is, (A-9) [Q=H, and other symbols are each as defined above] can be converted to (A-10) [Q=X, and other symbols are each as defined above] by reaction with a generally known halogenating reagent such as bromine, N-bromosuccinimide, N-iodosuccinimide, N-chlorosuccinimide or sulfuryl chloride and the like (formula 12).

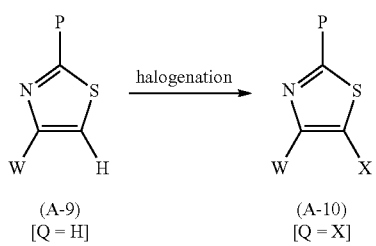

(A-9) [Q = H]   halogenation   (A-10) [Q = X]

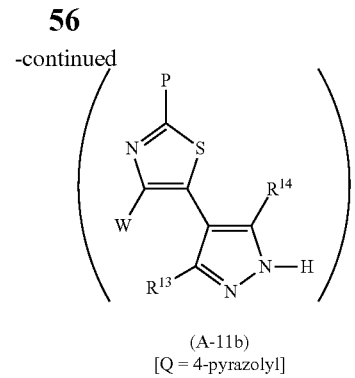

(A-11b) [Q = 4-pyrazolyl]

The reaction here can be performed under the conditions described for the formula 2.

Pyrazole derivative (A-11a) and/or (A-11b) [Q=4-pyrazolyl, and other symbols are each as defined above] can be obtained by reacting (A-10) [each symbol is as defined above] obtained by (formula 12) with an organic boronic acid reagent (VI) wherein $R^{12}$ is a hydrogen atom, or an alkyl group, an aryl group or a heterocyclic group, each of which is optionally substituted, or a known pyrazole-protecting group conventionally used such as Boc (tert-butoxycarbonyl), SEM (2-(trimethylsilyl)ethoxymethyl) and the like; and $R^{13}$ and $R^{14}$ are each a hydrogen atom, or an alkyl group, an aryl group or a heterocyclic group, each of which is optionally substituted or a cyano group], which is commercially available or can be produced by a generally known method, together with a base in the presence of a catalytic amount of a palladium complex (formula 14).

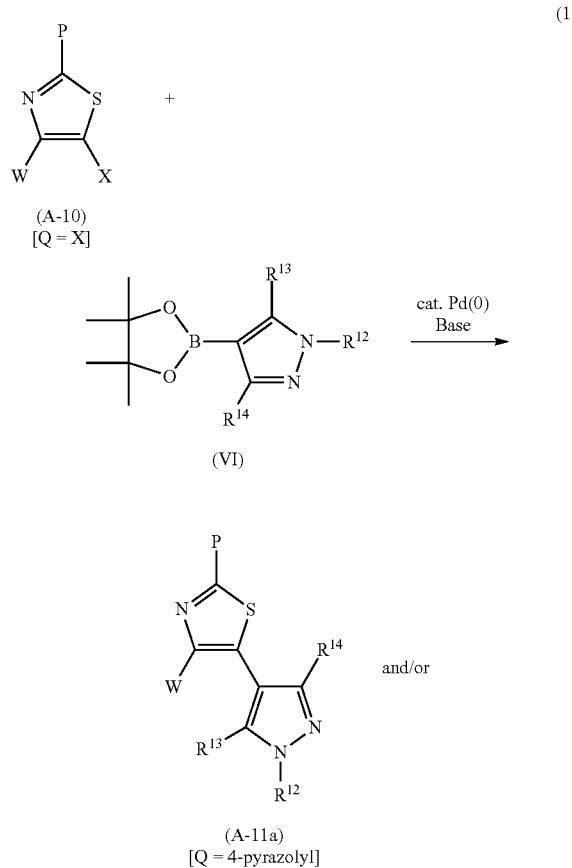

(A-11a) [Q = 4-pyrazolyl]

The reaction here is preferably performed in a solvent and using 1 to 10 equivalents, preferably 1 to 5 equivalents, of an organic boronic acid reagent (VI) [each symbol is as defined above], and 10 equivalents to a large excess, preferably 5 to 20 equivalents, of a base, relative to (A-10) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like are used. The aforementioned reaction is performed at room temperature or under heating (about 40 to 200° C., preferably about 40 to 160° C.), and the reaction time is generally about 1 to 30 hr, preferably about 1 to 20 hr, more preferably about 1 to 10 hr. As the base for the aforementioned reaction, an inorganic base, an organic base and the like are used, and specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium tert-butoxide, sodium hydride, sodium amide, diazabicycloundecene (DBU) and the like. As the palladium complex to be used as a catalyst, palladium acetate, palladium chloride, tris(dibenzylideneacetone)dipalladium(0) or [1,1'-bis(diphenylphosphino)ferrocene]dichloropalladium(II), dichlorobis(triphenylphosphine)palladium, tetrakis(triphenylphosphine)palladium and the like can be used. Where necessary, a phosphine ligand such as triphenylphosphine, 2,2'-bis(diphenylphosphino)-1,1'-binaphthyl (BINAP), dicyclohexyl(2',4',6'-triisopropylbiphenyl-2-yl)phosphine (X-Phos) or 1,1'-bis(diphenylphosphino)ferrocene (DPPF) and the like can also be added.

When $R^{12}$ of the organic boronic acid reagent (IV) is a hydrogen atom, (A-11a) and/or (A-11b) [$R^{12}$=H, and other symbols are each as defined above] can be obtained as resultant product(s), and (A-11a) and (A-11b) are tautomers to each other.

A compound wherein $R^3$ is a 4-(1,2,3-triazolyl) group can be produced by the method shown in (formula 14) and subsequent (formula 15).

That is, (A-12) [W=C:::$CR^{15}$, and other symbols are each as defined above] can be obtained by reacting (A-10) [each symbol is as defined above] obtained by (formula 12) with alkyne (VII) [H—C:::$CR^{15}$: wherein $R^{15}$ is a hydrogen atom, or an alkyl group, an aryl group or a heterocyclic group, each of which is optionally substituted, or a generally known alkyne-protecting group such as a trimethylsilyl group and the like], which is commercially available or can be produced by a generally known method, in the presence of a catalytic amount of a copper salt and a palladium complex, together with a base (formula 14),

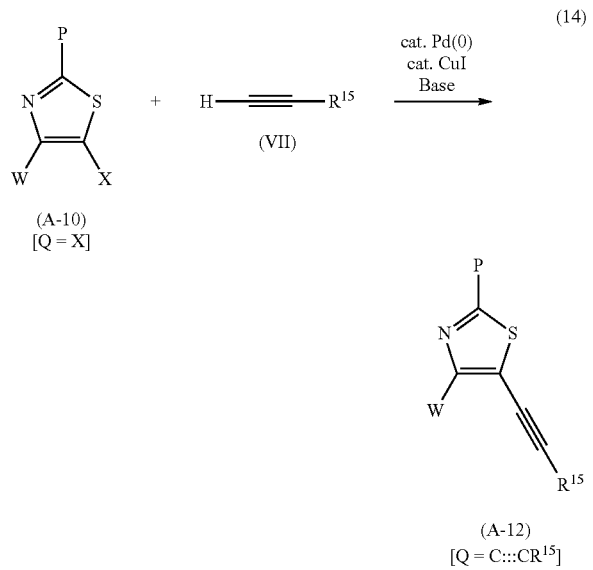

The reaction here is preferably performed in a solvent and using 1 to 10 equivalents, preferably 1 to 5 equivalents, of alkyne (VII) [each symbol is as defined above], and 1 equivalent to a large excess, preferably 5 to 20 equivalents, of a base, relative to (A-10) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction is performed at room temperature or under heating (about 40 to 200° C., preferably about 40 to 160° C.), and the reaction time is generally about 1 to 30 hr, preferably about 1 to 20 hr, more preferably about 1 to 10 hr. As the base for the aforementioned reaction, an organic base is generally used. Specifically, for example, triethylamine, N-ethyldiisopropylamine, pyridine, N,N-dimethylaminopyridine, 1,1,3,3-tetramethylguanidine, diazabicycloundecene (DBU) and the like are used. As the palladium complex to be used as a catalyst, palladium acetate, palladium chloride, tris(dibenzylideneacetone)dipalladium(0) or [1,1'-bis(diphenylphosphino)ferrocene]dichloropalladium(II), dichlorobis(triphenylphosphine)palladium, tetrakis(triphenylphosphine)palladium and the like can be used. Where necessary, a phosphine ligand such as triphenylphosphine, 2,2'-bis(diphenylphosphino)-1,1'-binaphthyl (BINAP), dicyclohexyl(2',4',6'-triisopropylbiphenyl-2-yl)phosphine (X-Phos) or 1,1'-bis(diphenylphosphino)ferrocene (DPPF) and the like can also be added. As the copper salt, copper iodide can be generally used.

(A-12) [each symbol is as defined above] obtained in (formula 14) can be led to 1,2,3-triazole derivative (A-13a) and/or (A-13b) and/or (A-13c) [Q=4-(1,2,3-triazolyl), and other symbols are each as defined above] by reaction with an azide compound [R16=N3: wherein R16 is an alkyl group, an aryl group or a heterocyclic group, each of which is optionally substituted, or a trimethylsilyl group or a sodium atom], which is commercially available or can be produced by a generally known method (formula 15).

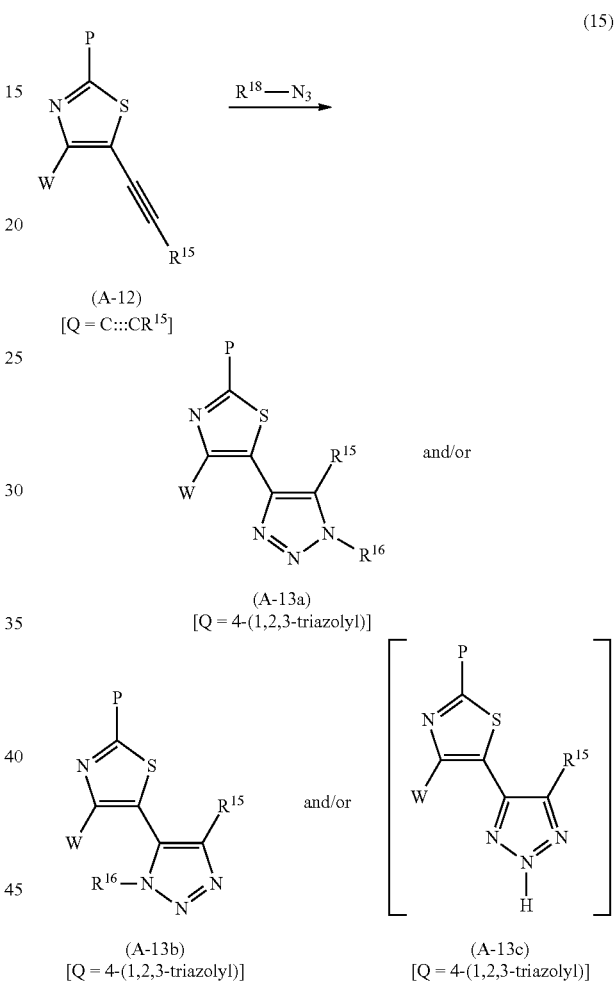

The reaction here is preferably performed in a solvent and using 1 to 10 equivalents, preferably 1 to 5 equivalents, of an azide compound [$R^{16}$—N3: wherein $R^{16}$ is as defined above], relative to (A-12) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction is performed at room temperature or under heating (about 40 to 200° C., preferably about 40 to 160° C.), and the reaction time is generally about 1 to 30 hr, preferably about 1 to 20 hr, more preferably about 1 to 10 hr. When azide compound ($R^{16}$—$N_3$) is sodium azide ($NaN_3$), 1 to 10 equivalents, preferably 1 to 5 equivalents, of ammonium chloride may be added relative to sodium azide ($NaN_3$) as necessary, to promote the reaction.

When the azide compound ($R^{16}$—$N_3$) is trimethylsilyl azide ($Me_3SiN_3$) or sodium azide ($NaN_3$), (A-13a) and/or (A-13b) and/or (A-13c) [$R^{16}$=H, and other symbols are each as defined above] are/is obtained as the resultant product(s), and (A-13a), (A-13b) and (A-13c) [$R^{16}$=H, and other symbols are each as defined above] are tautomers to each other.

A compound wherein $R^3$ is a 3-(1,2,4-triazolyl) group can be produced by the method shown in (formula 16) and subsequent (formula 17).

That is, (A-14) [Q=C(=O)O$R^{17}$ wherein $R^{17}$ is an alkyl group, an aryl group or a heterocyclic group, each of which is optionally substituted, and other symbols are each as defined above] obtained from (formula 1) can be led to (A-15) [Q=C(=O)NH$_2$, and other symbols are each as defined above] by generally known ester hydrolysis and subsequent amidation reaction (formula 16).

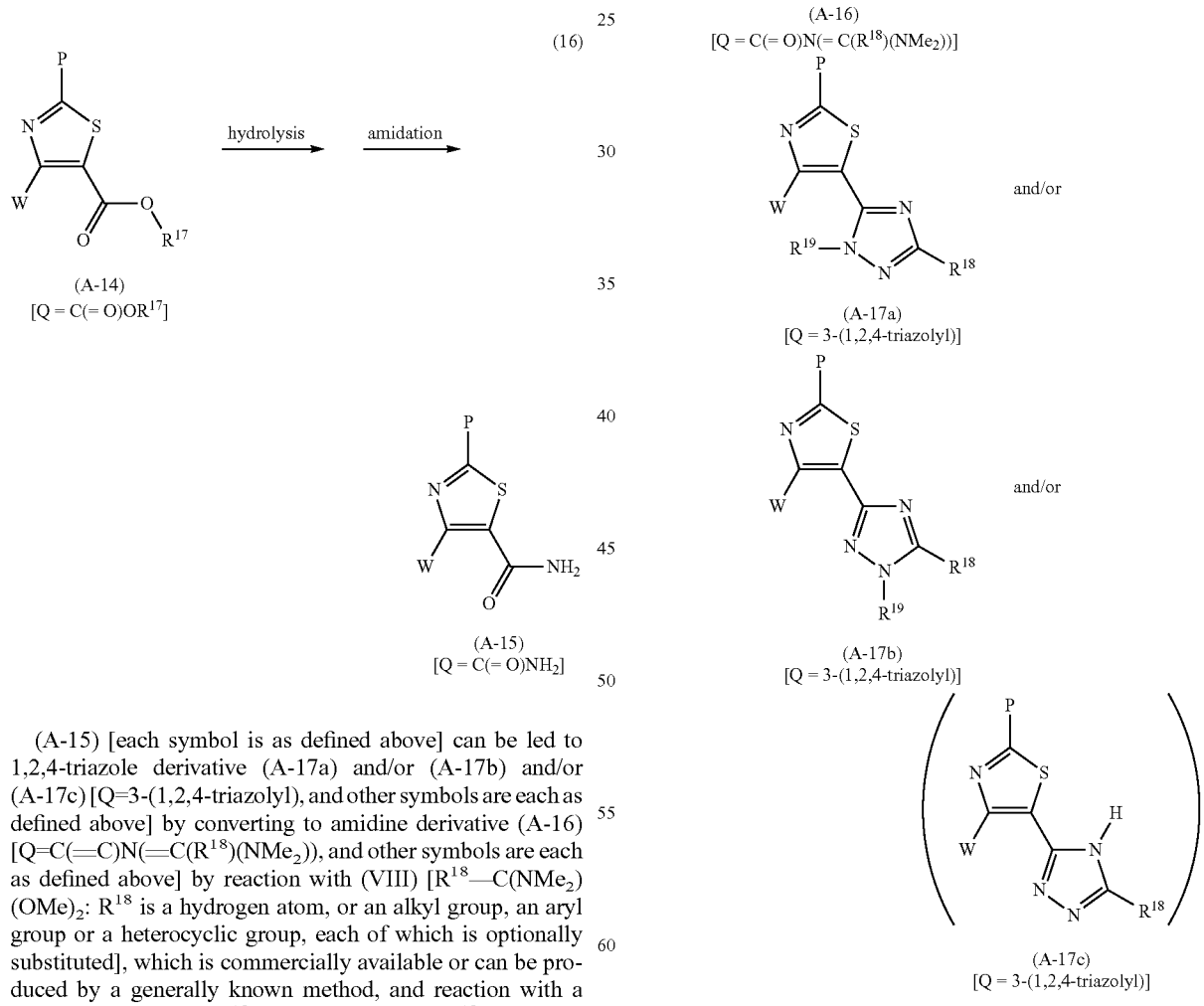

(A-15) [each symbol is as defined above] can be led to 1,2,4-triazole derivative (A-17a) and/or (A-17b) and/or (A-17c) [Q=3-(1,2,4-triazolyl), and other symbols are each as defined above] by converting to amidine derivative (A-16) [Q=C(=C)N(=C($R^{18}$)(NMe$_2$)), and other symbols are each as defined above] by reaction with (VIII) [$R^{18}$—C(NMe$_2$)(OMe)$_2$: $R^{18}$ is a hydrogen atom, or an alkyl group, an aryl group or a heterocyclic group, each of which is optionally substituted], which is commercially available or can be produced by a generally known method, and reaction with a hydrazine derivative [$R^{19}$—NHNH$_2$: wherein $R^{19}$ is a hydrogen atom, or an alkyl group, an aryl group or a heterocyclic group, each of which is optionally substituted], which is commercially available or can be produced by a generally known method (formula 17).

The reaction to produce (A-16) [each symbol is as defined above] in (formula 17) is preferably performed in a solvent as necessary and using 1 equivalent to a solvent amount, preferably 1 to 5 equivalents, of (VIII) [each symbol is as defined above] relative to (A-15) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr.

The reaction to produce (A-17a) and/or (A-17b) and/or (A-17c) [each symbol is as defined above] in (formula 17) is preferably performed in a solvent and using 1 equivalent to a large excess, preferably 1 to 10 equivalents, of a hydrazine derivative [$R^{19}$—NHNH$_2$: wherein $R^{19}$ is as defined above] relative to (A-16) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, acetic acid, water or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. When a hydrazine derivative [$R^{19}$—NHNH$_2$: wherein $R^{19}$ is as defined above] is used in the form of a hydrochloride, sodium acetate in an amount equivalent to the hydrazine derivative [$R^{19}$—NHNH$_2$: wherein $R^{19}$ is as defined above] can also be added as necessary.

When $R^{19}$ of the hydrazine derivative ($R^{19}$—NHNH$_2$) is a hydrogen atom, (A-17a) and/or (A-17b) and/or (A-17c) [$R^{19}$=H, and other symbols are each as defined above] are/is obtained as resultant product(s), and (A-17a), (A-17b) and (A-17c) [$R^{19}$=H, and other symbols are each as defined above] are tautomers to each other.

A compound wherein $R^3$ is a 5-tetrazolyl group can be produced by the method shown in (formula 18).

That is, (A-15) [each symbol is as defined above] obtained by (formula 16) can be converted to tetrazole derivative (A-19a) and/or (A-19b) [Q=5-tetrazolyl, and other symbols are each as defined above] by dehydration by a generally known method to lead to (A-18) [Q=CN] and reaction with an azide compound [$R^{16}$—N$_3$: wherein $R^{16}$ is as defined above], which is commercially available or can be produced by a generally known method (formula 18).

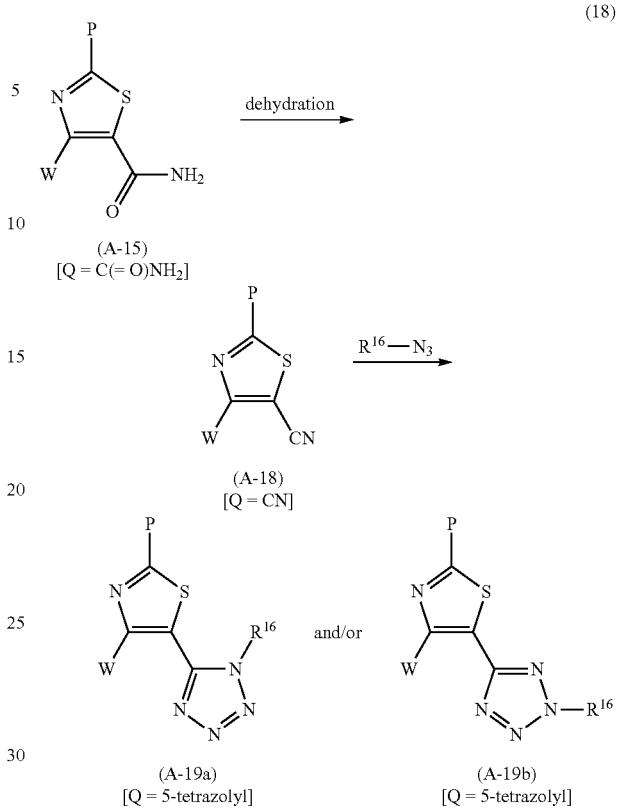

(18)

The reaction to produce (A-18) [each symbol is as defined above] in (formula 18) can be performed using 1 equivalent to a large excess, preferably 1 to 10 equivalents, of a dehydrating reagent such as phosphorus oxychloride or trifluoroacetic anhydride and the like, relative to (A-15) [each symbol is as defined above]. The reaction can also be performed without a solvent. When a solvent is used, halogenated hydrocarbons such as dichloromethane, chloroform, carbon tetrachloride, 1,2-dichloroethane and the like, aromatic hydrocarbons such as benzene, toluene, xylene and the like, ethers such as diethyl ether, tetrahydrofuran, dioxane and the like, acetonitrile, ethyl acetate, or a mixed solvent thereof and the like are used. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. The reaction is accelerated as necessary by adding a base. As the base, an organic base, and the like are generally used, and specifically, for example, triethylamine, N-ethyldiisopropylamine, pyridine, N,N-dimethylaminopyridine, diazabicycloundecene (DBU) and the like are used.

The reaction to produce (A-19a) and/or (A-19b) [each symbol is as defined above] in (formula 18) is preferably performed in a solvent and using 1 to 10 equivalents, preferably 1 to 5 equivalents, of an azide compound [$R^{16}$—N3: wherein $R^{16}$ is as defined above], relative to (A-18) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction is performed at room temperature or under heating (about 40 to 200° C., preferably about 40 to 160° C.), and the reaction time is generally about 1 to 30 hr, preferably about 1 to 20 hr, more preferably about 1 to 10 hr. When the azide compound ($R^{16}$—$N_3$) is sodium azide ($NaN_3$), 1 to 10 equivalents, preferably 1 to 5 equivalents, of ammonium chloride or tributyltin chloride, relative to sodium azide ($NaN_3$), can also be added as necessary to promote the reaction.

When the azide compound ($R^{16}$—$N_3$) is trimethylsilyl azide ($Me_3SiN_3$) or sodium azide ($NaN_3$), (A-19a) and/or (A-19b) [$R^{16}$=H, and other symbols are each as defined above] are/is obtained as resultant product(s), and (A-19a) and (A-19b) [$R^{16}$=H, and other symbols are each as defined above] are tautomers to each other.

A compound wherein $R^3$ is a 4-imidazolyl group can be produced by the method shown in (formula 19).

(A-18) [each symbol is as defined above] obtained by (formula 18) can be converted to (A-20a) and/or (A-20b) [Q=4-imidazolyl, and other symbols are each as defined above] by reaction with isonitrile derivative (IX) [$R^{20}$—$CH_2N+:::C$—: wherein $R^{20}$ is a hydrogen atom, or an alkyl group, an aryl group or a heterocyclic group, each of which is optionally substituted, an ester group, a cyano group, a nitro group or a trimethylsilyl group], which is commercially available or can be produced by a generally known method, in the presence of a base.

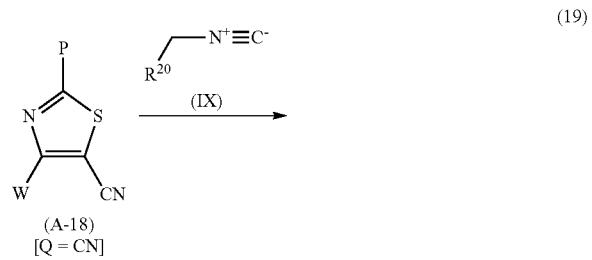

The reaction here is preferably performed in a solvent and using 1 to 10 equivalents, preferably 1 to 5 equivalents, of isonitrile derivative (IX) [$R^{20}$—$CH_2N+:::C$—: wherein $R^{20}$ is as defined above], and 1 equivalent to 10 equivalents, preferably 1 to 5 equivalents, of a base, relative to (A-18) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction is performed at room temperature or under heating (about 40 to 200° C., preferably about 40 to 160° C.), and the reaction time is generally about 1 to 30 hr, preferably about 1 to 20 hr, more preferably about 1 to 10 hr. As the base for the aforementioned reaction, an inorganic base, an organic base and the like are used, and specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium tert-butoxide, sodium hydride, sodium amide, diazabicycloundecene (DBU) and the like are used.

(A-20a) and (A-20b) [other symbols are each as defined above] produced by (formula 19) are tautomers to each other.

A compound wherein $R^3$ is a 2-(1,3-thiazolyl) group can be produced by the method shown in (formula 20).

That is, (A-15) [each symbol is as defined above] produced by (formula 16) is converted to thioamide derivative (A-21) [Q=(C=S)$NH_2$, and other symbols are each as defined above] by a generally known method using Lawesson's reagent and the like, and reacted with α-halocarbonyl compound (X) wherein each $R^{21}$ is a hydrogen atom, or an alkyl group, an aryl group or a heterocyclic group, each of which is optionally substituted, or an ester group, each $R^{22}$ is a hydrogen atom, or an alkyl group, an aryl group or a heterocyclic group, each of which is optionally substituted, an ester group, a nitro group or a cyano group], which is commercially available or can be produced by a generally known method, or a ketal- or acetal-protected compound thereof, whereby (A-15) is led to thiazole derivative (A-22) [Q=2-(1,3-thiazolyl), and other symbols are each as defined above] (formula 20).

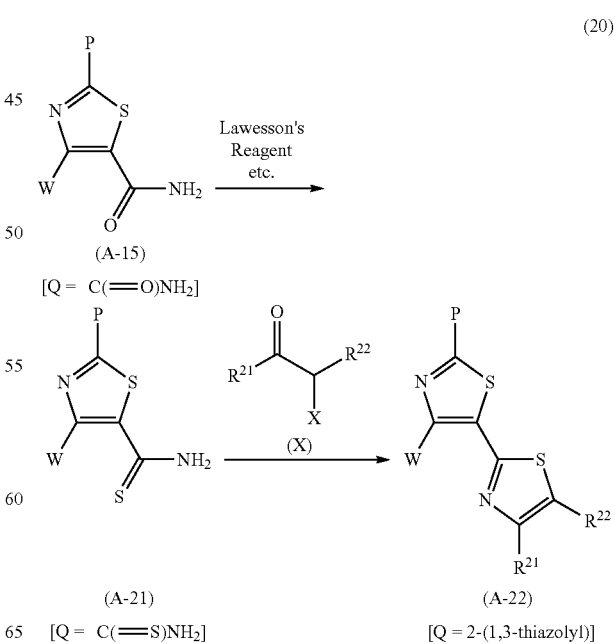

The reaction to produce (A-21) [each symbol is as defined above] in (formula 20) is preferably performed in a solvent and using 1 equivalent to a large excess, preferably 1 to 10 equivalents, of a thionation reagent such as Lawesson's reagent or diphosphorus pentasulfide and the like, relative to (A-15) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, ethers such as diethyl ether, tetrahydrofuran, dioxane and the like, acetonitrile, ethyl acetate, or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. A base can be added as necessary to the reaction. As the base, an organic base and the like are generally used. Specifically, for example, triethylamine, N-ethyldiisopropylamine, pyridine, N,N-dimethylaminopyridine, diazabicycloundecene (DBU) and the like are used.

(A-22) [each symbol is as defined above] in (formula 20) can be obtained by reacting (A-21) [each symbol is as defined above] with (X) [wherein $R^{21}$ and $R^{22}$ are as defined above] under the conditions of (formula 1). When a ketal or acetal-protected compound of α-halocarbonyl compound (X) is used, the reaction can be performed under acidic conditions with hydrochloric acid or aqueous acetic acid and the like.

A compound wherein $R^3$ is a 2-imidazolyl group can be produced by the method shown in (formula 21).

That is, the thioamide derivative (A-21) [each symbol is as defined above] obtained by (formula 20) is reacted with methyl iodide for conversion to imidothioate derivative (A-23) [Q=C(=NH)SMe], and reacted with amine (XI) [$R^{23}$—NHCH($R^{24}$)C($R^{25}$)(OMe)$_2$: wherein $R^{23}$ is a hydrogen atom, or an alkyl group, an aryl group or a heterocyclic group, each of which is optionally substituted, and $R^{24}$ and $R^{25}$ are each a hydrogen atom, or an alkyl group, an aryl group or a heterocyclic group, each of which is optionally substituted, or an ester group], which is commercially available or can be produced by a generally known method, whereby (A-21) can be led to (A-25a) and/or (A-25b) [Q=2-imidazolyl, and other symbols are each as defined above] via amidine derivative (A-24) [Q=C(=NH)NR$^{23}$CH(R$^{24}$)C(R$^{25}$)(OMe)$_2$, and other symbols are each as defined above] (formula 21).

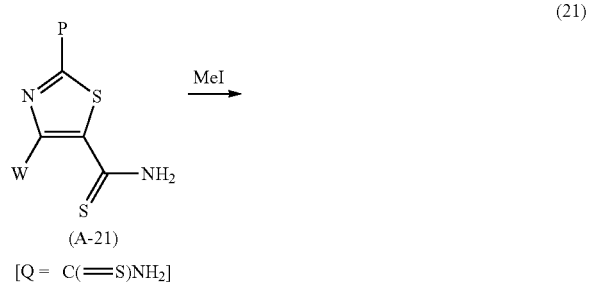

(21)

(A-21)

[Q = C(=S)NH$_2$]

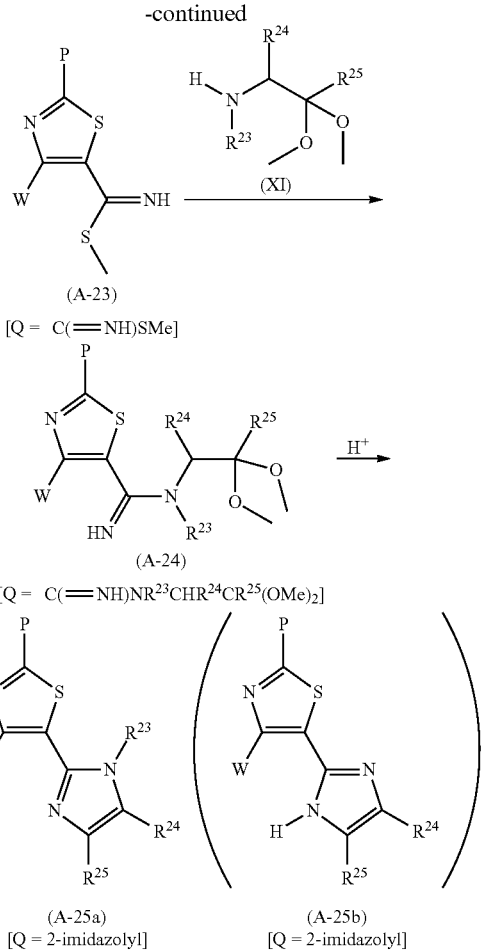

(A-23)

[Q = C(=NH)SMe]

(A-24)

[Q = C(=NH)NR$^{23}$CHR$^{24}$CR$^{25}$(OMe)$_2$]

(A-25a)          (A-25b)
[Q = 2-imidazolyl]   [Q = 2-imidazolyl]

The reaction to produce (A-23) [each symbol is as defined above] in (formula 21) is preferably performed in a solvent and using 1 to 10 equivalents, preferably 1 to 5 equivalents, of methyl iodide, relative to (A-21) [each symbol is as defined above]. Where necessary, a base may be added. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, ethers such as diethyl ether, tetrahydrofuran, dioxane and the like, acetonitrile, ethyl acetate, or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. As the base, an inorganic base and the like are generally used. Specifically, for example, sodium hydroxide, potassium hydroxide, sodium carbonate, potassium carbonate, cesium carbonate, sodium hydrogen carbonate, potassium hydrogen carbonate and the like are used.

The reaction to produce amidine derivative (A-24) [each symbol is as defined above] in (formula 21) is preferably performed in a solvent and using 1 equivalent to a large excess, preferably 1 to 5 equivalents, of amine (XI) [each symbol is as defined above], relative to (A-23) [each symbol is as defined above]. Where necessary, 1 equivalent to a large excess, preferably 1 to 5 equivalents, of a base or acid can also be added. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. As the base to be used for the reaction, an inorganic base, an organic base and the like are used, and specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium tert-butoxide, sodium hydride, sodium amide, diazabicycloundecene (DBU) and the like are used. The acid added as necessary is acetic acid and the like.

The reaction to produce (A-25a) and/or (A-25b) [each symbol is as defined above] in (formula 21) is achieved by reacting amidine derivative (A-24) [each symbol is as defined above] with an acid in a solvent in the presence of water. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. As the acid to be used for the aforementioned reaction, hydrochloric acid, sulfuric acid, acetic acid, trifluoroacetic acid and the like are used. When $R^{23}$ is a hydrogen atom, (A-25a) [$R^{23}$=H, and other symbols are each as defined above] and/or (A-25b) [other symbols are each as defined above] are/is obtained as resultant product(s), and (A-25a) [$R^{23}$=H, and other symbols are each as defined above] and (A-25b) [other symbols are each as defined above] are tautomers to each other.

A compound wherein $R^3$ is a 4-imidazolyl group can also be produced by the method shown in (formula 22) and subsequent (formula 23).

That is, (A-14) [each symbol is as defined above] obtained by (formula 1) can be led to ketone derivative (A-27) [Q=C(=O)CH$_2$R$^{26}$, and other symbols are each as defined above] by generally known hydrolysis of ester group, then an amidation reaction to give Weinreb amide (A-26) [Q=C(=O)NMeOMe, and other symbols are each as defined above] and reaction with an organic metal reagent such as an alkyllithium reagent [$R^{26}$CH$_2$Li: wherein $R^{26}$ is a hydrogen atom, or an alkyl group, an aryl group or a heterocyclic group, each of which is optionally substituted], or Grignard reagent [$R^{26}$CH$_2$MgX: wherein $R^{26}$ and X is as defined above] which is commercially available or can be produced by a generally known method, and the like (formula 22).

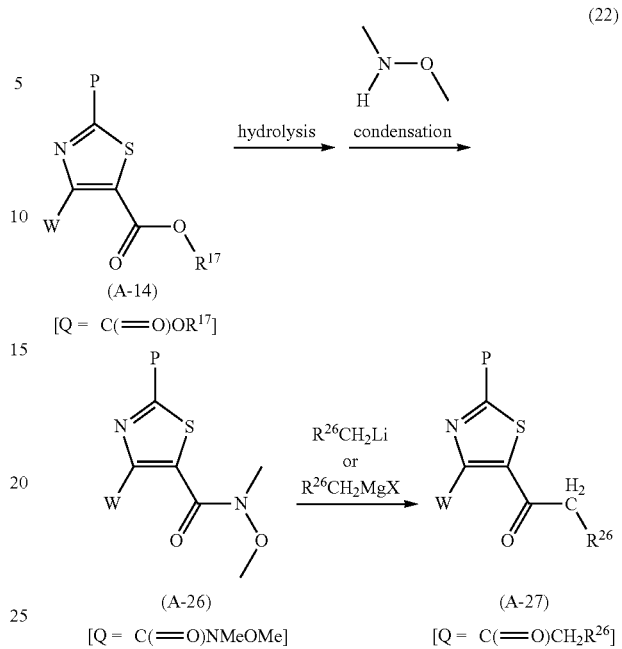

(A-27) [each symbol is as defined above] obtained by (formula 22) can be led to (A-29a) and/or (A-29b) [Q=4-imidazolyl, and other symbols are each as defined above] by a generally known bromination reaction using N-bromosuccinimide and the like to give (A-28) [Q=C(=O)CHBrR$^{26}$, and other symbols are each as defined above], and reacting (A-28) with an amidine reagent (XII) [$R^{27}$—C(=NR$^{28}$)NH$_2$: wherein $R^{27}$ and $R^{28}$ are each a hydrogen atom, or an alkyl group, an aryl group or a heterocyclic group, each of which is optionally substituted], which is commercially available or can be produced by a generally known method (formula 23).

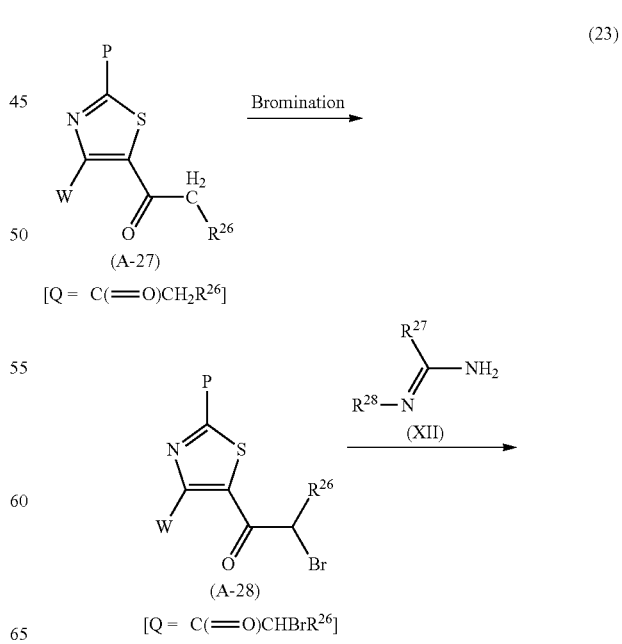

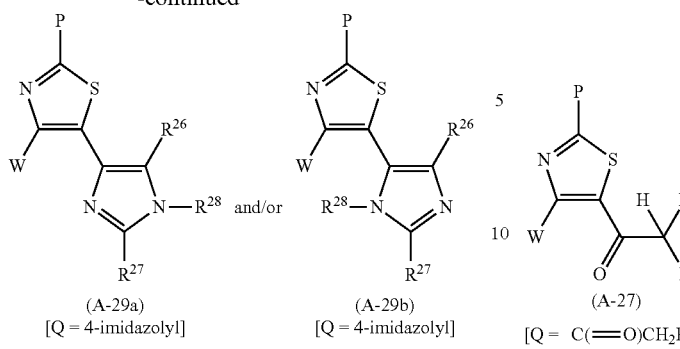

(A-29a) [Q = 4-imidazolyl]  (A-29b) [Q = 4-imidazolyl]  (A-27) [Q = C(=O)CH$_2$R$^{26}$]

Production of (A-28) [each symbol is as defined above] by the bromination reaction in (formula 23) can be performed under the conditions of (formula 2) and using bromine or N-bromosuccinimide as a brominating agent.

The reaction to produce (A-29a) and/or (A-29b) [each symbol is as defined above] in (formula 23) is preferably performed in a solvent and using 1 to 10 equivalents, preferably 1 to 5 equivalents, of amidine reagent (XII) [each symbol is as defined above], relative to (A-28) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. Where necessary, a base may be added. As the base, an inorganic base, an organic base and the like are used, and specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium tert-butoxide, sodium hydride, sodium amide, diazabicycloundecene (DBU) and the like are used.

When R$^{28}$ is a hydrogen atom, (A-29a) and (A-29b) [R$^{28}$=H, and other symbols are each as defined above] are obtained as resultant products, and they are tautomers to each other.

A compound wherein R$^3$ is a 3-pyrazolyl group can also be produced by the method shown in (formula 24).

That is, (A-27) [each symbol is as defined above] obtained by (formula 22) can be led to (A-31a) and/or (A-31b) [Q=3-pyrazolyl, and other symbols are each as defined above] by reaction with (VIII) [R$^{18}$—C(NMe$_2$)(OMe)$_2$: each symbol is as defined above] to give (A-30) [Q=C(=O)CR$^{26}$(=C(R$^{18}$)(NMe$_2$))] and each symbol is as defined above] and reacting (A-30) with a hydrazine derivative [R$^{19}$—NHNH$^2$: each symbol is as defined above] (formula 24).

(24)

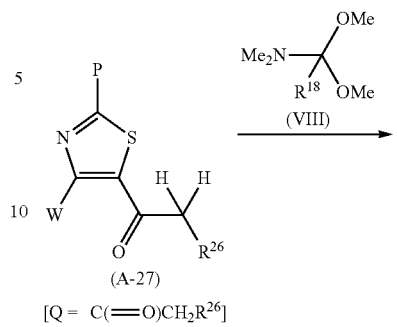

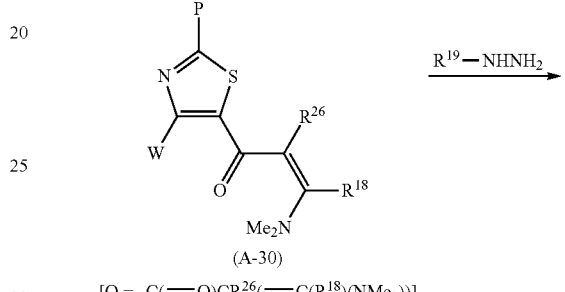

(A-30) [Q = C(=O)CR$^{26}$(=C(R$^{18}$)(NMe$_2$))]

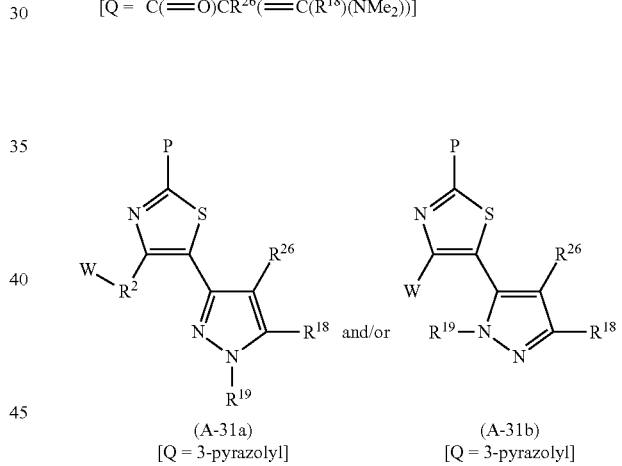

(A-31a) [Q = 3-pyrazolyl]  (A-31b) [Q = 3-pyrazolyl]

Conversion of (A-27) [each symbol is as defined above] to (A-30) [each symbol is as defined above] and conversion of (A-30) [each symbol is as defined above] to (A-31a) and/or (A-31b) [each symbol is as defined above] in (formula 24) can be performed under the conditions of (formula 17).

A compound wherein R$^3$ is a 2-(1,3,4-thiadiazolyl) group can also be produced by the method shown in (formula 25).

That is, (A-14) [each symbol is as defined above] can be led to 1,3,4-thiadiazole derivative (A-33) [Q=2-(1,3,4-thiadiazolyl), and other symbols are each as defined above] by generally known ester hydrolysis to give a carboxylic acid derivative, condensation with acyl hydrazide (XIII) [R$^{29}$—C(=O)NHNH$_2$: wherein R$^{29}$ is a hydrogen atom, or an alkyl group, an aryl group or a heterocyclic group, each of which is optionally substituted], which is commercially available or can be produced by a generally known method, to give (A-32) [Q=C(=O)NHNHC(=O)R$^{29}$, and other symbols are each as defined above] and reaction with Lawesson's reagent and the like (formula 25).

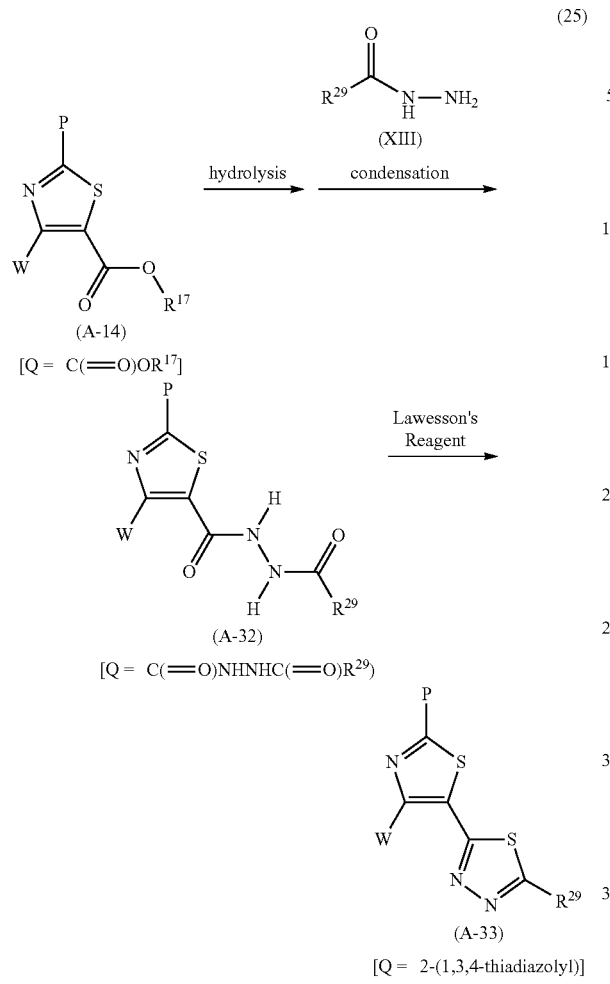

(25)

(A-14)   [Q = C(=O)OR¹⁷]

(A-32)   [Q = C(=O)NHNHC(=O)R²⁹]

(A-33)   [Q = 2-(1,3,4-thiadiazolyl)]

The conversion reaction of (A-14) [each symbol is as defined above] to (A-32) [each symbol is as defined above] in (formula 25) can be performed under the conditions of generally known ester hydrolysis and amidation reaction of carboxylic acid.

The conversion reaction of (A-32) [each symbol is as defined above] to 1,3,4-thiadiazole derivative (A-33) [each symbol is as defined above] in (formula 25) can be performed under the conditions of the conversion reaction of (A-15) [each symbol is as defined above] to (A-21) [each symbol is as defined above] in (formula 20).

The thioamide derivative (II) [P is as defined above], a starting material, can be obtained according to a generally known method by converting carboxylic acid (B) [P is as defined above] to amide derivative (C) [P is as defined above] and reacting the amide derivative with Lawesson's reagent or diphosphorus pentasulfide (formula 26).

(26)

In (formula 26), carboxylic acid (B) [P is as defined above] can be converted to amide (C) [P is as defined above] under the conditions of generally known amidation reaction. The conversion of amide derivative (C) [P is as defined above] to thioamide derivative (H) [P is as defined above] in (formula 26) can be performed under the conditions of the conversion reaction of (A-15) [each symbol is as defined above] to (A-21) [each symbol is as defined above] in (formula 20).

In addition, thioamide derivative (H) [P is as defined above] can also be produced according to a generally known method by reacting nitrite compound (D) [P is as defined above] that can be produced from carboxylic acid derivative (B) [P is as defined above] with ammonium sulfide or O,O'-diethyl dithiophosphate and the like (formula 27).

(27)

In (formula 27), conversion of carboxylic acid derivative (B) to nitrile compound (D) can be easily achieved under generally known reaction conditions.

In (formula 27), conversion of nitrile compound (D) [P is as defined above] to thioamide derivative (II) [P is as defined above] using ammonium sulfide is preferably performed in a solvent and using 1 to 20 equivalents, preferably 1 to 10 equivalents, of ammonium sulfide, relative to nitrile compound (D) [P is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr.

In (formula 27), conversion of nitrite compound (D) [P is as defined above] to thioamide derivative (II) [P is as defined above] using O,O'-diethyl dithiophosphate is preferably performed in a solvent and using 1 equivalent to a large excess, preferably 1 to 10 equivalents, of O,O'-diethyl dithiophosphate, relative to nitrile compound (D) [P is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. Where necessary, a base or acid can be added for the reaction. As the base, an organic base is general used. Specifically, for example, triethylamine, N-ethyldiisopropylamine, pyridine, N,N-dimethylaminopyridine, diazabicycloundecene (DBU) and the like are used. As the acid, hydrogen chloride and the like are generally used.

The α-halocarbonyl compound (III) [each symbol is as defined above], a starting material, can be produced by generally known halogenation of ketone (E) [each symbol is as defined above], which is a commercially available compound or can be produced by a generally known method, with N-chlorosuccinimide or sulfuryl chloride or N-bromosuccinimide and the like (formula 28).

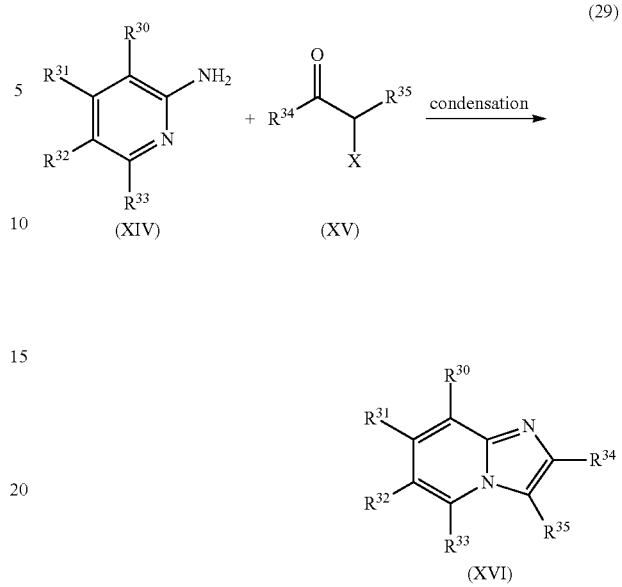

(29)

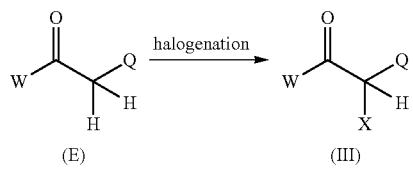

(28)

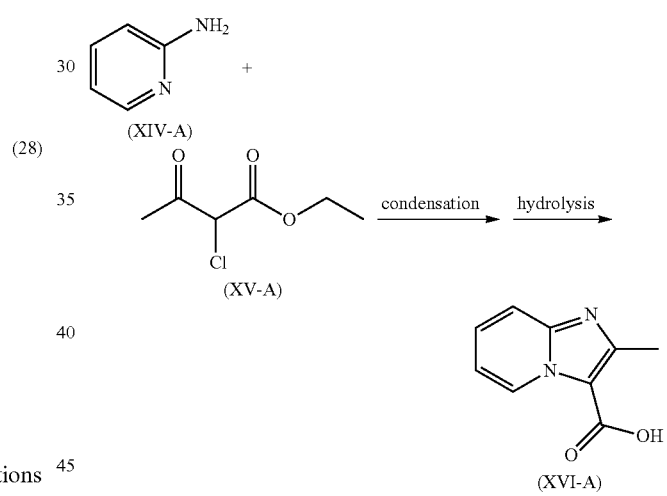

The reaction here can be performed under the conditions described for the formula 2.

The imidazo[1,2-a]pyridine skeleton (XVI) for $R^1$ can be constructed, for example, by condensation of 2-aminopyridine derivative (XIV) [$R^{30}$, $R^{31}$, $R^{32}$ and $R^{33}$ are each an optional substituent] wherein pyridine ring is optionally substituted and α-halo-keto compound (XV) [$R^{34}C(=O)$ CHXR$^{35}$:R$^{34}$ is a hydrogen atom, or an alkyl group, an aryl group or a heterocyclic group, each of which is optionally substituted, $R^{35}$ is a hydrogen atom, or an alkyl group, an aryl group or a heterocyclic group, each of which is optionally substituted, a cyano group, a nitro group or an alkoxycarbonyl group, and other symbols are each as defined above].

For example, commercially available 2-aminopyridine (XIV-A) is condensed with commercially available ethyl 2-chloro-3-oxobutanoate (XV-A), and subjected to generally known ester hydrolysis to give 2-methyl imidazo[1,2-a]pyridine-3-carboxylic acid (XVI-A) (formula 29). The carboxylic acid (XVI-A) can be led to thioamide derivative (II) according to a generally known method described in (formula 26) or (formula 27).

The condensation reaction of (XIV) [each symbol is as defined above] and (XV) [each symbol is as defined above] in (formula 29) is preferably performed in a solvent and using 1 to 10 equivalents, preferably 1 to 5 equivalents, of (XV) [each symbol is as defined above], relative to (XIV) [each symbol is as defined above]. As the reaction conditions, those described in (formula 1) can be applied.

The imidazo[1,2-b]pyridazine skeleton (XVIII) for $R^1$ can be constructed by condensation of, for example, 3-aminopyridazine derivative (XVII) [$R^{36}$, $R^{37}$ and $R^{38}$ are each an optional substituent] and x-halo-keto compound (XV) [each symbol is as defined above].

For example, commercially available 6-chloropyridazin-3-amine (XVII-A) is condensed with commercially available ethyl 2-chloro-3-oxobutanoate (XV-A), and subjected to generally known ester hydrolysis to give 2-methyl imidazo[1,2-b]pyridazine-3-carboxylic acid (XVIII-A) (formula 30). The carboxylic acid (XVIII-A) can be led to thioamide derivative (II) according to the generally known method described in (formula 26) or (formula 27).

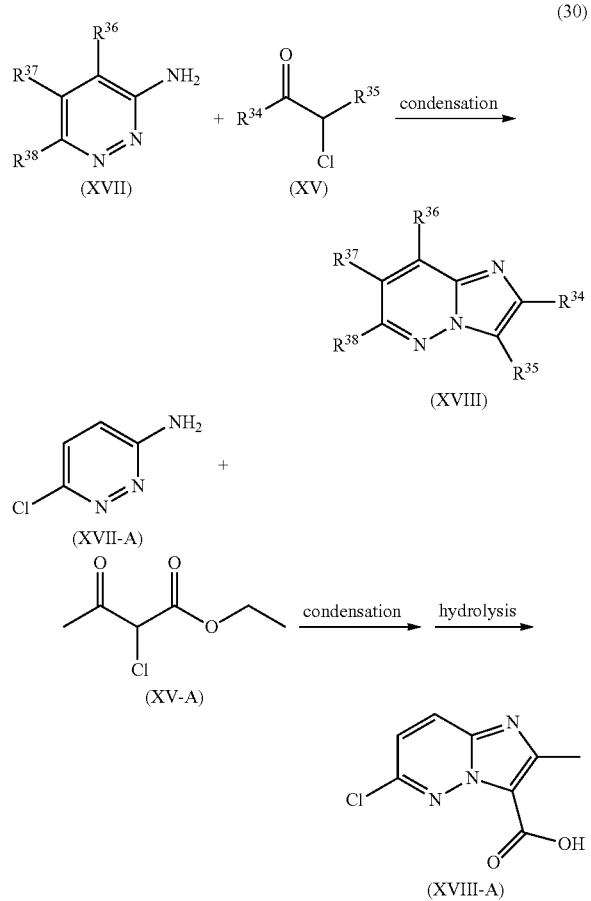

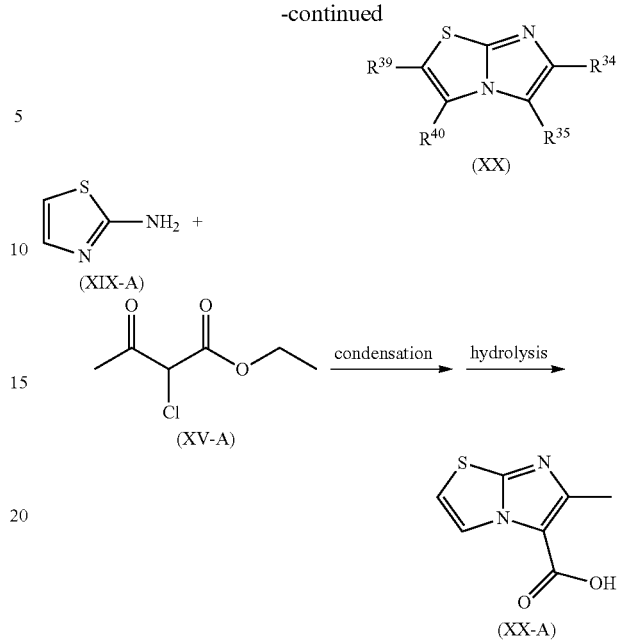

The condensation reaction of (XVII) [each symbol is as defined above] and (XV) [each symbol is as defined above] in (formula 30) is preferably performed in a solvent and using 1 to 10 equivalents, preferably 1 to 5 equivalents, of (XV) [each symbol is as defined above] relative to (XVII) [each symbol is as defined above]. The reaction can be performed under the conditions described for the formula 1.

The imidazo[2,1-b][1,3]thiazole skeleton (XX) for R1 can be constructed, for example, by condensation of 2-aminothiazole derivative (XIX) [R39 and R40 are each an optional substituent] and α-halo-keto compound (XV) [each symbol is as defined above].

For example, 6-methylimidazo[2,1-b][1,3]thiazole-5-carboxylic acid (XX-A) can be produced by condensation of commercially available 2-aminothiazole (XIX-A) and commercially available ethyl 2-chloro-3-oxobutanoate (XV-A), and subjecting to generally known ester hydrolysis (formula 31). The carboxylic acid (XX-A) can be led to thioamide derivative (II) according to the generally known method described in (formula 26) or (formula 27).

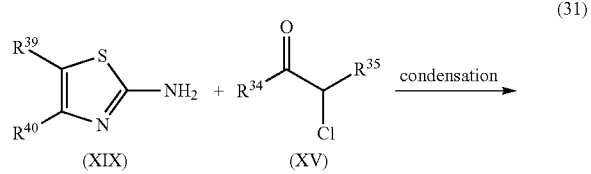

The condensation reaction of (XIX) [each symbol is as defined above] and (XV) [each symbol is as defined above] in (formula 31) is preferably performed in a solvent and using I to 10 equivalents, preferably 1 to 5 equivalents, of (XV) [each symbol is as defined above], relative to (XIX) [each symbol is as defined above]. The reaction can be performed under the conditions described for the formula 1.

The pyrazolo[1,5-a]pyridine skeleton (XXVI) for $R^1$ can be produced by the following method.

The pyrazolo[1,5-a]pyridine skeleton (XXVI-a) can be constructed by reacting pyridine derivative (XXI) [$R^{41}$, $R^{42}$, $R^{43}$ and $R^{44}$ are each an optional substituent] with a generally known aminating reagent (XXII) to give 1-aminopyridinium salt (XXIII) [Y— is a halogen ion or a sulfonate ion, and other symbols are each as defined above] and reacting the obtained salt with alkyne derivative (XXIV) [$R^{45}C:::R^{46}$; $R^{45}$ is a hydrogen atom, or an alkyl group, an aryl group or a heterocyclic group, each of which is optionally substituted, and $R^{46}$ is an aryl group or a heterocyclic group, each of which is optionally substituted, a cyano group or an alkoxycarbonyl group].

In addition, pyrazolo[1,5-a]pyridine skeleton (XXVI-b) can also be constructed by a condensation reaction of 1-aminopyridinium salt (XXIII) and ketone derivative (XXV) [$R^{48}CH_2C(=O)R^{47}$; $R^{47}$ is a hydrogen atom, or an alkyl group, an aryl group or a heterocyclic group, each of which is optionally substituted, and $R^{48}$ is a hydrogen atom, or an alkyl group, an aryl group or a heterocyclic group, each of which is optionally substituted, a cyano group, a nitro group or an alkoxycarbonyl group].

For example, 2-methylpyrazolo[1,5-a]pyridine-3-carboxylic acid (XXVI-A) can be produced by reacting 4-(benzyloxy)pyridine (XXI-A) which can be produced by a generally known method with 2-[(aminooxy)sulfonyl]-1,3,5-trimethylbenzene (XXII-A) which can be produced by a generally known method to give 1-amino-4-(benzyloxy)pyridinium 2,4,6-trimethylbenzenesulfonate (XXIII-A), condensing the obtained compound with ethyl 2-butynoate (XXIV-A), and subjecting the condensate to a generally known hydrolysis (formula 32). The carboxylic acid (XXVI- A) can be led to thioamide derivative (II) according to the generally known method described in (formula 26) or (formula 27).

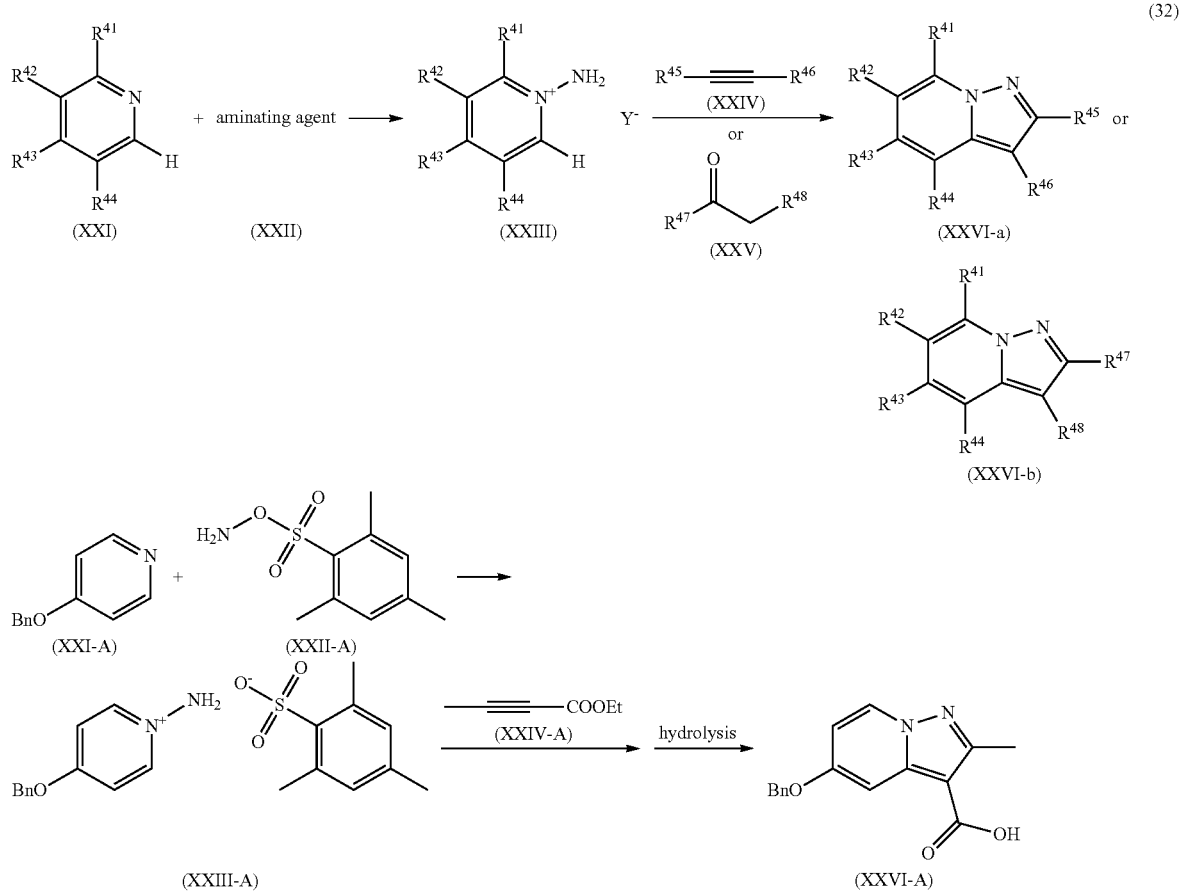

The amination reaction of pyridine (XXI) [each symbol is as defined above] in (formula 32) is preferably performed in a solvent and using 0.1 to 10 equivalents, preferably 1 equivalent, of 2-[(aminooxy)sulfonyl]-1,3,5-trimethylbenzene (XXII-A), which can be produced by a generally known method, relative to pyridine (XXI) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr.

The condensation cyclization reaction of 1-aminopyridinium salt (XXIII) [each symbol is as defined above] and alkyne derivative (XXIV) [each symbol is as defined above] in (formula 32) is preferably performed in a solvent and using 0.1 to 10 equivalents, preferably 1 to 5 equivalents, of alkyne derivative (XXIV) [each symbol is as defined above], relative to 1-aminopyridinium salt (XXIII) [each symbol is as defined above]. Examples of the solvent for the above-mentioned reaction include halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr. Where necessary, a base may be added. As the base, an inorganic base, an organic base and the like are used, and specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium tert-butoxide, sodium hydride, sodium amide, diazabicycloundecene (DBU) and the like are used.

The 4,5,6,7-tetrahydropyrazolo[1,5-a]pyridine skeleton (XXVII) [each symbol is as defined above] for $R^1$ can be obtained by catalytic hydrogenation of pyrazolo[1,5-a]pyridine derivative (XXVI) [each symbol is as defined above] produced above by a generally known technique (formula 33).

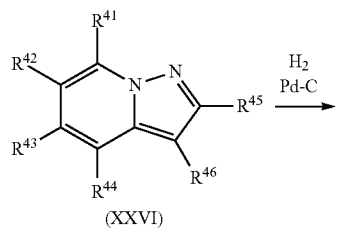
(XXVI)

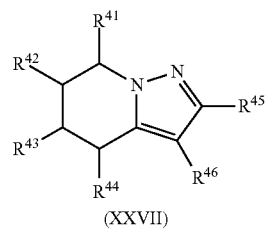
(XXVII)

The above-mentioned reaction can be easily performed under the conditions of generally known catalytic hydrogenation reaction.

The pyrazolo[5,1-b][1,3]thiazole skeleton (XXX) for $R^1$ can be constructed by, for example, reacting 2-methylthiazole derivative (XXVIII) [$R^{49}$ and $R^{50}$ are each an optional substituent] with a generally known aminating reagent (XXII) to give 3-amino-1,3-thiazol-3-ium salt (XXIX) [each symbol is as defined above], and reacting the obtained salt with acetic anhydride in the presence of sodium acetate.

For example, 1-(6-methylpyrazolo[5,1-b][1,3]thiazol-7-yl)ethanone (XXX-A) can be obtained by reacting commercially available 2-methylthiazole (XXVIII-A) with 2-[(aminooxy)sulfonyl]-1,3,5-trimethylbenzene (XXII-A), which can be produced by a generally known method, to give 3-amino-1,3-thiazol-3-ium 2,4,6-trimethylbenzenesulfonate (XXIX-A), and reacting the obtained compound with acetic anhydride in the presence of sodium acetate (formula 34), (XXX-A) can be led to thioamide derivative (II) by generally known functional group conversion.

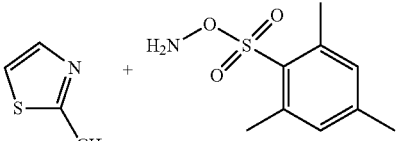
(XXVIII)    (XXII)

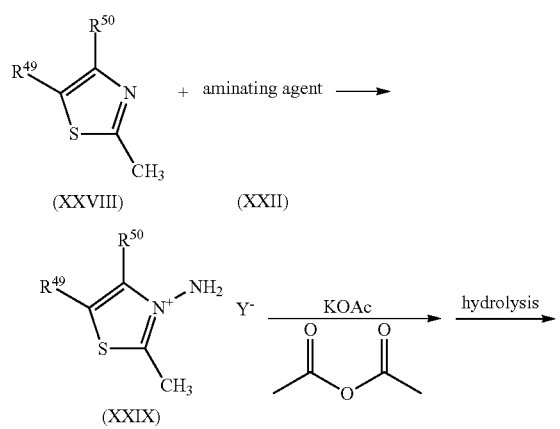
(XXIX)

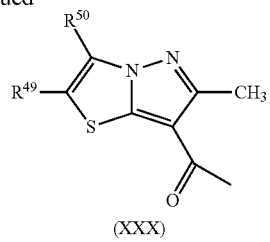
(XXX)

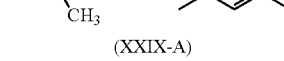

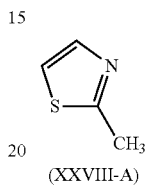
(XXVIII-A)

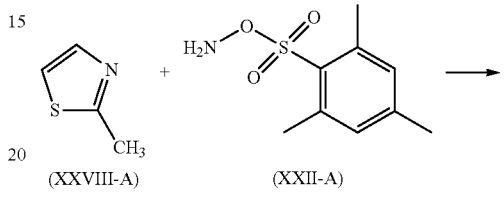
(XXII-A)

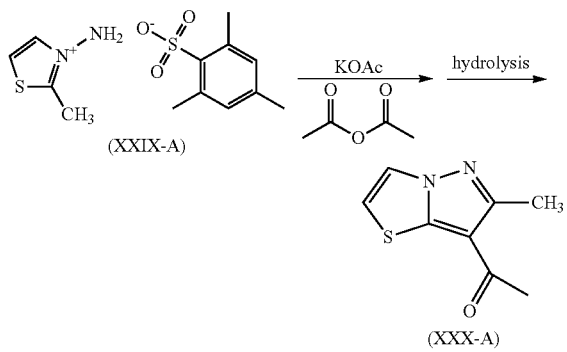
(XXX-A)

In the reaction of (formula 34), amination reaction of thiazole (XXVIII) [each symbol is as defined above] with 2-[(aminooxy)sulfonyl]-1,3,5-trimethylbenzene (XXII-A) can be similarly achieved by applying the conditions of amination reaction of pyridine (XXI) [each symbol is as defined above] with 2-[(aminooxy)sulfonyl]-1,3,5-trimethylbenzene (XXII-A) in (formula 32).

In the reaction of (formula 34), condensation cyclization reaction of (XXIX) [each symbol is as defined above] with potassium acetate and acetic anhydride can be performed using 1 to 10 equivalents, preferably 1 to 5 equivalents, of potassium acetate and 10 equivalents to solvent amount, preferably 10 to 50 equivalents, of acetic anhydride, relative to 3-amino-1,3-thiazol-3-ium salt (XXIX) [each symbol is as defined above] without solvent. The aforementioned reaction can be performed under cooling, at room temperature or under heating (about 40 to 200° C., preferably about 40 to 160° C.), and the reaction time is generally about 1 to 30 hr, preferably about 1 to 20 hr, more preferably about 1 to 10 hr.

The pyrazolo[1,5-a]pyrimidine skeleton (XXXIII) for $R^1$ can be constructed, for example, by a condensation reaction of 3-aminopyrazole derivative (XXXI) [$R^{51}$ and $R^{52}$ are each an optional substituent] and α,β-diketo compound (XXXII) [$R^{53}$, $R^{54}$ and $R^{55}$ are each an optional substituent], or an equivalent form thereto. The reaction conditions here are, for example, those described in Huppatz, John L.; Australian Journal of Chemistry; 38; 1; 1985; 221-230 (formula 35).

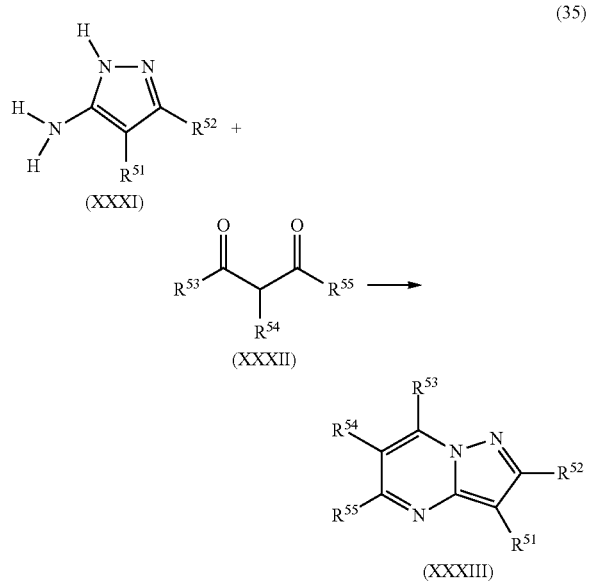

(35)

(XXXI)

(XXXII)

(XXXIII)

In addition, carboxylic acid derivative (B) having various hetero rings as P [P is as defined above] can be produced from commercially available starting materials according to a generally known method or a combination of generally known methods, and thioamide derivative (II) can be produced according to the method shown in (formula 26) or (formula 27), which can be led to thiazole derivative (I).

2-halothiazole key intermediates (A-34) can be obtained by the standard well known Sandmeyer conditions from 2-aminothiazole derivatives (A: wherein P=NH$_2$) which can be prepared by the procedure described in formula 1,

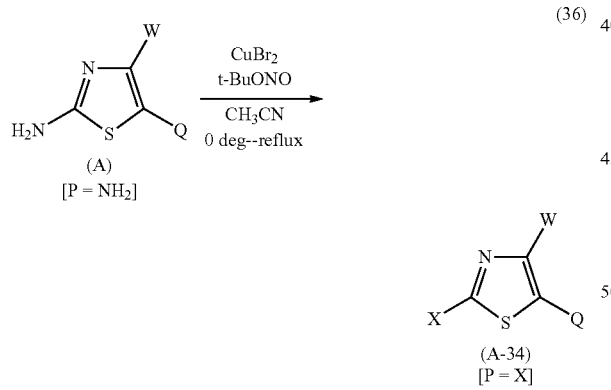

(36)

(A)
[P = NH$_2$]

(A-34)
[P = X]

Key intermediate, 2-halothiazoles (A-34), which can be prepared by the procedure described in formula 36, can be coupled with suitable partners, such as boronic acids or esters (IV'), stannanes (V'), wherein P' is $R^1$ itself or the functional group which can be converter $R^1$ by the well known organic reactions, under standard Suzuki conditions, such as Pd(PPh$_3$)$_4$, Na$_2$CO$_3$, DME/water, elevated temperature or microwave irradiation, or standard Stille conditions, such as Pd(PPh$_3$)$_4$, CuI, LiCl, dioxane at elevated temperature, followed by appropriate organic functional group transformation as described above to afford compounds (I). (formula 37).

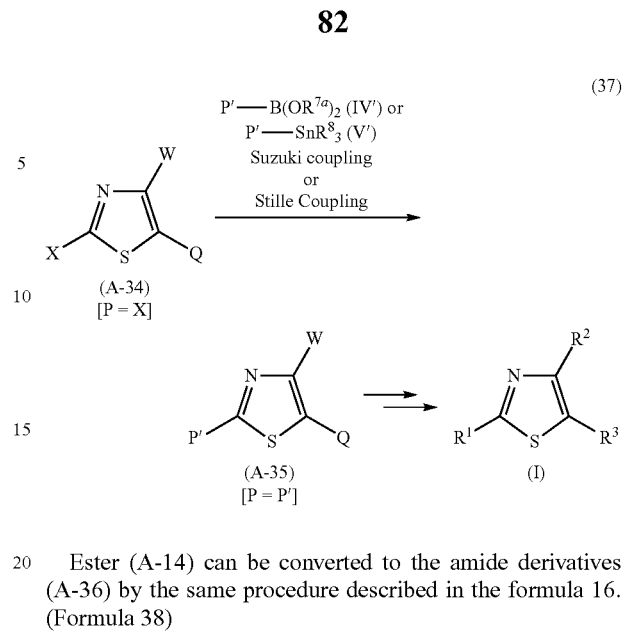

(37)

(A-34)
[P = X]

(A-35)
[P = P']

(I)

Ester (A-14) can be converted to the amide derivatives (A-36) by the same procedure described in the formula 16. (Formula 38)

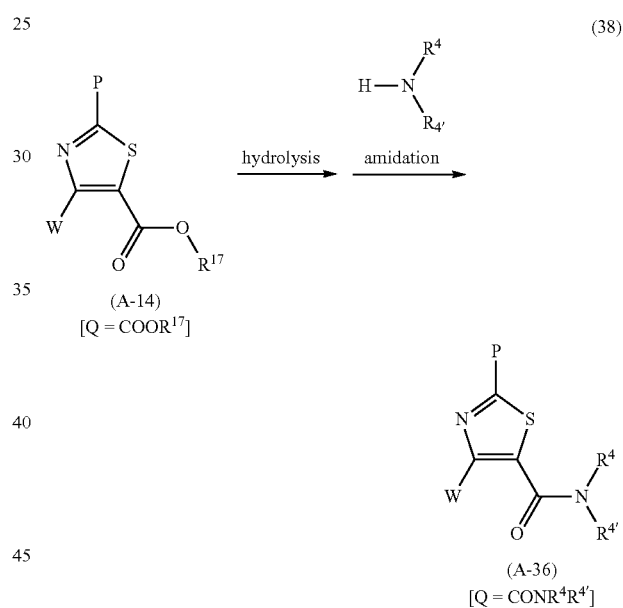

(38)

(A-14)
[Q = COOR$^{17}$]

(A-36)
[Q = CONR$^4$R$^{4'}$]

As shown in Formula 39, triazoles (A-17a-c: $R^{18}$=H), which can be prepared by the procedure described in Formula 17, are treated with a suitable halogenating agent, such as NBS in a suitable solvent, for example tetrachloromethane to afford compounds (A-37).

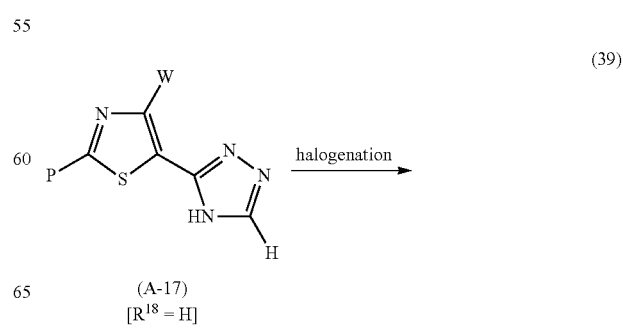

(39)

(A-17)
[$R^{18}$ = H]

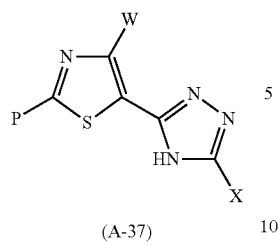
(A-37)

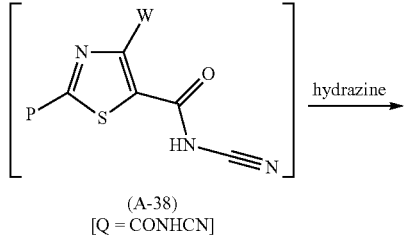
(A-38)
[Q = CONHCN]

As shown in Formula 40, Ester (A-14) are converted to acid by the standard manner, followed by resulting carboxylic acid is coupled with cyanamine (XXXIV), for example via an intermediate acid halide in a suitable solvent, such as DCM to cyanamides (A-38), that are in turn treated with hydrazine using appropriate conditions, for example acetic acid at elevated temperature to give compounds of formula (A-39),

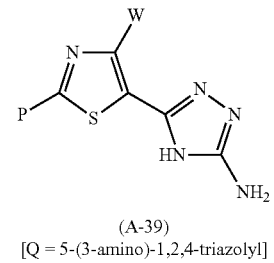
(A-39)
[Q = 5-(3-amino)-1,2,4-triazolyl]

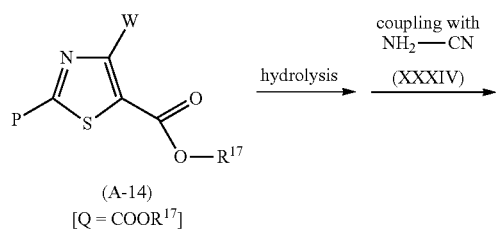
(A-14)
[Q = COOR$^{17}$]

As shown in Formula 41, Ester (A-14) can be converted to 2-imidazolyl via acids. For example, Ester (A-14) is converted to acid by standard procedure, followed by resulting acids are treated with Boc protected ethylenediamine (XXXV) using standard coupling conditions, such as EDCI and HOBt in DCM, Boc protective group is removed using an appropriate acid, for example TFA in DCM to give amide (A-40). Cyclization of (A-40) can be achieved using suitable conditions, for example POCl$_3$ to form dihydroimidazoles (A-41). Dihydroimidazoles (A-41) can be oxidized to imidazoles (A-25) using a suitable oxidative method, for example heating with Magtrieve.

(41)

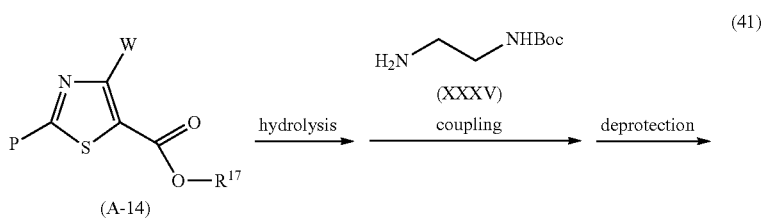
(A-14)

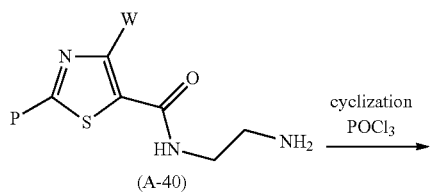
(A-40)

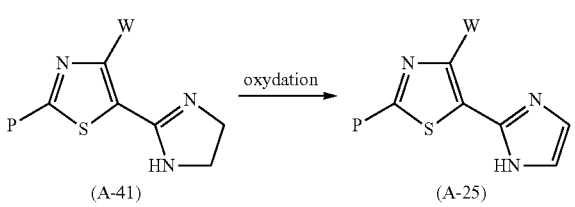
(A-41)  (A-25)

As shown in Formula 42, 2-imidazolyl functionality can be constructed by the coupling with aldehyde (A-42) and alfa, beta-dileto compounds (XXXVI). For example, aldehydes (A-42) are treated with alfa, beta-diketocompounds (XXXVI) such as diketones, ketoaldehydes, or glyoxal with an appropriate ammonia source, such as ammonium acetate, with suitable acid, such as acetic acid in solvent such as methanol to form imidazoles (A-25).

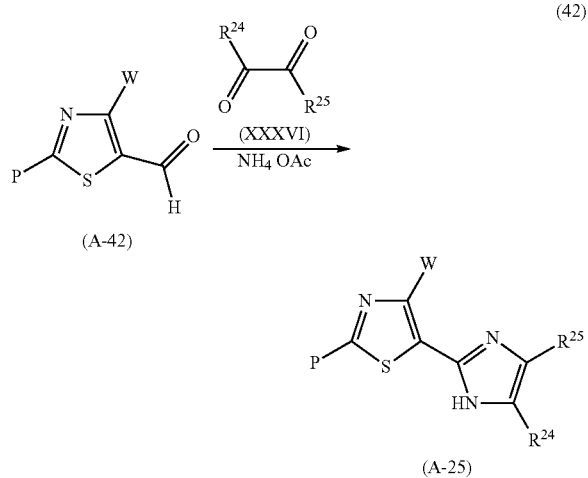

(42)

As shown in Formula 43, 2-imidazolyl functionality is also constructed by the coupling reaction between aldehydes (A-42) and alfa-dihalo carbonyl compounds (XXXVII). For example, aldehydes (A-42) can be treated with alfa-dihalogenketones (XXXVII) under suitable conditions, such as ammonium hydroxide, sodium acetate in an appropriate solvent, for example methanol and water to afford imidazoles (A-25).

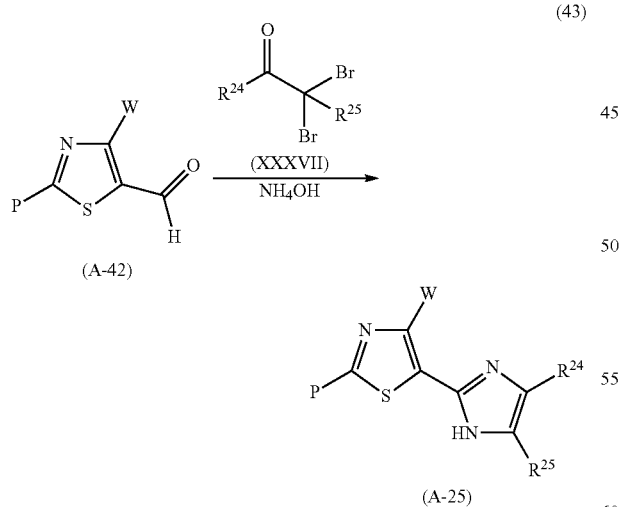

(43)

Formula 44 describes an alternative synthetic route for the preparing 2-imidazolyl analogs (A-25). For example, treatment of nitriles (A-18), which can be prepared by the procedure described in Formula 18, with LiHMDS in a suitable solvent mixture, such as THF/ether/hexane gives amidines (A-43) that can be treated with alfa-haloketones (XXXVIII) in the presence of a suitable base, such as potassium carbonate in an appropriate solvent, such as DCM under elevated temperature to give imidazoles (A-25).

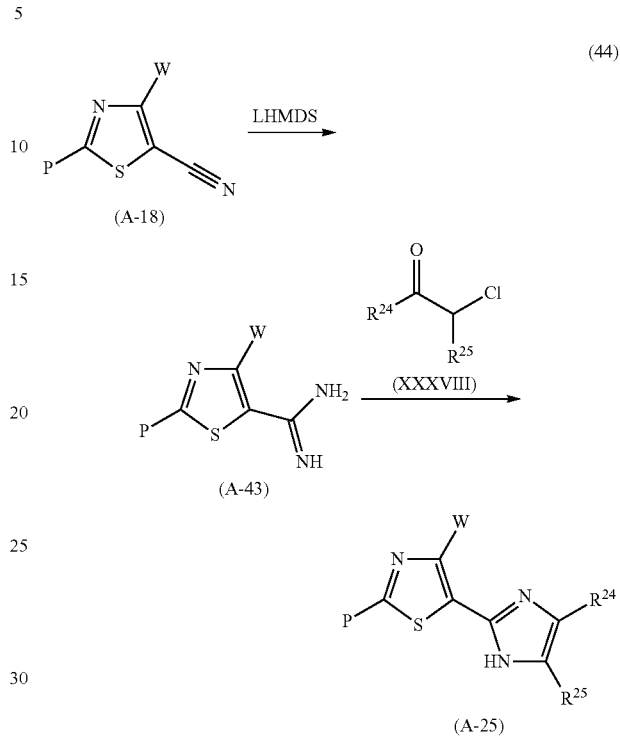

(44)

As shown in Formula 45, 2-imidazolyl functionality can be also constructed from the imidates (A-44). For example imidates (A-44), which can be obtained by the standard procedure from amide (A-15), are treated with diamines (XXXIX) using appropriate conditions, for example ethanol at elevated temperature to obtain dihydroimidazoles (A-41'). Resulting dihydroimidazoles (A-41') can be then oxidized in a same manner as in Formula 41 to afford 2-imidazole derivatives (A-25).

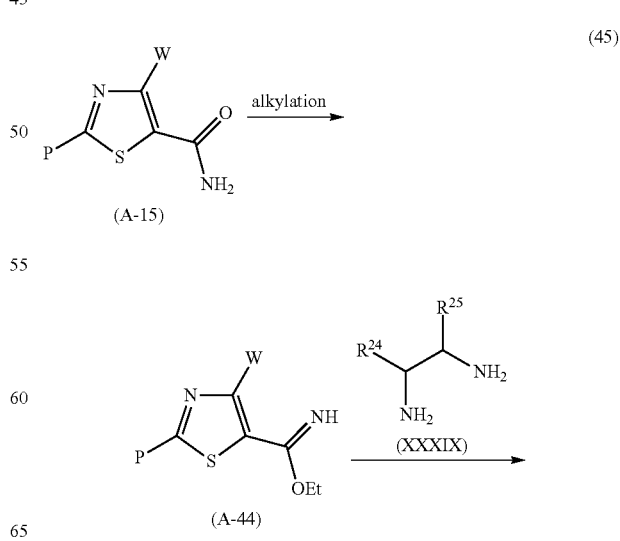

(45)

-continued

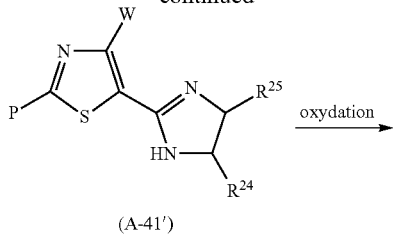

(A-41′)

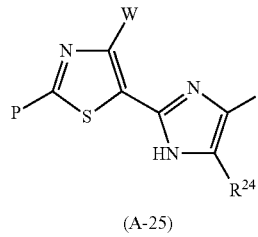

(A-25)

As shown in Formula 46, 4-oxazolyl functionality can be constructed from 2-haloketone (A-28), which can be prepared from ketone (A-27) by the procedure described in Formula 23. For example, ketone (A-27), which can be prepared by the procedure described in Formula 22, are halogenated with a suitable reagent, such as bromine or NBS in an appropriate solvent, such as acetic acid at elevated temperature to form 2-bromoketones (A-28). Treatment of 2-haloketone (A-28) with formamide under elevated temperature or microwave irradiation affords the 4-oxazoles (A-45).

(46)

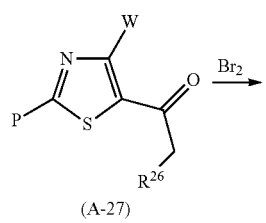

(A-27)

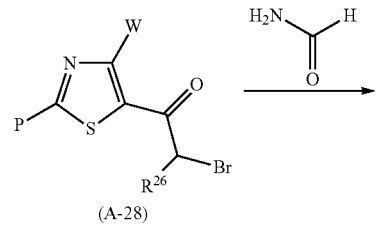

(A-28)

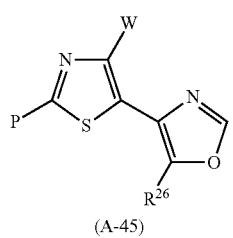

(A-45)

General Method for the Synthesis of Bicycle Lactam Building Blocks (47)

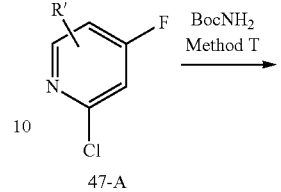

47-A

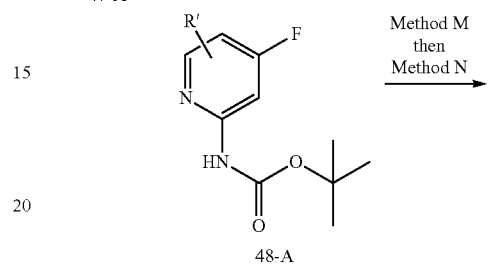

48-A

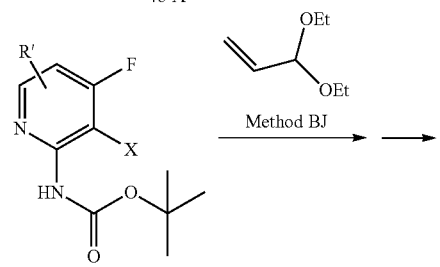

49-A

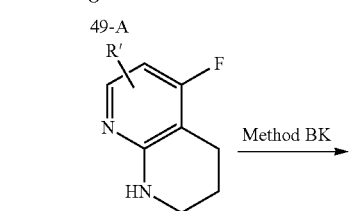

50-A

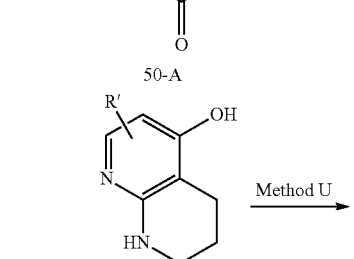

51-A

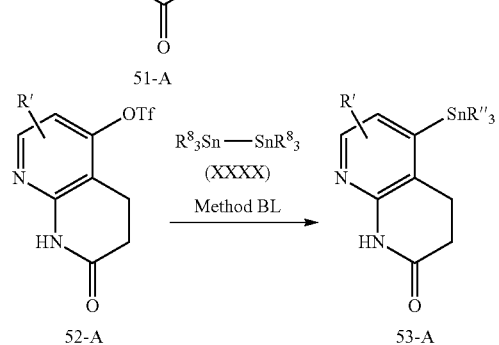

52-A       53-A

Formula 47 above shows a general method for the synthesis of bicyclic lactam building blocks 52-A and 53-A. As shown in Formula 47, substituted 2-chloro-4-fluoropyridines can be amidated, for example with BocNH$_2$, Pd$_2$ dba$_3$ and a suitable ligand, such as X-Phos in the presence of a base, for example cesium carbonate in an appropriate solvent, like dioxane to afford Boc-protected 2-aminopyridines 48-A (Method T). Compounds 48-A can be deprotonated, for example using n-BuLi/TMEDA in THF at low temperature (Method M) and then quenched with a molecule of halogen, such as iodine in THF (Method N) to give halogenated compounds 49-A. Compounds 49-A can be coupled with diethoxypropene using a suitable Pd catalyst, such as Di-mu-chlorobis[5-hydroxy-2-[1-(hydroxylmino-kappaN)ethyl]phenyl-kappaC] palladium(II) dimer with an appropriate base, like N,N-diisopropylethylamine in a suitable solvent, for example DMF-water mixture (Method BJ) to afford lactams of formula 50-A. Transformation of fluoro 50-A into hydroxyl analogs 51-A can be carried out using a standard procedure, for example treatment with benzyl alcohol in the presence of a base, such as sodium hydride at elevated temperature and subsequent debenzylation, such as using hydrogenation with Pd/C catalyst in a suitable solvent, such as ethanol (Method BK). Triflates 52-A can be formed by treatment of 51-A with a suitable reagent, for example triflic anhydride using appropriate conditions, such as pyridine as a base in DCM (Method U). The resulting triflates 52-A can be transformed into stannanes 53-A using a suitable method, such as heating with hexamethyldistannane (XXXX), Pd(PPh$_3$)$_4$ in a suitable solvent, like THF (Method BL). Stannanes 53-A can be then coupled with 2-halo-thiazole halides (A-34), which can be prepared by the procedures described in Formula 36 using standard Stille conditions described in the Formula 37.

Alternative Method for the Synthesis of Bicycle Lactam Building Blocks

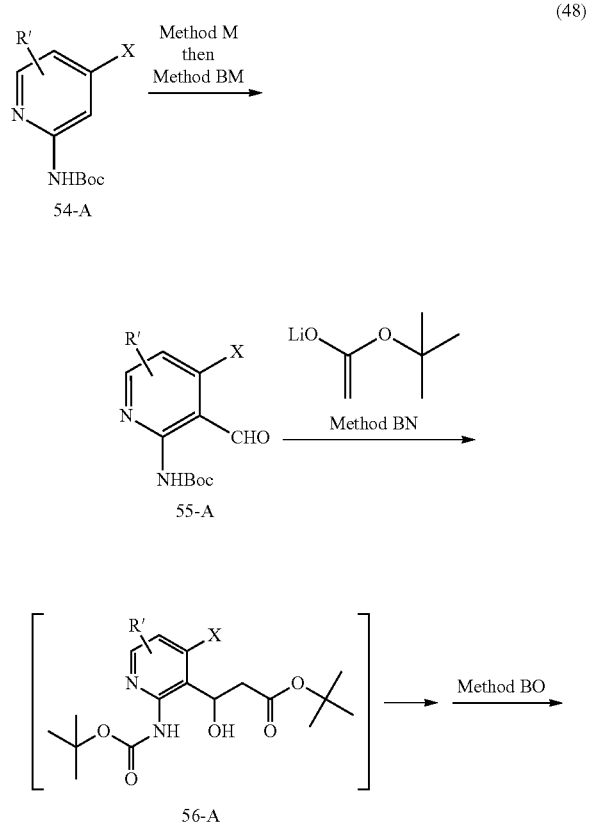

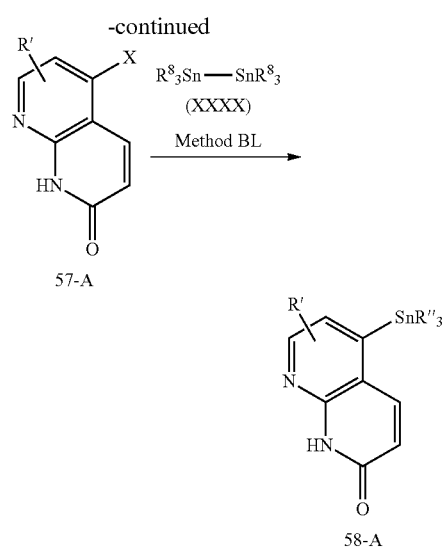

Formula 48 above shows an alternative method for the synthesis of bicyclic lactam building blocks 58-A. As shown in Formula 48, compounds 54-A can be deprotonated with a suitable reagent, such as n-BuLi in THF at low temperature (Method M) and then treated with DMF to produce carbaldehydes 55-A (Method BM), Aldehyde group in 55-A can be then treated with enolate generated from t-Butylacetate and LDA in a suitable solvent, such as THF at low temperature (Method BN) to form intermediate β-hydroxyesters 56-A, that can be cyclized to lactams 57-A using an acid, such as HCl in water at elevated temperature (Method BO). Transformation of aryl halides 57-A to stannanes 58-A can be carried out using hexamethyldistannane, Pd(PPh$_3$)$_4$ in a suitable solvent, like THF (Method BL). Stannanes 58-A can be then coupled with 2-halo-thiazole halides (A-34), which can be prepared by the procedures described in Formula 36 using standard Stille conditions described in the Formula 37.

The thus-obtained compound (I), (I'), or subsets thereof, can be isolated and purified by a separation means known per se, for example, concentration, concentration under reduced pressure, solvent extraction, crystallization, recrystallization, phase transfer, chromatography and the like.

When compound (I), (I'), or subsets thereof, is obtained in a free form, it can be converted to a desired salt by a method known per se or a method analogous thereto, and when it is obtained in a form of a salt, it can be converted to a free form or other desired salt by a method known per se or a method analogous thereto.

When compound (I), (I'), or subsets thereof, has an isomer such as optical isomer, stereoisomer, positional isomer, rotamer, tautomer and the like, any one of the isomers and a mixture thereof are also encompassed in compound (I), (I'), or subsets thereof. For example, when compound (I), (I'), or subsets thereof, has an optical isomer, an optical isomer resolved from racemate is also encompassed in compound (I), (I'), or subsets thereof. Each of these isomers can be obtained as a single product by a synthesis method, separation method (concentration, solvent extraction, column chromatography, recrystallization and the like) known per se.

Compound (I), (I'), or subsets thereof, may be a crystal, and is encompassed in compound (I), (I'), or subsets thereof, whether the crystal form is the same or it is a crystal mixture. A crystal can be produced by crystallization according to a crystallization method known per se.

Compound (I), (I'), or subsets thereof, may be a solvate (e.g., hydrate etc.) or non-solvate, both of which are encompassed in compound (I), (I'), or subsets thereof.

Compounds labeled with an isotope (e.g., $^3$H, $^{14}$C, $^{35}$S, $^{125}$I and the like) and the like are also encompassed in compound (I), (I'), or subsets thereof.

A prodrug of the compound (I), (I'), or subsets thereof, or a salt thereof (hereinafter to be abbreviated as compound (I), (I'), or subsets thereof) means a compound which is converted to the compound (I), (I'), or subsets thereof, with a reaction due to an enzyme, a gastric acid, etc. under the physiological condition in the living body, that is, a compound which is converted to the compound (I), (I'), or subsets thereof, with oxidation, reduction, hydrolysis, etc. according to an enzyme; a compound which is converted to the compound (I), (I'), or subsets thereof, by hydrolysis etc. due to gastric acid, etc. A prodrug of compound (I), (I'), or subsets thereof, may be a compound obtained by subjecting an amino group in compound ((I), (I'), or subsets thereof) to an acylation, alkylation or phosphorylation (e.g., a compound obtained by subjecting an amino group in compound (I), (I'), or subsets thereof, to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I), (I'), or subsets thereof, to an acylation, alkylation, phosphorylation or boration (e.g., a compound obtained by subjecting a hydroxy group in compound (I), (I'), or subsets thereof, to an acetylation, palmitoylation, propanoylation, pivaloylation, succinylation, fumarylation, alanylation, dimethylaminomethylcarbonylation, etc.); a compound obtained by subjecting a carboxyl group in compound (I), (I'), or subsets thereof, to an esterification or amidation (e.g., a compound obtained by subjecting a carboxyl group in compound (I), (I'), or subsets thereof, to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I), (I'), or subsets thereof, by a method known per se.

A prodrug of compound (I), (I'), or subsets thereof, may also be one which is converted into compound (I), (I'), or subsets thereof, under a physiological condition, such as those described in IYAKUHIN no KAIHATSU (Development of Pharmaceuticals), Vol. 7, Design of Molecules, p. 163-198, Published by HIROKAWA SHOTEN (1990).

Compound (I), (I'), or subsets thereof, of the present invention or a salt thereof or a prodrug thereof (hereinafter sometimes to be abbreviated as the compound of the present invention) has a PI3K inhibitory activity and(or) an mTOR inhibitory activity, and can be used for the prophylaxis or treatment of a PI3K and(or) mTOR dependent disease in mammals. Particularly, the compound of the present invention is useful as a therapeutic agent that suppresses growth of cancer expressing PI3K and(or) mTOR, as well as a prophylactic agent that prevents change of hormone dependent cancer into hormone independent cancer. In addition, since the compound shows low toxicity (e.g., acute toxicity, chronic toxicity, genetic toxicity, reproductive toxicity, cardiotoxicity, drug interaction, carcinogenicity and the like), high water-solubility, and superior stability, in vivo kinetics (absorption, distribution, metabolism, excretion and the like), and efficacy expression, it is useful as a pharmaceutical agent.

The compound of the present invention can be used as a safe prophylactic or therapeutic agent for diseases caused by abnormal cell proliferation, such as various cancers (particularly, breast cancer (e.g., invasive ductal carcinoma, non-invasive ductal carcinoma, inflammatory breast cancer and the like), prostate cancer (e.g., hormone-dependent prostate cancer, hormone-independent prostate cancer and the like), pancreatic cancer (e.g., pancreatic duct cancer and the like), gastric cancer (e.g., papillary adenocarcinoma, mucinous adenocarcinoma, adenosquamous carcinoma and the like), lung cancer (e.g., non-small cell lung cancer, small cell lung cancer, malignant mesothelioma and the like), colorectal cancer (e.g., familial colorectal cancer, hereditary nonpolyposis colorectal cancer, gastrointestinal stromal tumor and the like), small intestinal cancer, colon cancer (e.g., gastrointestinal stromal tumor and the like), rectal cancer (e.g., gastrointestinal stromal tumor and the like), esophagus cancer, duodenal cancer, cancer of the tongue, pharyngeal cancer (e.g., nasopharyngeal cancer, oropharyngeal cancer, hypopharyngeal cancer and the like), salivary gland cancer, brain tumor (e.g., pineal astrocytoma, pilocytic astrocytoma, diffuse astrocytoma, anaplastic astrocytoma and the like), neurinoma, non-small cell lung cancer, small cell lung cancer, liver cancer (e.g., primary liver cancer, extrahepatic bile duct cancer and the like), kidney cancer (e.g., renal cell carcinoma, transitional cell cancer of renal pelvis and ureter and the like), cancer of the bile duct, uterine body cancer, endometrial carcinoma, uterine cervical cancer, ovary cancer (e.g., ovarian epithelial carcinoma, extragonadal germ cell tumor, ovarian germ cell tumor, ovarian low malignant potential tumor and the like), urinary bladder cancer, urethral cancer, skin cancer (e.g., intraocular (ocular) melanoma, Merkel cell carcinoma and the like), hemangioma, malignant lymphoma, malignant melanoma, thyroid cancer (e.g., medullary thyroid carcinoma and the like), parathyroid cancer, nasal cavity cancer, paranasal sinus cancer, bone tumor (e.g., osteosarcoma, Ewing's tumor, uterus sarcoma, soft tissue sarcoma and the like), vascular fibroma, retinoblastoma, penile cancer, solid cancer in childhood, Kaposi's sarcoma, Kaposi's sarcoma derived from AIDS, maxillary tumor, fibrous histiocytoma, leiomyosarcoma, rhabdomyosarcoma, leukemia (e.g., acute myelocytic leukemia, acute lymphoblastic leukemia and the like) etc.), atherosclerosis, angiogenesis (e.g., angiogenesis associated with growth of solid cancer and sarcoma, angiogenesis associated with tumor metastasis, and angiogenesis associated with diabetic retinopathy etc.), viral diseases (HIV infection etc.) and the like.

Furthermore, the compound of the present invention is also useful as an agent for the prophylaxis or treatment of restenosis, arteriosclerosis, bone diseases, rheumatoid arthritis, rheumatic retinopathy, psoriasis, benign prostatic hyperplasia, atherosclerosis, inflammation, angiogenesis, renal diseases, allergic diseases, anaphylaxis, acute or chronic inflammation, autoimmune diseases, thrombosis, cardiac hypertrophy, hypertension, cardiac failure and the like.

The compound of the present invention is useful as an anticancer agent for the prophylaxis or treatment of cancers, particularly breast cancer, ovary cancer, colorectal cancer, gastric cancer, esophagus cancer, prostate cancer, lung cancer, pancreatic cancer and the like.

Since the compound of the present invention has low toxicity, it can be used for mammals (e.g., human, horse, bovine, dog, cat, rat, mouse, rabbit, swine, monkey etc.) as a pharmaceutical agent or as a pharmaceutical composition in admixture with pharmaceutically acceptable carrier etc. known per se.

The pharmaceutical composition may contain, together with the compound of the present invention, other active ingredients, such as the following hormonal therapeutic agent, anticancer agent (e.g., chemotherapeutic agent, immunotherapeutic agent, a pharmaceutical agent that inhibits the action of cell growth factor and receptor thereof etc.) and the like.

The administration method of the compound of the present invention as a pharmaceutical agent to mammals such as human and the like generally includes oral administration of, for example, tablet, capsule (including soft capsule, microcapsule), powder, granule etc., and parenteral administration of injection, suppository, pellet etc. The "parenteral administration" includes intravenous, intramuscular, subcutaneous, intraorgan, intranasal, intradermal, instillation, intracerebral, intrarectal, vaginal, intraperitoneal and intratumoral administrations, administration to the vicinity of tumor etc., and administration directly to the lesion.

While the dose of the compound of the present invention varies depending on the administration route, symptom and the like, it is, for example, 0.5 to 100 mg/kg body weight/day, preferably 1 to 50 mg/kg body weight/day, more preferably 1 to 25 mg/kg body weight/day, for oral administration as an anticancer agent to patients (body weight 40-80 kg) with breast cancer or prostate cancer. This amount can be administered once or in 2 or 3 portions a day.

The compound of the present invention can be safely administered orally or parenterally (e.g., topical, rectal, intravenous administration etc.) and alone or in the form of a pharmaceutical composition, for example, tablet (including sugar-coated tablet, film-coated tablet), powder, granule, capsule, liquid, emulsion, suspension, injection, suppository, sustained-release preparation, plaster and the like containing pharmacologically acceptable carriers according to a conventional method (e.g., the method described in the Japanese Pharmacopoeia etc.).

A combination of (1) administering an effective amount of a compound of the present invention and (2) 1 to 3 selected from the group consisting of (i) administering an effective amount of other anticancer agents, (ii) administering an effective amount of hormonal therapeutic agents and (iii) non-drug therapy can prevent and/or treat cancer more effectively. As the non-drug therapy, for example, surgery, radiotherapy, gene therapy, thermotherapy, cryotherapy, laser cauterization, and the like are exemplified and two or more of these may be combined.

For example, the compound of the present invention can be used in combination with other hormonal therapeutic agents, anticancer agents (e.g., chemotherapeutic agents, immunotherapeutic agents (including vaccine), antibody, gene therapy drugs, pharmaceutical agents inhibiting the action of cell growth factors or cell growth factor receptors or pharmaceutical agents'inhibiting angiogenesis) (hereafter to be briefly referred to as a concomitant drug).

While the compound of the present invention exhibits excellent anticancer action even when used as a simple agent, its effect can be enhanced by using it in combination with one or more of the concomitant drug(s) mentioned above (multi-agent co-administration).

Examples of said "hormonal therapeutic agents" include fosfestrol, diethylstylbestrol, chlorotrianisene, medroxyprogesterone acetate, megestrol acetate, chlormadinone acetate, cyproterone acetate, danazol, dienogest, asoprisnil, allylestrenol, gestrinone, nomegestrol, Tadenan, mepartricin, raloxifene, ormeloxifene, levormeloxifene, anti-estrogens (e.g., tamoxifen citrate, toremifene citrate, and the like), ER down regulator (e.g., fulvestrant, and the like), human menopausal gonadotrophin, follicle stimulating hormone, pill preparations, mepitiostane, testrolactone, aminoglutethimide, LH-RH derivative such as LH-RH agonists (e.g., goserelin acetate, buserelin, leuprorelin, and the like) and LH-RH antagonist, droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, dutasteride, epristeride, and the like), adrenocortical hormone drugs (e.g., dexamethasone, prednisolone, betamethasone, triamcinolone, and the like), androgen synthesis inhibitors (e.g., abiraterone, and the like), retinoid and drugs that retard retinoid metabolism (e.g., liarozole, and the like), etc. LH-RH agonists (e.g., goserelin acetate, buserelin, leuprorelin) are particularly preferable.

As the "chemotherapeutic agents", alkylating agents, antimetabolites, anticancer antibiotics, plant-derived anticancer agents, and other chemotherapeutic agents are used.

As the "alkylating agents", nitrogen mustard, nitrogen mustard-N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin and the like are used. As the "antimetabolites", mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur, and the like), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine and the like are used.

As the "anticancer antibiotics", actinomycin-D, actinomycin-C, mitomycin-C, chrornomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and the like are used.

As the "plant-derived anticancer agents", etoposide, etoposide phosphate, vinblastine sulfate, vincristine sulfate, vindesine sulfate, teniposide, paclitaxel (Taxol(trademark)), docetaxel, vinorelbine, irinotecan, topotecan, and the like are used.

As "other chemotherapeutic agents", sobuzoxane and the like are used.

As the "immunotherapeutic agents (BRM)", picibanil, krestin, sizofuran, lentinan, ubenimex, interferons, interleukins, macrophage colony-stimulating factor, granulocyte colony-stimulating factor, erythropoietin, lymphotoxin, *Corynebacterium parvum*, levamisole, polysaccharide K, procodazole, and the like are used. As the vaccine, BCG vaccine, PROVENGE, Onyvax-P, PROSTVAC-VF, GVAX, DCVax-Prostate, SAPOIMMUNE, VPM-4-001 and the like are used.

As the "antibody", antibody against EpiCAM, antibody against PSCA and antibody against PSMA are used.

Examples of the "cell growth factor" of the "pharmaceutical agents inhibiting the action of cell growth factors or cell growth factor receptors" include any substances that promote cell proliferation, which are normally peptides having a molecular weight of not more than 20,000 that are capable of exhibiting their action at low concentrations by binding to a receptor, including (1) EGF (epidermal growth factor) or substances possessing substantially the same activity as it [e.g., EGF, heregulin, TGF-α, HB-EGF, and the like], (2) insulin or substances possessing substantially the same activity as it [e.g., insulin, IGF (insulin-like growth factor)-1, IGF-2, and the like], (3) FGF (fibroblast growth factor) or substances possessing substantially the same activity as it [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HOF (hepatocyte growth factor), VEGF (vascular endothelial growth factor), and the like], and the like.

Examples of the "cell growth factor receptors" include any receptors capable of binding to the aforementioned cell growth factors, specifically, EGF receptor and HER2, HER3 and HER4 belonging to the same family, insulin receptor, IGF receptor, FGF receptor-1, FGF receptor-2 and the like.

Examples of the "pharmaceutical agents inhibiting the action of cell growth factor" include trastuzumab (Herceptin (trademark) HER2 antibody), imatinib mesylate, ZD1839 or EGFR antibody (cetuximab (Erbitux (trademark)) etc.), antibody against VEGF (e.g., bevacizumab (Avastin (trademark))), VEGFR antibody, VEGFR inhibitor, EGFR inhibitor (gefitinib (Iressa (trademark)), erlotinib (Tarceva (trademark)) etc.).

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), angiogenesis inhibitor (e.g., thalidomide, SU11248 etc.), α-blocker (e.g., tamsulosin hydrochloride, naftopidil, urapidil, alfuzosin, terazosin, prazosin, silodosin etc.), serine/threonine kinase inhibitor, endothelin receptor antagonist (e.g., atrasentan etc.), proteasome inhibitor (e.g., bortezomib etc.), Hsp90 inhibitor (e.g., 17-AAG etc.), spironolactone, minoxidil, 11α-hydroxyprogesterone, bone resorption inhibiting/metastasis suppressing agent (e.g., zoledronic acid, alendronic acid, pamidronic acid, etidronic acid, ibandronic acid, clodronic acid) and the like can also be used.

Among the aforementioned drugs, as a concomitant drug, LH-RH agonist (e.g., goserelin acetate, buserelin, leuprorelin etc.), HER2 antibody (trastuzumab (Herceptin (trademark))), EGFR antibody (cetuximab (Erbitux (trademark)) etc.), EGFR inhibitor (erlotinib (Tarceva (trademark)), gefitinib (Iressa (trademark)) etc.), VEGFR inhibitor or chemotherapeutic agent (paclitaxel (Taxol (trademark)) etc.) is preferable.

Particularly, trastuzumab (Herceptin (trademark)), cetuximab (Erbitux (trademark)), erlotinib (Tarceva (trademark)), gefitinib (Iressa (trademark)), paclitaxel (Taxol (trademark)) and the like are preferable.

When using the compound of the present invention and the concomitant drug in combination, the administration time of the compound of the present invention and the concomitant drug is not restricted, and the compound of the present invention and the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration mode of a combination of the compound of the present invention and the concomitant drug is not particularly limited, and the compound of the present invention and the concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

EXAMPLES

The present invention is explained in detail in the following by referring to Examples, Formulation Examples and Experimental Examples, which are not to be construed as limitative.

In Examples 47-B to 71-B, LC/MS analysis was performed under the following conditions.
Measurement instrument: Waters LC-MS system
Column: CAPCELL PAK C18 U0120, S-3 μM, 1.5×35 mm (Shiseido Co., Ltd.)
Solvent: Solution A; 0.05% trifluoroacetic acid-containing water, Solution B: 0.04% trifluoroacetic acid-containing acetonitrile
Gradient cycle: 0.00 min (Solution A/Solution B=90/10), 2.00 min (Solution A/Solution B=5/95), 2.75 min (Solution A/Solution B=5/95), 2.76 min (Solution A/Solution B=90/10), 3.60 min (Solution A/Solution B=90/10)
Flow rate: 0.5 mL/min, detection method: UV 220 nm
MS conditions: ionization method: ESI In Examples 47-B to 71-B, purification by large-scale preparative HPLC was performed under the following conditions.
Instrument: Gilson Inc. reversed-phase large-scale preparative purification system GX-281
Column: CombiPrep C18 RS S-5 μm, 50×30 mm (YMC)
Solvent: Solution A; 10% aqueous ammonium hydrogen carbonate solution, Solution B; acetonitrile
Gradient cycle: 0.00 min (Solution A/Solution B=95/5), 0.30 min (Solution A/Solution B=95/5), 3.50 min (Solution A/Solution B=0/100), 5.50 min (Solution A/Solution B=0/100), 5.60 min (Solution A/Solution B=95/5), 6.60 min (Solution A/Solution B=95/5)
Flow rate: 50 mL/min, detection method: UV 220 nm The elution by column chromatography was performed under observation by TLC (thin layer chromatography). For TLC observation, Kieselgel 60 F254 plate manufactured by Merck, or NH TLC plate manufactured by Fuji Silysia Chemical Ltd., or an equivalent product thereof was used as a TLC plate, and the solvent used as an elution solvent in column chromatography was used as the eluent. For detection, a UV detector was employed. As silica gel for the column, Kieselgel 60 F254 (70-230 mesh) manufactured by Merck, or CHROMATOREX NH DM1020 (basic silica gel, 100-200 mesh) manufactured by Fuji Silysia Chemical Ltd., or an equivalent product thereof was used. The ratio of solvents in silica gel chromatography shows the volume ratio of mixed solvents. Unless otherwise specified, % means weight percent.

NMR spectrum is shown by proton NMR, with tetramethylsilane as the internal standard and using VARIAN Gemini-200 (200 MHz spectrometer) or Gemini-300 (300 MHz spectrometer) or BRUKER AVANCE300 (300 MHz spectrometer) for the measurement; 5 values are expressed in ppm.

The abbreviations used in the Examples mean the following. s: singlet, br: broad, d: doublet, t: triplet, q: quartet, dd: double doublet, m: multiplet, J: coupling constant, Hz: hertz, DMSO: dimethyl sulfoxide, DME: 1,2-Dimethoxyethane, TFA: trifluoroacetic acid, DMAP: N,N-dimethylaminopyridine Genetic manipulation methods described in Experimental Example below are based on the methods described in Maniatis et al., Molecular Cloning, Cold Spring Harbor Laboratory, 1989, and the appended reagent protocol.

1-B

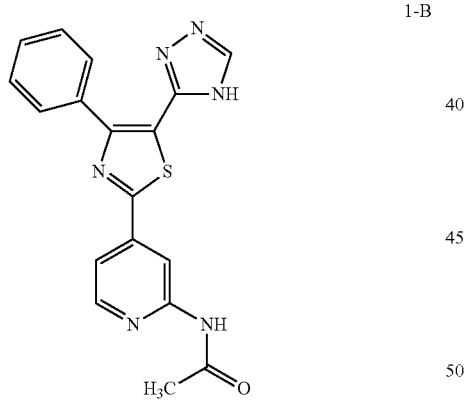

2-B

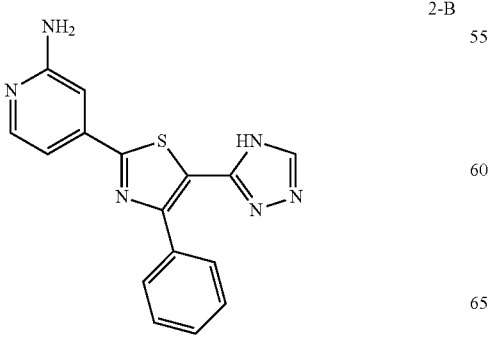

-continued

3-B

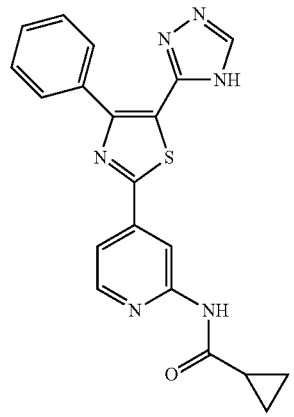

4-B

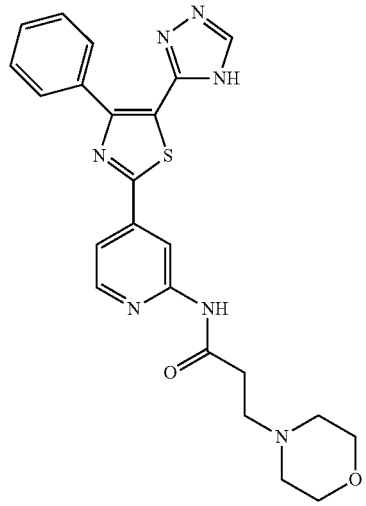

5-B

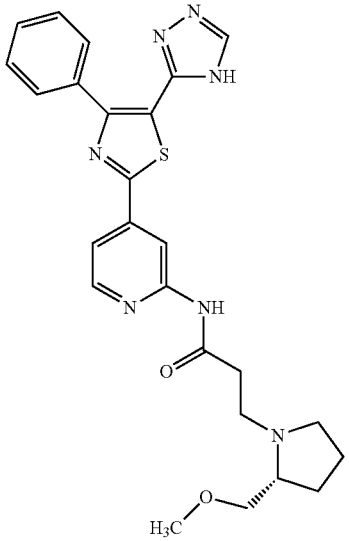

99
-continued
6-B
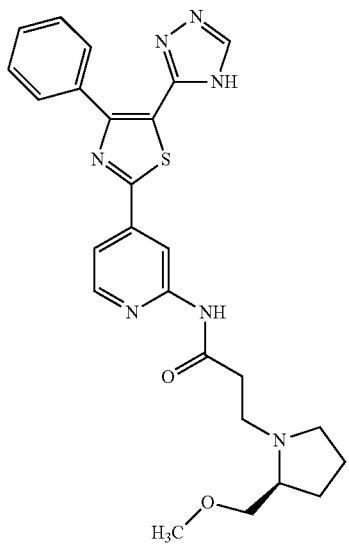
7-B
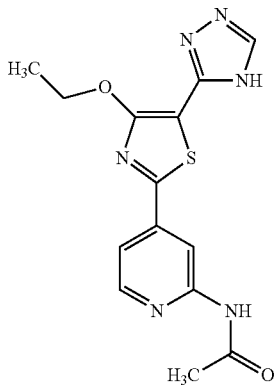
8-B
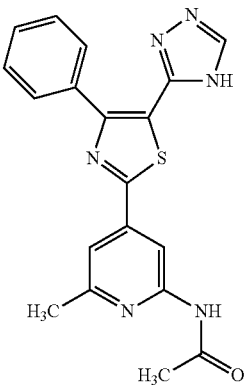
100
-continued
9-B
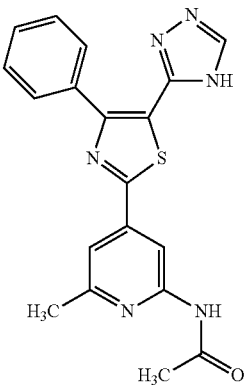
10-B
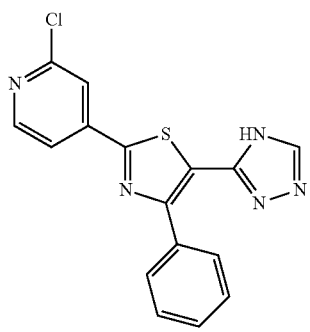
11-B
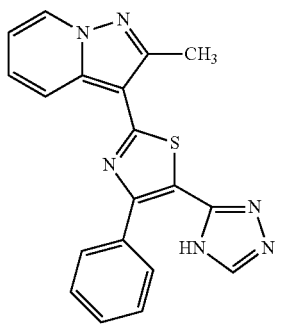
12-B
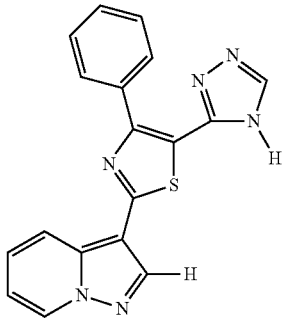

13-B
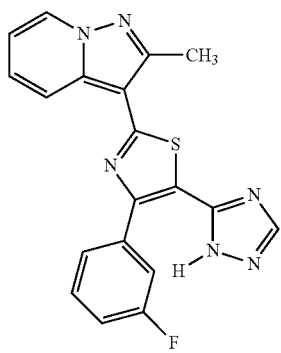
14-B
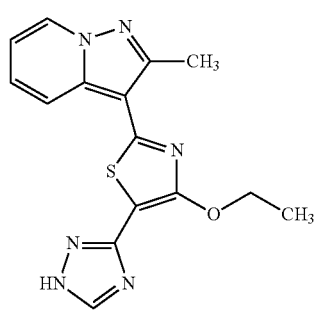
15-B
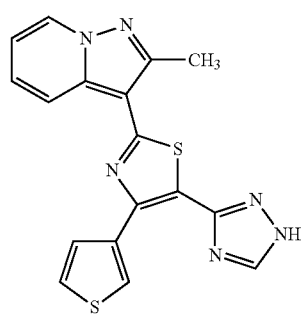
16-B
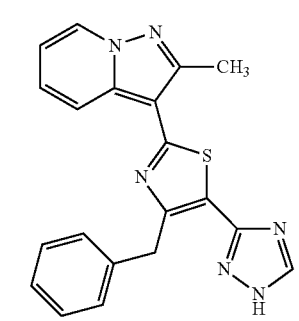
17-B
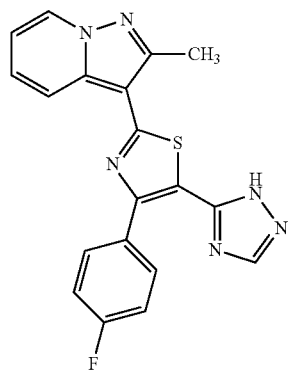
18-B
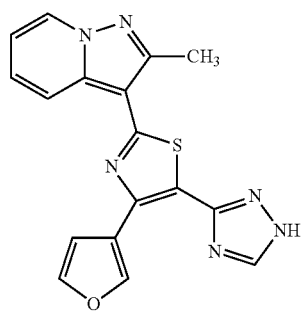
19-B
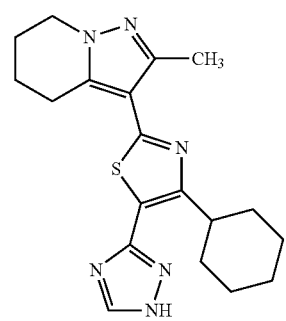
20-B
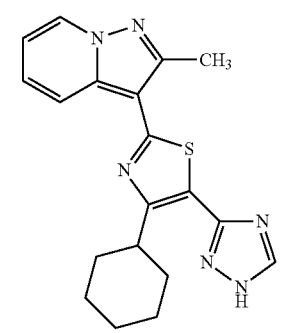
21-B
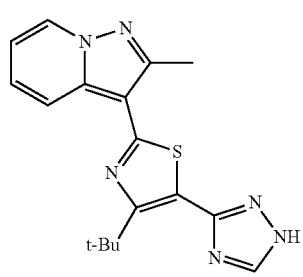

103
-continued
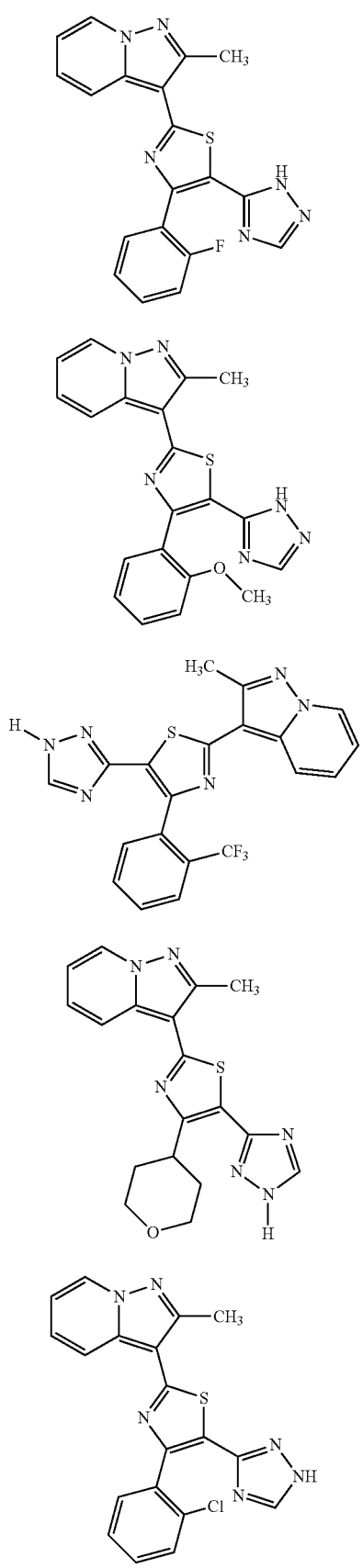
| | |
|---|---|
| 22-B | |
| 23-B | |
| 24-B | |
| 25-B | |
| 26-B | |
104
-continued
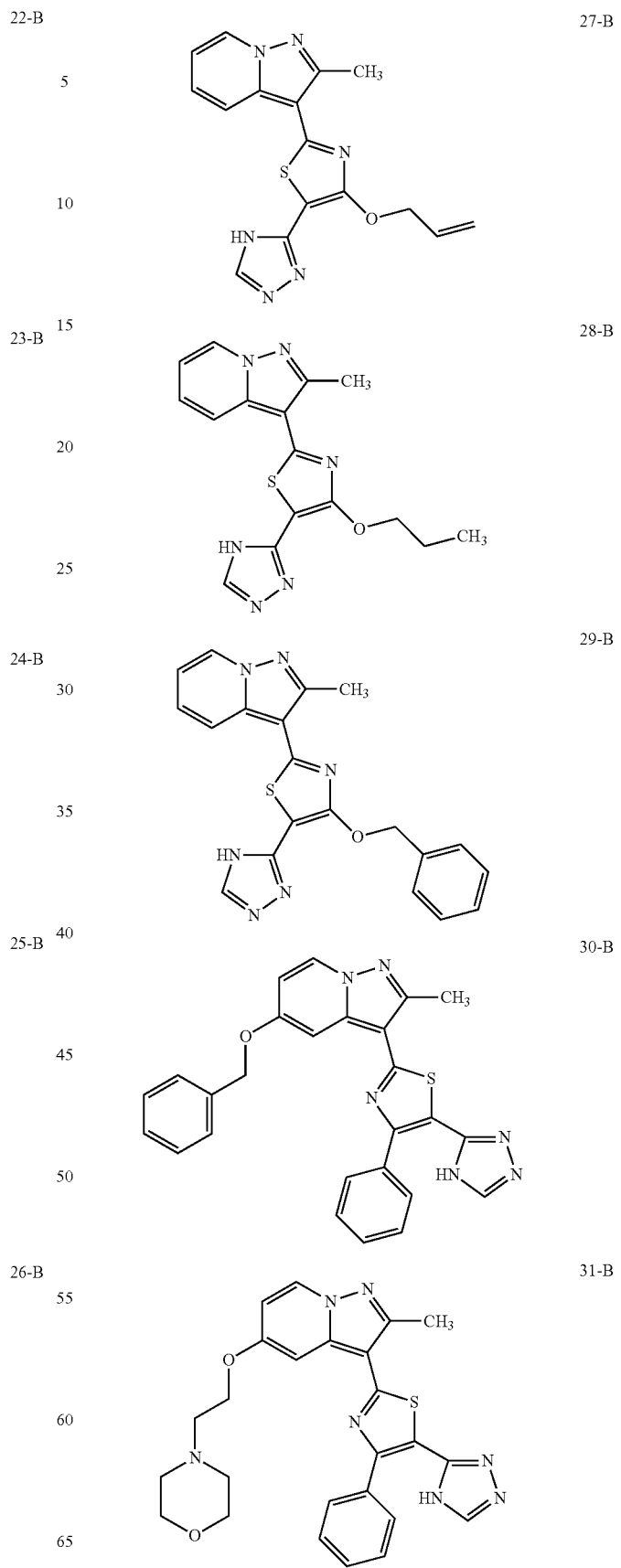
| | |
|---|---|
| 27-B | |
| 28-B | |
| 29-B | |
| 30-B | |
| 31-B | |

| | |
|---|---|
| 32-B 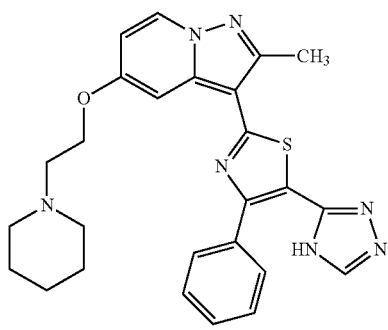 | 37-B 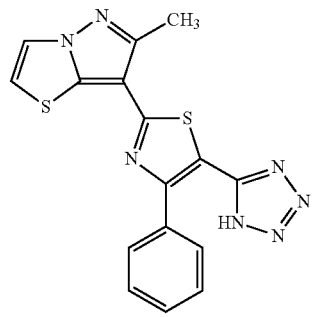 |
| 33-B 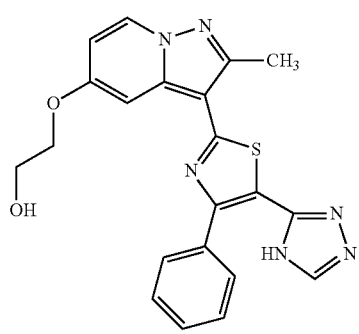 | 38-B 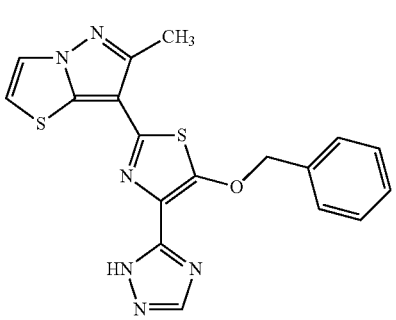 |
| 34-B 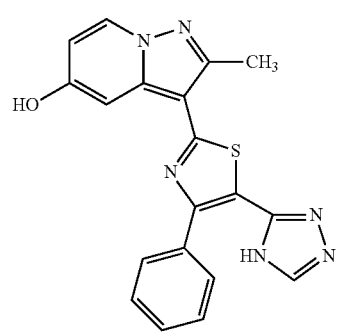 | 39-B 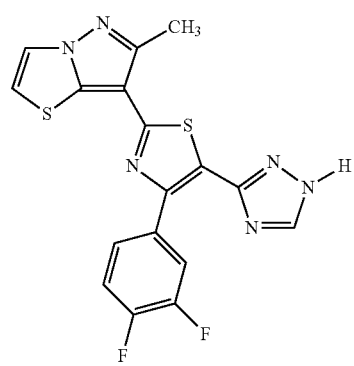 |
| 35-B 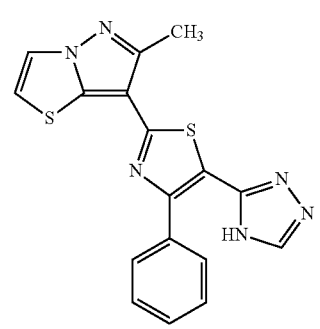 | 40-B 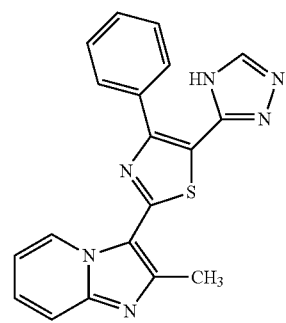 |
| 36-B 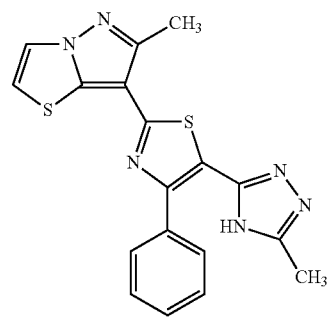 | 41-B 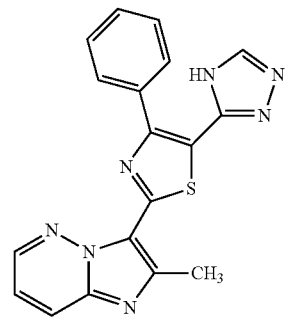 |

42-B 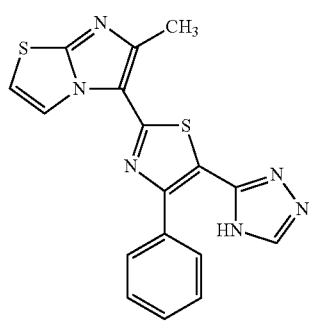
43-B 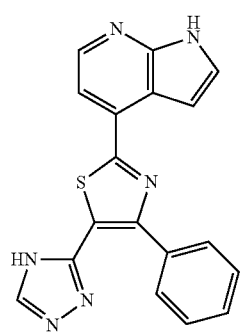
44-B 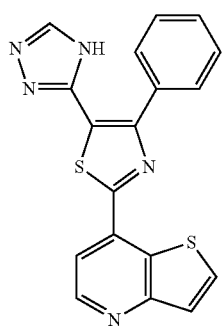
45-B 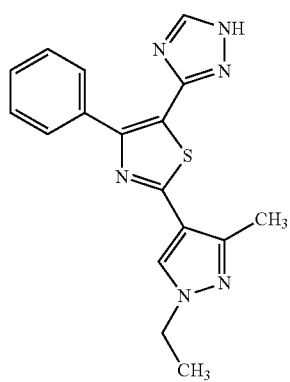
46-B 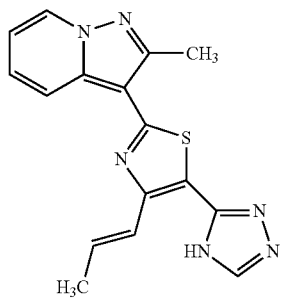
47-B 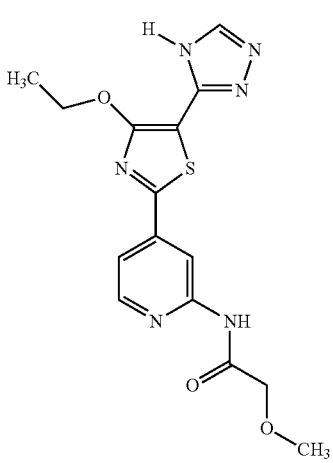
48-B 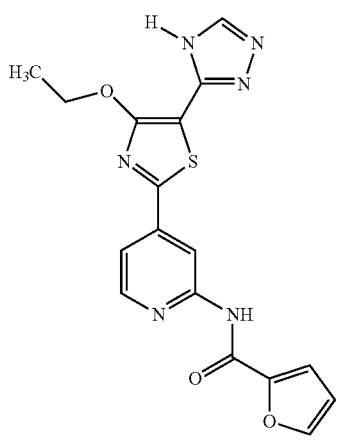
49-B 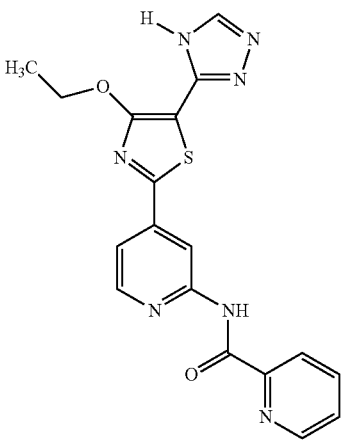

50-B
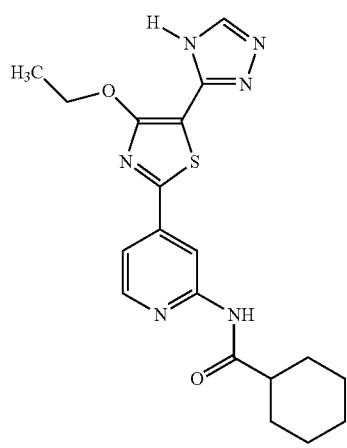
51-B
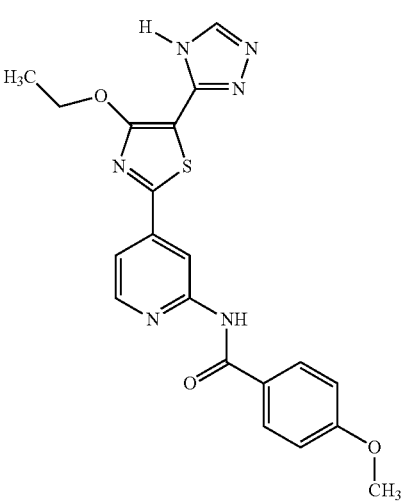
53-B
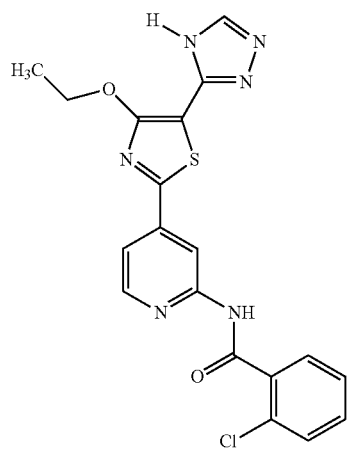
54-B
52-B
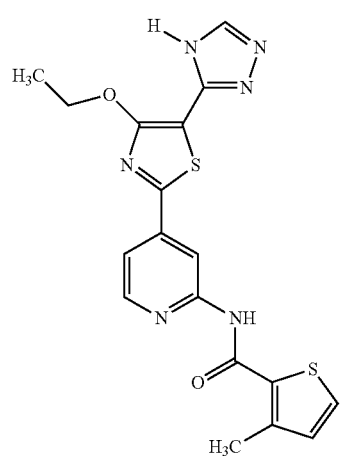
55-B
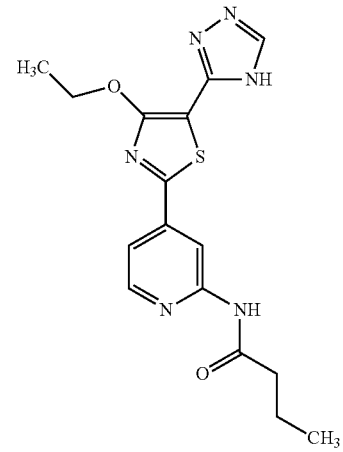

56-B
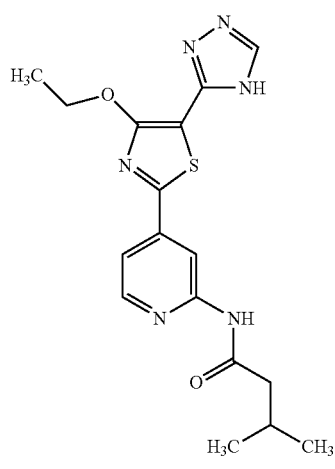
57-B
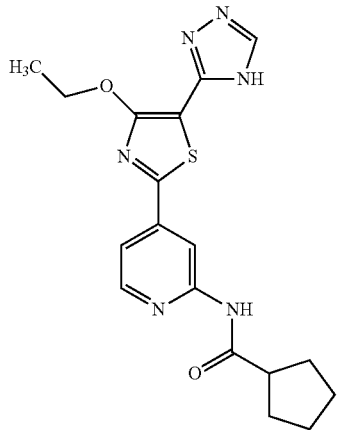
58-B
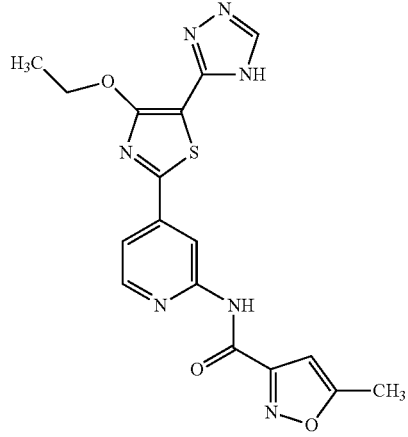
59-B
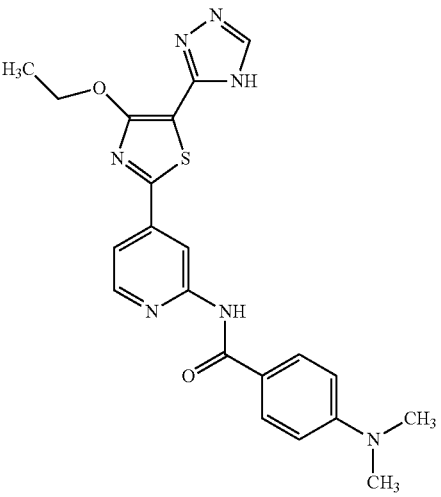
60-B
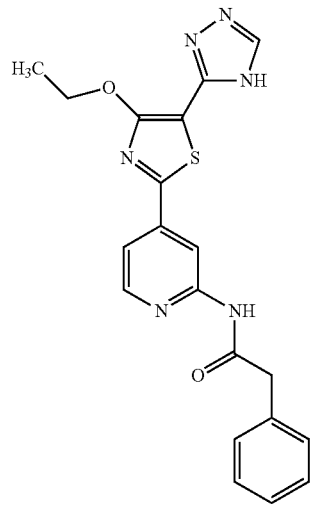
61-B
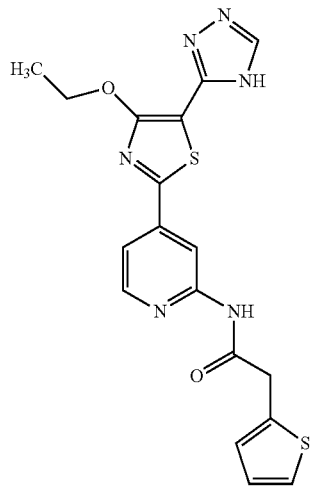

113
-continued
62-B
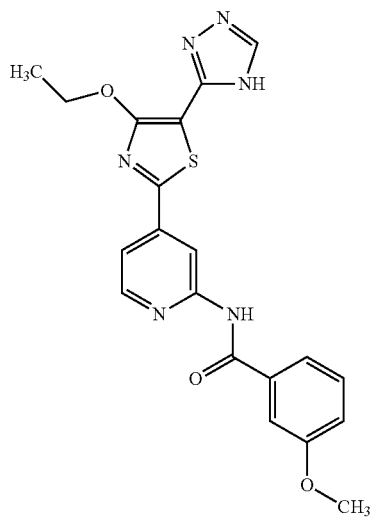
63-B
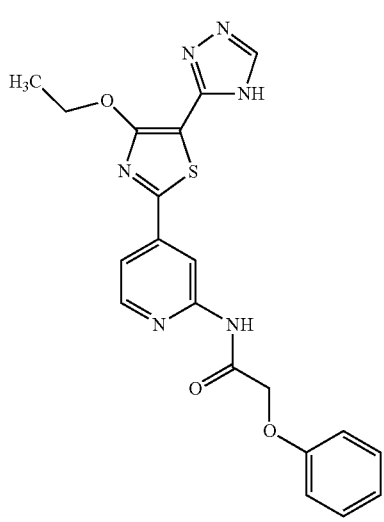
64-B
114
-continued
65-B
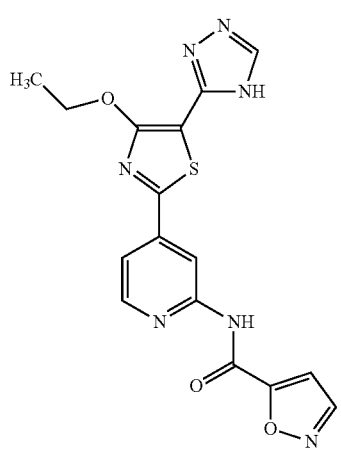
66-B
67-B
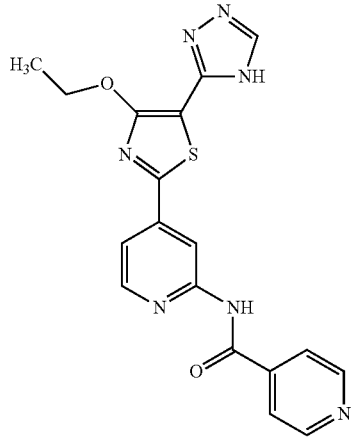

68-B
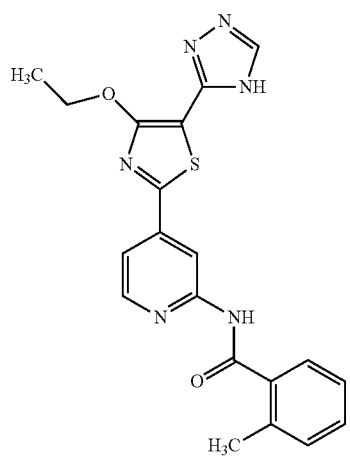
69-B
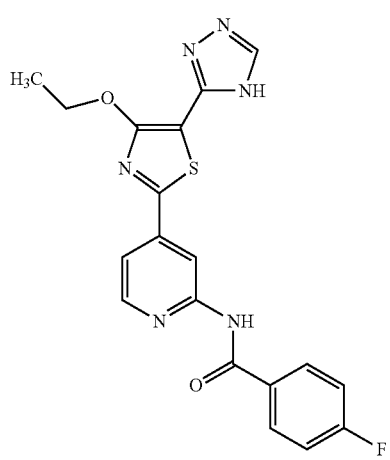
70-B
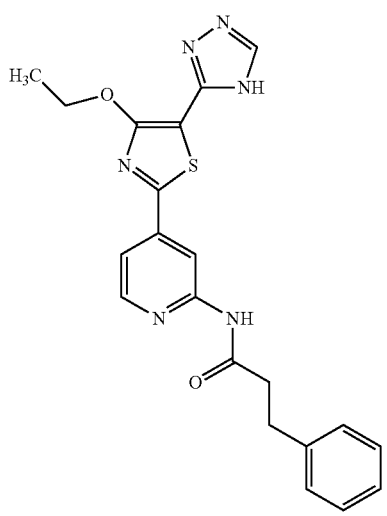
71-B
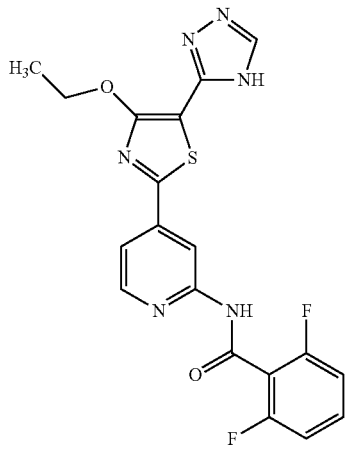
72-B
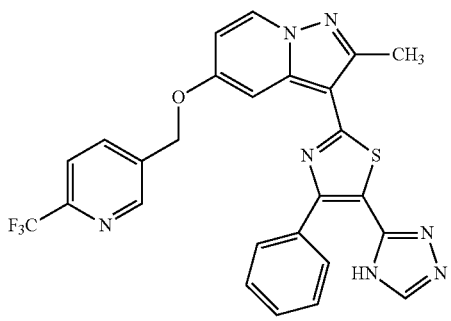
73-B
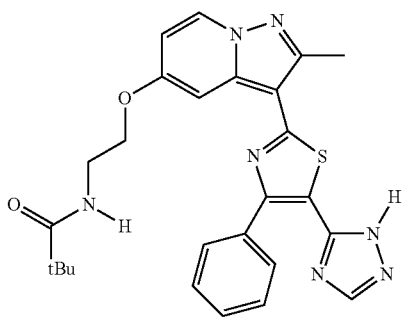
74-B
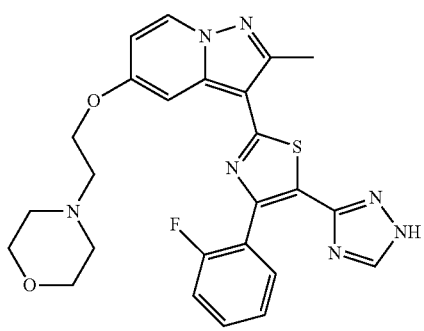

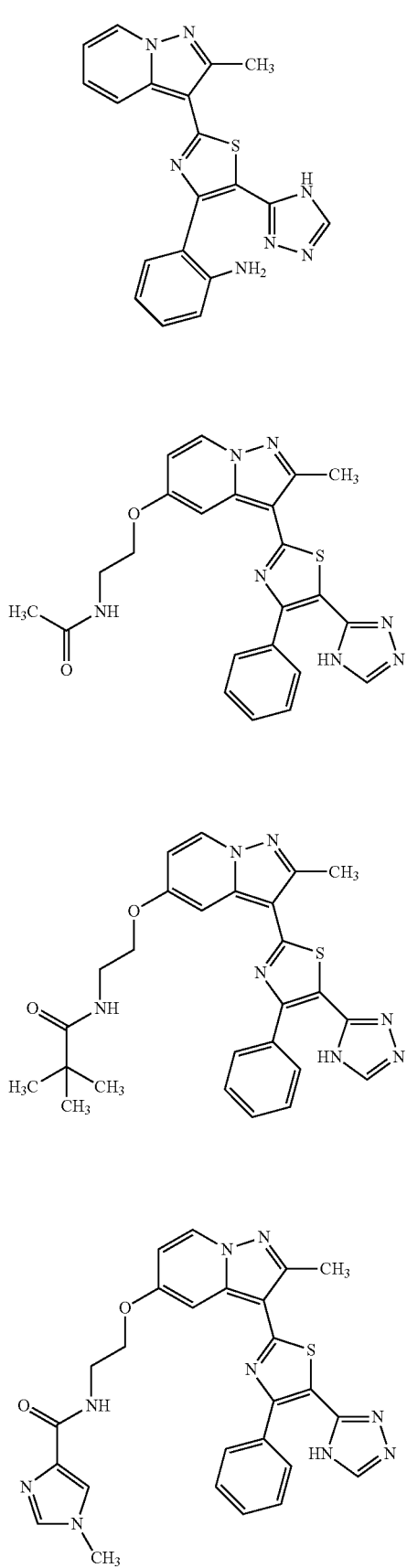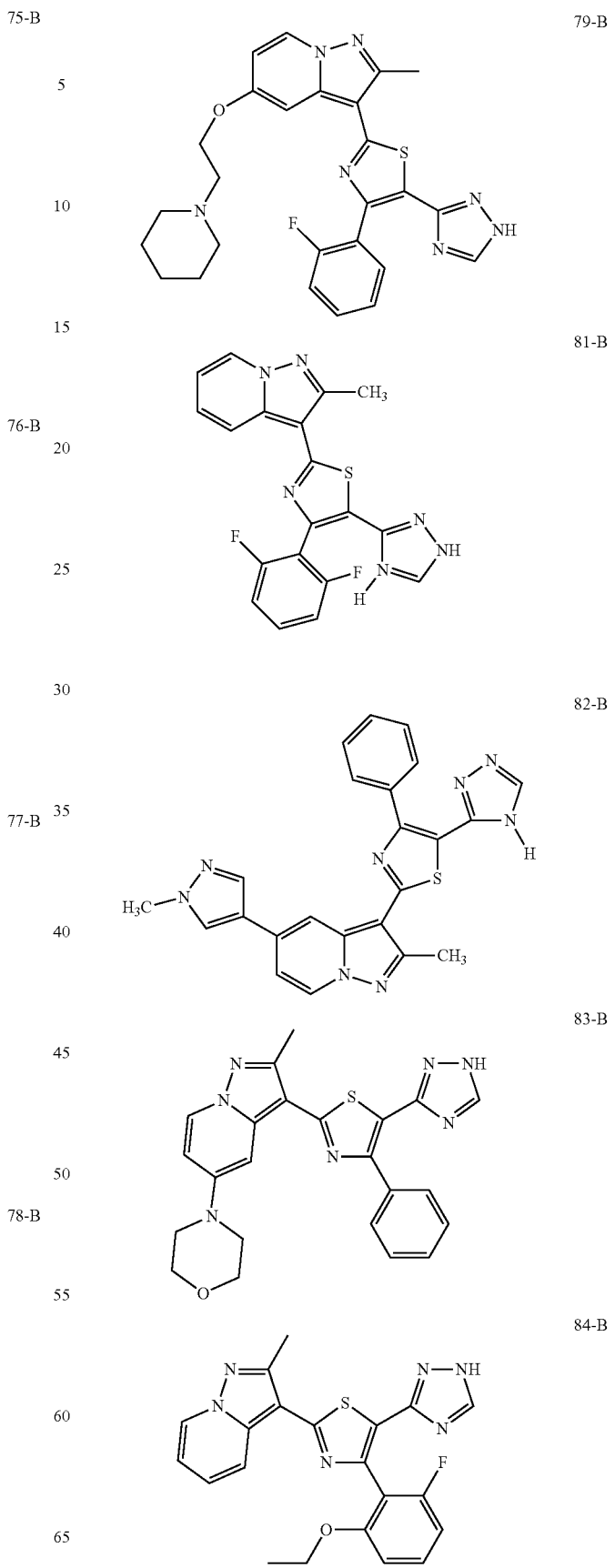

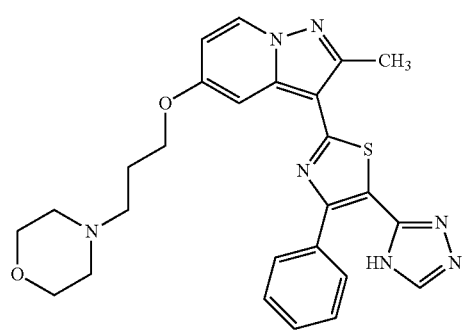
85-B
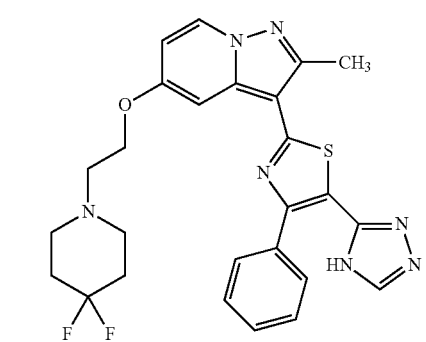
86-B
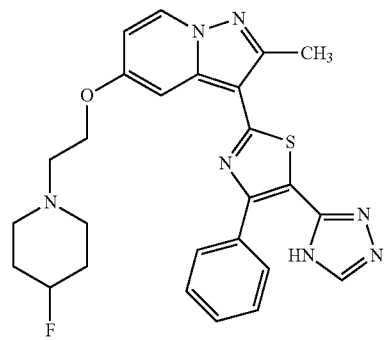
87-B
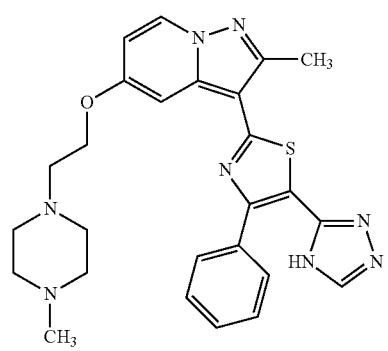
88-B
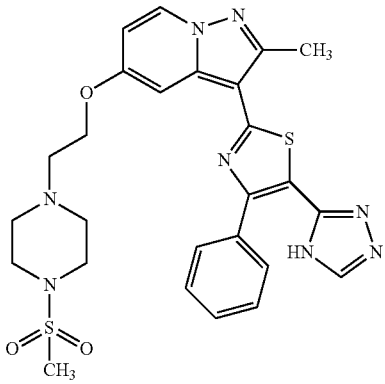
89-B
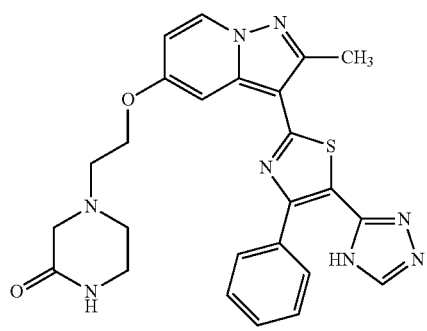
90-B
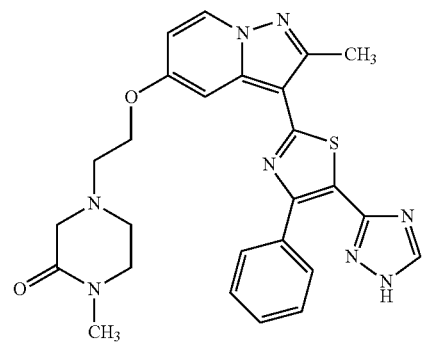
91-B
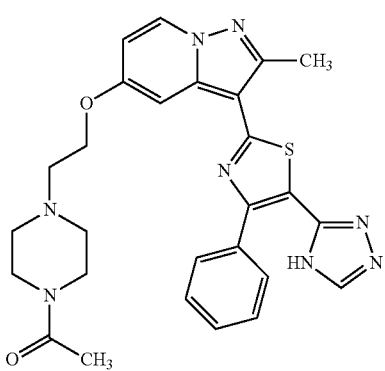
92-B 93-B
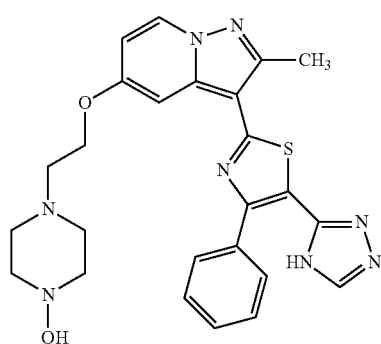
94-B
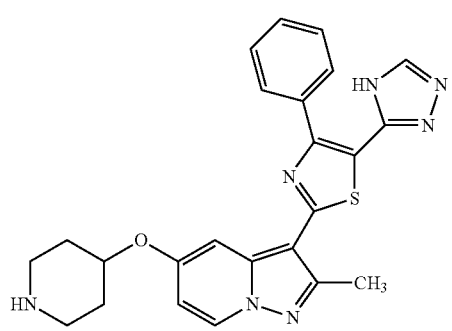
95-B
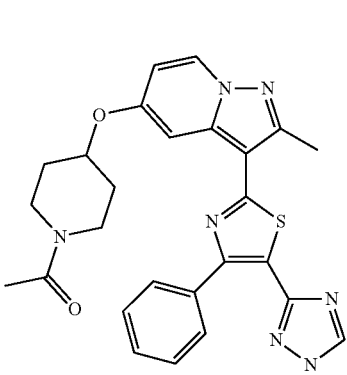
96-B
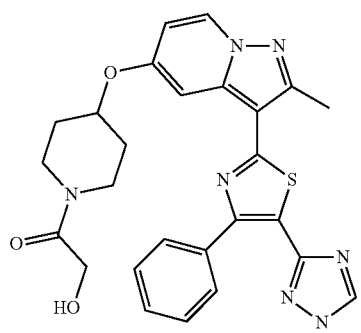
97-B
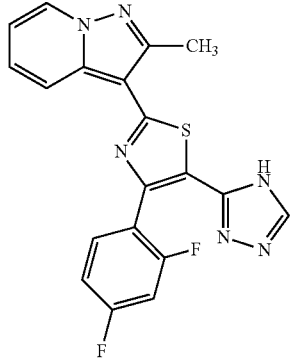
98-B
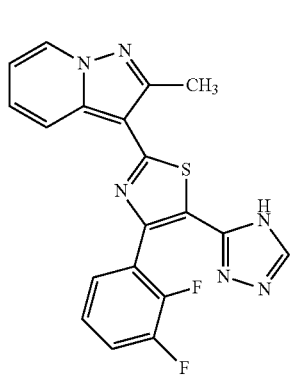
99-B
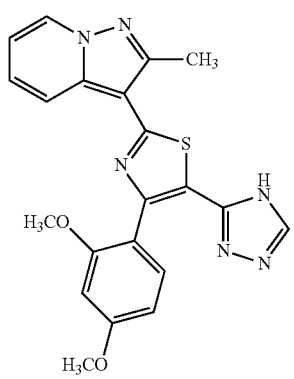
100-B
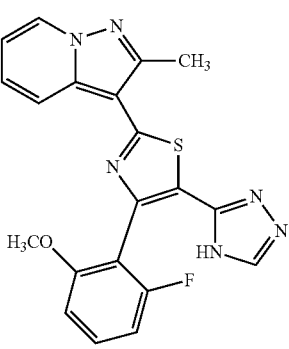

| | |
|---|---|
| 101-B 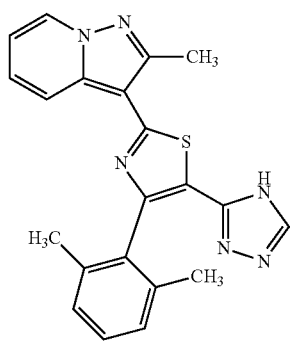 | 105-B 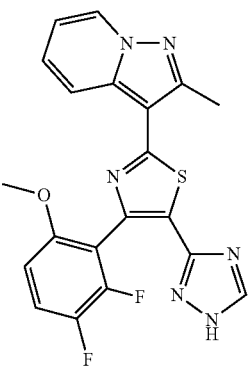 |
| 102-B 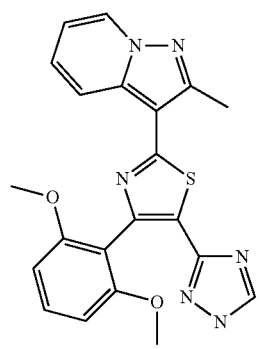 | 106-B 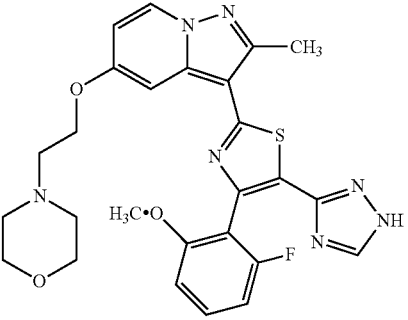 |
| 103-B 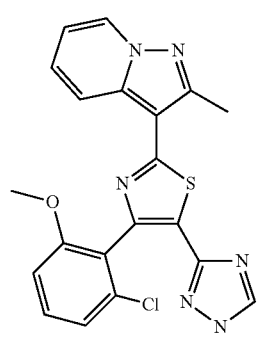 | 107-B 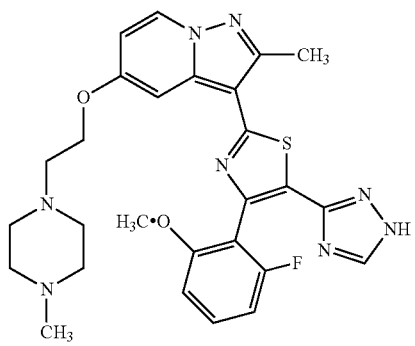 |
| 104-B 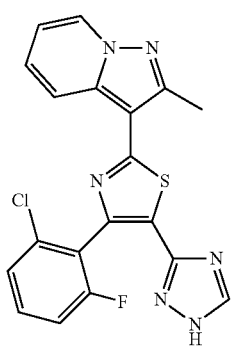 | 108-B 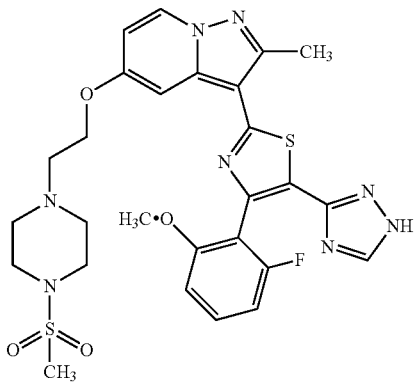 |

125
-continued
109-B
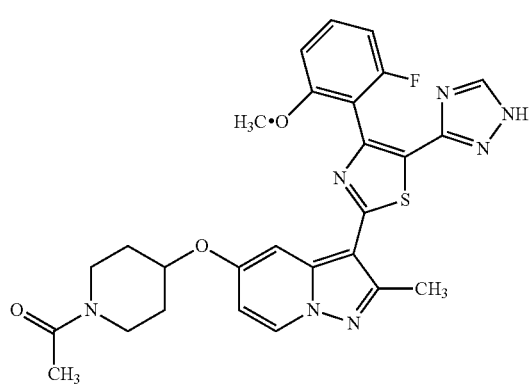
110-B
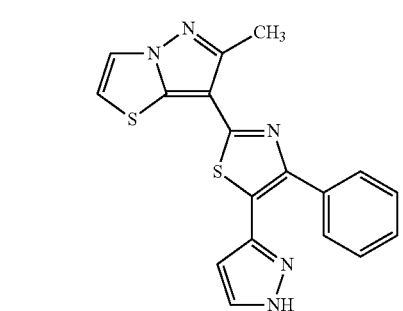
111-B
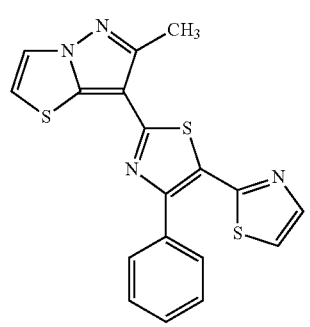
112-B
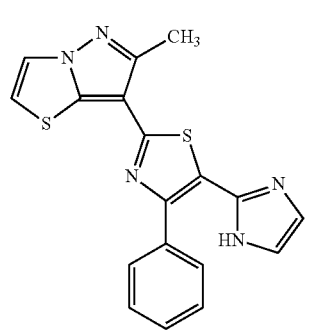
126
-continued
113-B
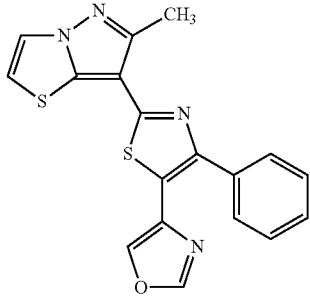
114-B
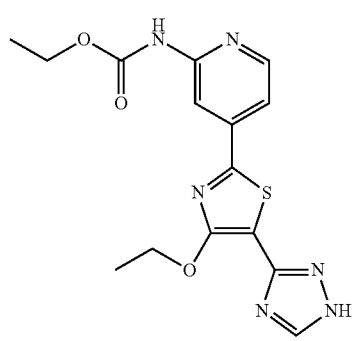
115-B
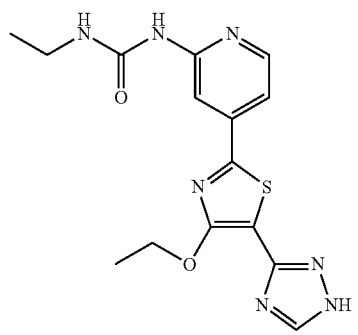
116-B
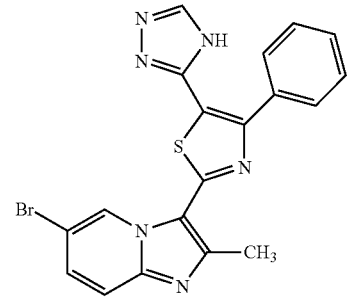
117-B
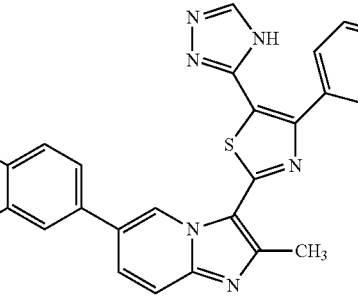

118-B
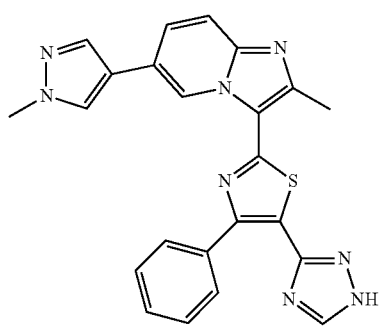
119-B
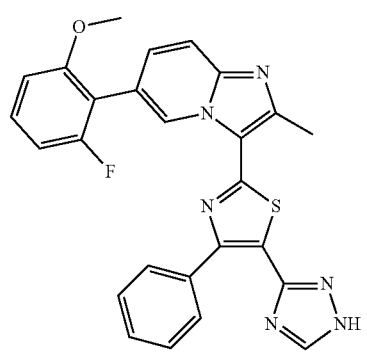
120-B
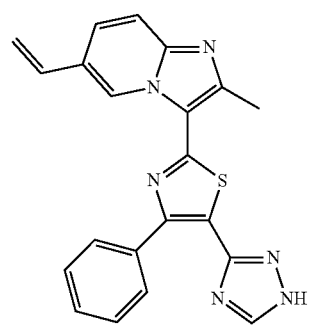
121-B
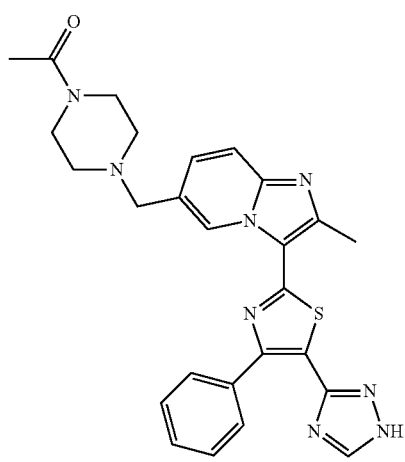
122-B
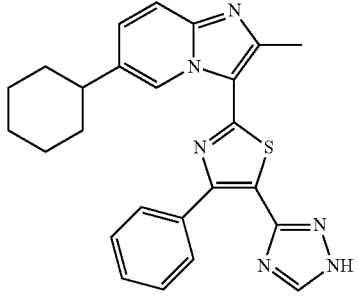
123-B
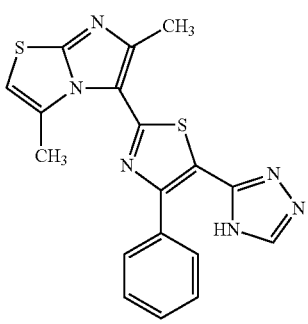
124-B
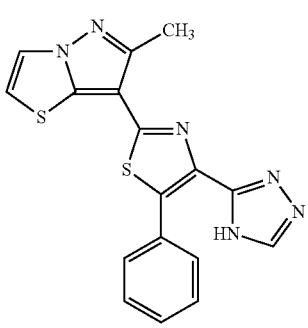
125-B
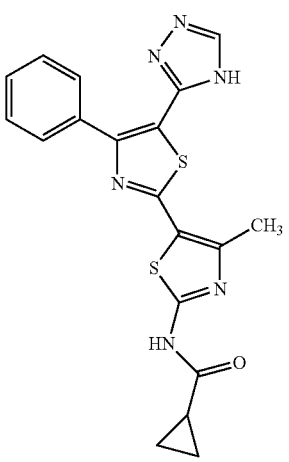

-continued
126-B
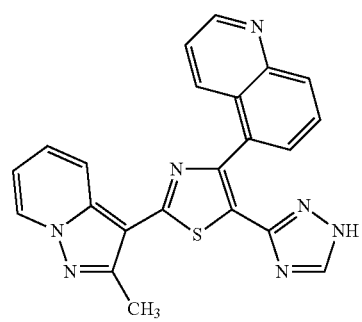
127-B
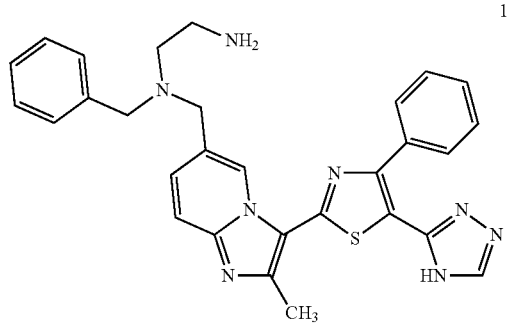
128-B
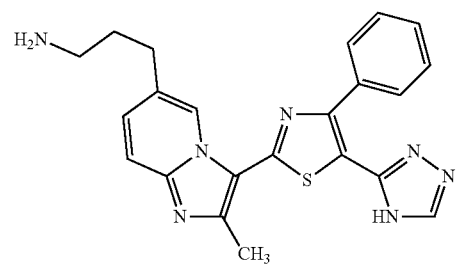
129-B
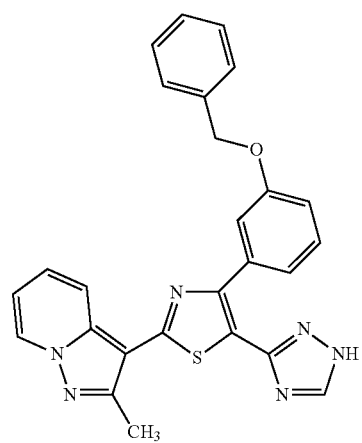
-continued
130-B
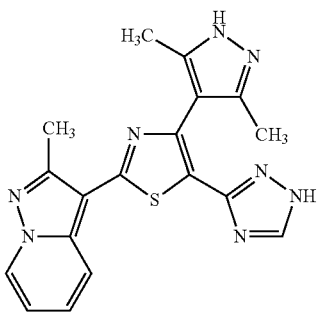
131-B
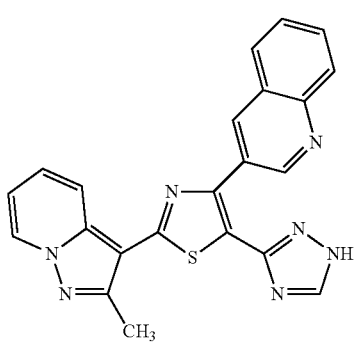
132-B
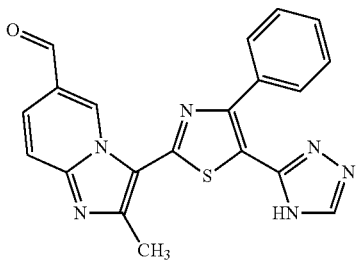
133-B
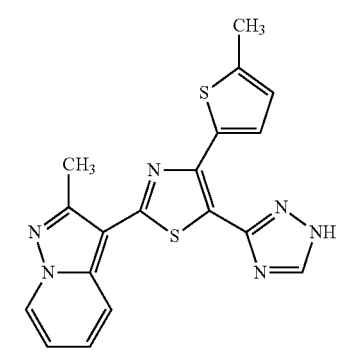
134-B
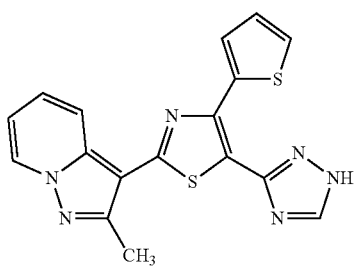

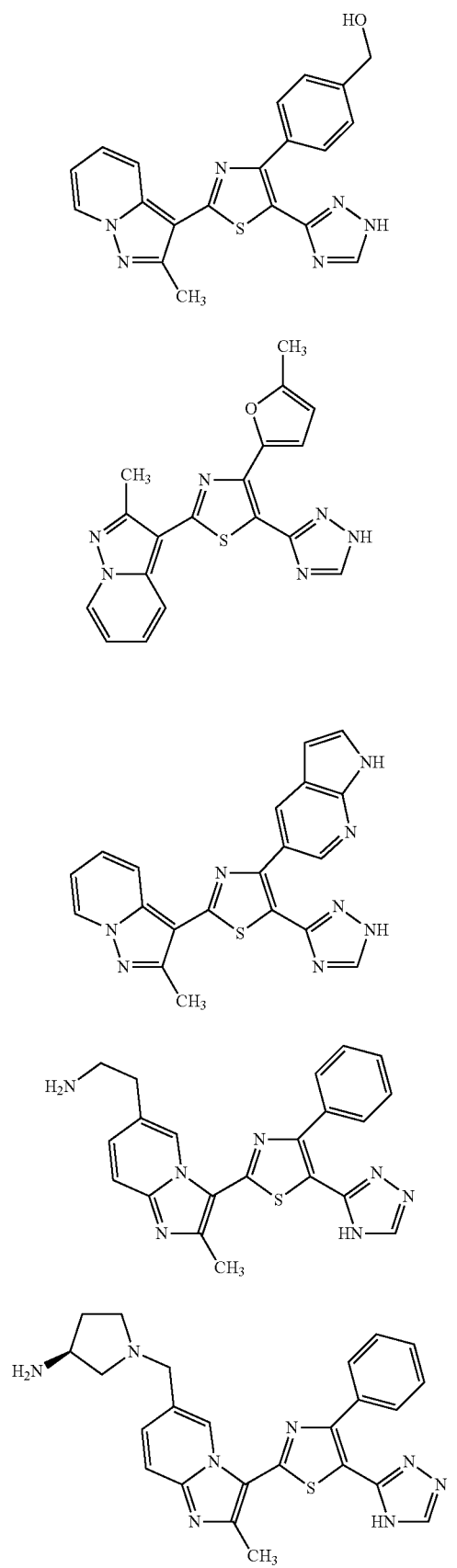
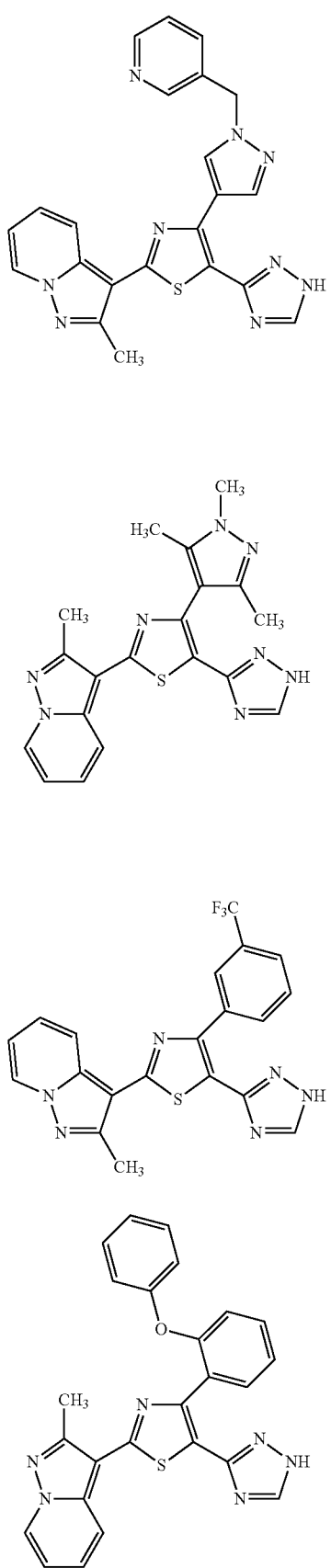

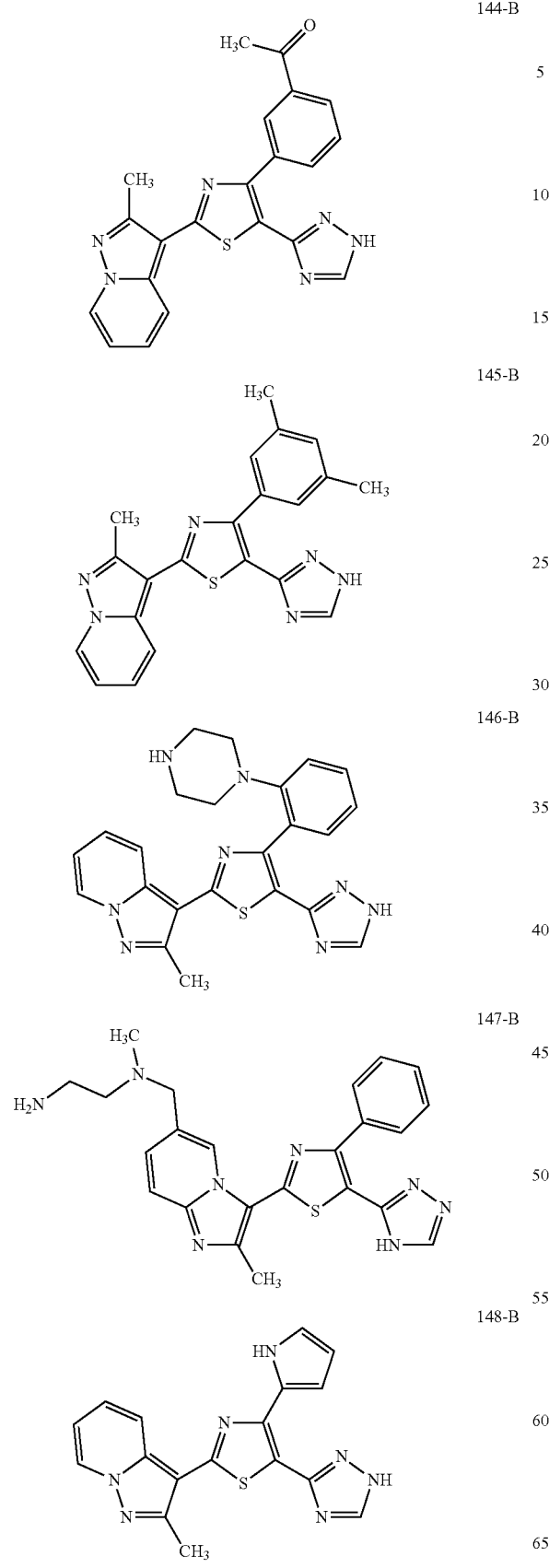
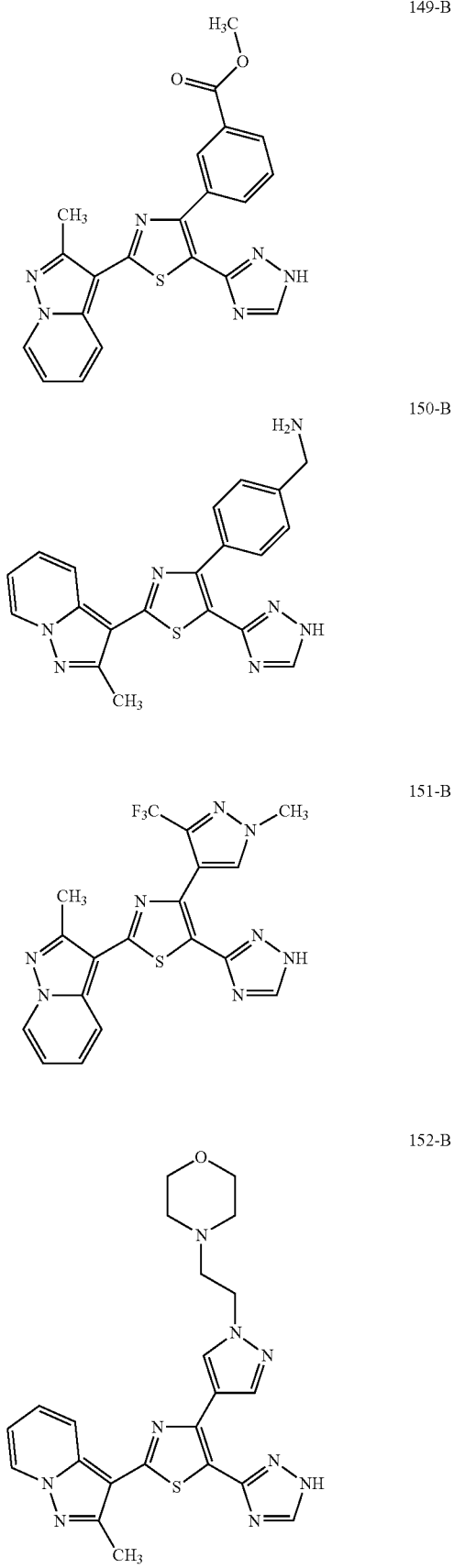

135
-continued
153-B
154-B
155-B
156-B
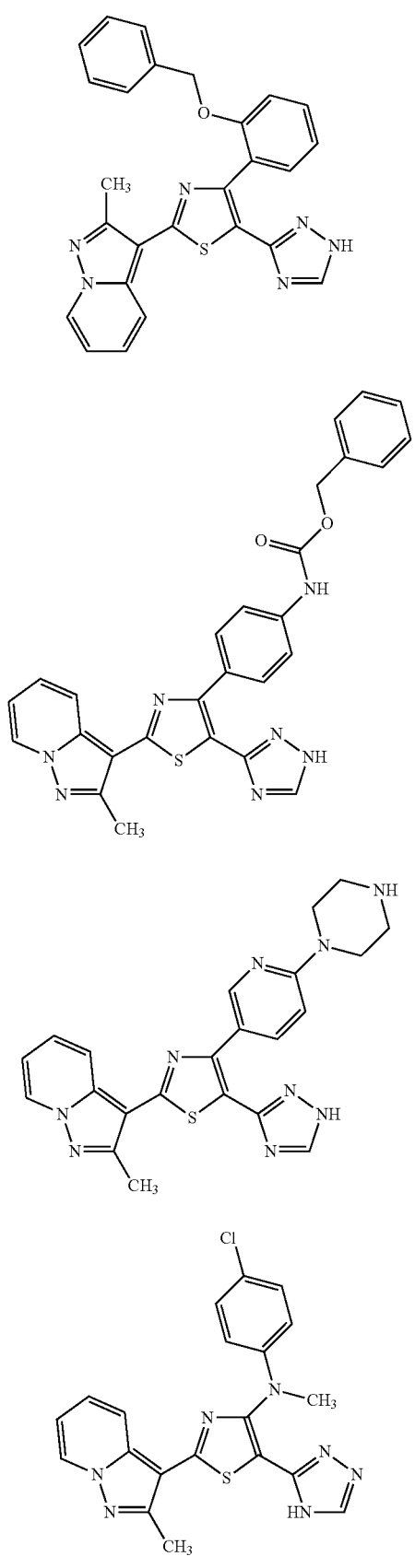
136
-continued
157-B
158-B
159-B
160-B
161-B
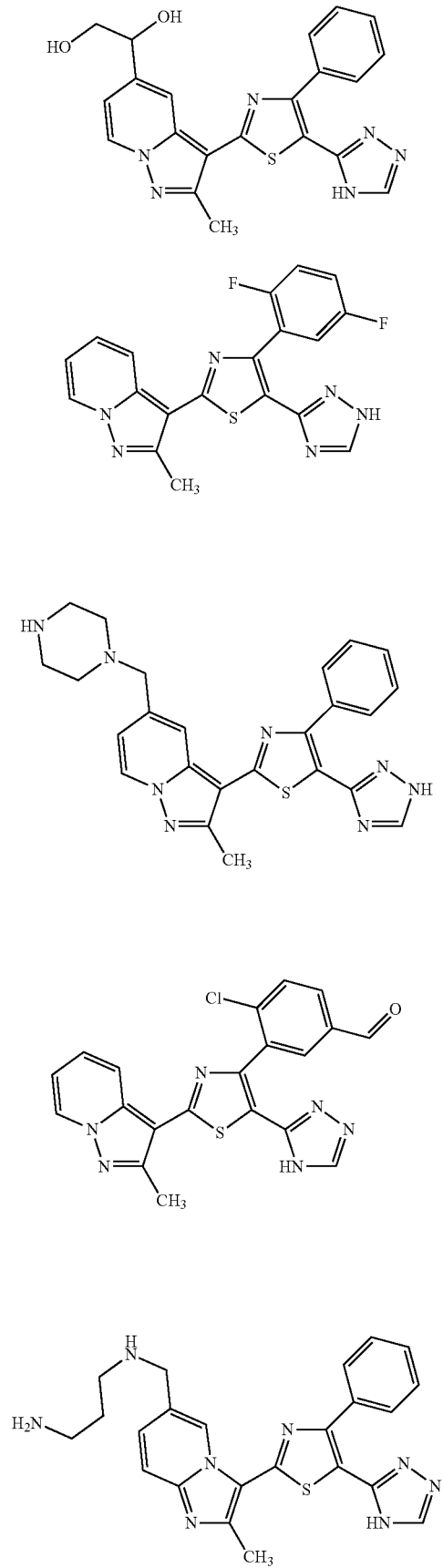

162-B
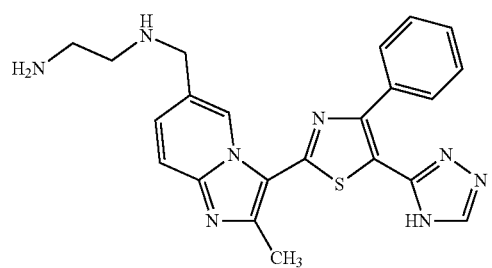
163-B
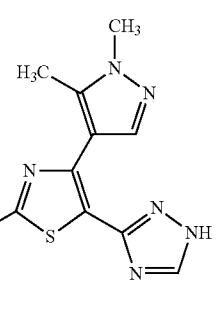
164-B
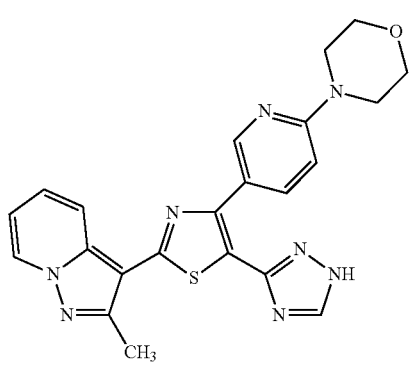
2-C
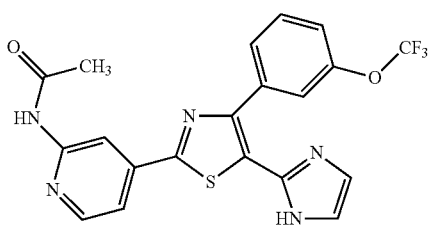
3-C
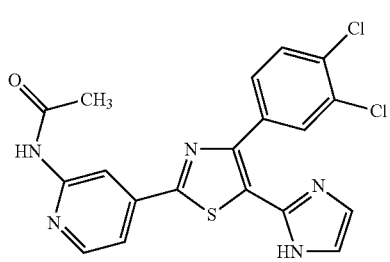
4-C
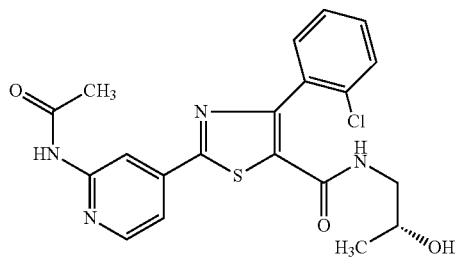
5-C
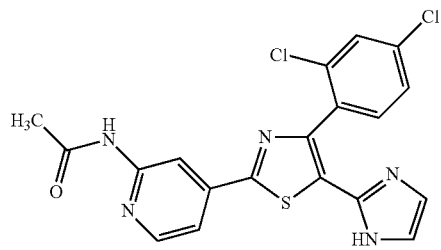
6-C
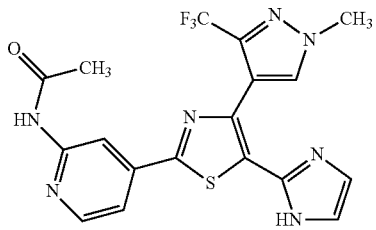
7-C
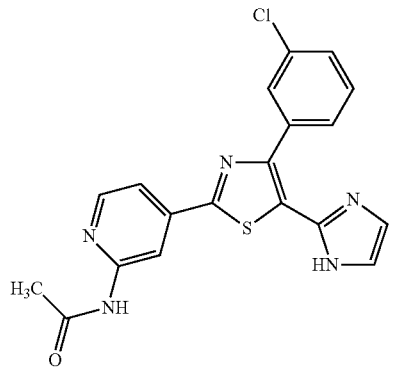
8-C
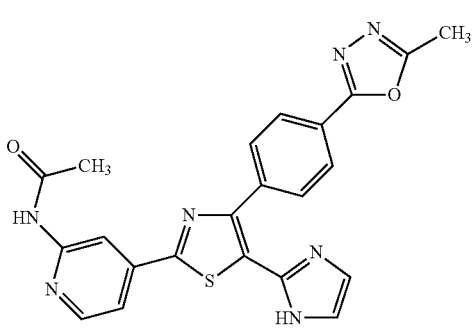

9-C
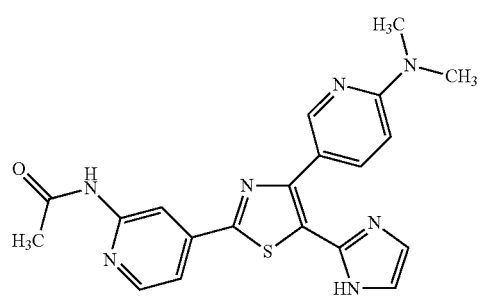
10-C
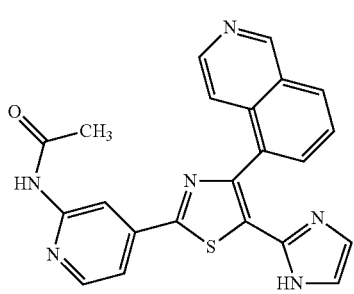
11-C
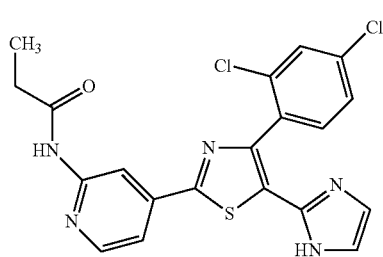
13-C
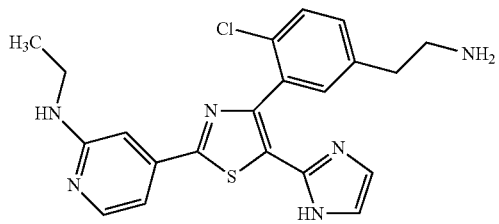
14-C
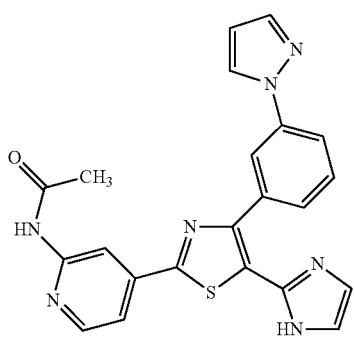
15-C
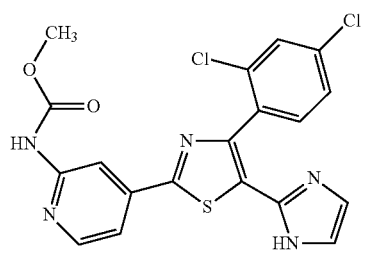
16-C
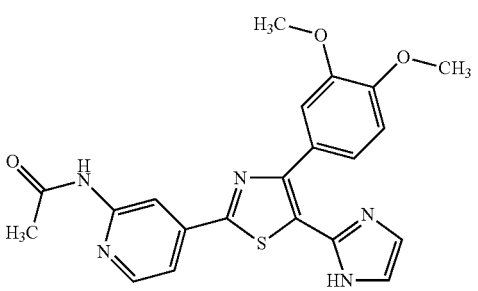
17-C
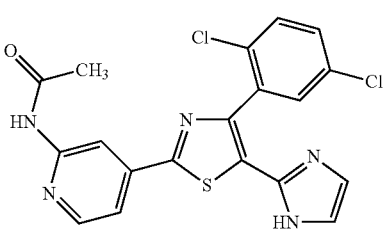
18-C
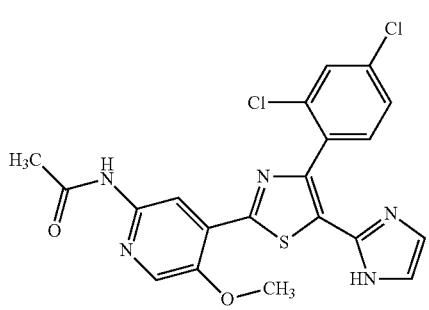
19-C
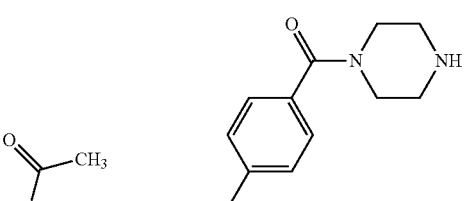
21-C
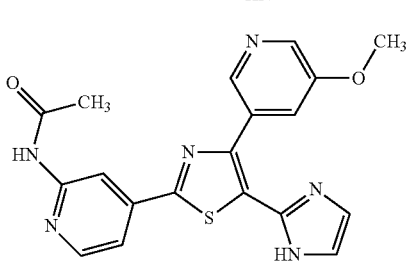

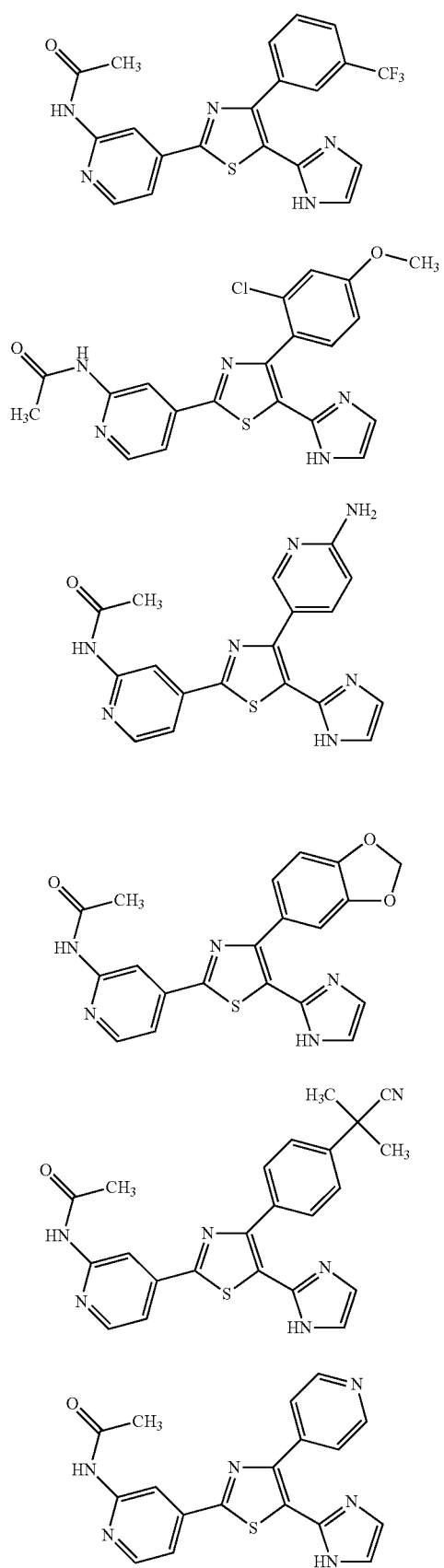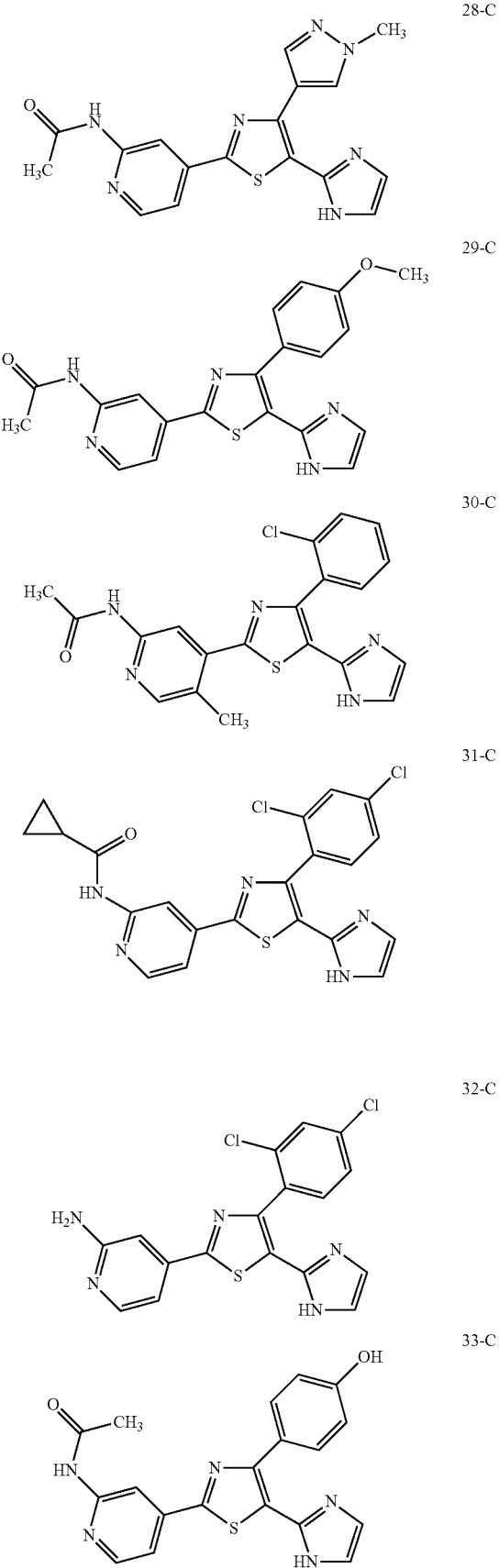

34-C
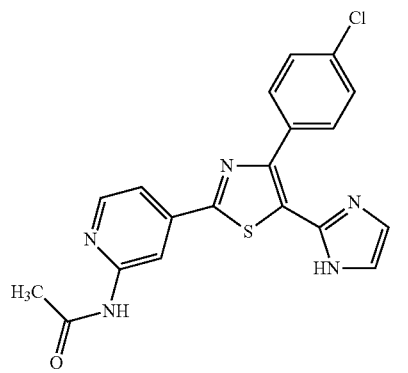
35-C
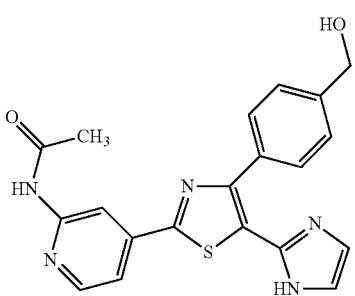
36-C
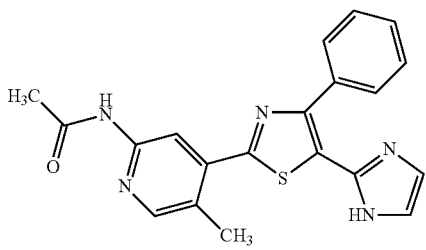
38-C
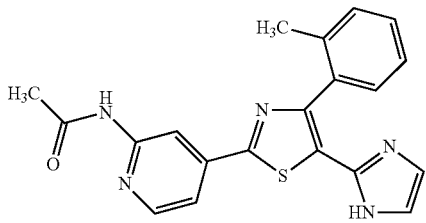
39-C
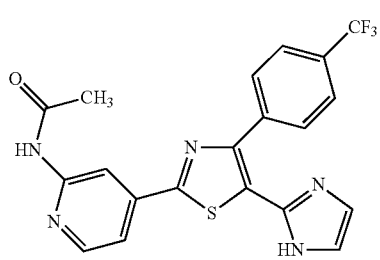
40-C
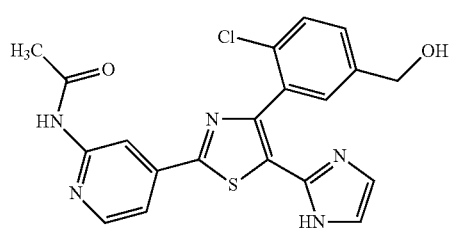
41-C
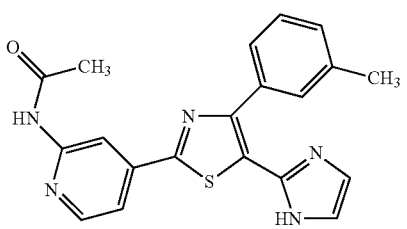
42-C
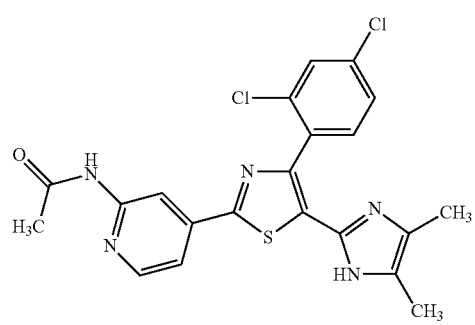
43-C
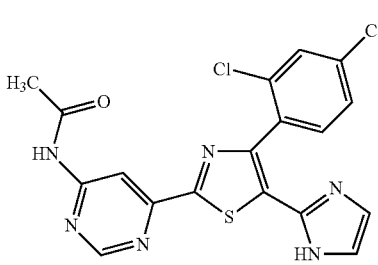
45-C
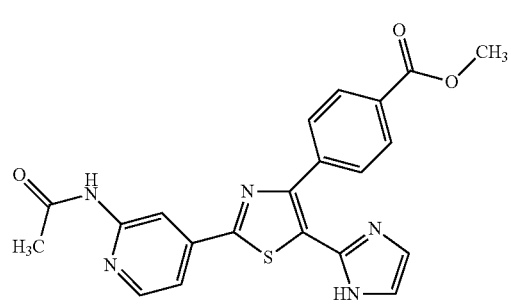
46-C
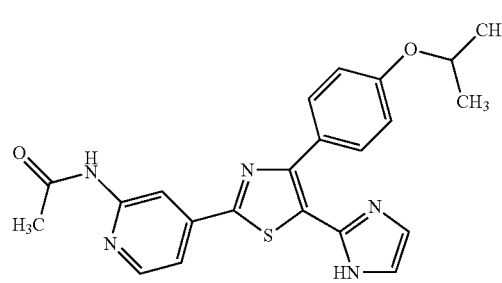
47-C
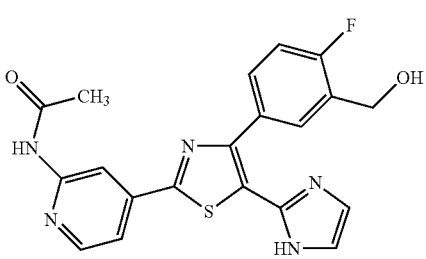

-continued
48-C
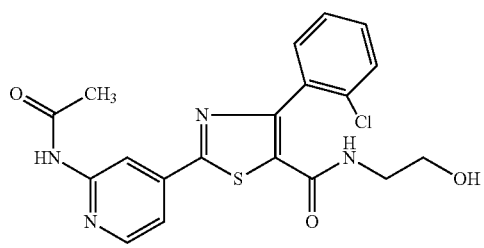
49-C
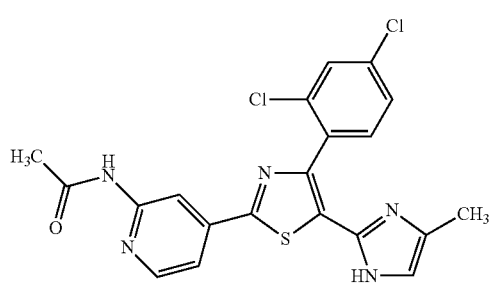
50-C
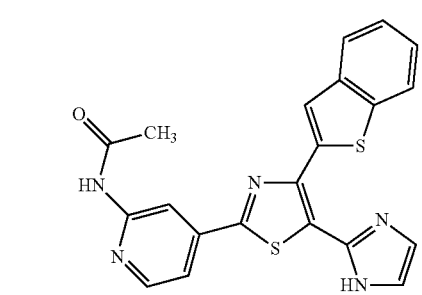
51-C
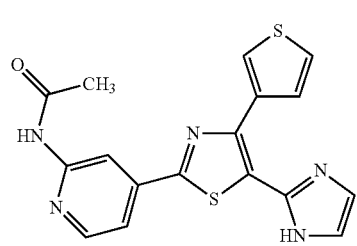
52-C
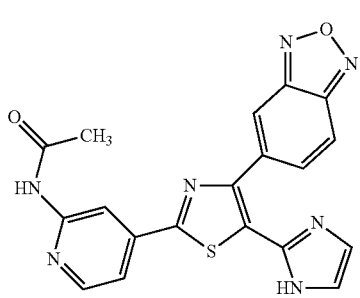
53-C
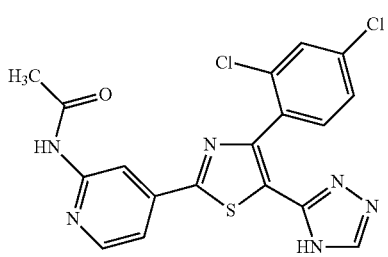
-continued
54-C
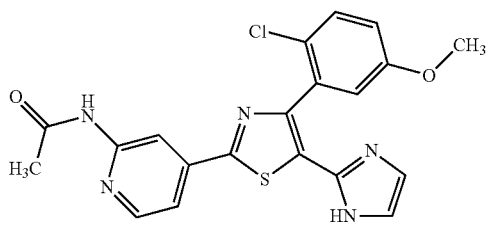
55-C
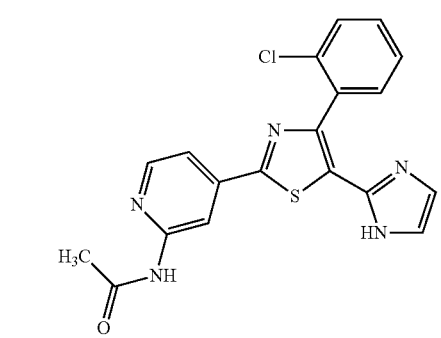
56-C
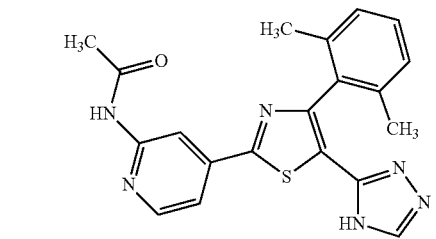
57-C
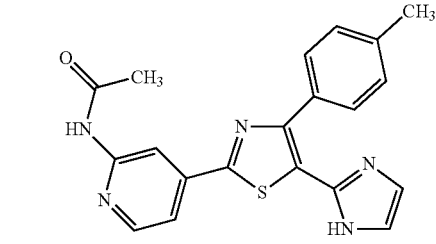
58-C
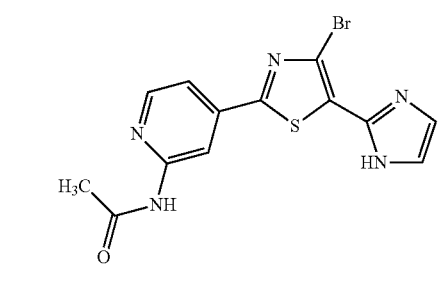

-continued
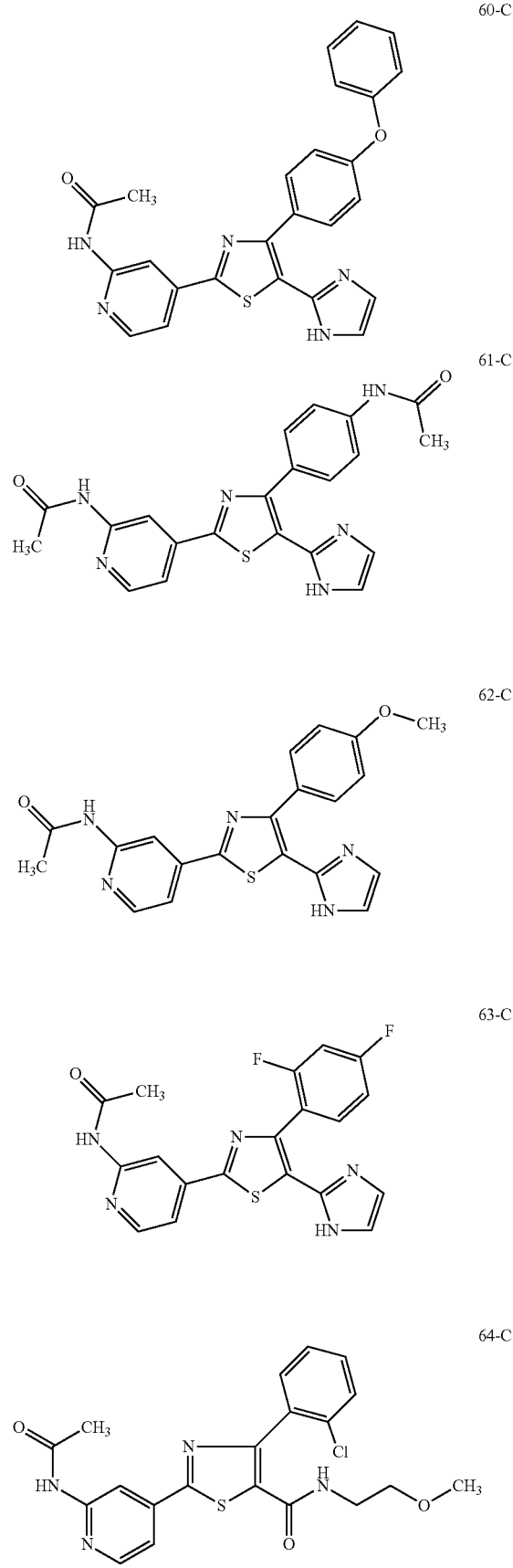
60-C
61-C
62-C
63-C
64-C
-continued
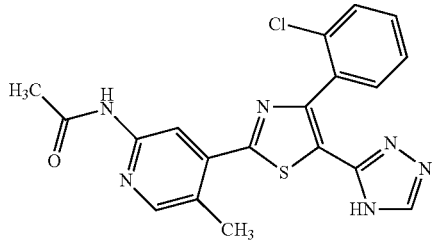
65-C
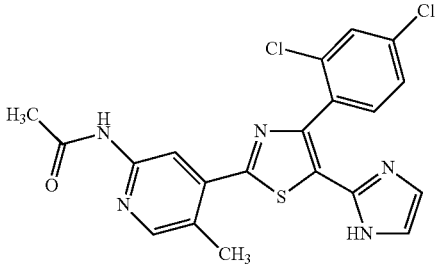
66-C
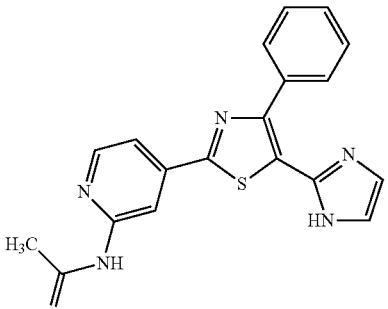
67-C
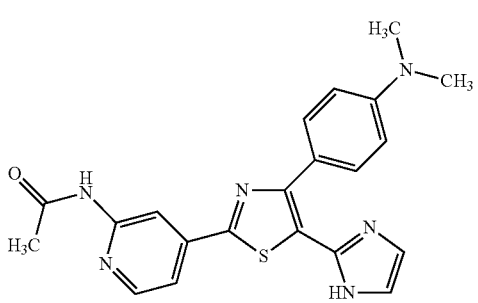
68-C
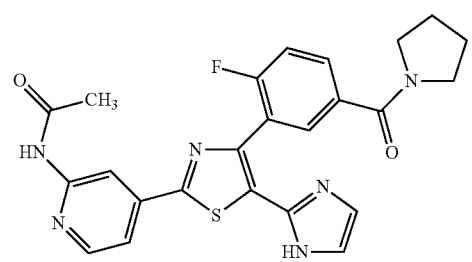
69-C

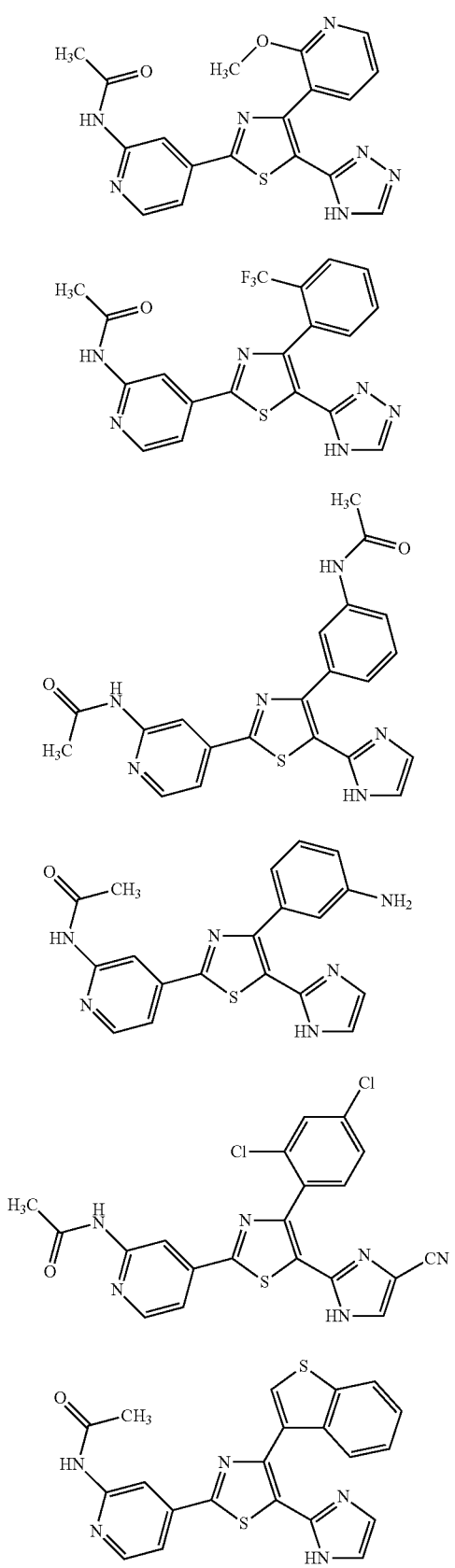
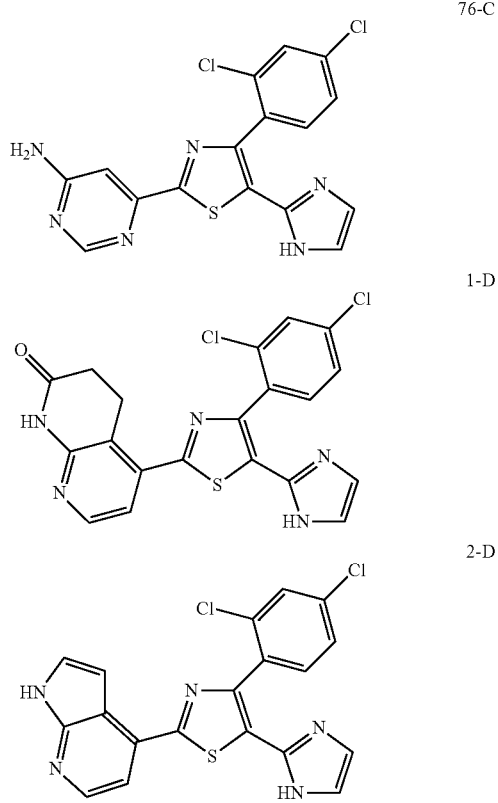
Example 1-B
Production of N-{4-[4-phenyl-5-(4H-1,2,4-triazol-3-yl)-1,3-thiazol-2-yl]pyridin-2-yl}acetamide
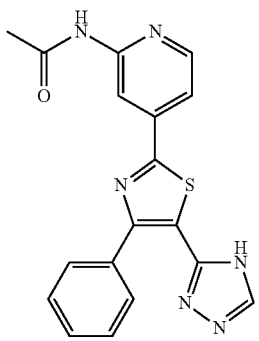 [SMILES: CC(=O)Nc1cc(-c2nc(-c3ccccc3)c(-c3nnc[nH]3)s2)ccn1]

(i) Production of 2-aminopyridine-4-carbothioamide

A mixture of 2-aminopyridine-4-carbonitrile (6.0 g, 50 mmol), O,O'-diethyl dithiophosphate (11 mL, 60 mmol), tetrahydrofuran (25 mL) and water (25 mL) was stirred at 60° C. for 4 hr. To the reaction mixture was added O,O'-diethyl dithiophosphate (2.8 mL, 15 mmol) and the mixture was stirred at 60° C. for 1 day. To the reaction mixture was added aqueous sodium bicarbonate solution, and the mixture was extracted with ethyl acetate. The combined organic layer was washed with saturated brine and dried over anhydrous magnesium sulfate, and the insoluble material was filtered off. The filtrate was concentrated under reduced pressure, and the obtained residue was washed with diisopropyl ether to give the title compound (6.2 g, 81%) as a yellow solid.

$^1$H-NMR (DMSO-$d_6$, 300 MHz) δ 6.12 (2H, s), 6.73 (1H, dd, J=1.7, 5.3 Hz), 6.77-6.81 (1H, m), 7.92 (1H, dd, J=0.6, 5.3 Hz), 9.53 (1H, br s), 9.95 (1H, br s).

(ii) Production of N-(4-carbamothioylpyridin-2-yl)acetamide

A mixture of 2-aminopyridine-4-carbothioamide (2.1 g, 18 mmol) obtained above, acetic anhydride (1.5 mL, 16 mmol) and pyridine (20 mL) was stirred at room temperature for 1 day. The reaction mixture was concentrated under reduced pressure, aqueous sodium bicarbonate solution was added to the obtained residue, and the mixture was extracted with ethyl acetate. The combined organic layer was washed with saturated brine and dried over anhydrous magnesium sulfate, and the insoluble material was filtered off. The filtrate was concentrated under reduced pressure, and the obtained residue was washed with ethyl acetate/diisopropyl ether to give the title compound (2.1 g, 76%) as a yellow solid.

$^1$H-NMR (DMSO-$d_6$, 300 MHz) δ 2.11 (3H, s), 7.29 (1H, dd, J=1.6, 5.2 Hz), 8.33 (1H, d, J=5.2 Hz), 8.36-8.42 (1H, m), 9.72 (1H, br s), 10.13 (1H, br s), 10.60 (1H, s).

(iii) Production of ethyl 2-[2-(acetylamino)pyridin-4-A-4-phenyl-1,3-thiazole-5-carboxylate A mixture of N-(4-carbamothioylpyridin-2-yl)acetamide (980 mg, 5.0 mmol) obtained above, ethyl 2-bromo-3-oxo-3-phenylpropanoate (1.4 g, 5.3 mmol) produced by the method described in K. Tanemura, et al.; Chemical Communications; 4; 2004; 470-471 and acetonitrile (20 mL) was stirred at 80° C. for 4 hr. To the reaction mixture was added aqueous sodium bicarbonate solution, and successively ethyl acetate and tetrahydrofuran, and the insoluble material was filtered off. The filtrate was extracted with a mixed solvent of ethyl acetate/tetrahydrofuran. The combined organic layer was washed with saturated brine and dried over anhydrous magnesium sulfate, and the insoluble material was filtered off. The filtrate was concentrated under reduced pressure, the obtained residue was purified by silica gel column chromatography (ethyl acetate/hexane=50/50→100/0) and the obtained crude product was washed with ethyl acetate/diisopropyl ether to give the title compound (910 mg, 49%) as a colorless solid.

$^1$H-NMR (DMSO-$d_6$, 300 MHz) δ 1.24 (3H, t, J=7.1 Hz), 2.14 (3H, s), 4.27 (2I-1, q, J=7.2 Hz), 7.46-7.53 (3H, m), 7.69 (1H, dd, J=1.7, 5.1 Hz), 7.75-7.84 (2H, m), 8.48 (1H, d, J=5.1 Hz), 8.71-8.75 (1H, m), 10.77 (1H, s).

(iv) Production of 2-[2-(acetylamino)pyridin-4-yl]-4-phenyl-1,3-thiazole-5-carboxylic acid A mixture of ethyl 2-[2-(acetylamino)pyridin-4-yl]-4-phenyl-1,3-thiazole-5-carboxylate (740 mg, 2.0 mmol) obtained above, 1N aqueous sodium hydroxide solution (2.4 mL), methanol (10 mL) and tetrahydrofuran (10 mL) was stirred at room temperature for 1 day. To the reaction mixture was added 1N hydrochloric acid (2.4 mL) and water, and the resulting precipitate was collected by filtration, washed with water and dried to give the title compound (670 mg, 99%) as a colorless solid.

$^1$H-NMR (DMSO-$d_6$, 300 MHz) δ2.14 (3H, s), 7.44-7.53 (3H, m), 7.67 (1H, dd, J=1.7, 5.2 Hz), 7.76-7.85 (2H, m), 8.47 (1H, dd, J=0.8, 5.2 Hz), 8.69-8.73 (1H, m), 10.75 (1H, s).

(v) Production of 2-[2-(acetylamino)pyridin-4-yl]-4-phenyl-1,3-thiazole-5-carboxamide A mixture of 2-[2-(acetylamino)pyridin-4-yl]-4-phenyl-1,3-thiazole-5-carboxylic acid (670 mg, 2.0 mmol) obtained above, ammonium chloride (320 mg, 6.0 mmol), triethylamine (0.84 mL, 6.0 mmol), N-[3-(dimethylamino)propyl]-N'-ethylcarbodiimide hydrochloride (580 mg, 3.0 mmol), 1-hydroxybenzotriazole (410 mg, 3.0 mmol) and N,N-dimethylformamide (20 mL) was stirred at room temperature for 1 day. To the reaction mixture was added water, and the resulting precipitate was collected by filtration, washed with water and diethyl ether and dried. The obtained crude product was suspended in N,N-dimethylformamide (5 mL) in a hot-water bath at 90° C. Water (20 mL) was added, and the mixture was stirred at room temperature. The precipitate was collected by filtration, washed with water and dried to give the title compound (540 mg, 80%) as a colorless solid.

$^1$H-NMR (DMSO-$d_6$, 300 MHz) δ 2.14 (3H, s), 7.41-7.55 (3H, m), 7.65 (1H, dd, J=1.6, 5.2 Hz), 7.78-7.85 (2H, m), 7.87 (1H, br s), 7.96 (1H, br s), 8.47 (1H, dd, J=0.8, 5.2 Hz), 8.68-8.73 (1H, m), 10.75 (1H, s).

(vi) Production of N-{-4-[4-phenyl-5-(4H-1,2,4-triazol-3-yl)-1,3-thiazol-2-yl]pyridin-2-yl}acetamide 2-[2-(Acetylamino)pyridin-4-yl]-4-phenyl-1,3-thiazole-5-carboxamide (630 mg, 1.9 mmol) obtained above was suspended in N,N-dimethylformamide dimethyl acetal (10 mL), and the mixture was stirred at 100° C. for 4 hr. The reaction mixture was concentrated under reduced pressure, hydrazine monohydrate (0.45 mL, 9.3 mmol) and acetic acid (10 mL) were added to the obtained residue, and the mixture was stirred at 100° C. for 1 hr. The reaction mixture was concentrated under reduced pressure, aqueous sodium bicarbonate solution was added to the obtained residue, and the precipitate was collected by filtration. The obtained solid was washed with water and diethyl ether and dried. The obtained crude product was purified by silica gel column chromatography (methanol/ethyl acetate=0/100→50/50), washed with water and dried to give the title compound (360 mg, 53%) as a colorless solid.

¹H-NMR (DMSO-d₆, 300 MHz) δ 2.14 (3H, s), 7.38-7.50 (3H, m), 7.67 (1H, dd, J=1.6, 5.2 Hz), 7.80-7.90 (2H, m), 8.47 (1H, dd, J=0.7, 5.2 Hz), 8.70 (1H, s), 8.71-8.74 (1H, m), 10.73 (1H, s), 14.37 (1H, s).

Example 2-B

Production of 4-[4-phenyl-5-(4H-1,2,4-triazol-3-yl)-1,3-thiazol-2-yl]pyridin-2-amine

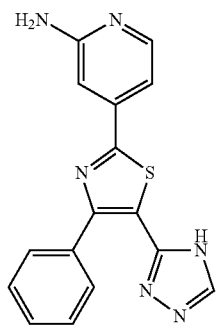 [SMILES: Nc1cc(-c2nc(-c3ccccc3)c(-c3nnc[nH]3)s2)ccn1]

A mixture of N-{4-[4-phenyl-5-(4H-1,2,4-triazol-3-yl)-1,3-thiazol-2-yl]pyridin-2-yl}acetamide (250 mg, 0.70 mmol) produced in Example 1-B (vi), 1N aqueous sodium hydroxide solution (3.5 mL), methanol (5 mL) and tetrahydrofuran (5 mL) was stirred at 60° C. for 3 hr. To the reaction mixture was added 1N aqueous sodium hydroxide solution (3.5 mL), and the mixture was stirred at 60° C. for 1 hr. The reaction mixture was neutralized with 1N hydrochloric acid, and concentrated under reduced pressure. The resulting precipitate was collected by filtration, washed with water and diethyl ether and dried to give the title compound (130 mg, 58%) as a yellow solid.

¹H-NMR (DMSO-d₆, 300 MHz) δ 7.38 (1H, dd, J=1.7, 6.6 Hz), 7.41-7.50 (3H, m), 7.60 (1H, s), 7.78-7.91 (2H, m), 8.15 (2H, br s), 8.09 (1H, d, J=6.6 Hz), 8.71 (1H, br s), 14.51 (1H, br s).

Example 3-B

Production of N-{4-[4-phenyl-5-(4H-1,2,4-triazol-3-yl)-1,3-thiazol-2-yl]pyridin-2-yl}cyclopropanecarboxamide

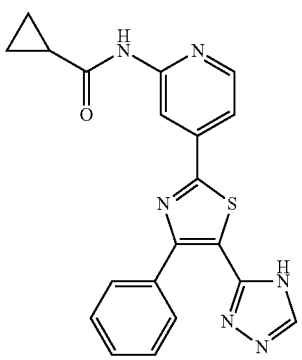 [SMILES: O=C(Nc1cc(-c2nc(-c3ccccc3)c(-c3nnc[nH]3)s2)ccn1)C1CC1]

A mixture of 4-[4-phenyl-5-(4H-1,2,4-triazol-3-yl)-1,3-thiazol-2-yl]pyridin-2-amine (150 mg, 0.47 mmol) produced in Example 2, cyclopropanecarbonyl chloride (0.13 mL, 1.40 mmol) and pyridine (5 mL) was stirred at room temperature for 6 hr. To the reaction mixture was added cyclopropanecarbonyl chloride (0.085 mL, 0.94 mmol) and the mixture was stirred at room temperature for 1 day. To the reaction mixture was added aqueous sodium bicarbonate solution, and the mixture was extracted with ethyl acetate. The combined organic layer was washed with saturated brine and dried over anhydrous magnesium sulfate, and the insoluble material was filtered off. The obtained residue was purified by silica gel column chromatography (ethyl acetate/hexane=20/80→100/0), and 1N aqueous sodium hydroxide solution (0.5 mL), methanol (5 mL) and tetrahydrofuran (10 mL) were added to the crude product. The mixture was stirred at room temperature for 1 hr. The reaction mixture was concentrated under reduced pressure, and water was added to the obtained residue. After neutralization with 1N hydrochloric acid, the resulting precipitate was collected by filtration, washed with water and diethyl ether and dried to give the title compound (145 mg, 80%) as a pale-yellow solid.

¹H-NMR (DMSO-d₆, 300 MHz) δ 0.79-0.93 (4H, m), 2.00-2.12 (1H, m), 7.38-7.49 (3H, m), 7.67 (1H, dd, J=1.6, 5.2 Hz), 7.80-7.90 (2H, m), 8.47 (1H, dd, J=0.8, 5.2 Hz), 8.63 (1H, s), 8.73-8.76 (1H, m), 11.05 (1H, s), 14.36 (1H, br s).

Example 4-B

Production of 3-morpholin-4-yl-N-{4-[4-phenyl-5-(4H-1,2,4-triazol-3-yl)-1,3-thiazol-2-yl]pyridin-2-yl}propanamide

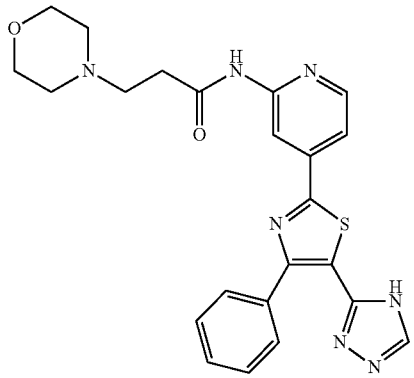 [SMILES: O=C(CCN1CCOCC1)Nc1cc(-c2nc(-c3ccccc3)c(-c3nnc[nH]3)s2)ccn1]

(i) Production of N-(4-{4-phenyl-5-[1-(tetrahydro-2H-pyran-2-yl)-1H-1,2,4-triazol-3-yl]-1,3-thiazol-2-yl}pyridin-2-yl)acetamide To a solution of N-{4-[4-phenyl-5-(4H-1,2,4-triazol-3-yl)-1,3-thiazol-2-yl]pyridin-2-yl}acetamide (65 mg, 0.18 mmol) produced in Example 1-B (vi) in tetrahydrofuran (3.0 mL) were added p-toluenesulfonic acid monohydrate (41 mg, 0.22 mmol) and 3,4-dihydro-2H-pyran (140 mg, 1.7 mmol), and the mixture was heated under reflux for 3 hr. The reaction mixture was cooled to room temperature, diluted with ethyl acetate (40 mL), and washed with saturated aqueous sodium bicarbonate solution (30 mL). The aqueous layer was extracted with ethyl acetate (40 mL), the combined organic layer was dried over anhydrous magnesium sulfate, and the insoluble material was filtered off. The filtrate was concentrated under reduced pressure, and the obtained residue was purified by silica gel column chromatography (ethyl acetate/hexane=20/80→100/0) to give the title compound (71.0 mg, 88%) as a white solid.

$^1$H-NMR (CDCl$_3$, 300 MHz) δ 1.54-1.84 (3H, m), 1.89-2.18 (3H, m), 2.24 (3H, s), 3.60-3.85 (1H, m), 3.98-4.11 (1H, m), 5.48 (1H, dd, J=3.4, 8.1 Hz), 7.32-7.47 (3H, m), 7.72 (1H, dd, J=1.6 Hz, 5.2 Hz), 7.82-7.99 (2H, m), 8.28 (1H, s), 8.35 (1H, d, J=5.2 Hz), 8.79 (2H, br s).

(ii) Production of 4-{4-phenyl-5-[1-(tetrahydro-2H-pyran-2-yl)-1H-1,2,4-triazol-3-yl]-1,3-thiazol-2-yl}pyridin-2-amine To N-(4-{4-phenyl-5-[1-(tetrahydro-2H-pyran-2-yl)-1H-1,2,4-triazol-3-yl]-1,3-thiazol-2-yl}pyridin-2-yl)acetamide (2.0 g, 4.4 mmol) prepared in the same manner as above in a mixed solvent (88 mL) of tetrahydrofuran/methanol (1:1) was added 1N aqueous sodium hydroxide solution (44 mL, 44.0 mmol), and the mixture was stirred at 60° C. for 3 hr. The reaction solution was cooled to room temperature, and diluted with ethyl acetate (300 mL) and water (150 mL). The aqueous layer was separated and extracted with ethyl acetate (200 mL), and the combined organic layer was dried over anhydrous magnesium sulfate. The insoluble material was filtered off, and the filtrate was concentrated under reduced pressure. The obtained solid was washed with diethyl ether (25 mL) and hexane (25 mL) to give the title compound (1.6 g, 87%) as a pale-yellow solid.

$^1$H-NMR (DMSO-d$_6$, 300 MHz) δ 1.47-1.70 (3H, m), 1.88-2.10 (3H, m), 3.59-3.72 (1H, m), 3.84-4.01 (1H, m), 5.61 (1H, dd, J=3.3 Hz, 8.4 Hz), 6.26 (2H, s), 7.03 (1H, dd, J=1.5 Hz, 5.1 Hz), 7.08 (1H, d, J=0.9 Hz), 7.38-7.49 (3H, m), 7.77-7.87 (2H, m), 8.06 (1H, d, J=5.1 Hz), 8.82 (1H, s).

(iii) Production of N-(4-{4-phenyl-5-[1-(tetrahydro-2H-pyran-2-yl)-1H-1,2,4-triazol-3-yl]-1,3-thiazol-2-yl}pyridin-2-yl)prop-2-enamide To a solution of 4-{4-phenyl-5-[1-(tetrahydro-2H-pyran-2-yl)-1H-1,2,4-triazol-3-yl]-1,3-thiazol-2-yl}pyridin-2-amine (680 mg, 1.7 mmol) produced in the above step in tetrahydrofuran (17 mL) were added triethylamine (190 mg, 1.9 mmol) and prop-2-enoyl chloride (770 mg, 8.5 mmol) at −78° C., and the mixture was stirred at the same temperature for 2 hr. The reaction mixture was warmed to 0° C., saturated aqueous sodium bicarbonate solution (50 mL) was added, and the mixture was stirred at room temperature for 12 hr. To the reaction mixture was further added saturated aqueous sodium bicarbonate solution (50 mL), and the mixture was stirred at room temperature for 3 hr. The aqueous layer was extracted with ethyl acetate (100 mL×2), the combined organic layer was dried over anhydrous magnesium sulfate, and the insoluble material was filtered off. The filtrate was concentrated under reduced pressure, and the residue was purified by silica gel column chromatography (ethyl acetate/hexane=20/80→100/0) to give the title compound (400 mg, 51%) as a yellow solid.

$^1$H-NMR (DMSO-d$_6$, 300 MHz) δ 1.45-1.74 (3H, m), 1.84-2.15 (3H, m), 3.62-3.72 (1H, m), 3.85-3.96 (1H, m), 5.62 (1H, dd, J=3.3 Hz, 8.4 Hz), 5.76-5.92 (1H, m), 6.36 (1H, dd, J=1.9, 17.0 Hz), 6.55-6.74 (1H, m), 7.38-7.53 (3H, m), 7.67-7.77 (1H, m), 7.82-7.93 (2H, m), 8.47-8.55 (1H, m), 8.82-8.93 (2H, m), 11.0 (1H, s).

(iv) Production of 3-morpholin-4-yl-N-{4-[4-phenyl-5-(4H-1,2,4-triazol-3-yl)-1,3-thiazol-2-yl]pyridin-2-yl}propanamide To a solution of N-(4-{4-phenyl-5-[1-(tetrahydro-2H-pyran-2-yl)-1H-1,2,4-triazol-3-yl]-1,3-thiazol-2-yl}pyridin-2-yl)prop-2-enamide (70 mg, 0.15 mmol) produced in the above in tetrahydrofuran (1.5 mL) was added morpholine (140 mg, 1.50 mmol), and the mixture was heated under reflux for 2 hr. The reaction mixture was cooled to room temperature and the solvent was evaporated under reduced pressure. The obtained residue was dissolved in trifluoroacetic acid (1.5 mL), and the mixture was stirred at room temperature for 3 hr. The reaction mixture was diluted with tetrahydrofuran (5.0 mL) and water (10 mL), and 25% aqueous ammonia (5.0 mL) was added. The aqueous layer was extracted with ethyl acetate (30 mL×2), and the combined organic layer was dried over anhydrous magnesium sulfate. The insoluble material was filtered off, the filtrate was concentrated under reduced pressure, and the obtained residue was purified by basic silica gel column chromatography (methanol/ethyl acetate=0/100→10/90) to give the title compound (50 mg, 72%) as a white solid.

$^1$H-NMR (DMSO-d$_6$, 300 MHz) δ 2.37-2.46 (4H, m), 2.57-2.70 (4H, m), 3.51-3.67 (4H, m), 7.35-7.53 (3H, m), 7.68 (1H, dd, J=1.6, 5.2 Hz), 7.78-7.92 (2H, m), 8.41-8.53 (1H, m), 8.66 (1H, s), 8.76 (1H, d, J=0.9 Hz), 10.92 (1H, s), 14.34 (1H, br s).

Example 5-B

Production of 3-[(2S)-2-(methoxymethyl)pyrrolidin-1-yl]-N-{4-[4-phenyl-5-(4H-1,2,4-triazol-3-yl)-1,3-thiazol-2-yl]pyridin-2-yl}propanamide

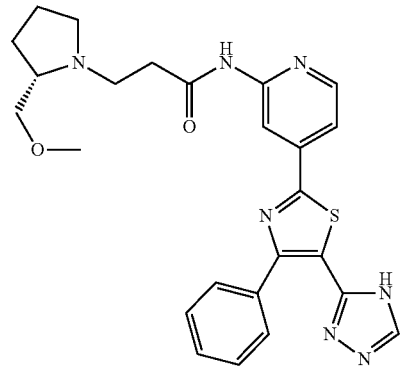 [SMILES: COC[C@@H]1CCCN1CCC(=O)Nc1cc(-c2nc(-c3ccccc3)c(-c3nnc[nH]3)s2)ccn1]

To a solution of N-(4-{4-phenyl-5-[1-(tetrahydro-2H-pyran-2-yl)-1H-1,2,4-triazol-3-yl]-1,3-thiazol-2-yl}pyridin-2-yl)prop-2-enamide (92 mg, 0.2 mmol) prepared in Example 4-B (iii) in tetrahydrofuran (2.0 mL) was added (2S)-2-(methoxymethyl)pyrrolidine (120 mg, 1.0 mmol), and the mixture was heated under reflux for 14 hr. The reaction solution was cooled to room temperature, and diluted with ethyl acetate (30 mL) and saturated aqueous sodium bicarbonate solution (30 mL). The aqueous layer was separated, extracted with ethyl acetate (40 mL), and the combined organic layer was dried over anhydrous magnesium sulfate. The insoluble material was filtered off, and the filtrate was concentrated. The obtained residue was dissolved in trifluoroacetic acid (4.0 mL), and the mixture was stirred at room temperature for 3 hr. Trifluoroacetic acid was evaporated under reduced pressure, and the residue was diluted with ethyl acetate (30 mL), and washed with saturated aqueous sodium bicarbonate solution (30 mL). The aqueous layer was separated and extracted with ethyl acetate (30 mL), and the combined organic layer was dried over anhydrous magnesium sulfate. The insoluble material was filtered off, the filtrate was concentrated under reduced pressure, and the obtained residue was purified by basic silica gel column chromatography (methanol/ethyl acetate=0/100→50/50) to give the title compound (60 mg, 62%) as a pale-yellow solid.

$^{1}$H-NMR (DMSO-d$_{6}$, 300 MHz) δ 1.43-1.55 (1H, m), 1.61-1.72 (2H, m), 1.79-1.90 (1H, m), 2.14-2.30 (1H, m), 2.53-2.76 (4H, m), 3.13-3.25 (6H, m), 3.40-3.44 (1H, m), 7.32-7.56 (3H, m), 7.67 (1H, dd, J=1.5, 5.1 Hz), 7.77-8.02 (2H, m), 8.31-8.55 (1H, m), 8.60-8.70 (1H, m), 8.74 (1H, d, J=0.8 Hz), 10.95 (1H, s), 14.36 (1H, br s).

Example 6-B

Production of 3-[(2R)-2-(methoxymethyl)pyrrolidin-1-yl]-N-{4-[4-phenyl-5-(4H-1,2,4-triazol-3-yl)-1,3-thiazol-2-yl]pyridin-2-yl}propanamide

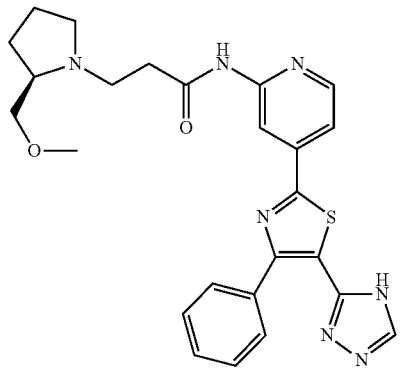 [SMILES: COC[C@H]1CCCN1CCC(=O)Nc1cc(-c2nc(-c3ccccc3)c(-c3nnc[nH]3)s2)ccn1]

In the same manner as in Example 5-B except that (2R)-2-(methoxymethyl)pyrrolidine (120 mg, 1.0 mmol) was used, the title compound (73 mg, 74%) was obtained as a pale-yellow solid from N-(4-{4-phenyl-5-[1-(tetrahydro-2H-pyran-2-yl)-1H-1,2,4-triazol-3-yl]-1,3-thiazol-2-yl}pyridin-2-yl)prop-2-enamide (91.6 mg, 0.2 mmol) prepared in Example 4-B (iii).

$^{1}$H-NMR (DMSO-d$_{6}$, 300 MHz) δ 1.39-1.57 (1H, m), 1.57-1.74 (2H, m), 1.76-1.96 (1H, m), 2.11-2.30 (1H, m), 2.53-2.68 (4H, m), 3.04-3.27 (6H, m), 3.35-3.46 (1H, m), 7.33-7.57 (3H, m), 7.67 (1H, dd, J=1.7, 5.1 Hz), 7.76-8.01 (2H, m), 8.47 (1H, dd, J=0.8, 5.1 Hz), 8.66-8.69 (1H, m), 8.75 (1H, d, J=0.8 Hz), 10.95 (1H, s), 14.37 (1H, br s).

Example 7-B

Production of 3-(phenylsulfanyl)-N-{4-[4-phenyl-5-(4H-1,2,4-triazol-3-yl)-1,3-thiazol-2-yl]pyridin-2-yl}propanamide

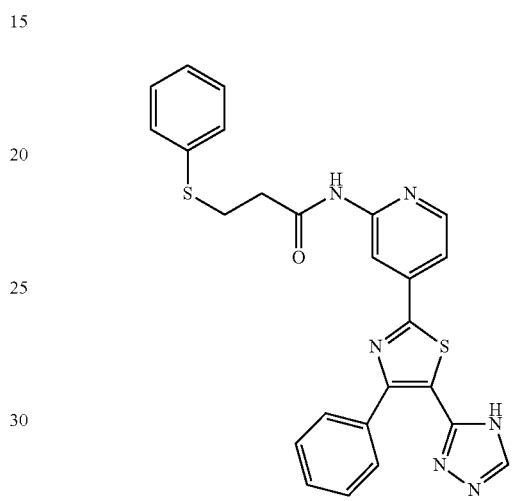

To a solution of N-(4-{4-phenyl-5-[1-(tetrahydro-2H-pyran-2-yl)-1H-1,2,4-triazol-3-yl]-1,3-thiazol-2-yl}pyridin-2-yl)prop-2-enamide (92 mg, 0.2 mmol) prepared in Example 4-B (iii) in tetrahydrofuran (2.0 mL) were added triethylamine (30 mg, 0.3 mmol) and thiophenol (29 mg, 0.26 mmol), and the mixture was stirred at room temperature for 15 hr. The reaction mixture was diluted with ethyl acetate (25 mL), and washed with saturated aqueous sodium bicarbonate solution (25 mL). The aqueous layer was extracted with ethyl acetate (25 mL), and the combined organic layer was dried over anhydrous magnesium sulfate. The insoluble material was filtered off, and the filtrate was concentrated under reduced pressure. The obtained residue was dissolved in trifluoroacetic acid (8.0 mL), and the mixture was stirred at room temperature for 6 hr. Trifluoroacetic acid was evaporated under reduced pressure, and the residue was diluted with ethyl acetate (40 mL) and washed with saturated aqueous sodium bicarbonate solution (30 mL). The aqueous layer was separated and extracted with ethyl acetate (40 mL), and the combined organic layer was dried over anhydrous magnesium sulfate. The insoluble material was filtered off, the filtrate was concentrated under reduced pressure, and the obtained residue was purified by silica gel column chromatography (ethyl acetate/hexane=50/50→100/0) to give the title compound (69 mg, 71%) as a white solid.

$^{1}$H-NMR (DMSO-d$_{6}$, 300 MHz) δ 2.81 (2H, t, 7.1 Hz), 3.26 (2H, t, J=7.1 Hz), 7.15-7.25 (1H, m), 7.27-739 (4H, m), 7.40-7.50 (3H, m), 7.68 (1H, dd, J=1.6, 5.2 Hz), 7.81-7.96

(2H, m), 8.39-8.56 (1H, m), 8.60-8.68 (1H, m), 8.71-8.82 (1H, m), 10.81 (1H, s), 14.33 (1H, s).

Example 8-B

Production of N-{4-[4-ethoxy-5-(4H-1,2,4-triazol-3-yl)-1,3-thiazol-2-yl]pyridin-2-yl}acetamide

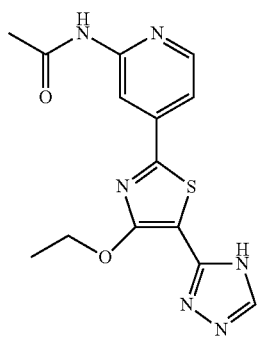 [SMILES: CCOc1nc(-c2ccnc(NC(C)=O)c2)sc1-c1nnc[nH]1]

(i) Production of ethyl 2-[2-(acetylamino)pyridin-4-yl]-4-hydroxy-1,3-thiazole-5-carboxylate To a suspension of N-(4-carbamothioylpyridin-2-yl)acetamide (15 g, 77 mmol) produced in the same manner as in Example 1(ii) in 2-propanol (136 mL) was added ethyl 2-chloro-3-oxo-3-phenylpropanoate, and the mixture was stirred with heating at 90° C. for 12 hr. Tetrabutylammonium bromide (1.2 g, 3.9 mmol) was added to the reaction solution, and the mixture was further stirred with heating at the same temperature for 10 hr. The reaction mixture was cooled to room temperature and diluted with ethyl acetate (200 mL), and saturated aqueous sodium bicarbonate solution (200 mL) was added. The resulting solid was collected by filtration, and washed with water (200 mL), ethanol (100 mL) and diethyl ether (100 mL×2). The obtained crude product was suspended in acetic anhydride (150 mL), concentrated sulfuric acid (0.05 mL) was added, and the mixture was heated under reflux at 120° C. for 2 hr. The reaction mixture was cooled to room temperature, and acetic anhydride was evaporated under reduced pressure. The residue was suspended in methanol (50 mL), and after stirring, methanol was evaporated under reduced pressure. The obtained residue was suspended in tetrahydrofuran (300 mL), 25% aqueous ammonia solution (150 mL) was added, and the mixture was stirred at room temperature for 1 hr. To the reaction mixture was added methanol (100 mL), and the mixture was further stirred at room temperature for 30 min. The resulting solid was collected by filtration, and washed with water (100 mL) and diethyl ether (100 mL) to give the title compound (7.4 g, 31%) as a yellow solid. The combined filtrate and washing solution was concentrated under reduced pressure, the resulting yellow solid was collected by filtration, and washed with water (500 mL), ethanol (100 mL) and diethyl ether (200 mL) to give a second crop (2.9 g, 12%) of the title compound as a yellow solid.
$^1$H-NMR (DMSO-$d_6$, 300 MHz) δ 1.22 (3H, t, J=7.2 Hz), 2.12 (3H, s), 4.11 (2H, q, J=7.2 Hz), 7.45 (1H, br s), 7.48 (1H, dd, J=1.6 Hz, 5.2 Hz), 8.30-8.44 (1H, m), 8.53-8.62 (1H, m), 10.64 (1H, s).

(ii) Production of ethyl 2-[2-(acetylamino)pyridin-4-yl]-4-ethoxy-1,3-thiazole-5-carboxylate To a solution of ethyl 2-[2-(acetylamino)pyridin-4-yl]-4-hydroxy-1,3-thiazole-5-carboxylate (11 g, 34 mmol) produced in the above in N,N-dimethylformamide (350 mL) were added potassium carbonate (24 g, 170 mmol) and iodoethane (15.8 g, 103 mmol), and the mixture was stirred at 50° C. for 3 hr. The reaction mixture was cooled to room temperature, water (400 mL) was added, and the mixture was cooled to 0° C. The resulting solid was collected by filtration, and washed with water (1.0 L) and diethyl ether (100 mL) to give the title compound (8.8 g, 77%) as a yellow solid.
$^1$H-NMR (DMSO-$d_6$, 300 MHz) δ 1.28 (3H, t, J=7.2 Hz), 1.39 (3H, t, J=7.1 Hz), 2.13 (3H, s), 4.25 (21-1, q, J=7.2 Hz), 4.56 (2H, q, J=7.1 Hz), 7.66 (1H, dd, J=1.7 Hz, 5.2 Hz), 8.46 (1H, dd, J=0.8 Hz, 5.2 Hz), 8.60-8.69 (1H, m), 10.76 (1H, s).

(iii) Production of 2-[2-(acetylamino)pyridin-4-yl]-4-ethoxy-1,3-thiazole-5-carboxylic acid To ethyl 2-[2-(acetylamino)pyridin-4-yl]-4-ethoxy-1,3-thiazole-5-carboxylate (8.8 g, 26 mmol) produced in the above in a mixed solvent (240 mL) of tetrahydrofuran/methanol (1:1) was added 1N aqueous sodium hydroxide solution (29 mL, 29 mmol), and the mixture was stirred at 40° C. for 3 hr. 1N Aqueous sodium hydroxide solution (2.7 mL, 2.7 mmol) was further added, and the mixture was stirred at 40° C. for 7 hr. The reaction solution was cooled to room temperature, tetrahydrofuran and methanol were evaporated, and the residue was concentrated to about 120 mL. The residue was diluted with water (300 mL), and 1N hydrochloric acid (30 mL) was added. The resulting white solid was collected by filtration, and washed with water (100 mL) and diethyl ether (100 mL×2). After drying, the obtained white solid was suspended in acetic anhydride (100 mL), concentrated sulfuric acid (0.05 mL) was added, and the mixture was stirred at 100° C. for 5 hr. Acetic anhydride (25 mL) and concentrated sulfuric acid (1.0 mL) were further added, and the mixture was stirred for 30 min. The reaction mixture was cooled to room temperature, and acetic anhydride was evaporated under reduced pressure. The residue was suspended in methanol, and after stirring, methanol was evaporated under reduced pressure. The obtained residue was dissolved in a mixed solvent (500 mL) of tetrahydrofuran/methanol (3:7), 25% aqueous ammonia solution (150 mL) was added, and the mixture was stirred at room temperature for 1 hr. Under reduced pressure, tetrahydrofuran and methanol were evaporated, water (300 mL) was added, and the mixture was neutralized to pH 5 with 1N hydrochloric acid (30 mL). The resulting solid was collected by filtration, and washed with water (100 mL) and diethyl ether (50 mL×2) to give the title compound (7.5 g, 93%) as a yellow solid.
$^1$H-NMR (DMSO-$d_6$, 300 MHz) δ 1.39 (3H, t, J=7.0 Hz), 2.13 (3H, s), 4.54 (2H, q, J=7.0 Hz), 7.59 (1H, dd, J=1.6, 5.2 Hz), 8.45 (1H, dd, J=0.8, 5.2 Hz), 8.59-8.68 (1H, m), 10.75 (1H, s), 13.04 (1H, br s).

(iv) Production of 2-[2-(acetylamino)pyridin-4-yl]-4-ethoxy-1,3-thiazole-5-carboxamide To a solution of 2-[2-(acetylamino)pyridin-4-yl]-4-ethoxy-1,3-thiazole-5-carboxylic acid (7.5 g, 24 mmol) produced in the above in N,N-dimethylformamide (240 mL) were added triethylamine (10 mL, 73 mmol), ammonium chloride (3.9 g, 73 mmol), 1-hydroxybenzotriazole (5.0 g, 36 mmol) and N-[3-(dimethylamino)propyl]-N'-ethylcarbodiimide hydrochloride (7.0 g, 37 mmol), and the mixture was stirred at room temperature for 2.5 days. Under reduced pressure, the solvent was evaporated, and the residue was diluted with water (200 mL). The resulting solid was collected by filtration, and washed with water (100 mL) and diethyl ether (100 mL) to give a pale-yellow solid. The obtained solid was washed with water (300 mL) and diethyl ether (100 mL) to give the title compound (7.0 g, 94%) as a pale-yellow solid.

$^1$H-NMR (DMSO-d$_6$, 300 MHz) δ 1.43 (3H, t, J=7.0 Hz), 2.13 (3H, s), 4.59 (2H, q, J=7.0 Hz), 7.04 (1H, br s), 7.57 (1H, dd, J=1.7, 5.1 Hz), 7.82 (1H, br s), 8.39-8.50 (1H, m), 8.63 (1H, d, J=5.1 Hz), 10.73 (1H, s).

(v) Production of N-{4-[4-ethoxy-5-(4H-1,2,4-triazol-3-yl)-1,3-thiazol-2-yl]pyridin-2-yl}acetamide 2-[2-(Acetylamino)pyridin-4-yl]-4-ethoxy-1,3-thiazole-5-carboxamide (7.0 g, 23 mmol) produced in the above was suspended in N,N-dimethylformamide dimethyl acetal (250 mL), and the mixture was stirred at 100° C. for 2 hr. The reaction mixture was cooled to room temperature, and the solvent was evaporated under reduced pressure. The residue was suspended in acetic acid (260 mL), hydrazine monohydrate (5.7 g, 110 mmol) was added under ice-cooling, and the mixture was stirred at 90° C. for 1 hr. The reaction mixture was cooled to room temperature, and acetic acid was evaporated under reduced pressure. The obtained residue was suspended in diethyl ether (100 mL) and saturated aqueous sodium bicarbonate solution (1.2 L). The resulting solid was collected by filtration, and washed with water (500 mL) and diethyl ether (200 mL) to give the title compound (7.2 g, 96%) as a yellow solid.

$^1$H-NMR (DMSO-d$_6$, 300 MHz) δ 1.42 (3H, t, J=7.0 Hz), 2.13 (3H, s), 4.56 (2H, q, J=7.0 Hz), 7.59 (1H, dd, J=1.6 Hz, 5.2 Hz), 8.21-8.53 (2H, m), 8.57-8.72 (1H, m), 10.72 (1H, s), 14.04 (1H, br s).

Example 9-B

Production of N-{6-methyl-4-[4-phenyl-5-(4H-1,2,4-triazol-3-yl)-1,3-thiazol-2-yl]pyridin-2-yl}acetamide

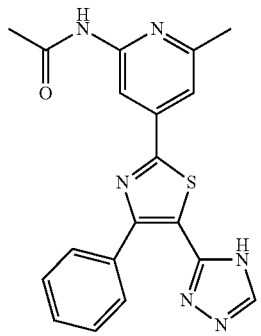 [SMILES: CC(=O)Nc1cc(-c2nc(-c3ccccc3)c(-c3nnc[nH]3)s2)cc(C)n1]

(i) Production of 2-chloro-6-methylpyridine-4-carboxamide

A mixture of 2-chloro-6-methylpyridine-4-carboxylic acid (9.6 g, 56 mmol), ammonium chloride (8.9 g, 170 mmol), triethylamine (23 mL, 170 mmol), N-[3-(dimethylamino)propyl]-N'-ethylcarbodiimide hydrochloride (13 g, 67 mmol), 1-hydroxybenzotriazole (9.1 g, 67 mmol) and N,N-dimethylformamide (100 mL) was stirred at room temperature for 1 day. The reaction mixture was concentrated under reduced pressure, aqueous sodium bicarbonate solution was added to the obtained residue, and the mixture was extracted with ethyl acetate. The combined organic layer was washed with saturated brine and dried over anhydrous magnesium sulfate, and the insoluble material was filtered off. The obtained residue was washed with diisopropyl ether to give the title compound (5.6 g, 59%) as a pale-brown solid.

$^1$H-NMR (DMSO-d$_6$, 300 MHz) δ 2.51 (3H, s), 7.64-7.67 (2H, m), 7.81 (1H, br s), 8.25 (1H, br s).

(ii) Production of 2-chloro-6-methylpyridine-4-carbonitrile

To a mixture of 2-chloro-6-methylpyridine-4-carboxamide (5.1 g, 30 mmol) obtained above, pyridine (7.3 mL, 90 mmol) and tetrahydrofuran (50 mL) was added dropwise a solution of trifluoroacetic anhydride (6.4 mL, 45 mmol) in tetrahydrofuran (10 mL) under ice-cooling, and the mixture was stirred under ice-cooling for 0.5 hr and at room temperature for 1 hr. The reaction mixture was concentrated under reduced pressure, aqueous sodium bicarbonate solution was added to the obtained residue, and the mixture was extracted with ethyl acetate. The combined organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=5/95→10/90). The obtained solution was concentrated under reduced pressure to give the title compound (4.3 g, 95%) as a colorless solid.

$^1$H-NMR (DMSO-d$_6$, 300 MHz) δ 2.52 (3H, s), 7.81 (1H, s), 7.94 (1H, s).

(iii) Production of 2-[(4-methoxybenzyl)amino]-6-methylpyridine-4-carbonitrile

A mixture of 2-chloro-6-methylpyridine-4-carbonitrile (1.5 g, 10 mmol) obtained above, 4-methoxybenzylamine (2.7 g, 20 mmol), potassium carbonate (2.1 g, 15 mmol), potassium iodide (830 mg, 5.0 mmol) and 1-methyl-2-pyrrolidone (20 mL) was stirred at 100° C. for 1 day. To the reaction mixture was added water, and the mixture was extracted with ethyl acetate. The combined organic layer was washed with saturated brine and dried over anhydrous magnesium sulfate, and the insoluble material was filtered off. The obtained residue was purified by silica gel column chromatography (ethyl acetate/hexane=10/90→20/80), and the obtained solution was concentrated under reduced pressure to give the title compound (1.4 g, 56%) as a colorless solid.

$^1$H-NMR (DMSO-d$_6$, 300 MHz) δ 2.30 (3H, s), 3.72 (3H, s), 4.39 (2H, d, J=5.9 Hz), 6.62 (1H, s), 6.67 (1H, s), 6.88 (2H, d, J=8.8 Hz), 7.26 (2H, d, J=8.8 Hz), 7.43 (1H, t, J=5.9 Hz).

(iv) Production of 2-amino-6-methylpyridine-4-carbothioamide

A mixture of 2-[(4-methoxybenzyl)amino]-6-methylpyridine-4-carbonitrile (1.3 g, 5.2 mmol) obtained above, and trifluoroacetic acid (5 mL) was stirred at 80° C. for 1.5 hr. The reaction mixture was concentrated under reduced pressure, water, tetrahydrofuran and ethyl acetate were added to the obtained residue, and the mixture was stirred. 8N Aqueous sodium hydroxide solution was added, and the mixture was extracted with a mixed solvent of ethyl acetate and tetrahydrofuran. The organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate) to give a crude product (762 mg) of 2-amino-6-methylpyridine-4-carbonitrile.

A mixture of 2-amino-6-methylpyridine-4-carbonitrile (740 mg) obtained above, O,O'-diethyl dithiophosphate (1.5 mL, 7.8 mmol), tetrahydrofuran (5 mL) and water (5 mL) was stirred at 60° C. for 8 hr. To the reaction mixture was added aqueous sodium bicarbonate solution, and the mixture was extracted with ethyl acetate. The combined organic layer was washed with saturated brine and dried over anhydrous magnesium sulfate, and the insoluble material was filtered off. The filtrate was concentrated under reduced pressure, and the obtained residue was washed with diisopropyl ether to give the title compound (770 mg, 89%) as a pale-yellow solid.

$^1$H-NMR (DMSO-$d_6$, 300 MHz) δ 2.25 (3H, s), 6.04 (2H, s), 6.58 (1H, s), 6.60 (1H, s), 9.48 (1H, br s), 9.90 (1H, br s).

(v) Production of N-(4-carbamothioyl-6-methylpyridin-2-yl)acetamide

A mixture of 2-amino-6-methylpyridine-4-carbothioamide (740 mg, 4.4 mmol) obtained above, acetic anhydride (0.62 mL, 6.6 mmol) and pyridine (10 mL) was stirred at room temperature for 1 day. The reaction mixture was concentrated under reduced pressure, aqueous sodium bicarbonate solution was added to the obtained residue, and the mixture was extracted with ethyl acetate. The combined organic layer was washed with saturated brine and dried over anhydrous magnesium sulfate, and the insoluble material was filtered off. The filtrate was concentrated under reduced pressure, and the obtained residue was washed with diisopropyl ether to give the title compound (860 mg, 93%) as a pale-yellow orange solid.

$^1$H-NMR (DMSO-$d_6$, 300 MHz) δ 2.08 (3H, s), 2.43 (3H, s), 7.16 (1H, d, J=0.9 Hz), 8.19 (1H, s), 9.67 (1H, br s), 10.09 (1H, br s), 10.56 (1H, s).

(vi) Production of ethyl 2-[2-(acetylamino)-6-methylpyridin-4-yl]-4-phenyl-1,3-thiazole-5-carboxylate A mixture of N-(4-carbamothioyl-6-methylpyridin-2-yl)acetamide (840 mg, 4.0 mmol) obtained above, ethyl 2-bromo-3-oxo-3-phenylpropanoate (1.3 g, 4.8 mmol) and acetonitrile (30 mL) was stirred at 80° C. for 1 day. To the reaction mixture were added aqueous sodium bicarbonate solution, ethyl acetate and tetrahydrofuran, and the insoluble material was filtered off. The filtrate was extracted with a mixed solvent of ethyl acetate and tetrahydrofuran. The combined organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=50/50→100/0). The obtained solution was concentrated under reduced pressure. The obtained residue was washed with ethyl acetate/diisopropyl ether to give the title compound (890 mg, 58%) as a colorless solid.

$^1$H-NMR (DMSO-$d_6$, 300 MHz) δ 1.24 (3H, t, J=7.2 Hz), 2.11 (3H, s), 2.50 (3H, s), 4.26 (2H, q, J=7.2 Hz), 7.46-7.53 (3H, m), 7.59 (1H, d, J=0.9 Hz), 7.74-7.83 (2H, m), 8.53-8.56 (1H, m), 10.72 (1H, s).

(vii) Production of 2-[2-(acetylamino)-6-methylpyridin-4-yl]-4-phenyl-1,3-thiazole-5-carboxylic acid A mixture of ethyl 2-[2-(acetylamino)-6-methylpyridin-4-yl]-4-phenyl-1,3-thiazole-5-carboxylate (760 mg, 2.0 mmol) obtained above, 1N aqueous sodium hydroxide solution (2.2 mL), methanol (10 mL) and tetrahydrofuran (10 mL) was stirred at 40° C. for 3 hr. To the reaction mixture were added 1N hydrochloric acid (2.2 mL) and water, and the resulting precipitate was collected by filtration, washed successively with water and diethyl ether and dried to give the title compound (650 mg, 93%) as a colorless solid.

$^1$H-NMR (DMSO-$d_6$, 300 MHz) δ 2.11 (3H, s), 2.50 (3H, s), 7.43-7.50 (3H, m), 7.56 (1H, d, J=0.9 Hz), 7.76-7.84 (2H, m), 8.53 (1H, s), 10.71 (1H, s), 13.65 (1H, br s).

(viii) Production of 2-[2-(acetylamino)-6-methylpyridin-4-yl]-4-phenyl-1,3-thiazole-5-carboxamide A mixture of 2-[2-(acetylamino)-6-methylpyridin-4-yl]-4-phenyl-1,3-thiazole-5-carboxylic acid (650 mg, 1.9 mmol) obtained above, ammonium chloride (320 mg, 6.0 mmol), triethylamine (0.84 mL, 6.0 mmol), N-[3-(dimethylamino)propyl]-N'-ethylcarbodiimide hydrochloride (580 mg, 3.0 mmol), 1-hydroxybenzotriazole (410 mg, 3.0 mmol) and N,N-dimethylformamide (20 mL) was stirred at room temperature for 1 day. The reaction mixture was concentrated under reduced pressure, and water was added to the obtained residue. The resulting precipitate was collected by filtration, washed successively with water and diethyl ether and dried to give the title compound (610 mg, 93%) as a colorless solid.

$^1$H-NMR (DMSO-$d_6$, 300 MHz) δ 2.12 (3H, s), 2.51 (3H, s), 7.41-7.54 (3H, m), 7.55 (1H, d, J=0.9 Hz), 7.78-7.85 (2H, m), 7.87 (1H, br s), 7.95 (1H, br s), 8.52 (1H, s), 10.70 (1H, s).

(ix) Production of N-{6-methyl-4-[4-phenyl-5-(4H-1,2,4-triazol-3-yl)-1,3-thiazol-2-yl]pyridin-2-yl}acetamide A mixture of 2-[2-(acetylamino)-6-methylpyridin-4-yl]-4-phenyl-1,3-thiazole-5-carboxamide (560 mg, 1.6 mmol) obtained above and N,N-dimethylformamide dimethyl acetal (10 mL) was stirred at 100° C. for 2 hr. The reaction mixture was concentrated under reduced pressure, hydrazine monohydrate (0.39 mL, 8.0 mmol) and acetic acid (10 mL) were added to the obtained residue, and the mixture was stirred at 100° C. for 1 hr. The reaction mixture was concentrated under reduced pressure, and aqueous sodium bicarbonate solution was added to the obtained residue. The resulting precipitate was collected by filtration, washed with water and diethyl ether and dried. The obtained crude product was purified by silica gel column chromatography (methanol/ethyl acetate=0/100→50/50), and the crude product was treated with ethanol and water. The obtained solid was collected by filtration, washed successively with water and diethyl ether and dried to give the title compound (220 mg, 36%) as a colorless solid.

¹H-NMR (DMSO-d₆, 300 MHz) δ 2.12 (3H, s), 2.51 (3H, s), 7.38-7.49 (3H, m), 7.55-7.59 (1H, m), 7.79-7.88 (2H, m), 8.54 (1H, s), 8.66 (1H, s), 10.68 (1H, s), 14.37 (1H, br s).

Example 10-B

Production of 2-chloro-4-[4-phenyl-5-(4H-1,2,4-triazol-3-yl)-1,3-thiazol-2-yl]pyridine

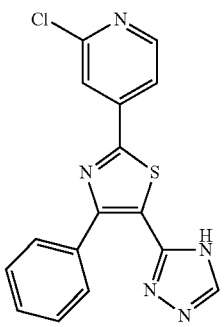 [SMILES: Clc1cc(-c2nc(-c3ccccc3)c(-c3nnc[nH]3)s2)ccn1]

(i) Production of ethyl 4-phenyl-2-pyridin-4-yl-1,3-thiazole-5-carboxylate

To a suspension of pyridine-4-carbothioamide (2.9 g, 21 mmol) in ethanol (150 mL) was added ethyl 2-bromo-3-oxo-3-phenylpropanoate (5.9 g, 22 mmol), and the mixture was heated under reflux for 8 hr. The reaction solution was allowed to cool to room temperature, and the solid was collected by filtration, washed with diethyl ether, dried, suspended in ethyl acetate (250 mL), and washed with saturated aqueous sodium bicarbonate solution (150 mL×2). The combined aqueous layer was extracted with ethyl acetate (100 mL×2). The combined organic layer was dried over anhydrous magnesium sulfate, the insoluble material was filtered off, and the filtrate was concentrated under reduced pressure. The residue was washed with diethyl ether, and collected by filtration to give the title compound (3.7 g, 57%) as a colorless solid.

¹H-NMR (DMSO-d₆, 300 MHz) δ 1.24 (3H, t, J=7.2 Hz), 4.27 (2H, q, J=7.2 Hz), 7.47-7.52 (3H, m), 7.79-7.82 (2H, m), 8.00-8.02 (2H, m), 8.77-8.79 (2H, m).

(ii) Production of ethyl 2-(1-oxidopyridin-4-yl)-4-phenyl-1,3-thiazole-5-carboxylate To a suspension of ethyl 4-phenyl-2-pyridin-4-yl-1,3-thiazole-5-carboxylate (2.6 g, 8.5 mmol) produced in the above in acetonitrile (300 mL) was added m-chloroperbenzoic acid (containing water, about 70%, 3.9 g, about 16.0 mmol), and the mixture was stirred at room temperature for 2 days. The reaction solution was concentrated under reduced pressure to about 100 mL, and the obtained suspension was diluted with ethyl acetate (300 mL), and washed successively with saturated aqueous sodium bisulfite solution (150 mL×2) and saturated aqueous sodium carbonate solution (150 mL×2). The combined aqueous layer was extracted with ethyl acetate (200 mL×2). The combined organic layer was dried over anhydrous magnesium sulfate, the insoluble material was filtered off, and the filtrate was concentrated under reduced pressure. The obtained solid was washed with ethyl acetate, and collected by filtration to give the title compound (2.0 g, 72%) as a yellow solid.

¹H-NMR (DMSO-d₆, 300 MHz) δ 1.23 (3H, t, J=6.9 Hz), 4.26 (2H, q, J=6.9 Hz), 7.46-7.51 (3H, m), 7.76-7.82 (2H, m), 8.03-8.07 (2H, m), 8.31-8.35 (2H, m).

(iii) Production of ethyl 2-(2-chloropyridin-4-yl)-4-phenyl-1,3-thiazole-5-carboxylate Ethyl 2-(1-oxidopyridin-4-yl)-4-phenyl-1,3-thiazole-5-carboxylate (1.8 g, 5.6 mmol) produced in the above was suspended in phosphorus oxychloride (31 g), and the mixture was heated under reflux for 4 hr. The obtained solution was allowed to cool to room temperature, and concentrated under reduced pressure. The obtained residue was dissolved in tetrahydrofuran (100 mL), saturated aqueous sodium bicarbonate solution (100 mL) was added to the obtained solution, and the mixture was vigorously stirred at room temperature for 1 hr. Ethyl acetate (150 mL) was added, and the aqueous layer was separated. The organic layer was washed with saturated aqueous ammonium chloride solution (100 mL). The combined aqueous layer was extracted with ethyl acetate (100 mL×2). The combined organic layer was dried over anhydrous magnesium sulfate, the insoluble material was filtered off, and the filtrate was concentrated under reduced pressure to give the title compound (1.9 g, 100%) as a yellow solid.

¹H-NMR (CDCl₃, 300 MHz) δ 1.24 (3H, t, J=7.2 Hz), 4.28 (2H, q, J=7.2 Hz), 7.48-7.52 (3H, m), 7.80-7.83 (2H, m), 8.05 (1H, dd, J=1.5, 5.3 Hz), 8.09-8.16 (1H, m), 8.61 (1H, dd, J=0.7, 5.3 Hz).

(iv) Production of 2-(2-chloropyridin-4-yl)-4-phenyl-1,3-thiazole-5-carboxylic acid To a solution of ethyl 2-(2-chloropyridin-4-yl)-1,3-thiazole-5-carboxylate (540 mg, 1.6 mmol) produced in the above in tetrahydrofuran (20 mL) and methanol (20 mL) were added water (20 mL) and 8N aqueous sodium hydroxide solution (1 mL), and the mixture was heated under reflux for 90 min. The reaction solution was cooled to 0° C., and 6N hydrochloric acid (1.5 mL) was added to adjust the solution to about pH 5.0. The resulting solid was collected by filtration, washed with water, ethanol and diethyl ether and dried to give the title compound (260 mg, 52%) as a pale-yellow solid. The filtrate was extracted with ethyl acetate (100 mL×2), and the organic layer was washed with saturated ammonium chloride (50 mL) and dried over anhydrous magnesium sulfate. The insoluble material was filtered off, and the filtrate was concentrated under reduced pressure to give a second crop (260 mg) of the title compound.

¹H-NMR (DMSO-d₆, 300 MHz) δ 7.43-7.53 (3H, m), 7.77-7.88 (2H, m), 8.02 (1H, dd, J=1.5, 5.3 Hz), 8.09 (1H, dd, J=0.6, 1.5 Hz), 8.60 (1H, dd, J=0.6, 5.3 Hz), 13.76 (1H, br s).

(v) Production of 2-(2-chloropyridin-4-yl)-4-phenyl-1,3-thiazole-5-carboxamide

To a suspension of 2-(2-chloropyridin-4-yl)-4-phenyl-1,3-thiazole-5-carboxylic acid (480 mg, 1.5 mmol) produced in the above in toluene (50 mL) was added thionyl chloride (5.0 mL, 68 mmol), and the mixture was heated under reflux for 8 hr. The obtained solution was allowed to cool to room temperature, and concentrated under reduced pressure, and the obtained residue was dissolved in tetrahydrofuran (50 mL). 25% Aqueous ammonia (50 mL) was added, and the mixture was vigorously stirred for 90 min. The aqueous layer was separated, and the organic layer was diluted with ethyl acetate (150 mL), and washed with saturated aqueous ammonium chloride solution (100 mL). The combined aqueous layer was extracted with ethyl acetate (100 mL). The combined organic layer was dried over anhydrous magnesium sulfate, and decolorized with activated carbon, and the insoluble material was filtered off. The filtrate was concentrated under reduced pressure, and the obtained solid was recrystallized from ethyl acetate to give the title compound (250 mg, 53%) as a pale-yellow solid. The mother liquor was concentrated to give a second crop (220 mg, 46%) of the title compound (total yield 99%).

$^1$H-NMR (DMSO-$d_6$, 300 MHz) δ 7.40-7.57 (3H, m), 7.78-7.88 (2H, m), 7.88-8.05 (3H, m), 8.08 (1H, d, J=0.6 Hz), 8.59 (1H, dd, J=0.6, 5.1 Hz).

(vi) Production of 2-chloro-4-[4-phenyl-5-(4H-1,2,4-triazol-3-yl)-1,3-thiazol-2-yl)pyridine 2-(2-Chloropyridin-4-yl)-4-phenyl-1,3-thiazole-5-carboxamide (370 mg, 1.2 mmol) produced in the above was suspended in N,N-dimethylformamide dimethyl acetal (10 mL), and the mixture was stirred at 120° C. for 3 hr. The obtained solution was allowed to cool to room temperature, and concentrated under reduced pressure. The obtained solid was suspended in acetic acid (50 mL), hydrazine monohydrate (2 mL, 41 mmol) was added, and the mixture was stirred at 100° C. for 8 hr. The reaction solution was allowed to cool to room temperature, and concentrated under reduced pressure. The residue was diluted with saturated aqueous sodium bicarbonate solution (100 mL), and extracted with a mixed solvent of ethyl acetate-methanol (9:1, 50 mL×2). The combined organic layer was washed with saturated aqueous ammonium chloride solution (50 mL) and dried over anhydrous magnesium sulfate, and the insoluble material was filtered off. The filtrate was concentrated under reduced pressure. The obtained residue was purified by silica gel column chromatography (ethyl acetate/hexane=80/20→100/0) to give the title compound (130 mg, 33%) as a yellow solid.

$^1$H-NMR (DMSO-$d_6$, 300 MHz) δ 7.38-7.50 (3H, m), 7.82-7.91 (2H, m), 8.01 (1H, dd, J=1.5, 5.3 Hz), 8.06-8.11 (1H, m), 8.58 (1H, dd, J=0.6, 5.3 Hz), 8.67 (1H, s), 14.39 (1H, br s).

Example 11-B

Production of 2-methyl-3-[4-phenyl-5-(4H-1,2,4-triazol-3-yl)-1,3-thiazol-2-yl]pyrazolo[1,5-a]pyridine p-toluenesulfonate

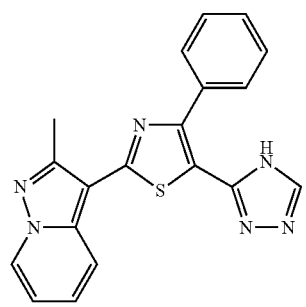

TsOH (i) Production of ethyl 2-methylpyrazolo[1,5-a]pyridine-3-carboxylate

To a suspension of 1-aminopyridinium iodide (125g, 0.56 mmol) in N,N-dimethylformamide (1.2 L) were added ethyl 2-butynoate (54.0 g, 0.48 mmol) and potassium carbonate (79 g, 0.56 mmol) and the mixture was stirred at room temperature for 3 days. The reaction mixture was diluted with water (500 mL), ethyl acetate (500 mL) and hexane (500 mL), and the precipitated solid was collected by filtration, and washed with water (500 mL). The filtrate was extracted with a mixed solvent (1.5 L×2) of ethyl acetate/hexane (1:1) and dried over anhydrous magnesium sulfate, and the insoluble material was filtered off. The residue obtained by concentration of the filtrate and the solid collected by filtration in the above were combined, washed with diethyl ether (25 mL) and hexane (25 mL) and dried to give the title compound (36.0 g, 37%) as a white solid. The washing solution was concentrated, and the obtained residue was washed with diethyl ether (10 mL) and hexane (10 mL) and dried to give a second crop (11.0 g, 11%) of the title compound as a white solid. The washing solution of the second crop was concentrated, and the obtained residue was purified using a pad (elution solvent: ethyl acetate/hexane=1/1) with silica gel and activated carbon in 2 layers, washed with diethyl ether (5.0 mL) and hexane (5.0 mL) and dried to give a third crop (6.5 g, 7%) of the title compound as a white solid (total yield 55%).

$^1$H-NMR (DMSO-$d_6$, 300 MHz) δ 1.35 (3H, t, J=7.2 Hz), 2.57 (3H, s), 4.30 (2H, q, J=7.2 Hz), 7.09 (1H, dt, J=1.5, 6.9 Hz), 7.49-7.61 (1H, m), 8.00 (1H, td, J=1.3 Hz), 8.75 (1H, td, J=1.0, 6.9 Hz).

(ii) Production of 2-methylpyrazolo[1,5-a]pyridine-3-carboxylic acid

To a solution of ethyl 2-methylpyrazolo[1,5-a]pyridine-3-carboxylate (52 g, 260 mmol) produced in the above in tetrahydrofuran (300 mL) and methanol (200 mL) was added 8N aqueous sodium hydroxide solution (100 mL, 800 mmol), and the mixture was stirred at 70° C. for 3.5 hr. The reaction solution was cooled to room temperature, tetrahydrofuran and methanol were evaporated under reduced pressure, and the mixture was concentrated to about 150 mL. 6N Hydrochloric acid (130 mL, 780 mmol) and 1N hydrochloric acid (20.0 mL, 20.0 mmol) were added to the residue, and the mixture was diluted with water (500 mL). The resulting white precipitate was collected by filtration, washed with water (600 mL), ethanol (300 mL) and diethyl ether (300 mL) and dried to give the title compound (43g, 96%) as a white solid.

$^1$H-NMR (DMSO-$d_6$, 300 MHz) δ 2.57 (3H, s), 6.94-7.16 (1H, m), 7.50 (1H, ddd, J=1.1, 6.9, 8.8 Hz), 8.01 (1H, td, J=1.3, 8.8 Hz), 8.72 (1H, td, J=1.1, 6.9 Hz), 12.31 (1H, br s).

(iii) Production of 2-methylpyrazolo[1,5-a]pyridine-3-carboxamide

To a suspension of 2-methylpyrazolo[1,5-a]pyridine-3-carboxylic acid (41 g, 230 mmol) produced in the above in toluene (500 mL) was added dropwise thionyl chloride (150 g, 1.2 mol), and the mixture was heated under reflux for 2 hr. The reaction mixture was cooled to room temperature, and toluene and thionyl chloride were evaporated under reduced pressure. The obtained solid was dissolved in tetrahydrofuran (400 mL), 25% aqueous ammonia solution (180 mL) was gradually added under ice-cooling, and the mixture was stirred at room temperature for 12 hr. The resulting yellow solid was collected by filtration, washed with water (100 mL) and dried to give the title compound (38 g, 89%) as a yellow solid. The filtrate and washing solution were extracted with ethyl acetate (300 mL×2), and a mixed solvent of ethyl acetate (200 mL) and tetrahydrofuran (100 mL), and the extract was dried over anhydrous magnesium sulfate. The insoluble material was filtered off, and the filtrate was concentrated to give a second crop (2.7 g, 6.0%) of the title compound as a yellow solid (total yield 95%).

$^1$H-NMR (DMSO-$d_6$, 300 MHz) δ 2.56 (3H, s), 6.96 (1H, dt, J=1.2, 6.9 Hz), 7.09 (2H, br s), 7.38 (1H, ddd, J=1.2, 6.9, 9.0 Hz), 7.96 (1H, td, J=1.2, 9.0 Hz), 8.64 (1H, td, J=1.2, 6.9 Hz)

(iv) Production of 2-methylpyrazolo[1,5-a]pyridine-3-carbonitrile

2-Methylpyrazolo[1,5-a]pyridine-3-carboxamide (41 g, 233 mmol) produced in the above was suspended in phosphorus oxychloride (270 g, 1.8 mol), and the mixture was heated under reflux at 80° C. for 2 hr. The reaction mixture was cooled to room temperature, and phosphorus oxychloride was evaporated under reduced pressure. The obtained residue was diluted with toluene (100 mL) and ice-cooled saturated aqueous sodium bicarbonate solution (200 mL). Then, ethyl acetate (200 mL) and 1N aqueous sodium hydroxide solution (1.00 L) were added, and the mixture was stirred. The aqueous layer was separated, and extracted 3 times with a mixed solvent of ethyl acetate (300 mL) and tetrahydrofuran (100 mL). The collected organic layer was dried over anhydrous magnesium sulfate, and decolorized with activated carbon. The insoluble material was filtered off, and the filtrate was concentrated to give the title compound (35 g, 95%) as a white solid.

$^1$H-NMR (DMSO-$d_6$, 300 MHz) δ 2.50 (3H, s), 7.15 (1H, dt, J=1.2, 6.9 Hz), 7.59 (1H, ddd, J=1.2, 6.9, 8.8 Hz), 7.81 (1H, td, J=1.2, 8.8 Hz), 8.83 (1H, td, J=1.2, 6.9 Hz, 1H).

(v) Production of 2-methylpyrazolo[1,5-a]pyridine-3-carbothioamide hydrochloride To a solution of 2-methylpyrazolo[1,5-a]pyridine-3-carbonitrile (34.9 g, 220 mmol) produced in the above in methanol (300 mL) were added 4N hydrogen chloride ethyl acetate solution (150 mL, 600 mmol) and O,O'-diethyl dithiophosphate (250 g, 1.3 mol), and the mixture was stirred at 60° C. for 75 min. The reaction solution was diluted with ethyl acetate (50 mL), and cooled to room temperature. Diisopropyl ether (350 mL) was added, and the mixture was stirred at 0° C. for 1 hr. The resulting yellow solid was collected by filtration, washed with diethyl ether (150 mL) and dried to give the title compound (39 g, 77%) as a yellow solid.

$^1$H-NMR (DMSO-$d_6$, 300 MHz) δ 2.57 (3H, s), 6.99 (1H, dt, J=1.4, 6.9 Hz), 7.42 (1H, ddd, J=1.1, 6.9, 9.0 Hz), 8.24 (1H, td, J=1.2, 8.9 Hz), 8.65 (1H, td, J=1.1, 6.9 Hz), 8.74 (1H, br s).

(vi) Production of ethyl 2-(2-methylpyrazolo[1,5-a]pyridin-3-yl)-4-phenyl-1,3-thiazole-5-carboxylate A mixture of 2-methylpyrazolo[1,5-a]pyridine-3-carbothioamide (400 mg, 2.1 mmol) produced in the same manner as above, ethyl 2-bromo-3-oxo-3-phenylpropanoate (569 mg, 2.1 mmol) and ethanol (10 mL) was stirred at 80° C. for 4 hr. To the reaction mixture were added aqueous sodium bicarbonate solution, ethyl acetate and tetrahydrofuran, and the insoluble material was filtered off. The filtrate was extracted with a mixed solvent of ethyl acetate and tetrahydrofuran. The collected organic layer was washed with saturated brine and dried over anhydrous magnesium sulfate, and the insoluble material was filtered off. The filtrate was concentrated under reduced pressure, the obtained residue was purified by silica gel column chromatography (ethyl acetate/hexane=20/80→100/0), and the crude purified product was washed with diisopropyl ether to give the title compound (273 mg, 36%) as a pale-yellow solid.

$^1$H-NMR (DMSO-$d_6$, 300 MHz) δ 1.24 (3H, t, J=7.2 Hz), 2.71 (3H, s), 4.25 (2H, q, J=7.2 Hz), 7.12 (1H, dt, J=1.2, 6.8 Hz), 7.45-7.55 (3H, m), 7.59 (1H, ddd, J=1.2, 6.8, 8.9 Hz), 7.80-7.89 (2H, m), 8.36 (1H, td, J=1.2, 8.9 Hz), 8.80 (1H, td, J=1.2, 6.8 Hz).

(vii) Production of 2-(2-methylpyrazolo[1,5-a]pyridin-3-yl)-4-phenyl-1,3-thiazole-5-carboxylic acid A mixture of ethyl 2-(2-methylpyrazolo[1,5-a]pyridin-3-yl)-4-phenyl-1,3-thiazole-5-carboxylate (250 mg, 0.7 mmol) produced in the above, 1N aqueous sodium hydroxide solution (2 mL), methanol (5 mL) and tetrahydrofuran (5 mL) was stirred at 60° C. for 1 hr. The reaction mixture was concentrated under reduced pressure to about ½ volume, and 1N hydrochloric acid (2 mL) and water were added. The resulting precipitate was collected by filtration, washed with water and diethyl ether and dried to give the title compound (230 mg, 98%) as a pale-yellow solid.

$^1$H-NMR (DMSO-$d_6$, 300 MHz) δ 2.70 (3H, s), 7.11 (1H, dt, J=1.2, 6.8 Hz), 7.42-7.53 (3H, m), 7.57 (1H, ddd, J=1.2, 6.8, 8.9 Hz), 7.83-7.92 (2H, m), 8.35 (1H, td, J=1.2, 8.9 Hz), 8.79 (1H, td, J=1.2, 6.8 Hz), 13.24 (1H, br s).

(viii) Production of 2-(2-methylpyrazolo[1,5-a]pyridin-3-yl)-4-phenyl-1,3-thiazole-5-carboxamide A mixture of 2-(2-methylpyrazolo[1,5-a]pyridin-3-yl)-4-phenyl-1,3-thiazole-5-carboxylic acid (230 mg, 0.69 mmol) produced in the above, ammonium chloride (110 mg, 2.1 mmol), triethylamine (0.29 mL, 2.1 mmol), N-[3-(dimethylamino)propyl]-N'-ethylcarbodiimide hydrochloride (200 mg, 1.1 mmol), 1-hydroxybenzotriazole (140 mg, 1.1 mmol) and N,N-dimethylformamide (10 mL) was stirred at room temperature for 1 day. The reaction mixture was concentrated under reduced pressure, and water was added to the obtained residue. The resulting precipitate was collected by filtration, washed with water and diethyl ether and dried to give the title compound (210 mg, 93%) as a colorless solid.

$^1$H-NMR (DMSO-$d_6$, 300 MHz) δ 2.70 (3H, s), 7.09 (1H, dt, J=1.2, 6.8 Hz), 7.40-7.60 (4H, m), 7.68 (2H, br s), 7.83-7.90 (2H, m), 8.35 (1H, td, J=1.2, 8.8 Hz), 8.78 (1H, td, J=1.2, 6.8 Hz).

(ix) Production of 2-methyl-3-[4-phenyl-5-(4H-1,2,4-triazol-3-yl)-1,3-thiazol-2-yl]pyrazolo[1,5-a]pyridine p-toluenesulfonate A mixture of 2-(2-methylpyrazolo[1,5-a]pyridin-3-yl)-4-phenyl-1,3-thiazole-5-carboxamide (200 mg, 0.6 mmol) produced in the above and N,N-dimethylformamide dimethyl acetal (5 mL) was stirred at 100° C. for 2 hr. The reaction mixture was concentrated under reduced pressure, hydrazine monohydrate (0.29 mL, 6.0 mmol) and acetic acid (10 mL) were added to the obtained residue, and the mixture was stirred at 100° C. for 2 hr. The reaction mixture was concentrated under reduced pressure, and aqueous sodium bicarbonate solution and diethyl ether were added to the obtained residue. The resulting precipitate was collected by filtration, washed with water and diethyl ether and dried to give 2-methyl-3-[4-phenyl-5-(4H-1,2,4-triazol-3-yl)-1,3-thiazol-2-yl]pyrazolo[1,5-a]pyridine (210 mg, 98%) as a pale-yellow solid. The obtained 2-methyl-3-[4-phenyl-5-(4H-1,2,4-triazol-3-yl)-1,3-thiazol-2-yl]pyrazolo[1,5-a]pyridine (90 mg, 0.25 mmol) and p-toluenesulfonic acid monohydrate (57 mg, 0.3 mmol) were dissolved in ethanol (6 mL) by heating, and the mixture was concentrated under reduced pressure. The obtained residue was crystallized from ethanol and ethyl acetate to give the title compound (93 mg, 70%) as a pale-orange solid.

$^1$H-NMR (DMSO-d$_6$, 300 MHz) δ 2.29 (3H, s), 2.73 (3H, s), 7.05-7.15 (3H, m), 7.36-7.51 (5H, m), 7.55 (1H, ddd, J=1.0, 6.8, 8.8 Hz), 7.87-7.94 (2H, m), 8.38 (1H, td, J=1.0, 8.8 Hz), 8.62 (1H, s), 8.78 (1H, d, J=6.8 Hz).

Example 12-B

Production of 3-[4-phenyl-5-(4H-1,2,4-triazol-3-yl)-1,3-thiazol-2-yl]pyrazolo[1,5-a]pyridine

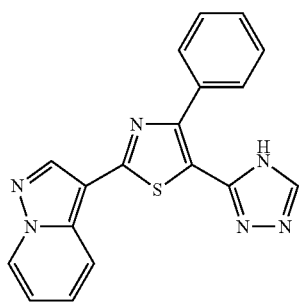 [SMILES: c1ccc(-c2nc(-c3cnn4ccccc34)sc2-c2nnc[nH]2)cc1]

(i) Production of ethyl 2-(pyrazolo[1,5-a]pyridin-3-yl)-4-phenyl-1,3-thiazole-5-carboxylate To a suspension of commercially available pyrazolo[1,5-a]pyridine-3-carbothioamide (580 mg, 3.3 mmol) in ethanol (20 mL) was added ethyl 2-bromo-3-oxo-3-phenylpropanoate (1.0 g, 3.7 mmol), and the mixture was heated under reflux for 11 hr. The reaction solution was allowed to cool to room temperature, and the resulting solid was collected by filtration and washed with methanol. The collected filtrate and washing solution was concentrated under reduced pressure, and the obtained residue was suspended in ethyl acetate (100 mL). The obtained suspension was washed with saturated aqueous sodium bicarbonate solution (50 mL×2), and the collected aqueous layer was extracted with ethyl acetate (50 mL). The collected organic layer was dried over anhydrous magnesium sulfate, the insoluble material was filtered off, and the filtrate was concentrated under reduced pressure. The obtained residue was purified by silica gel column chromatography (ethyl acetate/hexane=5/95→100/0) to give the title compound (360 mg, 31%) as a yellow solid.

$^1$H-NMR (DMSO-d$_6$, 300 MHz) δ 1.23 (3H, t, J=7.1 Hz), 4.24 (2H, q, J=7.1 Hz), 7.17 (1H, dt, J=1.2, 6.9 Hz), 7.44-7.53 (3H, m), 7.62 (1H, ddd, 1.2, 6.9, 8.9 Hz), 7.78-7.88 (2H, m), 8.33 (1H, d, J=8.9 Hz), 8.77 (1H, s), 8.90 (1H, d, J=6.9 Hz).

(ii) Production of 2-(pyrazolo[1,5-a]pyridin-3-yl)-4-phenyl-1,3-thiazole-5-carboxylic acid To a solution of ethyl 2-(pyrazolo[1,5-a]pyridin-3-yl)-4-phenyl-1,3-thiazole-5-carboxylate produced in the above in hot methanol (20 mL) was added 1N aqueous sodium hydroxide solution (5 mL), and the mixture was heated under reflux for 30 min. The reaction solution was cooled to 0° C., and 6N hydrochloric acid (1 mL) was added to adjust the solution to about pH 5.0. The resulting solid was collected by filtration, and washed with methanol and diethyl ether to give the title compound (192 mg, 58%). The combined filtrate and washing solution was concentrated under reduced pressure to give a second crop (110 mg, including slight amount of sodium chloride) of the title compound.

$^1$H-NMR (DMSO-d$_6$, 300 MHz) δ 7.16 (1H, dt, J=1.2, 6.9 Hz), 7.42-7.52 (3H, m), 7.60 (1H, ddd, 1.2, 6.9, 8.9 Hz), 7.80-7.90 (2H, m), 8.33 (1H, d, J=8.9 Hz), 8.73 (1H, s), 8.89 (1H, d, J=6.9 Hz), 13.25 (1H, br s).

(iii) Production of 2-(pyrazolo[1,5-a]pyridin-3-yl)-4-phenyl-1,3-thiazole-5-carboxamide To a suspension of 2-(pyrazolo[1,5-a]pyridin-3-yl)-4-phenyl-1,3-thiazole-5-carboxylic acid (263 mg, 0.82 mmol) produced in the above in toluene (50 mL) was added thionyl chloride (3 mL, 41 mol), and the mixture was heated under reflux for 2 hr. The obtained solution was allowed to cool to room temperature, and concentrated under reduced pressure, and the obtained residue was used as an acid chloride for the next reaction.

The acid chloride produced in the above was dissolved in tetrahydrofuran (50 mL), 25% aqueous ammonia (30 mL) was added, and the mixture was vigorously stirred for 1 hr. The aqueous layer was separated, and extracted with ethyl acetate (50 mL×2). The collected organic layer was dried over anhydrous magnesium sulfate, and the insoluble material was filtered off. The filtrate was concentrated under reduced pressure to give the title compound (260 mg, 99%) as a yellow solid.

$^1$H-NMR (DMSO-d$_6$, 300 MHz) δ 7.15 (1H, dt, J=1.3, 6.9 Hz), 7.38-7.54 (3H, m), 7.59 (1H, ddd, 0.9, 6.9, 8.8 Hz), 7.69 (2H, br s), 7.82-7.91 (2H, m), 8.35 (1H, ddd, J=0.9, 1.3, 8.8 Hz), 8.67 (1H, s), 8.88 (1H, d, J=6.9 Hz).

(iv) Production of 3-[4-phenyl-5-(4H-1,2,4-triazol-3-yl)-1,3-thiazol-2-yl]pyrazolo[1,5-a]pyridine 2-(Pyrazolo[1,5-a]pyridin-3-yl)-4-phenyl-1,3-thiazole-5-carboxamide (200 mg, 0.62 mmol) produced in the above was suspended in N,N-dimethylformamide dimethyl acetal (20 mL), and the mixture was heated under reflux for 1 hr. The obtained solution was allowed to cool to room temperature, and concentrated under reduced pressure. The obtained residue was suspended in acetic acid (10 mL), hydrazine monohydrate (0.5 mL) was added, and the mixture was stirred at 100° C. for 30 min. The reaction solution was allowed to cool to room temperature, and acetic acid was evaporated under reduced pressure. Saturated aqueous sodium bicarbonate solution (50 mL), tetrahydrofuran (20 mL) and ethyl acetate (50 mL) were added to the obtained residue, and the mixture was vigorously stirred for 15 min. The organic layer was separated, and the aqueous layer was extracted with ethyl acetate (50 mL). The collected organic layer was dried over anhydrous magnesium sulfate, the insoluble material was filtered off, and the filtrate was concentrated under reduced pressure. The residue was crystallized from tetrahydrofuran, ethyl acetate and diethyl ether to give the title compound (160 mg, 74%) as a colorless solid.

$^1$H-NMR (DMSO-d$_6$, 300 MHz) δ 7.14 (1H, dt, J=1.2, 6.8 Hz), 7.36-7.50 (3H, m), 7.59 (1H, ddd, J=1.2, 6.8, 8.8 Hz), 7.84-7.97 (2H, m), 8.37 (1H, td, J=1.2, 8.8 Hz), 8.61 (1H, s), 8.69 (1H, s), 8.88 (1H, d, J=6.8 Hz), 14.25 (1H, br s).

Example 13-B

Production of 3-[4-(3-fluorophenyl)-5-(4H-1,2,4-triazol-3-yl)-1,3-thiazol-2-yl]-2-methylpyrazolo[1,5-a]pyridine

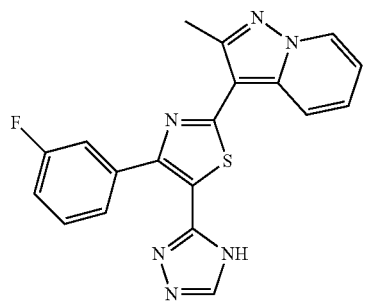 [SMILES: Cc1nn2ccccc2c1-c1nc(-c2cccc(F)c2)c(-c2nnc[nH]2)s1]

(i) Production of methyl 4-hydroxy-2-(2-methylpyrazolo[1,5-a]pyridin-3-yl)-1,3-thiazole-5-carboxylate A suspension of 2-methylpyrazolo[1,5-a]pyridine-3-carbothioamide hydrochloride (3.0 g, 13 mmol) produced in Example 11-B (v) and dimethyl chloromalonate (6.6 g, 40 mmol) in 2-propanol (40 mL) was stirred at 90° C. for 7 hr. The reaction mixture was cooled to room temperature, and the precipitated solid was collected by filtration, washed with ethyl acetate and diisopropyl ether and dried to give the title compound (3.1 g, 82%) as a yellow solid.
$^1$H-NMR (DMSO-$d_6$, 300 MHz) δ 2.64 (3H, s), 3.73 (3H, s), 7.11 (1H, dt, J=1.3, 6.8 Hz), 7.58 (1H, ddd, J=1.3, 6.8, 8.8 Hz), 8.36 (1H, td, J=1.3, 8.8 Hz), 8.76 (1H, td, J=1.3, 6.8 Hz), 11.78 (1H, s).

(ii) Production of methyl 2-(2-methylpyrazolo[1,5-a]pyridin-3-yl)-4-{[(trifluoromethyl)sulfonyl]oxy}-1,3-thiazole-5-carboxylate To a solution of methyl 4-hydroxy-2-(2-methylpyrazolo[1,5-a]pyridin-3-yl)-1,3-thiazole-5-carboxylate (2.0 g, 6.9 mmol) produced in the above in pyridine (150 mL) was added trifluoromethanesulfonic anhydride (9.4 g, 33 mmol) at 0° C., and the mixture was stirred at room temperature for 4 hr. The reaction solution was cooled to 0° C., saturated aqueous ammonium chloride solution (500 mL) and ethyl acetate (500 mL) were added, and the mixture was stirred for 30 min. The organic layer was washed with saturated brine and dried over anhydrous magnesium sulfate, and the insoluble material was filtered off. The filtrate was concentrated under reduced pressure. The obtained residue was purified by silica gel column chromatography (ethyl acetate) to give the title compound (2.8 g, 94%) as a yellow solid.
$^1$H-NMR (DMSO-$d_6$, 300 MHz) δ 2.67 (3H, s) 3.89 (3H, s) 7.21 (1H, dt, J=1.2, 6.8 Hz) 7.71 (1H, ddd, J=1.2, 6.8, 8.8 Hz), 8.18 (1H, td, J=1.2, 8.8 Hz), 8.87 (1H, td, J=1.2, 6.8 Hz).

(iii) Production of methyl 4-(3-fluorophenyl)-2-(2-methylpyrazolo[1,5-a]pyridin-3-yl)-1,3-thiazole-5-carboxylate Methyl 2-(2-methylpyrazolo[1,5-a]pyridin-3-yl)-4-{[(trifluoromethyl)sulfonyl]oxy}-1,3-thiazole-5-carboxylate (350 mg, 0.83 mmol) produced in the above, (3-fluorophenyl)boronic acid (480 mg, 3.4 mmol), [1,1-bis(diphenylphosphino)ferrocene]palladium(II) dichloride dichloromethane complex (75 mg, 0.092 mmol) and cesium carbonate (700 mg, 2.2 mmol) were suspended in 1,2-dimethoxyethane (30 mL), water (2 mL) was added, and the mixture was stirred at 80° C. for 1 hr. The reaction solution was cooled to room temperature, water (50 mL) was added, and the mixture was extracted with ethyl acetate (50 mL×2). The collected organic layer was dried over anhydrous magnesium sulfate, the insoluble material was filtered off, and the filtrate was concentrated. The obtained residue was purified by silica gel column chromatography (ethyl acetate) to give the title compound (127 mg, 42%) as a brown solid.
$^1$H-NMR (DMSO-$d_6$, 300 MHz) δ 2.65 (3H, s), 3.73 (3H, s), 7.00-7.85 (6H, m), 8.41-8.53 (1H, m), 8.88 (1H, d, J=6.8 Hz).

(iv) Production of 4-(3-fluorophenyl)-2-(2-methylpyrazolo[1,5-a]pyridin-3-yl)-1,3-thiazole-5-carboxylic acid To a solution of methyl 4-(3-fluorophenyl)-2-(2-methylpyrazolo[1,5-a]pyridin-3-yl)-1,3-thiazole-5-carboxylate (120 mg; 0.27 mmol) purified above in methanol (15 mL) and tetrahydrofuran (25 mL) was added 8N aqueous sodium hydroxide solution (6 mL), and the mixture was stirred at 70° C. for 1 hr. The reaction solution was cooled to 0° C., 6N hydrochloric acid was added to adjust the solution to about pH 3.0, and the reaction solution was extracted with ethyl acetate (100 mL×2). The collected organic layer was dried over anhydrous magnesium sulfate, the insoluble material was filtered off, and the filtrate was concentrated to give the title compound (105 mg, 91%) as a yellow solid.
$^1$H-NMR (DMSO-$d_6$, 300 MHz) δ 2.76 (3H, s), 7.02-7.78 (6H, m), 8.43-8.51 (1H, m), 8.87 (1H, d, J=6.8 Hz), (v) Production of 4-(3-fluorophenyl)-2-(2-methylpyrazolo[1,5-a]pyridin-3-yl)-1,3-thiazole-5-carboxamide A mixture of 4-(3-fluorophenyl)-2-(2-methylpyrazolo[1,5-a]pyridin-3-yl)-1,3-thiazole-5-carboxylic acid (120 mg, 0.34 mmol) produced in the above, ammonium chloride (4.0 g, 75 mmol), triethylamine (3 mL), 1-hydroxybenzotriazole (100 mg, 0.74 mmol), N-[3-(dimethylamino)propyl]-N'-ethylcarbodiimide hydrochloride (450 mg, 2.3 mmol) and N,N-dimethylformamide (15 mL) was stirred at room temperature for 10 hr. Water (100 mL) and ethyl acetate (100 mL) were added to the reaction solution, and the mixture was stirred for 30 min. The organic layer was washed with saturated brine and dried over anhydrous magnesium sulfate, the insoluble material was filtered off, and the filtrate was concentrated under reduced pressure. The obtained residue was purified by basic silica gel column chromatography (ethyl acetate) to give the title compound (76 mg, 63%) as a brown solid.
$^1$H-NMR (DMSO-$d_6$, 300 MHz) δ 2.76 (3H, s), 7.02-7.38 (4H, m), 7.46-7.84 (4H, m), 8.47 (1H, d, J=8.9 Hz), 8.88 (1H, d, J=6.8 Hz).

(vi) Production of 3-[4-(3-fluorophenyl)-5-(4H-1,2,4-triazol-3-yl)-1,3-thiazol-2-yl]-2-methylpyrazolo[1,5-a]pyridine A solution of 4-(3-fluorophenyl)-2-(2-methylpyrazolo[1,5-a]pyridin-3-yl)-1,3-thiazole-5-carboxamide (75 mg, 0.21 mmol) produced in the above in N,N-dimethylformamide dimethyl acetal (7 mL) was stirred with heating at 90° C. for 1 hr. The reaction solution was cooled to room temperature, the solvent was evaporated, and the residue was washed with hexane (5 mL) and diethyl ether (2 mL). The solvent was removed. The obtained residue was dissolved in acetic acid (10 mL), hydrazine monohydrate (0.3 mL) was added, and the mixture was stirred with heating at 80° C. for 1 hr. The reaction solution was cooled to room temperature, saturated aqueous sodium bicarbonate solution (50 mL) and ethyl acetate (50 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was washed with ethyl acetate (2 mL) and diethyl ether (10 mL) to give the title compound (43 mg, 54%) as a brown solid.

$^1$H-NMR (DMSO-$d_6$, 300 MHz) δ 2.73 (3H, s), 7.09 (1H, dt, J=1.3, 6.9 Hz), 7.19-7.30 (1H, m), 7.42-7.63 (2H, m), 7.76-7.92 (2H, m), 8.37 (1H, d, J=8.9 Hz), 8.61 (1H, s), 8.78 (1H, d, J=6.9 Hz).

Example 14-B

Production of 3-[4-ethoxy-5-(4H-1,2,4-triazol-3-yl)-1,3-thiazol-2-yl]-2-methylpyrazolo[1,5-a]pyridine

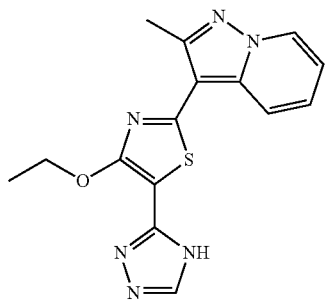 [SMILES: CCOc1nc(-c2c(C)nn3ccccc23)sc1-c1nnc[nH]1]

(i) Production of ethyl 4-hydroxy-2-(2-methylpyrazolo[1,5-a]pyridin-3-yl)-1,3-thiazole-5-carboxylate and ethyl 4-ethoxy-2-(2-methylpyrazolo[1,5-a]pyridin-3-yl)-1,3-thiazole-5-carboxylate A suspension of 2-methylpyrazolo[1,5-a]pyridine-3-carbothioamide hydrochloride (1.7 g, 7.5 mmol) produced in Example 11-B (v) and diethyl chloromalonate (2.0 g, 11 mmol) in 2-propanol (25 mL) was stirred at 90° C. for 4 hr with heating. The reaction mixture was cooled to room temperature, and the precipitated solid was collected by filtration and dried to give ethyl 4-hydroxy-2-(2-methylpyrazolo[1,5-a]pyridin-3-yl)-1,3-thiazole-5-carboxylate (1.45 g, 64%) as a yellow solid.

$^1$H-NMR (DMSO-$d_6$, 300 MHz) δ 1.27 (3H, t, J=7.1 Hz), 2.65 (3H, s), 4.23 (2H, q, J=7.1 Hz), 7.12 (1H, dt, J=1.3, 6.8 Hz), 7.51-7.65 (1H, m), 8.36 (1H, d, J=8.9 Hz), 8.79 (1H, d, J=6.8 Hz), 11.76 (1H, s).

Saturated aqueous sodium bicarbonate solution (100 mL) and ethyl acetate (100 mL) were added to the filtrate, and the mixture was stirred for 30 min. The organic layer was dried over anhydrous magnesium sulfate, the insoluble material was filtered off, and the filtrate was concentrated. The obtained residue was purified by silica gel column chromatography (ethyl acetate) to give ethyl 4-ethoxy-2-(2-methylpyrazolo[1,5-a]pyridin-3-yl)-1,3-thiazole-5-carboxylate (200 mg, 32%) as a yellow solid.

$^1$H-NMR (DMSO-$d_6$, 300 MHz) δ 1.27 (3H, t, J=7.1 Hz), 1.42 (3H, t, J=6.9 Hz), 2.65 (3H, s), 4.23 (2H, q, J=7.1 Hz), 4.61 (2H, q, J=6.9 Hz), 7.12 (1H, dt, J=1.3, 6.9 Hz), 7.55-7.69 (1H, m), 8.32 (1H, d, J=8.9 Hz), 8.79 (1H, d, J=6.9 Hz).

(ii) Production of 4-ethoxy-2-(2-methylpyrazolo[1,5-a]pyridin-3-yl)-1,3-thiazole-5-carboxylic acid Using ethyl 4-ethoxy-2-(2-methylpyrazolo[1,5-a]pyridin-3-yl)-1,3-thiazole-5-carboxylate (500 mg, 0.27 mmol) produced in the above, methanol (10 mL), tetrahydrofuran (10 mL) and 8N aqueous sodium hydroxide solution (5 mL) as starting materials and in the same manner as in Example 13-B (iv), the title compound (435 mg, 95%) was obtained as a yellow solid.

$^1$H-NMR (DMSO-$d_6$, 300 MHz) δ 1.41 (3H, t, J=7.0 Hz), 2.65 (3H, s), 4.59 (2H, q, J=7.0 Hz), 7.12 (1H, dt, J=1.0, 6.8 Hz), 7.59 (1H, ddd, J=1.0, 6.8, 8.7 Hz), 8.29 (1H, d, J=8.7 Hz), 8.80 (1H, d, J=6.8 Hz), 12.54 (1H, s), (iii) Production of 4-ethoxy-2-(2-methylpyrazolo[1,5-a]pyridin-3-yl)-1,3-thiazole-5-carboxamide Using 4-ethoxy-2-(2-methylpyrazolo[1,5-a]pyridin-3-yl)-1,3-thiazole-5-carboxylic acid (400 mg, 1.3 mmol) produced in the above, ammonium chloride (2.5 g, 47 mmol), triethylamine (3 mL), 1-hydroxybenzotriazole (250 mg, 1.9 mmol), N-[3-(dimethylamino)propyl]-N'-ethylcarbodiimide hydrochloride (1.2 g, 6.3 mmol) and N,N-dimethylformamide (50 mL) as starting materials and in the same manner as in Example 13-B(v), the title compound (390 mg, 98%) was obtained as a yellow solid.

$^1$H-NMR (DMSO-$d_6$, 300 MHz) δ 1.42-1.49 (3H, m), 2.65 (3H, s), 4.63 (2H, q, J=7.0 Hz), 6.87 (1H, s), 7.11 (1H, dt, J=1.3, 6.8 Hz) 7.50-7.63 (2H, m), 8.25-8.35 (1H, m), 8.79 (1H, d, J=6.8 Hz).

(iv) Production of 3-[4-ethoxy-5-(4H-1,2,4-triazol-3-yl)-1,3-thiazol-2-yl]-2-methylpyrazolo[1,5-a]pyridine Using 4-ethoxy-2-(2-methylpyrazolo[1,5-a]pyridin-3-yl)-1,3-thiazole-5-carboxamide (200 mg, 0.66 mmol) produced in the above, N,N-dimethylformamide dimethyl acetal (45 mL), acetic acid (50 mL) and hydrazine monohydrate (0.5 mL) as starting materials and in the same manner as in Example 13-B(vi), the title compound (145 mg, 67%) was obtained as a yellow solid.

$^1$H-NMR (DMSO-$d_6$, 300 MHz) δ 1.46 (3H, t, J=7.0 Hz), 2.68 (3H, s), 4.62 (2H, q, J=7.0 Hz), 7.10 (1H, dt, J=1.2, 6.9

Hz), 7.57 (1H, ddd, J=1.2, 6.9, 8.9 Hz), 8.19 (1H, s), 8.28-8.38 (1H, m), 8.78 (1H, d, J=6.9 Hz), 13.83 (1H, s).

Example 15-B

Production of 2-methyl-3-[4-thiophen-3-yl-5-(4H-1,2,4-triazol-3-yl)-1,3-thiazol-2-yl]pyrazolo[1,5-a]pyridine

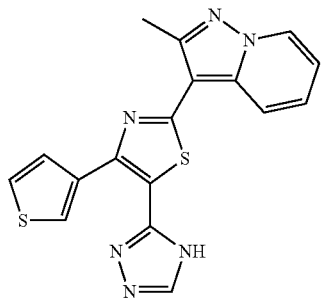 [SMILES: Cc1nn2ccccc2c1-c1nc(-c2ccsc2)c(-c2nnc[nH]2)s1]

(i) Production of ethyl 2-(2-methylpyrazolo[1,5-a]pyridin-3-yl)-4-{[(trifluoromethyl)sulfonyl]oxy}-1,3-thiazole-5-carboxylate Using ethyl 4-hydroxy-2-(2-methylpyrazolo[1,5-a]pyridin-3-yl)-1,3-thiazole-5-carboxylate (1.4 g, 4.7 mmol) produced in Example 14-B (i), pyridine (30 mL) and trifluoromethanesulfonic anhydride (3.3 g, 12 mmol) as starting materials and in the same manner as in Example 13-B (ii), the title compound (1.1 g, 53%) was obtained as a yellow solid.

$^1$H-NMR (DMSO-d$_6$, 300 MHz) δ 1.33 (3H, t, J=7.1 Hz), 2.68 (3H, s), 4.37 (2H, q, J=7.1 Hz), 7.21 (1H, dt, J=1.2, 6.9 Hz), 7.72 (1H, ddd, J=1.2, 6.9, 8.9 Hz), 8.16-8.21 (1H, m), 8.86-8.89 (1H, m), (ii) Production of ethyl 2-(2-methylpyrazolo[1,5-a]pyridin-3-yl)-4-thiophen-3-yl-1,3-thiazole-5-carboxylate Using ethyl 2-(2-methylpyrazolo[1,5-a]pyridin-3-yl)-4-{[(trifluoromethyl)sulfonyl]oxy}-1,3-thiazole-5-carboxylate (170 mg, 0.39 mmol) produced in the above, thiophen-3-ylboronic acid (100 mg, 0.78 mmol), [1,1-bis(diphenylphosphino)ferrocene]palladium(II) dichloride dichloromethane complex (52 mg, 0.092 mmol), cesium carbonate (450 mg, 2.15 mmol), water (0.5 mL) and 1,2-dimethoxyethane (10 mL) as starting materials and in the same manner as in Example 13-B (iii), the title compound (121 mg, 83%) was obtained as a yellow solid.

$^1$H-NMR (DMSO-d$_6$, 300 MHz) δ 1.31 (3H, t, J=7.1 Hz), 2.71 (3H, s), 4.32 (2H, q, J=7.1 Hz), 7.14 (1H, dt, J=1.3, 6.9 Hz), 7.58-7.68 (2H, m), 7.86 (1H, dd, J=1.2, 5.1 Hz), 8.43 (1H, d, J=8.7 Hz), 8.48 (1H, dd, J=-1.2, 3.0 Hz), 8.82 (1H, d, J=6.9 Hz), (iii) Production of 2-(2-methylpyrazolo[1,5-a]pyridin-3-yl)-4-thiophen-3-yl-1,3-thiazole-5-carboxylic acid Using ethyl 2-(2-methylpyrazolo[1,5-a]pyridin-3-yl)-4-thiophen-3-yl-1,3-thiazole-5-carboxylate (150 mg, 0.27 mmol) produced in the above, methanol (5 mL), tetrahydrofuran (5 mL) and 8N aqueous sodium hydroxide solution (1 mL) as starting materials and in the same manner as in Example 13-B (iv), the title compound (139 mg, 99%) was obtained as a yellow solid.

$^1$H-NMR (DMSO-d$_6$, 300 MHz) δ 2.71 (3H, s), 7.11 (1H, dt, J=1.3, 6.9 Hz), 7.48-7.63 (2H, m), 7.94 (1H, d, J=5.1 Hz), 8.42 (1H, d, J=8.9 Hz), 8.56 (1H, s), 8.79 (1H, d, J=6.9 Hz).

(iv) Production of 2-(2-methylpyrazolo[1,5-a]pyridin-3-yl)-4-thiophen-3-yl-1,3-thiazole-5-carboxamide Using 2-(2-methylpyrazolo[1,5-a]pyridin-3-yl)-4-thiophen-3-yl-1,3-thiazole-5-carboxylic acid (110 mg, 0.32 mmol) produced in the above, ammonium chloride (1.2 g, 22 mmol), triethylamine (1.5 mL), 1-hydroxybenzotriazole (52 mg, 0.38 mmol), N-[3-(dimethylamino)propyl]-N'-ethylcarbodiimide hydrochloride (400 mg, 2.1 mmol) and N,N-dimethylformamide (25 mL) as starting materials and in the same manner as in Example 13-B (v), the title compound (95 mg, 87%) was obtained as a brown solid.

$^1$H-NMR (DMSO-d$_6$, 300 MHz) δ 2.70 (3H, s), 7.10 (1H, dt, J=1.3, 6.9 Hz), 7.53-7.97 (5H, m), 8.22 (1H, dd, J=1.3, 3.0 Hz), 8.40 (1H, dd, J=1.3, 8.9 Hz), 8.79 (1H, d, J=6.9 Hz).

v) Production of 2-methyl-3-[4-thiophen-3-yl-5-(4H-1,2,4-triazol-3-yl)-1,3-thiazol-2-yl]pyrazolo[1,5-a]pyridine Using 2-(2-methylpyrazolo[1,5-a]pyridin-3-yl)-4-thiophen-3-yl-1,3-thiazole-5-carboxamide (90 mg, 0.26 mmol) produced in the above, N,N-dimethylformamide dimethyl acetal (15 mL), acetic acid (15 mL) and hydrazine monohydrate (0.2 mL) as starting materials and in the same manner as in Example 13-B (vi), the title compound (71 mg, 74%) was obtained as a white solid.

$^1$H-NMR (DMSO-d$_6$, 300 MHz) δ 2.73 (3H, s), 7.09 (1H, dt, J=1.4, 6.8 Hz), 7.53-7.62 (2H, m), 7.91 (1H, d, J=5.1 Hz), 8.40-8.46 (1H, m), 8.60-8.68 (2H, m), 8.78 (1H, d, J=6.8 Hz).

Example 16-B

Production of 3-[4-benzyl-5-(4H-1,2,4-triazol-3-yl)-1,3-thiazol-2-yl]-2-methylpyrazolo[1,5-a]pyridine

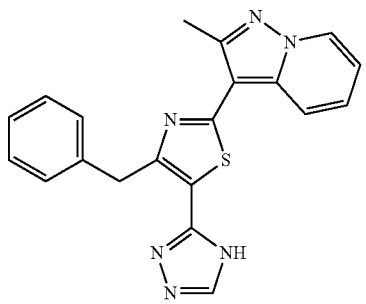 [SMILES: Cc1nn2ccccc2c1-c1nc(Cc2ccccc2)c(-c2nnc[nH]2)s1]

(i) Production of ethyl 4-benzyl-2-(2-methylpyrazolo[1,5-a]pyridin-3-yl)-1,3-thiazole-5-carboxylate Using ethyl 2-(2-methylpyrazolo[1,5-a]pyridin-3-yl)-4-{[(trifluoromethyl)sulfonyl]oxy}-1,3-thiazole-5-carboxylate (450 mg, 1.1 mmol) produced in Example 15(i), 2-benzyl-4, 4,5,5-tetramethyl-1,3,2-dioxaborolane (1.0 g, 4.6 mmol), [1,1-bis(diphenylphosphino)ferrocene]palladium(II) dichloride dichloromethane complex (70 mg, 0.086 mmol), cesium carbonate (670 mg, 2.1 mmol), water (5 mL) and 1,2-dimethoxyethane (30 mL) as starting materials and in the same manner as in Example 13-B (iii), the title compound (174 mg, 43%) was obtained as a brown solid.

$^1$H-NMR (DMSO-d$_6$, 300 MHz) δ 1.32 (3H, t, J=7.1 Hz), 2.65 (3H, s), 4.34 (2H, q, J=7.1 Hz), 4.46-4.55 (2H, m), 7.05-7.42 (6H, m), 7.57 (1H, ddd, J=1.1, 6.8, 8.9 Hz), 8.24-8.33 (1H, m), 8.78 (1H, d, J=6.8 Hz).

(ii) Production of 4-benzyl-2-(2-methylpyrazolo[1,5-a]pyridin-3-yl)-1,3-thiazole-5-carboxylic acid Using ethyl 4-benzyl-2-(2-methylpyrazolo[1,5-a]pyridin-3-yl)-1,3-thiazole-5-carboxylate (150 mg, 0.41 mmol) produced in the above, methanol (10 mL), tetrahydrofuran (15 mL) and 8N aqueous sodium hydroxide solution (1 mL) as starting materials and in the same manner as in Example 13-B (iv), the title compound (92 mg, 64%) was obtained as a yellow solid.

$^1$H-NMR (DMSO-d$_6$, 300 MHz) δ 2.63 (3H, s), 4.52 (2H, s), 7.00-7.23 (2H, m), 7.23-7.44 (4H, m), 7.47-7.58 (1H, m), 8.23-8.31 (1H, m), 8.67-8.81 (1H, m).

(iii) Production of 4-benzyl-2-(2-methylpyrazolo[1,5-a]pyridin-3-yl)-1,3-thiazole-5-carboxamide Using 4-benzyl-2-(2-methylpyrazolo[1,5-a]pyridin-3-yl)-1,3-thiazole-5-carboxylic acid (90 mg, 0.26 mmol) produced in the above, ammonium chloride (300 mg, 5.6 mmol), triethylamine (2 mL), 1-hydroxybenzotriazole (70 mg, 0.5 mmol), N-[3-(dimethylamino)propyl]-N'-ethylcarbodiimide hydrochloride (250 mg, 1.3 mmol) and N,N-dimethylformamide (25 mL) as starting materials and in the same manner as in Example 13-B (v), the title compound (88 mg, 98%) was obtained as a yellow solid.

$^1$H-NMR (DMSO-d$_6$, 300 MHz) δ 2.64 (3H, s), 4.48 (2H, s), 7.04-7.42 (6H, m), 7.44-7.75 (3H, m), 8.20-8.26 (1H, m), 8.69-8.79 (1H, m).

(iv) Production of 3-[4-benzyl-5-(4H-1,2,4-triazol-3-yl)-1,3-thiazol-2-yl]-2-methylpyrazolo[1,5-a]pyridine Using 4-benzyl-2-(2-methylpyrazolo[1,5-a]pyridin-3-yl)-1,3-thiazole-5-carboxamide (85 mg, 0.73 mmol) produced in the above, N,N-dimethylformamide dimethyl acetal (25 mL), acetic acid (25 mL) and hydrazine monohydrate (0.4 mL) as starting materials and in the same manner as in Example 13-B(vi), the title compound (63 mg, 69%) was obtained as a yellow solid.

$^1$H-NMR (DMSO-d$_6$, 300 MHz) δ 2.67 (3H, s), 4.66 (2H, s), 7.05 (1H, dt, J=1.4, 6.9 Hz), 7.14-7.21 (1H, m), 7.24-7.32 (2H, m), 7.39-7.44 (2H, m), 7.47-7.55 (1H, m), 8.28 (1H, d, J=8.8 Hz), 8.67-8.80 (2H, m), 14.30 (1H, s).

Example 17-B

Production of 3-[4-(4-fluorophenyl)-5-(4H-1,2,4-triazol-3-yl)-1,3-thiazol-2-yl]-2-methylpyrazolo[1,5-a]pyridine

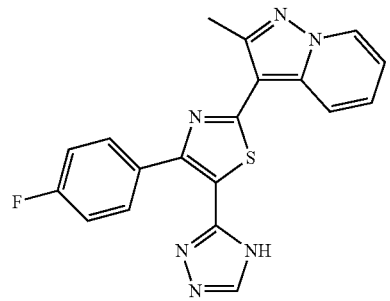 [SMILES: Cc1nn2ccccc2c1-c1nc(-c2ccc(F)cc2)c(-c2nnc[nH]2)s1]

(i) Production of ethyl 4-(4-fluorophenyl)-2-(2-methylpyrazolo[1,5-a]pyridin-3-yl)-1,3-thiazole-5-carboxylate Using ethyl 2-(2-methylpyrazolo[1,5-a]pyridin-3-yl)-4-{[(trifluoromethyl)sulfonyl]oxy}-1,3-thiazole-5-carboxylate (500 mg, 1.2 mmol) produced in Example 15-B(i), (4-fluorophenyl)boronic acid (480 mg, 3.4 mmol), [1,1-bis(diphenylphosphino)ferrocene]palladium(II) dichloride dichloromethane complex (75 mg, 0.091 mmol), cesium carbonate (700 mg, 2.2 mmol), water (2 mL) and 1,2-dimethoxyethane (30 mL) as starting materials and in the same manner as in Example 13-B(iii), the title compound (310 mg, 73%) was obtained as a brown solid.

$^1$H-NMR (DMSO-d$_6$, 300 MHz) δ 1.25 (3H, t, J=7.1 Hz), 2.69-2.72 (3H, s), 4.26 (2H, q, J=7.1 Hz), 7.09-7.39 (3H, m), 7.60 (1H, ddd, J=1.1, 7.2, 8.7 Hz), 7.79-8.00 (2H, m), 8.32-8.40 (1H, m), 8.75-8.85 (1H, m).

(ii) Production of 4-(4-fluorophenyl)-2-(2-methylpyrazolo[1,5-a]pyridin-3-yl)-1,3-thiazole-5-carboxylic acid Using ethyl 4-(4-fluorophenyl)-2-(2-methylpyrazolo[1,5-a]pyridin-3-yl)-1,3-thiazole-5-carboxylate (150 mg, 0.39 mmol) produced in the above, methanol (15 mL), tetrahydrofuran (15 mL) and 8N aqueous sodium hydroxide solution (1 mL) as starting materials and in the same manner as in Example 13-B (iv), the title compound (105 mg, 76%) was obtained as a white solid.

$^1$H-NMR (DMSO-d$_6$, 300 MHz) δ 2.70 (3H, s), 7.05-7.40 (3H, m), 7.52-7.64 (1H, m), 7.79-7.98 (2H, m), 8.35 (1H, d, J=8.6 Hz), 8.80 (1H, d, J=6.9 Hz), 13.29 (1H, s).

(iii) Production of 4-(4-fluorophenyl)-2-(2-methylpyrazolo[1,5-a]pyridin-3-yl)-1,3-thiazole-5-carboxamide Using 4-(4-fluorophenyl)-2-(2-methylpyrazolo[1,5-a]pyridin-3-yl)-1,3-thiazole-5-carboxylic acid (120 mg, 0.34 mmol) produced in the above, ammonium chloride (1.5 g, 28 mmol), N,N-dimethylformamide (30 mL), triethylamine (3 mL), 1-hydroxybenzotriazole (50 mg, 0.37 mmol) and N-[3-(dimethylamino)propyl]-N'-ethylcarbodiimide hydrochloride (1.0 g, 5.0 mmol) as starting materials and in the same manner as in Example 13-B(v), the title compound (101 mg, 84%) was obtained as a yellow solid.

$^1$H-NMR (DMSO-$d_6$, 300 MHz) δ 2.69 (3H, s), 7.10 (1H, dt, J=1.3, 6.9 Hz), 7.27-7.39 (2H, m), 7.51-7.61 (1H, m), 7.73 (2H, s), 7.88-7.95 (2H, m), 8.34 (1H, d, J=8.6 Hz), 8.79 (1H, d, J=6.9 Hz).

(iv) Production of 3-[4-(4-fluorophenyl)-5-(4H-1,2,4-triazol-3-yl)-1,3-thiazol-2-yl]-2-methylpyrazolo[1,5-a]pyridine Using 4-(4-fluorophenyl)-2-(2-methylpyrazolo[1,5-a]pyridin-3-yl)-1,3-thiazole-5-carboxamide (100 mg, 0.73 mmol) produced in the above, N,N-dimethylformamide dimethyl acetal (15 mL), acetic acid (25 mL) and hydrazine monohydrate (0.4 mL) as starting materials and in the same manner as in Example 13(vi), the title compound (73 mg, 68%) was obtained as a white solid.

$^1$H-NMR (DMSO-$d_6$, 300 MHz) δ 2.72 (3H, s), 7.09 (1H, dt, J=1.4, 6.8 Hz), 7.23-7.34 (2H, m), 7.55 (1H, ddd, J=1.1, 7.0, 8.9 Hz), 7.94-8.05 (2H, m), 8.32-8.41 (1H, m), 8.61 (1H, s), 8.75-8.81 (1H, m).

Example 18-B

Production of 3-[4-furan-3-yl-5-(4H-1,2,4-triazol-3-yl)-1,3-thiazol-2-yl]-2-methylpyrazolo[1,5-a]pyridine

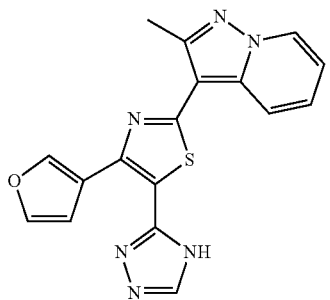 [SMILES: Cc1nn2ccccc2c1-c1nc(-c2ccoc2)c(-c2nnc[nH]2)s1]

(i) Production of methyl 4-furan-3-yl-2-(2-methylpyrazolo[1,5-a]pyridin-3-yl)-1,3-thiazole-5-carboxylate Using methyl 2-(2-methylpyrazolo[1,5-a]pyridin-3-yl)-4-{[(trifluoromethyl)sulfonyl]oxy}-1,3-thiazole-5-carboxylate (300 mg, 0.71 mmol) produced in Example 13-B (ii), furan-3-ylboronic acid (160 mg, 1.4 mmol), [1,1-bis(diphenylphosphino)ferrocene]palladium(II) dichloride dichloromethane complex (70 mg, 0.086 mmol), cesium carbonate (830 mg, 2.6 mmol), 1,2-dimethoxyethane (20 mL) and water (0.5 mL) as starting materials and in the same manner as in Example 13-B(iii), the title compound (225 mg, 93%) was obtained as a yellow solid.

$^1$H-NMR (DMSO-$d_6$, 300 MHz) δ 2.70 (3H, s), 3.87 (3H, s), 7.14 (1H, dt, J=1.3, 6.9 Hz), 7.31 (1H, dd, J=0.8, 1.9 Hz), 7.62 (1H, ddd, J=1.1, 7.0, 8.9 Hz), 7.84 (1H, t, J=1.8 Hz), 8.43-8.49 (1H, m), 8.70-8.72 (1H, m), 8.81 (1H, d, J=7.0 Hz).

(ii) Production of 4-furan-3-yl-2-(2-methylpyrazolo[1,5-a]pyridin-3-yl)-1,3-thiazole-5-carboxylic acid Using methyl 4-furan-3-yl-2-(2-methylpyrazolo[1,5-a]pyridin-3-yl)-1,3-thiazole-5-carboxylate (220 mg, 1.5 mmol) produced in the above, methanol (15 mL), tetrahydrofuran (15 mL) and 8N aqueous sodium hydroxide solution (1.5 mL) as starting materials and in the same manner as in Example 13(iv), the title compound (192 mg, 91%) was obtained as a white solid.

$^1$H-NMR (DMSO-$d_6$, 300 MHz) δ 2.70 (3H, s), 7.12 (1H, dt, J=1.3, 6.9 Hz), 7.32 (1H, d, J=1.9 Hz), 7.54-7.66 (1H, m), 7.80 (1H, t, J=1.9 Hz), 8.44 (1H, d, J=8.9 Hz), 8.70-8.72 (1H, m), 8.79 (1H, d, J=6.9 Hz).

(iii) Production of 4-furan-3-yl-2-(2-methylpyrazolo[1,5-a]pyridin-3-yl)-1,3-thiazole-5-carboxamide Using 4-furan-3-yl-2-(2-methylpyrazolo[1,5-a]pyridin-3-yl)-1,3-thiazole-5-carboxamide (200 mg, 0.61 mmol) produced in the above, ammonium chloride (2.1 g, 39 mmol), N,N-dimethylformamide (35 mL), triethylamine (3.0 mL), 1-hydroxybenzotriazole (50 mg, 0.37 mmol) and N-[3-(dimethylamino)propyl]-N'-ethylcarbodiimide hydrochloride (1.5 g, 7.8 mmol) as starting materials and in the same manner as in Example 13-B(v), the title compound (183 mg, 92%) was obtained as a white solid.

$^1$H-NMR (DMSO-$d_6$, 300 MHz) δ 2.70 (3H, s), 7.05-7.16 (2H, m), 7.57 (1H, ddd, J=1.0, 6.9, 8.9 Hz), 7.64-7.89 (3H, m), 8.37-8.44 (1H, m), 8.45-8.50 (1H, m), 8.78 (1H, d, J=6.9 Hz).

(iv) Production of 3-[4-furan-3-yl-5-(4H-1,2,4-triazol-3-yl)-1,3-thiazol-2-yl]-2-methylpyrazolo[1,5-a]pyridine Using 4-furan-3-yl-2-(2-methylpyrazolo[1,5-a]pyridin-3-yl)-1,3-thiazole-5-carboxamide (180 mg, 0.55 mmol) produced in the above, N,N-dimethylformamide dimethyl acetal (15 mL), acetic acid (25 mL) and hydrazine monohydrate (0.5 mL) as starting materials and in the same manner as in Example 13(vi), the title compound (143 mg, 74%) was obtained as a white solid.

$^1$H-NMR (DMSO-$d_6$, 300 MHz) δ 2.72 (3H, s), 7.07 (1H, dt, J=1.3, 6.9 Hz), 7.40 (1H, d, J=1.3 Hz), 7.55 (1H, ddd, J=1.1, 6.8, 8.9 Hz), 7.75 (1H, t, J=1.8 Hz), 8.37 (1H, d, J=1.3 Hz), 8.39-8.50 (1H, m), 8.76 (1H, d, J=6.8 Hz), 9.06 (1H, s).

Example 19-B

Production of 3-[4-cyclohexyl-5-(4H-1,2,4-triazol-3-yl)-1,3-thiazol-2-yl]-2-methyl-4,5,6,7-tetrahydropyrazolo[1,5-a]pyridine

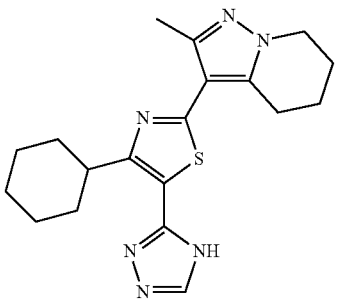 [SMILES: Cc1nn2c(c1-c1nc(C3CCCCC3)c(-c3nnc[nH]3)s1)CCCC2]

(i) Production of ethyl 4-cyclohex-1-en-1-yl-2-(2-methylpyrazolo[1,5-a]pyridin-3-yl)-1,3-thiazole-5-carboxylate Using ethyl 2-(2-methylpyrazolo[1,5-a]pyridin-3-yl)-4-{[(trifluoromethyl)sulfonyl]oxy}-1,3-thiazole-5-carboxylate (220 mg, 0.5 mmol) produced in Example 15(i), 2-cyclohex-1-en-1-yl-4,4,5,5-tetramethyl-1,3,2-dioxaborolane (620 mg, 3.0 mmol), [1,1-bis(diphenylphosphino)ferrocene]palladium (II) dichloride dichloromethane complex (72 mg, 0.088 mmol), cesium carbonate (620 mg, 1.9 mmol), water (0.5 mL) and 1,2-dimethoxyethane (15 mL) as starting materials and in the same manner as in Example 13(iii), the title compound (176 mg, 95%) was obtained as a yellow solid.

$^1$H-NMR (DMSO-$d_6$, 300 MHz) δ 1.25-1.34 (3H, m), 1.48-2.29 (8H, m), 2.67 (3H, s), 4.21-4.30 (2H, m), 6.21-6.48 (1H, m), 7.11 (1H, dt, J=1.4, 6.9 Hz), 7.55-7.63 (1H, m), 8.32 (1H, d, J=8.9 Hz), 8.79 (1H, d, J=6.8 Hz).

(ii) Production of ethyl 4-cyclohexyl-2-(2-methyl-4,5,6,7-tetrahydropyrazolo[1,5-a]pyridin-3-yl)-1,3-thiazole-5-carboxylate To a solution of ethyl 4-cyclohex-1-en-1-yl-2-(2-methylpyrazolo[1,5-a]pyridin-3-yl)-1,3-thiazole-5-carboxylate (150 mg, 6.5 mmol) produced in the above in methanol (10 mL)-tetrahydrofuran (5 mL) was added 10% palladium-carbon powder (350 mg), and the mixture was stirred at room temperature for 5 hr under a hydrogen atmosphere (1 atm). The palladium-carbon powder was filtered off, and the filtrate was concentrated under reduced pressure. The obtained residue was washed with diisopropyl ether to give the title compound (150 mg, 99%) as a gray solid.

$^1$H-NMR (DMSO-$d_6$, 300 MHz) δ 1.22-2.02 (17H, m), 2.42 (3H, s), 2.95-3.04 (2H, m), 3.49-3.64 (1H, m), 4.04 (2H, t, J=5.9 Hz), 4.27 (2H, q, J=7.2 Hz).

(iii) Production of 4-cyclohexyl-2-(2-methyl-4,5,6,7-tetrahydropyrazolo[1,5-a]pyridin-3-yl)-1,3-thiazole-5-carboxylic acid Using ethyl 4-cyclohexyl-2-(2-methyl-4,5,6,7-tetrahydropyrazolo[1,5-a]pyridin-3-yl)-1,3-thiazole-5-carboxylate (160 mg, 0.4 mmol) produced in the above, methanol (5 mL), tetrahydrofuran (20 mL) and 8N aqueous sodium hydroxide solution (1 mL) as starting materials and in the same manner as in Example 13(iv), the title compound was obtained (115 mg, 80%) as a yellow solid.

$^1$H-NMR (DMSO-$d_6$, 300 MHz) δ 1.19-2.04 (14H, m), 2.40 (3H, s), 2.93-3.02 (2H, m), 3.54-3.68 (1H, m), 3.97-4.08 (2H, m), 12.92 (1H, s).

(iv) Production of 4-cyclohexyl-2-(2-methyl-4,5,6,7-tetrahydropyrazolo[1,5-a]pyridin-3-yl)-1,3-thiazole-5-carboxamide Using 4-cyclohexyl-2-(2-methyl-4,5,6,7-tetrahydropyrazolo[1,5-a]pyridin-3-yl)-1,3-thiazole-5-carboxylic acid (105 mg, 0.3 mmol) produced in the above, ammonium chloride (500 mg, 9.3 mmol), N,N-dimethylformamide (15 mL), triethylamine (3 mL), 1-hydroxybenzotriazole (70 mg, 0.5 mmol) and N-[3-(dimethylamino)propyl]-N'-ethylcarbodiimide hydrochloride (1.0 g, 5.2 mmol) as starting materials and in the same manner as in Example 13-B (v), the title compound (65 mg, 62%) was obtained as a white solid.

$^1$H-NMR (DMSO-$d_6$, 300 MHz) δ 1.22-2.01 (14H, m), 2.40 (3H, s), 2.94-3.02 (2H, m), 3.41-3.52 (1H, m), 4.00-4.07 (2H, m), 7.36-7.49 (2H, m).

(v) Production of 3-[4-cyclohexyl-5-(4H-1,2,4-triazol-3-yl)-1,3-thiazol-2-yl]-2-methyl-4,5,6,7-tetrahydropyrazolo[1,5-a]pyridine Using 4-cyclohexyl-2-(2-methyl-4,5,6,7-tetrahydropyrazolo[1,5-a]pyridin-3-yl)-1,3-thiazole-5-carboxamide (65 mg, 0.19 mmol) produced in the above, N,N-dimethylformamide dimethyl acetal (20 mL), acetic acid (15 mL) and hydrazine monohydrate (0.4 mL) as starting materials and in the same manner as in Example 13-B (vi), the title compound (61 mg, 88%) was obtained as a white solid.

$^1$H-NMR (DMSO-$d_6$, 300 MHz) δ 1.21-2.04 (14H, m), 2.42 (3H, s), 3.00 (2H, t, J=6.2 Hz), 3.65-3.80 (1H, m), 4.00-4.10 (2H, m), 8.61 (1H, s).

Example 20-B

Production of 3-[4-cyclohexyl-5-(4H-1,2,4-triazol-3-yl)-1,3-thiazol-2-yl]-2-methylpyrazolo[1,5-a]pyridine

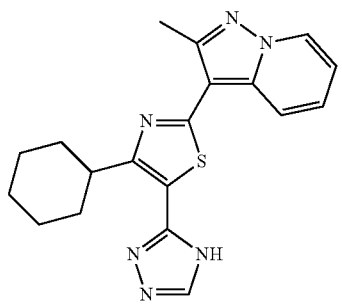 [SMILES: Cc1nn2ccccc2c1-c1nc(C2CCCCC2)c(-c2nnc[nH]2)s1]

(i) Production of ethyl 2-chloro-3-cyclohexyl-3-oxopropanoate

To a solution of ethyl 3-cyclohexyl-3-oxopropanoate (1.0 g, 5.0 mmol) in diethyl ether (15 mL) was added sulfuryl chloride (750 mg, 5.5 mmol) at 0° C., and the mixture was stirred at room temperature for 1 hr. Saturated aqueous sodium bicarbonate solution (150 mL) and ethyl acetate (150 mL) were added to the reaction solution, and the mixture was stirred for 30 min. The organic layer was washed with saturated brine (10 mL) and dried over anhydrous magnesium sulfate, and the insoluble material was filtered off. The filtrate was concentrated under reduced pressure to give the title compound (870 mg, 60%) as a colorless oil.

$^1$H-NMR (DMSO-d$_6$, 300 MHz) δ 1.08-1.34 (8H, m), 1.54-1.89 (5H, m), 2.67-2.79 (1H, m), 4.21 (2H, q, J=7.0 Hz), 5.81 (1H, s).

(ii) Production of ethyl 4-cyclohexyl-2-(2-methylpyrazolo[1,5-a]pyridin-3-yl)-1,3-thiazole-5-carboxylate Using 2-methylpyrazolo[1,5-a]pyridine-3-carbothioamide hydrochloride (300 mg, 1.3 mmol) produced in Example 11(v), ethyl 2-chloro-3-cyclohexyl-3-oxopropanoate (870 mg, 3.7 mmol) produced in the above and 2-propanol (50 mL) as starting materials and in the same manner as in Example 11-B (vi), the title compound (455 mg, 74%) was obtained as a yellow solid.

$^1$H-NMR (DMSO-d$_6$, 300 MHz) δ 1.13-1.92 (13H, m), 2.67 (3H, s), 3.57-3.67 (1H, m), 4.30 (2H, q, J=7.1 Hz), 7.11 (1H, dt, J=1.3, 6.9 Hz), 7.61 (1H, ddd, J=1.1, 7.2, 8.7 Hz), 8.33-8.39 (1H, m), 8.76-8.81 (1H, m).

(iii) Production of 4-cyclohexyl-2-(2-methylpyrazolo[1,5-a]pyridin-3-yl)-1,3-thiazole-5-carboxylic acid Using ethyl 4-cyclohexyl-2-(2-methylpyrazolo[1,5-a]pyridin-3-yl)-1,3-thiazole-5-carboxylate (350 mg, 0.95 mmol) produced in the above, methanol (10 mL), tetrahydrofuran (25 mL) and 8N aqueous sodium hydroxide solution (1 mL) as starting materials and in the same manner as in Example 13-B (iv), the title compound (275 mg, 85%) was obtained as a white solid.

$^1$H-NMR (DMSO-d$_6$, 300 MHz) δ 1.35 (10H, s), 2.65 (3H, s), 3.62-3.78 (1H, m), 7.08 (1H, dt, J=1.3, 6.9 Hz), 7.53-7.61 (1H, m), 8.31-8.38 (1H, m), 8.75 (1H, d, J=6.8 Hz), (iv) Production of 4-cyclohexyl-2-(2-methylpyrazolo[1,5-a]pyridin-3-yl)-1,3-thiazole-5-carboxamide Using 4-cyclohexyl-2-(2-methylpyrazolo[1,5-a]pyridin-3-yl)-1,3-thiazole-5-carboxylic acid (250 mg, 0.73 mmol) produced in the above, ammonium chloride (1.6 g, 19 mmol), dimethylformamide (25 mL), triethylamine (5 mL), 1-hydroxybenzotriazole (100 mg, 0.73 mmol) and N-[3-(dimethylamino)propyl]-N'-ethylcarbodiimide hydrochloride (2.0 g, 10 mmol) as starting materials and in the same manner as in Example 13-B (v), the title compound (215 mg, 86%) was obtained as a white solid.

$^1$H-NMR (DMSO-d$_6$, 300 MHz) δ 1.27-1.47 (3H, m), 1.66-1.94 (7H, m), 2.65 (3H, s), 3.62-3.78 (1H, m), 7.08 (1H, dt, J=1.3, 6.9 Hz), 7.53-7.61 (3H, m), 8.31-8.38 (1H, m), 8.75 (1H, d, J=6.8 Hz).

(v) Production of 3-[4-cyclohexyl-5-(4H-1,2,4-triazol-3-yl)-1,3-thiazol-2-yl]-2-methylpyrazolo[1,5-a]pyridine Using 4-cyclohexyl-2-(2-methylpyrazolo[1,5-a]pyridin-3-yl)-1,3-thiazole-5-carboxamide (200 mg, 0.6 mmol), N,N-dimethylformamide dimethyl acetal (15 mL), acetic acid (25 mL) and hydrazine monohydrate (0.3 mL) as starting materials and in the same manner as in Example 13-B (vi), the title compound (146 mg, 68%) was obtained as a white solid.

$^1$H-NMR (DMSO-d$_6$, 300 MHz) δ 1.28-1.50 (3H, m), 1.66-1.94 (7H, m), 2.66-2.71 (3H, s), 3.71-3.86 (1H, m), 7.06 (1H, dt, J=1.4, 6.8 Hz), 7.55 (1H, ddd, J=1.0, 6.8, 8.9 Hz), 8.31-8.40 (1H, m), 8.62 (1H, s), 8.74 (1H, d, J=7.0 Hz).

Example 21-B

Production of 3-[4-tert-butyl-5-(4H-1,2,4-triazol-3-yl)-1,3-thiazol-2-yl]-2-methylpyrazolo[1,5-a]pyridine

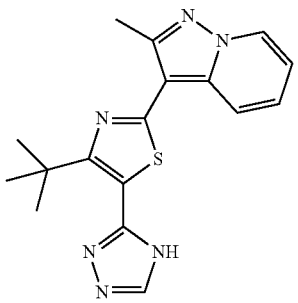 [SMILES: Cc1nn2ccccc2c1-c1nc(C(C)(C)C)c(-c2nnc[nH]2)s1]

(i) Production of methyl 2-chloro-4,4-dimethyl-3-oxopentanoate

Using 4,4-dimethyl-3-oxopentanoic acid (1.0 g, 6.3 mmol), sulfuryl chloride (940 mg, 7.0 mmol) and diethyl ether (20 mL) as starting materials and in the same manner as in Example 20(i), the title compound (980 mg, 80%) was obtained as a colorless oil.

$^1$H-NMR (DMSO-d$_6$, 300 MHz) δ 1.18 (9H, s), 3.71 (3H, s), 6.08 (1H, s).

(ii) Production of methyl 4-tert-butyl-2-(2-methylpyrazolo[1,5-a]pyridin-3-yl)-1,3-thiazole-5-carboxylate Using 2-methylpyrazolo[1,5-a]pyridine-3-carbothioamide hydrochloride (300 mg, 1.3 mmol) produced in Example 11-B(v), methyl 2-chloro-4,4-dimethyl-3-oxopentanoate (950 mg, 4.9 mmol) produced in the above and 2-propanol (25 mL) as starting materials and in the same manner as in Example 11(vi), the title compound (330 mg, 76%) was obtained as a yellow solid.

$^1$H-NMR (DMSO-d$_6$, 300 MHz) δ 1.54 (9H, s), 2.66 (3H, s), 3.83 (3H, s), 7.11 (1H, dt, J=1.3, 6.9 Hz), 7.55-7.66 (1H, m), 8.34 (1H, d, J=8.9 Hz), 8.79 (1H, d, J=6.9 Hz), (iii) Production of 4-tert-butyl-2-(2-methylpyrazolo[1,5-a]pyridin-3-yl)-1,3-thiazole-5-carboxylic acid Using methyl 4-tert-butyl-2-(2-methylpyrazolo[1,5-a]pyridin-3-yl)-1,3-thiazole-5-carboxylate (320 mg, 0.41 mmol) produced in the above, methanol (15 mL), tetrahydrofuran (20 mL) and 8N aqueous sodium hydroxide solution (3 mL) as starting materials and in the same manner as in Example 13-B(iv), the title compound (271 mg, 88%) was obtained as a yellow solid.

$^1$H-NMR (DMSO-d$_6$, 300 MHz) δ 1.54 (9H, s), 2.66 (3H, s), 7.08 (1H, dt, J=1.3, 6.8 Hz), 7.56 (1H, ddd, J=1.1, 6.8, 8.9 Hz), 8.33 (1H, d, J=8.9 Hz), 8.77 (1H, d, J=6.8 Hz).

(iv) Production of 4-tert-butyl-2-(2-methylpyrazolo[1,5-a]pyridin-3-yl)-1,3-thiazole-5-carboxamide Using 4-tert-butyl-2-(2-methylpyrazolo[1,5-a]pyridin-3-yl)-1,3-thiazole-5-carboxylic acid (250 mg, 0.79 mmol) produced in the above, ammonium chloride (1.5 g, 28 mmol), N,N-dimethylformamide (30 mL), triethylamine (4 mL), 1-hydroxybenzotriazole (50 mg, 0.37 mmol) and N-[3-(dimethylamino)propyl]-N'-ethylcarbodiimide hydrochloride (1.5 g, 7.8 mmol) as starting materials and in the same manner as in Example 13(v), the title compound (240 mg, 96%) was obtained as a brown solid.
$^1$H-NMR (DMSO-d$_6$, 300 MHz) δ 1.47 (9H, s), 2.64 (3H, s), 7.05 (1H, dt, J=1.4, 6.8 Hz), 7.53 (1H, ddd, J=1.0, 6.8, 8.9 Hz), 7.66 (1H, s), 7.99 (1H, s), 8.26 (1H, d, J=8.9 Hz), 8.74 (1H, d, J=6.8 Hz).

(v) Production of 3-[4-tert-butyl-5-(4H-1,2,4-triazol-3-yl)-1,3-thiazol-2-yl]-2-methylpyrazolo[1,5-a]pyridine Using 4-tert-butyl-2-(2-methylpyrazolo[1,5-a]pyridin-3-yl)-1,3-thiazole-5-carboxamide (230 mg, 0.73 mmol), N,N-dimethylformamide dimethyl acetal (25 mL), acetic acid (25 mL) and hydrazine monohydrate (0.5 mL) as starting materials and in the same manner as in Example 13(vi), the title compound (210 mg, 85%) was obtained as a brown solid.
$^1$H-NMR (DMSO-d$_6$, 300 MHz) δ 1.48 (9H, s), 2.66 (3H, s), 7.05 (1H, dt, J=1.4, 6.8 Hz), 7.53 (1H, ddd, J=1.0, 6.8, 8.9 Hz), 8.32 (1H, d, J=8.9 Hz), 8.62 (1H, s), 8.74 (1H, d, J=6.8 Hz), 14.18 (1H, s).

Example 22-B

Production of 3-[4-(2-fluorophenyl)-5-(4H-1,2,4-triazol-3-yl)-1,3-thiazol-2-yl]-2-methylpyrazolo[1,5-a]pyridine monoacetate

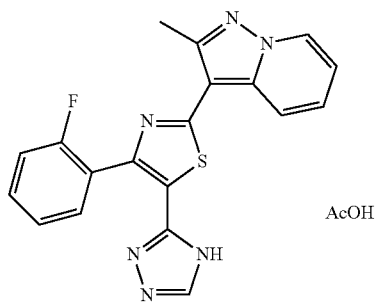 [SMILES: "AcOH" ; Cc1nn2ccccc2c1-c1nc(-c2ccccc2F)c(-c2nnc[nH]2)s1]

(i) Production of ethyl 2-chloro-3-(2-fluorophenyl)-3-oxopropanoate

Using ethyl 3-(2-fluorophenyl)-3-oxopropanoate (1.0 g, 4.75 mmol), sulfuryl chloride (771 mg, 5.7 mmol) and diethyl ether (50 mL) as starting materials and in the same manner as in Example 20(i), the title compound (1.13 g, 97%) was obtained as a colorless oil.

$^1$H-NMR (DMSO-d$_6$, 300 MHz) δ 1.11-1.22 (3H, m), 4.06-4.20 (2H, m), 6.28 (1H, d, J=0.8 Hz), 7.30-7.48 (2H, m), 7.64-8.03 (2H, m).

(ii) Production of ethyl 4-(2-fluorophenyl)-2-(2-methylpyrazolo[1,5-a]pyridin-3-yl)-1,3-thiazole-5-carboxylate Using 2-methylpyrazolo[1,5-a]pyridine-3-carbothioamide hydrochloride (300 mg, 1.3 mmol) produced in Example 11(v), ethyl 2-chloro-3-(2-fluorophenyl)-3-oxopropanoate (1.0 g, 4.09 mmol) produced in the above and 2-propanol (25 mL) as starting materials and in the same manner as in Example 11(vi), the title compound (341 mg, 68%) was obtained as a yellow solid.
$^1$H-NMR (DMSO-d$_6$, 300 MHz) δ 1.18 (3H, t, J=7.2 Hz), 2.70 (3H, s), 4.21 (2H, q, J=7.2 Hz), 7.12 (1H, dt, J=1.3, 6.9 Hz), 7.28-7.40 (2H, m), 7.49-7.62 (2H, m), 7.67-7.71 (1H, m), 8.27-8.37 (1H, m), 8.81 (1H, d, J=7.0 Hz).

(iii) Production of 4-(2-fluorophenyl)-2-(2-methylpyrazolo[1,5-a]pyridin-3-yl)-1,3-thiazole-5-carboxylic acid Using ethyl 4-(2-fluorophenyl)-2-(2-methylpyrazolo[1,5-a]pyridin-3-yl)-1,3-thiazole-5-carboxylate (340 mg, 0.89 mmol) produced in the above, methanol (15 mL), tetrahydrofuran (20 mL) and 8N aqueous sodium hydroxide solution (1 mL) as starting materials and in the same manner as in Example 13-B(iv), the title compound (312 mg, 99%) was obtained as a white solid.
$^1$H-NMR (DMSO-d$_6$, 300 MHz) δ 2.70 (3H, s), 7.11 (1H, dt, J=1.4, 6.9 Hz), 7.27-7.38 (2H, m), 7.48-7.62 (2H, m), 7.65-7.69 (1H, m), 8.31 (1H, d, J=8.9 Hz), 8.80 (1H, d, J=6.9 Hz).

(iv) Production of 4-(2-fluorophenyl)-2-(2-methylpyrazolo[1,5-a]pyridin-3-yl)-1,3-thiazole-5-carboxamide Using 4-(2-fluorophenyl)-2-(2-methylpyrazolo[1,5-a]pyridin-3-yl)-1,3-thiazole-5-carboxylic acid (300 mg, 0.85 mmol) produced in the above, ammonium chloride (1.5 g, 28 mmol), N,N-dimethylformamide (40 mL), triethylamine (6 mL), 1-hydroxybenzotriazole (70 mg, 0.52 mmol) and N-[3-(dimethylamino)propyl]-N'-ethylcarbodiimide hydrochloride (1.0 g, 5.2 mmol) as starting materials and in the same manner as in Example 13(v), the title compound (290 mg, 97%) was obtained as a white solid.
$^1$H-NMR (DMSO-d$_6$, 300 MHz) δ 2.70 (3H, s) 7.09 (1H, dt, J=1.3, 6.9 Hz), 7.24-7.42 (2H, m), 7.44-7.59 (4H, m), 7.68-7.77 (1H, m), 8.29 (1H, d, J=8.9 Hz), 8.78 (1H, d, J=6.9 Hz).

(v) Production of 3-[4-(2-fluorophenyl)-5-(4H-1,2,4-triazol-3-yl)-1,3-thiazol-2-yl]-2-methylpyrazolo[1,5-a]pyridine acetate Using 4-(2-fluorophenyl)-2-(2-methylpyrazolo[1,5-a]pyridin-3-yl)-1,3-thiazole-5-carboxamide (290 mg, 0.73 mmol) produced in the above, N,N-dimethylformamide dimethyl acetal (30 mL), acetic acid (40 mL) and hydrazine monohydrate (0.5 mL) as starting materials and in the same manner as in Example 13(vi), the title compound (221 mg, 62%) was obtained as a white solid.

$^1$H-NMR (DMSO-d$_6$, 300 MHz) δ 1.90 (3H, s), 2.72 (3H, s), 7.08 (1H, dt, J=1.4, 6.8 Hz), 7.21-7.35 (2H, m), 7.44-7.56 (2H, m), 7.65-7.75 (1H, m), 8.23-8.37 (1H, m), 8.54 (1H, s), 8.77 (1H, d, J=6.8 Hz).

Example 23-B

Production of 3-[4-(2-methoxyphenyl)-5-(4H-1,2,4-triazol-3-yl)-1,3-thiazol-2-yl]-2-methylpyrazolo[1,5-a]pyridine

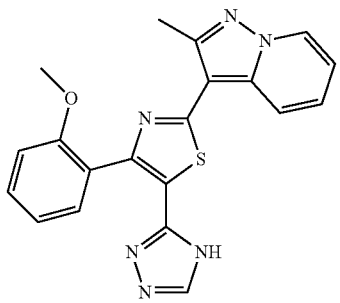 [SMILES: COc1ccccc1-c1nc(-c2c(C)nn3ccccc23)sc1-c1nnc[nH]1]

(i) Production of ethyl 2-chloro-3-(2-methoxyphenyl)-3-oxopropanoate

Using ethyl 3-(2-methoxyphenyl)-3-oxopropanoate (1.7 g, 7.4 mmol), sulfuryl chloride (1.2 g, 8.9 mmol) and diethyl ether (100 mL) as starting materials and in the same manner as in Example 20(i), the title compound (1.8 g, 97%) was obtained as a colorless oil.

$^1$H-NMR (DMSO-d$_6$, 300 MHz) δ 1.11-1.23 (3H, m), 3.87 (3H, s), 4.17 (2H, q, J=7.0 Hz), 6.07 (1H, s), 7.11 (1H, t, J=7.5 Hz), 7.23 (1H, d, J=8.3 Hz), 7.59-7.72 (1H, m), 7.80 (1H, dd, J=1.8, 7.7 Hz).

(ii) Production of ethyl 4-(2-methoxyphenyl)-2-(2-methylpyrazolo[1,5-a]pyridin-3-yl)-1,3-thiazole-5-carboxylate Using 2-methylpyrazolo[1,5-a]pyridine-3-carbothioamide hydrochloride (300 mg, 1.3 mmol) produced in Example 11-B(v), ethyl 2-chloro-3-(2-methoxyphenyl)-3-oxopropanoate (600 mg, 2.3 mmol) produced in the above and 2-propanol (40 mL) as starting materials and in the same manner as in Example 11-B(vi), the title compound (1.8 g, 71%) was obtained as a yellow solid.

$^1$H-NMR (DMSO-d$_6$, 300 MHz) δ 1.07-1.15 (3H, m), 2.70 (3H, s), 3.74 (3H, s), 4.15 (2H, q, J=7.1 Hz), 7.02-7.17 (3H, m), 7.40-7.60 (3H, m), 8.23-8.34 (1H, m), 8.77-8.83 (1H, m).

(iii) Production of 4-(2-methoxyphenyl)-2-(2-methylpyrazolo[1,5-a]pyridin-3-yl)-1,3-thiazole-5-carboxylic acid Using ethyl 4-(2-methoxyphenyl)-2-(2-methylpyrazolo[1,5-a]pyridin-3-yl)-1,3-thiazole-5-carboxylate (320 mg, 0.81 mmol) produced in the above, methanol (15 mL), tetrahydrofuran (20 mL) and 8N aqueous sodium hydroxide solution (1 mL) as starting materials and in the same manner as in Example 13-B(iv), the title compound (296 mg, 99%) was obtained as a white solid.

$^1$H-NMR (DMSO-d$_6$, 300 MHz) δ 2.69 (3H, s), 3.74 (3H, s), 6.99-7.15 (3H, m), 7.37-7.47 (2H, m), 7.48-7.57 (1H, m), 8.28 (1H, d, J=8.9 Hz), 8.78 (1H, d, J=6.8 Hz), (iv) Production of 4-(2-methoxyphenyl)-2-(2-methylpyrazolo[1,5-a]pyridin-3-yl)-1,3-thiazole-5-carboxamide Using 4-(2-methoxyphenyl)-2-(2-methylpyrazolo[1,5-a]pyridin-3-yl)-1,3-thiazole-5-carboxylic acid (300 mg, 0.82 mmol) produced in the above, ammonium chloride (1.5 g, 28 mmol), triethylamine (6 mL), 1-hydroxybenzotriazole (70 mg, 0.52 mmol), N-[3-(dimethylamino)propyl]-N'-ethylcarbodiimide hydrochloride (1.0 g, 5.2 mmol) and N,N-dimethylformamide (20 mL) as starting materials and in the same manner as in Example 13-B(v), the title compound (285 mg, 95%) was obtained as a white solid.

$^1$H-NMR (DMSO-d$_6$, 300 MHz) δ 2.69 (3H, s), 3.77 (3H, s), 6.86-7.23 (4H, m), 7.31-7.70 (4H, m), 8.26 (1H, d, J=8.7 Hz), 8.71-8.80 (1H, m).

(v) Production of 3-[4-(2-methoxyphenyl)-5-(4H-1,2,4-triazol-3-yl)-1,3-thiazol-2-yl]-2-methylpyrazolo[1,5-a]pyridine Using 4-(2-methoxyphenyl)-2-(2-methylpyrazolo[1,5-a]pyridin-3-yl)-1,3-thiazole-5-carboxamide (200 mg, 0.55 mmol) produced in the above, N,N-dimethylformamide dimethyl acetal (25 mL), acetic acid (40 mL) and hydrazine monohydrate (0.5 mL) as starting materials and in the same manner as in Example 13(vi), the title compound (145 mg, 68%) was obtained as a white solid.

$^1$H-NMR (DMSO-d$_6$, 300 MHz) δ 2.71 (3H, s), 3.52 (3H, s), 6.97-7.11 (3H, m), 7.35-7.55 (3H, m), 8.24-8.34 (1H, m), 8.45 (1H, s), 8.72-8.79 (1H, m).

Example 24-B

Production of 2-methyl-3-{5-(4H-1,2,4-triazol-3-yl)-4-[2-(trifluoromethyl)phenyl]-1,3-thiazol-2-yl}pyrazolo[1,5-a]pyridine

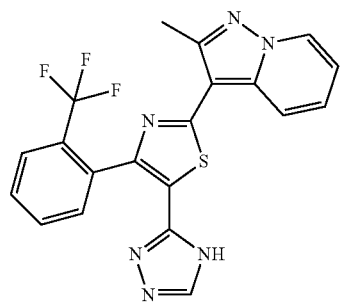 [SMILES: Cc1nn2ccccc2c1-c1nc(-c2ccccc2C(F)(F)F)c(-c2nnc[nH]2)s1]

(i) Production of ethyl 2-chloro-3-oxo-3-[2-(trifluoromethyl)phenyl]propanoate

Using ethyl 3-oxo-3-[2-(trifluoromethyl)phenyl]propanoate (1.0 g, 3.8 mmol), sulfuryl chloride (620 mg, 4.9 mmol) and diethyl ether (50 mL) as starting materials and in the same manner as in Example 20-B(i), the title compound (720 mg, 64%) was obtained as a colorless oil.

¹H-NMR (DMSO-d₆, 300 MHz) δ 1.01-1.11 (3H, m), 4.08 (2H, q, J=7.1 Hz), 6.60 (1H, s), 7.60-7.99 (4H, m).

(ii) Production of ethyl 2-(2-methylpyrazolo[1,5-a]pyridin-3-yl)-4-[2-(trifluoromethyl)phenyl]-1,3-thiazole-5-carboxylate Using 2-methylpyrazolo[1,5-a]pyridine-3-carbothioamide hydrochloride (100 mg, 0.44 mmol) produced in Example 11-B(v), ethyl 2-chloro-3-oxo-3-[2-(trifluoromethyl)phenyl]propanoate (250 mg, 0.85 mmol) produced in the above and 2-propanol (25 mL) as starting materials and in the same manner as in Example 11-B(vi), the title compound (158 mg, 84%) was obtained as a yellow solid.

¹H-NMR (DMSO-d₆, 300 MHz) δ 1.04 (3H, t, J=7.1 Hz), 2.70 (3H, s), 4.10 (2H, q, J=7.1 Hz), 7.08-7.15 (1H, m), 7.50-7.64 (2H, m), 7.69-7.92 (3H, m), 8.24 (1H, dt, J=1.2, 8.8 Hz), 8.81 (1H, d, J=6.8 Hz).

(iii) Production of 2-(2-methylpyrazolo[1,5-a]pyridin-3-yl)-4-[2-(trifluoromethyl)phenyl]-1,3-thiazole-5-carboxylic acid Using ethyl 2-(2-methylpyrazolo[1,5-a]pyridin-3-yl)-4-[2-(trifluoromethyl)phenyl]-1,3-thiazole-5-carboxylate (140 mg, 1.5 mmol) produced in the above, methanol (5 mL), tetrahydrofuran (15 mL) and 8N aqueous sodium hydroxide solution (2 mL) as starting materials and in the same manner as in Example 13-B(iv), the title compound (130 mg, 99%) was obtained as a white solid.

¹H-NMR (DMSO-d₆, 300 MHz) δ 2.68 (3H, s), 7.03-7.13 (1H, m), 7.46-7.77 (4H, m), 7.81-7.90 (1H, m), 8.19-8.28 (1H, m), 8.78 (1H, d, J=7.0 Hz).

(iv) Production of 2-(2-methylpyrazolo[1,5-a]pyridin-3-yl)-4-[2-(trifluoromethyl)phenyl]-1,3-thiazole-5-carboxamide Using 2-(2-methylpyrazolo[1,5-a]pyridin-3-yl)-4-[2-(trifluoromethyl)phenyl]-1,3-thiazole-5-carboxylic acid (130 mg, 0.32 mmol) produced in the above, ammonium chloride (2.0 g, 37 mmol), triethylamine (5.0 mL), 1-hydroxybenzotriazole (80 mg, 0.59 mmol), N-[3-(dimethylamino)propyl]-N'-ethylcarbodiimide hydrochloride (2.5 g, 13 mmol) and N,N-dimethylformamide (50 mL) as starting materials and in the same manner as in Example 13-B(v), the title compound (105 mg, 81%) was obtained as a white solid.

¹H-NMR (DMSO-d₆, 300 MHz) δ 2.69 (3H, s), 6.96-7.21 (2H, m), 7.37-7.62 (3H, m), 7.65-7.81 (2H, m), 7.84-7.92 (1H, m), 8.16-8.27 (1H, m), 8.77 (1H, d, J=6.8 Hz), (v) Production of 2-methyl-3-{5-(4H-1,2,4-triazol-3-yl)-4-[2-(trifluoromethyl)phenyl]-1,3-thiazol-2-yl}pyrazolo[1,5-a]pyridine Using 2-(2-methylpyrazolo[1,5-a]pyridin-3-yl)-4-[2-(trifluoromethyl)phenyl]-1,3-thiazole-5-carboxamide (105 mg, 0.82 mmol) produced in the above, N,N-dimethylformamide dimethyl acetal (15 mL), acetic acid (20 mL) and hydrazine monohydrate (0.4 mL) as starting materials and in the same manner as in Example 13-B(vi), the title compound (72 mg, 65%) was obtained as a white solid.

¹H-NMR (DMSO-d₆, 300 MHz) δ 2.71 (3H, s), 7.06 (1H, dt, J=1.3, 6.8 Hz), 7.42-7.62 (2H, m), 7.63-7.77 (2H, m), 7.81-7.92 (1H, m), 8.19-8.31 (1H, m), 8.49 (1H, s), 8.76 (1H, d, J=6.8 Hz), 14.08 (1H, s).

Example 25-B

Production of 2-methyl-3-[4-(tetrahydro-2H-pyran-4-yl)-5-(4H-1,2,4-triazol-3-yl)-1,3-thiazol-2-yl]pyrazolo[1,5-a]pyridine

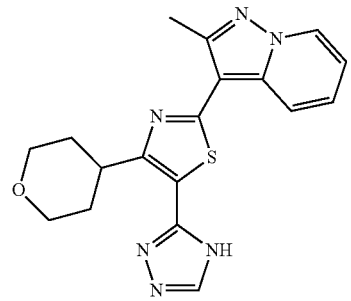 [SMILES: Cc1nn2ccccc2c1-c1nc(C2CCOCC2)c(-c2nnc[nH]2)s1]

(i) Production of ethyl 2-chloro-3-oxo-3-(tetrahydro-2H-pyran-4-yl)propanoate

Using ethyl 3-oxo-3-(tetrahydro-2H-pyran-4-yl)propanoate (1.0 g, 5.0 mmol), sulfuryl chloride (810 mg, 6.0 mmol) and diethyl ether (50 mL) as starting materials and in the same manner as in Example 20-B(i), the title compound (1.0 g, 85%) was obtained as a colorless oil.

¹H-NMR (DMSO-d₆, 300 MHz) δ 1.16-1.25 (3H, m), 1.39-1.60 (2H, m), 1.66-1.84 (2H, m), 2.95-3.10 (1H, m), 3.31-3.41 (2H, m), 3.79-3.91 (2H, m), 4.22 q, J=7.1 Hz), 5.85 (1H, s).

(ii) Production of ethyl 2-(2-methylpyrazolo[1,5-a]pyridin-3-yl)-4-(tetrahydro-2H-pyran-4-yl)-1,3-thiazole-5-carboxylate Using 2-methylpyrazolo[1,5-a]pyridine-3-carbothioamide hydrochloride (400 mg, 1.8 mmol) produced in Example 11-B(v), ethyl 2-chloro-3-oxo-3-(tetrahydro-2H-pyran-4-yl)propanoate (1.0 g, 4.3 mmol) produced in the above and 2-propanol (40 mL) as starting materials and in the same manner as in Example 11-B(vi), the title compound (530 mg, 81%) was obtained as a yellow solid.

¹H-NMR (DMSO-d₆, 300 MHz) δ 1.32 (3H, t, J=7.1 Hz), 1.75 (2H, d, J=14.7 Hz), 1.93-2.12 (2H, m), 2.67 (3H, s), 3.43-3.55 (2H, m), 3.81-3.96 (1H, m), 3.96-4.07 (2H, m), 4.31 (2H, q, J=7.1 Hz), 7.12 (1H, dt, J=1.3, 7.0 Hz), 7.63 OH, ddd, J=1.3, 7.0, 8.9 Hz), 8.13-8.42 (1H, m), 8.79 (1H, d, J=7.0 Hz).

(iii) Production of 2-(2-methylpyrazolo[1,5-a]pyridin-3-yl)-4-(tetrahydro-2H-pyran-4-yl)-1,3-thiazole-5-carboxylic acid Using ethyl 2-(2-methylpyrazolo[1,5-a]pyridin-3-yl)-4-(tetrahydro-2H-pyran-4-yl)-1,3-thiazole-5-carboxylate (500 mg, 1.5 mmol) produced in the above, methanol (20 mL), tetrahydrofuran (20 mL) and 8N aqueous sodium hydroxide solution (2 mL) as starting materials and in the same manner as in Example 13(iv), the title compound (431 mg, 93%) was obtained as a yellow solid.

$^1$H-NMR (DMSO-d$_6$, 300 MHz) δ 1.68-1.80 (2H, m), 1.94-2.11 (2H, m), 2.67 (3H, s), 3.40-3.53 (2H, m), 3.83-4.05 (3H, m), 7.11 (1H, dt, J=1.3, 6.9 Hz), 7.55-7.66 (1H, m), 8.37 (1H, d, J=8.9 Hz), 8.78 (1H, d, J=6.9 Hz), 13.20 (1H, s).

(iv) Production of 2-(2-methylpyrazolo[1,5-a]pyridin-3-yl)-4-(tetrahydro-2H-pyran-4-yl)-1,3-thiazole-5-carboxamide Using 2-(2-methylpyrazolo[1,5-a]pyridin-3-yl)-4-(tetrahydro-2H-pyran-4-yl)-1,3-thiazole-5-carboxylic acid (400 mg, 1.2 mmol) produced in the above, ammonium chloride (1.0 g, 19 mmol), triethylamine (4.0 mL), 1-hydroxybenzotriazole (150 mg, 1.7 mmol), N-[3-(dimethylamino)propyl]-N'-ethylcarbodiimide hydrochloride (850 mg, 4.4 mmol) and N,N-dimethylformamide (70 mL) as starting materials and in the same manner as in Example 13(v), the title compound (347 mg, 87%) was obtained as a white solid.

$^1$H-NMR (DMSO-d$_6$, 300 MHz) δ 1.69-1.80 (2H, m), 1.95-2.05 (2H, m), 2.67 (3H, s), 3.40-3.50 (2H, m), 3.72-3.88 (1H, m), 3.92-4.01 (2H, m), 7.09 (1H, dt, J=1.3, 6.9 Hz), 7.45-7.70 (3H, m), 8.33 (1H, d, J=8.7 Hz), 8.77 (1H, d, J=6.9 Hz).

(v) Production of 2-methyl-3-[4-(tetrahydro-2H-pyran-4-yl)-5-(4H-1,2,4-triazol-3-yl)-1,3-thiazol-2-yl]pyrazolo[1,5-a]pyridine Using 2-(2-methylpyrazolo[1,5-a]pyridin-3-yl)-4-(tetrahydro-2H-pyran-4-yl)-1,3-thiazole-5-carboxamide (300 mg, 0.82 mmol) produced in the above, N,N-dimethylformamide dimethyl acetal (20 mL), acetic acid (30 mL) and hydrazine monohydrate (0.3 mL) as starting materials and in the same manner as in Example 13(vi), the title compound (221 mg, 69%) was obtained as a white solid.

$^1$H-NMR (DMSO-d$_6$, 300 MHz) δ 1.78 (2H, d, J=11.0 Hz), 2.00-2.16 (2H, m), 2.69 (3H, s), 3.49 (2H, t, J=11.0 Hz), 3.94-4.12 (3H, m), 7.07 (1H, dt, J=1.2, 6.8 Hz), 7.57 (1H, ddd, J=1.2, 6.8, 8.8 Hz), 8.29-8.41 (1H, m), 8.66 (1H, s), 8.76 (1H, d, J=6.8 Hz), 14.27 (1H, s).

Example 26-B

Production of 3-[4-(2-chlorophenyl)-5-(4H-1,2,4-triazol-3-yl)-1,3-thiazol-2-yl]-2-methylpyrazolo[1,5-a]pyridine

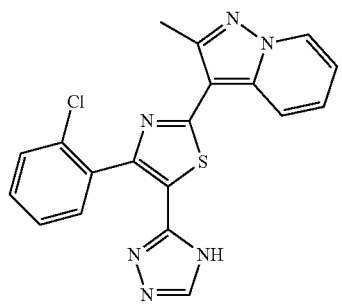 [SMILES: Cc1nn2ccccc2c1-c1nc(-c2ccccc2Cl)c(-c2nnc[nH]2)s1]

(i) Production of ethyl 2-chloro-3-(2-chlorophenyl)-3-oxopropanoate

Using ethyl 3-(2-chlorophenyl)-3-oxopropanoate (1.0 g, 5.0 mmol), sulfuryl chloride (810 mg, 6.0 mmol) and diethyl ether (50 mL) as starting materials and in the same manner as in Example 20(i), the title compound (1.0 g, 85%) was obtained as a colorless oil.

$^1$H-NMR (DMSO-d$_6$, 300 MHz) δ 1.22-1.31 (3H, m), 4.17-4.27 (2H, m), 6.47 (1H, s) 7.35-7.94 (4H, m).

(ii) Production of ethyl 4-(2-chlorophenyl)-2-(2-methylpyrazolo[1,5-a]pyridin-3-yl)-1,3-thiazole-5-carboxylate Using 2-methylpyrazolo[1,5-a]pyridine-3-carbothioamide hydrochloride (300 mg, 1.3 mmol) produced in Example 11(v), ethyl 2-chloro-3-(2-chlorophenyl)-3-oxopropanoate (1.0 g, 3.9 mmol) produced in the above and 2-propanol (20 mL) as starting materials and in the same manner as in Example 11-B(vi), the title compound (475 mg, 91%) was obtained as a yellow solid.

$^1$H-NMR (DMSO-d$_6$, 300 MHz) δ 1.12 (3H, t, J=7.2 Hz), 2.71 (3H, s), 4.16 (2H, q, J=7.2 Hz), 7.12 (1H, dt, J=1.3, 6.9 Hz), 7.41-7.65 (5H, m), 8.24-8.34 (1H, m), 8.81 (1H, d, J=6.9 Hz).

(iii) Production of 4-(2-chlorophenyl)-2-(2-methylpyrazolo[1,5-a]pyridin-3-yl)-1,3-thiazole-5-carboxylic acid Using ethyl 4-(2-chlorophenyl)-2-(2-methylpyrazolo[1,5-a]pyridin-3-yl)-1,3-thiazole-5-carboxylate (400 mg, 1.0 mmol) produced in the above, methanol (10 mL), tetrahydrofuran (20 mL) and 8N aqueous sodium hydroxide solution (2.0 mL) as starting materials and in the same manner as in Example 13-B(iv), the title compound (355 mg, 96%) was obtained as a white solid.

$^1$H-NMR (DMSO-d$_6$, 300 MHz) δ 2.70 (3H, s), 7.09 (1H, dt, J=1.3, 6.8 Hz), 7.38-7.61 (5H, m), 8.23-8.32 (1H, m), 8.78 (1H, d, J=6.8 Hz).

(iv) Production of 4-(2-chlorophenyl)-2-(2-methylpyrazolo[1,5-a]pyridin-3-yl)-1,3-thiazole-5-carboxamide Using 4-(2-chlorophenyl)-2-(2-methylpyrazolo[1,5-a]pyridin-3-yl)-1,3-thiazole-5-carboxylic acid (350 mg, 0.94 mmol) produced in the above, ammonium chloride (3.0 g, 56 mmol), triethylamine (4.5 mL), 1-hydroxybenzotriazole (70 mg, 0.52 mmol), N-[3-(dimethylamino)propyl]-N'-ethylcarbodiimide hydrochloride (2.0 g, 10 mmol) and N,N-dimethylformamide (50 mL) as starting materials and in the same manner as in Example 13-B(v), the title compound (341 mg, 97%) was obtained as a yellow solid.

$^1$H-NMR (DMSO-d$_6$, 300 MHz) δ 2.70 (3H, s), 7.06-7.20 (2H, m), 7.43-7.64 (6H, m), 8.26 (1H, d, J=8.7 Hz), 8.78 (1H, d, J=6.8 Hz).

(v) Production of 3-[4-(2-chlorophenyl)-5-(4H-1,2,4-triazol-3-yl)-1,3-thiazol-2-yl]-2-methylpyrazolo[1,5-a]pyridine Using 4-(2-chlorophenyl)-2-(2-methylpyrazolo[1,5-a]pyridin-3-yl)-1,3-thiazole-5-carboxamide (340 mg, 0.92 mmol) produced in the above, N,N-dimethylformamide dimethyl acetal (20 mL), acetic acid (25 mL) and hydrazine monohydrate (0.7 mL) as starting materials and in the same manner as in Example 13-B(vi), the title compound (322 mg, 89%) was obtained as a white solid.

$^1$H-NMR (DMSO-$d_6$, 300 MHz) δ 2.72 (3H, s), 7.05 (1H, dt, J=1.5, 6.8 Hz), 7.38-7.61 (5H, m), 8.25-8.31 (1H, m), 8.33 (1H, s), 8.76 (1H, d, J=6.8 Hz).

Example 27-B

Production of 2-methyl-3-[4-(prop-2-en-1-yloxy)-5-(4H-1,2,4-triazol-3-yl)-1,3-thiazol-2-yl]pyrazolo[1,5-a]pyridine

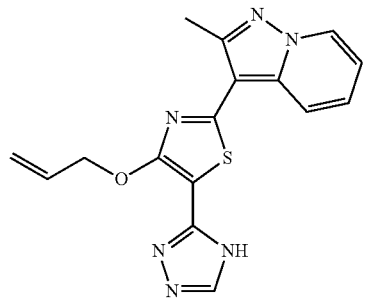 [SMILES: C=CCOc1nc(-c2c(C)nn3ccccc23)sc1-c1nnc[nH]1]

(i) Production of methyl 2-(2-methylpyrazolo[1,5-a]pyridin-3-yl)-4-(prop-2-en-1-yloxy)-1,3-thiazole-5-carboxylate Methyl 4-hydroxy-2-(2-methylpyrazolo[1,5-a]pyridin-3-yl)-1,3-thiazole-5-carboxylate (1.0 g, 3.5 mmol) produced in Example 13-B(i) was dissolved in N,N-dimethylformamide (50 mL), potassium carbonate (3.2 g, 9.7 mmol) and 3-bromoprop-1-ene (2.8 g, 23 mmol) were added, and the mixture was stirred at room temperature for 2 hr. Water (100 mL) and ethyl acetate (100 mL) were added to the reaction solution, and the mixture was stirred for 30 min. The organic layer was washed with water (100 mL×3) and saturated brine (10 mL) and dried over anhydrous sodium sulfate. The insoluble material was filtered off, and the filtrate was concentrated under reduced pressure. The obtained residue was purified by silica gel column chromatography (hexane/ethyl acetate=100/0→0/100) to give the title compound (760 mg, 67%) as a brown solid.

$^1$H-NMR (DMSO-$d_6$, 300 MHz) δ 2.66 (3H, s), 3.76 (3H, s), 5.10 (2H, td, J=1.5, 5.1 Hz), 5.30 (1H, ddd, J=1.5, 3.2, 10.5 Hz), 5.50 (1H, ddd, J=1.5, 3.2, 17.2 Hz), 6.08-6.22 (1H, m), 7.14 (1H, dt, J=1.2, 6.9 Hz), 7.62 (1H, ddd, J=1.2, 6.9, 8.8 Hz), 8.25-8.38 (1H, m), 8.81 (1H, d, J=6.9 Hz).

(ii) Production of 2-(2-methylpyrazolo[1,5-a]pyridin-3-yl)-4-(prop-2-en-1-yloxy)-1,3-thiazole-5-carboxylic acid Using methyl 2-(2-methylpyrazolo[1,5-a]pyridin-3-yl)-4-(prop-2-en-1-yloxy)-1,3-thiazole-5-carboxylate (670 mg, 2.0 mmol) produced in the above, methanol (10 mL), tetrahydrofuran (30 mL) and 8N aqueous sodium hydroxide solution (1.5 mL) as starting materials and in the same manner as in Example 13-B(iv), the title compound (610 mg, 95%) was obtained as a yellow solid.

$^1$H-NMR (DMSO-$d_6$, 300 MHz) δ 2.65 (3H, s), 5.08 (2H, td, J=1.5, 5.3 Hz), 5.29 (1H, ddd, J=1.5, 3.2, 10.5 Hz), 5.50 (1H, ddd, J=1.5, 3.2, 17.2 Hz), 6.11-6.17 (1H, m), 7.12 (1H, dt, J=1.3, 6.9 Hz), 7.54-7.66 (1H, m), 8.30 (1H, d, J=8.9 Hz), 8.79 (1H, d, J=6.9 Hz).

(iii) Production of 2-(2-methylpyrazolo[1,5-a]pyridin-3-yl)-4-(prop-2-en-1-yloxy)-1,3-thiazole-5-carboxamid Using 2-(2-methylpyrazolo[1,5-a]pyridin-3-yl)-4-(prop-2-en-1-yloxy)-1,3-thiazole-5-carboxylic acid (600 mg, 1.9 mmol) produced in the above, ammonium chloride (2.0 g, 37 mmol), triethylamine (3.5 mL), 1-hydroxybenzotriazole (40 mg, 0.3 mmol), N-[3-(dimethylamino)propyl]-N'-ethylcarbodiimide hydrochloride (2.1 g, 11 mmol) and N,N-dimethylformamide (50 mL) as starting materials and in the same manner as in Example 13(v), the title compound (415 mg, 69%) was obtained as a yellow solid.

$^1$H-NMR (DMSO-$d_6$, 300 MHz) δ 2.65 (3H, s), 5.12 (2H, td, J=1.3, 5.7 Hz), 5.28-5.39 (1H, m), 5.41-5.53 (1H, m), 6.09-6.30 (1H, m), 6.88 (1H, s), 7.11 (1H, dt, J=1.3, 6.9 Hz), 7.50-7.65 (2H, m), 8.31 (1H, d, J=8.9 Hz), 8.78 (1H, d, J=6.9 Hz), (iv) Production of 2-methyl-3-[4-(prop-2-en-1-yloxy)-5-(4H-1,2,4-triazol-3-yl)-1,3-thiazol-2-yl]pyrazolo[1,5-a]pyridine Using 2-(2-methylpyrazolo[1,5-a]pyridin-3-yl)-4-(prop-2-en-1-yloxy)-1,3-thiazole-5-carboxamide (400 mg, 0.55 mmol) produced in the above, N,N-dimethylformamide dimethyl acetal (20 mL), acetic acid (30 mL) and hydrazine monohydrate (0.4 mL) as starting materials and in the same manner as in Example 13-B(vi), the title compound (277 mg, 68%) was obtained as a yellow solid.

$^1$H-NMR (DMSO-$d_6$, 300 MHz) δ 2.68 (3H, s), 5.10 (2H, td, J=1.5, 5.3 Hz), 5.28 (1H, ddd, J=1.5, 3.2, 10.6 Hz), 5.50 (1H, ddd, J=1.5, 3.2 17.3 Hz), 6.12-6.24 (1H, m), 7.05-7.15 (1H, m), 7.57 (1H, ddd, J=1.1, 6.9, 9.0 Hz), 8.24-8.35 (2H, m), 8.78 (1H, d, J=6.9 Hz).

Example 28-B

Production of 2-methyl-3-[4-propoxy-5-(4H-1,2,4-triazol-3-yl)-1,3-thiazol-2-yl]pyrazolo[1,5-a]pyridine

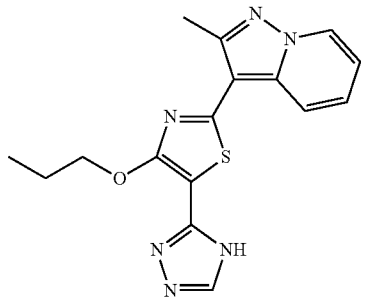 [SMILES: CCCOc1nc(-c2c(C)nn3ccccc23)sc1-c1nnc[nH]1]

To a solution of 2-methyl-3-[4-(prop-2-en-1-yloxy)-5-(4H-1,2,4-triazol-3-yl)-1,3-thiazol-2-yl]pyrazolo[1,5-a]pyridine (70 mg, 0.55 mmol) produced in Example 27 in ethanol (15 mL)-tetrahydrofuran (15 mL) was added 10% palladium/carbon (73 mg), and the mixture was stirred at room temperature for 5 hr under a hydrogen atmosphere (1 atm). Palladium/carbon was filtered off, and the filtrate was concentrated under reduced pressure. The obtained residue was washed with diisopropyl ether to give the title compound (43 mg, 61%) as a yellow solid.

¹H-NMR (DMSO-d₆, 300 MHz) δ 1.03 (3H, t, J=7.5 Hz), 1.75-1.94 (2H, m), 2.68 (3H, s), 4.51 (2H, t, J=6.6 Hz), 7.04-7.11 (1H, m), 7.50-7.63 (1H, m), 8.18 (1H, s), 8.29 (1H, d, J=8.9 Hz), 8.77 (1H, d, J=7.0 Hz).

Example 29-B

Production of 3-[4-(benzyloxy)-5-(4H-1,2,4-triazol-3-yl)-1,3-thiazol-2-yl]-2-methylpyrazolo[1,5-a]pyridine

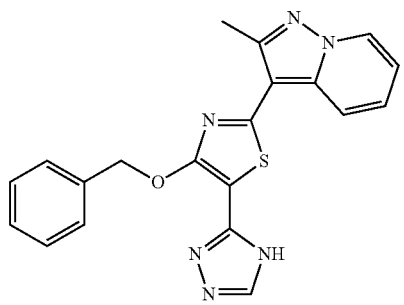 [SMILES: Cc1nn2ccccc2c1-c1nc(OCc2ccccc2)c(-c2nnc[nH]2)s1]

(i) Production of methyl 4-(benzyloxy)-2-(2-methylpyrazolo[1,5-a]pyridin-3-yl)-1,3-thiazole-5-carboxylate Using methyl 4-hydroxy-2-(2-methylpyrazolo[1,5-a]pyridin-3-yl)-1,3-thiazole-5-carboxylate (800 mg, 2.5 mmol) produced in Example 13-B(i), potassium carbonate (1.9 g, 5.9 mmol), benzyl bromide (2.8 g, 12 mmol) and N,N-dimethylformamide (50 mL) as starting materials and in the same manner as in Example 27-B(i), the title compound (560 mg, 60%) was obtained as a yellow solid.

¹H-NMR (DMSO-d₆, 300 MHz) δ 2.64 (3H, s), 3.77 (3H, s), 5.67 (2H, s), 7.14 (1H, dt, J=1.3, 6.8 Hz), 7.30-7.45 (3H, m), 7.49-7.64 (3H, m), 8.24-8.30 (1H, m), 8.80 d, J=6.8 Hz).

(ii) Production of 4-(benzyloxy)-2-(2-methylpyrazolo[1,5-a]pyridin-3-yl)-1,3-thiazole-5-carboxylic acid Using methyl 4-(benzyloxy)-2-(2-methylpyrazolo[1,5-a]pyridin-3-yl)-1,3-thiazole-5-carboxylate (560 mg, 1.5 mmol) produced in the above, methanol (15 mL), tetrahydrofuran (25 mL) and 8N aqueous sodium hydroxide solution (1.5 mL) as starting materials and in the same manner as in Example 13-B(iv), the title compound (515 mg, 96%) was obtained as a yellow solid.

¹H-NMR (DMSO-d₆, 300 MHz) δ 2.64 (3H, s), 5.63 (2H, s), 7.11 (1H, dt, J=1.3, 6.9 Hz), 7.28-7.45 (3H, m), 7.50-7.62 (3H, m), 8.21-8.29 (1H, m), 8.78 (1H, d, J=6.9 Hz), (iii) Production of 4-(benzyloxy)-2-(2-methylpyrazolo[1,5-a]pyridin-3-yl)-1,3-thiazole-5-carboxamide Using 4-(benzyloxy)-2-(2-methylpyrazolo[1,5-a]pyridin-3-yl)-1,3-thiazole-5-carboxylic acid (500 mg, 1.4 mmol) produced in the above, ammonium chloride (2.0 g, 37 mmol), triethylamine (5.3 mL), 1-hydroxybenzotriazole (80 mg, 0.6 mmol), N-[3-(dimethylamino)propyl]-N'-ethylcarbodiimide hydrochloride (2.5 g, 13 mmol) and N,N-dimethylformamide (50 mL) as starting materials and in the same manner as in Example 13-B(v), the title compound (430 mg, 86%) was obtained as a yellow solid.

¹H-NMR (DMSO-d₆, 300 MHz) δ 2.63 (3H, s), 5.67 (2H, s), 6.93 (1H, s), 7.10 (1H, dt, J=1.4, 6.8 Hz), 7.30-7.45 (3H, m), 7.49-7.62 (4H, m), 8.21-8.29 (1H, m), 8.77 (1H, d, J=6.8 Hz).

(iv) Production of 3-[4-(benzyloxy)-5-(4H-1,2,4-triazol-3-yl)-1,3-thiazol-2-yl]-2-methylpyrazolo[1,5-a]pyridine Using 4-(benzyloxy)-2-(2-methylpyrazolo[1,5-a]pyridin-3-yl)-1,3-thiazole-5-carboxamide (300 mg, 0.82 mmol) produced in the above, N,N-dimethylformamide dimethyl acetal (25 mL), acetic acid (50 mL) and hydrazine monohydrate (0.5 mL) as starting materials and in the same manner as in Example 13-B(vi), the title compound (249 mg, 79%) was obtained as a yellow solid.

¹H-NMR (DMSO-d₆, 300 MHz) δ 2.65 (3H, s), 5.66 (2H, s), 7.08 (1H, dt, J=1.2, 6.8 Hz), 7.25-7.45 (3H, m), 7.49-7.63 (3H, m), 8.19-8.35 (2H, m), 8.76 (1H, d, J=6.8 Hz).

Example 30-B

Production of 5-(benzyloxy)-2-methyl-3-[4-phenyl-5-(4H-1,2,4-triazol-3-yl)-1,3-thiazol-2-yl]pyrazolo[1,5-a]pyridine p-toluenesulfonate

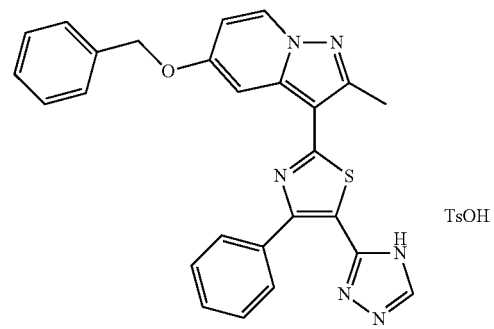

(i) Production of 4-(benzyloxy)pyridine

To 4-chloropyridine hydrochloride (15.0 g, 100 mmol) was added aqueous sodium bicarbonate solution, and the mixture was extracted with ethyl acetate. The collected organic layer was washed with saturated brine and dried over anhydrous magnesium sulfate, and the insoluble material was filtered off. The filtrate was concentrated under reduced pressure to give 4-chloropyridine. To a suspension of sodium hydride (60% in oil, 4.20 g, 105 mmol) in dimethyl sulfoxide (20 mL) was added dropwise benzyl alcohol (11.3 g, 105 mmol) under ice-cooling. The mixture was stirred at room temperature for 1 hr, 4-chloropyridine produced in the above was added, and the mixture was stirred at room temperature for 1 day. Water was added to the reaction mixture, and the mixture was extracted with diethyl ether. The collected organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=10/90→70/30). The obtained solution was concentrated under reduced pressure to give the title compound (10 g, 55%) as a pale-yellow solid.

$^1$H-NMR (DMSO-$d_6$, 300 MHz) δ 5.19 (2H, s), 7.00-7.07 (2H, m), 7.31-7.51 (5H, m), 8.36-8.43 (2H, m), (ii) Production of ethyl 5-(benzyloxy)-2-methylpyrazolo[1,5-a]pyridine-3-carboxylate To a solution of ethyl (1E)-N-{[(2,4,6-trimethylphenyl)sulfonyl]oxy}ethanimidate (11 g, 37 mmol) in 1,2-dimethoxyethane (15 mL) was slowly added dropwise perchloric acid (5 mL) under ice-cooling. The mixture was stirred for 0.5 hr under ice-cooling, and water (20 mL) was added. Water (10 mL) was further added, and the mixture was stirred. The resulting precipitate was collected by filtration and washed with water. The obtained white solid was dissolved in ethyl acetate. The aqueous layer was separated and dried over anhydrous magnesium sulfate. The insoluble material was filtered off, and the obtained solution was added dropwise to a solution of 4-(benzyloxy)pyridine (5.6 g, 30 mmol) produced in the above in ethyl acetate (30 mL) under ice-cooling. After stirring at room temperature for 1 day, the reaction mixture was concentrated under reduced pressure. Ethyl acetate and diethyl ether were added to the obtained residue. The separated oil was washed with ethyl acetate/diethyl ether and diethyl ether, and concentrated under reduced pressure. To a solution of the obtained residue in N,N-dimethylformamide (50 mL) were added potassium carbonate (5.0 g, 36 mmol) and ethyl 2-butynoate (3.4 g, 30 mmol), and the mixture was stirred at room temperature for 1 day. The reaction mixture was concentrated under reduced pressure, water was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, the obtained residue was purified by silica gel column chromatography (ethyl acetate/hexane=10/90→50/50), and the obtained solution was concentrated under reduced pressure. The obtained residue was washed with diisopropyl ether to give the title compound (1.5 g, 16%) as a colorless solid.

$^1$H-NMR (DMSO-$d_6$, 300 MHz) δ 1.33 (3H, t, J=7.0 Hz), 2.50 (3H, s), 4.26 (2H, q, J=7.0 Hz), 5.26 (2H, s), 6.82 (1H, dd, J=2.8, 7.6 Hz), 7.32-7.47 (4H, m), 7.47-7.54 (2H, m), 8.61 (1H, d, J=7.6 Hz).

(iii) Production of 5-(benzyloxy)-2-methylpyrazolo[1,5-a]pyridine-3-carboxylic acid A mixture of ethyl 5-(benzyloxy)-2-methylpyrazolo[1,5-a]pyridine-3-carboxylate (1.6 g, 5.2 mmol) produced in the above, 1N aqueous sodium hydroxide solution (10 mL), methanol (20 mL) and tetrahydrofuran (10 mL) was stirred at 70° C. for 1 day. To the reaction mixture was added 1N aqueous sodium hydroxide solution (10 mL), and the mixture was stirred at 70° C. for 2 hr. To the reaction mixture was added 8N aqueous sodium hydroxide solution (1 mL), and the mixture was stirred at 70° C. for 2 hr. The reaction mixture was concentrated under reduced pressure, water and 6N hydrochloric acid (2.7 mL) were added to the obtained residue, and the resulting precipitate was collected by filtration, washed with water and dried to give the title compound (1.4 g, 99%) as a colorless solid.

$^1$H-NMR (DMSO-$d_6$, 300 MHz) δ 2.50 (3H, s), 5.22 (2H, s), 6.79 (1H, dd, J=2.8, 7.5 Hz), 7.32-7.47 (4H, m), 7.47-7.55 (2H, m), 8.59 (1H, d, J=7.5 Hz), 12.20 (1H, br s).

(iv) Production of 5-(benzyloxy)-2-methylpyrazolo[1,5-a]pyridine-3-carboxamide

A mixture of 5-(benzyloxy)-2-methylpyrazolo[1,5-a]pyridine-3-carboxylic acid (1.4 g, 5.0 mmol) produced in the above, thionyl chloride (1.1 mL, 15 mmol) and toluene (10 mL) was stirred at 100° C. for 1.5 hr. The reaction mixture was concentrated under reduced pressure, toluene was added to the obtained residue, and the mixture was concentrated again under reduced pressure. The obtained residue was dissolved in tetrahydrofuran (10 mL), concentrated aqueous ammonia (5 mL) and tetrahydrofuran (20 mL) were added, and the mixture was stirred at room temperature for 1 hr. To the reaction mixture were added water and ethyl acetate, and the resulting precipitate was collected by filtration, washed with water and ethyl acetate and dried to give the title compound (917 mg, 65%) as a colorless solid. The filtrate was extracted with a mixed solvent of ethyl acetate and tetrahydrofuran, and the collected organic layer was dried over anhydrous magnesium sulfate. The insoluble material was filtered off. The filtrate was concentrated under reduced pressure, and the obtained residue was washed with diisopropyl ether to give a second crop (490 mg, 35%) of the title compound as a pale-brown solid.

$^1$H-NMR (DMSO-$d_6$, 300 MHz) δ 2.51 (3H, s), 5.21 (2H, s), 6.70 (1H, dd, J=2.7, 7.6 Hz), 6.96 (2H, br s), 7.32-7.47 (4H, m), 7.46-7.55 (2H, m), 8.51 (1H, d, J=7.6 Hz).

(v) Production of 5-(benzyloxy)-2-methylpyrazolo[1,5-a]pyridine-3-carbonitrile

To a mixture of 5-(benzyloxy)-2-methylpyrazolo[1,5-a]pyridine-3-carboxamide (1.3 g, 4.8 mmol) produced in the above, pyridine (1.2 mL, 14 mmol) and tetrahydrofuran (20 mL) was added dropwise under ice-cooling a solution of trifluoroacetic anhydride (1.0 mL, 7.2 mmol) in tetrahydrofuran (2 mL), and the mixture was stirred under ice-cooling for 0.5 hr. Triethylamine (2.0 mL, 14 mmol) was added, and the mixture was stirred at room temperature for 0.5 hr. Trifluoroacetic anhydride (1.0 mL, 7.2 mmol) was added dropwise at room temperature, and the mixture was stirred at room temperature for 0.5 hr and concentrated under reduced pressure. Aqueous sodium bicarbonate solution was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=20/80→100/0). The obtained solution was concentrated under reduced pressure, and the obtained residue was washed with diisopropyl ether/hexane to give the title compound (1.0 g, 79%) as a colorless solid.

$^1$H-NMR (DMSO-$d_6$, 300 MHz) δ 2.44 (3H, s), 5.28 (2H, s), 6.86 (1H, dd, J=2.5, 7.8 Hz), 7.26 (1H, d, J=2.5 Hz), 7.33-7.53 (5H, m), 8.68 (1H, d, J=7.8 Hz).

(vi) Production of 5-(benzyloxy)-2-methylpyrazolo[1,5-a]pyridine-3-carbothioamide A mixture of 5-(benzyloxy)-2-methylpyrazolo[1,5-a]pyridine-3-carbonitrile (950 mg, 3.6 mmol) produced in the above, O,O'-diethyl dithiophosphate (1.3 mL, 7.2 mmol), 4N hydrogen, chloride/ethyl acetate (12 mL) and methanol (4 mL) was stirred at 50° C. for 3 hr. To the reaction mixture was added methanol (8 mL), and the mixture was stirred for 2 hr. To the reaction mixture were added O,O'-diethyl dithiophosphate (0.67 mL, 3.6 mmol) and methanol (6 mL), and the mixture was stirred for 4 hr. To the reaction mixture were added aqueous sodium bicarbonate solution and diethyl ether, and the resulting precipitate was collected by filtration, washed with water and diethyl ether and dried to give the title compound (1.0 g, 95%) as a pale-brown solid.

$^1$H-NMR (DMSO-d$_6$, 300 MHz) δ 2.53 (3H, s), 5.19 (2H, s), 6.76 (1H, dd, J=2.7, 7.6 Hz), 7.32-7.46 (3H, m), 7.47-7.54 (2H, m), 7.86 (1H, d, J=2.7 Hz), 8.47 (1H, br s), 8.54 (1H, d, J=7.6 Hz), 9.28 (1H, br s).

(vii) Production of ethyl 2-[5-(benzyloxy)-2-methylpyrazolo[1,5-a]pyridin-3-yl]-4-phenyl-1,3-thiazole-5-carboxylate A mixture of 5-(benzyloxy)-2-methylpyrazolo[1,5-a]pyridine-3-carbothioamide (950 mg, 3.2 mmol) produced in the above, ethyl 2-bromo-3-oxo-3-phenylpropanoate (1.30 g, 4.8 mmol) and ethanol (50 mL) was stirred at 80° C. for 1 day. To the reaction mixture was added aqueous sodium bicarbonate solution, ethyl acetate and tetrahydrofuran, and the insoluble material was filtered off. The filtrate was extracted with a mixed solvent of ethyl acetate and tetrahydrofuran. The collected organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=50/50→100/0). The crude product was washed with diisopropyl ether to give the title compound (800 mg, 54%) as a pale-yellow solid.

$^1$H-NMR (DMSO-d$_6$, 300 MHz) δ 1.24 (3H, t, J=7.0 Hz), 2.63 (3H, s), 4.24 (2H, q, J=7.0 Hz), 5.28 (2H, s), 6.86 (1H, dd, J=2.7, 7.5 Hz), 7.28-7.34 (3H, m), 7.41-7.56 (5H, m), 7.77 (1H, d, J=2.7 Hz), 7.82-7.90 (2H, m), 8.68 (1H, d, J=7.5 Hz).

(viii) Production of 2-[5-(benzyloxy)-2-methylpyrazolo[1,5-a]pyridin-3-yl]-4-phenyl-1,3-thiazole-5-carboxylic acid A mixture of ethyl 2-[5-(benzyloxy)-2-methylpyrazolo[1,5-a]pyridin-3-yl]-4-phenyl-1,3-thiazole-5-carboxylate (770 mg, 1.6 mmol) produced in the above, 1N aqueous sodium hydroxide solution (4 mL), methanol (10 mL) and tetrahydrofuran (20 mL) was stirred at 60° C. for 1 hr. To the reaction mixture were added 1N hydrochloric acid (4 mL) and water. The resulting precipitate was collected by filtration, washed with water and diethyl ether and dried to give the title compound (725 mg) as a colorless solid.

$^1$H-NMR (DMSO-d$_6$, 300 MHz) δ 2.63 (3H, s), 5.29 (2H, s), 6.85 (1H, dd, J=2.6, 7.6 Hz), 7.28-7.36 (3H, m), 7.41-7.55 (5H, m), 7.78 (1H, d, J=2.6 Hz), 7.87-7.95 (2H, m), 8.66 (1H, d, J=7.6 Hz), 13.17 (1H, br s).

(ix) Production of 2-[5-(benzyloxy)-2-methylpyrazolo[1,5-a]pyridin-3-yl]-4-phenyl-1,3-thiazole-5-carboxamide A mixture of 2-[5-(benzyloxy)-2-methylpyrazolo[1,5-a]pyridin-3-yl]-4-phenyl-1,3-thiazole-5-carboxylic acid (660 mg, 1.5 mmol) produced in the above, ammonium chloride (240 mg, 4.5 mmol), triethylamine (0.75 mL, 5.4 mmol), N-[3-(dimethylamino)propyl]-N'-ethylcarbodiimide hydrochloride (440 mg, 2.3 mmol), 1-hydroxybenzotriazole (311 mg, 2.3 mmol) and N,N-dimethylformamide (20 mL) was stirred at room temperature for 1 day. To the reaction mixture were added ammonium chloride (558 mg, 10.5 mmol), triethylamine (1.8 mL, 13 mmol), N-[3-(dimethylamino)propyl]-N'-ethylcarbodiimide hydrochloride (440 mg, 2.3 mmol), 1-hydroxybenzotriazole (310 mg, 2.3 mmol) and N,N-dimethylformamide (20 mL), and the mixture was stirred at room temperature for 1 day. The reaction mixture was concentrated under reduced pressure, and water was added to the obtained residue. The resulting precipitate was collected by filtration, washed with water and diethyl ether and dried to give the title compound (630 mg, 95%) as a pale-yellow solid.

$^1$H-NMR (DMSO-d$_6$, 300 MHz) δ 2.63 (3H, s), 5.31 (2H, s), 6.84 (1H, dd, J=2.6, 7.6 Hz), 7.28-7.56 (8H, m), 7.64 (2H, br s), 7.75 (1H, d, J=2.6 Hz), 7.82-7.89 (2H, m), 8.65 (1H, d, J=7.6 Hz).

(x) Production of 5-(benzyloxy)-2-methyl-3-[4-phenyl-5-(4H-1,2,4-triazol-3-yl)-1,3-thiazol-2-yl]pyrazolo[1,5-a]pyridine A mixture of 2-[5-(benzyloxy)-2-methylpyrazolo[1,5-a]pyridin-3-yl]-4-phenyl-1,3-thiazole-5-carboxamide (590 mg, 1.3 mmol) produced in the above and N,N-dimethylformamide dimethyl acetal (20 mL) was stirred at 100° C. for 3 hr. The reaction mixture was concentrated under reduced pressure, toluene was added to the obtained residue, and the mixture was concentrated again under reduced pressure. Hydrazine monohydrate (0.33 mL, 6.7 mmol) and acetic acid (20 mL) were added to the obtained residue, and the mixture was stirred at 100° C. for 2 hr. The reaction mixture was concentrated under reduced pressure, and aqueous sodium bicarbonate solution and diethyl ether were added to the obtained residue. The resulting precipitate was collected by filtration, washed with water and diethyl ether and dried to give the title compound (566 mg, 91%) as a pale-brown solid.

$^1$H-NMR (DMSO-d$_6$, 300 MHz) δ 2.65 (3H, s), 5.31 (2H, s), 6.83 (1H, dd, J=2.6, 7.6 Hz), 7.30-7.56 (8H, m), 7.80 (1H, d, J=2.6 Hz), 7.90-7.97 (2H, m), 8.55 (1H, s), 8.65 (1H, d, J=7.6 Hz), 14.17 (1H, br s).

(xi) Production of 5-(benzyloxy)-2-methyl-3-[4-phenyl-5-(4H-1,2,4-triazol-3-yl)-1,3-thiazol-2-yl]pyrazolo[1,5-a]pyridine p-toluenesulfonate A mixture of 5-(benzyloxy)-2-methyl-3-[4-phenyl-5-(4H-1,2,4-triazol-3-yl)-1,3-thiazol-2-yl]pyrazolo[1,5-a]pyridine (100 mg, 0.22 mmol) produced in the above, p-toluenesulfonic acid monohydrate (49 mg, 0.26 mmol) and ethanol (40 mL) was dissolved by heating, and concentrated under reduced pressure. The obtained residue was crystallized from ethanol and ethyl acetate to give the title compound (90 mg, 66%) as a pale-yellow solid.

$^1$H-NMR (DMSO-d$_6$, 300 MHz) δ 2.29 (3H, s), 2.65 (3H, s), 5.31 (2H, s), 6.83 (1H, dd, J=2.6, 7.6 Hz), 7.11 (2H, d,

J=7.7 Hz), 7.30-7.53 (10H, m), 7.80 (1H, d, J=2.6 Hz), 7.86-7.95 (2H, m), 8.61 (1H, s), 8.65 (1H, d, J=7.6 Hz).

Example 31-B

Production of 2-methyl-5-(2-morpholin-4-ylethoxy)-3-[4-phenyl-5-(4H-1,2,4-triazol-3-yl)-1,3-thiazol-2-yl]pyrazolo[1,5-a]pyridine di-p-toluenesulfonate

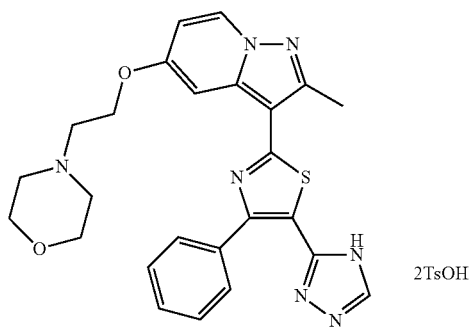

2TsOH (i) Production of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol A mixture of 5-(benzyloxy)-2-methyl-3-[4-phenyl-5-(4H-1,2,4-triazol-3-yl)-1,3-thiazol-2-yl]pyrazolo[1,5-a]pyridine (440 mg, 0.94 mmol) produced in Example 30-B(x), 3,4-dihydro-2H-pyran (0.17 mL, 1.9 mmol), p-toluenesulfonic acid monohydrate (38 mg, 0.2 mmol) and tetrahydrofuran (10 mL) was stirred at 60° C. for 1 day. The reaction mixture was concentrated under reduced pressure, aqueous sodium bicarbonate solution was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=30/70→100/0). The obtained solution was concentrated under reduced pressure, and the obtained residue was washed with diisopropyl ether to give 5-(benzyloxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (430 mg, 84%) as a colorless solid.

To a solution of 5-(benzyloxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (410 mg, 0.75 mmol) produced in the above in tetrahydrofuran (30 mL)/ethanol (30 mL) was added 10% palladium-carbon (50% wet with water, 80 mg). The mixture was stirred at room temperature for 3 hr under a hydrogen atmosphere (1 atm), and 10% palladium-carbon was filtered off. 10% Palladium-carbon (50% wet with water, 120 mg) was added to the filtrate, and the mixture was stirred at room temperature for 14 hr under a hydrogen atmosphere (1 atm). 10% Palladium-carbon was filtered off. 10% Palladium-carbon (50% wet with water, 120 mg) was added to the filtrate, and the mixture was stirred at room temperature for 3 hr under a hydrogen atmosphere (1 atm). 10% Palladium-carbon was filtered off, and the filtrate was concentrated under reduced pressure. The obtained residue was purified by silica gel column chromatography (ethyl acetate/hexane=50/50→100/0), and the obtained solution was concentrated under reduced pressure. The obtained residue was washed with diisopropyl ether to give the title compound (273 mg, 79%) as a colorless solid.

$^1$H-NMR (DMSO-d$_6$, 300 MHz) δ 1.48-1.77 (3H, m), 1.86-2.17 (3H, m), 2.64 (3H, s), 3.55-3.73 (1H, m), 3.89-3.98 (1H, m), 5.59 (1H, dd, J=3.0, 8.9 Hz), 6.63 (1H, dd, J=2.6, 7.5 Hz), 7.36-7.51 (3H, m), 7.65 (1H, d, J=2.6 Hz), 7.88-7.96 (2H, m), 8.57 (1H, d, J=7.5 Hz), 8.77 (1H, s), 10.78 (1H, s).

(ii) Production of 2-methyl-5-(2-morpholin-4-ylethoxy)-3-[4-phenyl-5-(4H-1,2,4-triazol-3-yl)-1,3-thiazol-2-yl]pyrazolo[1,5-a]pyridine di-p-toluenesulfonate A mixture of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (60 mg, 0.13 mmol) produced in the above, 4-(2-chloroethyl)morpholine hydrochloride (48 g, 0.26 mmol), potassium carbonate (72 mg, 0.52 mmol) and N,N-dimethylformamide (3 mL) was stirred at room temperature for 1 hr and at 60° C. for 5 hr. To the reaction mixture was added water, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by basic silica gel column chromatography (ethyl acetate/hexane=50/50→100/0), and the obtained solution was concentrated under reduced pressure. 1N Hydrochloric acid (2 mL), methanol (2 mL) and tetrahydrofuran (2 mL) were added to the obtained residue, and the mixture was stirred at room temperature for 1 hr and at 60° C. for 2 hr. To the reaction mixture was added aqueous sodium bicarbonate solution, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with diisopropyl ether to give 2-methyl-5-(2-morpholin-4-ylethoxy)-3-[4-phenyl-5-(4H-1,2,4-triazol-3-yl)-1,3-thiazol-2-yl]pyrazolo[1,5-a]pyridine (55 mg, 87%) as a colorless solid.

A mixture of 2-methyl-5-(2-morpholin-4-ylethoxy)-3-[4-phenyl-5-(4H-1,2,4-triazol-3-yl)-1,3-thiazol-2-yl]pyrazolo[1,5-a]pyridine (55 mg, 0.11 mmol) produced in the above, p-toluenesulfonic acid monohydrate (46 mg, 0.24 mmol) and ethanol (80 mL) was dissolved by heating, and concentrated under reduced pressure. The obtained residue was crystallized from ethanol and ethyl acetate to give the title compound (73 mg, 78%) as a yellow solid.

$^1$H-NMR (DMSO-d$_6$, 300 MHz) δ 2.28 (6H, s), 2.69 (3H, s), 3.14-3.35 (2H, m), 3.51-3.62 (2H, m), 3.62-4.09 (6H, m), 4.52-4.61 (2H, m), 6.83 (1H, dd, J=2.7, 7.6 Hz), 7.11 (4H, d,

J=7.7 Hz), 7.39-7.50 (7H, m), 7.75 (1H, d, J=2.7 Hz), 7.88-7.99 (2H, m), 8.63 (1H, br s), 8.72 (1H, d, J=7.6 Hz), 9.85 (1H, br s).

Example 32-B

Production of 2-methyl-3-[4-phenyl-5-(4H-1,2,4-triazol-3-yl)-1,3-thiazol-2-yl]-5-(2-piperidin-1-ylethoxy)pyrazolo[1,5-a]pyridine di-p-toluenesulfonate

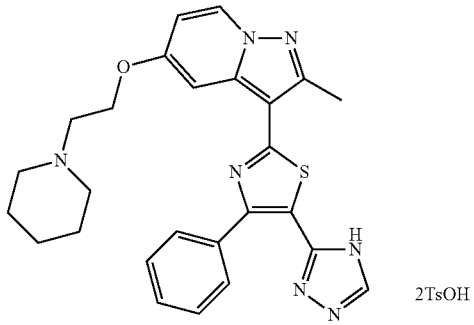

2TsOH

A mixture of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (60 mg, 0.13 mmol) produced in Example 31-B(i), 1-(2-chloroethyl)piperidine hydrochloride (48 mg, 0.26 mmol), potassium carbonate (72 mg, 0.52 mmol) and N,N-dimethylformamide (3 mL) was stirred at 60° C. for 5 hr. To the reaction mixture was added water, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by basic silica gel column chromatography (ethyl acetate/hexane=40/60→100/0), and the obtained solution was concentrated under reduced pressure. 1N Hydrochloric acid (2 mL), methanol (2 mL) and tetrahydrofuran (2 mL) were added to the obtained residue, and the mixture was stirred at 60° C. for 2 hr. To the reaction mixture was added aqueous sodium bicarbonate solution, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with diisopropyl ether, 2-methyl-3-[4-phenyl-5-(4H-1,2,4-triazol-3-yl)-1,3-thiazol-2-yl]-5-(2-piperidin-1-ylethoxy)pyrazolo[1,5-a]pyridine (57 mg, 90%) as a colorless solid.

A mixture of 2-methyl-3-[4-phenyl-5-(4H-1,2,4-triazol-3-yl)-1,3-thiazol-2-yl]-5-(2-piperidin-1-ylethoxy)pyrazolo[1,5-a]pyridine (57 mg, 0.12 mmol) produced in the above, p-toluenesulfonic acid monohydrate (49 mg, 0.26 mmol) and ethanol (10 mL) was dissolved by heating, and concentrated under reduced pressure. The obtained residue was crystallized from ethanol and ethyl acetate to give the title compound (85 mg, 87%) as a yellow solid.

$^1$H-NMR (DMSO-$d_6$, 300 MHz) δ 1.29-1.50 (1H, m), 1.56-1.93 (5H, m), 2.28 (6H, s), 2.68 (3H, s), 2.96-3.14 (2H, m), 3.49-3.67 (4H, m), 4.54 (2H, t, J=4.4 Hz), 6.83 (1H, dd, J=2.6, 7.6 Hz), 7.11 (4H, d, J=7.9 Hz), 7.36-7.53 (7H, m), 7.74 (1H, d, J=2.6 Hz), 7.89-7.98 (2H, m), 8.62 (1H, s), 8.71 (1H, d, J=7.6 Hz), 9.26 (1H, br s).

Example 33-B

Production of 2-({2-methyl-3-[4-phenyl-5-(4H-1,2,4-triazol-3-yl)-1,3-thiazol-2-yl]pyrazolo[1,5-a]pyridin-5-yl}oxy)ethanol

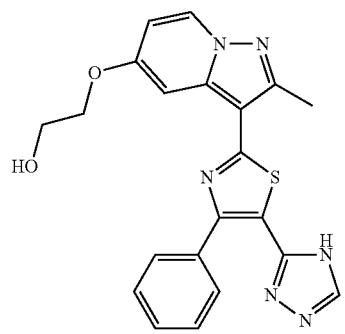 [SMILES: Cc1nn2ccc(OCCO)cc2c1-c1nc(-c2ccccc2)c(-c2nnc[nH]2)s1]

A mixture of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (73 mg, 0.16 mmol) produced in Example 31-B(i), (2-iodoethyl)benzoate (88 mg, 0.32 mmol), potassium carbonate (44 mg, 0.32 mmol) and N,N-dimethylformamide (3 mL) was stirred at 60° C. for 4 hr. To the reaction mixture was added water, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by basic silica gel column chromatography (ethyl acetate/hexane=30/70→100/0). The obtained solution was concentrated under reduced pressure. 1N Hydrochloric acid (2 mL), methanol (2 mL) and tetrahydrofuran (2 mL) were added to the obtained residue, and the mixture was stirred at 60° C. for 1 hr. To the reaction mixture were added methanol (1 mL) and tetrahydrofuran (1 mL), and the mixture was stirred at 60° C. for 2 hr. To the reaction mixture was added 2N aqueous sodium hydroxide solution (2 mL), and the mixture was stirred at room temperature for 1 hr. To the reaction mixture was added water, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with diisopropyl ether to give the title compound (54 mg, 81%) as a colorless solid.

$^1$H-NMR (DMSO-$d_6$, 300 MHz) δ 2.66 (3H, s), 3.81 (2H, q, J=4.8 Hz), 4.17 (2H, t, J=4.8 Hz), 4.98 (1H, t, J=4.8 Hz), 6.78 (1H, dd, J=2.7, 7.6 Hz), 7.34-7.49 (3H, m), 7.73 (1H, d, J=2.7 Hz), 7.91-7.99 (2H, m), 8.58 (1H, s), 8.64 (1H, d, J=7.6 Hz), 14.24 (1H, br s).

Example 34-B

Production of 2-methyl-3-[4-phenyl-5-(4H-1,2,4-triazol-3-yl)-1,3-thiazol-2-yl]pyrazolo[1,5-a]pyridin-5-ol

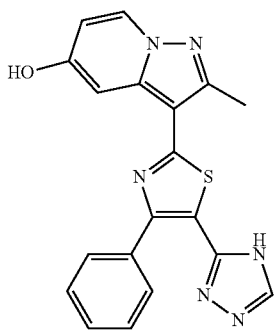 [SMILES: Cc1nn2ccc(O)cc2c1-c1nc(-c2ccccc2)c(-c2nnc[nH]2)s1]

To a solution of 5-(benzyloxy)-2-methyl-3-[4-phenyl-5-(4H-1,2,4-triazol-3-yl)-1,3-thiazol-2-yl]pyrazolo[1,5-a]pyridine (220 mg, 0.47 mmol) produced in Example 30(x) in tetrahydrofuran (20 mL) and methanol (10 mL) was added 10% palladium-carbon (50% wet with water, 110 mg). Under a hydrogen atmosphere (1 atm), the mixture was stirred at room temperature for 31 hr, and 10% palladium-carbon was filtered off. The filtrate was concentrated under reduced pressure, the obtained residue was purified by silica gel column chromatography (ethyl acetate/hexane=50/50→100/0), and the obtained solution was concentrated under reduced pressure. The obtained residue was washed with tetrahydrofuran/ethyl acetate. The obtained crude product was dissolved in ethanol, and concentrated under reduced pressure. The obtained residue was crystallized from ethanol and ethyl acetate to give the title compound (68 mg, 38%) as a pale yellow-brown solid.

$^1$H-NMR (DMSO-d$_6$, 300 MHz) δ 2.64 (3H, s), 6.63 (1H, dd, J=2.5, 7.5 Hz), 7.31-7.51 (3H, m), 7.65 (1H, d, J=15 Hz), 7.81-8.03 (2H, m), 8.57 (1H, d, J=7.5 Hz), 8.63 (1H, br s), 10.79 (1H, br s), 14.23 (1H, br s).

Example 35-B

Production of 6-methyl-7-[4-phenyl-5-(4H-1,2,4-triazol-3-yl)-1,3-thiazol-2-yl]pyrazolo[5,1-b][1,3]thiazole acetate (i) Production of 3-amino-2-methyl-1,3-thiazol-3-ium 2,4,6-trimethylbenzenesulfonate A solution of ethyl (1E)-N-{[(2,4,6-trimethylphenyl)sulfonyl]oxy}ethanimidate (19 g, 67 mmol) in 1,4-dioxane (20 mL) was ice-cooled, and perchloric acid (8 mL) was slowly added dropwise with stirring so that the inside temperature would not exceed 10° C. After stirring for 20 min, water (80 mL) was added to the reaction system, and the resulting solid was collected by filtration and washed with water. The obtained solid was added to a suspension of ethyl acetate (80 mL) and anhydrous magnesium sulfate (20 g) under ice-cooling, and the mixture was stirred for 10 min. The insoluble material was filtered off, and washed with toluene (100 mL). The obtained filtrate was used for the next reaction without purification as a solution of 2-[(aminooxy)sulfonyl]-1,3,5-trimethylbenzene in ethyl acetate-toluene.

To a solution of 2-methyl-1,3-thiazole (6.6 g, 67 mmol) in toluene (60 mL) was added a solution of 2-[(aminooxy)sulfonyl]-1,3,5-trimethylbenzene obtained in the above in ethyl acetate-toluene under ice-cooling, and the mixture was stirred for 2 hr. Diisopropyl ether (200 mL) was added to the reaction system, and the resulting solid was collected by filtration to give the title compound (13 g, 63%) as a white solid. The filtrate was concentrated under reduced pressure to about 100 mL, diisopropyl ether (100 mL) was added, and the resulting solid was collected by filtration to give the title compound (3.8 g, 18%) as a white solid (total yield 81%).

$^1$H-NMR (DMSO-d$_6$, 300 MHz) δ 2.17 (3H, s), 2.49 (6H, s), 2.83 (3H, s), 6.74 (2H, s), 7.46 (2H, br s), 8.03 (1H, d, J=3.9 Hz), 8.19 (1H, d, J=3.9 Hz).

(ii) Production of 1-(6-methylpyrazolo[5,1-b][1,3]thiazol-7-yl)ethanone

A mixture of 3-amino-2-methyl-1,3-thiazol-3-ium 2,4,6-trimethylbenzenesulfonate (17 g, 54 mmol) produced in the above, potassium acetate (16 g, 160 mmol) and acetic anhydride (70 mL, 740 mmol) was stirred at 140° C. for 2 hr. The reaction mixture was cooled to room temperature, 2M aqueous potassium carbonate solution (400 mL) was added, and the mixture was extracted with ethyl acetate. The organic layer was dried over anhydrous magnesium sulfate, the insoluble material was filtered off, and the filtrate was concentrated under reduced pressure. The residue was purified by silica gel column chromatography (ethyl acetate/hexane=2/98→100/0) to give the title compound (4.8 g, 50%) as an orange solid.

$^1$H-NMR (DMSO-d$_6$, 300 MHz) δ 2.51 (3H, s), 2.65 (3H, s), 7.00 (1H, d, J=3.9 Hz), 7.76 (1H, d, J=3.9 Hz).

(iii) Production of 6-methylpyrazolo[5,1-b][1,3]thiazole 1-(6-Methylpyrazolo[5,1-b][1,3]thiazol-7-yl)ethanone (2.8 g, 16 mmol) produced in the above was added to concentrated hydrochloric acid (28 mL), and the mixture was stirred at 100° C. for 4 days. The reaction mixture was cooled to room temperature, neutralized with an excess amount of aqueous potassium carbonate solution and extracted with ethyl acetate. The organic layer was washed with saturated brine and dried over anhydrous magnesium sulfate, and the insoluble material was filtered off. The filtrate was concentrated under reduced pressure, and the residue was purified by silica gel column chromatography (ethyl acetate/hexane=2/98→50/50) to give the title compound (1.3 g, 61%) as a yellow liquid.

$^1$H-NMR (DMSO-d$_6$, 300 MHz) δ 2.41 (3H, s), 6.51 (1H, s), 6.72 (1H, d, J=4.2 Hz), 7.66 (1H, d, J=4.2 Hz).

(iv) Production of 6-methylpyrazolo[5,1-b][1,3]thiazole-7-carbaldehyde

To a solution of 6-methylpyrazolo[5,1-b][1,3]thiazole (1.3 g, 9.5 mmol) produced in the above in N,N-dimethylformamide (10 mL) was added N-(chloromethylidene)-N-methylmethanaminium chloride (1.8 g, 14 mmol) with stirring, and the mixture was stirred for 30 min. The reaction solution was added to an excess amount of an aqueous sodium bicarbonate solution, and the mixture was extracted with ethyl acetate. The organic layer was washed with saturated brine and dried over anhydrous magnesium sulfate, and the insoluble material was filtered off. The filtrate was concentrated under reduced pressure, hexane was added to the residue, and the resulting solid was collected by filtration to give the title compound (1.2 g, 79%) as a white solid.

$^1$H-NMR (DMSO-d$_6$, 300 MHz) δ 2.64 (3H, s), 7.06 (1H, d, J=4.2 Hz), 7.78 (1H, d, J=3.9 Hz), 9.92 (1H, s).

(v) Production of 6-methylpyrazolo[5,1-b][1,3]thiazole-7-carbonitrile

A suspension of 6-methylpyrazolo[5,1-b][1,3]thiazole-7-carbaldehyde (170 mg, 1.0 mmol) produced in the above and hydroxylamine hydrochloride (83 mg, 1.2 mmol) in N,N-dimethylformamide (5 mL) was stirred at 80° C. for 30 min, Triethylamine (0.7 mL, 5 mmol) and 2-chloro-1,3-dimethyl-4,5-dihydro-1H-imidazol-3-ium chloride (250 mg, 1.5 mmol) were added to the reaction solution, and the mixture was further stirred for 30 min. The reaction mixture was cooled to room temperature, an excess amount of an aqueous sodium bicarbonate solution was added, and the mixture was extracted with ethyl acetate. The organic layer was washed with saturated brine and dried over anhydrous magnesium sulfate, and the insoluble material was filtered off. The filtrate was concentrated under reduced pressure, and the residue was purified by silica gel column chromatography (ethyl acetate/hexane=2/98→100/0) to give the title compound (80 mg, 49%) as a white solid.

$^1$H-NMR (DMSO-d$_6$, 300 MHz) δ 2.53 (3H, s), 6.99 (1H, d, J=4.2 Hz), 7.77 (1H, d, J=4.2 Hz).

(vi) Production of 6-methylpyrazolo[5,1-b][1,3]thiazole-7-carbothioamide

A mixture of 6-methylpyrazolo[5,1-b][1,3]thiazole-7-carbonitrile (470 mg, 2.9 mmol) produced in the above, O,O'-diethyl dithiophosphate (640 mg, 3.4 mmol) and 4N hydrogen chloride/ethyl acetate solution (5 mL) was stirred at room temperature for 30 min. Methanol (5 mL) was added to the reaction solution, and the mixture was heated to 50° C. and stirred for 30 min. The reaction mixture was cooled to room temperature, an excess amount of aqueous sodium hydrogen bicarbonate solution, was added, and the mixture was extracted with ethyl acetate. The organic layer was washed with saturated brine and dried over anhydrous magnesium sulfate, and the insoluble material was filtered off. The filtrate was concentrated under reduced pressure, hexane was added to the residue, and the resulting solid was collected by filtration to give the title compound (530 mg, 94%) as a gray solid.

$^1$H-NMR (DMSO-d$_6$, 300 MHz) δ 2.56 (3H, s), 7.39 (1H, d, J=4.2 Hz), 8.04 (1H, br s), 8.19 (1H, d, J=4.2 Hz), 9.34 (1H, br s).

(vii) Production of ethyl 2-(6-methylpyrazolo[5,1-b][1,3]thiazol-7-yl)-4-phenyl-1,3-thiazole-5-carboxylate 6-Methylpyrazolo[5,1-b][1,3]thiazole-7-carbothioamide (570 mg, 2.9 mmol) produced in the above and separately produced ethyl 2-bromo-3-oxo-3-phenylpropanoate (860 mg, 3.2 mmol) were added to ethanol (10 mL), and the mixture was stirred at 80° C. for 1 hr. The reaction mixture was cooled to room temperature, an aqueous sodium bicarbonate solution was added, and the mixture was extracted with ethyl acetate. The organic layer was washed with saturated brine and dried over anhydrous magnesium sulfate, and the insoluble material was filtered off. The filtrate was concentrated under reduced pressure, hexane was added to the residue, and the resulting solid was collected by filtration to give the title compound (670 mg, 63%) as a yellow solid.

$^1$H-NMR (DMSO-d$_6$, 300 MHz) δ 1.24 (3H, t, J=7.2 Hz), 2.63 (3H, s), 4.25 (2H, q, J=7.2 Hz), 7.45-7.54 (4H, m), 7.83-7.87 (2H, m), 8.33 (1H, d, J=4.2 Hz).

(viii) Production of 2-(6-methylpyrazolo[5,1-b][1,3]thiazol-7-yl)-4-phenyl-1,3-thiazole-5-carboxylic acid To a solution of ethyl 2-(6-methylpyrazolo[5,1-b][1,3]thiazol-7-yl)-4-phenyl-1,3-thiazole-5-carboxylate (780 mg, 2.1 mmol) produced in the above in tetrahydrofuran (5 mL) were added methanol (5 mL) and 1N aqueous sodium hydroxide solution (2.4 mL), and the mixture was stirred at 60° C. for 2 hr. The reaction solution was concentrated under reduced pressure, distilled water (10 mL) and 1N hydrochloric acid (2.5 mL) were added to the residue, and the mixture was concentrated under reduced pressure. Ethanol was added to the residue, and the resulting solid was collected by filtration to give the title compound (520 mg) as a yellow solid. The obtained compound was used for the next reaction without further purification.

(ix) Production of 2-(6-methylpyrazolo[5,1-b][1,3]thiazol-7-yl)-4-phenyl-1,3-thiazole-5-carboxamide A suspension of 2-(6-methylpyrazolo[5,1-b][1,3]thiazol-7-yl)-4-phenyl-1,3-thiazole-5-carboxylic acid (85 mg, 0.25 mmol) produced in the above, ammonium chloride (27 mg, 0.5 mmol) and triethylamine (51 mg, 0.5 mmol) in N,N-dimethylformamide (5 mL) was stirred at room temperature for 10 min. 1-Hydroxybenzotriazole (51 mg, 0.38 mmol) and N-[3-(dimethylamino)propyl]-N'-ethylcarbodiimide hydrochloride (72 mg, 0.38 mmol) were added to the reaction solution, and the mixture was further stirred at room temperature for 1 day. The reaction mixture was added to a mixed solution of ethyl acetate and saturated aqueous sodium bicarbonate solution, and the resulting solid was collected by filtration to give the title compound (10 mg, 10%) as a white solid.

The organic layer was separated from the filtrate and dried over anhydrous magnesium sulfate, and the insoluble material was filtered off. The filtrate was concentrated under reduced pressure to give the title compound (79 mg) as a white solid. The obtained compound contained a small amount of impurity, but was used for the next reaction without further purification.

$^1$H-NMR (DMSO-d$_6$, 300 MHz) δ 2.61 (3H, s), 7.44-7.52 (4H, m), 7.69 (2H, br s), 7.84-7.87 (2H, m), 8.32 (1H, d, J=4.2 Hz).

(x) Production of 6-methyl-7-[4-phenyl-5-(4H-1,2,4-triazol-3-yl)-1,3-thiazol-2-yl]pyrazolo[5,1-b][1,3]thiazole acetate A suspension of 2-(6-methylpyrazolo[5,1-b][1,3]thiazol-7-yl)-4-phenyl-1,3-thiazole-5-carboxamide (79 mg, about 0.23 mmol) produced in the above in N,N-dimethylformamide dimethyl acetal (2 mL) was stirred at 90° C. for 2 hr. The reaction mixture was concentrated under reduced pressure, hydrazine monohydrate (0.017 mL, 0.35 mmol) and acetic acid (2 mL) were added to the residue, and the mixture was stirred at 90° C. for 1 hr. The reaction mixture was cooled to room temperature, and the resulting solid was collected by filtration and washed with ethyl acetate to give the title compound (27.8 mg, 33%) as a white solid.

$^1$H-NMR (DMSO-d$_6$, 300 MHz) δ 1.91 (3H, s), 2.64 (3H, s), 7.39-7.52 (4H, m), 7.94 (2H, br s), 8.31 (1H, d, J=4.2 Hz), 8.66 (1H, br s), 11.95 (1H, br s), 14.28 (1H, br s).

Example 36-B

Production of 6-methyl-7-[5-(5-methyl-4H-1,2,4-triazol-3-yl)-4-phenyl-1,3-thiazol-2-yl]pyrazolo[5,1-b][1,3]thiazole acetate

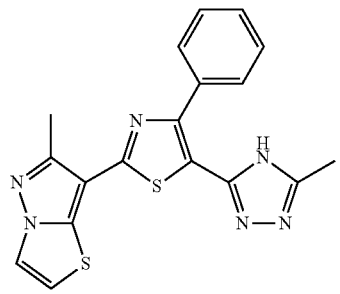 [SMILES: Cc1nnc(-c2sc(-c3c(C)nn4ccsc34)nc2-c2ccccc2)[nH]1]

2-(6-Methylpyrazolo[5,1-b][1,3]thiazol-7-yl)-4-phenyl-1,3-thiazole-5-carboxamide (79 mg, about 0.23 mmol) produced in the same manner as in Example 35-B(ix) was suspended in N,N-dimethylacetamide dimethyl acetal (2 mL), and the mixture was stirred at 90° C. for 2 hr. The reaction mixture was concentrated under reduced pressure, hydrazine monohydrate (0.017 mL, 0.35 mmol) and acetic acid (2 mL) were added to the residue, and the mixture was stirred at 90° C. for 1 hr. The reaction mixture was cooled to room temperature, and the resulting solid was collected by filtration and washed with ethyl acetate to give the title compound (72 mg, 70%) as a white solid.

$^1$H-NMR (DMSO-d$_6$; 300 MHz) δ 1.91 (3H, s), 2.39 (3H, s), 2.64 (3H, s), 7.39-7.51 (4H, m), 7.97-8.00 (2H, m), 8.31 (1H, d, J=4.2 Hz), 11.92 (1H, br s), 13.82 (1H, br s).

Example 37-B

Production of 6-methyl-7-[4-phenyl-5-(1H-tetrazol-5-yl)-1,3-thiazol-2-yl]pyrazolo[5,1-b][1,3]thiazole

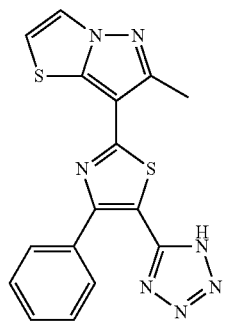 [SMILES: Cc1nn2ccsc2c1-c1nc(-c2ccccc2)c(-c2nnn[nH]2)s1]

(i) Production of 2-(6-methylpyrazolo[5,1-b][1,3]thiazol-7-yl)-4-phenyl-1,3-thiazole-5-carbonitrile To a suspension of 2-(6-methylpyrazolo[5,1-b][1,3]thiazol-7-yl)-4-phenyl-1,3-thiazole-5-carboxamide (270 mg, 0.80 mmol) produced in the same manner as in Example 35-B (ix) in tetrahydrofuran (20 mL) was added Burgess reagent (230 mg, 0.96 mmol), and the mixture was stirred for 30 min. The reaction solution was added to ethyl acetate (100 mL) and saturated aqueous sodium bicarbonate solution (100 mL). The resulting solid was collected by filtration, washed with water and dried to give the title compound (110 mg, 42%) as a colorless solid.

$^1$H-NMR (DMSO-d$_6$, 300 MHz) δ 2.64 (3H, s), 7.57-7.65 (4H, m), 8.15-8.17 (2H, m), 8.39 (1H, d, J=4.2 Hz).

(ii) Production of 6-methyl-7-[4-phenyl-5-(1H-tetrazol-5-yl)-1,3-thiazol-2-yl]pyrazolo[5,1-b][1,3]thiazole A suspension of 2-(6-methylpyrazolo[5,1-b][1,3]thiazol-7-yl)-4-phenyl-1,3-thiazole-5-carbonitrile (108 mg, 0.335 mmol) produced in the above, sodium azide (87 mg, 1.3 mmol) and ammonium chloride (72 mg, 1.3 mmol) in N,N-dimethylformamide (10 mL) was stirred at 120° C. for 1 day. The reaction solution was cooled to room temperature, sodium azide (100 mg, 1.5 mmol) and ammonium chloride (80 mg, 1.5 mmol) were added, and the mixture was stirred at 120° C. for 4 hr. The reaction solution was cooled to room temperature, the insoluble material was filtered off, and the filtrate was concentrated under reduced pressure. N,N-Dimethylformamide (10 mL), sodium azide (200 mg, 3.1 mmol) and ammonium chloride (160 mg, 3.0 mmol) were added to the residue, and the mixture was stirred at 140° C. for 3 hr. The reaction solution was concentrated under reduced pressure, water (about 5 mL) was added and the insoluble material was filtered off. The filtrate was concentrated under reduced pressure, and water (5 mL), ethyl acetate (5 mL) and 0.1N hydrochloric acid (3 mL) were added. The resulting solid was collected by filtration, washed with water and ethyl acetate and dried to give the title compound (67 mg, 55%).

$^1$H-NMR (DMSO-d$_6$, 300 MHz) δ 2.65 (3H, s), 7.43-7.49 (3H, m), 7.54 (1H, d, J=4.2 Hz), 7.74-7.76 (2H, m), 8.34 (1H, d, J=4.2 Hz).

Example 38-B

Production of 7-[4-(benzyloxy)-5-(4H-1,2,4-triazol-3-yl)-1,3-thiazol-2-yl]-6-methylpyrazolo[5,1-b][1,3]thiazole

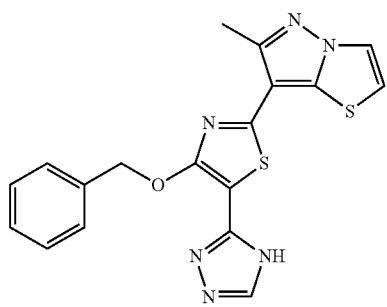 [SMILES: Cc1nn2ccsc2c1-c1nc(OCc2ccccc2)c(-c2nnc[nH]2)s1]

(i) Production of Dibenzyl Bromomalonate

To a solution of dibenzyl malonate (10.0 g, 35.0 mmol) in diethyl ether (20 mL) were added ammonium acetate (270 mg, 3.5 mmol) and N-bromosuccinimide (6.9 g, 39 mmol), and the mixture was stirred at room temperature for 2 hr. Saturated aqueous sodium bicarbonate solution (100 mL) and ethyl acetate (100 mL) were added to the reaction solution, and the mixture was stirred for 30 min. The organic layer was washed with saturated aqueous potassium carbonate solution (100 mL) and saturated brine (10 mL) and dried over anhydrous magnesium sulfate, and the insoluble material was filtered off. The filtrate was concentrated under reduced pressure, and the obtained residue was purified by silica gel column chromatography (ethyl acetate/hexane=0/100→50/50) to give the title compound (3.8 g, 29%) as a brown oil.

$^1$H-NMR (DMSO-d$_6$, 300 MHz) δ 5.23 (4H, s), 5.76 (1H, s), 7.27-7.42 (10H, m).

(ii) Production of benzyl 4-hydroxy-2-(6-methylpyrazolo[5,1-b][1,3]thiazol-7-yl)-1,3-thiazole-5-carboxylate hydrobromide A suspension of 6-methylpyrazolo[5,1-b][1,3]thiazole-7-carbothioamide (600 mg, 3.0 mmol) produced in Example 35-B(vi) and dibenzyl bromomalonate (980 mg, 2.7 mmol) produced in the above in 2-propanol (300 mL) was stirred at 80° C. for 3 hr. The reaction mixture was cooled to room temperature, and the precipitated solid was collected by filtration, washed with ethyl acetate and diisopropyl ether and dried to give the title compound (570 mg, 61%) as a yellow solid. This compound was used for the next reaction without further purification.

$^1$H-NMR (DMSO-d$_6$, 300 MHz) δ 2.60 (3H, m), 5.26 (2H, m), 7.22-7.64 (6H, m), 8.27-8.42 (1H, m), 11.95 (1H, s).

(iii) Production of benzyl 4-(benzyloxy)-2-(6-methylpyrazolo[5,1-b][1,3]thiazol-7-yl)-1,3-thiazole-5-carboxylate To a solution of benzyl 4-hydroxy-2-(6-methylpyrazolo[5,1-b][1,3]thiazol-7-yl)-1,3-thiazole-5-carboxylate hydrobromide (300 mg, 0.66 mmol) produced in the above and benzyl bromide (120 mg, 0.70 mmol) in N,N-dimethylformamide (30 mL) was added potassium carbonate (600 mg, 4.3 mmol), and the mixture was stirred at room temperature for 2 hr. The reaction solution was diluted with water (50 mL), and the mixture was extracted with ethyl acetate (150 mL). The organic layer was washed with saturated brine and dried over anhydrous magnesium sulfate. The insoluble material was filtered off, and the filtrate was concentrated under reduced pressure. The obtained residue was purified by silica gel column chromatography (ethyl acetate/hexane=0/100→100/0) to give the title compound (240 mg, 78%) as a yellow solid.

$^1$H-NMR (DMSO-d$_6$, 300 MHz) δ 2.57 (3H, s), 5.27 (2H, s), 5.64 (2H, s), 7.30-7.44 (8H, m), 7.47-7.55 (2H, m), 7.57 (1H, d, J=4.1 Hz), 8.35 (1H, d, J=4.1 Hz), (iv) Production of 4-(benzyloxy)-2-(6-methylpyrazolo[5,1-b][1,3]thiazol-7-yl)-1,3-thiazole-5-carboxylic acid To a solution of benzyl 4-(benzyloxy)-2-(6-methylpyrazolo[5,1-b][1,3]thiazol-7-yl)-1,3-thiazole-5-carboxylate (300 mg, 0.65 mmol) produced in the above in ethanol (8 mL)—tetrahydrofuran (10 mL) were added sodium hydroxide (940 mg, 23.5 mmol) and water (4 mL), and the mixture was stirred at 80° C. for 3 hr. The reaction solution was cooled to room temperature, and the mixture was acidified with 6N hydrochloric acid to about pH 3.0 and extracted with ethyl acetate (100 mL×2). The collected organic layer was dried over anhydrous magnesium sulfate, and the insoluble material was filtered off. The filtrate was concentrated to give the title compound (220 mg, 89%) as a yellow solid.

$^1$H-NMR (DMSO-$d_6$, 300 MHz) δ 2.56 (3H, s), 5.61 (2H, s), 7.28-7.62 (6H, m), 8.33 (1H, d, J=3.9 Hz), 12.65 (1H, s).

(v) Production of 4-(benzyloxy)-2-(6-methylpyrazolo[5,1-b][1,3]thiazol-7-yl)-1,3-thiazole-5-carboxamide To a suspension of 4-(benzyloxy)-2-(6-methylpyrazolo[5,1-b][1,3]thiazol-7-yl)-1,3-thiazole-5-carboxylic acid (200 mg, 0.54 mmol) produced in the above in toluene (8 mL) was added thionyl chloride (0.5 mL, 6.9 mmol), and the mixture was heated under reflux for 2 hr. The solvent was evaporated under reduced pressure, and the obtained residue was dissolved in tetrahydrofuran (20 mL). 25% Aqueous ammonia (2 mL) was added, and the mixture was stirred for 30 min. The reaction solution was diluted with saturated aqueous sodium bicarbonate solution (100 mL) and extracted with ethyl acetate (100 mL). The organic layer was washed with saturated brine and dried over anhydrous magnesium sulfate, and the insoluble material was filtered off. The filtrate was concentrated under reduced pressure, and the obtained residue was washed with diisopropyl ether and dried to give the title compound (130 mg, 61%) as a yellow solid.

$^1$H-NMR (DMSO-$d_6$, 300 MHz) δ 2.55 (3H, s), 5.64 (2H, s), 7.31-7.46 (4H, m), 7.51-7.63 (4H, m), 8.32 (1H, d, J=4.1 Hz).

(vi) Production of 7-[4-(benzyloxy)-5-(4H-1,2,4-triazol-3-yl)-1,3-thiazol-2-yl]-6-methylpyrazolo[5,1-b][1,3]thiazole A solution of 4-(benzyloxy)-2-(6-methylpyrazolo[5,1-b][1,3]thiazol-7-yl)-1,3-thiazole-5-carboxamide (100 mg, 0.27 mmol) produced in the above in N,N-dimethylformamide dimethyl acetal (5 mL) was stirred at 85° C. for 1 hr. The reaction solution was cooled to room temperature, and the solvent was evaporated. The residue was washed with diisopropyl ether, the solvent was removed, and the residue was dried. The obtained solid was dissolved in acetic acid (5 mL), hydrazine monohydrate (0.2 mL) was added, and the mixture was stirred at 80° C. for 1 hr. The reaction solution was cooled to room temperature, saturated aqueous sodium bicarbonate solution (100 mL) and ethyl acetate (100 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=100/0) to give the title compound (52 mg, 49%) as a yellow solid.

$^1$H-NMR (DMSO-$d_6$, 300 MHz) δ 2.58 (3H, s), 5.63 (2H, s), 7.26-7.42 (3H, m), 7.50-7.63 (3H, m), 8.24 (1H, s), 8.31 (1H, d, J=4.1 Hz).

Example 39-B

Production of 7-[4-(3,4-difluorophenyl)-5-(4H-1,2,4-triazol-3-yl)-1,3-thiazol-2-yl]-6-methylpyrazolo[5,1-b][1,3]thiazole

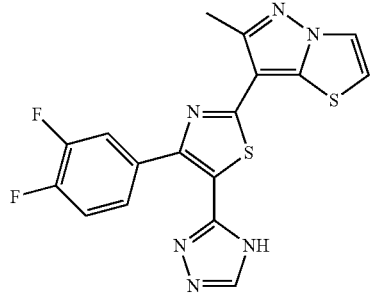 [SMILES: Cc1nn2ccsc2c1-c1nc(-c2ccc(F)c(F)c2)c(-c2nnc[nH]2)s1]

(i) Production of benzyl 2-(6-methylpyrazolo[5,1-b][1,3]thiazol-7-yl)-4-{[(trifluoromethyl)sulfonyl]oxy}-1,3-thiazole-5-carboxylate To a solution of benzyl 4-hydroxy-2-(6-methylpyrazolo[5,1-b][1,3]thiazol-7-yl)-1,3-thiazole-5-carboxylate hydrobromide (1.0 g, 2.2 mmol) produced in Example 38-B(ii) in pyridine (20 mL) was added trifluoromethanesulfonic anhydride (1.5 mL, 8.9 mmol) at 0° C., and the mixture was stirred at room temperature for 1 hr. The reaction solution was cooled to 0° C., saturated aqueous sodium bicarbonate solution (500 mL) and ethyl acetate (500 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was purified by basic silica gel column chromatography (ethyl acetate) to give the title compound (1.0 g, 90%) as a yellow solid.

$^1$H-NMR (DMSO-$d_6$, 300 MHz) δ 2.58 (3H, s), 5.39 (2H, s), 7.36-7.51 (5H, m), 7.60 (1H, d, J=3.9 Hz), 8.39 (1H, d, J=3.9 Hz), (ii) Production of benzyl 4-(3,4-difluorophenyl)-2-(6-methylpyrazolo[5,1-b][1,3]thiazol-7-yl)-1,3-thiazole-5-carboxylate Benzyl 2-(6-methylpyrazolo[5,1-b][1,3]thiazol-7-yl)-4-{[(trifluoromethyl)sulfonyl]oxy}-1,3-thiazole-5-carboxylate (430 mg, 0.85 mmol) produced in the above, (3,4-difluorophenyl)boronic acid (220 mg, 1.4 mmol), [1,1-bis(diphenylphosphino)ferrocene]palladium(II) dichloride dichloromethane complex (45 mg, 0.055 mmol) and cesium carbonate (850 mg, 2.6 mmol) were suspended in 1,2-dimethoxyethane (15 mL), water (2 mL) was added, and the mixture was stirred at 80° C. for 1 hr. The reaction solution was cooled to room temperature, water (50 mL) was added, and the mixture was extracted with ethyl acetate (50 mL×2). The collected organic layer was dried over anhydrous magnesium sulfate, and the insoluble material was filtered off. The filtrate was concentrated under reduced pressure, and the obtained residue was subjected to silica gel column chromatography (ethyl acetate) to give the title compound (200 mg, 51%) as a brown solid.

$^1$H-NMR (DMSO-$d_6$, 300 MHz) δ 2.61 (3H, s), 5.41 (2H, s), 7.35-7.44 (5H, m), 7.45-7.62 (2H, m), 7.75-7.88 (1H, m), 7.99-8.07 (1H, m), 8.33 (1H, d, J=4.1 Hz).

(iii) Production of 4-(3,4-difluorophenyl)-2-(6-methylpyrazolo[5,1-b][1,3]thiazol-7-yl)-1,3-thiazole-5-carboxylic acid To a solution of benzyl 4-(3,4-difluorophenyl)-2-(6-methylpyrazolo[5,1-b][1,3]thiazol-7-yl)-1,3-thiazole-5-carboxylate (130 mg, 0.27 mmol) produced in the above in methanol (5 mL)—tetrahydrofuran (5 mL) was added 8N aqueous sodium hydroxide solution (1.5 mL), and the mixture was stirred at 70° C. for 1 hr. The reaction solution was cooled to 0° C., and 1N hydrochloric acid (10 mL) was added. The precipitated solid was collected by filtration and dried to give the title compound (102 mg, 97%) as a yellow solid.

$^1$H-NMR (DMSO-$d_6$, 300 MHz) δ 2.61 (3H, s), 7.46-7.61 (2H, n), 7.78-7.86 (1H, m), 7.98-8.07 (1H, m), 8.33 (1H, d, J=4.1 Hz).

(iv) Production of 4-(3,4-difluorophenyl)-2-(6-methylpyrazolo[5,1-b][1,3]thiazol-7-yl)-1,3-thiazole-5-carboxamide To a suspension of 4-(3,4-difluorophenyl)-2-(6-methylpyrazolo[5,1-b][1,3]thiazol-7-yl)-1,3-thiazole-5-carboxylic acid (70 mg, 0.19 mmol) produced in the above in toluene (5 mL) was added thionyl chloride (1.0 mL, 14 mmol), and the mixture was heated under reflux for 1 hr. The solvent was evaporated, and the obtained residue was dissolved in tetrahydrofuran (7 mL). 25% Aqueous ammonia (3 mL) was added, and the mixture was stirred for 30 min. The reaction solution was diluted with water (50 mL), and the mixture was extracted with ethyl acetate (50 mL×2). The organic layer was washed with saturated brine and dried over anhydrous magnesium sulfate, and the insoluble material was filtered off. The filtrate was concentrated under reduced pressure, and the obtained residue was washed with diisopropyl ether and dried to give the title compound (52 mg, 74%) as a yellow solid.

$^1$H-NMR (DMSO-$d_6$, 300 MHz) δ 2.62 (3H, s), 7.52 (1H, d, J=4.1 Hz), 7.53-7.65 (1H, m), 7.68-7.97 (4H, m), 8.33 (1H, d, J=4.1 Hz).

(v) Production of 7-[4-(3,4-difluorophenyl)-5-(4H-1,2,4-triazol-3-yl)-1,3-thiazol-2-yl]-6-methylpyrazolo[5,1-b][1,3]thiazole A solution of 4-(3,4-difluorophenyl)-2-(6-methylpyrazolo[5,1-b][1,3]thiazol-7-yl)-1,3-thiazole-5-carboxamide (50 mg, 0.13 mmol) produced in the above in N,N-dimethylformamide dimethyl acetal (5 mL) was stirred at 90° C. for 1 hr. The reaction solution was cooled to room temperature, and the solvent was evaporated. The residue was washed with hexane (5 mL) and diethyl ether (2 mL) and dried. The obtained residue was dissolved in acetic acid (10 mL), hydrazine monohydrate (0.3 mL) was added, and the mixture was stirred at 80° C. for 1 hr. The reaction solution was cooled to room temperature, saturated aqueous sodium bicarbonate solution (50 mL) and ethyl acetate (50 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was washed with ethyl acetate (2 mL) and diethyl ether (10 mL) to give the title compound (32 mg, 60%) as a yellow solid.

$^1$H-NMR (DMSO-$d_6$, 300 MHz) δ 2.64 (3H, s), 7.45-7.62 (2H, m), 7.88-7.97 (1H, m), 8.14-8.24 (1H, m), 8.32 (1H, d, J=4.1 Hz), 8.63 (1H, s)

Example 40-B

Production of 2-methyl-3-[4-phenyl-5-(4H-1,2,4-triazol-3-yl)-1,3-thiazol-2-yl]imidazo[1,2-a]pyridine

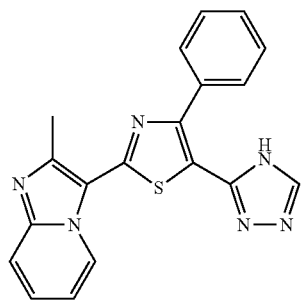 [SMILES: Cc1nc2ccccn2c1-c1nc(-c2ccccc2)c(-c2nnc[nH]2)s1]

(i) Production of 2-methylimidazo[1,2-a]pyridine-3-carboxylic acid

A mixture of pyridin-2-amine (10 g, 106 mmol), ethyl 2-chloro-3-oxobutanoate (16 g, 97 mmol) and ethanol (200 mL) was stirred at 80° C. for 2 days. The reaction mixture was concentrated under reduced pressure, saturated aqueous sodium bicarbonate solution was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, 8N aqueous sodium hydroxide solution (25 mL), water (75 mL) and ethanol (200 mL) were added to the obtained residue, and the mixture was stirred at 70° C. for 1 hr. 6N Hydrochloric acid (34 mL) was added dropwise to the reaction mixture under ice-cooling. The resulting precipitate was collected by filtration, washed with water, ethanol and diethyl ether and dried to give the title compound (7.6 g, 44%) as a pale-pink solid.

$^1$H-NMR (DMSO-$d_6$, 300 MHz) δ 2.60 (3H, s), 7.14 (1H, dt, J=1.3, 6.9 Hz), 7.50 (1H, ddd, J=1.3, 7.0, 8.7 Hz), 7.65 (1H, td, J=1.0, 9.0 Hz), 9.27 (1H, td, J=1.1, 7.0 Hz), 13.04 (1H, br s).

(ii) Production of 2-methylimidazo[1,2-a]pyridine-3-carboxamide

A mixture of 2-methylimidazo[1,2-a]pyridine-3-carboxylic acid (7.1 g, 40 mmol) produced in the above, thionyl chloride (30 mL, 410 mmol) and toluene (50 mL) was stirred at 100° C. for 1 day, and the reaction mixture was concentrated under reduced pressure. A suspension of the obtained residue in tetrahydrofuran (50 mL) was added to 25% aqueous ammonia (50 mL), and the mixture was stirred at room temperature for 3 hr. Water was added to the reaction mixture, and the mixture was extracted with a mixed solvent of ethyl acetate and tetrahydrofuran. The collected organic layer was washed with saturated brine and dried over anhydrous sodium sulfate, and the insoluble material was filtered off. The filtrate was concentrated under reduced pressure to give the title compound (6.86 g, 98%) as a colorless solid.

$^1$H-NMR (DMSO-$d_6$, 300 MHz) δ 2.58 (3H, s), 7.02 (1H, dt, J=1.3, 6.9 Hz), 7.24-7.52 (2H, m), 7.39 (1H, ddd, J=1.3, 6.8, 8.9 Hz), 7.57 (1H, td, J=1.1, 8.9 Hz), 9.16 (1H, td, J=1.1, 7.0 Hz).

(iii) Production of 2-methylimidazo[1,2-a]pyridine-3-carbonitrile

To a mixture of 2-methylimidazo[1,2-a]pyridine-3-carboxamide (3.50 g, 20 mmol) produced in the above, pyridine (4.85 mL, 60 mmol) and tetrahydrofuran (50 mL) was added dropwise a solution of trifluoroacetic anhydride (4.24 mL, 30 mmol) in tetrahydrofuran (10 mL) under ice-cooling. The mixture was stirred at room temperature for 1 hr, saturated aqueous sodium bicarbonate solution was added, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with ethyl acetate/diisopropyl ether to give the title compound (2.5 g, 80%) as a pale-brown solid.

$^1$H-NMR (DMSO-$d_6$, 300 MHz) δ 2.49 (3H, s), 7.19 (1H, dt, J=1.1, 6.8 Hz), 7.56 (1H, ddd, J=1.2, 7.0, 9.0 Hz), 7.73 (1H, td, J=1.1, 9.0 Hz), 8.59 (1H, td, J=1.1, 6.8 Hz).

(iv) Production of 2-methylimidazo[1,2-a]pyridine-3-carbothioamide

A mixture of 2-methylimidazo[1,2-a]pyridine-3-carbonitrile (2.76 g, 18 mmol) produced in the above, O,O'-diethyl dithiophosphate (3.9 mL, 21 mmol), 4N hydrogen chloride ethyl acetate solution (30 mL) and methanol (30 mL) was stirred at 60° C. for 5 hr. Saturated aqueous sodium bicarbonate solution, ethyl acetate and tetrahydrofuran were added to the reaction mixture, and the resulting precipitate was collected by filtration. The obtained solid was washed with water and ethyl acetate and dried to give the title compound (805 mg, 24%) as a pale-yellow solid. The filtrate was extracted with a mixed solvent of ethyl acetate and tetrahydrofuran. The collected organic layer was washed with saturated brine and dried over anhydrous sodium sulfate, and the insoluble material was filtered off. The filtrate was concentrated under reduced pressure, and the obtained residue was washed with ethyl acetate/diisopropyl ether to give the title compound (1.9 g, 55%) as a pale-yellow solid.

$^1$H-NMR (DMSO-$d_6$, 300 MHz) δ 2.52 (3H, s), 7.03 (1H, dt, J=1.3, 6.9 Hz), 7.39 (1H, ddd, J=1.3, 6.8, 8.9 Hz), 7.56 (1H, td, J=1.1, 9.1 Hz), 9.10 (1H, br s), 9.40 (1H, td, J=1.2, 7.0 Hz), 9.78 (1H, br s).

(iv) Production of ethyl 2-(2-methylimidazo[1,2-a]pyridin-3-yl)-4-phenyl-1,3-thiazole-5-carboxylate hydrobromide A mixture of 2-methylimidazo[1,2-a]pyridine-3-carbothioamide (2.5 g, 13 mmol) produced in the above, ethyl 2-bromo-3-oxo-3-phenylpropanoate (3.5 g, 13 mmol) and ethanol (50 mL) was stirred at 80° C. for 5 hr. The reaction mixture was concentrated under reduced pressure, and ethyl acetate was added. The resulting precipitate was collected by filtration, washed with ethyl acetate and dried to give the title compound (3.0 g, 51%) as a colorless solid.

$^1$H-NMR (DMSO-$d_6$, 300 MHz) δ 1.25 (3H, t, J=7.1 Hz), 2.80 (3H, s), 4.29 (2H, q, J=7.1 Hz), 7.44-7.59 (4H, m), 7.79-8.02 (4H, m), 9.84 (1H, d, J=6.8 Hz).

(v) Production of 2-(2-methylimidazo[1,2-a]pyridin-3-yl)-4-phenyl-1,3-thiazole-5-carboxylic acid A mixture of ethyl 2-(2-methylimidazo[1,2-a]pyridin-3-yl)-4-phenyl-1,3-thiazole-5-carboxylate hydrobromide (2.7 g, 6.0 mmol) produced in the above, 8N aqueous sodium hydroxide solution (3 mL), water (9 mL), methanol (20 mL) and tetrahydrofuran (20 mL) was stirred at 60° C. for 2 hr. The reaction mixture was concentrated under reduced pressure, and 6N hydrochloric acid (4 mL) was added. The resulting precipitate was collected by filtration, washed with water and ethanol and dried to give the title compound (1.6 g, 81%) as a colorless solid.

$^1$H-NMR (DMSO-$d_6$, 300 MHz) δ 2.71 (3H, s), 7.23 (1H, dt, J=1.2, 6.9 Hz), 7.46-7.58 (4H, m), 7.73 (1H, d, J=8.9 Hz), 7.83-7.92 (2H, m), 9.77 (1H, d, J=6.8 Hz), 13.41 (1H, br s).

(vi) Production of 2-(2-methylimidazo[1,2-a]pyridin-3-yl)-4-phenyl-1,3-thiazole-5-carboxamide hydrochloride A mixture of 2-(2-methylimidazo[1,2-a]pyridin-3-yl)-4-phenyl-1,3-thiazole-5-carboxylic acid (1.6 g, 4.9 mmol) produced in the above, ammonium chloride (1.6 g, 30 mmol), triethylamine (4.2 mL, 30 mmol), N-[3-(dimethylamino)propyl]-N'-ethylcarbodiimide hydrochloride (1.2 g, 6.0 mmol), 1-hydroxybenzotriazole (810 mg, 6.0 mmol) and N,N-dimethylformamide (50 mL) was stirred at room temperature for 1 day. The reaction mixture was concentrated under reduced pressure, water, ethyl acetate and tetrahydrofuran were added to the obtained residue, and the resulting precipitate was collected by filtration, washed with water, tetrahydrofuran and ethyl acetate and dried to give 2-(2-methylimidazo[1,2-a]pyridin-3-yl)-4-phenyl-1,3-thiazole-5-carboxamide (665 mg, 41%) as a colorless solid. The filtrate was extracted with a mixed solvent of ethyl acetate and tetrahydrofuran. The collected organic layer was washed with saturated brine and dried over anhydrous magnesium sulfate, and the insoluble material was filtered off. The filtrate was concentrated under reduced pressure, and the obtained residue was washed with ethyl acetate/diisopropyl ether to give a crude product (1.1 g) of 2-(2-methylimidazo[1,2-a]pyridin-3-yl)-4-phenyl-1,3-thiazole-5-carboxamide as a yellow solid. 2-(2-Methylimidazo[1,2-a]pyridin-3-yl)-4-phenyl-1,3-thiazole-5-carboxamide (200 mg, 0.60 mmol) produced in the above was dissolved in 4N hydrogen chloride ethyl acetate solution (0.3 mL) and methanol (10 mL), and the mixture was concentrated under reduced pressure. The obtained residue was washed with methanol/ethyl acetate to give the title compound (185 mg, 83%) as a gray solid.

$^1$H-NMR (DMSO-$d_6$, 300 MHz) δ 2.81 (3H, s), 7.44-7.64 (4H, m), 7.84-8.05 (6H, m), 9.87 (1H, d, J=7.0 Hz).

(vii) Production of 2-methyl-3-[4-phenyl-5-(4H-1,2,4-triazol-3-yl)-1,3-thiazol-2-yl]imidazo[1,2-a]pyridine hydrochloride A mixture of 2-(2-methylimidazo[1,2-a]pyridin-3-yl)-4-phenyl-1,3-thiazole-5-carboxamide (670 mg, 2.0 mmol) produced in the above and N,N-dimethylformamide dimethyl acetal (20 mL) was stirred at 120° C. for 2 hr. The reaction mixture was concentrated under reduced pressure, and the obtained residue was washed with ethyl acetate to give a solid (628 mg). Hydrazine monohydrate (0.4 mL, 8.0 mmol) and acetic acid (20 mL) were added to the obtained solid (312 mg), and the mixture was stirred at 100° C. for 1 day. The reaction mixture was concentrated under reduced pressure, and saturated aqueous sodium bicarbonate solution and ethanol were added to the obtained residue. The resulting precipitate was collected by filtration, washed with water and ethanol and dried. A mixture of the obtained crude product (254 mg), 4N hydrogen chloride ethyl acetate solution (0.3 mL) and methanol (30 mL) was dissolved by heating, and the mixture was concentrated under reduced pressure. The obtained residue was washed with methanol/ethyl acetate to give the title compound (143 mg, 36%) as a pale-brown solid.

$^1$H-NMR (DMSO-$d_6$, 300 MHz) δ 2.83 (3H, s), 7.40-7.62 (4H, m), 7.85-8.02 (4H, m), 8.70 (1H, s), 9.91 (1H, d, J=7.0 Hz).

Example 41B

Production of 2-methyl-3-[4-phenyl-5-(4H-1,2,4-triazol-3-yl)-1,3-thiazol-2-yl]imidazo[1,2-b]pyridazine

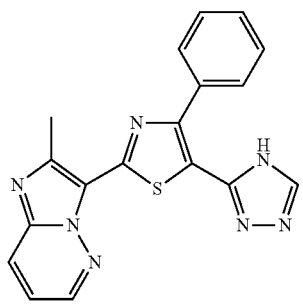

(i) Production of ethyl 6-chloro-2-methylimidazo[1,2-b]pyridazine-3-carboxylate

A mixture of 6-chloropyridazin-3-amine (5.3 g, 41 mmol), ethyl 2-chloro-3-oxobutanoate (6.7 g, 41 mmol) and ethanol (50 mL) was heated under reflux for 2 days. The reaction mixture was concentrated under reduced pressure, saturated aqueous sodium bicarbonate solution and ethyl acetate were added to the obtained residue, and the insoluble material was filtered off. The filtrate was extracted with ethyl acetate, and the collected organic layer was washed with saturated brine and dried over anhydrous magnesium sulfate. The insoluble material was filtered off, and the filtrate was concentrated under reduced pressure. Ethyl acetate and diisopropyl ether were added to the obtained residue, and the insoluble material was filtered off. The obtained residue was purified by silica gel column chromatography (ethyl acetate/hexane=50/50→100/0) and washed with ethyl acetate/diisopropyl ether to give the title compound (3.2 g, 32%) as a colorless solid.

$^1$H-NMR (DMSO-$d_6$, 300 MHz) δ 1.35 (3H, t, J=7.1 Hz), 2.63 (3H, s), 4.37 (2H, q, J=7.1 Hz), 7.59 (1H, d, J=9.4 Hz), 8.25 (1H, d, J=9.4 Hz).

(ii) Production of 6-chloro-2-methylimidazo[1,2-b]pyridazine-3-carboxamide

A mixture of ethyl 6-chloro-2-methylimidazo[1,2-b]pyridazine-3-carboxylate (2.4 g, 10 mmol) produced in the above, 8N aqueous sodium hydroxide solution (2 mL) and methanol (50 mL) was stirred at 70° C. for 1.5 hr. To the reaction mixture was added 6N hydrochloric acid (2.6 mL), and the resulting precipitate was collected by filtration, washed with ethanol and dried. Thionyl chloride (3.7 mL, 50 mmol) and toluene (20 mL) were added to the obtained solid, and the mixture was stirred at 80° C. for 1.5 hr. The reaction mixture was concentrated under reduced pressure, toluene was added to the obtained residue, and the mixture was concentrated again under reduced pressure. A suspension of the obtained residue in tetrahydrofuran (20 mL) was added to 25% aqueous ammonia (20 mL), and the mixture was stirred at room temperature for 1 hr. The resulting precipitate was collected by filtration, washed with water and ethyl acetate and dried to give the title compound (1.0 g, 49%) as a colorless solid. The filtrate was extracted with a mixed solvent of ethyl acetate and tetrahydrofuran, and the collected organic layer was washed with saturated brine and dried over anhydrous sodium sulfate, and the insoluble material was filtered off. The filtrate was concentrated under reduced pressure to give the title compound (0.5 g, 23%) as a colorless solid.

$^1$H-NMR (DMSO-$d_6$, 300 MHz) δ 2.65 (3H, s), 7.55 (1H, d, J=9.4 Hz), 7.82 (1H, br s), 7.95 (1H, br s), 8.27 (1H, d, J=9.4 Hz).

(iii) Production of 6-chloro-2-methylimidazo[1,2-b]pyridazine-3-carbonitrile

To a mixture of 6-chloro-2-methylimidazo[1,2-b]pyridazine-3-carboxamide (1.5 g, 7.0 mmol) produced in the above, pyridine (1.7 mL, 21 mmol) and tetrahydrofuran (20 mL) was added dropwise under ice-cooling a solution of trifluoroacetic anhydride (1.5 mL, 11 mmol) in tetrahydrofuran (5 mL), and the mixture was stirred at room temperature for 2 hr. A saturated aqueous sodium bicarbonate solution was added to the reaction mixture, and the mixture was extracted with ethyl acetate. The collected organic layer was washed with saturated brine and dried over anhydrous magnesium sulfate, and the insoluble material was filtered off. The filtrate was concentrated under reduced pressure, the obtained residue was purified by silica gel column chromatography (ethyl acetate/hexane=50/50→100/0), and the obtained solution was concentrated under reduced pressure. The obtained residue was washed with diisopropyl ether to give the title compound (887 mg, 66%) as a colorless solid.

$^1$H-NMR (DMSO-$d_6$, 300 MHz) δ 2.54 (3H, s), 7.68 (1H, d, J=9.6 Hz), 8.34 (1H, d, J=9.6 Hz).

(iv) Production of 6-chloro-2-methylimidazo[1,2-b]pyridazine-3-carbothioamide

A mixture of 6-chloro-2-methylimidazo[1,2-b]pyridazine-3-carbonitrile (830 mg, 4.3 mmol) produced in the above, O,O'-diethyl dithiophosphate (1.0 mL, 5.2 mmol), 4N hydrogen chloride ethyl acetate solution (10 mL) and methanol (10 mL) was stirred at 60° C. for 1 day. To the reaction mixture was added saturated aqueous sodium bicarbonate solution, and the resulting precipitate was collected by filtration, washed with water and diethyl ether and dried to give the title compound (766 mg, 79%) as a yellow solid.

$^1$H-NMR (DMSO-$d_6$, 300 MHz) δ 2.70 (3H, s), 7.53 (1H, d, J=9.4 Hz), 8.25 (1H, d, J=9.4 Hz), 9.55 (1H, br s), 10.13 (1H, br s).

(v) Production of ethyl 2-(6-chloro-2-methylimidazo[1,2-b]pyridazin-3-yl)-4-phenyl-1,3-thiazole-5-carboxylate A mixture of 6-chloro-2-methylimidazo[1,2-b]pyridazine-3-carbothioamide (725 mg, 3.2 mmol) produced in the above, ethyl 2-bromo-3-oxo-3-phenylpropanoate (868 mg, 3.2 mmol) and ethanol (20 mL) was stirred at 80° C. for 5 hr. To the reaction mixture were added saturated aqueous sodium bicarbonate solution, ethyl acetate and tetrahydrofuran, and the insoluble material was filtered off. The filtrate was extracted with a mixed solvent of ethyl acetate and tetrahydrofuran. The collected organic layer was washed with saturated brine and dried over anhydrous sodium sulfate, and the insoluble material was filtered off. The filtrate was concentrated under reduced pressure, the obtained residue was purified by silica gel column chromatography (methanol/ethyl acetate=0/100→100/0), and the obtained solution was concentrated under reduced pressure. The obtained residue was washed with ethyl acetate/diisopropyl ether to give the title compound (564 mg, 44%) as a yellow solid.

$^1$H-NMR (DMSO-$d_6$, 300 MHz) δ 1.26 (3H, t, J=7.2 Hz), 2.86 (3H, s), 4.29 (2H, q, J=7.2 Hz), 7.45-7.55 (3H, m), 7.64 (1H, d, J=9.4 Hz), 7.80-7.90 (2H, m), 8.37 (1H, d, J=9.3 Hz).

(vi) Production of 2-(6-chloro-2-methylimidazo[1,2-b]pyridazin-3-yl)-4-phenyl-1,3-thiazole-5-carboxamide hydrochloride A mixture of ethyl 2-(6-chloro-2-methylimidazo[1,2-b]pyridazin-3-yl)-4-phenyl-1,3-thiazole-5-carboxylate (520 mg, 1.3 mmol) produced in the above, 1N aqueous sodium hydroxide solution (1.6 mL), ethanol (5 mL) and tetrahydrofuran (10 mL) was stirred at 50° C. for 3 hr. To the reaction mixture were added 1N hydrochloric acid (1.6 mL) and water, and the resulting precipitate was collected by filtration, washed with water and diethyl ether and dried. Ammonium chloride (346 mg, 6.5 mmol), triethylamine (0.9 mL, 6.5 mmol), N-[3-(dimethylamino)propyl]-N'-ethylcarbodiimide hydrochloride (383 mg, 2.0 mmol), 1-hydroxybenzotriazole (270 mg, 2.0 mmol) and N,N-dimethylformamide (10 mL) were added to the obtained 2-(6-chloro-2-methylimidazo[1,2-b]pyridazin-3-yl-4-phenyl-1,3-thiazole-5-carboxylic acid (408 mg), and the mixture was stirred at room temperature for 3 days. The reaction mixture was concentrated under reduced pressure, water and ethyl acetate were added to the obtained residue, and the resulting precipitate was collected by filtration, washed with water and ethyl acetate and dried. 4N Hydrogen chloride ethyl acetate solution (0.5 mL) and methanol (10 mL) were added to the obtained crude product (379 mg), and the mixture was heated, and concentrated under reduced pressure. The obtained residue was washed with methanol to give the title compound (294 mg, 56%) as a yellow solid.

$^1$H-NMR (DMSO-$d_6$, 300 MHz) δ 2.91 (3H, s), 7.40-7.56 (3H, m), 7.61 (1H, d, J=9.4 Hz), 7.72-8.00 (4H, m), 8.36 (1H, d, J=9.4 Hz), (vii) Production of 2-(2-methylimidazo[1,2-b]pyridazin-3-yl)-4-phenyl-1,3-thiazole-5-carboxamide To a solution of 2-(6-chloro-2-methylimidazo[1,2-b]pyridazin-3-yl)-4-phenyl-1,3-thiazole-5-carboxamide hydrochloride (162 mg, 0.40 mmol) produced in the above and triethylamine (0.28 mL, 2 mmol) in N,N-dimethylformamide (30 mL) was added 10% palladium-carbon (50% wet with water, 50 mg). Under a hydrogen atmosphere (1 atm), the mixture was stirred at room temperature for 1 day, and 10% palladium-carbon was filtered off. The filtrate was concentrated under reduced pressure, and the obtained residue was washed with water and ethyl acetate to give the title compound (144 mg, quantitative) as a gray solid.

$^1$H-NMR (DMSO-$d_6$, 300 MHz) δ 2.92 (3H, s), 7.39-7.55 (4H, m), 7.69-7.94 (4H, m), 8.29 (1H, dd, J=1.5, 9.1 Hz), 8.86 (1H, dd, J=1.6, 4.6 Hz), (viii) Production of 2-methyl-3-[4-phenyl-5-(4H-1,2,4-triazol-3-yl)-1,3-thiazol-2-yl]imidazo[1,2-b]pyridazine A mixture of 2-(2-methylimidazo[1,2-b]pyridazin-3-yl)-4-phenyl-1,3-thiazole-5-carboxamide (124 mg, 0.37 mmol) produced in the above and N,N-dimethylformamide dimethyl acetal (10 mL) was stirred at 120° C. for 4 hr. The reaction mixture was concentrated under reduced pressure, and the obtained residue was washed with ethyl acetate/diethyl ether. Hydrazine monohydrate (0.18 mL, 3.7 mmol) and acetic acid (10 mL) were added to the obtained solid, and the mixture was stirred at 100° C. for 2 hr. The reaction mixture was concentrated under reduced pressure, and water and saturated aqueous sodium bicarbonate solution were added to the obtained residue. The resulting precipitate was collected by filtration, washed with water and ethyl acetate and dried. The obtained crude product was purified by silica gel column chromatography (methanol/ethyl acetate=20/80→100/0), and the obtained solution was concentrated under reduced pressure. Water was added to the obtained residue, and the precipitate was collected by filtration, washed with water, ethanol and ethyl acetate and dried to give the title compound (93 mg, 71%) as a yellow solid.

$^1$H-NMR (DMSO-$d_6$, 300 MHz) δ 2.94 (3H, s), 7.36-7.51 (4H, m), 7.92-8.00 (2H, m), 8.29 (1H, dd, J=1.6, 9.2 Hz), 8.61 (1H, br s), 8.86 (1H, dd, J=1.6, 4.6 Hz), 14.31 (1H, br s).

Example 42-B

Production of 6-methyl-5-[4-phenyl-5-(4H-1,2,4-triazol-3-yl)-1,3-thiazol-2-yl]imidazo[2,1-b][1,3]thiazole p-toluenesulfonate

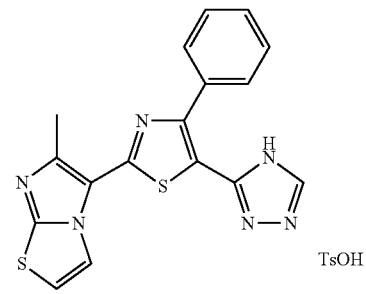

(i) Production of ethyl 6-methylimidazo[2,1-b][1,3]thiazole-5-carboxylate

A mixture of 1,3-thiazol-2-amine (10 g, 100 mmol), ethyl 2-chloro-3-oxobutanoate (16 g, 100 mmol) and ethanol (100 mL) was stirred at 80° C. for 1 day. The reaction mixture was concentrated under reduced pressure, saturated aqueous sodium bicarbonate solution was added to the obtained residue, and the mixture was extracted with ethyl acetate. The collected organic layer was washed with saturated brine and dried over anhydrous magnesium sulfate. The insoluble material was filtered off, and the filtrate was concentrated under reduced pressure. The obtained residue was purified by silica gel column chromatography (ethyl acetate/hexane=20/

80→350/50) and washed with diisopropyl ether to give the title compound (5.5 g, 26%) as a colorless solid.

$^1$H-NMR (DMSO-$d_6$, 300 MHz) δ 1.34 (3H, t, J=7.2 Hz), 2.51 (3H, s), 4.33 (2H, q, J=7.2 Hz), 7.44 (1H, d, J=4.3 Hz), 8.08 (1H, d, J=4.3 Hz).

(ii) Production of
6-methylimidazo[2,1-b][1,3]thiazole-5-carboxamide

A mixture of ethyl 6-methylimidazo[2,1-b][1,3]thiazole-5-carboxylate (2.1 g, 10 mmol) produced in the above, 8N aqueous sodium hydroxide solution (2 mL) and methanol (10 mL) was stirred at room temperature for 1 day. To the reaction mixture was added 6N hydrochloric acid (2.6 mL), and the mixture was concentrated under reduced pressure. Toluene was added to the obtained residue, and the mixture was concentrated again under reduced pressure. Thionyl chloride (3.7 mL, 50 mmol) and toluene (30 mL) were added to the obtained solid, and the mixture was stirred at 100° C. for 1 day. The reaction mixture was concentrated under reduced pressure, toluene was added to the obtained residue, and the mixture was concentrated again under reduced pressure. To a suspension of the obtained residue in tetrahydrofuran (20 mL) was added 25% aqueous ammonia (10 mL), and the mixture was stirred at room temperature for 2 hr. The reaction mixture was concentrated under reduced pressure, tetrahydrofuran was added to the obtained residue, and the insoluble material was filtered off. The filtrate was concentrated under reduced pressure, and the obtained residue was purified by silica gel column chromatography (methanol/ethyl acetate=0/100→20/80). The obtained solution was concentrated under reduced pressure to give the title compound (588 mg, 32%) as a brown solid.

$^1$H-NMR (DMSO-$d_6$, 300 MHz) δ 2.48 (3H, s), 7.24 (2H, br s), 7.31 (1H, d, J=4.3 Hz), 8.11 (1H, d, J=4.3 Hz).

(iii) Production of
6-methylimidazo[2,1-b][1,3]thiazole-5-carbonitrile

To a mixture of 6-methylimidazo[2,1-b][1,3]thiazole-5-carboxamide (544 mg, 3.0 mmol) produced in the above, pyridine (0.7 mL, 9.0 mmol) and tetrahydrofuran (10 mL) was added dropwise under ice-cooling trifluoroacetic anhydride (0.6 mL, 4.5 mmol). After stirring at room temperature for 1 day, saturated aqueous sodium bicarbonate solution was added, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=30/70→50/50). The obtained solution was concentrated under reduced pressure to give the title compound (433 mg, 86%) as a pale-brown solid.

$^1$H-NMR (DMSO-$d_6$, 300 MHz) δ 2.40 (3H, s), 7.51 (1H, d, J=4.5 Hz), 8.17 (1H, d, J=4.5 Hz).

(iv) Production of ethyl 2-(6-methylimidazo[2,1-b][1,3]thiazol-5-yl)-4-phenyl-1,3-thiazole-5-carboxylate A mixture of 6-methyl imidazo[2,1-b][1,3]thiazole-5-carbonitrile (408 mg, 2.5 mmol) produced in the above, O,O'-diethyl dithiophosphate (0.6 mL, 3.0 mmol), 4N hydrogen chloride ethyl acetate solution (5 mL) and methanol (5 mL) was stirred at 50° C. for 2 hr. To the reaction mixture was added saturated aqueous sodium bicarbonate solution, and the resulting precipitate was collected by filtration, washed with water and diethyl ether and dried. To the obtained crude product of 6-methylimidazo[2,1-b][1,3]thiazole-5-carbothioamide were added ethyl 2-bromo-3-oxo-3-phenylpropanoate (542 mg, 2.0 mmol) and ethanol (10 mL), and the mixture was stirred at 80° C. for 2 hr. The reaction mixture was concentrated under reduced pressure, saturated aqueous sodium bicarbonate solution was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, the obtained residue was washed with ethyl acetate/diisopropyl ether, and the filtrate was concentrated under reduced pressure. The obtained residue was purified by silica gel column chromatography (ethyl acetate/hexane=50/50→100/0). The obtained solution was concentrated under reduced pressure to give the title compound (115 mg, 12%) as a colorless solid.

$^1$H-NMR (DMSO-$d_6$, 300 MHz) δ 1.24 (3H, t, J=7.1 Hz), 2.59 (3H, s), 4.26 (2H, q, J=7.2 Hz), 7.46-7.53 (4H, m), 7.81-7.89 (2H, m), 8.45 (1H, d, J=4.5 Hz).

(v) Production of 2-(6-methylimidazo[2,1-b][1,3]thiazol-5-yl)-4-phenyl-1,3-thiazole-5-carboxylic acid A mixture of ethyl 2-(6-methylimidazo[2,1-b][1,3]thiazol-5-yl)-4-phenyl-1,3-thiazole-5-carboxylate (111 mg, 0.30 mmol) produced in the above, 1N aqueous sodium hydroxide solution (1 mL), methanol (5 mL) and tetrahydrofuran (5 mL) was stirred at room temperature for 1 day. The reaction mixture was concentrated under reduced pressure, and water and 1N hydrochloric acid (1 mL) were added. The resulting precipitate was collected by filtration, washed with water and diethyl ether and dried to give the title compound (80 mg, 78%) as a pale-brown solid.

$^1$H-NMR (DMSO-$d_6$, 300 MHz) δ 2.59 (3H, s), 7.44-7.53 (4H, m), 7.82-7.90 (2H, m), 8.45 (1H, d, J=4.5 Hz), 13.39 (1H, br s).

(vi) Production of 2-(6-methylimidazo[2,1-b][1,3]thiazol-5-yl)-4-phenyl-1,3-thiazole-5-carboxamide A mixture of 2-(6-methylimidazo[2,1-b][1,3]thiazol-5-yl)-4-phenyl-1,3-thiazole-5-carboxylic acid (60 mg, 0.18 mmol) produced in the above, ammonium chloride (53 mg, 1.0 mmol), triethylamine (0.14 mL, 1.0 mmol), N-[3-(dimethylamino)propyl]-N'-ethylcarbodiimide hydrochloride (77 mg, 0.4 mmol), 1-hydroxybenzotriazole (54 mg, 0.4 mmol) and N,N-dimethylformamide (5 mL) was stirred at room temperature for 3 days. The reaction mixture was concentrated under reduced pressure, and water and diethyl ether were added to the obtained residue. The resulting precipitate was collected by filtration, washed with water and diethyl ether and dried to give the title compound (56 mg, 94%) as a colorless solid.

$^1$H-NMR (DMSO-$d_6$, 300 MHz) δ 2.58 (3H, s), 7.41-7.55 (4H, m), 7.75 (2H, s), 7.82-7.90 (2H, m), 8.49 (1H, d, J=4.3 Hz).

(vii) Production of 6-methyl-5-[4-phenyl-5-(4H-1,2,4-triazol-3-yl)-1,3-thiazol-2-yl]imidazo[2,1-b][1,3]thiazole p-toluenesulfonate A mixture of 2-(6-methylimidazo[2,1-b][1,3]thiazol-5-yl)-4-phenyl-1,3-thiazole-5-carboxamide (150 mg, 0.44 mmol) produced in the above and N,N-dimethylformamide dimethyl acetal (10 mL) was stirred at 100° C. for 3 hr. The reaction mixture was concentrated under reduced pressure, and the obtained residue was washed with diethyl ether. Hydrazine monohydrate (0.22 mL, 4.4 mmol) and acetic acid (10 mL) were added to the obtained solid, and the mixture was stirred at 100° C. for 2 hr. The reaction mixture was concentrated under reduced pressure, saturated aqueous sodium bicarbonate solution and diethyl ether were added to the obtained residue, and the mixture was stirred. The resulting precipitate was collected by filtration, washed with water and diethyl ether and dried to give 6-methyl-5-[4-phenyl-5-(4H-1,2,4-triazol-3-yl)-1,3-thiazol-2-yl]imidazo[2,1-b][1,3]thiazole (123 mg, 77%) as a pale-yellow solid.

A mixture of 6-methyl-5-[4-phenyl-5-(4H-1,2,4-triazol-3-yl)-1,3-thiazol-2-yl]imidazo[2,1-b][1,3]thiazole (51 mg, 0.14 mmol) produced in the above, p-toluenesulfonic acid monohydrate (32 mg, 0.17 mmol) and ethanol (40 mL) was dissolved by heating and concentrated under reduced pressure. The obtained residue was crystallized from ethanol to give the title compound (72 mg, 96%) as a pale-pink solid.

$^1$H-NMR (DMSO-$d_6$, 300 MHz) δ 2.29 (3H, s), 2.63 (3H, s), 7.11 (2H, d, J=7.9 Hz), 7.38-7.51 (5H, m), 7.53 (1H, d, J=4.5 Hz), 7.87-7.95 (2H, m), 8.55 (1H, d, J=4.3 Hz), 8.65 (1H, s).

Example 43-B

Production of 4-[4-phenyl-5-(4H-1,2,4-triazol-3-yl)-1,3-thiazol-2-yl]-1H-pyrrolo[2,3-b]pyridine p-toluenesulfonate

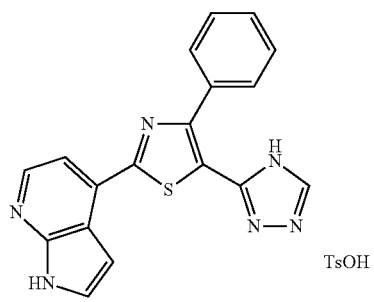

(i) Production of 1H-pyrrolo[2,3-b]pyridine-4-carbonitrile

A mixture of 4-chloro-1H-pyrrolo[2,3-b]pyridine (3.1 g, 20 mmol), zinc cyanide (1.4 g, 12 mmol), zinc (130 mg, 2.0 mmol), tris(dibenzylideneacetone)dipalladium(0) (370 mg, 0.40 mmol), 1,1'-bis(diphenylphosphino)ferrocene (440 mg, 0.80 mmol) and N,N-dimethylacetamide (20 mL) was stirred at 120° C. for 1.5 hr under an argon atmosphere. The reaction mixture was purified by silica gel column chromatography (ethyl acetate/hexane=20/80→100/0), and the obtained solution was concentrated under reduced pressure. The obtained residue was washed with diisopropyl ether to give the title compound (2.60 g, 91%) as a red-brown solid.

$^1$H-NMR (DMSO-$d_6$, 300 MHz) δ 6.65 (1H, dd, J=1.7, 3.4 Hz), 7.56 (1H, d, J=4.9 Hz), 7.81-7.87 (1H, m), 8.41 (1H, d, J=4.9 Hz), 12.38 (1H, br s).

(ii) Production of 1H-pyrrolo[2,3-b]pyridine-4-carbothioamide

A mixture of 1H-pyrrolo[2,3-b]pyridine-4-carbonitrile (1.0 g, 7.0 mmol) produced in the above, O,O'-diethyl dithiophosphate (1.6 mL, 8.4 mmol), 4N hydrogen chloride ethyl acetate solution (15 mL) and methanol (15 mL) was stirred at 50° C. for 3.5 hr and at 60° C. for 4.5 hr. Saturated aqueous sodium bicarbonate solution was added to the reaction mixture, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with diisopropyl ether to give the title compound (751 mg, 61%) as a yellow solid.

$^1$H-NMR (DMSO-$d_6$, 300 MHz) δ 6.67 (1H, dd, J=1.7, 3.4 Hz), 7.18 (1H, d, J=5.1 Hz), 7.55 (1H, dd, J=2.5, 3.2 Hz), 8.24 (1H, d, J=4.9 Hz), 9.58 (1H, br s), 10.11 (1H, br s), 11.82 (1H, br s).

(iii) Production of 4-phenyl-2-(1H-pyrrolo[2,3-b]pyridin-4-yl)-1,3-thiazole-5-carboxylic acid A mixture of 1H-pyrrolo[2,3-b]pyridine-4-carbothioamide (710 mg, 4.0 mmol) produced in the above, ethyl 2-bromo-3-oxo-3-phenylpropanoate (1.2 g, 4.4 mmol) and ethanol (20 mL) was stirred at 80° C. for 1 day. Saturated aqueous sodium bicarbonate solution and water were added to the reaction mixture, and the resulting precipitate was collected by filtration, washed with water and diethyl ether and dried. 1N Aqueous sodium hydroxide solution (4.5 mL), methanol (10 mL) and tetrahydrofuran (10 mL) were added to the obtained solid, and the mixture was stirred at 60° C. for 2 hr. Water was added to the reaction mixture, the insoluble material was filtered off, and 1N hydrochloric acid (4.5 mL) was added to the filtrate. The resulting precipitate was collected by filtration, washed with water and diethyl ether and dried to give the title compound (678 mg, 53%) as a yellow solid.

$^1$H-NMR (DMSO-$d_6$, 300 MHz) δ 7.08 (1H, dd, J=1.9, 3.4 Hz), 7.44-7.56 (3H, m), 7.70-7.76 (2H, m), 7.84-7.93 (2H, m), 8.38 (1H, d, J=4.9 Hz), 12.09 (1H, br s), 13.59 (1H, br s).

(iv) Production of 4-phenyl-2-(1H-pyrrolo[2,3-b]pyridin-4-yl)-1,3-thiazole-5-carboxamide A mixture of 4-phenyl-2-(1H-pyrrolo[2,3-b]pyridin-4-yl)-1,3-thiazole-5-carboxylic acid (640 mg, 2.0 mmol) produced in the above, ammonium chloride (320 mg, 6.0 mmol), triethylamine (0.84 mL, 6.0 mmol), N-[3-(dimethylamino)propyl]-N'-ethylcarbodiimide hydrochloride (580 mg, 3.0 mmol), 1-hydroxybenzotriazole (410 mg, 3.0 mmol) and N,N-dimethylformamide (20 mL) was stirred at room temperature for 6 hr. The reaction mixture was concentrated under reduced pressure, and water, ethyl acetate and diethyl ether were added to the obtained residue. The resulting precipitate was collected by filtration, washed with water and diethyl ether and dried to give the title compound (507 mg, 79%) as a yellow solid.

$^1$H-NMR (DMSO-$d_6$, 300 MHz) δ 7.11 (1H, dd, J=1.9, 3.4 Hz), 7.38-7.58 (3H, m), 7.69 (1H, d, J=5.1 Hz), 7.71-7.76 (1H, m), 7.81-8.09 (4H, m), 8.38 (1H, d, J=5.1 Hz), 12.07 (1H, br s).

(v) Production of 4-[4-phenyl-5-(4H-1,2,4-triazol-3-yl)-1,3-thiazol-2-yl]-1H-pyrrolo[2,3-b]pyridine A mixture of 4-phenyl-2-(1H-pyrrolo[2,3-b]pyridin-4-yl)-1,3-thiazole-5-carboxamide (320 mg, 1.0 mmol) produced in the above and N,N-dimethylformamide dimethyl acetal (20 mL) was stirred at 100° C. for 1 day. The reaction mixture was concentrated under reduced pressure, hydrazine monohydrate (0.49 mL, 10 mmol) and acetic acid (10 mL) were added to the obtained residue, and the mixture was stirred at 100° C. for 2 hr. The reaction mixture was concentrated under reduced pressure, saturated aqueous sodium bicarbonate solution was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, the obtained residue was purified by silica gel column chromatography (methanol/ethyl acetate=0/100→100/0), and the obtained solution was concentrated under reduced pressure. The obtained residue was washed with ethyl acetate/diisopropyl ether to give the title compound (244 mg, 71%) as a yellow solid.

$^1$H-NMR (DMSO-$d_6$, 300 MHz) δ 7.13 (1H, dd, J=1.9, 3.4 Hz), 7.39-7.52 (3H, m), 7.68-7.75 (2H, m), 7.85-8.01 (2H, m), 8.38 (1H, d, J=5.1 Hz), 8.71 (1H, br s), 12.04 (1H, br s), 14.38 (1H, br s).

(vi) Production of 4-[4-phenyl-5-(4H-1,2,4-triazol-3-yl)-1,3-thiazol-2-yl]-1H-pyrrolo[2,3-b]pyridine p-toluenesulfonate A mixture of 4-[4-phenyl-5-(4H-1,2,4-triazol-3-yl)-1,3-thiazol-2-yl]-1H-pyrrolo[2,3-b]pyridine (69 mg, 0.20 mmol) produced in the above, p-toluenesulfonic acid monohydrate (46 mg, 0.24 mmol) and ethanol (5 mL) was dissolved by heating, and the mixture was concentrated under reduced pressure. The obtained residue was crystallized from ethanol and ethyl acetate to give the title compound (88 mg, 85%) as a yellow solid.

$^1$H-NMR (DMSO-$d_6$, 300 MHz) δ 2.29 (3H, s), 7.11 (2H, d, J=7.7 Hz), 7.15 (1H, dd, J=1.9, 3.4 Hz), 7.39-7.52 (5H, m), 7.71-7.77 (2H, m), 7.88-7.95 (2H, m), 8.39 (1H, d, J=5.3 Hz), 8.68 (1H, s), 12.11 (1H, br s).

Example 44-B

Production of 7-[4-phenyl-5-(4H-1,2,4-triazol-3-yl)-1,3-thiazol-2-yl]thieno[3,2-b]pyridine p-toluenesulfonate

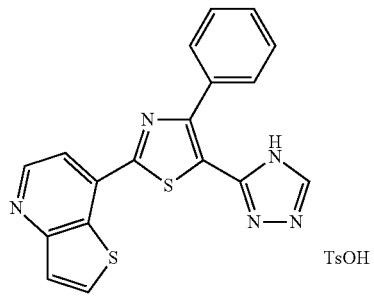

(i) Production of 7-chlorothieno[3,2-b]pyridine

A mixture of thieno[3,2-b]pyridin-7-ol (3.8 g, 25 mmol) and phosphorus oxychloride (18 g, 120 mmol) was stirred at 105° C. for 2 hr. The reaction mixture was added to ice water, and basified with 8N aqueous sodium hydroxide solution. Ethyl acetate was added, the insoluble material was filtered off, and the filtrate was extracted with ethyl acetate. The collected organic layer was washed with saturated brine and dried over anhydrous magnesium sulfate, and the insoluble material was filtered off. The filtrate was concentrated under reduced pressure, the obtained residue was purified by silica gel column chromatography (ethyl acetate/hexane=10/90→30/70), and the obtained solution was concentrated under reduced pressure to give the title compound (2.8 g, 66%) as a pale-yellow solid.

$^1$H-NMR (DMSO-$d_6$, 300 MHz) δ 7.59 (1H, d, J=5.1 Hz), 7.69 (1H, d, J=5.5 Hz), 8.28 (1H, d, J=5.5 Hz), 8.67 (1H, d, J=5.1 Hz), (ii) Production of thieno[3,2-b]pyridine-7-carbonitrile A mixture of 7-chlorothieno[3,2-b]pyridine (1.7 g, 10 mmol) produced in the above, zinc cyanide (0.71 g, 6.0 mmol), zinc (65 mg, 1.0 mmol), tris(dibenzylideneacetone)dipalladium(0) (180 mg, 0.20 mmol), 1,1'-bis(diphenylphosphino)ferrocene (220 mg, 0.40 mmol) and N,N-dimethylacetamide (10 mL) was stirred at 120° C. for 2 hr under an argon atmosphere. The reaction mixture was purified by silica gel column chromatography (ethyl acetate/hexane=5195→50/50), and the obtained solution was concentrated under reduced pressure. The obtained residue was washed with hexane to give the title compound (1.1 g, 72%) as a colorless solid.

$^1$H-NMR (DMSO-$d_6$, 300 MHz) δ 7.77 (1H, d, J=5.5 Hz), 7.95 (1H, d, J=4.7 Hz), 8.40 (1H, d, J=5.5 Hz), 8.91 (1H, d, J=4.7 Hz).

(iii) Production of thieno[3,2-b]pyridine-7-carbothioamide

A mixture of thieno[3,2-b]pyridine-7-carbonitrile (800 mg, 5.0 mmol) produced in the above, O,O'-diethyl dithiophosphate (1.4 mL, 7.5 mmol), 4N hydrogen chloride ethyl acetate solution (10 mL) and methanol (2 mL) was stirred at room temperature for 15 min and at 50° C. for 2 hr. Saturated aqueous sodium bicarbonate solution was added to the reaction mixture, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with diisopropyl ether to give the title compound (715 mg, 74%) as a yellow solid.

$^1$H-NMR (DMSO-$d_6$, 300 MHz) δ 7.49 (1H, d, J=4.9 Hz), 7.59 (1H, d, J=5.7 Hz), 8.20 (1H, d, J=5.7 Hz), 8.77 (1H, d, J=4.9 Hz), 9.92 (1H, br s), 10.34 (1H, br s), (iv) Production of ethyl 4-phenyl-2-thieno[3,2-b]pyridin-7-yl-1,3-thiazole-5-carboxylate A mixture of thieno[3,2-b]pyridine-7-carbothioamide (680 mg, 3.5 mmol) produced in the above, ethyl 2-bromo-3-oxo-3-phenylpropanoate (950 mg, 3.5 mmol) and ethanol (10 mL) was stirred at 80° C. for 2 hr. Saturated aqueous sodium bicarbonate solution and ethyl acetate were added to the reaction mixture, the insoluble material was filtered off, and the filtrate was extracted with ethyl acetate. The collected organic layer was washed with saturated magnesium sulfate, and the insoluble material was filtered off. The filtrate was concentrated under reduced pressure, the obtained residue was purified by silica gel column chromatography (ethyl acetate/hexane=20/80→100/0), and the obtained solution was concentrated under reduced pressure. The obtained residue was washed with ethyl acetate/hexane to give the title compound (510 mg, 40%) as a colorless solid.

$^1$H-NMR (DMSO-d$_6$, 300 MHz) δ 1.28 (3H, t, J=7.1 Hz), 4.32 (2H, q, J=7.1 Hz), 7.51-7.60 (3H, m), 7.69 (1H, d, J=5.7 Hz), 7.92-8.02 (2H, m), 8.06 (1H, d, J=4.9 Hz), 8.30 (1H, dd, J=0.4, 5.7 Hz), 8.87 (1H, d, J=4.9 Hz).

(v) Production of 4-phenyl-2-thieno[3,2-b]pyridin-7-yl-1,3-thiazole-5-carboxylic acid A mixture of ethyl 4-phenyl-2-thieno[3,2-b]pyridin-7-yl-1,3-thiazole-5-carboxylate (480 mg, 1.3 mmol) produced in the above, 1N aqueous sodium hydroxide solution (3 mL), methanol (5 mL) and tetrahydrofuran (5 mL) was stirred at 60° C. for 1 hr. The reaction mixture was concentrated under reduced pressure to about half volume, and 1N hydrochloric acid (3 mL) was added. The resulting precipitate was collected by filtration, washed with water and diethyl ether and dried to give the title compound (433 mg, 98%) as a pale yellow-white solid.

$^1$H-NMR (DMSO-d$_6$, 300 MHz) δ 7.47-7.59 (3H, m), 7.68 (1H, d, J=5.7 Hz), 7.94-8.06 (3H, m), 8.29 (1H, d, J=5.7 Hz), 8.86 (1H, d, J=4.9 Hz), 13.81 (1H, br s).

(vi) Production of 4-phenyl-2-thieno[3,2-b]pyridin-7-yl-1,3-thiazole-5-carboxamide A mixture of 4-phenyl-2-thieno[3,2-b]pyridin-7-yl-1,3-thiazole-5-carboxylic acid (380 mg, 1.1 mmol) produced in the above, ammonium chloride (180 mg, 3.4 mmol), triethylamine (0.5 mL, 3.4 mmol), N-[3-(dimethylamino)propyl]-N'-ethylcarbodiimide hydrochloride (330 mg, 1.7 mmol), 1-hydroxybenzotriazole (230 mg, 1.7 mmol) and N,N-dimethylformamide (10 mL) was stirred at room temperature for 1 day. The reaction mixture was concentrated under reduced pressure, and water was added to the obtained residue. The resulting precipitate was collected by filtration, washed with water and diethyl ether and dried to give the title compound (348 mg, 91%) as a colorless solid.

$^1$H-NMR (DMSO-d$_6$, 300 MHz) δ 7.45-7.60 (3H, m), 7.69 (1H, d, J=5.7 Hz), 7.94-8.03 (4H, m), 8.17 (1H, br s), 8.31 (1H, d, J=5.7 Hz), 8.86 (1H, d, J=4.9 Hz).

(vii) Production of 7-[4-phenyl-5-(4H-1,2,4-triazol-3-yl)-1,3-thiazol-2-yl]thieno[3,2-b]pyridine p-toluenesulfonate A mixture of 4-phenyl-2-thieno[3,2-b]pyridin-7-yl-1,3-thiazole-5-carboxamide (300 mg, 0.90 mmol) produced in the above and N,N-dimethylformamide dimethyl acetal (10 mL) was stirred at 100° C. for 2 hr. The reaction mixture was concentrated under reduced pressure, and the obtained residue was washed with diethyl ether. Hydrazine monohydrate (0.4 mL, 9.0 mmol) and acetic acid (10 mL) were added to the obtained solid, and the mixture was stirred at 100° C. for 1 hr. The reaction mixture was concentrated under reduced pressure, and saturated aqueous sodium bicarbonate solution and diethyl ether were added to the obtained residue. The resulting precipitate was collected by filtration, washed with water and diethyl ether and dried to give 7-[4-phenyl-5-(4H-1,2,4-triazol-3-yl)-1,3-thiazol-2-yl]thieno[3,2-b]pyridine (301 mg, 93%) as a pale-yellow solid.

A mixture of 7-[4-phenyl-5-(4H-1,2,4-triazol-3-yl)-1,3-thiazol-2-yl]thieno[3,2-b]pyridine (110 mg, 0.30 mmol) produced in the above, p-toluenesulfonic acid monohydrate (68 mg, 0.36 mmol) and ethanol (25 mL) was dissolved by heating, and the mixture was concentrated under reduced pressure. The obtained residue was crystallized from ethanol to give the title compound (132 mg, 82%) as a yellow solid.

$^1$H-NMR (DMSO-d$_6$, 300 MHz) δ 2.29 (3H, s), 7.11 (2H, d, J=7.9 Hz), 7.42-7.55 (5H, m), 7.71 (1H, d, J=5.7 Hz), 8.00-8.10 (3H, m), 8.37 (1H, d, J=5.7 Hz), 8.74 (1H, s), 8.90 (1H, d, J=5.1 Hz).

Example 45-B

Production of 3-[2-(1-ethyl-3-methyl-1H-pyrazol-4-yl)-4-phenyl-1,3-thiazol-5-yl]-4H-1,2,4-triazole

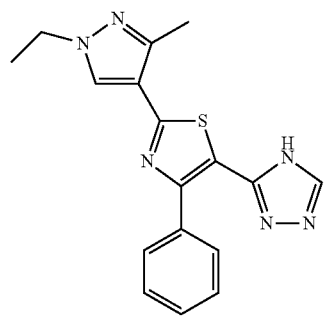 [SMILES: CCn1cc(-c2nc(-c3ccccc3)c(-c3nnc[nH]3)s2)c(C)n1]

(1) Production of 1-ethyl-3-methyl-1H-pyrazole-4-carboxamide

To a suspension of 1-ethyl-3-methyl-1H-pyrazole-4-carboxylic acid (2.0 g, 13 mmol) in toluene (50 mL) was added thionyl chloride (5 mL, 69 mmol), and the mixture was heated under reflux for 2 hr. The solvent was evaporated, and the obtained residue was dissolved in tetrahydrofuran (30 mL). 25% Aqueous ammonia (15 mL) was added, and the mixture was stirred for 30 min. Ethyl acetate (100 mL) was added to the reaction solution, and the mixture was stirred for 30 min. The organic layer was washed with saturated brine and dried over anhydrous magnesium sulfate, and the insoluble material was filtered off. The filtrate was concentrated under reduced pressure, the obtained residue was purified by silica gel column chromatography (methanol/ethyl acetate=0/100→20/80), and the obtained solution was concentrated under reduced pressure. The residue was triturated with ethyl acetate/diisopropyl ether to give the title compound (1.7 g, 86%) as a colorless solid.

$^1$H-NMR (DMSO-d$_6$, 300 MHz) δ 1.34 (3H, t, J=7.4 Hz), 2.29 (3H, s), 4.03 (2H, q, 7.4 Hz), 6.82 (1H, s), 7.24 (1H, s), 8.09 (1H, s).

(ii) Production of 1-ethyl-3-methyl-1H-pyrazole-4-carbothioamide

To a suspension of 1-ethyl-3-methyl-1H-pyrazole-4-carboxamide (1.7 g, 11 mmol) produced in the above in toluene (80 mL) was added Lawesson's reagent (7.0 g, 17 mmol), and the mixture was heated under reflux for 1.5 hr. The reaction solution was cooled to room temperature and purified by basic silica gel column chromatography (ethyl acetate/hexane=0/100→20/80) to give the title compound (445 mg, 24%) as a yellow oil.

$^1$H-NMR (DMSO-d$_6$, 300 MHz) δ 1.27-1.38 (3H, m), 2.40 (3H, s), 3.97-4.08 (2H, m), 8.09 (1H, s), 8.69 (1H, s), 9.16 (1H, s).

(iii) Production of 2-(1-ethyl-3-methyl-1H-pyrazol-4-yl)-4-phenyl-1,3-thiazole-5-carboxylic acid A solution of 1-ethyl-3-methyl-1H-pyrazole-4-carbothioamide (230 mg, 1.3 mmol) produced in the above and ethyl 2-bromo-3-oxo-3-phenylpropanoate (1.7 g, 6.3 mmol) in 2-propanol (30 mL) was stirred at 80° C. for 2 hr. The reaction solution was cooled to room temperature, saturated aqueous sodium bicarbonate solution (100 mL) and ethyl acetate (100 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was dissolved in tetrahydrofuran (15 mL). Methanol (5 mL) and 1N aqueous sodium hydroxide solution (2.0 mL) were added, and the mixture was stirred at 70° C. for 1 hr. The reaction solution was cooled to 0° C., 1N hydrochloric acid (1.9 mL) was added, and the mixture was extracted with ethyl acetate (100 mL). The organic layer was washed with saturated brine and dried over anhydrous magnesium sulfate, and the insoluble material was filtered off. The filtrate was concentrated under reduced pressure, and the obtained residue was triturated with ethyl acetate and diisopropyl ether to give the title compound (190 mg, 46%) as a white solid.

$^1$H-NMR (DMSO-d$_6$, 300 MHz) δ 1.39 (3H, t, J=7.4 Hz), 2.45 (3H, s), 4.12 (2H, q, J=7.4 Hz), 7.35-7.50 (3H, m), 7.71-7.85 (2H, m), 8.42 (1H, s), 13.23 (1H, s).

(iv) Production of 2-(1-ethyl-3-methyl-1H-pyrazol-4-yl)-4-phenyl-1,3-thiazole-5-carboxamide To a suspension of 2-(1-ethyl-3-methyl-1H-pyrazol-4-yl)-4-phenyl-1,3-thiazole-5-carboxylic acid (160 mg, 13 mmol) produced in the above in toluene (25 mL) was added thionyl chloride (1.5 mL, 21 mmol), and the mixture was heated under reflux for 1 hr. The solvent was evaporated, and the obtained residue was dissolved in tetrahydrofuran (25 mL), 25% Aqueous ammonia (2.5 mL) was added, and the mixture was stirred for 30 min, Ethyl acetate (100 mL) was added to the reaction solution, and the mixture was stirred for 30 min. The organic layer was washed with saturated brine and dried over anhydrous magnesium sulfate, and the insoluble material was filtered off. The filtrate was concentrated under reduced pressure, and the obtained residue was washed with diisopropyl ether and dried to give the title compound (155 mg, 97%) as a white solid.

$^1$H-NMR (DMSO-d$_6$, 300 MHz) δ 1.35-1.45 (3H, m), 2.46 (3H, s), 4.12 (2H, q, J=7.4 Hz), 7.38-7.50 (3H, m), 7.61-7.73 (2H, m), 7.74-7.82 (2H, m), 8.37 (1H, s).

(v) Production of 3-[2-(1-ethyl-3-methyl-1H-pyrazol-4-yl)-4-phenyl-1,3-thiazol-5-yl]-4H-1,2,4-triazole A solution of 2-(1-ethyl-3-methyl-1H-pyrazol-4-yl)-4-phenyl-1,3-thiazole-5-carboxamide (130 mg, 0.41 mmol) produced in the above in N,N-dimethylformamide dimethyl acetal (20 mL) was stirred with heating at 100° C. for 1 hr. The reaction solution was cooled to room temperature, the solvent was evaporated, and the residue was washed with hexane (5 mL) and diethyl ether (2 mL). The obtained residue was dissolved in acetic acid (10 mL), hydrazine monohydrate (0.4 mL) was added, and the mixture was stirred with heating at 80° C. for 1 hr. The reaction solution was cooled to room temperature, saturated aqueous sodium bicarbonate solution (150 mL) and ethyl acetate (100 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was washed with ethyl acetate (2 mL) and diisopropyl ether (10 mL) to give the title compound (105 mg, 75%) as a white solid.

$^1$H-NMR (DMSO-d$_6$, 300 MHz) δ 1.40 (3H, t, J=7.3 Hz), 2.48 (3H, s), 4.13 (2H, q, J=7.3 Hz), 7.33-7.46 (3H, m), 7.78-7.86 (2H, m), 8.38 (1H, s), 8.57 (1H, s).

Example 46-B

Production of 2-methyl-3-{4-[(1E)-prop-1-en-1-yl]-5-(4H-1,2,4-triazol-3-yl)-1,3-thiazol-2-yl}pyrazolo[1,5-a]pyridine

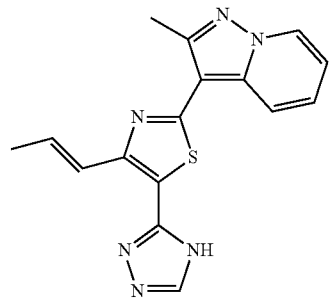 [SMILES: C/C=C/c1nc(-c2c(C)nn3ccccc23)sc1-c1nnc[nH]1]

(i) Production of methyl 2-(2-methylpyrazolo[1,5-a]pyridin-3-yl)-4-prop-2-en-1-yl-1,3-thiazole-5-carboxylate Using methyl 2-(2-methylpyrazolo[1,5-a]pyridin-3-yl)-4-{[(trifluoromethyl)sulfonyl]oxy}-1,3-thiazole-5-carboxylate (1.5 g, 3.6 mmol) produced in Example 13(ii), 4,4,5,5-tetramethyl-2-prop-2-en-1-yl-1,3,2-dioxaborolane (897 mg, 5.3 mmol), [1,1-bis(diphenylphosphino)ferrocene]palladium (H) dichloride dichloromethane complex (180 mg, 0.22 mmol), cesium carbonate (3.5 g, 11 mmol), 1,2-dimethoxyethane (50 mL) and water (3 mL) as starting materials and in the same manner as in Example 13-B (iii), the title compound (815 mg, 73%) was obtained as a yellow solid.

$^1$H-NMR (DMSO-d$_6$, 300 MHz) δ 2.68 (3H, s), 3.84 (3H, s) 3.93 (2H, dt, J=1.5, 6.6 Hz), 5.02-5.24 (2H, m), 5.99-6.21 (1H, m), 7.12 (1H, dt, J=1.3, 6.9 Hz), 7.59 (1H, ddd, J=1.1, 6.9, 8.9 Hz), 8.30-8.40 (1H, m), 8.71-8.84 (1H, m).

(ii) Production of 2-(2-methylpyrazolo[1,5-a]pyridin-3-yl)-4-[(1E)-prop-1-en-1-yl]-1,3-thiazole-5-carboxylic acid Using methyl 2-(2-methylpyrazolo[1,5-a]pyridin-3-yl)-4-prop-2-en-1-yl-1,3-thiazole-5-carboxylate (800 mg, 2.6 mmol) produced in the above, methanol (15 mL), tetrahydrofuran (15 mL) and 8N aqueous sodium hydroxide solution (1.5 mL) as starting materials and in the same manner as in Example 13-B (iv), the title compound (470 mg, 62%) was obtained as a white solid.

$^1$H-NMR (DMSO-d$_6$, 300 MHz) δ 1.98 (3H, dd, J=1.7, 6.8 Hz), 2.67 (3H, s), 6.97-7.36 (3H, m), 7.60 (1H, ddd, J=1.0, 6.8, 8.9 Hz), 8.34-8.48 (1H, m), 8.73-8.84 (1H, m).

(iii) Production of 2-(2-methylpyrazolo[1,5-a]pyridin-3-yl)-4-[(1E)-prop-1-en-1-yl]-1,3-thiazole-5-carboxamide Using 2-(2-methylpyrazolo[1,5-a]pyridin-3-yl)-4-[(1E)-prop-1-en-1-yl]-1,3-thiazole-5-carboxylic acid (400 mg, 1.3 mmol) produced in the above, ammonium chloride (2.0 g, 37 mmol), triethylamine (4.0 mL), 1-hydroxybenzotriazole (100 mg, 0.74 mmol) and N-[3-(dimethylamino)propyl]-N'-ethylcarbodiimide hydrochloride (750 mg, 3.9 mmol) and N,N-dimethylformamide (20 mL) as starting materials and in the same manner as in Example 13-B (v), the title compound (383 mg, 96%) was obtained as a white solid.
$^1$H-NMR (DMSO-d$_6$, 300 MHz) δ 1.95 (3H, dd, J=1.5, 6.8 Hz), 2.69 (3H, s), 6.85-7.00 (1H, m), 7.04-7.26 (2H, m), 7.42-7.73 (2H, m), 7.95 (1H, s), 8.33-8.42 (1H, m), 8.71-8.82 (1H, m).

(iv) Production of 2-methyl-3-{4-[(1E)-prop-1-en-1-yl]-5-(4H-1,2,4-triazol-3-yl)-1,3-thiazol-2-yl}pyrazolo[1,5-a]pyridine Using 2-(2-methylpyrazolo[1,5-a]pyridin-3-yl)-4-[(1E)-prop-1-en-1-yl]-1,3-thiazole-5-carboxamide (150 mg, 0.50 mmol) produced in the above, N,N-dimethylformamide dimethyl acetal (20 mL), acetic acid (20 mL) and hydrazine monohydrate (0.3 mL) as starting materials and in the same manner as in Example 13(vi), the title compound (78 mg, 48%) was obtained as a white solid.
$^1$H-NMR (DMSO-d$_6$, 300 MHz) δ 1.98 (3H, dd, J=1.7, 6.9 Hz), 2.71 (3H, s), 6.91 (1H, dd, J=6.9, 15.4 Hz), 7.08 (1H, dt, J=1.4, 6.8 Hz), 7.48-7.60 (2H, m), 8.41 (1H, d, J=8.9 Hz), 8.65 (1H, s), 8.77 (1H, d, J=7.0 Hz).

Example 47-B

N-{4-[4-ethoxy-5-(4H-1,2,4-triazol-3-yl)-1,3-thiazol-2-yl]pyridin-2-yl}-2-methoxyacetamide

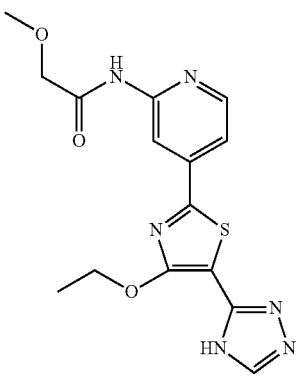 [SMILES: CCOc1nc(-c2ccnc(NC(=O)COC)c2)sc1-c1nnc[nH]1]

(i) Production of N-(4-{4-ethoxy-5-[1-(tetrahydro-2H-pyran-2-yl)-1H-1,2,4-triazol-3-yl]-1,3-thiazol-2-yl}pyridin-2-yl)acetamide Using N-{4-[4-ethoxy-5-(4H-1,2,4-triazol-3-yl)-1,3-thiazol-2-yl]pyridin-2-yl}acetamide (6.2 g, 19 mmol) produced in Example 8-B (v), p-toluenesulfonic acid monohydrate (4.3 g, 23 mmol), 3,4-dihydro-2H-pyran (7.9 g, 94 mmol) and tetrahydrofuran (188 mL) as starting materials and in the same manner as in Example 4-B(i), the title compound (4.7 g, 60%) was obtained as a yellow solid.
$^1$H-NMR (DMSO-d$_6$, 300 MHz) δ 1.40 (3H, t, J=7.1 Hz), 1.50-1.80 (3H, m), 1.89-2.15 (3H, m), 2.13 (3H, s), 3.60-3.78 (1H, m), 3.90-4.03 (1H, m), 4.54 (2H, q, J=7.1 Hz), 5.60 (1H, dd, J=2.6 Hz, 9.4 Hz), 7.58 (1H, dd, J=1.6 Hz, 5.2 Hz), 8.31-8.55 (1H, m), 8.64 (1H, d, J=0.8 Hz), 8.78 (1H, s), 10.70 (1H, s).

(ii) Production of 4-{4-ethoxy-5-[1-(tetrahydro-2H-pyran-2-yl)-1H-1,2,4-triazol-3-yl]-1,3-thiazol-2-yl}pyridin-2-amine To N-(4-{4-ethoxy-5-[1-(tetrahydro-2H-pyran-2-yl)-1H-1,2,4-triazol-3-yl]-1,3-thiazol-2-yl}pyridin-2-yl)acetamide (4.6 g, 11 mmol) produced in the above in a mixed solvent (224 mL) of tetrahydrofuran/methanol (1:1) was added 8N aqueous sodium hydroxide solution (19 mL, 152 mmol), and the mixture was stirred at 80° C. for 1 hr. The reaction solution was cooled to room temperature and diluted with ethyl acetate (500 mL) and water (300 mL). The aqueous layer was separated and extracted with ethyl acetate (300 mL×2), and the combined organic layer was dried over anhydrous magnesium sulfate. The insoluble material was filtered off, and the filtrate was concentrated under reduced pressure to give the title compound (4.1 g, 98%) as a yellow solid.
$^1$H-NMR (DMSO-d$_6$, 300 MHz) δ 1.39 (3H, t, J=7.0 Hz), 1.53-1.78 (3H, m), 1.90-2.19 (3H, m), 3.59-3.74 (1H, m), 3.92-4.01 (1H, m), 4.52 (2H, q, J=7.0 Hz), 5.99 (1H, dd, J=2.6 Hz, 9.4 Hz), 6.23 (2H, s), 6.88-7.06 (2H, m), 8.03 (1H, dd, J=0.8, 5.3 Hz), 8.76 (1H, s).

(iii) Production of N-{4-[4-ethoxy-5-(4H-1,2,4-triazol-3-yl)-1,3-thiazol-2-yl]pyridin-2-yl}-2-methoxyacetamide To a solution of 4-{4-ethoxy-5-[1-(tetrahydro-2H-pyran-2-yl)-1H-1,2,4-triazol-3-yl]-1,3-thiazol-2-yl}pyridin-2-amine (110 mg, 0.3 mmol) produced in the above in N,N-dimethylacetamide (2 mL) was added methoxyacetyl chloride (160 mg, 1.4 mmol), and the mixture was stirred at 40° C. for 60 hr. The reaction mixture was diluted with 2% aqueous sodium bicarbonate solution (5.0 mL) and ethyl acetate (10.0 mL), and the organic layer was dehydrated with Presep Tube, Wako Pure Chemical Industries, Ltd., and concentrated. The obtained residue was dissolved in 1N methanesulfonic acid acetonitrile solution (5.0 mL, 5.0 mmol), and the mixture was stirred at room temperature for 16 hr. The reaction solution was neutralized by adding 1N diisopropylamine acetonitrile solution (5.0 mL, 5.0 mmol). Water (2.0 mL) and dimethyl sulfoxide (5.0 mL) were added, and the mixture was purified by preparative HPLC to give the title compound (71.2 mg, yield 66%) as a yellow solid. LC-MS 361.15 (ESI+)

Examples 48-B to 71-B were each produced in the same manner as in Example 47-B(iii) and using 4-{4-ethoxy-5-[1-(tetrahydro-2H-pyran-2-yl)-1H-1,2,4-triazol-3-yl]-1,3-thiazol-2-yl}pyridin-2-amine produced in Example 47-B(ii), and corresponding acid chloride as starting materials.

The structural formula, name, m/z value detected by LC-MS, yield and yield (%) in Examples 48-B to 71-B are collectively shown in Table 2-1 to Table 2-8.

TABLE 2-1

| Example | structure | name | molecular formula | molecular weight | LCMS m/z | yield (mg) | yield (%) |
| --- | --- | --- | --- | --- | --- | --- | --- |
| 48-B | 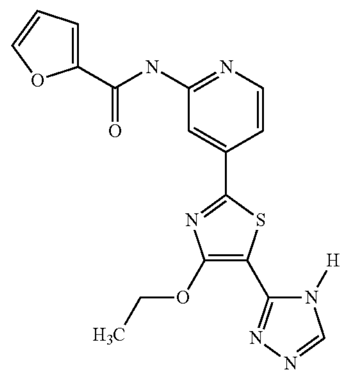 [SMILES: CCOc1nc(-c2ccnc(NC(=O)c3ccco3)c2)sc1-c1nnc[nH]1] | N-{4-[4-ethoxy-5-(4H-1,2,4-triazol-3-yl)-1,3-thiazol-2-yl]pyridin-2-yl}furan-2-carboxamide | C17H14N6O3S | 382.40 | 383.12 | 18.7 | 16 |
| 49-B | 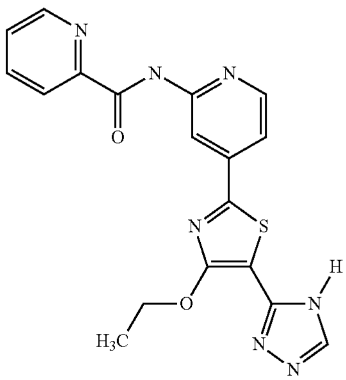 [SMILES: CCOc1nc(-c2ccnc(NC(=O)c3ccccn3)c2)sc1-c1nnc[nH]1] | N-{4-[4-ethoxy-5-(4H-1,2,4-triazol-3-yl)-1,3-thiazol-2-yl]pyridin-2-yl}pyridine-2-carboxamide | C18H15N7O2S | 393.42 | 394.15 | 54.4 | 46 |
| 50-B | 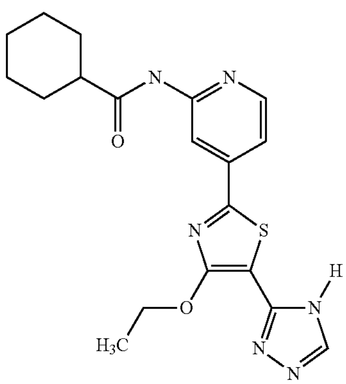 [SMILES: CCOc1nc(-c2ccnc(NC(=O)C3CCCCC3)c2)sc1-c1nnc[nH]1] | N-{4-[4-ethoxy-5-(4H-1,2,4-triazol-3-yl)-1,3-thiazol-2-yl]pyridin-2-yl}cyclohexanecarboxamide | C19H22N6O2S | 398.48 | 399.2 | 60.9 | 51 |

TABLE 2-2

| Example | structure | name | molecular formula | molecular weight | LCMS m/z | yield (mg) | yield (%) |
|---|---|---|---|---|---|---|---|
| 51-B | 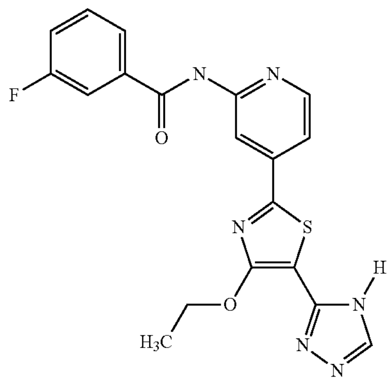 [SMILES: CCOc1nc(-c2ccnc(NC(=O)c3cccc(F)c3)c2)sc1-c1nnc[nH]1] | N-{4-[4-ethoxy-5-(4H-1,2,4-triazol-3-yl)-1,3-thiazol-2-yl]pyridin-2-yl}-3-fluorobenzamide | C19H15FN6O2S | 410.43 | 411.15 | 40.5 | 33 |
| 52-B | 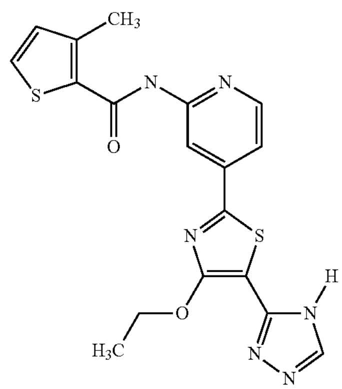 [SMILES: CCOc1nc(-c2ccnc(NC(=O)c3sccc3C)c2)sc1-c1nnc[nH]1] | N-{4-[4-ethoxy-5-(4H-1,2,4-triazol-3-yl)-1,3-thiazol-2-yl]pyridin-2-yl}-3-methylthiophene-2-carboxamide | C18H16N6O2S2 | 412.49 | 413.15 | 6.40 | 5 |
| 53-B | 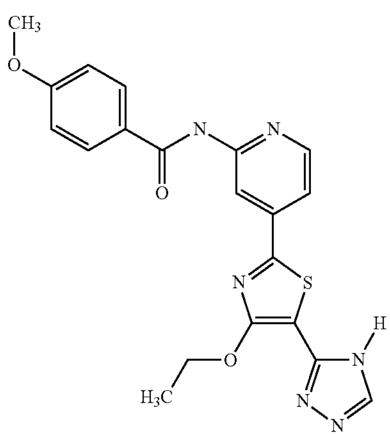 [SMILES: CCOc1nc(-c2ccnc(NC(=O)c3ccc(OC)cc3)c2)sc1-c1nnc[nH]1] | N-{4-[4-ethoxy-5-(4H-1,2,4-triazol-3-yl)-1,3-thiazol-2-yl]pyridin-2-yl}-4-methoxybenzamide | C20H18N6O3S | 422.46 | 423.16 | 46.0 | 36 |

TABLE 2-3

| Example | structure | name | molecular formula | molecular weight | LCMS m/z | yield (mg) | yield (%) |
|---|---|---|---|---|---|---|---|
| 54-B | 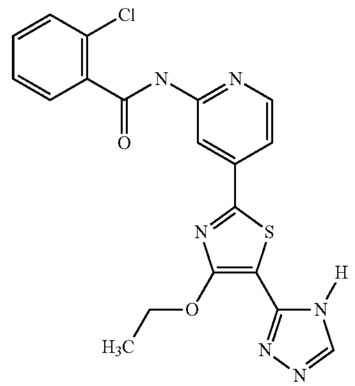 [SMILES: CCOc1nc(-c2ccnc(NC(=O)c3ccccc3Cl)c2)sc1-c1nnc[nH]1] | 2-chloro-N-{4-[4-ethoxy-5-(4H-1,2,4-triazol-3-yl)-1,3-thiazol-2-yl]pyridin-2-yl}benzamide | C19H15ClN6O2S | 426.88 | 427.11 | 19.7 | 15 |
| 55-B | 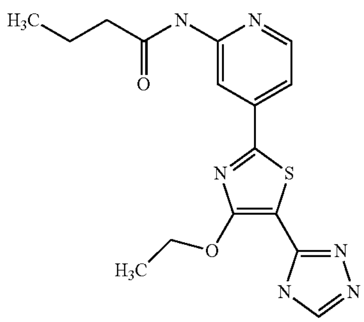 [SMILES: CCCC(=O)Nc1cc(-c2nc(OCC)c(-c3nnc[nH]3)s2)ccn1] | N-{4-[4-ethoxy-5-(4H-1,2,4-triazol-3-yl)-1,3-thiazol-2-yl]pyridin-2-yl}butanamide | C16H18N6O2S | 358.42 | 359.17 | 70.8 | 66 |
| 56-B | 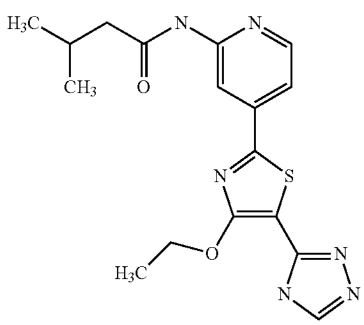 [SMILES: CCOc1nc(-c2ccnc(NC(=O)CC(C)C)c2)sc1-c1nnc[nH]1] | N-{4-[4-ethoxy-5-(4H-1,2,4-triazol-3-yl)-1,3-thiazol-2-yl]pyridin-2-yl}-3-methylbutanamide | C17H20N6O2S | 372.45 | 373.18 | 56.5 | 51 |

TABLE 2-4

| Example | structure | name | molecular formula | molecular weight | LCMS m/z | yield (mg) | yield (%) |
|---|---|---|---|---|---|---|---|
| 57-B | 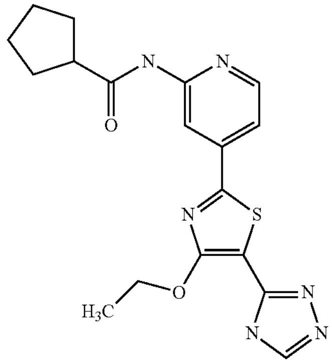 [SMILES: CCOc1nc(-c2ccnc(NC(=O)C3CCCC3)c2)sc1-c1nnc[nH]1] | N-{4-[4-ethoxy-5-(4H-1,2,4-triazol-3-yl)-1,3-thiazol-2-yl]pyridin-2-yl}cyclopentanecarboxamide | C18H20N6O2S | 384.46 | 385.19 | 70.0 | 61 |

TABLE 2-4-continued

| Example | structure | name | molecular formula | molecular weight | LCMS m/z | yield (mg) | yield (%) |
|---|---|---|---|---|---|---|---|
| 58-B | 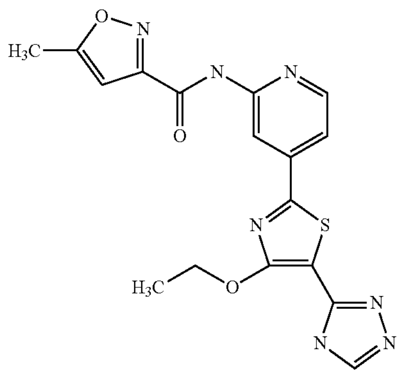 [SMILES: CCOc1nc(-c2ccnc(NC(=O)c3cc(C)on3)c2)sc1-c1nnc[nH]1] | N-{4-[4-ethoxy-5-(4H-1,2,4-triazol-3-yl)-1,3-thiazol-2-yl]pyridin-2-yl}-5-methylisoxazole-3-carboxamide | C17H15N7O3S | 397.41 | 398.15 | 57.0 | 48 |
| 59-B | 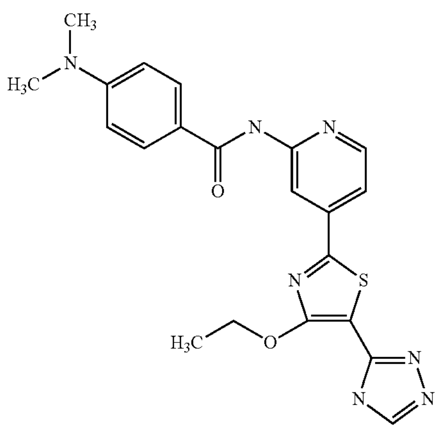 [SMILES: CCOc1nc(-c2ccnc(NC(=O)c3ccc(N(C)C)cc3)c2)sc1-c1nnc[nH]1] | 4-(dimethylamino)-N-{4-[4-ethoxy-5-(4H-1,2,4-triazol-3-yl)-1,3-thiazol-2-yl]pyridin-2-yl}benzamide | C21H21N7O2S | 435.50 | 436.19 | 11.3 | 9 |

TABLE 2-5

| Example | structure | name | molecular formula | molecular weight | LCMS m/z | yield (mg) | yield (%) |
|---|---|---|---|---|---|---|---|
| 60-B | 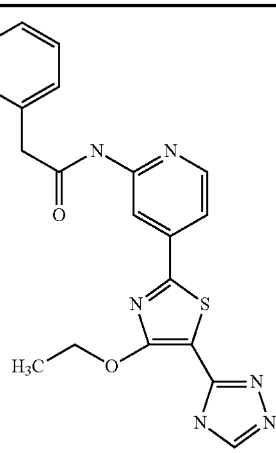 | N-{4-[4-ethoxy-5-(4H-1,2,4-triazol-3-yl)-1,3-thiazol-2-yl]pyridin-2-yl}-2-phenylacetamide | C20H18N6O2S | 406.46 | 407.16 | 91.1 | 75 |

TABLE 2-5-continued

| Example | structure | name | molecular formula | molecular weight | LCMS m/z | yield (mg) | yield (%) |
|---|---|---|---|---|---|---|---|
| 61-B | 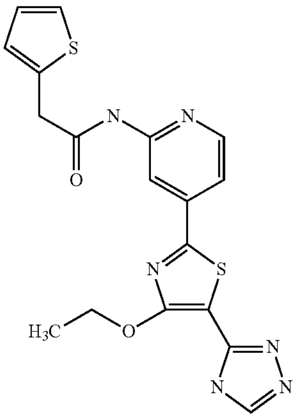 [SMILES: CCOc1nc(-c2ccnc(NC(=O)Cc3cccs3)c2)sc1-c1nnc[nH]1] | N-{4-[4-ethoxy-5-(4H-1,2,4-triazol-3-yl)-1,3-thiazol-2-yl]-pyridin-2-yl}-2-thiophen-2-ylacetamide | C18H16N6O2S2 | 412.49 | 413.13 | 21.6 | 17 |
| 62-B | 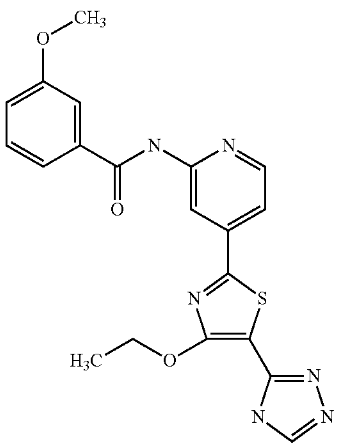 [SMILES: CCOc1nc(-c2ccnc(NC(=O)c3cccc(OC)c3)c2)sc1-c1nnc[nH]1] | N-{4-[4-ethoxy-5-(4H-1,2,4-triazol-3-yl)-1,3-thiazol-2-yl]pyridin-2-yl}-3-methoxybenzamide | C20H18N6O3S | 422.46 | 423.18 | 24.9 | 20 |

TABLE 2-6

| Example | structure | name | molecular formula | molecular weight | LCMS m/z | yield (mg) | yield (%) |
|---|---|---|---|---|---|---|---|
| 63-B | 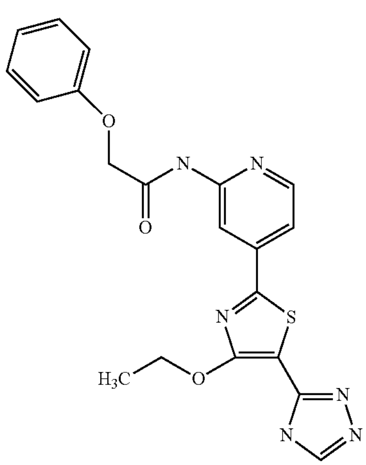 [SMILES: CCOc1nc(-c2ccnc(NC(=O)COc3ccccc3)c2)sc1-c1nnc[nH]1] | N-{4-[4-ethoxy-5-(4H-1,2,4-triazol-3-yl)-1,3-thiazol-2-yl]pyridin-2-yl}-2-phenoxyacetamide | C20H18N6O3S | 422.46 | 423.17 | 60.3 | 48 |

TABLE 2-6-continued

| Example | structure | name | molecular formula | molecular weight | LCMS m/z | yield (mg) | yield (%) |
|---------|-----------|------|-------------------|------------------|----------|------------|-----------|
| 64-B | 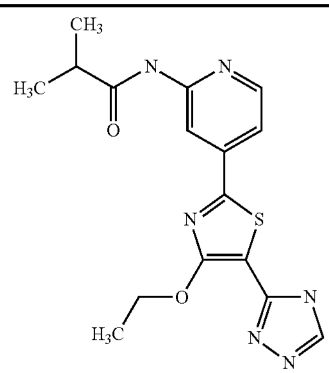 | N-{4-[4-ethoxy-5-(4H-1,2,4-triazol-3-yl)-1,3-thiazol-2-yl]pyridin-2-yl}-2-methylpropanamide | C16H18N6O2S | 358.42 | 359.19 | 27.0 | 25 |
| 65-B | 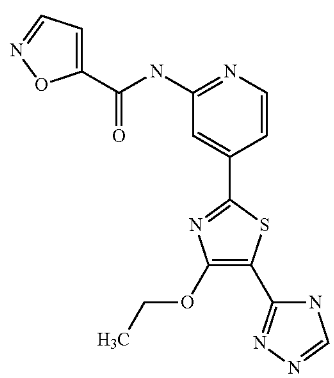 [SMILES: CCOc1nc(-c2ccnc(NC(=O)c3ccno3)c2)sc1-c1nnc[nH]1] | N-{4-[4-ethoxy-5-(4H-1,2,4-triazol-3-yl)-1,3-thiazol-2-yl]pyridin-2-yl}-isoxazole-5-carboxamide | C16H13N7O3S | 383.39 | 384.08 | 30.9 | 27 |

TABLE 2-7

| Example | structure | name | molecular formula | molecular weight | LCMS m/z | yield (mg) | yield (%) |
|---------|-----------|------|-------------------|------------------|----------|------------|-----------|
| 66-B | 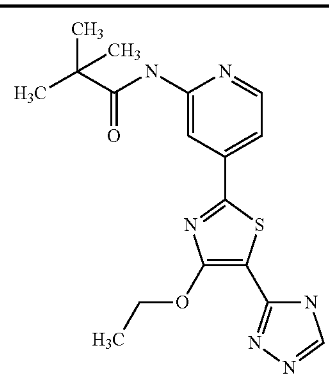 | N-{4-[4-ethoxy-5-(4H-1,2,4-triazol-3-yl)-1,3-thiazol-2-yl]pyridin-2-yl}-2,2-dimethylpropanamide | C17H20N6O2S | 372.45 | 373.17 | 33.9 | 30 |

TABLE 2-7-continued

| Example | structure | name | molecular formula | molecular weight | LCMS m/z | yield (mg) | yield (%) |
|---|---|---|---|---|---|---|---|
| 67-B | 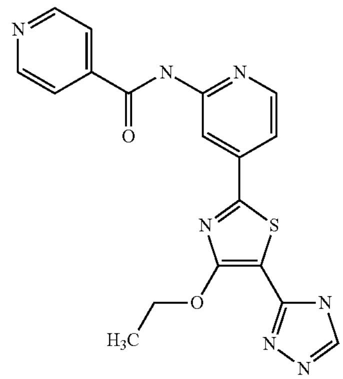 [SMILES: CCOc1nc(-c2ccnc(NC(=O)c3ccncc3)c2)sc1-c1nnc[nH]1] | N-{4-[4-ethoxy-5-(4H-1,2,4-triazol-3-yl)-1,3-thiazol-2-yl]pyridin-2-yl}pyridine-4-carboxamide | C18H15N7O2S | 393.42 | 394.16 | 56.8 | 48 |
| 68-B | 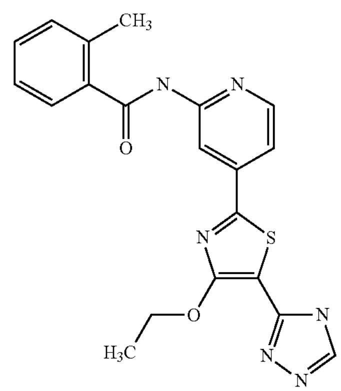 [SMILES: CCOc1nc(-c2ccnc(NC(=O)c3ccccc3C)c2)sc1-c1nnc[nH]1] | N-{4-[4-ethoxy-5-(4H-1,2,4-triazol-3-yl)-1,3-thiazol-2-yl]pyridin-2-yl}-2-methylbenzamide | C20H18N6O2S | 406.46 | 407.16 | 14.7 | 12 |

TABLE 2-8

| Example | structure | name | molecular formula | molecular weight | LCMS m/z | yield (mg) | yield (%) |
|---|---|---|---|---|---|---|---|
| 69-B | 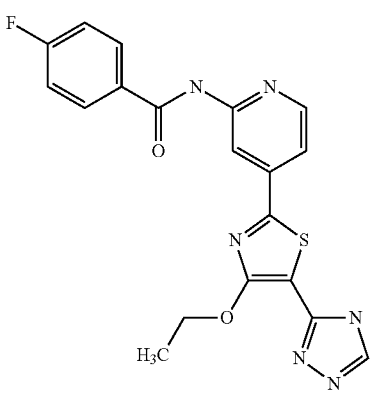 [SMILES: CCOc1nc(-c2ccnc(NC(=O)c3ccc(F)cc3)c2)sc1-c1nnc[nH]1] | N-{4-[4-ethoxy-5-(4H-1,2,4-triazol-3-yl)-1,3-thiazol-2-yl]pyridin-2-yl}-4-fluorobenzamide | C19H15FN6O2S | 410.43 | 411.15 | 39.7 | 32 |

TABLE 2-8-continued

| Example | structure | name | molecular formula | molecular weight | LCMS m/z | yield (mg) | yield (%) |
|---|---|---|---|---|---|---|---|
| 70-B | 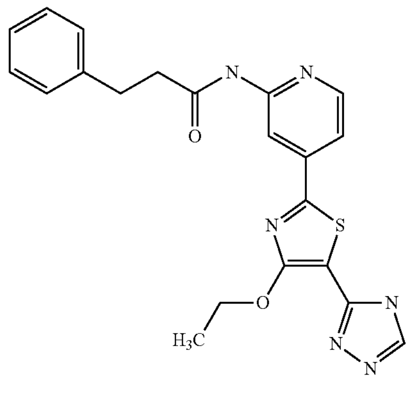 [SMILES: CCOc1nc(-c2ccnc(NC(=O)CCc3ccccc3)c2)sc1-c1nnc[nH]1] | N-{4-[4-ethoxy-5-(4H-1,2,4-triazol-3-yl)-1,3-thiazol-2-yl]pyridin-2-yl}-3-phenylpropanamide | C21H20N6O2S | 420.49 | 421.19 | 57.1 | 45 |
| 71-B | 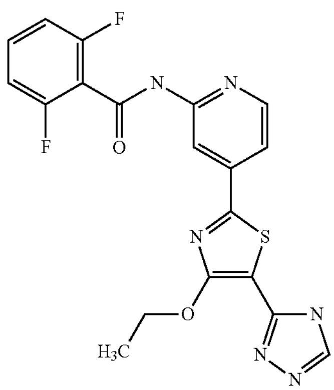 [SMILES: CCOc1nc(-c2ccnc(NC(=O)c3c(F)cccc3F)c2)sc1-c1nnc[nH]1] | N-{4-[4-ethoxy-5-(4H-1,2,4-triazol-3-yl)-1,3-thiazol-2-yl]pyridin-2-yl}-2,6-difluorobenzamide | C19H14F2N6O2S | 428.42 | 429.14 | 25.7 | 20 |

Example 72-B

Production of 2-methyl-3-[4-phenyl-5-(1H-1,2,4-triazol-3-yl)-1,3-thiazol-2-yl]-5-{[6-(trifluoromethyl)pyridin-3-yl]methoxy}pyrazolo[1,5-a]pyridine

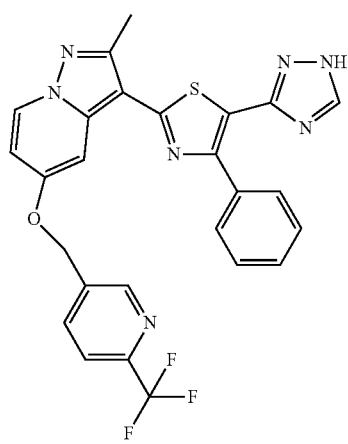 [SMILES: Cc1nn2ccc(OCc3ccc(C(F)(F)F)nc3)cc2c1-c1nc(-c2ccccc2)c(-c2nc[nH]n2)s1]

A mixture of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (100 mg, 0.22 mmol) obtained in Example 31-B(i), 5-(chloromethyl)-2-(trifluoromethyl)pyridine (64 mg, 0.33 mmol), potassium carbonate (60 mg, 0.44 mmol) and DMF (4 mL) was stirred at 60° C. for 2 h. Water (100 mL) and EtOAc (100 mL) were added to the reaction mixture, and the mixture was stirred for 30 min. The organic layer was washed with brine and dried over anhydrous magnesium sulfate. Insoluble materials were removed by filtration, and the filtrate was concentrated under reduced pressure. The residue was dissolved in MeOH (5 mL) and THF (30 mL), 6 N hydrochloric acid (3 mL) was added, and the mixture was stirred at 70° C. for 3 h. The reaction mixture was allowed to cool to rt, and the mixture was concentrated under reduced pressure. To the residue were added EtOAc (50 mL), THF (50 mL), 8 N aqueous sodium hydroxide solution (3 mL) and water (30 mL), and the mixture was stirred for 30 min. The organic layer was washed with brine and dried over anhydrous magnesium sulfate, and insoluble materials were removed by filtration. The filtrate was concentrated under reduced pressure. The residue was crystallized from EtOAc to give the title compound (107 mg, 92%) as a white solid.

$^1$H-NMR (DMSO-d$_6$, 300 MHz) δ 2.67 (3H, s), 5.51 (2H, s), 6.88 (1H, dd, J=2.6, 7.6, Hz), 7.31-7.53 (3H, m), 7.80 (1H, d, J=2.6 Hz), 7.84-7.98 (3H, m), 8.21 (1H, d, J=8.1 Hz), 8.52-8.64 (1H, m), 8.70 (1H, d, J=7.7 Hz), 8.92 (1H, s), 13.99 (1H, br s).

Example 73-B

Production of 2,2-dimethyl-N-[2-({2-methyl-3-[4-phenyl-5-(1H-1,2,4-triazol-3-yl)-1,3-thiazol-2-yl]pyrazolo[1,5-a]pyridin-5-yl}oxy)ethyl]propanamide

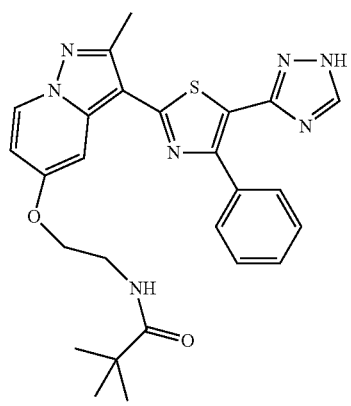 [SMILES: Cc1nn2ccc(OCCNC(=O)C(C)(C)C)cc2c1-c1nc(-c2ccccc2)c(-c2nc[nH]n2)s1]

(i) Production of 2-({2-methyl-3-[4-phenyl-5-(1H-1,2,4-triazol-3-yl)-1,3-thiazol-2-yl]pyrazolo[1,5-a]pyridin-5-yl}oxy)ethanamine di-hydrochloride (165-B)

A mixture of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (150 mg, 0.33 mmol) obtained in Example 31-B(i), 2-(BOC-amino)ethyl bromide (103 mg, 0.46 mmol), potassium carbonate (90 mg, 0.65 mmol) and DMF (5 mL) was stirred at 60° C. for 2 h. The reaction mixture was allowed to cool to rt, water (100 mL) and EtOAc (50 mL) were added, and the mixture was stirred for 30 min. The organic layer was washed with brine and dried over anhydrous magnesium sulfate. Insoluble materials were removed by filtration, and the filtrate was concentrated under reduced pressure. The residue was dissolved in MeOH (15 mL) and THF (10 mL), and then 6N hydrochloric acid (1.5 mL) was added. The mixture was stirred at 70° C. for 3 h. The reaction mixture was allowed to cool to rt, and the mixture was concentrated under reduced pressure. The residue was washed with diisopropyl ether and dried to give the title compound (132 mg, 79%) as a white solid.

$^1$H-NMR (DMSO-$d_6$, 300 MHz) δ 3.27-3.39 (2H, m), 4.34-4.39 (2H, m), 6.80 (1H, dd, J=2.7, 7.5 Hz), 7.37-7.50 (3H, m), 7.73 (1H, d, J=2.7 Hz), 7.87-7.97 (2H, m), 8.14 (3H, br s), 8.62 (1H, s), 8.71 (1H, d, J=7.6 Hz).

(ii) Production of 2,2-dimethyl-N-[2-({2-methyl-3-[4-phenyl-5-(1H-1,2,4-triazol-3-yl)-1,3-thiazol-2-yl]pyrazolo[1,5-a]pyridin-5-yl}oxy)ethyl]propanamide To a solution of 2-({2-methyl-3-[4-phenyl-5-(1H-1,2,4-triazol-3-yl)-1,3-thiazol-2-yl]pyrazolo[1,5-a]pyridin-5-yl}oxy)ethanamine di-hydrochloride (130 mg, 0.27 mmol) obtained above in TEA (430 mg, 4.3 mmol) and THF (5 mL) was added 2,2-dimethylpropanoyl chloride (76 mg, 0.51 mmol) at 0° C., and the mixture was stirred at 0° C. for 1 h. To the reaction mixture, were added saturated aqueous solution of sodium bicarbonate (50 mL) and EtOAc (50 mL), and the mixture was stirred for 30 min. The organic layer was washed with brine and dried over anhydrous magnesium sulfate. Insoluble materials were removed by filtration, and the filtrate was concentrated under reduced pressure.

The residue was washed with EtOAc and diisopropyl ether, and dried to give the title compound (120 mg, 90%) as a white solid.

$^1$H-NMR (DMSO-$d_6$, 300 MHz) δ 1.09 (9H, s), 2.66 (3H, s), 3.51 (2H, q, J=5.8 Hz), 4.16 (2H, t, J=5.8 Hz), 6.75 (1H, dd, J=2.7, 7.5 Hz), 7.31-7.48 (3H, m), 7.74 (2H, d, J=2.7 Hz), 7.99-8.08 (2H, m), 8.43 (1H, s), 8.64 (1H, d, J=7.5 Hz).

Example 74-B

Production of 3-[4-(2-fluorophenyl)-5-(1H-1,2,4-triazol-3-yl)-1,3-thiazol-2-yl]-2-methyl-5-(2-morpholin-4-ylethoxy)pyrazolo[1,5-a]pyridine di-p-toluenesulfonate

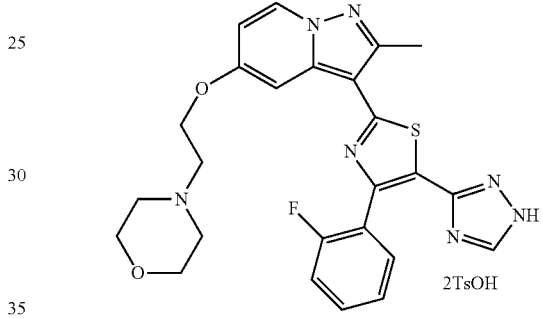

(i) Production of ethyl 2-[5-(benzyloxy)-2-methylpyrazolo[1,5-a]pyridin-3-yl]-4-(2-fluorophenyl)-1,3-thiazole-5-carboxylate A suspension of 5-(benzyloxy)-2-methylpyrazolo[1,5-a]pyridine-3-carbothioamide (820 mg, 2.8 mmol) obtained in Example 30-B(vi) and ethyl 2-chloro-3-(2-fluorophenyl)-3-oxopropanoate (3.1 g, 13 mmol) obtained in Example 22-B(i) in 2-propanol (50 mL) was stirred at 90° C. for 7 h. The reaction mixture was allowed to cool to room temperature, and the precipitated solid was collected by filtration. The solid was washed with EtOAc and diisopropyl ether, and dried to give the title compound (1.0 g, 75%) as a yellow solid.

$^1$H-NMR (DMSO-$d_6$, 300 MHz) δ 1.13-1.21 (3H, m), 2.62 (3H, s), 4.20 (2H, q, J=7.2 Hz), 5.25 (2H, s), 6.86 (1H, dd, J=2.8, 7.4 Hz), 7.22-7.61 (8H, m), 7.67-7.77 (2H, m), 8.67 (1H, d, J=7.4 Hz).

(ii) Production of 2-[5-(benzyloxy)-2-methylpyrazolo[1,5-a]pyridin-3-yl]-4-(2-fluorophenyl)-1,3-thiazole-5-carboxylic acid To a solution of ethyl 2-[5-(benzyloxy)-2-methylpyrazolo[1,5-a]pyridin-3-yl]-4-(2-fluorophenyl)-1,3-thiazole-5-carboxylate (1.0 g, 2.1 mmol) obtained above in MeOH (10 mL) and THF (25 mL), was added 8N aqueous sodium hydroxide solution (2.5 mL), and the mixture was stirred at 70° C. for 1 h. The reaction mixture was allowed to cool to 0° C., 1N hydrochloric acid was added to adjust the solution to about pH 3.0, and the reaction mixture was extracted with a 1:1 mixture of THF and EtOAc. The combined organic layers were dried over anhydrous magnesium sulfate and insoluble materials were removed by filtration, and the filtrate was concentrated to give the title compound (810 mg, 86%) as a yellow solid.

$^1$H-NMR (DMSO-$d_6$, 300 MHz) δ 2.59 (3H, s), 5.21 (2H, s), 6.77 (1H, dd, J=2.8, 7.6 Hz), 7.19-7.33 (5H, m), 7.37-7.52 (3H, m), 7.58-7.68 (1H, m), 7.72 (1H, d, J=2.6 Hz), 8.59 (1H, d, J=7.6 Hz), (iii) Production of 2-[5-(benzyloxy)-2-methylpyrazolo[1,5-a]pyridin-3-yl]-4-(2-fluorophenyl)-1,3-thiazole-5-carboxamide A mixture of 2-[5-(benzyloxy)-2-methylpyrazolo[1,5-a]pyridin-3-yl]-4-(2-fluorophenyl)-1,3-thiazole-5-carboxylic acid (750 mg, 1.6 mmol) obtained above, TEA (3.2 mL), ammonium chloride (1.5 g, 28 mmol), HOBT (150 mg, 1.1 mmol), EDCI (2.5 g, 13 mmol) and DMF (50 mL) was stirred at rt for 16 h. To the reaction mixture were added water (200 mL) and EtOAc (200 mL), and the mixture was stirred for 30 min. The organic layer was washed with brine and dried over anhydrous magnesium sulfate. Insoluble materials were removed by filtration, and the filtrate was concentrated under reduced pressure. The residue was washed with EtOAc and diisopropyl ether, and dried to give the title compound (520 mg, 69%) as a yellow solid.

$^1$H-NMR (DMSO-$d_6$, 300 MHz) δ 2.62 (3H, s), 5.26 (2H, s), 6.83 (1H, dd, J=2.8, 7.6 Hz), 7.26-7.56 (10H, m), 7.69-7.78 (2H, m), 8.65 (1H, d, J=7.6 Hz).

(iv) Production of 5-(benzyloxy)-3-[4-(2-fluorophenyl)-5-(1H-1,2,4-triazol-3-yl)-1,3-thiazol-2-yl]-2-methylpyrazolo[1,5-a]pyridine A suspension of 2-[5-(benzyloxy)-2-methylpyrazolo[1,5-a]pyridin-3-yl]-4-(2-fluorophenyl)-1,3-thiazole-5-carboxamide (500 mg, 1.1 mmol) obtained above in N,N-dimethylformamide dimethylacetal (50 mL) was stirred at 90° C. for 2 h. The reaction mixture was allowed to cool to rt, the solvent was evaporated and the residue was washed with diisopropyl ether (5 mL). The residue was dissolved in AcOH (50 mL) and then hydrazine monohydrate (0.5 mL) was added. The mixture was stirred at 90° C. for 1 h and then the reaction mixture was allowed to cool to rt. Then the mixture was concentrated under reduced pressure. To the residue were added saturated aqueous solution of sodium bicarbonate (150 mL) and EtOAc (100 mL), and then the mixture was stirred for 30 min. The organic layer was washed with brine and dried over anhydrous magnesium sulfate. Insoluble materials were removed by filtration and the filtrate was concentrated under reduced pressure. The residue was washed with EtOAc and diisopropyl ether, and dried to give the title compound (395 mg, 75%) as a white solid.

$^1$H-NMR (DMSO-$d_6$, 300 MHz) δ 2.65 (3H, s), 5.25 (2H, s), 6.81 (1H, dd, J=2.6, 7.4 Hz), 7.23-7.59 (8H, m), 7.67-7.80 (2H, m), 8.51 (1H, s), 8.64 (1H, d, J=7.6 Hz), 14.08 (1H, s).

(v) Production of 5-(benzyloxy)-3-{4-(2-fluorophenyl)-5-[1-(tetrahydro-2H-pyran-2-yl)-1H-1,2,4-triazol-3-yl]-1,3-thiazol-2-yl}-2-methylpyrazolo[1,5-a]pyridine A mixture of 5-(benzyloxy)-3-[4-(2-fluorophenyl)-5-(1H-1,2,4-triazol-3-yl)-1,3-thiazol-2-yl]-2-methylpyrazolo[1,5-a]pyridine (395 mg, 0.82 mmol) obtained above, 3,4-dihydro-2H-pyran (344 mg, 4.1 mmol), p-toluenesulfonic acid monohydrate (78 mg, 0.41 mmol) and THF (30 mL) was stirred at 70° C. for 17 h. The reaction mixture was concentrated under reduced pressure. To the residue, saturated aqueous solution of sodium bicarbonate was added and the mixture was extracted with EtOAc. The organic layer was washed with brine and dried over anhydrous magnesium sulfate. Insoluble materials were removed by filtration and the filtrate was concentrated under reduced pressure. The residue was washed with diisopropyl ether and dried to give the title compound (412 mg, 88%) as a white solid.

$^1$H-NMR (DMSO-$d_6$, 300 MHz) δ 1.42-1.63 (3H, m), 1.84-2.06 (3H, m), 2.64 (3H, s), 3.36-3.96 (2H, m), 5.25 (2H, s), 5.56 (1H, dd, J=3.2, 8.3 Hz), 6.82 (1H, dd, J=2.7, 7.5 Hz), 7.22-7.58 (8H, m), 7.68-7.82 (2H, m), 8.64 (1H, d, J=7.6 Hz), 8.69 (1H, s).

(vi) Production of 3-{4-(2-fluorophenyl)-5-[1-(tetrahydro-2H-pyran-2-yl)-1H-1,2,4-triazol-3-yl]-1,3-thiazol-2-yl}-2-methylpyrazolo[1,5-a]pyridin-5-ol To a solution of 5-(benzyloxy)-3-{4-(2-fluorophenyl)-5-[1-(tetrahydro-2H-pyran-2-yl)-1H-1,2,4-triazol-3-yl]-1,3-thiazol-2-yl}-2-methylpyrazolo[1,5-a]pyridine (400 mg, 0.71 mmol) obtained above in THF (15 mL) and EtOH (3 mL), was added 10% palladium-carbon (50% wet with water, 120 mg). The mixture was stirred at rt for 49 h under hydrogen atmosphere (1 atm), and then 10% palladium-carbon was removed by filtration. The filtrate was concentrated under reduced pressure and the residue was purified by silica gel column chromatography (EtOAc/hexane=50/50→100/0) to give the title compound (321 mg, 96%) as a brown syrup.

$^1$H-NMR (DMSO-$d_6$, 300 MHz) δ 1.40-1.73 (3H, m), 1.80-2.04 (3H, m), 2.63 (3H, s), 3.54-3.72 (1H, m), 3.82-3.94 (1H, m), 5.55 (1H, dd, J=3.3, 8.0 Hz), 6.61 (1H, dd, J=2.7, 7.5 Hz), 7.19-7.37 (2H, m), 7.44-7.53 (1H, m), 7.56 (1H, s), 7.68 (1H, dt, J=1.8, 7.5 Hz), 8.56 (1H, d, J=7.4 Hz), 8.67 (1H, s), 10.81 (1H, br s).

(vii) Production of 3-[4-(2-fluorophenyl)-5-(1H-1,2,4-triazol-3-yl)-1,3-thiazol-2-yl]-2-methyl-5-(2-morpholin-4-ylethoxy)pyrazolo[1,5-a]pyridine A mixture of 3-{4-(2-fluorophenyl)-5-[1-(tetrahydro-2H-pyran-2-yl)-1H-1,2,4-triazol-3-yl]-1,3-thiazol-2-yl}-2-methylpyrazolo[1,5-a]pyridin-5-ol (150 mg, 0.31 mmol) obtained above, 2-(4-morpholine)ethyl bromide (122 mg, 0.63 mmol), potassium carbonate (130 mg, 0.94 mmol) and DMF (10 mL) was stirred at 50° C. for 1 h. The mixture was allowed to cool to rt. To the reaction mixture were added water (100 mL) and EtOAc (100 mL), and the mixture was stirred for 30 min. The organic layer was washed with brine and dried over anhydrous magnesium sulfate. Insoluble materials were removed by filtration and the filtrate was concentrated under reduced pressure. The residue was purified by basic silica gel column chromatography (MeOH/EtOAc=0/100→5/95) to give 3-{4-(2-fluorophenyl)-5-[1-(tetrahydro-2H-pyran-2-yl)-1H-1,2,4-triazol-3-yl]-1,3-thiazol-2-yl}-2-methyl-5-(2-morpholin-4-ylethoxy)pyrazolo[1,5-a]pyridine (181 mg, 97%) as a white solid.

To a solution of 3-{4-(2-fluorophenyl)-5-[1-(tetrahydro-2H-pyran-2-yl)-1H-1,2,4-triazol-3-yl]-1,3-thiazol-2-yl}-2-methyl-5-(2-morpholin-4-ylethoxy)pyrazolo[1,5-a]pyridine (180 mg, 0.31 mmol) obtained above in MeOH (5 mL) and THF (2 mL), was added 2N hydrochloric acid (2.5 mL), and the mixture was stirred for 1 h at 70° C. The reaction mixture was allowed to cool to rt, and the solvent was evaporated. To the residue were added EtOAc (50 mL), THF (50 mL), 8N aqueous sodium hydroxide solution (2 mL) and water (30 mL), and the mixture was stirred for 30 min. The organic layer was washed with brine and dried over anhydrous magnesium sulfate. Insoluble materials were removed by filtration and the filtrate was concentrated under reduced pressure. The residue was washed with diisopropyl ether and dried to give the title compound (141 mg, 92%) as a white solid.

$^1$H-NMR (DMSO-$d_6$, 300 MHz) δ 2.42-2.47 (4H, m), 2.65 (3H, s), 2.74 (2H, t, J=5.9 Hz), 3.51-3.60 (4H, m), 4.22 (2H, t, J=5.9 Hz), 6.77 (1H, dd, J=2.8, 7.6 Hz), 7.16-7.38 (2H, m), 7.40-7.58 (1H, m), 7.60-7.82 (2H, m), 8.37-8.78 (2H, m), 14.14 (1H, br s).

(viii) Production of 3-[4-(2-fluorophenyl)-5-(1H-1,2,4-triazol-3-yl)-1,3-thiazol-2-yl]-2-methyl-5-(2-morpholin-4-ylethoxy)pyrazolo[1,5-a]pyridine di-p-toluenesulfonate A mixture of 3-[4-(2-fluorophenyl)-5-(1H-1,2,4-triazol-3-yl)-1,3-thiazol-2-yl]-2-methyl-5-(2-morpholin-4-ylethoxy)pyrazolo[1,5-a]pyridine (138 mg, 0.27 mmol) obtained above, p-toluenesulfonic acid monohydrate (114 mg, 0.60 mmol), EtOH (1.5 mL) and THF (5 mL) was heated to obtain clear solution, and then concentrated under reduced pressure. The residue was crystallized from EtOH to give the title compound (181 mg, 78%) as a pale yellow solid.

$^1$H-NMR (DMSO-$d_6$, 300 MHz) δ 2.28 (6H, s), 2.68 (3H, s), 3.11-3.32 (2H, m), 3.47-3.78 (6H, m), 3.93-4.05 (2H, m), 4.45-4.59 (2H, m), 6.83 (1H, dd, J=2.7, 7.5 Hz), 7.11 (5H, d, J=7.9 Hz), 7.20-7.35 (2H, m), 7.43-7.55 (6H, m), 7.61-7.76 (2H, m), 8.54 (1H, s), 8.72 (1H, d, J=7.6 Hz), 9.81 (1H, br s).

Example 75-B

Production of 2-[2-(2-methylpyrazolo[1,5-a]pyridin-3-yl)-5-(1H-1,2,4-triazol-3-yl)-1,3-thiazol-4-yl]aniline

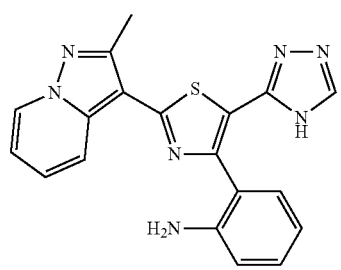 [SMILES: Cc1nn2ccccc2c1-c1nc(-c2ccccc2N)c(-c2nnc[nH]2)s1]

(i) Production of ethyl 2-chloro-3-(2-nitrophenyl)-3-oxopropanoate

To a solution of ethyl 3-(2-nitrophenyl)-3-oxopropanoate (2.0 g, 8.4 mmol) in diethyl ether (50 mL), was added sulfuryl chloride (1.37 g, 10 mmol) at 0° C., and the mixture was stirred for 3 h at rt. To the reaction mixture were added water (200 mL) and EtOAc (100 mL), and the mixture was stirred for 30 min. The organic layer was washed with brine (10 mL) and dried over anhydrous magnesium sulfate. Insoluble materials were removed by filtration and the filtrate was concentrated under reduced pressure to give the title compound (1.7 g, 75%) as colorless oil.

$^1$H-NMR (DMSO-$d_6$, 300 MHz) δ 1.13-1.27 (3H, m), 4.00-4.14 (2H, m), 4.99 (1H, s), 7.27-7.90 (4H, m).

(ii) Production of 2-(2-methylpyrazolo[1,5-a]pyridin-3-yl)-4-(2-nitrophenyl)-1,3-thiazole-5-carboxylic acid A mixture of 2-methylpyrazolo[1,5-a]pyridine-3-carbothioamide hydrochloride (1.2 g, 5.2 mmol) obtained in Example 11-B(v), ethyl 2-chloro-3-(2-nitrophenyl)-3-oxopropanoate (1.7 g, 8.4 mmol) obtained above and 2-propanol (20 mL) was stirred at 80° C. for 4 h. To the reaction mixture were added saturated aqueous solution of sodium bicarbonate, EtOAc and THF. Insoluble materials were removed by filtration and the filtrate was extracted with a 1:1 mixture of EtOAc and THF. The organic layer was washed with brine and dried over anhydrous magnesium sulfate. Insoluble materials were removed by filtration and the filtrate was concentrated under reduced pressure. To the residue were added MeOH (10 mL), THF (25 mL) and 8N aqueous sodium hydroxide solution (2.5 mL), and the mixture was stirred at 70° C. for 1 h. The reaction mixture was allowed to, cool to 0° C., 6N hydrochloric acid was added to adjust the solution to about pH 3.0. The resulting precipitate was collected by filtration, washed with diisopropyl ether, and dried to give the title compound (620 mg, 31%) as a yellow solid.

$^1$H-NMR (DMSO-$d_6$, 300 MHz) δ 2.69 (3H, s), 7.11 (1H, dt, J=1.3, 6.9 Hz), 7.55 (1H, ddd, J=1.1, 7.0, 8.9 Hz), 7.69-7.89 (3H, m), 8.13 (1H, dd, J=0.9, 8.1 Hz), 8.21 (1H, dt, J=1.3, 8.8 Hz), 8.77-8.83 (1H, m), 13.36 (1H, br s).

(iii) Production of 2-(2-methylpyrazolo[1,5-a]pyridin-3-yl)-4-(2-nitrophenyl)-1,3-thiazole-5-carboxamide A mixture of 2-(2-methylpyrazolo[1,5-a]pyridin-3-yl)-4-(2-nitrophenyl)-1,3-thiazole-5-carboxylic acid (600 mg, 1.6 mmol) obtained above, TEA (4.2 mL), ammonium chloride (2.5 g, 47 mmol), HOBT (170 mg, 1.3 mmol), EDCI (1.1 g, 5.7 mmol) and DMF (200 mL) was stirred for 14 h at rt. To the reaction mixture were added water (200 mL) and EtOAc (200 mL), and the mixture was stirred for 30 min. The organic layer was washed with water and brine, and dried over anhydrous magnesium sulfate. Insoluble materials were removed by filtration and the filtrate was concentrated under reduced pressure. The residue was washed with EtOAc and diisopropyl ether, and dried to give the title compound (592 mg, 99%) as a yellow solid.

$^1$H-NMR (DMSO-$d_6$, 300 MHz) δ2.66 (3H, s), 7.09 (1H, dt, J=1.3, 6.9 Hz), 7.47-7.85 (5H, m), 7.95 (1H, s), 8.04-8.19 (2H, m), 8.78 (1H, d, J=6.9 Hz).

(iv) Production of 2-methyl-3-[4-(2-nitrophenyl)-5-(1H-1,2,4-triazol-3-yl)-1,3-thiazol-2-yl]pyrazolo[1,5-a]pyridine A suspension of 2-(2-methylpyrazolo[1,5-a]pyridin-3-yl)-4-(2-nitrophenyl)-1,3-thiazole-5-carboxamide (500 mg, 1.3 mmol) obtained above in N,N-dimethylformamide dimethylacetal (25 mL) was stirred at 90° C. for 2 h. The reaction mixture was allowed to cool to rt, and the solvent was evaporated. The residue was washed with diisopropyl ether (5 mL) and then the solvent was removed. The residue was dissolved in AcOH (25 mL) and hydrazine monohydrate (0.5 mL) was added. The mixture was stirred at 90° C. for 1 h and then allowed to cool to rt. The mixture was concentrated under reduced pressure and the residue was suspended in saturated aqueous solution of sodium bicarbonate (150 mL) and EtOAc (100 mL). The mixture was stirred for 30 min and the organic layer was washed with brine, then dried over anhydrous magnesium sulfate. Insoluble materials were removed by filtration and the filtrate was concentrated under reduced pressure. The residue was washed with EtOAc and diisopropyl ether, and dried to give the title compound (363 mg, 68%) as a white solid.

$^1$H-NMR (DMSO-$d_6$, 300 MHz) δ 2.70 (3H, s), 7.08 (1H, dt, J=1.4, 6.9, Hz), 7.51 (1H, ddd, J=1.0, 6.9, 8.9 Hz), 7.65-7.85 (3H, m), 8.10 (1H, d, J=7.9 Hz), 8.16-8.23 (1H, m), 8.55 (1H, br s), 8.77 (1H, d, J=7.0 Hz), 14.21 (1H, br s).

(v) Production of 2-[2-(2-methylpyrazolo[1,5-a]pyridin-3-yl)-5-(1H-1,2,4-triazol-3-yl)-1,3-thiazol-4-yl]aniline To a solution of 2-methyl-3-[4-(2-nitrophenyl)-5-(1H-1,2,4-triazol-3-yl)-1,3-thiazol-2-yl]pyrazolo[1,5-a]pyridine (500 mg, 1.3 mmol) obtained above in THF (30 mL), were added EtOH (10 mL), reduced iron (2.2 g, 39 mmol) and 1N hydrochloric acid (3 mL), and the mixture was stirred at 80° C. for 3 h. The reaction mixture was allowed to cool to rt and insoluble materials were removed by filtration. To the filtrate, were added EtOAc (100 mL), 1N aqueous sodium hydroxide solution (5 mL) and water (50 mL). The mixture was stirred for 30 min. The organic layer was washed with brine, and dried over anhydrous magnesium sulfate. Insoluble materials were removed by filtration, and the filtrate was concentrated under reduced pressure. The residue was purified by basic silica gel column chromatography (EtOAc/hexane=50/50→100/0) to give the title compound (302 mg, 93%) as a yellow solid.

$^1$H-NMR (DMSO-$d_6$, 300 MHz) δ 2.72 (3H, s), 5.25 (2H, br s), 6.55 (1H, t, J=7.7 Hz), 6.78 (1H, d, J=7.4 Hz), 6.99-7.15 (2H, m), 7.21 (1H, d, J=7.4 Hz), 7.52 (1H, t, J=7.7 Hz), 8.28 (1H, d, J=9.6 Hz), 8.50 (1H, br s), 8.70-8.83 (1H, m), 14.02 (1H, br s).

Example 76-B

Production of N-[2-({2-methyl-3-[4-phenyl-5-(1H-1,2,4-triazol-3-yl)-1,3-thiazol-2-yl]pyrazolo[1,5-a]pyridin-5-yl}oxy)ethyl]acetamide

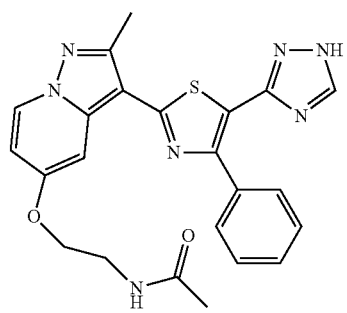 [SMILES: CC(=O)NCCOc1ccn2nc(C)c(-c3nc(-c4ccccc4)c(-c4nc[nH]n4)s3)c2c1]

To a suspension of 2-({2-methyl-3-[4-phenyl-5-(1H-1,2,4-triazol-3-yl)-1,3-thiazol-2-yl]pyrazolo[1,5-a]pyridin-5-yl}oxy)ethanamine di-hydrochloride (100 mg, 0.20 mmol) obtained in Example 73-B(i) and TEA (0.75 mL) in THF (10 mL), was added acetic anhydride (0.5 mL, 5.3 mmol) at 0° C., and the mixture was stirred at 0° C. for 1 h. To the reaction mixture were added saturated aqueous solution of sodium bicarbonate (50 mL) and EtOAc (50 mL), and the mixture was stirred for 30 min. The organic layer was washed with brine and dried over anhydrous magnesium sulfate. Insoluble materials were removed by filtration, and the filtrate was concentrated under reduced pressure. The residue was washed with EtOAc and diisopropyl ether, and dried to give the title compound (33 mg, 35%) as a white solid.

$^1$H-NMR (DMSO-$d_6$, 300 MHz) δ 1.84 (3H, s), 2.67 (3H, s), 3.44-3.55 (2H, m), 4.11-4.23 (2H, m), 6.77 (1H, dd, J=2.8, 7.7 Hz), 7.35-7.51 (3H, m), 7.72 (1H, s), 7.87-8.00 (2H, m), 8.16 (1H, s), 8.64-8.68 (2H, m).

Example 77-B

Production of 2-amino-2-methyl-N-[2-({2-methyl-3-[4-phenyl-5-(1H-1,2,4-triazol-3-yl)-1,3-thiazol-2-yl]pyrazolo[1,5-a]pyridin-5-yl}oxy)ethyl]propanamide

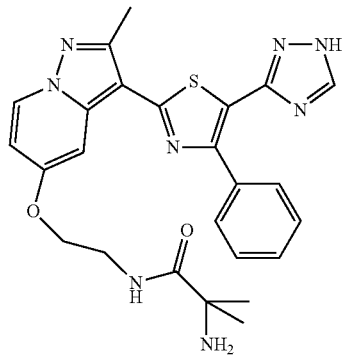 [SMILES: Cc1nn2ccc(OCCNC(=O)C(C)(C)N)cc2c1-c1nc(-c2ccccc2)c(-c2nc[nH]n2)s1]

A mixture of 2-({2-methyl-3-[4-phenyl-5-(1H-1,2,4-triazol-3-yl)-1,3-thiazol-2-yl]pyrazolo[1,5-a]pyridin-5-yl}oxy)ethanamine di-hydrochloride (100 mg, 0.20 mmol) obtained in Example 73-B(i), TEA (1.5 mL), 2-[(tert-butoxycarbonyl)amino]-2-methylpropanoic acid (75 mg, 0.37 mmol), HOBT (50 mg, 0.37 mmol), EDCI (210 mg, 1.1 mmol) and DMF (20 mL) was stirred at rt for 14 h. To the reaction mixture were added water (200 mL) and EtOAc (200 mL) and the mixture was stirred for 30 min. The organic layer was washed with water and brine, and dried over anhydrous magnesium sulfate. Insoluble materials were removed by filtration, and the filtrate was concentrated under reduced pressure. To a solution of the above residue in MeOH (10 mL) and THF (15 mL) was added 6N hydrochloric acid (3 mL), and the mixture was stirred at 70° C. for 1 h. The reaction mixture was allowed to cool to rt and then the solvent was evaporated. To the reaction mixture were added EtOAc (100 mL), 8N aqueous sodium hydroxide solution (3 mL) and water (100 mL), and the mixture was stirred for 30 min. The organic layer was washed with brine and dried over anhydrous magnesium sulfate. Insoluble materials were removed by filtration, and the filtrate was concentrated under reduced pressure. The residue was washed with diisopropyl ether and dried to give the title compound (46 mg, 45%) as a white solid.

$^1$H-NMR (DMSO-$d_6$, 300 MHz) δ 1.19 (6H, s), 2.66 (3H, s), 3.32 (2H, br s), 3.47-3.59 (2H, m), 4.12-4.23 (2H, m), 6.77

(1H, dd, J=2.8, 7.4 Hz), 7.35-7.49 (3H, m), 7.72 (1H, d, J=2.6 Hz), 7.94 (2H, dd, J=1.5, 8.1 Hz), 8.16 (1H, br s), 8.58 (1H, s), 8.65 (1H, d, J=7.6 Hz).

Example 78-B

Production of 1-methyl-N-[2-({2-methyl-3-[4-phenyl-5-(1H-1,2,4-triazol-3-yl)-1,3-thiazol-2-yl]pyrazolo[1,5-a]pyridin-5-yl}oxy)ethyl]-1H-imidazole-4-carboxamide

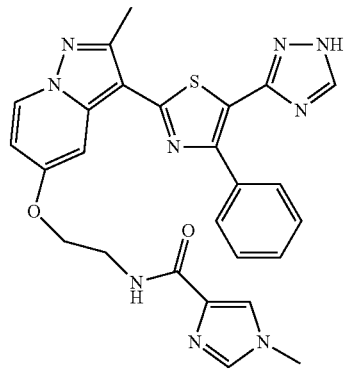 [SMILES: Cc1nn2ccc(OCCNC(=O)c3cn(C)cn3)cc2c1-c1nc(-c2ccccc2)c(-c2nc[nH]n2)s1]

A mixture of 2-({2-methyl-3-[4-phenyl-5-(1H-1,2,4-triazol-3-yl)-1,3-thiazol-2-yl]pyrazolo[1,5-a]pyridin-5-yl}oxy)ethanamine di-hydrochloride (100 mg, 0.20 mmol) obtained in Example 73-B(i), TEA (1.5 mL), 1-methyl-1H-imidazole-4-carboxylic acid (120 mg, 0.95 mmol), HOBT (220 mg, 1.6 mmol), EDCI (350 mg, 1.8 mmol) and DMF (10 mL) was stirred at rt for 14 h. To the reaction mixture were added water (200 mL) and EtOAc (200 mL) and the mixture was stirred for 30 min. The organic layer was washed with water and brine, and dried over anhydrous magnesium sulfate. Insoluble materials were removed by filtration, and the filtrate was concentrated under reduced pressure. The residue was washed with EtOAc and diisopropyl ether, and dried to give the title compound (31 mg, 29%) as a yellow solid.

$^1$H-NMR (DMSO-d$_6$, 300 MHz) δ 2.66 (3H, s), 3.52-3.75 (5H, m), 4.19-4.32 (2H, m), 6.78 (1H, dd, J=2.8, 7.7 Hz), 7.27-7.44 (3H, m), 7.61-7.71 (2H, m), 7.74-7.81 (1H, 7.89-8.00 (2H, m), 8.09-8.18 (1H, m), 8.53-8.62 (1H, m), 8.64 (1H, d, J=7.7 Hz).

Example 79-B

Production of 3-[4-(2-fluorophenyl)-5-(1H-1,2,4-triazol-3-yl)-1,3-thiazol-2-yl]-2-methyl-5-(2-piperidin-1-ylethoxy)pyrazolo[1,5-a]pyridine p-toluenesulfonate

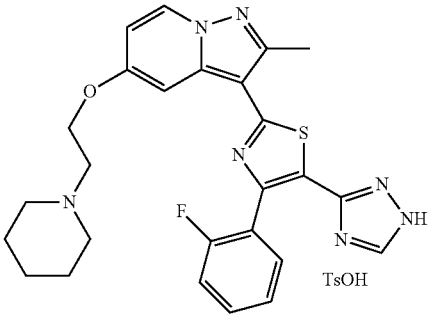

(i) Production of 3-{4-(2-fluorophenyl)-5-[1-(tetrahydro-2H-pyran-2-yl)-1H-1,2,4-triazol-3-yl]-1,3-thiazol-2-yl}-2-methyl-5-(2-piperidin-1-ylethoxy)pyrazolo[1,5-a]pyridine A mixture of 3-{4-(2-fluorophenyl)-5-[1-(tetrahydro-2H-pyran-2-yl)-1H-1,2,4-triazol-3-yl]-1,3-thiazol-2-yl}-2-methylpyrazolo[1,5-a]pyridin-5-ol (100 mg, 0.20 mmol) obtained in Example 74-B(vi), 1-(2-chloroethyl)piperidine hydrochloride (112 mg, 0.61 mmol), potassium carbonate (260 mg, 1.9 mmol) and DMF (10 mL) was stirred at 50° C. for 1 h. The mixture was allowed to cool to rt. To the reaction mixture were added water (100 mL) and EtOAc (100 mL), and the mixture was stirred for 30 min. The organic layer was washed with brine and dried over anhydrous magnesium sulfate. Insoluble materials were removed by filtration, and the filtrate was concentrated under reduced pressure. The residue was purified by basic silica gel column chromatography (MeOH/EtOAc=0/100→5/95) to give the title compound (112 mg, 95%) as a yellow solid.

$^1$H-NMR (DMSO-d$_6$, 300 MHz) δ 1.31-1.69 (9H, m), 1.69-2.11 (3H, m), 2.32-2.47 (4H, m), 2.66 (3H, s), 2.68-2.76 (2H, m), 3.55-3.70 (1H, m), 3.81-3.95 (1H, m), 4.20 (2H, t, J=6.2 Hz), 5.51-5.61 (1H, m), 6.76 (1H, dd, J=2.7, 7.5 Hz), 7.18-7.35 (2H, m), 7.41-7.56 (1H, m), 7.66-7.80 (2H, m), 8.63 (1H, d, J=7.5 Hz), 8.69 (1H, s).

(ii) Production of 3-[4-(2-fluorophenyl)-5-(1H-1,2,4-triazol-3-yl)-1,3-thiazol-2-yl]-2-methyl-5-(2-piperidin-1-ylethoxy)pyrazolo[1,5-a]pyridine p-toluenesulfonate To a solution of 3-{4-(2-fluorophenyl)-5-[1-(tetrahydro-2H-pyran-2-yl)-1H-1,2,4-triazol-3-yl]-1,3-thiazol-2-yl}-2-methyl-5-(2-piperidin-1-ylethoxy)pyrazolo[1,5-a]pyridine (110 mg, 0.19 mmol) obtained above in EtOH (5 mL) and THF (15 mL), was added 6N hydrochloric acid (1.5 mL), and the mixture was stirred at 70° C. for 1 h. The reaction mixture was allowed to cool to rt, and the solvent was evaporated. To the residue were added EtOAc (50 mL), THF (30 mL), 8N aqueous sodium hydroxide solution (1 mL) and saturated aqueous solution of sodium bicarbonate (300 mL), and the mixture was stirred for 30 min. The organic layer was washed with brine and dried over anhydrous magnesium sulfate. Insoluble materials were removed by filtration, and the filtrate was concentrated under reduced pressure. The residue was washed with EtOAc and diisopropyl ether, and dried to give 3-[4-(2-fluorophenyl)-5-(1H-1,2,4-triazol-3-yl)-1,3-thiazol-2-yl]-2-methyl-5-(2-piperidin-1-ylethoxy)pyrazolo[1,5-a]pyridine (81 mg, 86%) as a white solid, which was used in the next step without further purification.

A mixture of 3-[4-(2-fluorophenyl)-5-(1H-1,2,4-triazol-3-yl)-1,3-thiazol-2-yl]-2-methyl-5-(2-piperidin-1-ylethoxy)pyrazolo[1,5-a]pyridine (40 mg, 0.079 mmol) obtained above, p-toluenesulfonic acid monohydrate (33 mg, 0.17 mmol) and EtOH (1.5 mL) was heated to obtain clear solution. The solution was allowed to cool to rt and the resulting precipitate was collected by filtration to give the title compound (41 mg, 76%) as a pale yellow solid.

$^1$H-NMR (DMSO-$d_6$, 300 MHz) δ 1.24-1.94 (6H, m), 2.28 (3H, s), 2.68 (3H, s), 2.91-3.11 (2H, m), 3.47-3.65 (4H, m) 4.49 (2H, br s), 6.83 (1H, dd, J=2.6, 7.6, Hz), 7.04-7.17 (2H, m), 7.20-7.35 (2H, m), 7.44-7.58 (3H, m), 7.62-7.81 (2H, m), 8.57 (1H, s), 8.72 (1H, d, J=7.6 Hz), 9.22 (1H, br 14.15 (1H, br s).

Example 81-B

Production of 3-[4-(2,6-difluorophenyl)-5-(1H-1,2,4-triazol-3-yl)-1,3-thiazol-2-yl]-2-methylpyrazolo[1,5-a]pyridine

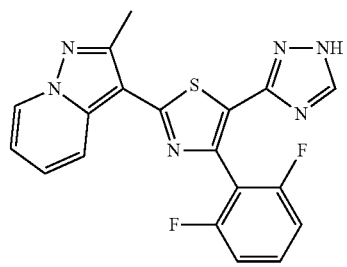 [SMILES: Cc1nn2ccccc2c1-c1nc(-c2c(F)cccc2F)c(-c2nc[nH]n2)s1]

(i) Production of methyl 4-(2,6-difluorophenyl)-2-(2-methylpyrazolo[1,5-a]pyridin-3-yl)-1,3-thiazole-5-carboxylate To a mixture of Methyl 2-(2-methylpyrazolo[1,5-a]pyridin-3-yl)-4-{[(trifluoromethyl)sulfonyl]oxy}-1,3-thiazole-5-carboxylate (500 mg, 1.2 mmol) obtained in Example 13-B (ii), 2,6-difluorophenylboronic acid (375 mg, 2.4 mmol), [1,1-bis(diphenylphosphino)ferrocene]palladium(II) dichloride dichloromethane complex (97 mg, 0.12 mmol) and cesium carbonate (1.2 g, 3.6 mmol) in DME (20 mL), was added water (1 mL) and the mixture was stirred at 80° C. for 3 h. The reaction mixture was allowed to cool to room temperature, and then water (100 mL) was added. The aqueous mixture was extracted with EtOAc (100 mL×2) and the combined organic layer was dried over anhydrous magnesium sulfate. Insoluble materials were removed by filtration and the filtrate was concentrated. The residue was purified by silica gel column chromatography (EtOAc) to give the title compound (147 mg, 32%) as a yellow solid.

$^1$H-NMR (DMSO-$d_6$, 300 MHz) δ 2.72 (3H, s), 3.76 (3H, s), 7.03-7.19 (1H, m), 7.20-7.36 (2H, m), 7.52-7.69 (2H, m), 8.23-8.33 (1H, m), 8.76-8.87 (1H, m).

(ii) Production of 4-(2,6-difluorophenyl)-2-(2-methylpyrazolo[1,5-a]pyridin-3-yl)-1,3-thiazole-5-carboxylic acid Using methyl 4-(2,6-difluorophenyl)-2-(2-methylpyrazolo[1,5-a]pyridin-3-yl)-1,3-thiazole-5-carboxylate (140 mg, 0.36 mmol) obtained above, MeOH (5 mL), THF (20 mL) and 8N aqueous sodium hydroxide solution (1.5 mL) as starting materials and in the similar manner described in Example 13-B(iv), the title compound (125 mg, 93%) was obtained as a white solid.

$^1$H-NMR (DMSO-$d_6$, 300 MHz) δ 2.70 (3H, s), 6.99-7.35 (3H, m), 7.45-7.72 (2H, m), 8.26 (1H, d, J=8.9 Hz), 8.80 (1H, d, J=6.8 Hz), 13.34 (1H, s).

(iii) Production of 4-(2,6-difluorophenyl)-2-(2-methylpyrazolo[1,5-a]pyridin-3-yl)-1,3-thiazole-5-carboxamide Using 4-(2,6-difluorophenyl)-2-(2-methylpyrazolo[1,5-a]pyridin-3-yl)-1,3-thiazole-5-carboxylic acid (120 mg, 11 mmol) obtained above, ammonium chloride (560 mg, 21 mmol), TEA (3 mL), HOBT (130 mg, 0.96 mmol), EDCI (350 mg, 1.8 mmol) and DMF (20 mL) as starting materials and in the similar manner described in Example 13-B(v), the title compound (105 mg, 88%) was obtained as a white solid.

$^1$H-NMR (DMSO-$d_6$, 300 MHz) δ 2.70 (3H, s), 7.09 (1H, dt, J=1.3, 6.9 Hz), 7.16-7.33 (2H, m), 7.41-7.83 (4H, m), 8.20-8.29 (1H, m), 8.79 (1H, d, J=6.9 Hz).

(iv) Production of 3-[4-(2,6-difluorophenyl)-5-(1H-1,2,4-triazol-3-yl)-1,3-thiazol-2-yl]-2-methylpyrazolo[1,5-a]pyridine Using 4-(2,6-difluorophenyl)-2-(2-methylpyrazolo[1,5-a]pyridin-3-yl)-1,3-thiazole-5-carboxamide (100 mg, 0.27 mmol) obtained above, N,N-dimethylformamide dimethylacetal (20 mL), AcOH (25 mL) and hydrazine monohydrate (0.4 mL) as starting materials and in the similar manner described in Example 13-B(vi), the title compound (70 mg, 66%) was obtained as a brown solid.

$^1$H-NMR (DMSO-d$_6$, 300 MHz) δ 2.70 (3H, s), 7.05 (1H, dt, J=1.3, 6.8 Hz), 7.13-7.26 (2H, m), 7.44-7.58 (2H, m), 8.17 (1H, s), 8.25 (1H, d, J=8.9 Hz), 8.75 (1H, d, J=6.8 Hz).

Example 82-B

Production of 2-methyl-5-(1-methyl-1H-pyrazol-4-yl)-3-[4-phenyl-5-(1H-1,2,4-triazol-3-yl)-1,3-thiazol-2-yl]pyrazolo[1,5-a]pyridine

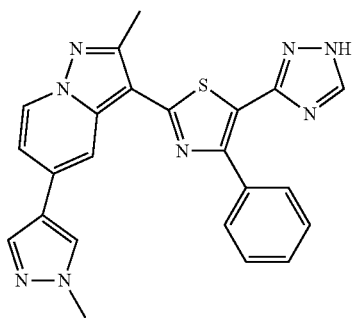 [SMILES: Cc1nn2ccc(-c3cnn(C)c3)cc2c1-c1nc(-c2ccccc2)c(-c2nc[nH]n2)s1]

(i) Production of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl trifluoromethanesulfonate To a solution of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (300 mg, 0.65 mmol) obtained in Example 31-B(i) in pyridine (15 mL), was added trifluoromethanesulfonic anhydride (280 mg, 1.0 mmol) at 0° C., and the mixture was stirred at 50° C. for 4 h. The reaction mixture was allowed to cool to 0° C., and then were added water (200 mL) and EtOAc (200 mL). The mixture was stirred for 30 min and then the organic layer was washed with brine and dried over anhydrous magnesium sulfate. Insoluble materials were removed by filtration and the filtrate was concentrated under reduced pressure. The residue was purified by silica gel column chromatography (EtOAc) to give the title compound (303 mg, 78%) as a yellow solid.

$^1$H-NMR (DMSO-d$_6$, 300 MHz) δ 1.50-1.81 (3H, m), 1.87-2.14 (3H, m), 2.74 (3H, s), 3.60-3.75 (1H, m), 3.88-3.99 (1H, m), 5.61 (1H, dd, =2.9, 8.8 Hz), 7.27-7.49 (3H, m), 7.90-7.99 (2H, m), 8.50 (1H, d, J=2.6 Hz), 8.58 (1H, dd, J=1.8, 5.8 Hz), 8.82 (1H, s), 9.03 (1H, d, J=7.6 Hz).

(ii) Production of 2-methyl-5-(1-methyl-1H-pyrazol-4-yl)-3-[4-phenyl-5-(1H-1,2,4-triazol-3-yl)-1,3-thiazol-2-yl]pyrazolo[1,5-a]pyridine To a mixture of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl trifluoromethanesulfonate (150 mg, 0.25 mmol) obtained above, 1-methyl-4-(4,4,5,5-tetramethyl-1,3,2-dioxaborolan-2-yl)-1H-pyrazole (106 mg, 0.51 mmol), [1,1-bis(diphenylphosphino)ferrocene]palladium(II) dichloride dichloromethane complex (41 mg, 0.052 mmol) and cesium carbonate (248 mg, 0.76 mmol) in DME (15 mL) was added water (3 mL) and the mixture was stirred at 80° C. for 2 h. The reaction mixture was allowed to cool to room temperature, water (100 mL) was added, and the mixture was extracted with EtOAc (100 mL×2). The combined organic layer was dried over anhydrous magnesium sulfate and insoluble materials were removed by filtration. The filtrate was concentrated. The residue was dissolved in THF (25 mL), and then were added EtOH (5 mL) and 2N hydrochloric acid (3 mL). The mixture was stirred at 70° C. for 1 h. The reaction mixture was allowed to cool to rt. To the reaction mixture were added EtOAc (200 mL), 1N aqueous sodium hydroxide solution (10 mL) and water (100 mL), and the mixture was stirred for 1 h. The organic layer was washed with brine and dried over anhydrous magnesium sulfate. Insoluble materials were removed by filtration and the filtrate was concentrated under reduced pressure. The residue was crystallized from EtOAc to give the title compound (77 mg, 69%) as a yellow solid.

$^1$H-NMR (DMSO-d$_6$, 300 MHz) δ 2.71 (3H, s), 3.92 (3H, s), 7.30 (1H, dd, J=1.9, 7.2, Hz), 7.32-7.59 (3H, m), 7.83-8.07 (3H, m), 8.24-8.47 (2H, m), 8.62 (1H, br s), 8.75 (1H, d, J=7.2 Hz), 14.27 (1H, br s).

Example 83-B

Production of 2-methyl-5-morpholin-4-yl-3-[4-phenyl-5-(1H-1,2,4-triazol-3-yl)-1,3-thiazol-2-yl]pyrazolo[1,5-a]pyridine

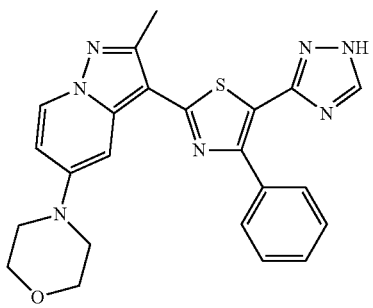 [SMILES: Cc1nn2ccc(N3CCOCC3)cc2c1-c1nc(-c2ccccc2)c(-c2nc[nH]n2)s1]

(i) Product ion of 2-methyl-5-morpholin-4-yl-3-{4-phenyl-5-[1-(tetrahydro-2H-pyran-2-yl)-1H-1,2,4-triazol-3-yl]-1,3-thiazol-2-yl}pyrazolo[1,5-a]pyridine A suspension 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl trifluoromethanesulfonate (150 mg, 0.25 mmol) obtained in Example 82-13(i), morpholine (501 mg, 5.73 mmol), tris(dibenzylideneacetone)dipalladium (0) (45 mg, 0.049 mmol), (R)-BINAP (50 mg, 0.080 mmol) and cesium carbonate (720 mg, 2.21 mmol) in toluene (30 mL) was stirred at 110° C. for 1 h. The reaction mixture was allowed to cool to room temperature, and then water (150 mL) was added. The mixture was extracted with EtOAc (150 mL×2). The combined organic layers were dried over anhydrous magnesium sulfate and insoluble materials were removed by filtration. The filtrate was concentrated and the residue was purified by silica gel column chromatography (EtOAc/hexane=10/90→100/0) to give the title compound (75 mg, 56%) as a yellow solid.

$^1$H-NMR (DMSO-d$_6$, 300 MHz) δ 1.47-1.78 (3H, m), 1.86-2.17 (3H, m), 2.64 (3H, s), 3.21-3.36 (4H, m), 3.59-3.72 (1H, m), 3.75-3.85 (4H, m), 3.88-4.00 (1H, m), 5.60 (1H, dd,

J=3.0, 8.8 Hz), 6.96 (1H, dd, J=2.5, 7.7 Hz), 7.32-7.50 (3H, m), 7.54 (1H, d, J=2.5 Hz), 7.88-8.03 (2H, m), 8.54 (1H, d, J=7.7 Hz), 8.79 (1H, s).

(ii) Production of 2-methyl-5-morpholin-4-yl-3-[4-phenyl-5-(1H-1,2,4-triazol-3-yl)-1,3-thiazol-2-yl]pyrazolo[1,5-a]pyridine To a solution of 2-methyl-5-morpholin-4-yl-3-{4-phenyl-5-[1-(tetrahydro-2H-pyran-2-yl)-1H-1,2,4-triazol-3-yl]-1,3-thiazol-2-yl}pyrazolo[1,5-a]pyridine (75 mg, 0.14 mmol) obtained above in THF (25 mL), were added EtOH (5 mL) and 4N solution of hydrogen chloride in EtOAc (3 mL), and the mixture was stirred at 70° C. for 2 h. The reaction mixture was allowed to cool to rt. To the reaction mixture were added EtOAc (200 mL), saturated aqueous solution of sodium bicarbonate (200 mL) and 1N aqueous sodium hydroxide solution (10 mL), and the mixture was stirred for 30 min. The organic layer was washed with brine and dried over anhydrous magnesium sulfate. Insoluble materials were removed by filtration, and the filtrate was concentrated under reduced pressure. The residue was crystallized from 2-propanol to give the title compound (48 mg, 76%) as a white solid.

$^1$H-NMR (DMSO-$d_6$, 300 MHz) δ 2.64 (3H, s), 3.40-3.48 (4H, m), 3.73-3.87 (4H, m), 6.96 (1H, dd, J=2.6, 2.6 Hz), 7.31-7.62 (4H, m), 7.88-8.04 (2H, m), 8.54 (1H, d, J=7.7 Hz), 8.66 (1H, s), 14.25 (1H, s).

Example 84-B

Production of 3-[4-(2-ethoxy-6-fluorophenyl)-5-(1H-1,2,4-triazol-3-yl)-1,3-thiazol-2-yl]-2-methylpyrazolo[1,5-a]pyridine

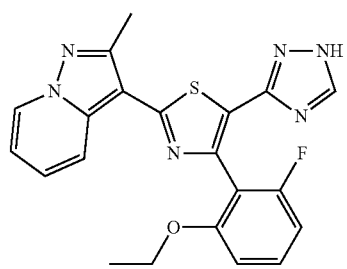 [SMILES: CCOc1cccc(F)c1-c1nc(-c2c(C)nn3ccccc23)sc1-c1nc[nH]n1]

(i) Production of methyl 4-(2-ethoxy-6-fluorophenyl)-2-(2-methylpyrazolo[1,5-a]pyridin-3-yl)-1,3-thiazole-5-carboxylate A suspension of Methyl 2-(2-methylpyrazolo[1,5-a]pyridin-3-yl)-4-{[(trifluoromethyl)sulfonyl]oxy}-1,3-thiazole-5-carboxylate (306 mg, 0.72 mmol) obtained in Example 13-B(ii), (2-ethoxy-6-fluorophenyl)boronic acid (262 mg, 1.4 mmol), [1,1-bis(diphenylphosphino)ferrocene]palladium (II) dichloride dichloromethane complex (80 mg, 0.098 mmol) and cesium carbonate (850 mg, 2.6 mmol) in DME (20 mL), was added water (2 mL), and the mixture was stirred at 90° C. for 5 h. The reaction mixture was allowed to cool to rt, water (200 mL) was added, and the mixture was extracted with EtOAc (100 mL×2). The combined organic layers were dried over anhydrous magnesium sulfate, insoluble materials were removed by filtration, and the filtrate was concentrated. The residue was purified by silica gel column chromatography (EtOAc/hexane=50/50→100/0) to give the title compound (295 mg, 100%) as a yellow solid.

$^1$H-NMR (DMSO-$d_6$, 300 MHz) δ 1.07-1.23 (3H, m), 2.70 (3H, s), 3.72 (3H, s), 3.97-4.13 (2H, m), 6.85-7.61 (5H, m), 8.29 (1H, d, J=8.9 Hz), 8.80 (1H, d, J=6.8 Hz).

(ii) Production of 4-(2-ethoxy-6-fluorophenyl)-2-(2-methylpyrazolo[1,5-a]pyridin-3-yl)-1,3-thiazole-5-carboxylic acid Using methyl 4-(2-ethoxy-6-fluorophenyl)-2-(2-methylpyrazolo[1,5-a]pyridin-3-yl)-1,3-thiazole-5-carboxylate (295 mg, 0.72 mmol) obtained above, MeOH (5 mL), THF (25 mL) and 8N aqueous sodium hydroxide solution (2 mL) as starting materials and in the similar manner described in Example 13-B(iv), the title compound (281 mg, 98%) was obtained as a yellow solid.

$^1$H-NMR (DMSO-$d_6$, 300 MHz) δ 1.11-1.26 (3H, m), 2.69 (3H, s), 3.94-4.16 (2H, m), 6.81-7.01 (2H, m), 7.04-7.18 (1H, m), 7.35-7.67 (2H, m), 8.13-8.36 (1H, m), 8.78 (1H, d, J=7.0 Hz), 13.04 (1H, br s).

(iii) Production of 4-(2-ethoxy-6-fluorophenyl)-2-(2-methylpyrazolo[1,5-a]pyridin-3-yl)-1,3-thiazole-5-carboxamide Using 4-(2-ethoxy-6-fluorophenyl)-2-(2-methylpyrazolo[1,5-a]pyridin-3-yl)-1,3-thiazole-5-carboxylic acid (280 mg, 0.70 mmol) obtained above, ammonium chloride (1.4 g, 26 mmol), TEA (2 mL), HOBT (150 mg, 1.1 mmol), EDCI (720 mg, 3.6 mmol) and DMF (5 mL) as starting materials and in the similar manner described in Example 13-B(v), the title compound (277 mg, 99%) was obtained as a white solid.

$^1$H-NMR (DMSO-$d_5$, 300 MHz) δ 1.16-1.28 (3H, m), 2.69 (3H, s), 3.91-4.14 (2H, m), 6.80-7.13 (4H, m), 7.33-7.59 (3H, m), 8.13-8.34 (1H, m), 8.77 (1H, d, J=6.8 Hz).

(iv) Production of 3-[4-(2-ethoxy-6-fluorophenyl)-5-(1H-1,2,4-triazol-3-yl)-1,3-thiazol-2-yl]-2-methylpyrazolo[1,5-a]pyridine Using 4-(2-ethoxy-6-fluorophenyl)-2-(2-methylpyrazolo[1,5-a]pyridin-3-yl)-1,3-thiazole-5-carboxamide (270 mg, 0.68 mmol) obtained above, N,N-dimethylformamide dimethylacetal (15 mL), AcOH (25 mL) and hydrazine monohydrate (0.4 mL) as starting materials and in the similar manner described in Example 13-B(vi), the title compound (147 mg, 51%) was obtained as a pale yellow solid.

$^1$H-NMR (DMSO-$d_6$, 300 MHz) δ 0.86-1.05 (3H, m), 2.72 (3H, s), 3.80-4.09 (2H, m), 6.83-6.97 (2H, m), 7.01-7.11 (1H, m), 7.33-7.55 (2H, m), 8.20-8.34 (1H, m), 8.52 (1H, br s), 8.76 (1H, d, J=7.0 Hz), 14.07 (1H, s).

Example 85-B

Production of 2-methyl-5-(3-morpholin-4-ylpropoxy)-3-[4-phenyl-5-(1H-1,2,4-triazol-3-yl)-1,3-thiazol-2-yl]pyrazolo[1,5-a]pyridine p-toluenesulfonate

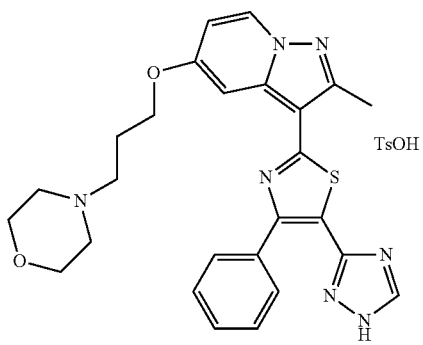

(i) Production of 4-(3-chloropropyl)morpholine

To a solution of morpholine (2.00 g, 23.0 mmol) in toluene (200 mL), was added 1-bromo-3-chloropropane (4.55 mL, 45.9 mmol) and the mixture was stirred for 4 h at 70° C. Insoluble materials were removed by filtration and the filtrate has been concentrated under reduced pressure. The residue was purified by silica gel column chromatography (EtOAc/hexane=70/30→100/0) to give the title compound (1.27 g, 68%) as a colorless oil.

$^1$H-NMR (DMSO-d$_6$, 300 MHz) δ 1.95 (2 H, quin, J=6.6 Hz), 2.34-2.55 (6 H, m), 3.61 (2 H, t, J=6.6 Hz), 3.66-3.77 (4 H, m), (ii) Production of 2-methyl-5-(3-morpholin-4-ylpropoxy)-3-{4-phenyl-5-[1-(tetrahydro-2H-pyran-2-yl)-1H-1,2,4-triazol-3-yl]-1,3-thiazol-2-yl}pyrazolo[1,5-a]pyridine To a suspension of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (100 mg, 0.218 mmol) obtained in Example 31-B-(i) and potassium carbonate (60.3 mg, 0.436 mmol) in DMF (4 mL), was added 4-(3-chloropropyl)morpholine (71.3 mg, 0.436 mmol) obtained above and the mixture was stirred for 5 h at 60° C. To the reaction mixture, were added EtOAc (20 mL) and saturated aqueous solution of sodium bicarbonate (15 mL). The organic layer was separated and then aqueous layer was extracted with EtOAc (5 mL). The combined organic layers were washed with brine (5 mL) and then dried over anhydrous sodium sulfate. Insoluble materials were removed by filtration and the filtrate was concentrated under reduced pressure. The residue was purified by silica gel column chromatography (EtOAc/hexane=30/70→60/40) to give the title compound (128 mg, quant) as a colorless solid $^1$H-NMR (DMSO-d$_6$, 300 MHz) δ 1.51-1.62 (2 H, m), 1.79-2.12 (6 H, m), 2.28-2.41 (2 H, m), 2.30-2.40 (1 H, m), 2.45 (2 H, t, J=7.0 Hz), 2.66 (3 H, s), 3.48-3.61 (6 H, m), 3.84-4.01 (1 H, m), 4.19 (2 H, t, J=6.5 Hz), 5.60 (1 H, dd, J=3.0, 8.9 Hz), 6.75 (1 H, dd, J=7.7 Hz), 7.30-7.53 (3 H, m), 7.74 (1 H, d, J=2.7 Hz), 7.85-8.03 (2 H, m), 8.63 (1 H, d, J=7.7 Hz), 8.79 (1 H, s).

(iii) Production of 2-methyl-5-(3-morpholin-4-ylpropoxy)-3-[4-phenyl-5-(1H-1,2,4-triazol-3-yl)-1,3-thiazol-2-yl]pyrazolo[1,5-a]pyridine To a solution of 2-methyl-5-(3-morpholin-4-ylpropoxy)-3-{4-phenyl-5-[1-(tetrahydro-2H-pyran-2-yl)-1H-1,2,4-triazol-3-yl]-1,3-thiazol-2-yl}pyrazolo[1,5-a]pyridine (128 mg, 0.218 mmol) obtained above in THF (3 mL) and MeOH (1 mL), was added 3N hydrochloric acid (1 mL) and the mixture was stirred for 1 h at 60° C. To the reaction mixture was added a 3:1 mixture of EtOAc and THF (20 mL) and saturated aqueous solution of sodium bicarbonate (15 mL) and then organic layer was separated. The organic layer was concentrated under reduced pressure and the residue was washed with EtOAc (5 mL) to give title compound (86 mg, 79%) as a pale yellow solid.

$^1$H-NMR (DMSO-d$_6$, 300 MHz) δ 1.91-2.03 (2 H, m), 2.33-2.40 (4 H, m), 2.45 (2 H, t, J=7.2 Hz), 2.66 (3 H, s), 3.49-3.58 (4 H, m), 4.19 (2 H, t, J=6.5 Hz), 6.76 (1 H, dd, J=2.7, 7.6 Hz), 7.36-7.48 (3 H, m), 7.74 (1 H, d, J=2.7 Hz), 7.89-8.00 (2 H, m), 8.61 (1 H, br s), 8.63 (1 H, d, J=7.6 Hz), 14.25 (1 H, br s).

(iv) Production of 2-methyl-5-(3-morpholin-4-ylpropoxy)-3-[4-phenyl-5-(1H-1,2,4-triazol-3-yl)-1,3-thiazol-2-yl]pyrazolo[1,5-a]pyridine p-toluenesulfonate To a suspension of 2-methyl-5-(3-morpholin-4-ylpropoxy)-3-[4-phenyl-5-(1H-1,2,4-triazol-3-yl)-1,3-thiazol-2-yl]pyrazolo[1,5-a]pyridine (85.8 mg, 0.171 mmol) obtained above in EtOH (10 mL), was added a solution of p-toluene sulfonic acid monohydrate (71.6 mg, 0.376 mmol) in EtOH (2 mL) and then resulting mixture was concentrated under reduced pressure. The residue was crystallized from EtOH (2 mL) and EtOAc (6 mL) to obtain title compound (106 mg, 92%) as a pale yellow solid.

$^1$H-NMR (DMSO-d$_6$, 300 MHz) δ 2.17-2.26 (2 H, m), 2.27 (3 H, s), 2.67 (3 H, s), 2.95-3.21 (2 H, m), 3.35-3.41 (2 H, m), 3.42-3.56 (2 H, m), 3.56-3.75 (2 H, m), 3.93-4.08 (2 H, m), 4.19-4.36 (2 H, m), 6.76 (1 H, dd, J=2.7, 7.6 Hz), 7.11 (2 H, d, J=7.9 Hz), 7.30-7.54 (5H, m), 7.71 (1 H, d, J=2.7 Hz), 7.90-8.02 (2 H, m), 8.58-8.74 (2 H, m), 9.51 (1 H, br s), 14.27

(1 H, br s). Acidic proton from p-toluenesulfonic acid has been observed with intensity of 1 H.

Example 86-B

Production of 5-[2-(4,4-difluoropiperidin-1-yl)ethoxy]-2-methyl-3-[4-phenyl-5-(1H-1,2,4-triazol-3-yl)-1,3-thiazol-2-yl]pyrazolo[1,5-a]pyridine di-p-toluenesulfonate

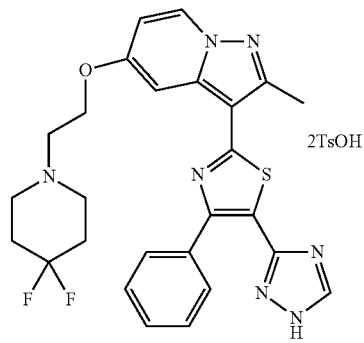

(i) Production of 1-(2-chloroethyl)-4,4-difluoropiperidine

To a solution of 4,4-difluoropiperidine (1.00 g, 6.35 mmol) in acetone (15 mL), were added potassium carbonate (2.19 g, 15.9 mmol) and 1-bromo-2-chloroethane (635 μL, 7.62 mmol) and the mixture was stirred for 8 h at 50° C. Insoluble materials were removed by filtration and the filtrate was concentrated under reduced pressure. The residue was purified by silica gel column chromatography (EtOAc/hexane=0/100→30/70) to obtain title compound (188 mg, 16%) as a pale yellow oil.

$^1$H-NMR (DMSO-$d_6$, 300 MHz) δ 1.92-2.09 (4 H, m), 2.58-2.68 (4 H, m), 2.78 (2 H, t, J=6.9 Hz), 3.57 (2 H, t, J=6.9 Hz).

(ii) Production of 5-[2-(4,4-difluoropiperidin-1-yl)ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine The title compound has been prepared according to the similar manner described in 85-B (ii) using 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (100 mg, 0.218 mmol) obtained in Example 31-B-(i), potassium carbonate (75.3 mg, 0.545 mmol) and 1-(2-chloroethyl)-4,4-difluoropiperidine (80.0 mg, 0.436 mmol) obtained above. The crude product was purified by basic silica gel column chromatography (EtOAc/hexane=20/80→50/50) to give pure title compound (120 mg, 91%) as a colorless solid.

$^1$H-NMR (DMSO-$d_6$, 300 MHz) δ 1.50-1.62 (2 H, m), 1.62-1.76 (1 H, m), 1.82-2.14 (7 H, m), 2.58-2.69 (4 H, m), 2.66 (3 H, s), 2.87 (2 H, t, J=5.9 Hz), 3.61-3.73 (1 H, m), 3.84-4.04 (1 H, m), 4.27 (2 H, t, J=5.9 Hz), 5.60 (1 H, dd, J=3.0, 8.9 Hz), 6.77 (1 H, dd, J=2.7, 7.6 Hz), 7.26-7.54 (3 H, m), 7.76 (1 H, d, J=2.7 Hz), 7.90-8.04 (2 H, m), 8.64 (1 H, d, J=7.6 Hz), 8.80 (1 H, s).

(iii) Production of 5-[2-(4,4-difluoropiperidin-1-yl)ethoxy]-2-methyl-3-[4-phenyl-5-(1H-1,2,4-triazol-3-yl)-1,3-thiazol-2-yl]pyrazolo[1,5-a]pyridine The title compound has been prepared according to the similar manner described in 85-B (iii) using 5-[2-(4,4-difluoropiperidin-1-yl)ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (120 mg, 0.198 mmol) obtained above. The crude product was purified by washing with EtOAc (3 mL) to give pure title compound (89 mg, 86%) as a colorless solid.

$^1$H-NMR (DMSO-$d_6$, 300 MHz) δ 1.83-2.05 (4 H, m), 2.60-2.66 (4 H, m), 2.66 (3 H, s), 2.87 (2 H, t, J=5.9 Hz), 4.28 (2 H, t, J=5.9 Hz), 6.77 (1 H, dd, J=2.7, 7.5 Hz), 7.35-7.52 (3 H, m), 7.75 (1 H, d, J=2.7 Hz), 7.91-8.06 (2 H, m), 8.52 (1 H, br s), 8.63 (1 H, d, J=7.6 Hz). No acidic proton of triazole.

(iv) Production of 5-[2-(4,4-difluoropiperidin-1-yl)ethoxy]-2-methyl-3-[4-phenyl-5-(1H-1,2,4-triazol-3-yl)-1,3-thiazol-2-yl]pyrazolo[1,5-a]pyridine di-p-toluenesulfonate The title compound has been prepared according to the similar manner described in 85-B (iv) from 5-[2-(4,4-difluoropiperidin-1-yl)ethoxy]-2-methyl-3-[4-phenyl-5-(1H-1,2,4-triazol-3-yl)-1,3-thiazol-2-yl]pyrazolo[1,5-a]pyridine (87.8 mg, 0.168 mmol) and p-toluenesulfonic acid monohydrate (70.3 mg, 0.370 mmol). The crude product was washed with EtOH (4 mL) to give pure title compound (100 mg, 69%) as a yellow solid.

$^1$H-NMR (DMSO-$d_6$, 300 MHz) δ 2.20-2.50 (4 H, m), 2.29 (6 H, s), 2.69 (3 H, s), 3.18-3.39 (2 H, m), 3.74 (4 H, br s), 4.47-4.66 (2 H, m), 6.84 (1 H, dd, J=2.6, 7.5 Hz), 7.11 (4H, d, J=7.9 Hz), 7.33-7.55 (7 H, m), 7.75 (1 H, d, J=2.6 Hz), 7.87-8.01 (2 H, m), 8.63 (1 H, br s), 8.73 (1 H, d, J=7.5 Hz), 9.75 (1 H, br s), 14.28 (1 H, br s). acidic proton of p-toluenesulfonic acid has been observed with intensity of 1H.

Example 87-B

Production of 5-[2-(4-fluoropiperidin-1-yl)ethoxy]-2-methyl-3-[4-phenyl-5-(1H-1,2,4-triazol-3-yl)-1,3-thiazol-2-yl]pyrazolo[1,5-a]pyridine di-p-toluenesulfonate

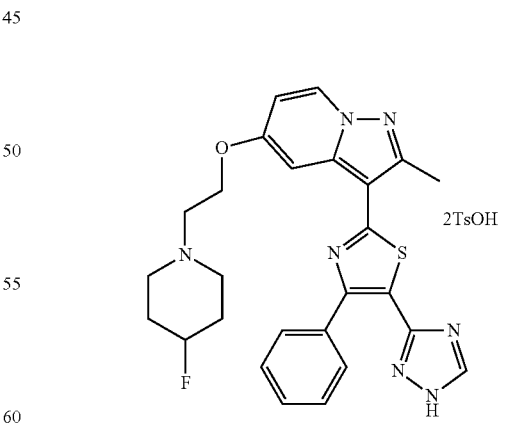

(i) Production of 1-(2-chloroethyl)-4-fluoropiperidine

The title compound has been prepared according to the similar manner described in 86-B (i) using 4-fluoropiperidine hydrochloride (1.00 g, 7.16 mmol) and 1-bromo-2-chloroethane (717 µL, 8.60 mmol). The crude product has been purified by silica gel column chromatography (EtOAc/hexane=10/90→40/60) to obtain pure title compound (250 mg, 21%) as a pale yellow oil.

$^1$H-NMR (DMSO-d$_6$, 300 MHz) δ 1.80-2.02 (4 H, m), 2.41-2.54 (2 H, m), 2.57-2.69 (2 H, m), 2.73 (2 H, t, J=7.1 Hz), 3.58 (2 H, t, J=7.1 Hz), 4.56-4.81 (1 H, m).

(ii) Production of 5-[2-(4-fluoropiperidin-1-yl)ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine The title compound has been prepared according to the similar manner described in 85-B (ii) from 1-(2-chloroethyl)-4-fluoropiperidine (72.2 mg, 0.436 mmol) obtained above, 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (100 mg, 0.218 mmol) obtained in Example 31-B-(i) and potassium carbonate (75.3 mg, 0.545 mmol). The crude product has been roughly purified by simple filtration through basic silica gel pad and was used without further purification (pale yellow oil).

$^1$H-NMR (DMSO-d$_6$, 300 MHz) δ 1.48-2.15 (10 H, m), 2.30-2.58 (4 H, m), 2.66 (3 H, s), 2.78 (2 H, t, J=6.0 Hz), 3.54-3.75 (1 H, m), 3.87-4.00 (1 H, m), 4.26 (2 H, t, J=6.0 Hz), 4.48-4.86 (1 H, m), 5.60 (1 H, dd, J=2.8, 8.9 Hz), 6.77 (1 H, dd, J=2.7, 7.6 Hz), 7.35-7.51 (3H, m), 7.77 (1 H, d, J=2.7 Hz), 7.90-8.03 (2 H, m), 8.63 (1 H, d, J=7.6 Hz), 8.80 (1 H, s).

(iii) Production of 5-[2-(4-fluoropiperidin-1-yl)ethoxy]-2-methyl-3-[4-phenyl-5-(1H-1,2,4-triazol-3-yl)-1,3-thiazol-2-yl]pyrazolo[1,5-a]pyridine The title compound has been prepared according to the similar manner described in 85-B (iii) from 5-[2-(4-fluoropiperidin-1-yl)ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine obtained above. The crude product was purified by washing with EtOAc (5 mL) to give pure title compound (89 mg, 81%) as a colorless solid.

$^1$H-NMR (DMSO-d$_6$, 300 MHz) δ 1.60-1.95 (4 H, m), 2.37-2.46 (2 H, m), 2.60-2.70 (2 H, m), 2.66 (3 H, s), 2.79 (2 H, t, J=5.9 Hz), 4.26 (2 H, t, J=5.9 Hz), 4.50-4.84 (1 H, m), 6.76 (1 H, dd, J=2.7, 7.6 Hz), 7.32-7.48 (3 H, m), 7.76 (1 H, d, J=2.7 Hz), 7.94-8.10 (2 H, m), 8.50 (1 H, br s), 8.63 (1 H, d, J=7.6 Hz). Acidic proton of triazole was not observed.

(iv) Production of 5-[2-(4-fluoropiperidin-1-yl)ethoxy]-2-methyl-3-[4-phenyl-5-(1H-1,2,4-triazol-3-yl)-1,3-thiazol-2-yl]pyrazolo[1,5-a]pyridine di-p-toluenesulfonate The title compound has been prepared according to the similar manner described in 85-B (iv) from 5-[2-(4-fluoropiperidin-1-yl)ethoxy]-2-methyl-3-[4-phenyl-5-(1H-1,2,4-triazol-3-yl)-1,3-thiazol-2-yl]pyrazolo[1,5-a]pyridine (89.3 mg, 0.177 mmol) and p-toluenesulfonic acid monohydrate (74.1 mg, 0.389 mmol). The crude product was crystallized from EtOH (1 mL) and EtOAc (4 mL) to give pure title compound (137 mg, 91%) as a yellow solid.

$^1$H-NMR (DMSO-d$_6$, 300 MHz) δ 2.05-2.17 (2 H, m), 2.21-2.36 (2 H, m), 2.29 (6 H, s), 2.69 (3 H, s), 3.50-3.74 (6 H, m), 4.49-4.61 (2 H, m), 4.87-5.12 (1 H, m), 6.80-6.89 (1 H, m), 7.11 (4 H, d, J=7.7 Hz), 7.36-7.53 (7 H, m), 7.72-7.77 (1 H, m), 7.88-8.01 (2 H, m), 8.64 (1 H, br s), 8.73 (1 H, d, J=7.4 Hz), 9.45 (1 H, br s), 14.24 (1 H, br s). Acidic proton of p-toluenesulfonic acid has been observed with intensity of 1H.

Example 88-B

Production of 2-methyl-5-[2-(4-methylpiperazin-1-yl)ethoxy]-3-[4-phenyl-5-(1H-1,2,4-triazol-3-yl)-1,3-thiazol-2-yl]pyrazolo[1,5-a]pyridinedi-p-toluenesulfonate

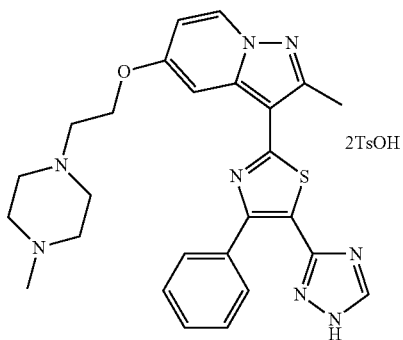

(i) Production of 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine The title compound has been prepared according to the similar manner described in 85-B (ii) from 1-bromo-2-chloroethane (163 µL, 1.96 mmol), 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (300 mg, 0.654 mmol) obtained in Example 31-B-(i) and cesium carbonate (639 mg, 1.96 mmol). The crude product has been roughly purified by simple filtration through silica gel pad (5 g) and then washed with diethyl ether (20 mL) to give title compound (319 mg, 93%) as a colorless solid.

$^1$H-NMR (DMSO-d$_6$, 300 MHz) δ 1.49-1.74 (3 H, m), 1.89-2.12 (3 H, m), 2.67 (3 H, s), 3.60-3.72 (1 H, m), 3.89-3.99 (1 H, m), 4.05 (2 H, t, J=5.2 Hz), 4.44 (2 H, t, J=5.2 Hz), 5.60 (1 H, dd, J=2.9, 8.8 Hz), 6.82 (1 H, dd, J=2.7, 7.6 Hz), 7.39-7.50 (3 H, m), 7.73 (1 H, d, J=2.7 Hz), 7.91-7.99 (2 H, m), 8.67 (1 H, d, J=7.6 Hz), 8.80 (1 H, s).

(ii) Production of 2-methyl-5-[2-(4-methylpiperazin-1-yl)ethoxy]-3-{4-phenyl-5-[1-(tetrahydro-2H-pyran-2-yl)-1H-1,2,4-triazol-3-yl]-1,3-thiazol-2-yl}pyrazolo[1,5-a]pyridine To a solution of 5-(2-chloroethoxy)-2-methyl-3-{4-phenyl-5-[1-(tetrahydro-2H-pyran-2-yl)-1H-1,2,4-triazol-3-yl]-

1,3-thiazol-2-yl}pyrazolo[1,5-a]pyridine (77.0 mg, 0.148 mmol) obtained above in DMF (2 mL), were added TEA (183 μL, 1.33 mmol) and 1-methylpiperazine (148 μL, 1.33 mmol) and the mixture was stirred for 18 h at 90° C. To the mixture were added EtOAc (20 mL) and saturated aqueous solution of sodium bicarbonate (15 mL) and then organic layer was separated. The organic layer was washed with brine (5 mL) and then dried over anhydrous sodium sulfate. Insoluble materials were removed by filtration and the filtrate was concentrated under reduced pressure. The residue was purified by basic silica gel column chromatography (EtOAc/hexane=80/20→100/0) to obtain crude title compound as a pale yellow syrup. This crude product has been used in the next step without further purification.

(iii) Production of 2-methyl-5-[2-(4-methylpiperazin-1-yl)ethoxy]-3-[4-phenyl-5-(1H-1,2,4-triazol-3-yl)-1,3-thiazol-2-yl]pyrazolo[1,5-a]pyridine The title compound has been prepared according to the similar manner described in 85-B (iii) from 2-methyl-5-[2-(4-methylpiperazin-1-yl)ethoxy]-3-{4-phenyl-5-[1-(tetrahydro-2H-pyran-2-yl)-1H-1,2,4-triazol-3-yl]-1,3-thiazol-2-yl}pyrazolo[1,5-a]pyridine obtained above. The crude product was purified by washing with EtOAc (4 mL) to give pure title compound (33 mg, 64%) as a colorless solid.

$^1$H-NMR (DMSO-$d_6$, 300 MHz) δ 2.14 (3 H, s), 2.25-2.38 (4 H, m), 2.41-2.50 (4 H, m), 2.66 (3 H, s), 2.77 (2 H, t, J=5.9 Hz), 4.25 (2 H, t, J=5.9 Hz), 6.76 (1 H, dd, J=2.7, 7.4 Hz), 7.35-7.47 (3 H, m), 7.76 (1 H, d, J=2.7 Hz), 7.92-8.04 (2 H, m), 8.56 (1 H, s), 8.63 (1 H, d, J=7.4 Hz), 14.24 (1 H, br s).

(iv) Production of 2-methyl-5-[2-(4-methylpiperazin-1-yl)ethoxy]-3-[4-phenyl-5-(1H-1,2,4-triazol-3-yl)-1,3-thiazol-2-yl]pyrazolo[1,5-a]pyridine di-p-toluenesulfonate The title compound has been prepared according to the similar manner described in 85-B (iv) from 2-methyl-5-[2-(4-methylpiperazin-1-yl)ethoxy]-3-[4-phenyl-5-(1H-1,2,4-triazol-3-yl)-1,3-thiazol-2-yl]pyrazolo[1,5-a]pyridine (32.5 mg, 0.0649 mmol) and p-toluenesulfonic acid monohydrate (27.2 mg, 0.143 mmol). Title compound (48 mg, 87%) has been obtained as a yellow solid by the addition of EtOAc to the reaction mixture followed by collection of the resulting precipitate by filtration.

$^1$H-NMR (DMSO-$d_6$, 300 MHz) δ 2.29 (6 H, s), 2.67 (3 H, s), 2.80 (3 H, br s), 2.92-3.54 (10 H, m), 4.34 (2 H, br s), 6.78 (1 H, dd, J=2.7, 7.5 Hz), 7.11 (4 H, d, J=7.7 Hz), 7.35-7.54 (7 H, m), 7.72 (1 H, d, J=2.7 Hz), 7.85-8.01 (2 H, m), 8.63 (1 H, br s), 8.67 (1 H, d, J=7.5 Hz), 9.37 (1 H, br s), 14.24 (1 H, br s). Acidic proton of p-toluenesulfonic acid has been observed with intensity of 1H.

Example 89-B

Production of 2-methyl-5-{2-[4-(methylsulfonyl)piperazin-1-yl]ethoxy}-3-[4-phenyl-5-(1H-1,2,4-triazol-3-yl)-1,3-thiazol-2-yl]pyrazolo[1,5-a]pyridine di-p-toluenesulfonate

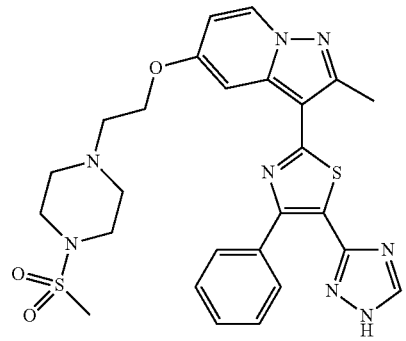 [SMILES: Cc1nn2ccc(OCCN3CCN(S(C)(=O)=O)CC3)cc2c1-c1nc(-c2ccccc2)c(-c2nc[nH]n2)s1]

(i) Production of 2-methyl-5-{2-[4-(methylsulfonyl)piperazin-1-yl]ethoxy}-3-{4-phenyl-5-[1-(tetrahydro-2H-pyran-2-yl)-1H-1,2,4-triazol-3-yl]-1,3-thiazol-2-yl}pyrazolo[1,5-a]pyridine Title compound has been prepared according to the similar manner described in 88-B (ii) from 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (120.0 mg, 0.230 mmol) obtained 88-B (i), 1-(methylsulfonyl)piperazine (75.7 mg, 0.461 mmol), potassium carbonate (63.7 mg, 0.461 mmol) as a base instead of TEA and sodium iodide (69.1 mg, 0.461 mmol) as an additive, Crude title compound has been obtained as yellow oil after extraction and was used in the next step without further purification.

(ii) Production of 2-methyl-5-{2-[4-(methylsulfonyl)piperazin-1-yl]ethoxy}-3-[4-phenyl-5-(1H-1,2,4-triazol-3-yl)-1,3-thiazol-2-yl]pyrazolo[1,5-a]pyridine The title compound has been prepared according to the similar manlier described in 85-B (iii) from 2-methyl-5-{2-[4-(methylsulfonyl)piperazin-1-yl]ethoxy}-3-{4-phenyl-5-[1-(tetrahydro-2H-pyran-2-yl)-1H-1,2,4-triazol-3-yl]-1,3-thiazol-2-yl}pyrazolo[1,5-a]pyridine obtained above. The crude product was purified by washing with EtOAc (5 mL) to give pure title compound (111 mg, 85%) as a colorless solid.

$^1$H-NMR (DMSO-$d_6$, 300 MHz) 12.57-2.65 (4 H, m), 2.67 (3 H, s), 2.81-2.90 (2 H, m), 2.87 (3 H, s), 3.05-3.16 (4 H, m), 4.28 (2 H, t, J=5.7 Hz), 6.77 (1 H, dd, J=2.6, 7.6 Hz), 7.37-7.48 (3 H, m), 7.74 (1 H, d, J=2.6 Hz), 7.88-8.04 (2 H, m), 8.56 (1 H, s), 8.63 (1 H, d, J=7.6 Hz), 14.25 (1 H, br s).

(iii) Production of 2-methyl-5-{2-[4-(methylsulfonyl)piperazin-1-yl]ethoxy}-3-[4-phenyl-5-(1H-1,2,4-triazol-3-yl)-1,3-thiazol-2-yl]pyrazolo[1,5-a]pyridine di-p-toluenesulfonate The title compound has been prepared according to the similar manner described in 85-B (iv) from 2-methyl-5-{2-

[4-(methylsulfonyl)piperazin-1-yl]ethoxy}-3-[4-phenyl-5-(1H-1,2,4-triazol-3-yl)-1,3-thiazol-2-yl]pyrazolo[1,5-a]pyridine (45.3 mg, 0.0802 mmol) and p-toluenesulfonic acid monohydrate (33.6 mg, 0.176 mmol). The pure title compound (62 mg, 85%) has been obtained as a yellow solid by crystallization from EtOH (1 mL) and EtOAc (3 mL).

$^1$H-NMR (DMSO-d$_6$, 300 MHz) δ 2.29 (6 H, s), 2.41-2.46 (2 H, m), 2.69 (3 H, s), 3.03 (3 H, s), 3.08-3.23 (4 H, m), 3.72 (4 H, br s), 4.57 (2 H, br s), 6.83 (1 H, dd, J=2.7, 7.6 Hz), 7.11 (4 H, d, J=7.7 Hz), 7.38-7.51 (7 H, m), 7.74 (1 H, d, J=2.7 Hz), 7.89-7.99 (2 H, m), 8.56-8.69 (1 H, m), 8.73 (1 H, d, J=7.6 Hz), 14.24 (1 H, br s).

Example 90-B

Production of 4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one p-toluenesulfonate

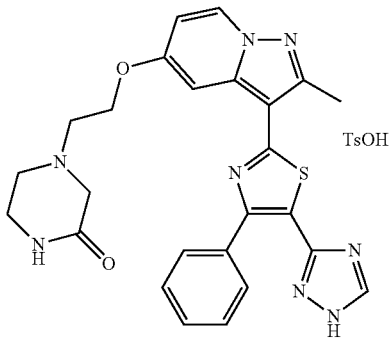

(i) Production of 4-{2-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]ethyl}piperazin-2-one Title compound has been prepared according to the similar manner described in 88-B (ii) from 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (78.0 mg, 0.150 mmol), piperazine-2-one (29.9 mg, 0.299 mmol) obtained 88-B (i), potassium carbonate (41.3 mg, 0.299 mmol) as a base instead of TEA and sodium iodide (44.8 mg, 0.299 mmol) as a additive. After extraction, the crude product has been washed with EtOAc (5 mL) to give title compound (66 mg, 75%) as a colorless solid.

$^1$H-NMR (DMSO-d$_6$, 300 MHz) δ 1.47-1.75 (3 H, m), 1.91-2.15 (3 H, m), 2.67 (3 H, s), 2.70-2.75 (2 H, m), 2.86 (2 H, t, J=5.6 Hz), 3.08 (2 H, s), 3.11-3.19 (2 H, m), 3.61-3.73 (1 H, m), 3.88-3.99 (1 H, m), 4.29 (2 H, t, J=5.6 Hz), 5.60 (1 H, dd, J=2.8, 8.7 Hz), 6.78 (1 H, dd, J=2.8, 7.6 Hz), 7.37-7.48 (3 H, m), 7.73-7.78 (2 H, m), 7.93-7.98 (2 H, m), 8.65 (1 H, d, 7.6 Hz), 8.80 (1 H, s).

(ii) Production of 4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one The title compound has been prepared according to the similar manner with the procedure described in 85-B (iii) from 4-{2-[(2-methyl-3-{4-phenyl-5-[1-(tetrahydro-2H-py-ran-2-yl)-1H-1,2,4-triazol-3-yl]-1,3-thiazol-2-yl}pyrazolo[1,5-a]pyridin-5-yl)oxy]ethyl}piperazin-2-one (65.0 mg, 0.111 mmol) obtained above. The crude product was purified by washing with EtOAc (5 mL) to give pure title compound (38 mg, 68%) as a colorless solid.

$^1$H-NMR (DMSO-d$_6$, 300 MHz) δ 2.64-2.75 (2 H, m), 2.67 (3 H, s), 2.86 (2 H, t, J=5.6 Hz), 3.08 (2 H, s), 3.11-3.21 (2 H, m), 4.30 (2 H, t, J=5.6 Hz), 6.78 (1 H, dd, J=2.7, 7.6 Hz), 7.29-7.54 (3 H, m), 7.75 (1 H, d, J=2.7 Hz), 7.75 (1 H, br s), 7.85-8.05 (2 H, m), 8.64 (1 H, d, J=7.6 Hz), 8.64 (1 H, br s), 14.24 (1 H, br s).

(iii) Production of 4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one p-toluenesulfonate The title compound has been prepared according to the similar manner described in 85-B (iv) from 4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one (38.0 mg, 0.0759 mmol) and p-toluenesulfonic acid (31.8 mg, 0.167 mmol). The pure title compound (35 mg, 68%) has been obtained as a pale yellow solid by crystallization from EtOH (8 mL) and EtOAc (2 mL).

$^1$H-NMR (DMSO-d$_6$, 300 MHz) δ 2.25-2.30 (2 H, m), 2.29 (3 H, s), 2.41-2.46 (2 H, m), 2.54-2.59 (2 H, m), 2.68 (3 H, s), 2.70-2.75 (2 H, m), 4.18-4.64 (2 H, m), 6.78-6.84 (1 H, m), 7.11 (2 H, d, J=7.7 Hz), 7.37-7.51 (5 H, m), 7.75 (1 H, d, J=2.8 Hz), 7.88-8.04 (2 H, m), 8.53-8.76 (2 H, m), 14.26 (1 H, br s). Lactam proton has not been observed.

Example 91-B

Production of 1-methyl-4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one hydrochloride

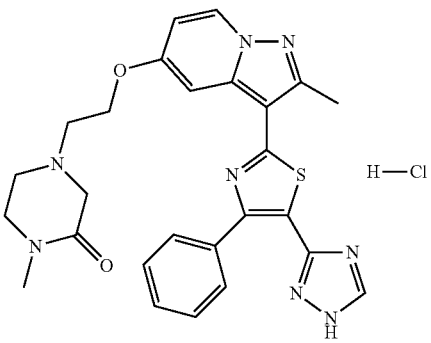 [SMILES: Cc1nn2ccc(OCCN3CCN(C)C(=O)C3)cc2c1-c1nc(-c2ccccc2)c(-c2nc[nH]n2)s1 ; Cl]

(i) Production of 4-benzyloxycarbonylpiperazine-2-one

To a suspension of piperazine-2-one (2.00 g, 20.0 mmol) in EtOAc (50 mL) and water (50 mL), were added sodium carbonate (6.36 g, 60.0 mmol) and 95% benzyl chloroformate (3.59 mL, 24.0 mmol) and the mixture was stirred for 3 days at rt. To the mixture were added EtOAc (50 mL) and water (20 mL) and then organic layer was separated. The aqueous layer was extracted with EtOAc (30 mL×2). The combined organic layer was washed with brine (20 mL) and then dried over anhydrous sodium sulfate. Insoluble materials were removed by filtration and the filtrate was concentrated under reduced pressure. The residue was washed with diethyl ether (50 mL) to give title compound (3.98 g, 85%) as a colorless solid.

$^1$H-NMR (CDCl$_3$, 300 MHz) δ 3.41 (2 H, br s), 3.71 (2 H, t, J=5.4 Hz), 4.18 (2 H, s), 5.16 (2 H, s), 6.02 (1 H, br s), 7.30-7.42 (5 H, m).

(ii) Production of benzyl 4-methyl-3-oxopiperazine-1-carboxylate

To a solution of 4-benzyloxycarbonylpiperazine-2-one (3.98 g, 17.0 mmol) obtained above in DMF (50 mL), was added 60% sodium hydride (815 mg, 20.4 mmol) and the mixture was stirred for 10 min at 0° C. To the mixture was added iodomethane (3.17 mL, 51.0 mmol) and the mixture was stirred for 4.5 h at rt. To the mixture were added EtOAc (100 mL) and water (50 mL) and then organic layer was separated. The aqueous layer was extracted with EtOAc (20 mL×4). The combined organic layer was washed with brine (15 mL) and then dried over anhydrous sodium sulfate. Insoluble materials were removed by filtration and the filtrate was concentrated under reduced pressure. The residue was purified by basic silica gel column chromatography (EtOAc/hexane=20/80→60/40) to give title compound (3.59 g, 85%) as a pale yellow oil.

$^1$H-NMR (CDCl$_3$, 300 MHz) δ 3.00 (3 H, s), 3.29-3.45 (2 H, m), 3.73 (2 H, t, J=5.4 Hz), 4.15 (2 H, s), 5.15 (2 H, s), 7.29-7.43 (5 H, m).

(iii) Production of 1-methylpiperazine-2-one

To a solution of benzyl 4-methyl-3-oxopiperazine-1-carboxylate (3.59 g, 14.5 mmol) in THF (30 mL) and EtOH (10 mL), was added 10% palladium-carbon (1.54 g, 1.45 mmol) and the mixture was stirred for 4 h at rt under hydrogen atmosphere (1 atm). The mixture was filtered through Celite pad and the filtrate was concentrated under reduced pressure to give title compound (1.61 g, 97%) as pale yellow oil.

$^1$H-NMR (CDCl$_3$, 300 MHz) δ 1.88 (1 H, br s), 2.97 (3 H, s), 3.08 (2 H, t, J=5.4 Hz), 3.32 (2 H, t, J=5.4 Hz), 3.51 (2 H, s).

(iv) Production of 1-methyl-4-{2-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]ethyl}piperazin-2-one Title compound has been prepared according to the similar manner described in 88-B (ii) from 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (236 mg, 0.453 mmol) obtained example 88-B (i), 1-methylpiperazine-2-one (129 mg, 1.13 mmol) obtained above, potassium carbonate (156 mg, 1.13 mmol) as a base instead of TEA and sodium iodide (169 mg, 1.13 mmol) as a additive. After extraction, the crude product has been purified by silica gel column chromatography (MeOH/EtOAc=0/100→10/90) to give title compound as a yellow syrup. This crude product was used in the next step without further purification.

(v) Production of 1-methyl-4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one hydrochloride To a suspension of 1-methyl-4-{2-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]ethyl}piperazin-2-one obtained above in THF (6 mL) and MeOH (2 mL), was added 2M hydrochloric acid (2 mL) and the mixture was stirred for 1 h at 60° C. To the mixture was added EtOAc (5 mL) and the resulting precipitate has been collected by filtration to obtain title compound (217 mg, 87%) as a yellow solid.

$^1$H-NMR (DMSO-d$_6$, 300 MHz) δ 2.68 (3 H, s), 2.90 (3 H, s), 3.39-3.79 (4 H, m), 3.70 (2 H, br s), 3.98 (2 H, br s), 4.55-4.66 (2 H, m), 6.84 (1 H, dd, J=2.7, 7.5 Hz), 7.35-7.51 (3 H, m), 7.74 (1 H, d, J=2.7 Hz), 7.88-7.99 (2 H, m), 8.62 (1 H, br s), 8.72 (1 H, d, J=7.5 Hz), 14.34 (1 H, br s).

Example 92-B

Production of 5-[2-(4-acetylpiperazin-1-yl)ethoxy]-2-methyl-3-[4-phenyl-5-(1H-1,2,4-triazol-3-yl)-1,3-thiazol-2-yl]pyrazolo[1,5-a]pyridine di-p-toluenesulfonate

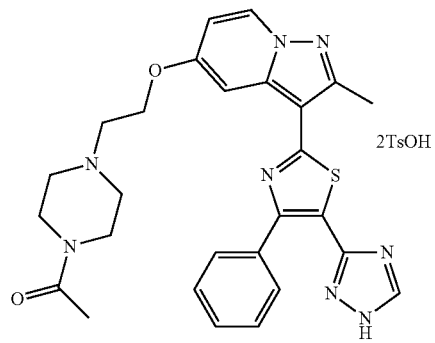

(i) Production of 5-[2-(4-acetylpiperazin-1-yl)ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine Title compound has been prepared according to the similar manner described in 88-B (ii) from 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-d]pyridine (100.0 mg, 0.192 mmol) obtained in Example 88-B (i), 1-acetylpiperazine (49.2 mg, 0.384 mmol) obtained above, potassium carbonate (53.1 mg, 0.384 mmol) as a base instead of TEA and sodium iodide (57.6 mg, 0.384 mmol) as a additive. After extraction, the crude product has been used in the next step without further purification.

(ii) Production of 5-[2-(4-acetylpiperazin-1-yl)ethoxy]-2-methyl-3-[4-phenyl-5-(1H-1,2,4-triazol-3-yl)-1,3-thiazol-2-yl]pyrazolo[1,5-a]pyridine The title compound has been prepared according to the similar manner described in 85-B (iii) from 5-[2-(4-acetylpiperazin-1-yl)ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine obtained above. The crude product was purified by silica gel column chromatography (MeOH/EtOAc=0/100→20/80) to give pure title compound (63 mg, 62%) as a colorless solid.

$^1$H-NMR (DMSO-d$_6$, 300 MHz) δ 1.98 (3 H, s), 2.41-2.47 (4 H, m), 2.66 (3 H, s), 2.82 (2 H, t, J=5.9 Hz), 3.38-3.49 (4 H, m), 4.29 (2H, t, J=5.9 Hz), 6.77 (1 H, dd, J=2.6, 7.6 Hz), 7.34-7.49 (3 H, m), 7.76 (1 H, d, J=2.6 Hz), 7.95-8.04 (2 H, m), 8.52 (1 H, s), 8.63 (1 H, d, J=7.6 Hz). Acidic proton of triazole was not observed.

(iii) Production of 5-[2-(4-acetylpiperazin-1-yl)ethoxy]-2-methyl-3-[4-phenyl-5-(1H-1,2,4-triazol-3-yl)-1,3-thiazol-2-yl]pyrazolo[1,5-a]pyridine di-p-toluenesulfonate The title compound has been prepared according to the similar manner described in 85-B (iv) from 5-[2-(4-acetylpiperazin-1-yl)ethoxy]-2-methyl-3-[4-phenyl-5-(1H-1,2,4-triazol-3-yl)-1,3-thiazol-2-yl]pyrazolo[1,5-a]pyridine (63.1 mg, 0.119 mmol) obtained above and p-toluenesulfonic acid monohydrate (50.0 mg, 0.263 mmol). The pure title compound (70 mg, 67%) has been obtained as a yellow solid by crystallization from EtOH (1 mL) and EtOAc (4 mL).

$^1$H-NMR (DMSO-$d_6$, 300 MHz) δ 2.05 (3 H, s), 2.28 (6 H, s), 2.69 (3 H, s), 2.86-3.32 (4 H, m), 3.33-3.54 (2 H, m), 3.73-3.88 (2 H, 3.95-4.12 (1 H, m), 4.36-4.51 (1 H, m), 4.52-4.64 (2 H, m), 6.83 (1 H, dd, J=2.7, 7.6 Hz), 7.11 (4 H, d, J=7.9 Hz), 7.33-7.56 (7 H, m), 7.74 (1 H, J=2.7 Hz), 7.85-8.03 (2 H, m), 8.64 (1 H, br s), 8.73 (1 H, d, J=7.6 Hz), 9.84 (1 H, br s), 14.32 (1 H, br s). Acidic proton of p-toluenesulfonic acid has been observed with intensity of 1H.

Example 93-B

Production of 1-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperidin-4-ol di-p-toluenesulfonate

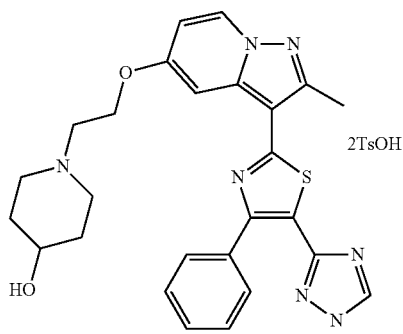

(i) Production of 1-{2-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]ethyl}piperidin-4-ol Title compound has been prepared according to the similar manner described in 88-B (ii) from 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (100.0 mg, 0.192 mmol) obtained in Example 88-B (i), 4-hydroxypiperazine (38.8 mg, 0.384 mmol), potassium carbonate (53.1 mg, 0.384 mmol) as a base instead of TEA and sodium iodide (57.6 mg, 0.384 mmol) as a additive. After extraction, the crude title product has been used in the next step without further purification.

(ii) Production of 1-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperidin-4-ol The title compound has been prepared according to the similar manner described in 85-B (iii) from 1-{2-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]ethyl}piperidin-4-ol obtained above. The crude product was purified by washing with EtOAc (5 mL) to give pure title compound (80 mg, 82%) as a colorless solid.

$^1$H-NMR (DMSO-$d_6$, 300 MHz) δ 1.30-1.48 (2 H, m), 1.63-1.78 (2 H, m), 2.08-2.23 (2 H, m), 2.66 (3 H, s), 2.70-2.86 (4 H, m), 3.40-3.50 (1 H, m), 4.24 (2 H, t, J=6.0 Hz), 4.55 (1 H, br s), 6.76 (1 H, dd, J=2.6, 7.5 Hz), 7.36-7.49 (3 H, m), 7.77 (1 H, d, J=2.6 Hz), 7.88-8.04 (2 H, m), 8.58 (1 H, s), 8.63 (1 H, d, J=7.5 Hz), 14.24 (1 H, br s).

(iii) Production of 1-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperidin-4-ol di-p-toluenesulfonate The title compound has been prepared according to the similar manner described in 85-B (iv) from 1-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperidin-4-ol (78.8 mg, 0.157 mmol) obtained above and p-toluenesulfonic acid monohydrate (65.7 mg, 0.345 mmol). The pure title compound (85 mg, 64%) has been obtained as a yellow solid by washing with EtOH (4 mL) and acetone (4 mL).

$^1$H-NMR (DMSO-$d_6$, 300 MHz) δ 1.52-2.05 (4 H, m), 2.28 (6 H, s), 2.68 (3 H, s), 3.03-3.48 (4 H, m), 3.50-3.62 (2 H, m), 3.94 (1 H, br s), 4.44-4.62 (2 H, m), 6.83 (1 H, td, J=2.4, 7.6 Hz), 7.11 (4 H, d, J=7.7 Hz), 7.34-7.55 (7 H, m), 7.74 (1 H, t, J=2.4 Hz), 7.83-8.07 (2H, m), 8.63 (1 H, br s), 8.72 (1 H, d, J=7.6 Hz), 9.29 (1 H, br s), 14.27 (1 H, br s). Acidic proton of p-toluenesulfonic acid has been observed with intensity of 1H. proton of OH has not been observed.

Example 94-B

Production of 2-methyl-3-[4-phenyl-5-(1H-1,2,4-triazol-3-yl)-1,3-thiazol-2-yl]-5-(piperidin-4-yloxy)pyrazolo[1,5-a]pyridine di-p-toluenesulfonate

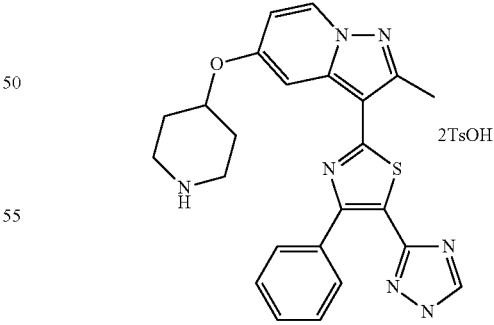

(i) Production of 1-[(tert-butoxycarbonyl)oxy]piperidin-4-yl methanesulfonate

To a solution of 1-[(tert-butoxycarbonyl)oxy]piperidin-4-ol (10.0 g, 49.7 mmol) in THF (200 mL), were added TEA (20.7 mL, 149 mmol) and methanesulfonyl chloride (7.69 mL, 99.4 mmol) at 0° C. The mixture was stirred for 2.5 h at the same temperature. To the mixture was added EtOAc (100 mL) and water (100 mL) and then organic layer has been separated. The aqueous layer has been extracted with EtOAc (50 mL) and the combined organic layer was washed with brine (30 mL). The organic layer was dried over anhydrous magnesium sulfate and then insoluble materials were removed by filtration. The filtrate was concentrated under reduced pressure, and the residue was purified by silica gel column chromatography (EtOAc/hexane 20/80→350/50). Concentration of appropriate fractions afforded crude product, which was washed with a 1:1 mixture of diethyl ether and hexane (50 mL) to give title compound (12.9 g, 92%) as a pale yellow solid.

$^1$H-NMR (DMSO-d$_6$, 300 MHz) δ 1.46 (9 H, s), 1.74-1.89 (2 H, m), 1.90-2.04 (2 H, m), 3.04 (3 H, s), 3.30 (2 H, ddd, J=3.8, 8.1, 13.7 Hz), 3.71 (2 H, ddd, J=4.0, 6.9, 13.7 Hz), 4.88 (1 H, tt, J=3.7, 7.7 Hz).

(ii) Production of tert-butyl 4-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]piperidine-1-carboxylate The title compound has been prepared according to the similar manner described in 85-B (ii) from 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (490 mg, 1.07 mmol) obtained in Example 31-B-(i), potassium carbonate (444 mg, 3.21 mmol) and 1-[(tert-butoxycarbonyl)oxy]piperidin-4-yl methanesulfonate (897 mg, 3.21 mmol) obtained above. The crude product was purified by basic silica gel column chromatography (EtOAc/hexane=20/80→50/50) to give pure title compound (630 mg, 92%) as a pale yellow solid.

$^1$H-NMR (DMSO-d$_6$, 300 MHz) δ 1.43 (9 H, s), 1.50-1.79 (5 H, m), 1.86-2.16 (5 H, m), 2.65 (3 H, s), 3.06-3.22 (2 H, m), 3.60-3.72 (1 H, m), 3.72-3.85 (2 H, m), 3.88-3.99 (1 H, m), 4.63-4.77 (1 H, m), 5.60 (1 H, dd, J=2.8, 8.9 Hz), 6.77 (1 H, dd, J=2.7, 7.6 Hz), 7.36-7.49 (3 H, m), 7.86 (1 H, d, J=2.7 Hz), 7.91-8.00 (2 H, m), 8.65 (1 H, d, J=7.6 Hz), 8.80 (1 H, s).

(iii) Production of 2-methyl-3-[4-phenyl-5-(1H-1,2,4-triazol-3-yl)-1,3-thiazol-2-yl]-5-(piperidin-4-yloxy)pyrazolo[1,5-a]pyridine A solution of tert-butyl 4-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]piperidine-1-carboxylate (630 mg, 0.982 mmol) obtained above in TFA (10 mL) was stirred for 2 h at rt and then the mixture was concentrated under reduced pressure. To the residue were added a 1:1 mixture of THF and EtOAc (30 mL) and saturated aqueous solution of sodium bicarbonate (20 mL). The organic layer has been separated and the aqueous layer was extracted with a 1:1 mixture of THF and EtOAc (10 mL). The combined organic layer has been dried over anhydrous sodium sulfate and then insoluble materials were removed by filtration. Concentration of the filtrate afforded crude product, which was washed with EtOAc (5 mL) to give title compound (383 mg, 85%) as a pale yellow solid.

$^1$H-NMR (DMSO-d$_6$, 300 MHz) δ 1.82-2.01 (2 H, m), 2.11-2.34 (2 H, m), 2.66 (3H, s), 3.00-3.17 (2 H, m), 3.27-3.31 (2 H, m), 4.74-4.90 (1 H, m), 6.80 (1 H, dd, J=2.8, 7.6 Hz), 7.35-7.54 (3 H, m), 7.84 (1 H, d, J=2.8 Hz), 7.90-8.01 (2 H, m), 8.63 (1 H, br s), 8.69 (1 H, d, J=7.6 Hz), 14.32 (1 H, br s). proton of NH was not observed.

(iv) Production of 2-methyl-3-[4-phenyl-5-(1H-1,2,4-triazol-3-yl)-1,3-thiazol-2-yl]-5-(piperidin-4-yloxy)pyrazolo[1,5-a]pyridine di-p-toluenesulfonate The title compound has been prepared according to the similar manner described in 85-B (iv) from 2-methyl-3-[4-phenyl-5-(1H-1,2,4-triazol-3-yl)-1,3-thiazol-2-yl]-5-(piperidin-4-yloxy)pyrazolo[1,5-a]pyridine (79.0 mg, 0.173 mmol) obtained above and p-toluenesulfonic acid monohydrate (72.4 mg, 0.381 mmol). The pure title compound (67 mg, 49%) has been obtained as a colorless solid by crystallization from EtOH (5 mL) and EtOAc (5 mL).

$^1$H-NMR (DMSO-d$_6$, 300 MHz) δ 1.89-2.05 (2 H, m), 2.17-2.26 (2 H, m), 2.29 (6H, s), 2.66 (3 H, s), 3.01-3.22 (2 H, m), 3.24-3.39 (2 H, m), 4.79-4.98 (1 H, m), 6.81 (1 H, dd, J=2.7, 7.5 Hz), 7.11 (4 H, d, J=7.9 Hz), 7.32-7.59 (7 H, m), 7.83 (1 H, d, J=2.7 Hz), 7.88-8.02 (2 H, m), 8.62 (1 H, br s), 8.69 (1 H, d, J=7.5 Hz), 8.80 (2 H, br s), 14.27 (1 H, br s).

Example 95-B

Production of 5-[(1-acetylpiperidin-4-yl)oxy]-2-methyl-3-[4-phenyl-5-(1H-1,2,4-triazol-3-yl)-1,3-thiazol-2-yl]pyrazolo[1,5-a]pyridine

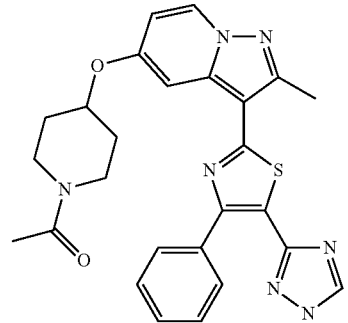 [SMILES: CC(=O)N1CCC(Oc2ccn3nc(C)c(-c4nc(-c5ccccc5)c(-c5nc[nH]n5)s4)c3c2)CC1]

To a solution of 2-methyl-3-[4-phenyl-5-(1H-1,2,4-triazol-3-yl)-1,3-thiazol-2-yl]-5-(piperidin-4-yloxy)pyrazolo[1,5-a]pyridine (100 mg, 0.219 mmol) obtained 85-B (iii) in DMF (3 mL), was added acetyl chloride (31.2 μL, 0.438 mmol) and the mixture was stirred for 2 h at rt. To the mixture, were added MeOH (1 mL) and potassium carbonate (90.8 mg, 0.657 mmol), and then the mixture was stirred for additional 1.5 h at the same temperature. To the mixture were added a 1:1 mixture of THF and EtOAc (20 mL) and saturated aqueous solution of sodium bicarbonate (15 mL), and then organic layer was separated. The aqueous layer was extracted with a 1:1 mixture of THF and EtOAc (5 mL×4) and the combined organic layer was washed with brine (5 mL). The organic layer was dried over anhydrous sodium sulfate and then insoluble materials were removed by filtration. The filtrate was concentrated under reduced pressure and the residue was purified by basic silica gel column chromatography (MeOH/EtOAc=0/100→15/85). Concentration of the appropriate fractions afforded crude product, which was crystallized from THF (1 mL) and EtOAc (5 mL) to obtain title compound (47 mg, 43%) as a colorless solid.

$^1$H-NMR (DMSO-d$_6$, 300 MHz) δ 1.51-1.81 (2 H, m), 2.00-2.19 (2 H, m), 2.05 (3 H, s), 2.65 (3 H, s), 3.11-3.22 (1 H, m), 3.30-3.40 (1 H, m), 3.72-3.83 (1 H, m), 3.95-4.07 (1 H, m), 4.71-4.84 (1 H, m), 6.78 (1 H, dd, J=2.7, 7.6 Hz), 7.35-7.49 (3 H, m), 7.87 (1 H, d, J=2.7 Hz), 7.93-8.03 (2 H, m), 8.54 (1 H, br s), 8.65 (1 H, d, J=7.6 Hz), 14.25 (1 H, br s).

Example 96-B

Production of 2-[4-({2-methyl-3-[4-phenyl-5-(4H-1,2,4-triazol-3-yl)-1,3-thiazol-2-yl]pyrazolo[1,5-a]pyridin-5-yl}oxy)piperidin-1-yl]-2-oxoethanol

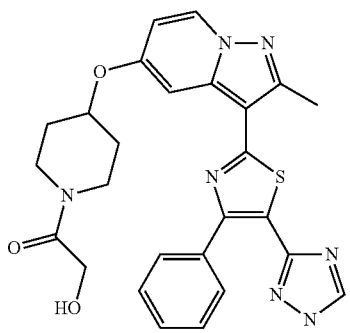 [SMILES: Cc1nn2ccc(OC3CCN(C(=O)CO)CC3)cc2c1-c1nc(-c2ccccc2)c(-c2nc[nH]n2)s1]

The title compound has been prepared according to the similar manner described in 85-B1 from 2-methyl-3-[4-phenyl-5-(1H-1,2,4-triazol-3-yl)-1,3-thiazol-2-yl]-5-(piperidin-4-yloxy)pyrazolo[1,5-a]pyridine (120 mg, 0.262 mmol) obtained 85-B0 (iii) and acetoxyacetyl chloride (56.4 μL, 0.524 mmol). The pure title compound (62 mg, 46%) has been obtained as a colorless solid after silica gel column chromatographic purification (MeOH/EtOAc=0/100→15/85) followed by crystallization from EtOAc (5 mL) and THF (1 mL).

$^1$H-NMR (DMSO-$d_6$, 300 MHz) δ 1.57-1.82 (2 H, m), 2.02-2.18 (2 H, m), 2.66 (3 H, s), 3.18-3.29 (2 H, m), 3.60-3.75 (1 H, m), 3.93-4.06 (1 H, m), 4.14 (2 H, d, J=5.4 Hz), 4.57 (1 H, t, J=5.4 Hz), 4.73-4.84 (1 H, m), 6.78 (1 H, dd, J=7.6, 2.7 Hz), 7.35-7.48 (3 H, m), 7.87 (1 H, d, J=2.7 Hz), 7.91-8.01 (2 H, m), 8.56 (1 H, br s), 8.65 (1 H, d, J=7.6 Hz), 14.25 (1 H, br s).

Example 97-B

Production of 3-[4-(2,4-difluorophenyl)-5-(1H-1,2,4-triazol-3-yl)-1,3-thiazol-2-yl]-2-methylpyrazolo[1,5-a]pyridine

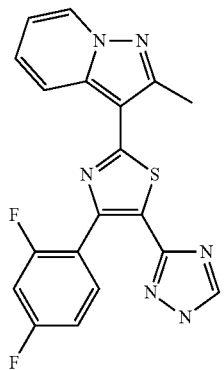 [SMILES: Cc1nn2ccccc2c1-c1nc(-c2ccc(F)cc2F)c(-c2nc[nH]n2)s1]

(i) Production of methyl 4-(2,4-difluorophenyl)-2-(2-methylpyrazolo[1,5-a]pyridin-3-yl)-1,3-thiazole-5-carboxylate To a suspension of methyl 2-(2-methylpyrazolo[1,5-a]pyridin-3-yl)-4-{[(trifluoromethyl)sulfonyl]oxy}-1,3-thiazole-5-carboxylate (100 mg, 0.237 mmol) obtained in Example 13-B (ii), 2,4-difluorophenylboronic acid (56.2 mg, 0.356 mmol), and cesium carbonate (154 mg, 0.474 mmol) in DME (5 mL) and water (1 mL) under argon atmosphere was added [1,1'-Bis(diphenylphosphino)ferrocene]palladium(II) dichloride complex with dichloromethane (1:1) (19.4 mg, 0.0237 mmol) and the mixture was stirred for 80° C. To the mixture were added EtOAc (20 mL) and saturated aqueous solution of sodium bicarbonate (15 mL) and then organic layer was separated. The aqueous layer was extracted with EtOAc (5 mL) and the combined organic layer was washed with brine (5 mL). The organic layer was separated and then filtered through silica gel pad (3 g). After the concentration of the filtrate, the residue was washed with EtOAc (2 mL) to obtain title compound (79 mg, 87%) as a colorless solid.

$^1$H-NMR (DMSO-$d_6$, 300 MHz) δ 2.71 (3 H, s), 3.77 (3 H, s), 7.13 (1 H, dt, J=1.2, 6.9 Hz), 7.25 (1 H, ddt, J=0.8, 2.5, 8.5 Hz), 7.40 (1 H, ddd, J=2.5, 9.5, 10.5 Hz), 7.59 (1 H, ddd, J=1.2, 6.9, 8.8 Hz), 7.77 (1 H, td, J=6.7, 8.5 Hz), 8.32 (1 H, td, J=1.2, 8.8 Hz), 8.82 (1 H, td, J=1.2, 6.9 Hz).

(ii) Production of 4-(2,4-difluorophenyl)-2-(2-methylpyrazolo[1,5-a]pyridin-3-yl)-1,3-thiazole-5-carboxylic acid To a suspension of methyl 4-(2,4-difluorophenyl)-2-(2-methylpyrazolo[1,5-a]pyridin-3-yl)-1,3-thiazole-5-carboxylate (250 mg, 0.649 mmol) obtained above in THF (5 mL) and MeOH (5 mL), was added 2N aqueous solution of sodium hydroxide (1 mL) and the mixture was stirred for 2 h at 60° C. To the mixture, was added a 2:1 mixture of EtOAc and THF (60 mL) and 1N hydrochloric acid. The organic layer was separated and the aqueous layer was extracted with a 2:1 mixture of EtOAc and THF (10 mL). The combined organic layers were washed with brine (5 mL) and then dried over anhydrous sodium sulfate. Insoluble materials were removed by filtration and the filtrate was concentrated under reduced pressure to obtain title compound (225 mg, 93%) as a pale yellow solid.

$^1$H-NMR (DMSO-$d_6$, 300 MHz) δ 2.70 (3 H, s), 7.11 (1 H, dt, J=1.2, 6.9 Hz), 7.17-7.27 (1 H, m), 7.37 (1 H, dt, J=2.5, 10.0 Hz), 7.56 (1 H, ddd, J=1.0, 6.9, 8.8 Hz), 7.68-7.78 (1 H, m), 8.30 (1 H, td, J=1.2, 8.8 Hz), 8.80 (1 H, ddd, J=1.0, 1.2, 6.9 Hz), 13.28 (1 H, br s).

(iii) Production of 4-(2,4-difluorophenyl)-2-(2-methylpyrazolo[1,5-a]pyridin-3-yl)-1,3-thiazole-5-carboxamide To a stirred suspension of 4-(2,4-difluorophenyl)-2-(2-methylpyrazolo[1,5-a]pyridin-3-yl)-1,3-thiazole-5-carboxylic acid (220 mg, 0.592 mmol) obtained above, ammonium chloride (126 mg, 2.37 mmol), EDCI (226 mg, 1.18 mmol) and HOBT (160 mg, 1.18 mmol) in DMF, (3 mL) was added TEA (329 μL, 2.37 mL) and the mixture was stirred for 3 h at rt. To the mixture were added a 1:1 mixture of THF and EtOAc (20 mL) and saturated aqueous solution of sodium bicarbonate (15 mL). The organic layer was separated and then washed with brine (5 mL). The organic layer was dried over anhydrous sodium sulfate and insoluble materials were removed by filtration. Concentration of the filtrate afforded pale yellow solid of title compound (182 mg, 76%) as adduct of 0.5 equivalent of DMF.

$^1$H-NMR (DMSO-$d_6$, 300 MHz) δ 2.70 (3 H, s), 7.09 (1 H, dt, J=1.4, 6.9 Hz), 7.18-7.27 (1 H, m), 7.35 (1 H, ddd, J=2.7, 9.6, 10.5 Hz), 7.55 (2 H, br s), 7.55 (1 H, ddd, J=1.0, 6.9, 8.9

Hz), 7.77 (1 H, dt, J=6.7, 8.5 Hz), 8.29 (1 H, ddd, J=1.0, 1.4, 8.9 Hz), 8.78 (1 H, td, J=1.0, 6.9 Hz).

(iv) Production of 3-[4-(2,4-difluorophenyl)-5-(1H-1,2,4-triazol-3-yl)-1,3-thiazol-2-yl]-2-methylpyrazolo[1,5-a]pyridine A suspension of 4-(2,4-difluorophenyl)-2-(2-methylpyrazolo[1,5-a]pyridin-3-yl)-1,3-thiazole-5-carboxamide (180 mg, 0.442 mmol, 0.5 equiv DMF adduct) obtained above in 1,1-Dimethoxy-N,N-dimethylmethanamine (3 mL) was stirred for 1 h at 100° C. and then the mixture was concentrated under reduced pressure. The residue was dissolved in AcOH (3 mL) and then was added hydrazine monohydrate (108 μL, 2.21 mmol). The resulting mixture was stirred for 1 h at 100° C. and then concentrated under reduced pressure. To the residue, were added a 1:1 mixture of EtOAc and THF (20 mL) and saturated aqueous solution of sodium bicarbonate (15 mL) and then the organic layer was separated, which was washed with brine (5 mL) and dried over anhydrous sodium sulfate. Insoluble materials were removed by filtration and the filtrate was concentrated under reduced pressure. The residue was crystallized from THF (3 mL) and hexane (6 mL) to obtain title compound (147 mg, 84%) as a yellow solid.
$^1$H-NMR (DMSO-$d_6$, 300 MHz) δ 2.72 (3 H, s), 7.08 (1 H, dt, J=1.4, 6.9 Hz), 7.15-7.25 (1 H, m), 7.31 (1 H, ddd, J=2.4, 9.7, 10.3 Hz), 7.52 (1 H, ddd, J=1.0, 6.9, 8.8 Hz), 7.75 (1 H, dt, J=6.7, 8.5 Hz), 8.30 (1 H, ddd, J=1.0, 1.4, 8.8 Hz), 8.52 (1 H, br s), 8.77 (1 H, td, J=1.0, 6.9 Hz), 14.15 (1 H, br s).

Example 98-B

Production of 3-[4-(2,3-difluorophenyl)-5-(1H-1,2,4-triazol-3-yl-1,3-thiazol-2-yl]-2-methylpyrazolo[1,5-a]pyridine

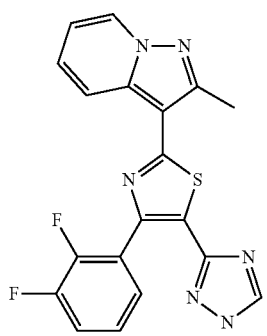 [SMILES: Cc1nn2ccccc2c1-c1nc(-c2cccc(F)c2F)c(-c2nc[nH]n2)s1]

(i) Production of 4-(2,3-difluorophenyl)-2-(2-methylpyrazolo[1,5-a]pyridin-3-yl)-1,3-thiazole-5-carboxylic acid According to the similar manner described in Example 97-B (i) and (ii), the title compound (193 mg, 93%) has been obtained as a colorless solid by the Suzuki coupling reaction using methyl 2-(2-methylpyrazolo[1,5-a]pyridin-3-yl)-4-{[(trifluoromethyl)sulfonyl]oxy}-1,3-thiazole-5-carboxylate (236 mg, 0.561 mmol) obtained in Example 13-B (ii) and 2,3-Difluorobenzeneboronic acid (133 mg, 0.842 mmol) followed by standard ester hydrolysis procedure.

$^1$H-NMR (DMSO-$d_6$, 300 MHz) δ 2.70 (3 H, s), 7.11 (1 H, dt, J=1.2, 6.9 Hz), 7.33 (1 H, m,), 7.45-7.62 (3 H, m), 8.30 (1 H, td, J=1.2, 8.8 Hz), 8.80 (1 H, td, J=1.2, 6.9 Hz), 13.40 (1 H, br s).

(ii) Production of 4-(2,3-difluorophenyl)-2-(2-methylpyrazolo[1,5-a]pyridin-3-yl)-1,3-thiazole-5-carboxamide According to the similar manner described in Example 97-B (iii), the title compound (134 mg, 70%) has been obtained as a pale yellow solid using 4-(2,3-difluorophenyl)-2-(2-methylpyrazolo[1,5-a]pyridin-3-yl)-1,3-thiazole-5-carboxylic acid (191 mg, 0.514 mmol) obtained above.
$^1$H-NMR (DMSO-$d_6$, 300 MHz) δ 2.70 (3 H, s), 7.10 (1 H, dt, J=1.2, 6.9 Hz), 7.28-7.39 (1 H, m), 7.46-7.75 (5 H, m), 8.29 (1 H, td, J=1.2, 8.8 Hz), 8.79 (1 H, td, J=1.2, 6.9 Hz).

(iii) Production of 3-[4-(2,3-difluorophenyl)-5-(1H-1,2,4-triazol-3-yl)-1,3-thiazol-2-yl]-2-methylpyrazolo[1,5-a]pyridine According to the similar manner described in Example 97-B (iv), the title compound (96 mg, 69%) has been obtained as a pale yellow solid using 4-(2,3-difluorophenyl)-2-(2-methylpyrazolo[1,5-a]pyridin-3-yl)-1,3-thiazole-5-carboxamide (130 mg, 0.351 mmol) obtained above.
$^1$H-NMR (DMSO-$d_6$, 300 MHz) δ 2.73 (3 H, s), 7.08 (1 H, dt, J=1.2, 6.8 Hz), 7.27-7.39 (1 H, m), 7.45-7.59 (3 H, m), 8.31 (1 H, td, J=1.2, 8.9 Hz), 8.56 (1 H, s), 8.78 (1 H, td, J=1.2, 6.8 Hz), 14.21 (1 H, br s).

Example 99-B

Production of 3-[4-(2,4-dimethoxyphenyl)-5-(1H-1,2,4-triazol-3-yl)-1,3-thiazol-2-yl]-2-methylpyrazolo[1,5-a]pyridine

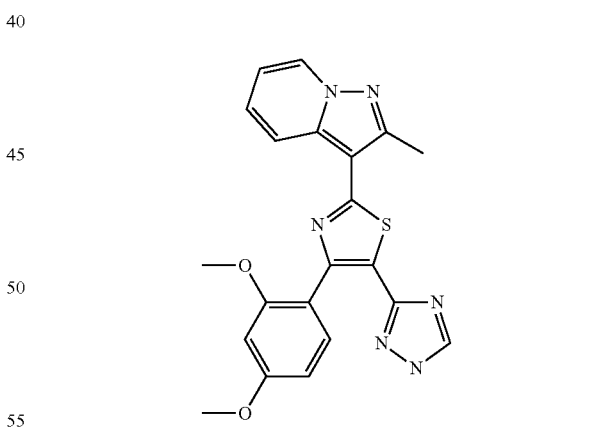

(i) Production of 4-(2,4-dimethoxyphenyl)-2-(2-methylpyrazolo[1,5-a]pyridin-3-yl)-1,3-thiazole-5-carboxylic acid According to the similar manner described in Example 97-B (i) and (ii), the title compound (205 mg, 92%) has been obtained as a colorless solid by the Suzuki coupling reaction using methyl 2-(2-methylpyrazolo[1,5-a]pyridin-3-yl)-4-{[(trifluoromethyl)sulfonyl]oxy}-1,3-thiazole-5-carboxylate (236 mg, 0.561 mmol)obtained in Example 13-B (ii) and 2,4-Dimethoxybenzeneboronic acid (153 mg, 0.842 mmol) followed by standard ester hydrolysis procedure.

$^1$H-NMR (DMSO-$d_6$, 300 MHz) δ 2.68 (3 H, s), 3.73 (3 H, s), 3.84 (3 H, s), 6.58-6.68 (2 H, m), 7.08 (1 H, dt, J=1.2, 7.0 Hz), 7.39 (1 H, d, J=8.3 Hz), 7.53 (1 H, ddd, J=1.2, 7.0, 8.7 Hz), 8.29 (1 H, td, J=1.2, 8.7 Hz), 8.77 (1 H, d, J=7.0 Hz), 12.77 (1 H, br s).

(ii) Production of 3-[4-(2,4-dimethoxyphenyl)-5-(1H-1,2,4-triazol-3-yl)-1,3-thiazol-2-yl]-2-methylpyrazolo[1,5-a]pyridine According to the similar manner described in Example 97-B (iii) and (iv), the title compound (131 mg, 61%) has been obtained as a pale yellow solid using 4-(2,4-dimethoxyphenyl)-2-(2-methylpyrazolo[1,5-a]pyridin-3-yl)-1,3-thiazole-5-carboxylic acid obtained above.

The pure title compound has been obtained by the crystallization of crude compound from THF (8 mL) and hexane (4 mL).

$^1$H-NMR (DMSO-$d_6$, 300 MHz) δ 2.71 (3 H, s), 3.50 (3 H, s), 3.83 (3 H, s), 6.58-6.66 (2 H, m), 7.05 (1 H, dt, J=1.2, 6.8 Hz), 7.43 (1 H, d, J=8.1 Hz), 7.49 (1 H, ddd, J=1.2, 6.8, 8.9 Hz), 8.29 (1 H, td, J=41.2, 8.9 Hz), 8.43 (1 H, br s), 8.75 (1 H, td, J=1.2, 6.8 Hz), 13.98 (1 H, br s).

Example 100-B

Production of 3-[4-(2-fluoro-6-methoxyphenyl)-5-(1H-1,2,4-triazol-3-yl)-1,3-thiazol-2-yl]-2-methylpyrazolo[1,5-a]pyridine

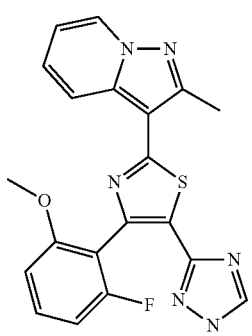 [SMILES: COc1cccc(F)c1-c1nc(-c2c(C)nn3ccccc23)sc1-c1nc[nH]n1]

(i) Production of methyl 4-(2-fluoro-6-methoxyphenyl)-2-(2-methylpyrazolo[1,5-a]pyridin-3-yl)-1,3-thiazole-5-carboxylate According to the similar manner described in Example 97-B (i), the title compound (86 mg, 93%) has been obtained as a yellow solid by the Suzuki coupling reaction using methyl 2-(2-methylpyrazolo[1,5-a]pyridin-3-yl)-4-{[(trifluoromethyl)sulfonyl]oxy}-1,3-thiazole-5-carboxylate (97.3 mg, 0.231 mmol) obtained in Example 13-B (ii) and (2-fluoro-6-methoxyphenyl)boronic acid (78.5 mg, 0.462 mmol). The pure title compound has been obtained by the basic silica gel column chromatographic purification (EtOAc/hexane=0/100→30/70).

$^1$H-NMR (DMSO-$d_6$, 300 MHz) δ 2.70 (3 H, s), 3.72 (3 H, s), 3.76 (3 H, s), 6.85-7.04 (2 H, m), 7.11 (1 H, dt, J=1.2, 6.9 Hz), 7.43-7.60 (2 H, m), 8.25 (1 H, td, J=1.2, 8.9 Hz), 8.80 (1 H, td, J=1.2, 6.9 Hz).

(ii) Production of 4-(2-fluoro-6-methoxyphenyl)-2-(2-methylpyrazolo[1,5-a]pyridin-3-yl)-1,3-thiazole-5-carboxylic acid According to the similar manner described in Example 97-B (ii), the title compound (129 mg, 83%) has been obtained as a pale blue solid by standard ester hydrolysis reaction using methyl 4-(2-fluoro-6-methoxyphenyl)-2-(2-methylpyrazolo[1,5-a]pyridin-3-yl)-1,3-thiazole-5-carboxylate (161 mg, 0.405 mmol) obtained above. The pure title compound has been obtained by washing of crude compound with EtOAc (5 mL).

$^1$H-NMR (DMSO-$d_6$, 300 MHz) δ 2.69 (3 H, s), 3.76 (3 H, s), 6.87-7.01 (2 H, m), 7.09 (1 H, dt, J=1.1, 6.9 Hz), 7.46 (1 H, dt, J=7.0, 8.4 Hz), 7.53 (1 H, ddd, J=1.1, 6.9, 8.9 Hz), 8.24 (1 H, td, J=1.1, 8.9 Hz), 8.78 (1 H, td, J=1.1, 6.8 Hz), 13.05 (1 H, br s).

(iii) Production of 4-(2-fluoro-6-methoxyphenyl)-2-(2-methylpyrazolo[1,5-a]pyridin-3-yl)-1,3-thiazole-5-carboxamide According to the similar manner described in Example 97-B (iii), the title compound (93 mg, 73%) has been obtained as a pale orange solid by the standard amidation reaction using 4-(2-fluoro-6-methoxyphenyl)-2-(2-methylpyrazolo[1,5-a]pyridin-3-yl)-1,3-thiazole-5-carboxylic acid (128 mg, 0.334 mmol) obtained above. The pure title compound has been obtained by washing of crude compound with diethyl ether (5 mL).

$^1$H-NMR (DMSO-$d_6$, 300 MHz) δ 2.69 (3 H, s), 3.77 (3 H, s), 6.88-7.03 (3 H, m), 7.07 (1 H, dt, J=1.2, 6.9 Hz), 7.42-7.57 (3 H, m), 8.21 (1 H, td, J=1.2, 8.9 Hz), 8.77 (1 H, td, J=1.2, 6.9 Hz).

(iv) Production of 3-[4-(2-fluoro-6-methoxyphenyl)-5-(1H-1,2,4-triazol-3-yl)-1,3-thiazol-2-yl]-2-methylpyrazolo[1,5-a]pyridine According to the similar manner described in Example 97-B (iv), the title compound (65 mg, 67%) has been obtained as a yellow solid using 4-(2-fluoro-6-methoxyphenyl)-2-(2-methylpyrazolo[1,5-a]pyridin-3-yl)-1,3-thiazole-5-carboxamide (91 mg, 0.238 mmol) obtained above. The pure title compound has been obtained by crystallization of the crude compound from THF (9 mL) and hexane (6 mL).

$^1$H-NMR (DMSO-$d_6$, 300 MHz) δ 2.71 (3 H, s), 3.66 (3 H, s), 6.83-6.99 (2 H, m), 7.06 (1 H, dt, J=1.2, 6.8 Hz), 7.38-7.55

(2 H, m), 8.24 (1 H, td, J=1.2, 8.8 Hz), 8.48 (1 H, br s), 8.76 (1 H, td, J=1.2, 6.8 Hz), 14.08 (1 H, br s).

Example 101-B

Production of 3-[4-(2,6-dimethylphenyl)-5-(1H-1,2,4-triazol-3-yl)-1,3-thiazol-2-yl]-2-methylpyrazolo[1,5-a]pyridine

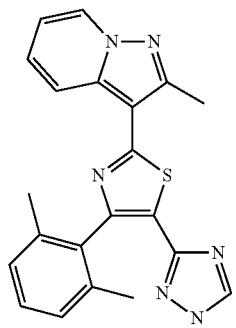 [SMILES: Cc1cccc(C)c1-c1nc(-c2c(C)nn3ccccc23)sc1-c1nc[nH]n1]

(i) Production of methyl 4-(2,6-dimethylphenyl)-2-(2-methylpyrazolo[1,5-a]pyridin-3-yl)-1,3-thiazole-5-carboxylate According to the similar manner described in Example 97-B (i), the title compound has been obtained as a yellow solid by the Suzuki coupling reaction using methyl 2-(2-methylpyrazolo[1,5-a]pyridin-3-yl)-4-({[(trifluoromethyl)sulfonyl]oxy}-1,3-thiazole-5-carboxylate (189 mg, 0.449 mmol) obtained in Example 13-B (ii) and 2,6-dimethylphenylboronic acid (135 mg, 0.898 mmol. The crude compound has been used in the next step without further purification.

$^1$H-NMR (DMSO-d$_6$, 300 MHz) δ 2.03 (6 H, s), 2.70 (3 H, s), 3.69 (3 H, s), 7.10 (1 H, td, J=1.3, 6.9 Hz), 7.12-7.16 (2 H, m), 7.24 (1 H, dd, J=6.6, 8.4 Hz), 7.54 (1 H, ddd, J=1.3, 6.9, 8.8 Hz), 8.24 (1 H, td, J=1.3, 8.8 Hz), 8.80 (1 H, td, J=1.3, 6.9 Hz).

(ii) Production of 4-(2,6-dimethylphenyl)-2-(2-methylpyrazolo[1,5-a]pyridin-3-yl)-1,3-thiazole-5-carboxamide According to the similar manner described in Example 97-B (ii) and (iii), the title compound (64 mg, 71%) has been obtained as a brown solid by the standard ester hydrolysis reaction followed by amidation reaction using methyl 4-(2,6-dimethylphenyl)-2-(2-methylpyrazolo[1,5-a]pyridin-3-yl)-1,3-thiazole-5-carboxylate obtained above.

$^1$H-NMR (DMSO-d$_6$, 300 MHz) δ 2.09 (6 H, s), 2.69 (3 H, s), 5.88 (1 H, br s), 7.08 (1H, dt, J=1.2, 6.9 Hz), 7.19-7.27 (2 H, m), 7.32 (1 H, dd, J=6.3, 8.4 Hz), 7.51 (1 H, br s), 7.51 (1 H, ddd, J=1.2, 6.9, 8.9 Hz), 8.22 (1 H, td, J=1.2, 8.9 Hz), 8.78 (1 H, td, J=1.2, 6.9 Hz).

(iii) Production of 3-[4-(2,6-dimethylphenyl)-5-(1H-1,2,4-triazol-3-yl)-1,3-thiazol-2-yl]-2-methylpyrazolo[1,5-a]pyridine According to the similar manner described in Example 97-B (iv), the title compound (58 mg, 88%) has been obtained as a yellow solid using 4-(2,6-dimethylphenyl)-2-(2-methylpyrazolo[1,5-a]pyridin-3-yl)-1,3-thiazole-5-carboxamide (62.0 mg, 0.171 mmol) obtained above. The pure compound has been obtained by crystallization from acetone and hexane.

$^1$H-NMR (DMSO-d$_6$, 300 MHz) δ 2.02 (6 H, s), 2.72 (3 H, s), 7.06 (1 H, dt, J=1.2, 6.8 Hz), 7.08-7.15 (2 H, m), 7.21 (1 H, dd, J=6.1, 8.3 Hz), 7.44-7.54 (1 H, m), 8.24 (1 H, td, J=1.2, 8.8 Hz), 8.51 (1 H, br s), 8.76 (1 H, td, J=1.2, 6.8 Hz), 14.05 (1 H, br s).

Example 102-B

Production of 3-[4-(2,6-dimethoxyphenyl)-5-(1H-1,2,4-triazol-3-yl)-1,3-thiazol-2-yl]-2-methylpyrazolo[1,5-a]pyridine

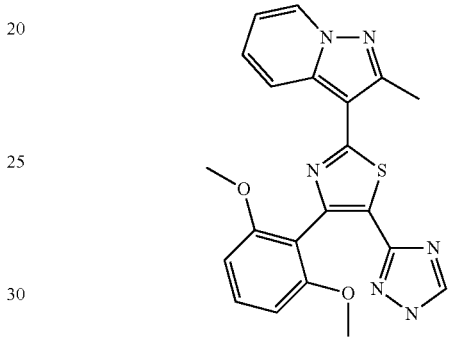

(i) Production of methyl 4-(2,6-dimethoxyphenyl)-2-(2-methylpyrazolo[1,5-a]pyridin-3-yl)-1,3-thiazole-5-carboxylate According to the similar manner described in Example 97-B (i), the title compound (174 mg, 89%) has been obtained as a gray solid by the Suzuki coupling reaction using methyl 2-(2-methylpyrazolo[1,5-a]pyridin-3-yl)-4-{[(trifluoromethyl)sulfonyl]oxy}-1,3-thiazole-5-carboxylate (200 mg, 0.475 mmol) obtained in Example 13-B (ii) and 2,6-dimethoxyphenylboronic acid (173 mg, 0.949 mmol. The pure compound has been obtained by washing of crude product with EtOAc (5 mL).

$^1$H-NMR (DMSO-d$_6$, 300 MHz) δ 2.69 (3 H, s), 3.67 (3 H, s), 3.68 (6 H, s), 6.76 (2 H, d, J=8.5 Hz), 7.09 (1 H, dt, J=1.2, 6.9 Hz), 7.39 (1 H, t, J=8.5 Hz), 7.53 (1 H, ddd, J=1.2, 6.9, 8.9 Hz), 8.24 (1 H, td, J=1.2, 8.9 Hz), 8.78 (1 H, td, J=1.2, 6.9 Hz)

(ii) Production of 4-(2,6-dimethoxyphenyl)-2-(2-methylpyrazolo[1,5-a]pyridin-3-yl)-1,3-thiazole-5-carboxylic acid According to the similar manner described in Example 97-B (ii), the title compound (144 mg, 87%) has been obtained as a pale yellow solid by standard ester hydrolysis reaction using methyl 4-(2,6-dimethoxyphenyl)-2-(2-methylpyrazolo[1,5-a]pyridin-3-yl)-1,3-thiazole-5-carboxylate (172 mg, 0.420 mmol) obtained above. The pure compound has been obtained by washing of crude product with EtOAc (5 mL).

$^1$H-NMR (DMSO-d$_6$, 300 MHz) δ 2.68 (3 H, s), 3.68 (6 H, s), 6.74 (2 H, d, J=8.5 Hz), 7.07 (1 H, dt, J=1.2, 6.9 Hz), 7.36

(1 H, t, J=8.5 Hz), 7.50 (1 H, ddd, J=1.2, 6.9, 8.9 Hz), 8.22 (1 H, td, J=1.2, 8.9 Hz), 8.76 (1 H, td, J=1.2, 6.9 Hz), 12.76 (1 H, br s).

(iii) Production of 4-(2,6-dimethoxyphenyl)-2-(2-methylpyrazolo[1,5-a]pyridin-3-yl)-1,3-thiazole-5-carboxamide According to the similar manner described in Example 97-B (iii), the title compound (113 mg, 80%) has been obtained as a pale yellow solid by standard amidation reaction using 4-(2,6-dimethoxyphenyl)-2-(2-methylpyrazolo[1,5-a]pyridin-3-yl)-1,3-thiazole-5-carboxylic acid (142 mg, 0.359 mmol) obtained above. The pure compound has been obtained by washing of crude product with EtOAc (5 mL).

$^1$H-NMR (DMSO-$d_6$, 300 MHz) δ 2.67 (3 H, s), 3.73 (6 H, s), 5.99 (1 H, br s), 6.83 (2 H, d, J=8.5 Hz), 7.06 (1 H, dt, J=1.2, 6.9 Hz), 7.31-7.58 (3 H, m), 8.20 (1 H, dt, J=1.2, 8.8 Hz), 8.76 (1 H, td, J=1.2, 6.9 Hz).

(iv) Production of 3-[4-(2,6-dimethoxyphenyl)-5-(1H-1,2,4-triazol-3-yl)-1,3-thiazol-2-yl]-2-methylpyrazolo[1,5-a]pyridine According to the similar manner described in Example 97-B (iv), the title compound (87 mg, 74%) has been obtained as a yellow solid using 4-(2,6-dimethoxyphenyl)-2-(2-methylpyrazolo[1,5-a]pyridin-3-yl)-1,3-thiazole-5-carboxamide (111 mg, 0.281 mmol) obtained above. The pure compound has been obtained by washing of crude product with EtOAc (5 mL).

$^1$H-NMR (DMSO-$d_6$, 300 MHz) δ 2.71 (3 H, s), 3.60 (6 H, s), 6.73 (2 H, d, J=8.4 Hz), 7.04 (1 H, dt, J=1.1, 6.8 Hz), 7.35 (1 H, t, J=8.4 Hz), 7.47 (1 H, ddd, J=1.1, 6.8, 8.9 Hz), 8.23 (1 H, td, J=1.1, 8.9 Hz), 8.42 (1 H, br s), 8.74 (1 H, td, J=1.1, 6.8 Hz), 13.94 (1 H, br s).

Example 103-B

Production of 3-[4-(2-chloro-6-methoxyphenyl)-5-(1H-1,2,4-triazol-3-yl)-1,3-thiazol-2-yl]-2-methylpyrazolo[1,5-a]pyridine

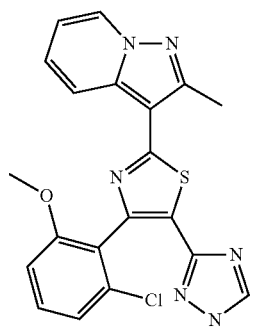 [SMILES: COc1cccc(Cl)c1-c1nc(-c2c(C)nn3ccccc23)sc1-c1nc[nH]n1]

(i) Production of methyl 4-(2-chloro-6-methoxyphenyl)-2-(2-methylpyrazolo[1,5-a]pyridin-3-yl)-1,3-thiazole-5-carboxylate According to the similar manner described in Example 97-B (i), the title compound (226 mg, 76%) has been obtained as a pale yellow solid by the Suzuki coupling reaction using methyl 2-(2-methylpyrazolo[1,5-a]pyridin-3-yl)-4-{[(trifluoromethyl)sulfonyl]oxy}-1,3-thiazole-5-carboxylate (300 mg, 0.712 mmol) obtained in Example 13-B (ii) and 2-Chloro-6-methoxyphenylboronic acid (265 mg, 1.42 mmol. The pure compound has been obtained by basic silicagel column chromatographic purification (EtOAc/hexane=10/90→40/60).

$^1$H-NMR (DMSO-$d_6$, 300 MHz) δ 2.70 (3 H, s), 3.70 (3 H, s), 3.72 (3 H, s), 7.06-7.22 (3 H, m), 7.47 (1 H, t, J=8.1 Hz), 7.55 (1 H, ddd, J=1.2, 6.9, 8.9 Hz), 8.25 (1 H, td, J=1.2, 8.9 Hz), 8.80 (1 H, td, J=1.2, 6.9 Hz).

(ii) Production of 4-(2-chloro-6-methoxyphenyl)-2-(2-methylpyrazolo[1,5-a]pyridin-3-yl)-1,3-thiazole-5-carboxylic acid According to the similar manner described in Example 97-B (ii), the title compound has been obtained as a pale yellow solid by standard ester hydrolysis reaction using methyl 4-(2-chloro-6-methoxyphenyl)-2-(2-methylpyrazolo[1,5-a]pyridin-3-yl)-1,3-thiazole-5-carboxylate (172 mg, 0.420 mmol) obtained above. The crude product has been used in the next step.

$^1$H-NMR (DMSO-$d_6$, 300 MHz) δ 2.69 (3 H, s), 3.73 (3 H, s), 7.05-7.20 (3 H, m), 7.44 (1 H, t, J=8.2 Hz), 7.53 (1 H, ddd, J=1.1, 6.9, 8.9 Hz), 8.24 (1 H, td, J=1.1, 8.9 Hz), 8.79 (1 H, td, J=1.1, 6.9 Hz), 12.97 (1 H, br s).

(iii) Production of 4-(2-chloro-6-methoxyphenyl)-2-(2-methylpyrazolo[1,5-a]pyridin-3-yl)-1,3-thiazole-5-carboxamide According to the similar manner described in Example 97-B (iii), the title compound (147 mg, 69%) has been obtained as a colorless solid by standard amidation reaction using 4-(2-chloro-6-methoxyphenyl)-2-(2-methylpyrazolo[1,5-a]pyridin-3-yl)-1,3-thiazole-5-carboxylic acid obtained above. The pure compound has been obtained by washing of crude product with a 1:1 mixture of EtOAc and diethyl ether (10 mL).

$^1$H-NMR (DMSO-$d_6$, 300 MHz) δ 2.69 (3 H, s), 3.75 (3 H, s), 6.66 (1 H, br s), 7.07 (1 H, td, J=1.2, 6.9 Hz), 7.12-7.25 (2 H, m), 7.30-7.61 (3 H, m), 8.21 (1 H, td, J=1.2, 8.9 Hz), 8.77 (1 H, td, J=1.2, 6.8 Hz),

(iv) Production of 3-[4-(2-chloro-6-methoxyphenyl)-5-(1H-1,2,4-triazol-3-yl)-1,3-thiazol-2-yl]-2-methylpyrazolo[1,5-a]pyridine According to the similar manner described in Example 97-B (iv), the title compound (94 mg, 61%) has been obtained as a yellow solid using 4-(2-chloro-6-methoxyphenyl)-2-(2-methylpyrazolo[1,5-a]pyridin-3-yl)-1,3-thiazole-5-carboxamide (145 mg, 0.364 mmol) obtained above. The pure compound has been obtained by crystallization from EtOAc (5 mL) and THF (1 mL).

$^1$H-NMR (DMSO-$d_6$, 300 MHz) δ 2.72 (3 H, s), 3.64 (3 H, s), 7.01-7.18 (3 H, m), 7.43 (1 H, t, J=8.2 Hz), 7.49 (1 H, ddd, J=1.1, 6.9, 8.9 Hz), 8.24 (1 H, td, J=1.1, 8.9 Hz), 8.48 (1 H, br s), 8.76 (1 H, td, J=1.1, 6.9 Hz), 14.05 (1 H, br s).

Example 104-B

Production of 3-[4-(2-chloro-6-fluorophenyl)-5-(1H-1,2,4-triazol-3-yl)-1,3-thiazol-2-yl]-2-methylpyrazolo[1,5-a]pyridine

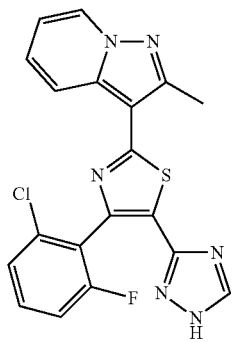 [SMILES: Cc1nn2ccccc2c1-c1nc(-c2c(F)cccc2Cl)c(-c2nc[nH]n2)s1]

(i) Production of methyl 4-(2-chloro-6-fluorophenyl)-2-(2-methylpyrazolo[1,5-a]pyridin-3-yl)-1,3-thiazole-5-carboxylate According to the similar manner described in Example 97-B (i), the title compound (315 mg, 33%) has been obtained as a yellow solid by the Suzuki coupling reaction using methyl 2-(2-methylpyrazolo[1,5-a]pyridin-3-yl)-4-{[(trifluoromethyl)sulfonyl]oxy}-1,3-thiazole-5-carboxylate (1.00 g, 2.37 mmol) obtained in Example 13-B (ii) and 2-Chloro-6-fluorophenylboronic acid (828 mg, 4.75 mmol. The pure compound has been obtained by washing of crude product with EtOAc (5 mL).
$^1$H-NMR (DMSO-$d_6$, 300 MHz) δ 2.71 (3 H, s), 3.75 (3 H, s), 7.13 (1 H, dt, J=1.2, 6.9 Hz), 7.39 (1 H, dt, J=1.2, 8.9 Hz), 7.47-7.65 (3 H, m), 8.27 (1 H, td, J=1.2, 8.9 Hz), 8.82 (1 H, td, J=1.2, 6.9 Hz).

(ii) Production of 4-(2-chloro-6-fluorophenyl)-2-(2-methylpyrazolo[1,5-a]pyridin-3-yl)-1,3-thiazole-5-carboxylic acid According to the similar manner described in Example 97-B (ii), the title compound (237 mg, 78%) has been obtained as a pale yellow solid by standard ester hydrolysis reaction using methyl 4-(2-chloro-6-fluorophenyl)-2-(2-methylpyrazolo[1,5-a]pyridin-3-yl)-1,3-thiazole-5-carboxylate (313 mg, 0.779 mmol) obtained above. The pure title compound has been obtained by washing of crude product with EtOAc (10 mL).
$^1$H-NMR (DMSO-$d_6$, 300 MHz) δ 2.70 (3 H, s), 7.11 (1 H, dt, J=1.2, 6.9 Hz), 7.32-7.42 (1 H, m), 7.44-7.51 (1 H, m), 7.51-7.62 (2 H, m), 8.26 (1 H, td, J=1.2, 8.9 Hz), 8.80 (1 H, td, J=1.2, 6.9 Hz), 13.35 (1 H, br s).

(iii) Production of 4-(2-chloro-6-fluorophenyl)-2-(2-methylpyrazolo[1,5-a]pyridin-3-yl)-1,3-thiazole-5-carboxamide According to the similar manner described in Example 97-B (iii), the title compound (124 mg, 53%) has been obtained as a brown solid by standard amidation reaction using 4-(2-chloro-6-fluorophenyl)-2-(2-methylpyrazolo[1,5-a]pyridin-3-yl)-1,3-thiazole-5-carboxylic acid (235 mg, 0.606 mmol) obtained above. The pure compound has been obtained by washing of crude product with EtOAc (3 mL).
$^1$H-NMR (DMSO-$d_6$, 300 MHz) δ 2.70 (3 H, s), 7.09 (1 H, dt, J=1.2, 6.9 Hz), 7.33 (1 H, dt, J=1.2, 8.8 Hz), 7.40-7.62 (5 H, m), 8.23 (1 H, td, J=1.2, 8.8 Hz), 8.79 (1 H, td, J=1.2, 6.9 Hz).

(iv) Production of 3-[4-(2-chloro-6-fluorophenyl)-5-(1H-1,2,4-triazol-3-yl)-1,3-thiazol-2-yl]-2-methylpyrazolo[1,5-a]pyridine According to the similar manner described in Example 97-B (iv), the title compound (92 mg, 71%) has been obtained as a pale yellow solid using 4-(2-chloro-6-fluorophenyl)-2-(2-methylpyrazolo[1,5-a]pyridin-3-yl)-1,3-thiazole-5-carboxamide (122 mg, 0.315 mmol) obtained above. The pure compound has been obtained by washing of crude compound with EtOAc (5 mL).
$^1$H-NMR (DMSO-$d_6$, 300 MHz) δ 2.73 (3 H, s), 7.07 (1 H, dt, J=1.2, 6.8 Hz), 7.34 (1H, dt, 1.2, 8.8 Hz), 7.42-7.59 (3 H, m), 8.26 (1 H, td, J=1.2, 8.8 Hz), 8.53 (1 H, br s), 8.77 (1H, td, J=1.2, 6.8 Hz), 14.17 (1 H, br s).

Example 105-B

Production of 3-[4-(2,3-difluoro-6-methoxyphenyl)-5-(1H-1,2,4-triazol-3-yl)-1,3-thiazol-2-yl]-2-methylpyrazolo[1,5-a]pyridine

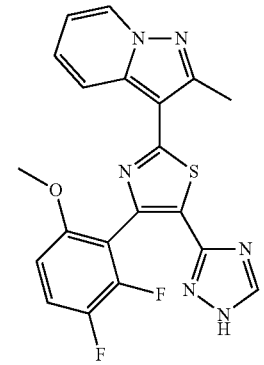 [SMILES: COc1ccc(F)c(F)c1-c1nc(-c2c(C)nn3ccccc23)sc1-c1nc[nH]n1]

(i) Production of 4-(2,3-difluoro-6-methoxyphenyl)-2-(2-methylpyrazolo[1,5-a]pyridin-3-yl)-1,3-thiazole-5-carboxylic acid According to the similar manner described in Example 97-B (i) and (ii), the title compound (237 mg, 78%) has been obtained as a brown solid by the Suzuki coupling reaction followed by standard ester hydrolysis reaction using methyl 2-(2-methylpyrazolo[1,5-a]pyridin-3-yl)-4-{[(trifluoromethyl)sulfonyl]oxy}-1,3-thiazole-5-carboxylate (339 mg, 0.805 mmol) obtained in Example 13-B (ii) and 2,3-difluoro-6-methoxyphenylboronic acid (303 mg, 1.61 mmol). The pure title compound has been obtained by washing with EtOAc (10 mL).
$^1$H-NMR (DMSO-$d_6$, 300 MHz) δ 2.69 (3 H, s), 3.75 (3 H, s), 6.96 (1 H, ddd, J=2.1, 3.7, 9.3 Hz), 7.10 (1 H, dt, J=1.2, 6.9

Hz), 7.43-7.63 (2 H, m), 8.24 (1 H, td, J=1.2, 8.9 Hz), 8.79 (1 H, td, J=1.2, 6.9 Hz), 13.21 (1 H, br s).

(ii) Production of 4-(2,3-difluoro-6-methoxyphenyl)-2-(2-methylpyrazolo[1,5-a]pyridin-3-yl)-1,3-thiazole-5-carboxamide According to the similar manner described in Example 97-B (iii), the title compound (102 mg, 59%) has been obtained as a brown solid by standard amidation reaction using 4-(2,3-difluoro-6-methoxyphenyl)-2-(2-methylpyrazolo[1,5-a]pyridin-3-yl)-1,3-thiazole-5-carboxylic acid (173 mg, 0.431 mmol) obtained above. The pure compound has been obtained by washing of crude product with EtOAc (5 mL)

$^1$H-NMR (DMSO-$d_6$, 300 MHz) δ 2.69 (3 H, s), 3.74 (3 H, s), 6.95 (1 H, ddd, J=2.0, 3.8, 9.3 Hz), 7.08 (1 H, dt, J=1.2, 6.9 Hz), 7.37 (2 H, br s), 7.44-7.58 (2 H, m), 8.22 (1 H, td, J=1.2, 8.8 Hz), 8.78 (1 H, td, J=1.2, 6.9 Hz).

(iii) Production of 3-[4-(2,3-difluoro-6-methoxyphenyl)-5-(1H-1,2,4-triazol-3-yl)-1,3-thiazol-2-yl]-2-methylpyrazolo[1,5-a]pyridine According to the similar manner described in Example 97-B (iv), the title compound (58 mg, 55%) has been obtained as a yellow solid using 4-(2,3-difluoro-6-methoxyphenyl)-2-(2-methylpyrazolo[1,5-a]pyridin-3-yl)-1,3-thiazole-5-carboxamide (100 mg, 0.250 mmol) obtained above. The pure compound has been obtained by crystallization from EtOAc (1 mL) and diethyl ether (1 mL).

$^1$H-NMR (DMSO-$d_6$, 300 MHz) δ 2.72 (3 H, s), 3.65 (3 H, s), 6.94 (1 H, ddd, J=1.8, 3.7, 9.4 Hz), 7.07 (1 H, dt, J=1.2, 6.9 Hz), 7.42-7.56 (2 H, m), 8.25 (1 H, d, J=8.9 Hz), 8.55 (1 H, s), 8.77 (1 H, d, J=6.9 Hz), 14.14 (1 H, s).

Example 106-B

Production of 3-[4-(2-fluoro-6-methoxyphenyl)-5-(1H-1,2,4-triazol-3-yl)-1,3-thiazol-2-yl]-2-methyl-5-(2-morpholin-4-ylethoxy)pyrazolo[1,5-a]pyridine

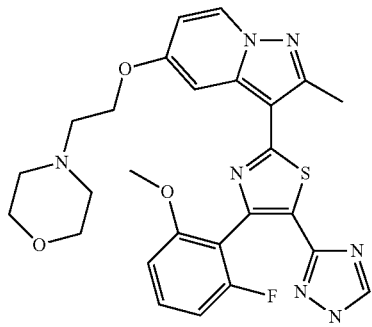 [SMILES: COc1cccc(F)c1-c1nc(-c2c(C)nn3ccc(OCCN4CCOCC4)cc23)sc1-c1nc[nH]n1]

(i) Production of methyl 2-[5-(benzyloxy)-2-methylpyrazolo[1,5-a]pyridin-3-yl]-4-{[(trifluoromethyl)sulfonyl]oxy}-1,3-thiazole-5-carboxylate To a suspension of 5-(benzyloxy)-2-methylpyrazolo[1,5-a]pyridine-3-carbothioamide hydrochloride(3.45 g, 10.3 mmol) in DMF (100 mL), was added 94% dimethyl chloromalonate (2.79 mL, 20.6 mmol) and the mixture was stirred for 7.5 h at 100° C. The reaction mixture was allowed to cool to 50° C. and then was dropwise added water (100 mL). The resulting precipitate was collected by filtration and then washed with EtOH (20 mL) and diethyl ether (20 mL) to obtain methyl 2-[5-(benzyloxy)-2-methylpyrazolo[1,5-a]pyridin-3-yl]-4-hydroxy-1,3-thiazole-5-carboxylate as a orange solid, which was used in the next step without further purification. $^1$H-NMR (DMSO-$d_6$, 300 MHz) δ 2.59 (3 H, s), 3.75 (3 H, s), 5.27 (2 H, s), 6.87 (1 H, dd, J=2.6, 7.6 Hz), 7.32-7.51 (3 H, m), 7.52-7.64 (2 H, m), 7.88 (1 H, d, J=2.6 Hz), 8.67 (1 H, d, J=7.6 Hz), 11.79 (1 H, br s).

To a suspension of methyl 2-[5-(benzyloxy)-2-methylpyrazolo[1,5-a]pyridin-3-yl]-4-hydroxy-1,3-thiazole-5-carboxylate obtained above in pyridine (100 mL), was added Trifluoromethanesulfonic anhydride (3.46 mL, 20.6 mmol) and the mixture was stirred for 3 h at 50° C. The mixture was concentrated under reduced pressure until half volume and then were added a 2:1 mixture of EtOAc and THF (150 mL) and saturated aqueous solution of ammonium chloride (100 mL). The organic layer was separated and the aqueous layer was extracted with a 2:1 mixture of EtOAc and THF (30 mL). The combined organic layer was washed with brine (20 mL) and then filtered through silica gel pad (100 g). The filtrate was concentrated under reduced pressure and the residue was washed with EtOAc (20 mL) to obtain title compound (2.51 g, 46%) as a red solid.

$^1$H-NMR (DMSO-$d_6$, 300 MHz) δ 2.62 (3 H, s), 3.89 (3 H, s), 5.26 (2 H, s), 6.96 (1 H, dd, J=2.6, 7.6 Hz), 7.35-7.48 (3 H, m), 7.48-7.55 (2 H, m), 7.63 (1 H, d, J=2.6 Hz), 8.76 (1 H, d, J=7.6 Hz), (ii) Production of 2-[5-(benzyloxy)-2-methylpyrazolo[1,5-a]pyridin-3-yl]-4-(2-fluoro-6-methoxyphenyl)-1,3-thiazole-5-carboxylic acid According to the similar manner described in Example 97-B (i) and (ii), the title compound (2.19 g, 73%) has been obtained as a pale purple solid by the Suzuki coupling reaction followed by standard ester hydrolysis reaction using methyl 2-[5-(benzyloxy)-2-methylpyrazolo[1,5-a]pyridin-3-yl]-4-{[(trifluoromethyl)sulfonyl]oxy}-1,3-thiazole-5-carboxylate (3.21 g, 6.09 mmol) obtained above and (2-fluoro-6-methoxyphenyl)boronic acid (2.07 g, 12.2 mmol). The pure title compound has been obtained by washing of the crude product, which was precipitated from reaction mixture after acidic work-up, with water (30 mL), MeOH (30 mL) and EtOAc (30 mL).

$^1$H-NMR (DMSO-$d_6$, 300 MHz) δ 2.61 (3 H, s), 3.78 (3 H, s), 5.19 (2 H, s), 6.83 (1 H, dd, J=2.6, 7.6 Hz), 6.95 (1 H, t, J=8.7 Hz), 7.02 (1 H, d, J=8.7 Hz), 7.19-7.34 (3 H, m), 7.35-7.42 (2 H, m), 7.48 (1 H, dt, J=6.9, 8.7 Hz), 7.67 (1 H, d, J=2.6 Hz), 8.65 (1 H, d, J=7.6 Hz), 13.03 (1 H, br s).

(iii) Production of 2-[5-(benzyloxy)-2-methylpyrazolo[1,5-a]pyridin-3-yl]-4-(2-fluoro-6-methoxyphenyl)-1,3-thiazole-5-carboxamide According to the similar manner described in Example 97-B (iii), the title compound (2.09 g, 89%) has been obtained as a yellow solid by standard amidation reaction using 2-[5-(benzyloxy)-2-methylpyrazolo[1,5-a]pyridin-3-yl]-4-(2-fluoro-6-methoxyphenyl)-1,3-thiazole-5-carboxylic acid (2.33 g, 4.76 mmol) obtained above. The pure title compound has been obtained by washing of the crude product, which was precipitated from reaction mixture after aqueous work-up, with water (50 mL) and EtOAc (20 mL).

¹H-NMR (DMSO-d₆, 300 MHz) δ 2.61 (3 H, s), 3.79 (3 H, s), 5.18 (2 H, s), 6.81 (1 H, dd, J=7.6, 2.7 Hz), 6.90-7.10 (1 H, m), 6.97 (1 H, t, J=8.6 Hz), 7.03 (1 H, d, J=8.6 Hz), 7.21-7.35 (3 H, m), 7.35-7.56 (3 H, m), 7.49 (1 H, dt, J=6.9, 8.6 Hz), 7.66 (1 H, d, J=2.7 Hz), 8.64 (1 H, d, J=7.6 Hz).

(iv) Production of 5-(benzyloxy)-3-[4-(2-fluoro-6-methoxyphenyl)-5-(1H-1,2,4-triazol-3-yl)-1,3-thiazol-2-yl]-2-methylpyrazolo[1,5-a]pyridine According to the similar manner described in Example 97-B (iv), the title compound has been obtained as a pale yellow solid using 2-[5-(benzyloxy)-2-methylpyrazolo[1,5-a]pyridin-3-yl]-4-(2-fluoro-6-methoxyphenyl)-1,3-thiazole-5-carboxamide (1.87 g, 3.83 mmol) obtained above. The crude compound has been used in the next step without further purification.

¹H-NMR (DMSO-d₆, 300 MHz) δ 2.64 (3 H, s), 3.68 (3 H, s), 5.19 (2 H, s), 6.79 (1 H, dd, J=2.7, 7.6 Hz), 6.92 (1 H, t, 8.4 Hz), 6.99 (1 H, d, J=8.4 Hz), 7.19-7.36 (3 H, m), 7.36-7.52 (3 H, m), 7.68 (1 H, d, J=2.7 Hz), 8.50 (1 H, br s), 8.62 (1 H, d, J=7.6 Hz), 14.04 (1 H, br s).

(v) Production of 5-(benzyloxy)-3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridine To a solution of 5-(benzyloxy)-3-[4-(2-fluoro-6-methoxyphenyl)-5-(1H-1,2,4-triazol-3-yl)-1,3-thiazol-2-yl]-2-methylpyrazolo[1,5-a]pyridine obtained above in THF (50 mL), were added 3,4-dihydro-2H-pyran (1.05 mL, 11.5 mmol) and p-toluenesulfonic acid monohydrate (364 mg, 1.92 mmol) and the mixture was stirred for 1.5 h at 70° C. To the mixture were added EtOAc (50 mL) and saturated aqueous solution of sodium bicarbonate (50 mL). The organic layer was separated and the aqueous layer was extracted with EtOAc (30 mL). The combined organic layer was washed with brine (20 mL) and then dried over anhydrous magnesium sulfate. Insoluble materials were removed by filtration and the filtrate was concentrated under reduced pressure. The residue was purified by basic silica gel column chromatography (EtOAc/hexane=40/60→70/30) to give title compound (1.68 g, 73%) as a pale yellow solid.

¹H-NMR (DMSO-d₆, 300 MHz) δ 1.43-1.70 (3 H, m), 1.80-2.00 (3 H, m), 2.64 (3 H, s), 3.56-3.66 (1 H, m), 3.68 (3 H, s), 3.80-3.92 (1 H, m), 5.20 (2 H, s), 5.54 (1 H, dd, J=3.4, 7.9 Hz), 6.80 (1 H, dd, J=2.7, 7.6 Hz), 6.92 (1 H, t, J=8.6 Hz), 6.99 (1 H, d, J=8.6 Hz), 7.22-7.34 (3 H, m), 7.38-7.52 (3 H, m), 7.68 (1 H, d, J=2.7 Hz), 8.63 (1 H, d, J=7.6 Hz), 8.64 (1 H, s).

(vi) Production of 3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridin-5-ol To a solution of 5-(benzyloxy)-3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridine (1.65 g, 2.77 mmol) obtained above in THF (60 mL) and EtOH (20 mL), was added 10% palladium-carbon (884 mg, 0.831 mmol) and the mixture was stirred for 2.5 h at rt under hydrogen atmosphere (1 atm). The mixture was filtered through Celite pad and the filtrate was concentrated under reduced pressure. The residue was crystallized from EtOAc (10 mL) to give title compound (1.30 g, 93%) as a pale yellow solid.

¹H-NMR (DMSO-d₆, 300 MHz) δ 1.43-1.69 (3 H, m), 1.78-1.97 (3 H, m), 2.63 (3 H, s), 3.55-3.65 (1 H, m), 3.66 (3 H, s), 3.79-3.89 (1 H, m), 5.53 (1 H, dd, J=3.5, 7.6 Hz), 6.60 (1 H, dd, J=2.6, 7.5 Hz), 6.89 (1 H, t, J=8.5 Hz), 6.95 (1 H, d, J=8.5 Hz), 7.44 (1 H, dt, J=7.0, 8.5 Hz), 7.53 (1 H, d, J=2.6 Hz), 8.55 (1 H, d, J=7.5 Hz), 8.61 (1 H, s), 10.70 (1 H, s).

(vii) Production of 3-[4-(2-fluoro-6-methoxyphenyl)-5-(1H-1,2,4-triazol-3-yl)-1,3-thiazol-2-yl]-2-methyl-5-(2-morpholin-4-ylethoxy)pyrazolo[1,5-a]pyridine According to the similar manner described in Example 85-B (ii) and (iii), the title compound (110 mg, 69%) has been obtained as a colorless solid using 3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridin-5-ol (150 mg, 0.296 mmol) obtained above and 4-(2-chloroethyl)morpholine hydrochloride (110 mg, 0.592 mmol) by standard alkylation reaction followed by deprotection of THP group using 2 N hydrochloric acid (2 mL) in THF (6 mL) and MeOH (2 mL) by standard manner. The pure title compound has been obtained by crystallization from THF (2 mL) and AcOEt (4 mL).

¹H-NMR (DMSO-d₆, 300 MHz) δ 2.41-2.48 (4 H, m), 2.65 (3 H, s), 2.73 (2 H, t, J=5.8 Hz), 3.50-3.59 (4 H, m), 3.67 (3 H, s), 4.19 (2 H, t, J=5.8 Hz), 6.75 (1 dd, J=2.8, 7.6 Hz), 6.87 (1 H, t, J=8.5 Hz), 6.96 (1 H, d, J=8.5 Hz), 7.43 (1 H, dt, J=6.9, 8.5 Hz), 7.59 (1 H, d, J=2.8 Hz), 8.49 (1 H, br s), 8.62 (1 H, d, J=7.6 Hz), 14.06 (1 H, br s).

Example 107-B

Production of 3-[4-(2-fluoro-6-methoxyphenyl)-5-(1H-1,2,4-triazol-3-yl)-1,3-thiazol-2-yl]-2-methyl-5-[2-(4-methylpiperazin-1-yl)ethoxy]pyrazolo[1,5-a]pyridine

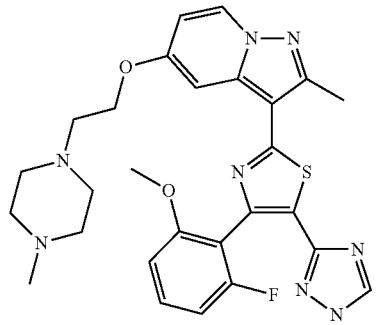 [SMILES: COc1cccc(F)c1-c1nc(-c2c(C)nn3ccc(OCCN4CCN(C)CC4)cc23)sc1-c1nc[nH]n1]

(i) Production of 5-(2-chloroethoxy)-3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridine According to the similar manner described in 85-B (ii), the title compound (429 mg, 95%) has been obtained as a pale yellow amorphous solid using 1-bromo-2-chloroethane (329 µL, 3.95 mmol) and 3-{4-(2-fluoro-6-methoxyphenyl)-5-[1-

(tetrahydro-2H-pyran-2-yl)-1H-1,2,4-triazol-3-yl]-1,3-thiazol-2-yl}-2-methylpyrazolo[1,5-a]pyridin-5-ol obtained in Example 86-B (vi) and cesium carbonate (1.29 g, 3.95 mmol) by standard alkylation reaction. The crude product has been purified by silica gel column chromatography (EtOAc/hexane=30/70→70/30).

$^1$H-NMR (DMSO-$d_6$, 300 MHz) δ 1.43-1.70 (3 H, m), 1.80-2.02 (3 H, m), 2.66 (3 H, s), 3.55-3.66 (1 H, m), 3.68 (3 H, s), 3.80-3.91 (1 H, m), 4.01 (2 H, t, J=5.3 Hz), 4.36 (2 H, t, J=5.3 Hz), 5.53 (1 H, dd, J=3.5, 7.8 Hz), 6.81 (1 H, dd, J=2.8, 7.6 Hz), 6.88 (1 H, t, J=8.6 Hz), 6.96 (1 H, d, J=8.6 Hz), 7.44 (1 H, dt, J=6.9, 8.6 Hz), 7.57 (1 H, d, J=2.8 Hz), 8.64 (1 H, s), 8.66 (1 H, d, J=7.6 Hz).¥

(ii) Production of 3-[4-(2-fluoro-6-methoxyphenyl)-5-(1H-1,2,4-triazol-3-yl)-1,3-thiazol-2-yl]-2-methyl-5-[2-(4-methylpiperazin-1-yl)ethoxy]pyrazolo[1,5-a]pyridine according to the similar manner described in Example 88-B (ii) and (iii), the title compound (104 mg, 50%) has been obtained as a colorless solid using 5-(2-chloroethoxy)-3-(4-(2-fluoro-6-methoxyphenyl)-5-[1-(tetrahydro-2H-pyran-2-yl)-1H-1,2,4-triazol-3-yl]-1,3-thiazol-2-yl)-2-methylpyrazolo[1,5-a]pyridine (213 mg, 0.374 mmol) obtained above, 1-methylpiperazine (83.4 µL, 0.749 mmol), potassium carbonate (104 mg, 0.749 mmol) and sodium iodide (112 mg, 0.749 mmol) by standard alkylation reaction followed by deprotection of THP group using 2 N hydrochloric acid (2 mL) in THF (6 mL) and MeOH (2 mL) by standard manner.

The pure title compound has been obtained by crystallization from EtOH (6 mL) and hexane (2 mL).

$^1$H-NMR (DMSO-$d_6$, 300 MHz) δ 2.14 (3 H, s), 2.28 (4 H, br s), 2.46 (4 H, br s), 2.65 (3 H, s), 2.72 (2 H, t, J=5.9 Hz), 3.67 (3 H, s), 4.16 (2 H, t, J=5.9 Hz), 6.75 (1 H, dd, J=2.7, 7.6 Hz), 6.87 (1 H, t, J=8.5 Hz), 6.95 (1 H, d, J=8.5 Hz), 7.43 (1 H, dt, J=6.9, 8.5 Hz), 7.58 (1 H, d, J=2.7 Hz), 8.48 (1 H, s), 8.61 (1 H, d, J=7.6 Hz), 14.05 (1 H, br s).

Example 108-B

Production of 3-[4-(2-fluoro-6-methoxyphenyl)-5-(1H-1,2,4-triazol-3-yl)-1,3-thiazol-2-yl]-2-methyl-5-{2-[4-(methylsulfonyl)piperazin-1-yl]ethoxy}pyrazolo[1,5-a]pyridine

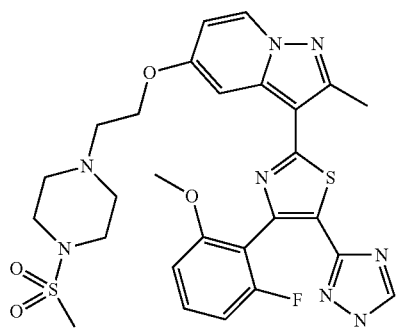 [SMILES: COc1cccc(F)c1-c1nc(-c2c(C)nn3ccc(OCCN4CCN(S(C)(=O)=O)CC4)cc23)sc1-c1nc[nH]n1]

According to the similar manner described in Example 88-B (ii) and (iii), the title compound (162 mg, 70%) has been obtained as a colorless solid using 5-(2-chloroethoxy)-3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridine (215 mg, 0.378 mmol) obtained in Example 86-B3 (i), 1-methanesulfonylpiperazine (124 mg, 0.756 mmol), potassium carbonate (104 mg, 0.756 mmol) and sodium iodide (113 mg, 0.756 mmol) by standard alkylation reaction followed by deprotection of THP group using 2 N hydrochloric acid (2 mL) in THF (6 mL) and MeOH (2 mL) by standard manner. The pure title compound has been obtained by crystallization from THF (2 mL) and EtOAc (4 mL).

$^1$H-NMR (DMSO-$d_6$, 300 MHz) δ 2.54-2.61 (4 H, m), 2.65 (3 H, s), 2.80 (2 H, t, J=5.8 Hz), 2.86 (3 H, s), 3.04-3.12 (4 H, m), 3.67 (3 H, s), 4.20 (2 H, t, J=5.8 Hz), 6.76 (1 H, dd, J=2.6, 7.6 Hz), 6.88 (1 H, t, J=8.5 Hz), 6.96 (1 H, d, J=8.5 Hz), 7.43 (1 H, dt, J=6.9, 8.5 Hz), 7.58 (1 H, d, J=2.6 Hz), 8.48 (1 H, br. s), 8.62 (1 H, d, J=7.6 Hz), 14.05 (1 H, br s).

Example 109-B

Production of 5-[(1-acetylpiperidin-4-yl)oxy]3-[4-(2-fluoro-6-methoxyphenyl)-5-(1H-1,2,4-triazol-3-yl)-1,3-thiazol-2-yl]-2-methylpyrazolo[1,5-a]pyridine

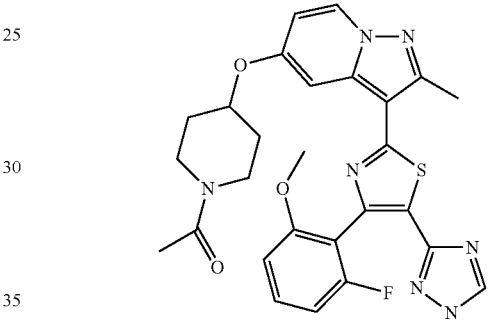

To a stirred solution of 3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridin-5-ol (250 mg, 0.494 mmol) obtained in Example 86-B2(vi) in DMF (4 mL) were added potassium carbonate (272 mg, 1.97 mmol) and 1-[(tert-butoxycarbonyl)oxy]piperidin-4-yl methanesulfonate (550 mg, 197 mmol) obtained in Example 85-B0 (i) and the mixture was stirred for 4.5 h at 80° C. To the mixture were added a 1:1 mixture of THF and EtOAc (20 mL) and saturated aqueous solution of sodium bicarbonate (15 mL). The organic layer was separated and the aqueous layer was extracted with a 1:1 mixture of THF and EtOAc (5 mL). The combined organic layer was washed with brine (5 mL) and then filtered through basic silica gel pad (3 g). The filtrate was concentrated under reduced pressure.

The residue was dissolved in TFA (10 mL) and the mixture was stirred for 2 h at rt. The mixture was concentrated under reduced pressure. To the residue were added a 1:1 mixture of THF and EtOAc (20 mL) and saturated aqueous solution of sodium carbonate (15 mL). The organic layer was separated and the aqueous layer was extracted with a 1:1 mixture of THF and EtOAc (5 mL×4). The combined organic layers were dried over anhydrous sodium sulfate. Insoluble materials were removed by filtration and the filtrate was concentrated under reduced pressure.

To the solution of above residue in DMF (3 mL), was added acetyl chloride (318 µL, 4.44 mmol) and the mixture was stirred for 2 h at rt. To the mixture, were added MeOH (3 mL) and potassium carbonate (820 mg, 5.72 mmol) and the mixture was stirred for 13 h at rt. To the mixture were added a 1:1 mixture of THF and EtOAc (20 mL) and saturated aqueous solution of sodium carbonate (15 mL). The organic layer was separated and the aqueous layer was extracted with a 1:1 mixture of THF and EtOAc (5 mL×2). The combined organic layer was washed with brine (5 mL) and then dried over anhydrous sodium sulfate. Insoluble materials were removed by filtration and the filtrate was concentrated under reduced pressure. The residue was purified by silica gel column chromatography (MeOH/AcOEt=0/100→10/90). Concentration of appropriate fractions afforded crude compound, which was crystallized from THF (2 mL) and EtOAc (4 mL) to obtain pure title compound (104 mg, 38%) as a colorless solid, $^1$H-NMR (DMSO-d$_6$, 300 MHz) δ 1.49-1.76 (2 H, m), 1.90-2.10 (2 H, m), 2.03 (3 H, s), 2.65 (3 H, s), 3.06-3.18 (1 H, m), 3.21-3.29 (1 H, m), 3.59-3.75 (1 H, m), 3.64 (3 H, s), 3.83-3.95 (1 H, m), 4.60-4.72 (1 H, m), 6.80 (1 H, dd, J=2.7, 7.6 Hz), 6.89 (1 H, t, J=8.5 Hz), 6.95 (1 H, d, J=8.5 Hz), 7.43 (1 H, dt, J=7.0, 8.5 Hz), 7.69 (1 H, d, J=2.7 Hz), 8.49 (1 H, br s), 8.65 (1 H, d, J=7.6 Hz), 14.05 (1 H, br s).

Example 110-B

Production of 6-methyl-7-[4-phenyl-5-(1H-pyrazol-5-yl)-1,3-thiazol-2-yl]pyrazolo[5,1-b][1,3]thiazole

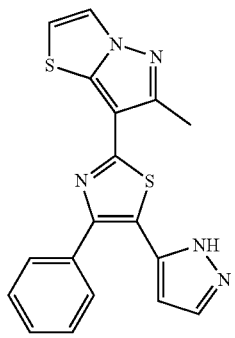 [SMILES: Cc1nn2ccsc2c1-c1nc(-c2ccccc2)c(-c2ccn[nH]2)s1]

(i) Production of N-methoxy-N-methyl-2-(6-methylpyrazolo[5,1-b][1,3]thiazol-7-yl)-4-phenyl-1,3-thiazole-5-carboxamide A mixture of 2-(6-methylpyrazolo[5,1-b][1,3]thiazol-7-yl)-4-phenyl-1,3-thiazole-5-carboxylic acid (1.53 g, 4.5 mmol) obtained in Example 35-B(viii), TEA (1.9 mL), N,O-dimethylamine hydrochloride (1.32 g, 13.5 mmol), HOBT (912 mg, 6.75 mmol), EDCI (1.30 g, 6.75 mmol) and DMF (45 mL) was stirred at rt for 16 h. The reaction mixture was concentrated under reduced pressure, and water (50 mL) was added to the reaction mixture. The aqueous layer was extracted with EtOAc (50 mL×2), and the combined organic layer was washed with saturated aqueous solution of sodium bicarbonate (50 mL) and dried over anhydrous magnesium sulfate. Insoluble materials were removed by filtration and the filtrate was concentrated under reduced pressure. The residue was purified by silica gel column chromatography (EtOAc/hexane=20/80→100/0) to give the title compound (1.43 g, 83%) as a yellow solid.

$^1$H-NMR (DMSO-d$_6$, 300 MHz) δ2.63 (3H, s), 3.23 (3H, s), 3.61 (3H, s), 7.35-7.58 (4H, m), 7.67-7.87 (2H, m), 8.33 (1H, d, J=4.2 Hz)

(ii) Production of 1-[2-(6-methylpyrazolo[5,1-b][1,3]thiazol-7-yl)-4-phenyl-1,3-thiazol-5-yl]ethanone To a solution of N-methoxy-N-methyl-2-(6-methylpyrazolo[5,1-b][1,3]thiazol-7-yl)-4-phenyl-1,3-thiazole-5-carboxamide (1.15 g, 3.0 mmol) obtained above in THF (20 mL) was added 2M methylmagnesium bromide in THF (7.2 mL, 7.2 mmol) at 0° C., the reaction mixture was stirred for 2 h at the same temperature, and then stirred for 1 h at rt. To the reaction mixture were added saturated aqueous solution of sodium bicarbonate (50 mL) and EtOAc (50 mL), the aqueous layer was extracted with EtOAc (50 mL), and the combined organic layers were dried over anhydrous magnesium sulfate. Insoluble materials were removed by filtration, and the filtrate was concentrated under reduced pressure to give the title compound (1.02 g, 99%) as a yellow solid.

$^1$H-NMR (DMSO-d$_6$, 300 MHz) δ 2.19 (3H, s), 2.62 (3H, s), 7.47-7.61 (4H, m), 7.63-7.82 (2H, m), 8.32 (1H, d, J=4.2 Hz).

(iii) Production of 6-methyl-7-[4-phenyl-5-(1H-pyrazol-5-yl)-1,3-thiazol-2-yl]pyrazolo[5,1-b][1,3]thiazole A solution of 1-[2-(6-methylpyrazolo[5,1-b][1,3]thiazol-7-yl)-4-phenyl-1,3-thiazol-5-yl]ethanone (170 mg, 0.5 mmol) obtained by similar manner with Example 110-B(ii) in N,N-dimethylformamide dimethylacetal (10 mL) was refluxed at 90° C. for 4 h. The reaction mixture was allowed to cool to rt, and the solvent was evaporated. The residue was suspended in EtOH (5 mL), and then was added hydrazine monohydrate (50 mg, 1.0 mmol). The mixture was stirred at 80° C. for 5 h. The mixture was allowed to cool to rt, and then concentrated. The residue was purified by silica gel column chromatography (EtOAc/hexane=30/70→100/0) to give the title compound (143 mg, 79%) as a yellow solid.

$^1$H-NMR (DMSO-d$_6$, 300 MHz) δ2.63 (3H, s), 6.05 (1H, d, J=2.3 Hz), 7.38-7.53 (4H, m), 7.66-7.79 (3H, m), 8.29 (1H, d, J=4.2 Hz), 13.08 (1H, br s).

Example 111-B

Production of 2'-(6-methylpyrazolo[5,1-b][1,3]thiazol-7-yl)-4'-phenyl-2,5'-bi-1,3-thiazole

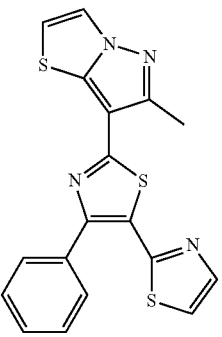 [SMILES: Cc1nn2ccsc2c1-c1nc(-c2ccccc2)c(-c2nccs2)s1]

(i) Production of 2-(6-methylpyrazolo[5,1-b][1,3]thiazol-7-yl)-4-phenyl-1,3-thiazole-5-carboxamide A mixture of 2-(6-methylpyrazolo[5,1-b][1,3]thiazol-7-yl)-4-phenyl-1,3-thiazole-5-carboxylic acid (1.70 g, 5.0 mmol) obtained in Example 35-B(viii), TEA (2.1 mL), ammonium chloride (803 mg, 15.0 mmol), HOBT (1.01 g, 7.5 mmol), EDCI (1.44 g, 7.5 mmol) and DMF (50 mL) was stirred at rt for 16 h. The reaction mixture was concentrated under reduced pressure. To the residue was added saturated aqueous solution of sodium bicarbonate (30 mL). The resulting precipitate was collected by filtration and was washed with water and diethyl ether to give the title compound (1.54 g, 90%) as a white solid.

$^1$H-NMR (DMSO-$d_6$, 300 MHz) δ2.62 (3H, s), 7.37-7.56 (4H, m), 7.68 (2H, br s), 7.81-7.90 (2H, m), 8.31 (1H, d, J=4.0 Hz).

(ii) Production of 2-(6-methylpyrazolo[5,1-b][1,3]thiazol-7-yl)-4-phenyl-1,3-thiazole-5-carbothioamide To a suspension of 2-(6-methylpyrazolo[5,1-b][1,3]thiazol-7-yl)-4-phenyl-1,3-thiazole-5-carboxamide (340 mg, 1.0 mmol) obtained above in DME (10 mL) was added 2,4-Bis(4-methoxyphenyl)-2,4-dithioxo-1,3,2,4-dithiadiphosphetane (485 mg, 1.2 mmol), and the mixture was stirred at 80° C. for 1 h. The reaction mixture was allowed to cool to rt, and then were added EtOAc (15 mL) and 1N hydrochloric acid (15 mL) and then the resulting suspension was filtered. The residue was washed with water (5 mL) and EtOAc (5 mL) to give the title compound (172 mg, 48%) as a yellow solid.

$^1$H-NMR (DMSO-$d_6$, 300 MHz) δ2.60 (3H, s), 7.33-7.58 (4H, m), 7.74-7.89 (2H, m), 8.31 (1H, d, J=4.2 Hz), 9.22 (1H, br s), 10.02 (1H, br s)

(iii) Production of 2'-(6-methylpyrazolo[5,1-b][1,3]thiazol-7-yl)-4'-phenyl-2,5'-bi-1,3-thiazole To a solution of 2-(6-methylpyrazolo[5,1-b][1,3]thiazol-7-yl)-4-phenyl-1,3-thiazole-5-carbothioamide (142 mg, 0.42 mmol) obtained above in AcOH (4 mL) were added p-toluenesulfonic acid monohydrate (3.8 mg, 0.02 mmol) and bromoacetaldehyde dimethylacetal (70 μL), and the reaction mixture was stirred at 100° C. for 2 h. The reaction mixture was allowed to cool to rt, and then solvent was evaporated. To the residue was added saturated aqueous solution of sodium bicarbonate (40 mL) and the mixture was extracted with EtOAc (40 mL×2). The combined organic layers were dried over anhydrous magnesium sulfate. Insoluble materials were removed by filtration, and the filtrate was concentrated under reduced pressure and the residue was purified by silica gel column chromatography (EtOAc/hexane=20/80→100/0) to give the title compound (83.2 mg, 54%) as a yellow solid.

$^1$H-NMR (DMSO-d6, 300 MHz) δ2.64 (3H, s), 7.51 (1H, d, J=4.2 Hz), 7.53-7.60 (3H, m), 7.63 (1H, d, J=3.2 Hz), 7.65-7.71 (2H, m), 7.84 (1H, d, J=3.2 Hz), 8.32 (1H, d, J=4.0 Hz).

Example 112-B

Production of 7-[5-(1H-imidazol-2-yl)-4-phenyl-1,3-thiazol-2-yl]-6-methylpyrazolo[5,1-b][1,3]thiazole

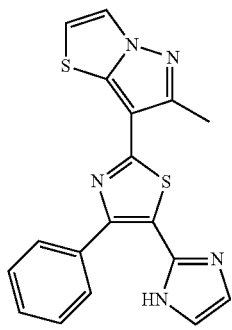 [SMILES: Cc1nn2ccsc2c1-c1nc(-c2ccccc2)c(-c2ncc[nH]2)s1]

To a suspension of 2-(6-methylpyrazolo[5,1-b][1,3]thiazol-7-yl)-4-phenyl-1,3-thiazole-5-carbothioamide (223 mg, 0.6 mmol) obtained in the similar manner described in Example 111-B(ii) in acetone (12 mL), was added iodomethane (75 μL, 1.2 mmol), and the mixture was stirred at rt for 2 h. The solvent was evaporated, and the residue was suspended in AcOH (12 mL). To the residue was added aminoacetaldehyde dimethylacetal (100 μL, 0.9 mmol), and the mixture was stirred at 90° C. for 16 h. The reaction mixture was allowed to cool to rt, then concentrated, and the residue was dissolved in THF (12 mL). To the solution was added 6N hydrochloric acid (400 μL, 2.4 mmol), and the mixture was stirred at 70° C. for 2 h. The reaction mixture was allowed to cool to rt, and then were added saturated aqueous solution of sodium bicarbonate (50 mL) and EtOAc (50 mL). The aqueous layer was extracted with EtOAc (50 mL), and the organic layer was dried over anhydrous magnesium sulfate. Insoluble materials were removed by filtration, and the filtrate was concentrated under reduced pressure. The residue was purified by silica gel column chromatography (EtOAc/hexane=20/80→100/0) to give the title compound (133 mg, 61%) as a yellow solid.

$^1$H-NMR (DMSO-$d_6$, 300 MHz) δ2.63 (3H, s), 7.05-7.15 (1H, m), 7.20-7.31 (1H, m), 7.34-7.46 (3H, m), 7.52 (1H, d, J=4.0 Hz), 7.63-7.76 (2H, m), 8.32 (1H, d, J=4.2 Hz), 12.30 (1H, br s)

Example 113-B

Production of 6-methyl-7-[5-(1,3-oxazol-4-yl)-4-phenyl-1,3-thiazol-2-yl]pyrazolo[5,1-b][1,3]thiazole

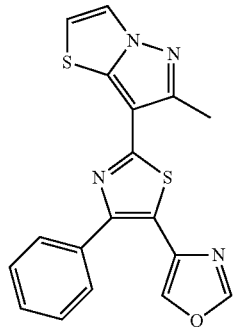 [SMILES: Cc1nn2ccsc2c1-c1nc(-c2ccccc2)c(-c2cocn2)s1]

To a solution of 1-[2-(6-methylpyrazolo[5,1-b][1,3]thiazol-7-yl)-4-phenyl-1,3-thiazol-5-yl]ethanone (136 mg, 0.4 mmol) obtained in the similar manner described in Example 110-B(ii) in AcOH (12 ml), was added 0.9N solution of bromine in AcOH (250 μL, 0.225 mmol) at 40° C., and the mixture was stirred at same temperature for 3 h. To the mixture was added 0.9N solution of bromine in AcOH (250 μL, 0.225 mmol), and the mixture was stirred for additional 1 h at the same temperature. The reaction mixture was allowed to cool to rt, and the mixture was concentrated under reduced pressure. To the residue, were added saturated aqueous solution of sodium bicarbonate (50 mL) and EtOAc (50 mL), and the aqueous layer was extracted with EtOAc (50 mL). The organic layer was dried over anhydrous magnesium sulfate. Insoluble materials were removed by filtration, and the filtrate was concentrated under reduced pressure. To the residue was added formamide (4 mL), and the mixture was stirred at 180° C. for 2 h. The reaction mixture was allowed to cool to rt, and then were added saturated aqueous solution of sodium bicarbonate (50 mL) and EtOAc (50 mL. The aqueous layer was extracted with EtOAc (50 mL), and the organic layer was dried over anhydrous magnesium sulfate. Insoluble materials were removed by filtration, and the filtrate was concentrated under reduced pressure. The residue was purified by silica gel column chromatography (EtOAc/hexane=30/70→100/0) to give the title compound (37.8 mg, 26%) as a yellow solid.

$^1$H-NMR (DMSO-$d_6$, 300 MHz) δ2.63 (3H, s), 7.37-7.58 (4H, m), 7.68-7.79 (2H, m), 8.08 (1H, d, J=1.0 Hz), 8.31 (1H, d, J=4.0 Hz), 8.54 (1H, d, J=1.0 Hz).

Example 114-B

Production of ethyl {4-[4-ethoxy-5-(1H-1,2,4-triazol-3-yl)-1,3-thiazol-2-yl]pyridin-2-yl}carbamate

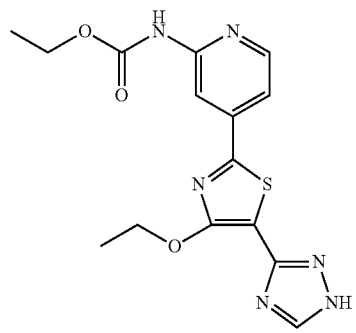 [SMILES: CCOC(=O)Nc1cc(-c2nc(OCC)c(-c3nc[nH]n3)s2)ccn1]

(i) Production of ethyl (4-{4-ethoxy-5-[1-(tetrahydro-2H-pyran-2-yl)-1H-1,2,4-triazol-3-yl]-1,3-thiazol-2-yl}pyridin-2-yl)carbamate To a solution of 4-{4-ethoxy-5-[1-(tetrahydro-2H-pyran-2-yl)-1H-1,2,4-triazol-3-yl]-1,3-thiazol-2-yl}pyridin-2-amine (100 mg, 0.268 mmol) obtained by similar manner with Example 47-B(ii) in pyridine (2.7 mL), was added ethyl chloroformate (100 μL, 1.08 mmol) at 0° C., and the mixture was stirred for 3 h. The reaction mixture was diluted with water (20 mL), and the mixture was stirred for 1 h. The resulting precipitate was collected by filtration and was washed with water and diethyl ether to give the title compound (99.1 mg, 83%) as a yellow solid.

$^1$H-NMR (DMSO-$d_6$, 300 MHz) δ1.27 (3H, t, J=7.1 Hz), 1.40 (3H, t, J=7.1 Hz), 1.49-1.79 (3H, m), 1.87-2.24 (3H, m), 3.60-3.78 (1H, m), 3.88-4.05 (1H, m), 4.19 (2H, q, J=7.0 Hz), 4.54 (2H, q, J=7.0 Hz), 5.60 (1H, dd, J=2.6, 9.4 Hz), 7.46-7.63 (1H, m), 8.24-8.51 (2H, m), 8.79 (1H, s), 10.36 (1H, s), (ii) Production of ethyl {-4-[4-ethoxy-5-(1H-1,2,4-triazol-3-yl)-1,3-thiazol-2-yl]pyridin-2-yl}carbamate A solution of ethyl (4-{4-ethoxy-5-[1-(tetrahydro-2H-pyran-2-yl)-1H-1,2,4-triazol-3-yl]-1,3-thiazol-2-yl}pyridin-2-yl)carbamate (99.0 mg, 0.222 mmol) obtained above in TFA (4 mL) was stirred at rt for 15 h. The solvent was evaporated under reduced pressure, and saturated aqueous solution of sodium bicarbonate (20 mL) and EtOAc (15 mL) were added to the residue. The resulting precipitate was collected by filtration and then washed with water, EtOH and diethyl ether sequentially, to give the title compound (99.1 mg, 83%) as a yellow solid.

$^1$H-NMR (DMSO-$d_6$, 300 MHz) δ1.27 (3H, t, J=7.1 Hz), 1.42 (3H, t, J=7.1 Hz), 4.19 (2H, q, J=7.0 Hz), 4.56 (2H, q, J=7.1 Hz), 7.54 (1H, dd, J=1.6, 5.2 Hz), 8.31-8.48 (3H, m), 10.37 (1H, s), 14.04 (1H, br s).

Example 115-B

Production of N-{4-[4-ethoxy-5-(1H-1,2,4-triazol-3-yl)-1,3-thiazol-2-yl]pyridin-2-yl}-N'-ethylurea

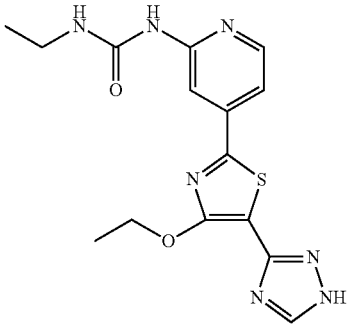 [SMILES: CCNC(=O)Nc1cc(-c2nc(OCC)c(-c3nc[nH]n3)s2)ccn1]

To a solution of 4-{4-ethoxy-5-[1-(tetrahydro-2H-pyran-2-yl)-1H-1,2,4-triazol-3-yl]-1,3-thiazol-2-yl}pyridin-2-amine (100 mg, 0.268 mmol) obtained in the similar manner described in Example 47-B(ii) in DMF (2 mL), was added ethyl isocyanate (36 μL, 0.457 mmol), and the mixture was stirred at rt for 15 h. To the reaction mixture, again was added ethyl isocyanate (100 μL, 1.27 mmol), and the mixture was stirred at 80° C. for 24 h. The reaction mixture was allowed to cool to rt, and then were added saturated aqueous solution of sodium bicarbonate (30 mL) and EtOAc (40 mL). The aqueous layer was extracted with EtOAc (40 mL), and the combined organic layer was dried over anhydrous magnesium sulfate. Insoluble materials were removed by filtration, and the filtrate was concentrated under reduced pressure. The residue was purified by silica gel column chromatography (EtOAc/hexane=20/80→100/0) to give a yellow solid.

The resulting yellow solid was dissolved in TFA (4 mL) and was stirred at rt for 3 h. The solvent was evaporated under reduced pressure, and were added saturated aqueous solution of sodium bicarbonate (8 mL) and EtOAc (3 mL). The resulting precipitate was collected by filtration and washed with water, EtOH and diethyl ether sequentially to give the title compound (34.0 mg, 29%) as a yellow solid.

$^1$H-NMR (DMSO-$d_6$, 300 MHz) δ1.10 (3H, t, J=7.2 Hz), 1.29-1.57 (3H, m), 3.11-3.28 (2H, m), 4.52 (1.2H, q, J=7.0 Hz), 4.62 (0.8H, q, J=6.9 Hz), 7.29-7.50 (1H, m), 7.67-7.90

(1H, m), 8.03 (1H, br s), 8.08 (0.4H, br s), 8.19-8.44 (1H, m), 8.63 (0.6H, br s), 9.18-9.47 (1H, m), 13.95 (0.6H, br s), 14.17 (0.4H, br s).

Example 116-B

Production of 6-bromo-2-methyl-3-[4-phenyl-5-(1H-1,2,4-triazol-3-yl)-1,3-thiazol-2-yl]imidazo[1,2-a]pyridine

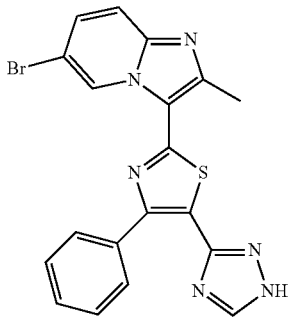 [SMILES: Cc1nc2ccc(Br)cn2c1-c1nc(-c2ccccc2)c(-c2nc[nH]n2)s1]

(i) Production of 2-methyl-4-phenyl-1,3-thiazole-5-carboxylic acid

To a solution of ethanethioamide (80.0 g, 1.06 mol) in EtOH (600 mL), was added ethyl 2-chloro-3-oxo-3-phenyl-propanoate (141.5 g, 0.64 mol), which was prepared by published procedure in M. Altuna-Urquijo, et al.; Tetrahedron; 65; 2009; 975-984, and the mixture was stirred at 80° C. for 2 h. The reaction mixture was allowed to cool to 50° C., 8N aqueous sodium hydroxide solution (120 mL) was added, and the mixture was stirred 80° C. for 2 h. The reaction mixture was allowed to cool to 50° C., 8N aqueous sodium hydroxide solution (240 mL) was added, and the mixture was stirred 80° C. for 1 h. The reaction mixture was allowed to cool to 0° C., and was then neutralized by the addition of 6N hydrochloric acid (400 mL). The mixture was stirred at rt for 12 h and the resulting precipitate was collected by filtration and washed with water, EtOH and diethyl ether sequentially to give the title compound (105.6 g, 75%) as a white solid.

$^1$H-NMR (DMSO-$d_6$, 300 MHz) δ 2.70 (3H, s), 7.30-7.50 (3H, m), 7.59 (2H, m), 13.22 (1H, br s).

(ii) Production of 2-methyl-4-phenyl-1,3-thiazole-5-carboxamide

A mixture of 2-methyl-4-phenyl-1,3-thiazole-5-carboxylic acid (104.6 g, 0.48 mol) obtained above, TEA (200 mL), ammonium chloride (76.1 g, 1.43 mol), HOBT (103.5 g, 0.77 mol), EDCI (146.8 g, 0.77 mol) and DMF (1.0 L) was stirred at 40° C. for 3 h. The reaction mixture was allowed to cool to rt, and insoluble materials were removed by filtration. The filtrate was concentrated under reduced pressure, and then were added water (1.6 L) and saturated aqueous solution of sodium bicarbonate (400 mL). The resulting precipitate was collected by filtration and sequentially washed with water, EtOH and diethyl ether to give the title compound (64.7 g, 61%) as a pale brown solid.

$^1$H-NMR (DMSO-$d_6$, 300 MHz) δ 2.69 (3H, s), 7.30-7.51 (3H, m), 7.64 (2H, br s), 7.67-7.75 (2H, m).

(iii) Production of 3-(2-methyl-4-phenyl-1,3-thiazol-5-yl)-1H-1,2,4-triazole

A suspension of 2-methyl-4-phenyl-1,3-thiazole-5-carboxamide (82.0 g, 0.377 mol) obtained above in N,N-dimethylformamide dimethylacetal (97.4 mL, 1.13 mmol) and toluene (1.8 L) was stirred at 50° C. for 3 h. The reaction mixture was allowed to cool to rt, decolorized with activated carbon. Insoluble materials were removed by filtration and the filtrate was concentrated under reduced pressure.

The residue was suspended in AcOH (900 mL), then was added hydrazine monohydrate (84 mL). The mixture was stirred at 90 C for 2 h and then allowed to cool to rt. The resulting precipitate was collected by filtration, and washed with EtOAc and diethyl ether to give the title compound (62.4 g, 68%) as a white solid.

$^1$H-NMR (DMSO-$d_6$, 300 MHz) δ 2.71 (3H, s), 7.20-7.53 (3H, m), 7.54-7.92 (2H, m), 8.55 (1H, s), 14.15 (1H, br s).

(iv) Production of 3-(2-methyl-4-phenyl-1,3-thiazol-5-yl)-1-(tetrahydro-2H-pyran-2-yl)-1H-1,2,4-triazole A mixture of 3-(2-methyl-4-phenyl-1,3-thiazol-5-yl)-1H-1,2,4-triazole (85.0 g, 0.351 mol) obtained above, 3,4-dihydro-2H-pyran (63.8 g, 0.702 mol), p-toluenesulfonic acid monohydrate (80.0 g, 0.423 mol) and THF (2.1 L) was stirred at 90° C. for 2 h. The reaction mixture was allowed to cool to rt, then the solvent was evaporated. To the residue, were added EtOAc (1.0 L) and 1N aqueous sodium hydroxide solution (600 mL). The aqueous layer was extracted with EtOAc, the combined organic layer was washed with saturated aqueous ammonium chloride and dried over anhydrous magnesium sulfate. Insoluble materials were removed by filtration and the filtrate was concentrated under reduced pressure. The residue was purified by a basic silica gel pad. The obtained solution was concentrated under reduced pressure, and the residue was washed with diethyl ether to give the title compound (61.2 g, 57%) as a pale yellow solid.

$^1$H-NMR (DMSO-$d_6$, 300 MHz) δ 1.45-1.77 (3H, m), 1.83-2.14 (3H, m), 2.71 (3H, s), 3.54-3.73 (1H, m), 3.80-3.98 (1H, m), 5.57 (1H, J=3.1, 8.6 Hz, d), 7.21-7.48 (3H, m), 7.63-7.87 (2H, m), 8.76 (1H, s).

(v) Production of 1-{4-phenyl-5-[1-(tetrahydro-2H-pyran-2-yl)-1H-1,2,4-triazol-3-yl]-1,3-thiazol-2-yl}acetone To a solution of 3-(2-methyl-4-phenyl-1,3-thiazol-5-yl)-1-(tetrahydro-2H-pyran-2-yl)-1H-1,2,4-triazole (32.6 g, 100 mmol) in THF (1.8 L), was dropwise added 1.6M solution of n-butyllithium in hexane (150 mL, 240 mmol) at −78° C. over 1 h, and the mixture was stirred for 1 h at the same temperature. To the reaction mixture was dropwise added a solution of N-methoxy-N-methylacetamide (10.3 g, 100 mmol) in THF (600 mL) at −78° C. over 3 h. After addition, the mixture was stirred for 30 min at the same temperature. The reaction mixture was neutralized by the addition of AcOH (13.8 mL), and the mixture was allowed to warm to rt. The solvent was evaporated under reduced pressure and then, to the residue, were added EtOAc (400 mL) and saturated aqueous ammonium chloride (300 mL). The aqueous layer was extracted with EtOAc, the combined organic layer was washed with saturated aqueous ammonium chloride, dried over anhydrous magnesium sulfate, and then insoluble materials were removed by filtration. The filtrate was concentrated under reduced pressure, and the residue was purified by silica gel column chromatography (EtOAc/hexane=5/95→80/20) to give the title compound (28.4 g, 74%) as a pale yellow oil.

¹H-NMR (DMSO-d₆, 300 MHz) δ 1.40-1.73 (3H, m), 1.84-2.14 (3H, m), 2.28 (3H, s), 3.54-3.73 (1H, m), 3.86-3.96 (1H, m), 4.38 (2H, s), 5.58 (1H, dd, J=3.0, 8.5 Hz), 7.29-7.48 (3H, m), 7.66-7.85 (2H, m), 8.75 (1H, br s).

(vi) Production of 1-bromo-1-{4-phenyl-5-[1-(tetrahydro-2H-pyran-2-yl)-1H-1,2,4-triazol-3-yl]-1,3-thiazol-2-yl}acetone A mixture of 1-{4-phenyl-5-[1-(tetrahydro-2H-pyran-2-yl)-1H-1,2,4-triazol-3-yl]-1,3-thiazol-2-yl}acetone (5.08 g, 13.8 mmol) obtained above, N-bromosuccinimide (2.69 g, 15.1 mmol), benzoyl peroxide (16.5 mg, 0.068 mmol) and benzotrifluoride (110 mL) was stirred at 80° C. for 2 h. The reaction mixture was allowed to cool to rt, and then were added saturated aqueous solution of sodium bicarbonate (30 mL) and EtOAc (100 mL). The aqueous layer was extracted with EtOAc (100 mL×2), and the combined organic layer was dried over anhydrous magnesium sulfate. Insoluble materials were removed by filtration, and the filtrate was concentrated under reduced pressure to give the title compound (5.66 g, 92%) as a brown solid.

¹H-NMR (DMSO-d₆, 300 MHz) δ1.47-1.70 (3H, m), 1.85-2.08 (3H, m), 2.47 (1.8H, s), 2.52 (1.2H, s), 3.55-3.73 (1H, m), 3.83-3.98 (1H, m), 5.54-5.70 (1H, m), 6.55 (0.4H, s), 7.29-7.48 (3H, m), 7.70-7.84 (2H, m), 8.82 (0.6H, s), 8.88 (0.4H, s), 11.08 (0.6H, br s).

(vii) Production of 6-bromo-2-methyl-3-[4-phenyl-5-(1H-1,2,4-triazol-3-yl)-1,3-thiazol-2-yl]imidazo[1,2-a]pyridine To a solution of 1-bromo-1-{4-phenyl-5-[1-(tetrahydro-2H-pyran-2-yl)-1H-1,2,4-triazol-3-yl]-1,3-thiazol-2-yl}acetone (448 mg, 1.0 mmol) obtained above in a mixed solvent of THF (5 mL) and 2-propanol (5 mL), was added 2-amino-5-bromopyridine (173 mg, 1.0 mmol), and the mixture was stirred at 80° C. for 14 h. The reaction mixture was allowed to cool to rt, and then were added saturated aqueous solution of sodium bicarbonate (50 mL) and EtOAc (50 mL). The aqueous layer was extracted with EtOAc (50 mL) and a 1:1 mixture of EtOAc and THF (60 mL×2). The combined organic layers were dried over anhydrous magnesium sulfate. Insoluble materials were removed by filtration, and the filtrate was concentrated under reduced pressure. The residue was purified by basic silica gel column chromatography (EtOAc/hexane=30/70→100/0; then MeOH/EtOAc=30/70). Concentration of appropriate fraction afforded crude product, which was washed with THF and diethyl ether to give the pure title compound (17.0 mg, 4%) as a brown solid.

¹H-NMR (DMSO-d₆, 300 MHz) δ2.73 (3H, s), 7.40-7.54 (3H, m), 7.64 (1H, dd, J=2.1 Hz, 9.4 Hz), 7.72 (1H, dd, J=0.8 Hz, 9.4 Hz), 7.86-7.95 (2H, m), 8.67 (1H, br s), 10.04 (1H, dd, J=0.8, 1.9 Hz), 14.35 (1H, br s).

Example 117-B

Production of 6-(3,4-dimethoxyphenyl)-2-methyl-3-[4-phenyl-5-(1H-1,2,4-triazol-3-yl)-1,3-thiazol-2-yl]imidazo[1,2-a]pyridine

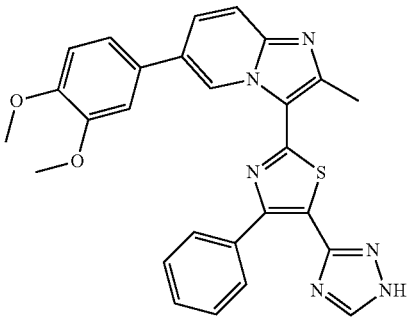 [SMILES: COc1ccc(-c2ccc3nc(C)c(-c4nc(-c5ccccc5)c(-c5nc[nH]n5)s4)n3c2)cc1OC]

(i) Production of 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine To a solution of 1-bromo-1-{4-phenyl-5-[1-(tetrahydro-2H-pyran-2-yl)-1H-1,2,4-triazol-3-yl]-1,3-thiazol-2-yl}acetone (2.96 g, 6.6 mmol) obtained in Example 116-B(vi) in THF (33 mL) and 2-propanol (33 mL), was added 2-amino-5-bromopyridine (5.71 g, 33.0 mmol), and the mixture was stirred at 80° C. for 3 h. The reaction mixture was allowed to cool to rt, and then were added saturated aqueous solution of sodium bicarbonate (60 mL) and EtOAc (150 mL). The aqueous layer was extracted with EtOAc (80 mL), and the combined organic layer was dried over anhydrous magnesium sulfate. Insoluble materials were removed by filtration, and the filtrate was concentrated under reduced pressure. The residue was purified by silica gel column chromatography (EtOAc/hexane=20/80→100/0; then MeOH/EtOAc=20/80), and then basic silica gel column chromatography (EtOAc/hexane=10/90→80/20) to give the title compound (520 mg, 15%) as a pale yellow solid.

¹H-NMR (DMSO-d₆, 300 MHz) δ 1.46-1.72 (3H, m), 1.88-2.13 (3H, m), 2.73 (3H, s), 3.58-3.73 (1H, m), 3.87-3.98 (1H, m), 5.62 (1H, dd, J=3.1, 8.8 Hz), 7.38-7.55 (3H, m), 7.64 (1H, dd, J=2.1, 9.4 Hz), 7.72 (1H, dd, J=0.8, 9.4 Hz), 7.83-7.99 (2H, m), 8.83 (1H, s), 10.04 (1H, dd, J=0.8, 1.9 Hz).

(ii) Production of 6-(3,4-dimethoxyphenyl)-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine To a suspension of 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (157 mg, 0.3 mmol) obtained above in DME (10 mL) and water (2 mL), were added (3,4-dimethoxyphenyl)boronic acid (81.9 mg, 0.45 mmol), [1,1-bis(diphenylphosphino)ferrocene]palladium(II) dichloride dichloromethane complex (24.5 mg, 0.03 mmol) and cesium carbonate (293 mg, 0.9 mmol) under a nitrogen atmosphere, and the mixture was stirred at 95° C. for 1 h. The reaction mixture was allowed to cool to rt, and then were added saturated aqueous solution of sodium bicarbonate (30 mL) and EtOAc (50 mL). The resulting precipitate was collected by filtration and washed with THF and diethyl ether to give the title compound (142 mg, 81%) as a white solid.

$^1$H-NMR (DMSO-d$_6$, 300 MHz) δ1.48-1.79 (3H, m), 1.88-2.16 (3H, m), 2.75 (3H, s), 3.55-3.73 (1H, m), 3.80 (3H, s), 3.82 (3H, s), 3.87-4.01 (1H, m), 5.62 (1H, dd, J=3.0, 8.7 Hz), 7.06-7.15 (1H, m), 7.25-7.32 (2H, m), 7.40-7.50 (3H, m), 7.77 (1H, dd, J=0.8, 9.3 Hz), 7.86 (1H, dd, J=1.9, 9.3 Hz), 7.93-8.03 (2H, m), 8.82 (1H, s), 10.10-10.33 (1H, m).

(iii) Production of 6-(3,4-dimethoxyphenyl)-2-methyl-3-[4-phenyl-5-(1H-1,2,4-triazol-3-yl)-1,3-thiazol-2-yl]imidazo[1,2-a]pyridine A solution of 6-(3,4-dimethoxyphenyl)-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (99.0 mg, 0.222 mmol) obtained above in TFA (5 mL) was stirred at rt for 3 h. To the mixture, again, was added TFA (2.5 mL), and the mixture was stirred at rt for 12 h. TFA was evaporated under reduced pressure, and the residue was treated with saturated aqueous solution of sodium bicarbonate (5 mL), EtOAc (5 mL) and water (5 mL). The resulting precipitate was collected by filtration and sequentially washed with water, EtOH and diethyl ether to give the title compound (109 mg, 90%) as a white solid.

$^1$H-NMR (DMSO-d$_6$, 300 MHz) δ2.74 (3H, s), 3.80 (3H, s), 3.82 (3H, s), 7.06-7.14 (1H, m), 7.24-7.32 (2H, m), 7.38-7.49 (3H, m), 7.75 (1H, dd, J=0.6, 9.3 Hz), 7.85 (1H, dd, J=1.9, 9.3 Hz), 7.93-8.03 (2H, m), 8.65 (1H, s), 10.01-10.49 (1H, m), 14.25 (1H, br s).

Example 118-B

Production of 2-methyl-6-(1-methyl-1H-pyrazol-4-yl)-3-[4-phenyl-5-(1H-1,2,4-triazol-3-yl)-1,3-thiazol-2-yl]imidazo[1,2-a]pyridine

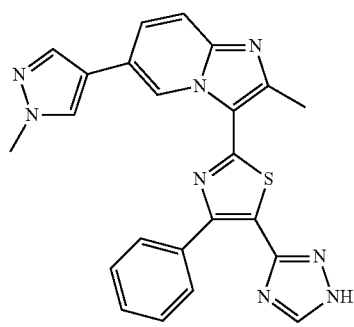 [SMILES: Cc1nc2ccc(-c3cnn(C)c3)cn2c1-c1nc(-c2ccccc2)c(-c2nc[nH]n2)s1]

(i) Production of 2-methyl-6-(1-methyl-1H-pyrazol-4-yl)-3-{4-phenyl-5-[1-(tetrahydro-2H-pyran-2-yl)-1H-1,2,4-triazol-3-yl]-1,3-thiazol-2-yl}imidazo[1,2-a]pyridine To a suspension of 6-bromo-2-methyl-3-{4-phenyl-5-[1-(tetrahydro-2H-pyran-2-yl)-1H-1,2,4-triazol-3-yl}-1,3-thiazol-2-yl]imidazo[1,2-a]pyridine (157 mg, 0.3 mmol) obtained in Example 117-B(i) in DME (10 mL) and water (2 mL), were added 1-methyl-4-(4,4,5,5-tetramethyl-1,3,2-dioxaborolan-2-yl)-1H-pyrazole (93.6 mg, 0.45 mmol), [1,1-bis(diphenylphosphino)ferrocene]palladium(II)dichloride dichloromethane complex (24.5 mg, 0.03 mmol) and cesium carbonate (293 mg, 0.9 mmol) under a nitrogen atmosphere, and the mixture was stirred at 95° C. for 12 h. The reaction mixture was allowed to cool to rt, and then were added water (40 mL) and EtOAc (40 mL). The aqueous layer was extracted with EtOAc (40 mL) and then a 1:1 mixture of EtOAc and THF (60 mL×2), and the combined organic layers were dried over anhydrous magnesium sulfate. Insoluble materials were removed by filtration, and the filtrate was concentrated under reduced pressure. The residue was washed with THF to give the title compound (64.0 mg, 41%) as a white solid.

$^1$H-NMR (DMSO-d$_6$, 300 MHz) δ1.52-1.79 (3H, m), 1.89-2.16 (3H, m), 2.72 (3H, s), 3.63-3.75 (1H, m), 3.86-4.01 (4H, m), 5.63 (1H, dd, J=3.0, 8.9 Hz), 7.45-7.54 (3H, m), 7.72-7.75 (2H, m), 7.79-7.82 (1H, m), 7.99-8.09 (2H, m), 8.17 (1H, br s), 8.84 (1H, s), 10.15 (1H, t, J=1.3 Hz).

(ii) Production of 2-methyl-6-(1-methyl-1H-pyrazol-4-yl)-3-[4-phenyl-5-(1H-1,2,4-triazol-3-yl)-1,3-thiazol-2-yl]imidazo[1,2-a]pyridine A solution of 2-methyl-6-(1-methyl-1H-pyrazol-4-yl)-3-{4-phenyl-5-[1-(tetrahydro-2H-pyran-2-yl)-1H-1,2,4-triazol-3-yl]-1,3-thiazol-2-yl}imidazo[1,2-a]pyridine (84 mg, 0.16 mmol) obtained above in TFA (10 mL) was stirred at rt for 4 h. TFA was evaporated under reduced pressure, and then were added saturated aqueous solution of sodium bicarbonate (10 mL), water (10 mL) and EtOAc (20 mL). The resulting precipitate was collected by filtration, and then purified by silica gel column chromatography (EtOAc/hexane=80/20→100/0; then MeOH/EtOAc=30/70) to give the title compound (49.5 mg, 70%) as a yellow solid.

$^1$H-NMR (DMSO-d$_6$, 300 MHz) δ2.72 (3H, s), 3.91 (3H, s), 7.41-7.55 (3H, m), 7.68-7.78 (2H, m), 7.79-7.83 (1H, m), 7.99-8.07 (2H, m), 8.16-8.20 (1H, m), 8.64-8.70 (1H, m), 10.12-10.18 (1H, m), 14.36 (1H, br s).

Example 119-B

Production of 6-(2-fluoro-6-methoxyphenyl)-2-methyl-3-[4-phenyl-5-(1H-1,2,4-triazol-3-yl)-1,3-thiazol-2-yl]imidazo[1,2-a]pyridine

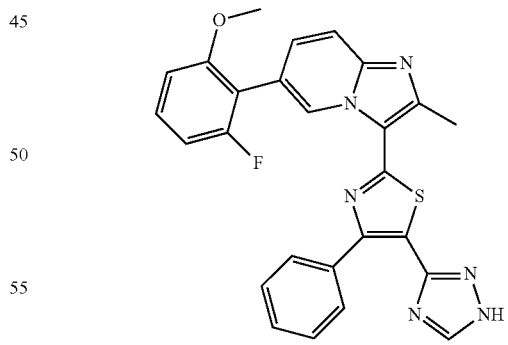

(i) Production of 6-(2-fluoro-6-methoxyphenyl)-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine To a suspension of 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (157 mg, 0.3 mmol)

obtained in Example 117-13(i) in DME (10 mL) and water (2 mL) were added (2-fluoro-6-methoxyphenyl)boronic acid (102 mg, 0.6 mmol), [1,1-bis(diphenylphosphino)ferrocene]palladium(II) dichloride dichloromethane complex (51 mg, 0.06 mmol) and cesium carbonate (293 mg, 0.9 mmol) under a nitrogen atmosphere, and the mixture was stirred at 95° C. for 2 h. The reaction mixture was allowed to cool to rt, and then were added water (40 mL) and EtOAc (40 mL). The aqueous layer was extracted with EtOAc (40 mL), and the combined organic layer was dried over anhydrous magnesium sulfate. Insoluble materials were removed by filtration, and the filtrate was concentrated under reduced pressure. The residue was purified by basic silica gel column chromatography (EtOAc/hexane=10/90→50/50) to give the title compound (156 mg, 92%) as a yellow solid.

$^1$H-NMR (DMSO-d$_6$, 300 MHz) δ1.51-1.73 (3H, m), 1.88-2.10 (3H, m), 2.76 (3H, s), 3.58-3.73 (1H, m), 3.81 (3H, s), 3.86-3.99 (1H, m), 5.62 (1H, dd, J=2.9, 8.8 Hz), 6.95-7.10 (2H, m), 7.39-7.50 (4H, m), 7.52-7.58 (1H, m), 7.78 (1H, dd, J=0.8 Hz, 9.3 Hz), 7.85-7.95 (2H, m), 8.83 (1H, m), 9.97-10.12 (1H, m).

(ii) Production of 6-(2-fluoro-6-methoxyphenyl)-2-methyl-3-[4-phenyl-5-(1H-1,2,4-triazol-3-yl)-1,3-thiazol-2-yl]imidazo[1,2-a]pyridine Using 6-(2-fluoro-6-methoxyphenyl)-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (156 mg, 0.275 mmol) obtained above and TFA (5.5 mL) as starting materials and in the similar manner described in Example 114-B(ii), the title compound (75 mg, 54%) was obtained as a white solid.

$^1$H-NMR (DMSO-d$_6$, 300 MHz) δ2.76 (3H, s), 3.81 (3H, s), 6.96-7.12 (2H, m), 7.36-7.51 (4H, m), 7.52-7.59 (1H, m), 7.75-7.82 (1H, m), 7.87-7.97 (2H, m), 8.57-8.78 (1H, m), 9.86-10.20 (1H, m), 14.34 (1H, br s).

Example 120-B

Production of 2-methyl-3-[4-phenyl-5-(1H-1,2,4-triazol-3-yl)-1,3-thiazol-2-yl]-6-vinylimidazo[1,2-a]pyridine

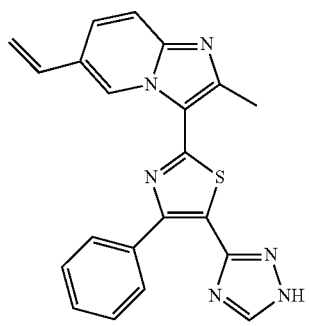 [SMILES: C=Cc1ccc2nc(C)c(-c3nc(-c4ccccc4)c(-c4nc[nH]n4)s3)n2c1]

(i) Production of 2-methyl-3-{4-phenyl-5-[1-(tetrahydro-2H-pyran-2-yl)-1H-1,2,4-triazol-3-yl]-1,3-thiazol-2-yl}-6-vinylimidazo[1,2-a]pyridine To a suspension of 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (1.04 g, 2.0 mmol) obtained by similar manner with Example 117-B(i) in DME (70 mL) and water (14 mL), were added potassiumvinyltrifluoroborate (410 mg, 3.0 mmol), [1,1-bis(diphenylphosphino)ferrocene]palladium(II)dichloride dichloromethane complex (170 mg, 0.2 mmol) and cesium carbonate (1.90 g, 6.0 mmol) under a nitrogen atmosphere, and the mixture was stirred at 95° C. for 4 h. The reaction mixture was allowed to cool to rt, and then was added EtOAc (40 mL). The resulting precipitate was collected by filtration and washed with water and diethyl ether to give the title compound (890 mg, 95%) as a gray solid.

$^1$H-NMR (DMSO-d$_6$, 300 MHz) δ 1.51-1.77 (3H, m), 1.89-2.15 (3H, m), 2.71 (3H, s), 3.62-3.74 (1H, m), 3.96-3.99 (1H, m), 5.39 (1H, d, J=11.0 Hz), 5.62 (1H, dd, J=2.8, 8.7 Hz), 5.93 (1H, d, J=17.6 Hz), 6.81 (1H, dd, J=11.1, 17.6 Hz), 7.40-7.59 (3H, m), 7.66-7.73 (1H, m), 7.75-7.82 (1H, m), 7.92-8.03 (2H, m), 8.83 (1H, s), 9.75-9.88 (1H, m).

(ii) Production of 2-methyl-3-[4-phenyl-5-(1H-1,2,4-triazol-3-yl)-1,3-thiazol-2-yl]-6-vinylimidazo[1,2-a]pyridine A solution of 2-methyl-3-(4-phenyl-5-[1-(tetrahydro-2H-pyran-2-yl)-1H-1,2,4-triazol-3-yl]-1,3-thiazol-2-yl)-6-vinylimidazo[1,2-a]pyridine (141 mg, 0.3 mmol) obtained above in TFA (6.0 mL), was stirred at rt for 2 h. TFA was evaporated under reduced pressure, and then were added saturated aqueous solution of sodium bicarbonate (5 mL), water (5 mL) and EtOAc (5 mL) were. The resulting precipitate was collected by filtration and dissolved in DMF (3 mL), which was subjected to basic silica gel column chromatography (EtOAc/hexane=20/80→100/0; then MeOH/EtOAc=30/70) to yield the title compound (70.5 mg, 61%) as a yellow solid.

$^1$H-NMR (DMSO-d$_6$, 300 MHz) δ 2.72 (3H, s), 5.40 (1H, d, J=11.0 Hz), 5.94 (1H, d, J=17.6 Hz), 6.82 (1H, dd, J=11.0, 17.4 Hz), 7.40-7.53 (3H, m), 7.68-7.74 (1H, m), 7.76-7.83 (1H, m), 7.93-7.98 (2H, m), 8.70 (1H, s), 9.84 (1H, s), 14.35 (1H, br s).

Example 121-B

Production of 6-[(4-acetylpiperazin-1-yl)methyl]-2-methyl-3-[4-phenyl-5-(1H-1,2,4-triazol-3-yl)-1,3-thiazol-2-yl]imidazo[1,2-a]pyridine

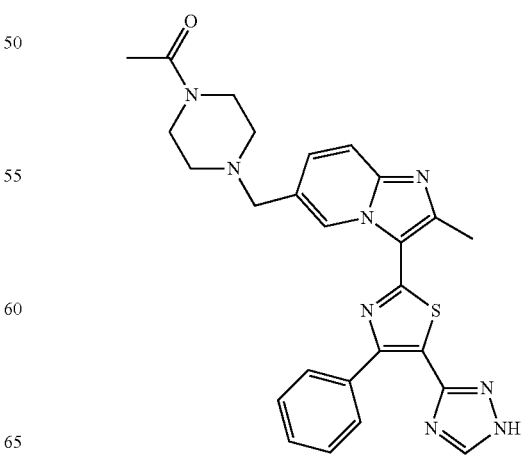

(i) Production of 6-[(4-acetylpiperazin-1-yl)methyl]-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine To a suspension of 2-methyl-3-{4-phenyl-5-[1-(tetrahydro-2H-pyran-2-yl)-1H-1,2,4-triazol-3-yl]-1,3-thiazol-2-yl}-6-vinylimidazo[1,2-a]pyridine (282 mg, 0.60 mmol) obtained in Example 110-B (i) in THF (21 mL) and water (6 mL), were added 4% aqueous osmium tetraoxide solution (375 μL, 0.03 mmol) and sodium periodate (320 mg, 1.5 mmol), and the mixture was stirred at rt for 24 h. To the reaction mixture was added water (50 mL), and the resulting precipitate was collected by filtration. The residue was washed with water and diethyl ether to obtain a gray solid.

The above solid was suspended in DMF (4.3 mL), and then were added AcOH (430 μL), 1-acetylpiperazine (300 mg, 2.6 mmol) and sodium triacetoxyborohydride (540 mg, 2.6 mmol). The mixture was stirred at 50° C. for 2 h, allowed to cool to rt, and then concentrated under reduced pressure. To the residue, were added saturated aqueous solution of sodium bicarbonate (50 mL) and EtOAc (50 mL). The aqueous layer was extracted with EtOAc (50 mL), and the combined organic layers were dried over anhydrous magnesium sulfate. Insoluble materials were removed by filtration, and the filtrate was concentrated under reduced pressure. The residue was purified by basic silica gel column chromatography (EtOAc/hexane=20/80→100/0; then MeOH/EtOAc=20/80) to give the title compound (79 mg, 23%) as a pale yellow solid.

¹H-NMR (DMSO-d₆, 300 MHz) δ1.53-1.73 (3H, m), 1.90-2.12 (6H, s), 2.37-2.47 (4H, m), 2.72 (3H, s), 3.39-3.48 (4H, m), 3.62 (2H, s), 3.65-3.73 (1H, m), 3.89-3.98 (1H, m), 5.62 (1H, dd, J=2.6, 8.4 Hz), 7.40-7.48 (4H, m), 7.65-7.71 (1H, m), 7.91-7.98 (2H, m), 8.80-8.83 (1H, m), 9.86 (1H, s).

(ii) Production of 6-[(4-acetylpiperazin-1-yl)methyl]-2-methyl-3-[4-phenyl-5-(1H-1,2,4-triazol-3-yl)-1,3-thiazol-2-yl]imidazo[1,2-a]pyridine A solution of 6-[(4-acetylpiperazin-1-yl)methyl]-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (77.0 mg, 0.13 mmol) obtained above in TFA (5.0 mL) was stirred at rt for 1 h, TFA was evaporated under reduced pressure, and the residue was again dissolved in TFA (5 mL). The mixture was stirred at rt for 1 h, and then TFA was evaporated under reduced pressure. To the residue were added saturated aqueous solution of sodium bicarbonate (5 mL), water (5 mL) and EtOAc (5 mL). The resulting precipitate was collected by filtration and washed with water and diethyl ether to give the title compound (25 mg, 38%) as a pale yellow solid.

¹H-NMR (DMSO-d₆, 300 MHz) δ 1.96 (3H, s), 2.33-2.48 (4H, S), 2.71 (3H, s), 3.34-3.48 (4H, m), 3.63 (2H, s), 7.34-7.48 (5H, m), 7.62-7.71 (1H, m), 8.05-8.16 (2H, m), 8.37 (1H, s), 9.87 (1H, s).

Example 122-B

Production of 6-cyclohexyl-2-methyl-3-[4-phenyl-5-(1H-1,2,4-triazol-3-yl)-1,3-thiazol-2-yl]imidazo[1,2-a]pyridine

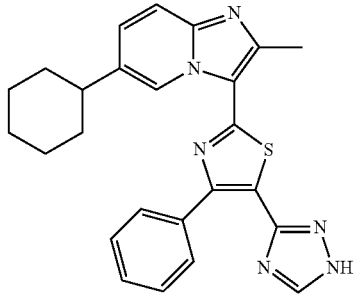 [SMILES: Cc1nc2ccc(C3CCCCC3)cn2c1-c1nc(-c2ccccc2)c(-c2nc[nH]n2)s1]

(i) Production of 6-bromo-2-methylimidazo[1,2-a]pyridine-3-carboxylic acid

To a solution of 2-amino-5-bromopyridine (25.0 g, 144.5 mmol) in EtOH (150 mL), was added methyl 2-chloro-3-acetoacetate (18.6 mL, 144.5 mmol), and the mixture was refluxed at 80° C. for 12 h. Then the reaction mixture was allowed to cool to rt, and then were added 8N aqueous sodium hydroxide solution (60 mL, 480 mmol) and water (30 mL). The mixture was stirred at 80° C. for 12 h, allowed to cool to 0° C., and then neutralized by the addition of 6N hydrochloric acid (300 mL). The resulting precipitate was collected by filtration and sequentially washed with water, EtOH and diethyl ether to give the title compound (11.1 g, 30%) as a brown solid.

¹H-NMR (DMSO-d₆, 300 MHz) δ2.59 (3H, s), 7.55-7.77 (2H, m), 9.41 (1H, dd, J=1.3, 1.3 Hz), 13.29 (1H, br s).

(ii) Production of 6-bromo-2-methylimidazo[1,2-a]pyridine-3-carboxamide

To a suspension of 6-bromo-2-methylimidazo[1,2-a]pyridine-3-carboxylic acid (11.0 g, 43.1 mmol) obtained above in toluene (200 mL), was added thionyl chloride (31.5 mL, 430 mmol), and the mixture was refluxed for 4 h. The mixture was allowed to cool to rt, and volatiles were removed under reduced pressure. The residue was dissolved in THF (200 mL), and was slowly added 25% aqueous ammonia solution (30 mL) at 0° C. The mixture was stirred at rt for 14 h. The resulting precipitate was collected by filtration and washed with water, EtOH and diethyl ether to give the title compound (5.0 g, 46%) as a brown solid.

¹H-NMR (DMSO-d₆, 300 MHz) δ2.56 (3H, s), 7.71-7.77 (1H, m), 7.82 (1H, dd, J=1.9, 9.4 Hz), 9.54 (1H, br s), 9.60 (1H, dd, J=0.9, 1.9 Hz), 10.22 (1H, br s).

(iii) Production of 6-bromo-2-methylimidazo[1,2-a]pyridine-3-carbonitrile 6-bromo-2-methylimidazo[1,2-a]pyridine-3-carboxamide (10.8 g, 42.4 mmol) obtained above was treated with phosphoryl chloride (85 mL) and DMF (50 µL) under reflux condition for 17 h. The mixture was allowed to cool to rt, and then volatiles were removed under reduced pressure. The residue was diluted with toluene (50 mL) and then was added ice-cooled saturated aqueous solution of sodium bicarbonate (200 mL). The mixture was neutralized by the addition of 1N aqueous sodium hydroxide solution (40 mL), the aqueous layer was extracted with EtOAc (250 mL×3), and the combined organic layer was dried over anhydrous magnesium sulfate and decolorized with activated carbon. Insoluble materials were removed by filtration and the filtrate was concentrated under reduced pressure to give the title compound (7.25 g, 73%) as a pale yellow solid.

$^1$H-NMR (DMSO-$d_6$, 300 MHz) δ 2.49 (3H, s), 7.63-7.77 (2H, m), 8.86 (1H, dd, J=1.3 Hz).

(iv) Production of 6-bromo-2-methylimidazo[1,2-a]pyridine-3-carbothioamide

To a suspension of 6-bromo-2-methylimidazo[1,2-a]pyridine-3-carbonitrile (6.2 g, 26.4 mmol) obtained above in MeOH (88 mL), were added 4N solution of hydrogen chloride in EtOAc (22 mL, 88.0 mmol) and O,O-diethyl hydrogen dithiophosphate (25 mL, 158 mol), and the mixture was stirred at 60° C. for 3 h. The mixture was allowed to cool to rt, and diluted with diisopropyl ether (100 mL). The resulting precipitate was collected by filtration and washed with diethyl ether to give the title compound (6.2 g, 77%) as a pale yellow solid.

$^1$H-NMR (DMSO-$d_6$, 300 MHz) δ2.56 (3H, s), 7.71-7.77 (1H, m), 7.82 (1H, dd, J=1.9, 9.4 Hz), 9.54 (1H, br s), 9.60 (1H, dd, 0.9, 1.9 Hz), 10.22 (1H, br s).

(v) Production of ethyl 2-(6-bromo-2-methylimidazo[1,2-a]pyridin-3-yl)-4-phenyl-1,3-thiazole-5-carboxylate To a suspension of 6-bromo-2-methylimidazo[1,2-a]pyridine-3-carbothioamide (700 mg, 2.59 mmol) obtained as described above in DMF (60 mL), was added ethyl 2-chloro-3-oxo-3-phenylpropanoate (1.76 g, 7.77 mmol), and the mixture was stirred at 90° C. for 21 h. The mixture was allowed to cool to rt, and the solvent was removed under reduced pressure. The residue was washed with water, EtOH and diethyl ether to give the titled compound (750 mg, 66%) as a pale yellow solid.

$^1$H-NMR (DMSO-$d_6$, 300 MHz) δ 1.25 (3H, t, J=7.1 Hz), 2.72 (3H, s), 4.27 (2H, q, J=7.0 Hz), 7.47-7.57 (3H, m), 7.69 (1H, dd, J=1.9, 9.4 Hz), 7.71-7.78 (1H, m), 7.82-7.90 (2H, m), 9.89-10.09 (1H, m).

(vi) Production of ethyl 2-(6-cyclohex-1-en-1-yl-2-methylimidazo[1,2-a]pyridin-3-yl)-4-phenyl-1,3-thiazole-5-carboxylate To a mixture of ethyl 2-(6-bromo-2-methylimidazo[1,2-a]pyridin-3-yl)-4-phenyl-1,3-thiazole-5-carboxylate (267 mg, 0.6 mmol) obtained above in DME (18 mL) and water (3.6 mL), were added 2-cyclohex-1-en-1-yl-4,4,5,5-tetramethyl-1,3,2-dioxaborolane (250 mg, 1.2 mmol), cesium carbonate (586 mg, 1.8 mmol) and [1,1-bis(diphenylphosphino)ferrocene]palladium(II) dichloride dichloromethane complex (49.1 mg, 0.06 mmol) under a nitrogen atmosphere, and the mixture was stirred at 95° C. for 3 h. The reaction mixture was allowed to cool to rt. The resulting precipitate was collected by filtration and washed with water and diethyl ether to give the title compound (223 mg, 84%) as a white solid.

$^1$H-NMR (DMSO-$d_6$, 300 MHz) δ 1.27 (3H, t, J=7.1 Hz), 1.58-1.69 (2H, m), 1.71-1.81 (2H, m), 2.17-2.30 (2H, m), 2.36-2.46 (2H, m), 2.69 (3H, s), 4.29 (2H, q, J=7.2 Hz), 6.38-6.48 (1H, m), 7.47-7.55 (3H, m), 7.62-7.68 (1H, m), 7.78 (1H, dd, J=1.9, 9.4 Hz), 7.93-7.99 (2H, m), 9.99-10.05 (1H, m).

(vii) Production of ethyl 2-(6-cyclohexyl-2-methylimidazo[1,2-a]pyridin-3-yl)-4-phenyl-1,3-thiazole-5-carboxylate To a mixture of ethyl 2-(6-cyclohex-1-en-1-yl-2-methylimidazo[1,2-a]pyridin-3-yl)-4-phenyl-1,3-thiazole-5-carboxylate (200 mg, 0.45 mmol) obtained above in acetic acid (18 mL) and MeOH (18 mL), was added 10% palladium-carbon (100 mg), and the mixture was stirred at rt for 15 h under a hydrogen atmosphere (1 atm). Insoluble materials were removed by filtration, and the filtrate was concentrated under reduced pressure. To the residue was added saturated aqueous solution of sodium bicarbonate (10 mL) and water (10 mL), and the resulting precipitate was collected by filtration, which was washed with diethyl ether to give the title compound (154 mg, 69%) as a black solid.

$^1$H-NMR (DMSO-$d_6$, 300 MHz) δ1.15-1.31 (4H, m), 135-1.47 (3H, m), 1.68-1.86 (3H, m), 1.92-2.06 (2H, m), 2.19-2.34 (1H, m), 2.55-2.66 (1H, m), 2.69 (3H, m), 4.28 (2H, q, 7.0 Hz), 7.45-7.57 (4H, m), 7.61-7.71 (1H, m), 7.88-8.02 (2H, m), 9.77-9.85 (1H, m).

(viii) Production of 2-(6-cyclohexyl-2-methylimidazo[1,2-a]pyridin-3-yl)-4-phenyl-1,3-thiazole-5-carboxylic acid A mixture of ethyl 2-(6-cyclohexyl-2-methylimidazo[1,2-a]pyridin-3-yl)-4-phenyl-1,3-thiazole-5-carboxylate (204 mg, 0.458 mmol) obtained above in THF (5 mL) and MeOH (5 mL), was added 2N aqueous sodium hydroxide (750 µL), and the mixture was stirred at 50° C. for 12 h. The mixture was allowed to cool to rt and then neutralized by the addition of 1N aqueous hydrochloric acid (1.5 mL). The resulting precipitate was collected by filtration and then washed with water and diethyl ether to give the title compound (159 mg, 83%) as a gray solid.

$^1$H-NMR (DMSO-$d_6$, 300 MHz) δ1.15-1.30 (1H, m),1.31-1.49 (3H, m), 1.67-1.87 (3H, m), 1.92-2.07 (2H, m), 2.36-2.45 (1H, m), 2.56-2.79 (4H, m), 7.41-7.59 (4H, m), 7.60-7.70 (1H, m), 7.90-8.06 (2H, m), 9.66-9.90 (1H, m), 13.38 (1H, br s).

(ix) Production of 2-(6-cyclohexyl-2-methylimidazo[1,2-a]pyridin-3-yl)-4-phenyl-1,3-thiazole-5-carboxamide To a suspension of 2-(6-cyclohexyl-2-methylimidazo[1,2-a]pyridin-3-yl)-4-phenyl-1,3-thiazole-5-carboxylic acid (169 mg, 0.405 mmol) obtained above in DMF (8 mL), were added TEA (170 µL, 1.22 mmol), ammonium chloride (65.0 mg 1.22 mmol), HOBT (82 mg, 0.61 mmol) and EDCI (120 mg, 0.61 mmol), and the mixture was stirred at rt for 12 h. To the mixture was added DMF (8.0 mL), and the mixture was stirred 40° C. for 2 h. The reaction mixture was allowed to cool to rt, DMF (30 mL) was added, and the mixture was warmed to 60° C. The solution was concentrated until ca 10 mL under reduced pressure. The residue was subjected to basic silica gel column chromatography (EtOAc/hexane=20/80→100/0; then MeOH/EtOAc=30/70). Concentration of the appropriate solution afforded crude product, which was suspended in saturated aqueous solution of sodium bicarbonate (10 mL) and water (10 mL). The resulting precipitate was collected by filtration and washed with water and diethyl ether to give the titled compound (104 mg, 62%) as a orange solid,
$^1$H-NMR (DMSO-$d_6$, 300 MHz) δ 1.21-1.33 (1H, m), 1.40-1.52 (3H, m), 1.69-1.91 (3H, m), 1.96-2.05 (2H, m), 2.23-2.32 (1H, m), 2.68 (3H, s), 2.71-2.76 (1H, m), 7.41-7.57 (4H, m), 7.61-7.68 (1H, m), 7.82 (2H, br s), 7.92 (2H, s), 9.76-9.83 (1H, m).

(x) Production of 6-cyclohexyl-2-methyl-3-[4-phenyl-5-(1H-1,2,4-triazol-3-yl)-1,3-thiazol-2-yl]imidazo[1,2-a]pyridine A suspension of 2-(6-cyclohexyl-2-methylimidazo[1,2-a]pyridin-3-yl)-4-phenyl-1,3-thiazole-5-carboxamide (104 mg, 0.25 mmol) obtained above in N,N-dimethylformamide dimethylacetal (20 mL) was stirred at 100° C. for 12 h. The reaction mixture was allowed to cool to rt and then concentrated under reduced pressure. The residue was suspended in AcOH (5 mL), and then was added hydrazine monohydrate (70 μL, 1.4 mmol) at 0° C., and the mixture was stirred at 90° C. for 1 h, allowed to cool to rt, and then concentrated under reduced pressure. The residue was diluted with EtOAc (20 mL), water (10 mL) and saturated aqueous solution of sodium bicarbonate (10 mL), and the aqueous layer was extracted with a 2:1 mixture of EtOAc and THF (30 mL). The combined organic layers were dried over anhydrous magnesium sulfate. Insoluble materials were removed by filtration, and the filtrate was concentrated under reduced pressure.
The residue was purified by silica gel column chromatography (EtOAc/hexane=20/80→100/0; then MeOH/EtOAc=20:80) to give the title compound (57.3 mg, 52%) as a pale yellow solid.
$^1$H-NMR (DMSO-$d_6$, 300 MHz) δ 1.20-1.32 (1H, m), 1.38-1.50 (3H, m), 1.70-1.88 (4H, m), 1.96-2.07 (2H, m), 2.59-2.78 (4H, m), 7.36-7.52 (4H, m), 7.60-7.68 (1H, m), 8.00-8.10 (2H, m), 8.60 (1H, s), 9.75-9.94 (1H, m), 14.13 (1H, br s).

Example 123-B

Production of 3,6-dimethyl-5-[4-phenyl-5-(1H-1,2,4-triazol-3-yl)-1,3-thiazol-2-yl]imidazo[2,1-b][1,3]thiazole

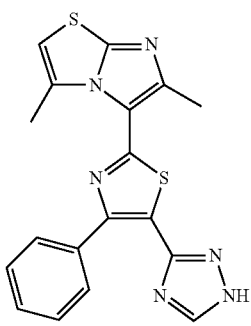 [SMILES: Cc1nc2scc(C)n2c1-c1nc(-c2ccccc2)c(-c2nc[nH]n2)s1]

To a mixture of 1-bromo-1-{4-phenyl-5-[1-(tetrahydro-2H-pyran-2-yl)-1H-1,2,4-triazol-3-yl]-1,3-thiazol-2-yl}acetone (1.15 g, 2.5 mmol) obtained by similar manner with Example 116-B(vi) in THF (12.5 mL) and 2-propanol (12.5 mL), was added 2-amino-4-methylthiazole (1.43 g, 12.5 mmol), the mixture was stirred at 80° C. for 4 h. The reaction mixture was allowed to cool to 50° C., 2N hydrochloric acid (12.5 mL) was added, and the mixture was stirred for 12 h. The reaction mixture was allowed to cool to rt, and then neutralized by the addition of 2N aqueous sodium hydroxide solution (12.5 mL). The mixture was extracted with EtOAc (50 mL×2), and the combined organic layers were dried over anhydrous magnesium sulfate. Insoluble materials were removed by filtration, and the filtrate was concentrated under reduced pressure. The residue was purified by basic silica gel column chromatography (EtOAc/hexane=50/50→100/0; then MeOH/EtOAc=30/70) followed by silica gel column chromatography (EtOAc/hexane=30/70→100/0) to give the title compound (88 mg, 9%) as a yellow solid.
$^1$H-NMR (DMSO-$d_6$, 300 MHz) δ2.45 (3H, d, J=1.1 Hz), 2.48 (3H, s), 6.98 (1H, d, J=1.3 Hz), 7.34-7.49 (3H, m), 7.76-7.86 (2H, m), 8.60-8.77 (1H, m), 14.34 (1H, br s).

Example 124-B

Production of 6-methyl-7-[5-phenyl-4-(1H-1,2,4-triazol-3-yl)-1,3-thiazol-2-yl]pyrazolo[5,1-b][1,3]thiazole

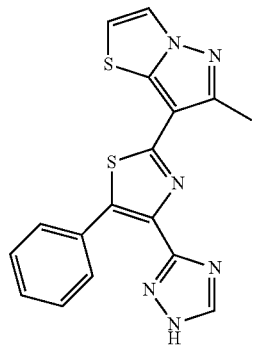 [SMILES: Cc1nn2ccsc2c1-c1nc(-c2nc[nH]n2)c(-c2ccccc2)s1]

(i) Production of 3-bromo-2-oxo-3-phenylpropanoic acid

To a stirred suspension of Phenylpyruvic acid (5.0 g, 30.5 mmol) in AcOH (20 ml), was added dropwise a solution of Bromine (1.57 mL, 30.5 mmol) in AcOH (5 ml) over 1 h at rt. After complete addition, stirring was continued for additional 30 min at the same temperature and then the reaction mixture was concentrated under reduced pressure. To the residue was added diisopropyl ether (30 ml) and the mixture was concentrated under reduced pressure. To the residue was added 1,2-dichloroethane (30 ml) and then the solution was kept on standing for 3 days at room temperature. The resultant precipitate was removed by filtration. To the filtrate was added hexane (20 mL) and the resulting precipitate was collected by filtration to obtain title compound (837 mg, 11%) as a colorless solid.
From the filtrate, second crop of the title compound (1.55 g, 21%) has been obtained as a colorless solid which was used in the next step without further purification. $^1$H-NMR (300 MHz, DMSO-d6) δ 6.53 (1H, s), 7.36-7.48 (6H, m).

(ii) Production of 2-(6-methylpyrazolo[5,1-h][1,3]thiazol-7-yl)-5-phenyl-1,3-thiazole-4-carboxylic acid A mixture of 3-bromo-2-oxo-3-phenylpropanoic acid (197 mg, 1.00 mmol) and 6-methylpyrazolo[5,1-b][1,3]thiazole- 7-carbothioamide (267 mg, 1.10 mmol) in EtOH (10 ml) was stirred at 50° C. for 1 h. The reaction mixture was allowed to cool to rt, the resulting precipitate was collected by filtration and then washed with EtOAc to obtain title compound (328 mg, 96%) as a colorless solid. 1H-NMR (DMSO-d6) δ 2.61 (3H, s), 7.43-7.59 (6H, m) 8.31 (1H, d, J=4.2 Hz), 12.99 (1H, br s).

(iii) Production of 2-(6-methylpyrazolo[5,1-h][1,3]thiazol-7-yl)-5-phenyl-1,3-thiazole-4-carboxamide According to the similar manner described in Example 97-B (iii), the title compound (126 mg, 45%) has been obtained as a colorless solid by standard amidation reaction using 2-(6-methylpyrazolo[5,1-b][1,3]thiazol-7-yl)-5-phenyl-1,3-thiazole-4-carboxylic acid (280 mg, 0.820 mmol) obtained above. The pure title compound has been obtained by washing of the crude product, which was precipitated from reaction mixture after aqueous work-up, with water and EtOAc. Second crop of the title compound (77.7 mg, 28%) has been obtained from above filtrate after standard extraction of the aqueous mixture. $^1$H-NMR (DMSO-d6) δ 2.62 (3H, s), 7.40-7.48 (3H, m), 7.54 (1H, d, J=3.9 Hz), 7.60-7.65 (3H, m), 7.69 (1H, br s), 8.32 (1H, d, J=4.2 Hz).

(iv) Production of 6-methyl-7-[5-phenyl-4-(1H-1,2,4-triazol-3-yl)-1,3-thiazol-2-yl]pyrazolo[5,1-b][1,3]thiazole According to the similar manner described in Example 97-B (iv), the title compound (24.2 mg, 18%) has been obtained as a pale yellow solid using 2-(6-methylpyrazolo[5,1-b][1,3]thiazol-7-yl)-5-phenyl-1,3-thiazole-4-carboxamide (126 mg, 0.370 mmol) obtained above. The pure title compound was obtained by extraction of the reaction mixture with EtOAc and then crystallized from EtOAc. The second crop of the title compound (34.2 mg, 25%) has been obtained from aqueous layer by spontaneous crystallization. $^1$H-NMR (DMSO-d6) δ 2.66 (3H, s), 7.39-7.54 (7H, m), 8.32 (1H, d, J=4.2 Hz), 14.26 (1H, brs).

Example 125-B

Production of N-[4'-methyl-4-phenyl-5-(1H-1,2,4-triazol-3-yl)-2,5'-bi-1,3-thiazol-2'-yl]cyclopropanecarboxamide hydrochloride

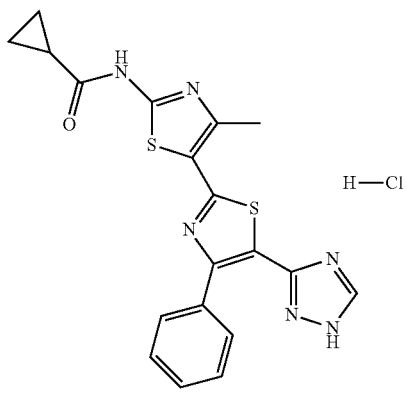 [SMILES: Cc1nc(NC(=O)C2CC2)sc1-c1nc(-c2ccccc2)c(-c2nc[nH]n2)s1 ; Cl]

To a solution of 1-bromo-1-{4-phenyl-5-[1-(tetrahydro-2H-pyran-2-yl)-1H-1,2,4-triazol-3-yl]-1,3-thiazol-2-yl}acetone (700 mg, 1.93 mmol) obtained in Example 116-B (vi) in THF (30 mL) and isopropyl alcohol (30 mL), was added thiourea (2.3 g, 30.2 mmol). The mixture was refluxed for 4 h with vigorous stirring. The mixture was allowed to cool to rt and the diluted with EtOAc (100 mL), which was washed with saturated aqueous solution of sodium bicarbonate (100 mL). The aqueous layer was extracted with EtOAc (100 mL). The combined organic layers were dried over anhydrous magnesium sulfate. Insoluble materials were removed by filtration and the filtrate was concentrated under reduced pressure. The residue (680 mg) has been used in the next step with out further purification.

To a solution of above residue (329 mg) in pyridine (10 mL) were added cyclopropanecarbonyl chloride (1.0 mL, 11.0 mmol) and DMAP (21.5 mg, 0.176 mmol) and the mixture was stirred for 1 h at rt. To the mixture, was added MeOH (30 mL) and the mixture was stirred for 10 h at rt. The mixture was concentrated under reduced pressure and the residue was suspended in water (50 mL). The aqueous mixture was extracted with EtOAc (50 mL×2) and the combined organic layers were washed with saturated aqueous solution of ammonium chloride (50 mL), dried over anhydrous magnesium sulfate. Insoluble materials were removed by filtration and the filtrate was concentrated under reduced pressure. The residue was suspended in EtOAc and insoluble materials were removed by filtration and the filtrate was purified by silica gel column chromatography (EtOAc/hexane 80/100→100/0) to obtain yellow foam (132 mg).

To a solution of above yellow foam in THF (3 mL) were added MeOH (3 mL) and 4 N solution of hydrogen chloride in EtOAc (3 mL). The mixture was refluxed for 2.5 h with vigorous stirring. The mixture was allowed to cool to rt and then concentrated under reduced pressure. The residual crystalline material was washed with hot EtOAc and the remaining precipitate was collected by filtration to obtain title compound (80 mg, 19%) as an off-white solid, $^1$H-NMR (DMSO-d$_6$, 300 MHz) δ 0.74-1.02 (4 H, m), 1.76-2.07 (1 H, m), 2.61 (3 H, s), 7.20-7.52 (3 H, m), 7.81 (2 H, d, J=9.6 Hz), 8.63 (1 H, s), 12.70 (1 H, br s).

Example 135-B

Synthesis of {4-[2-(2-methylpyrazolo[1,5-a]pyridin-3-yl)-5-(1H-1,2,4-triazol-3-yl)-1,3-thiazol-4-yl]phenyl}methanol (135-B)

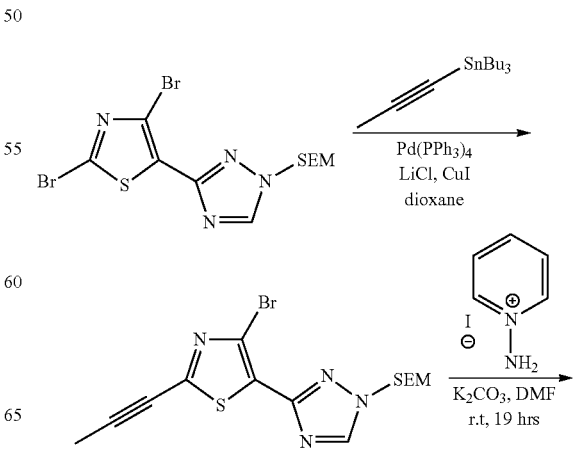

325

-continued

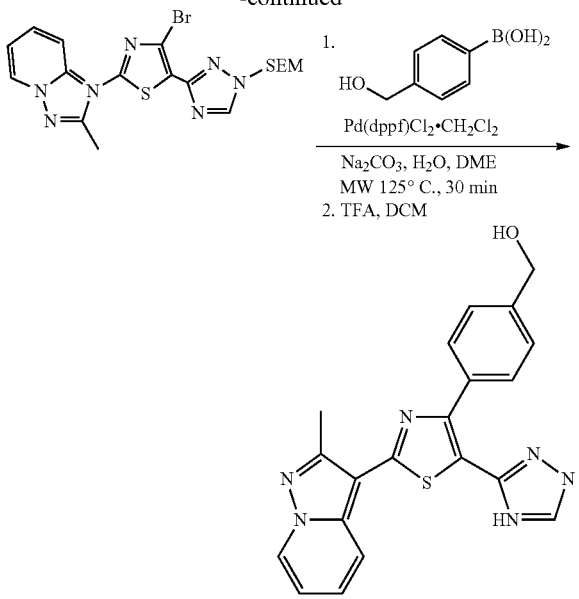

Step 1: Synthesis of 3-(4-bromo-2-prop-1-yn-1-yl-1,3-thiazol-5-yl)-1-{[2-(trimethylsilyl)ethoxy]methyl}-1H-1,2,4-triazole A mixture of 3-(2,4-dibromo-1,3-thiazol-5-yl)-1-{[2-(trimethylsilyl)ethoxy]methyl}-1H-1,2,4-triazole (6.00 g, 13.6 mmol), Lithium chloride (1.73 g, 40.9 mmol), Copper(I) iodide (0.779 g, 4.09 mmol) and Tetrakis(triphenylphosphine)platinum (0) (0.848 g, 0.681 mmol) in anhydrous 1,4-Dioxane (120 mL, 1500 mmol) was sonicated under Argon atmosphere for 2 minutes in a 250 mL RBF. Tributyl(1-propynyl)tin (4.80 mL, 15.0 mmol) was added. The mixture was heated to 100° C. for 1 hour under Argon atmosphere. The mixture was cooled to r.t., diluted with DCM (~150 mL), filtered through Celite, and washed with DCM. The filtrate was rotavaped to give a crude residue. Chromatograph in a 330 g ISCO column using EtOAc/hexane (0/100 to 50/50) gave a pure solid product (4.14 g, 76% yield). LCMS: (FA) ES+ 399, 401. $^1$H NMR (400 MHz, $d_1$-chloroform) δ 8.29 (s, 1H), 5.54 (s, 2H), 3.69-3.74 (m, 2H), 2.15 (s, 3H), 0.93-0.97 (m, 2H), 0.00 (s, 9H).

Step 2: Synthesis of 3-[4-bromo-5-(1-{[2-(trimethylsilyl)ethoxy]methyl}-1H-1,2,4-triazol-3-yl)-1,3-thiazol-2-yl]-2-methylpyrazolo[1,5-a]pyridine A mixture of 3-(4-bromo-2-prop-1-yn-1-yl-1,3-thiazol-5-yl)-1-{[2-(trimethylsilyl)ethoxy]methyl}-1H-1,2,4-triazole (0.514 g, 1.29 mmol), 1-Aminopyridinium iodide (0.343 g, 1.54 mmol) and Potassium carbonate (0.231 g, 1.67 mmol) in N,N-Dimethylformamide (8.0 mL, 1.0E2 mmol) was stirred at r.t. for 29 hours. The mixture was quenched with ice water (80 mL), extracted with EtOAc 3 times. The combined EtOAc solution was washed with water, brine, dried over Na$_2$SO$_4$, filtered and EtOAc/hexane (0/100 to 30/70) to afford a solid product. (0.410 g, 64.8% yield). LCMS: (FA) ES+ 491, 493. $^1$H NMR (400 MHz, $d_1$-chloroform) δ 8.43-8.46 (m, 2H), 8.32 (s, 1H), 7.39-7.42 (m, 1H), 6.90-6.93 (m, 1H), 5.57 (σ, 2H), 3.72-3.76 (m, 2H), 2.76 (s, 3H), 0.96-1.00 (m, 2H), 0.00 (s, 9H).

326

Step 3: Synthesis of {4-[2-(2-methylpyrazolo[1,5-a]pyridin-3-yl)-5-(1H-1,2,4-triazol-3-yl)-1,3-thiazol-4-yl]phenyl}methanol (135-B)

Into a microwave vial containing a mixture of 4-bromo-2-(2-methylpyrazolo[1,5-a]pyridin-3-yl)-5-(1-((2-(trimethylsilyl)ethoxy)methyl)-1H-1,2,4-triazol-3-yl)thiazole (0.030 g, 0.061 mmol) and 4-(hydroxymethyl)phenylboronic acid (0.026 g, 0.17 mmol) was added 1M aqueous NaHCO$_3$ (0.15 mL, 0.15 mmol), [1,1'-Bis(diphenylphosphino)ferrocene]palladium(II)dichloride (0.0021 g, 0.003 mmol) and 1,2-dimethoxyethane (0.60 mL). The vial was flushed with nitrogen gas and the reaction mixture was heated at 125° C. in a Biotage Microwave reactor for 30 minutes. Upon cooling to room temperature, the reaction was concentrated in vacuo and the residue obtained was partitioned between water (2 mL) & a mixture of CHCl$_3$/THF (4:1, 3 mL). Upon separation of the layers, the aqueous layer was extracted with additional CHCl$_3$/THF (4:1, 3 mL), the combined layers were filtered and concentrated. The material obtained was dissolved in methylene chloride (0.75 mL) and to this solution was added trifluoroacetic acid (0.5 mL, 6.4 mmol). The resulting reaction mixture was stirred overnight at room temperature. The reaction was concentrated in vacuo, the residue re-dissolved in DMSO (1 mL), filtered and purified on Agilent A2 prep instrument mass triggered reverse phase chromatography (Waters Sunfire prep C18 10 mm 19×150 mm column). Concentration of fractions containing desired product afforded product (0.0061 g, 26% yield). LCMS: (FA) ES+ 390.

Compounds in the following table were prepared from the appropriate starting materials in a method analogous to that of Example 135-B:

| | |
|---|---|
| 126-B | LCMS: (FA) ES+ 411. |
| 129-B | LCMS: (FA) ES+ 466. |
| 130-B | LCMS: (FA) ES+ 378. |
| 131-B | LCMS: (FA) ES+ 411. |
| 133-B | LCMS: (FA) ES+ 380. |
| 134-B | LCMS: (FA) ES+ 365. |
| 136-B | LCMS: (FA) ES+ 361. |
| 137-B | LCMS: (FA) ES+ 400. |
| 140-B | LCMS: (FA) ES+ 441. |
| 141-B | LCMS: (FA) ES+ 392. |
| 142-B | LCMS: (FA) ES+ 428. |
| 143-B | LCMS: (FA) ES+ 452. |
| 144-B | LCMS: (FA) ES+ 402. |
| 145-B | LCMS: (FA) ES+ 388. |
| 146-B | LCMS: (FA) ES+ 445. |
| 148-B | LCMS: (FA) ES+ 348. |
| 149-B | LCMS: (FA) ES+ 418. |
| 150-B | LCMS: (FA) ES+ 389. |
| 151-B | LCMS: (FA) ES+ 432. |
| 152-B | LCMS: (FA) ES+ 463. |
| 153-B | LCMS: (FA) ES+ 466. |
| 154-B | LCMS: (FA) ES+ 494. |
| 155-B | LCMS: (FA) ES+ 445. |
| 158-B | LCMS: (FA) ES+ 396. |
| 163-B | LCMS: (FA) ES+ 378. |
| 164-B | LCMS: (FA) ES+ 446. |

Example 160-B

Synthesis of 4-chloro-3-[2-(2-methylpyrazolo[1,5-a]pyridin-3-yl)-5-(1-{[2-(trimethylsilyl)ethoxy]methyl}-1H-1,2,4-triazol-3-yl)-1,3-thiazol-4-yl]benzaldehyde

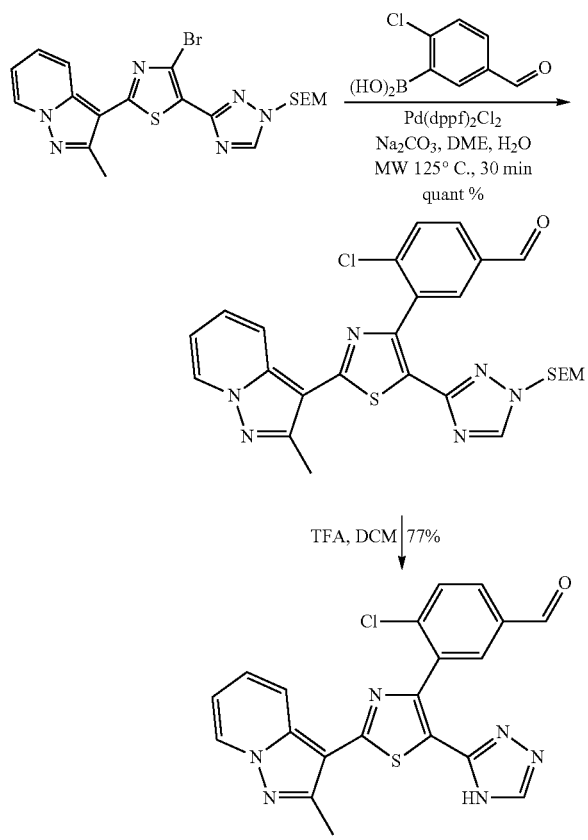

Step 1: Synthesis of 4-chloro-3-[2-(2-methylpyrazolo[1,5-a]pyridin-3-yl)-5-(1-{[2-(trimethylsilyl)ethoxy]methyl}-1H-1,2,4-triazol-3-yl)-1,3-thiazol-4-yl]benzaldehyde A mixture of 3-[4-bromo-5-(1-{[2-(trimethylsilyl)ethoxy]methyl}-1H-1,2,4-triazol-3-yl)-1,3-thiazol-2-yl]-2-methylpyrazolo[1,5-a]pyridine (0.0220 g, 0.0448 mmol), 2-Chloro-5-formylphenylboronic acid (15.0 mg, 0.0814 mmol), sodium carbonate (8.63 mg, 0.0814 mmol) and [1,1'-Bis(diphenylphosphino)ferrocene]dichloropalladium(II), complex with dichloromethane (1:1) (1.8 mg, 0.0022 mmol) in 1,2-Dimethoxyethane (0.50 mL, 4.8 mmol) with Water (0.050 mL, 2.8 mmol) in a MW vial was heated to 125° C. for 30 min. The mixture was cooled to r.t., diluted with DCM, filtered through Celite/Na₂SO₄. The filtrate was concentrated in rotavapor to give a crude product. Chromatograph in a 12 g ISCO column using EtOAc/hexane (0/100 to 40/60) to afford a solid product. (0.0265 g, 99.9% yield). LCMS: (FA) ES⁺ 551, 553. ¹H NMR (400 MHz, d₁-chloroform) δ 10.05 (σ, 1H), 8.44 (m, 2H), 8.13-8.15 (m, 2H), 7.90-7.93 (m, 1H), 7.64-7.66 (m, 1H), 7.33 (m, 1H), 6.88-6.90 (m, 1H), 5.40 (σ, 2H), 3.58 (t, J=8.03 Hz, 2H), 2.82 (s, 3H), 0.90 (t, J=8.03 Hz, 2H), δ 0.00 (s, 9H).

Step 2: Synthesis of 4-chloro-3-[2-(2-methylpyrazolo[1,5-a]pyridin-3-yl)-5-(4H-1,2,4-triazol-3-yl)-1,3-thiazol-4-yl]benzaldehyde (160-B)

-Chloro-3-[2-(2-methylpyrazolo[1,5-a]pyridin-3-yl)-5-(1-{[2-(trimethylsilyl)ethoxy]methyl}-1H-1,2,4-triazol-3-yl)-1,3-thiazol-4-yl]benzaldehyde (0.0230 g, 0.0388 mmol) was treated with Trifluoroacetic Acid (1.0 mL, 13 mmol) in Methylene chloride (1.0 mL, 16 mmol) at r.t. for 20 hours. The mixture was rotavaped. The residue was basified with saturated NaHCO₃, extracted with EtOAc. The EtOAc solution was washed with water, brine, dried over Na₂SO₄, filtered, rotavaped to give a crude product. Chromatograph in a 12 g ISCO column using MeOH/DCM (0/100 to 5/95) gave a solid product. (0.0125 g, 76.5% yield).

LCMS: (FA) ES⁺ 421, 423. ¹H NMR (400 MHz, d₁-chloroform & d4-methanol) δ 9.93 (σ, 1H), 8.32-8.37 (m, 2H), 8.04-8.07 (m, 2H), 7.82-7.85 (m, 1H), 7.57-7.60 (m, 1H), 7.26-7.30 (m, 1H), 6.82-6.86 (m, 1H), 2.72 (s, 3H).

Example 156-B

Synthesis of N-(4-chlorophenyl)-N-methyl-2-(2-methylpyrazolo[1,5-a]pyridin-3-yl)-5-(4H-1,2,4-triazol-3-yl)-1,3-thiazol-4-amine

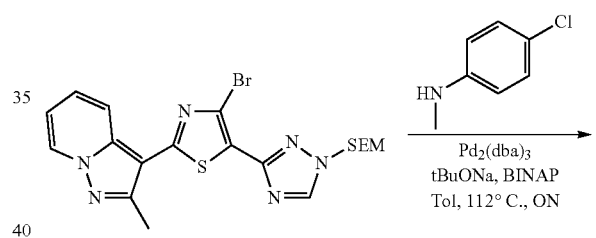

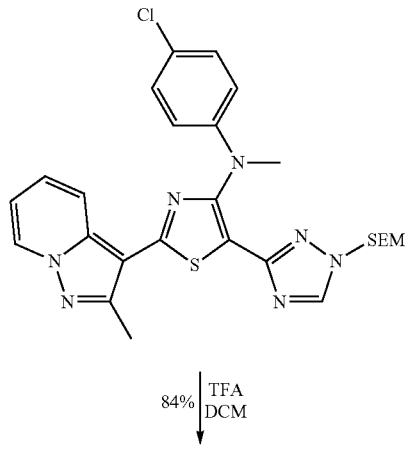

329
-continued

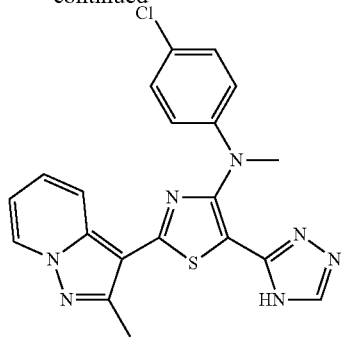

Step 1: Synthesis of N-(4-chlorophenyl)-N-methyl-2-(2-methylpyrazolo[1,5-a]pyridin-3-yl)-5-(1-{[2-(trimethylsilyl)ethoxy]methyl}-1H-1,2,4-triazol-3-yl)-1,3-thiazol-4-amine The mixture of 3-[4-bromo-5-(1-{[2-(trimethylsilyl)ethoxy]methyl}-1H-1,2,4-triazol-3-yl)-1,3-thiazol-2-yl]-2-methylpyrazolo[1,5-a]pyridine (0.0700 g, 0.142 mmol), p-Chloro-N-methylaniline (33.5 mg, 0.236 mmol), Tris(dibenzylideneacetone)dipalladium(0) (4.4 mg, 0.0048 mmol.), racemic 1,1'-binaphthalene-2,2'-diylbis(diphenylphosphine) (8.8 mg, 0.014 mmol) and Sodium tert-butoxide (22.7 mg, 0.236 mmol) in dry Toluene (2.0 mL, 19 mmol) was degassed by vacuum and backfilling with $N_2$ for 5 times, sonicated under $N_2$ for 1 min to dissolve all material, degassed for 5 more times. The resulted brown solution was heated under $N_2$ in a capped vial to 112° C. for 18 hours. The mixture was partitioned in EtOAc (80 mL) and water (30 mL). The EtOAc layer was washed with water, brine, dried over $Na_2SO_4$, filtered, rotavaped to give a crude product. Chromatograph in a 24 g ISCO column using EtOAc/hexane (0/100 to 40/60) afforded a solid product (0.059 g, 75% yield). LCMS: (FA) ES+ 552, 554. $^1$H NMR (400 MHz, $d_1$-chloroform) δ 8.43 (8, J=6.53 Hz, 1H), 8.32 (d, J=9.04 Hz, 1H), 8.13 (s, 1H), 7.29-7.33 (m, 1H), 7.10-7.12 (d, J=9.04 Hz, 2H), 6.84-6.88 (m, 1H), 6.82-6.84 (d, J=9.04 Hz, 2H), 5.39 (s, 2H), 3.55 (t, J=7.78 Hz, 2H), 3.51 (s, 3H), 2.78 (s, 3H), 0.90 (t, J=7.78 Hz, 2H), 0.00 (s, 9H).

Step 2: Synthesis of N-(4-chlorophenyl)-N-methyl-2-(2-methylpyrazolo[1,5-a]pyridin-3-yl)-5-(4H-1,2,4-triazol-3-yl)-1,3-thiazol-4-amine (156-B)

N-(4-chlorophenyl)-N-methyl-2-(2-methylpyrazolo[1,5-a]pyridin-3-yl)-5-(1-{[2-(trimethylsilyl)ethoxy]methyl}-1H-1,2,4-triazol-3-yl)-1,3-thiazol-4-amine (0.0566 g, 0.102 mmol) was treated with 4 M of Hydrochloric acid in 1,4-dioxane (6.0 mL, 24 mmol) and Water (1.0 mL, 56 mmol) at 35° C. to r.t. for 42 hours. The reaction solution was rotavaped, azeotroped with MeOH to give a crude residue. The material was dissolved in small amount of MeOH, diluted with $Et_2O$, filtered to give a solid product. (0.037 g, 84% yield). LCMS: (FA) ES+ 422. $^1$H NMR (400 MHz, $d_1$-chloroform & d4-methanol) δ 8.89 (0, 1H), 8.41 (d, J=6.78

330

Hz1-H8.26 (d, J=6.78 Hz, 1H), 7.36 (m, 1H), 7.10-7.12 (d, J=8.78 Hz, 2H), 6.87-6.90 (m, 3H), 3.51 (s, 3H), 2.72 (s, 3H).

Example 159-B

Synthesis of 2-methyl-3-[4-phenyl-5-(1H-1,2,4-triazol-3-yl)-1,3-thiazol-2-yl]-6-(piperazin-1-ylmethyl)imidazo[1,2-a]pyridine -continued

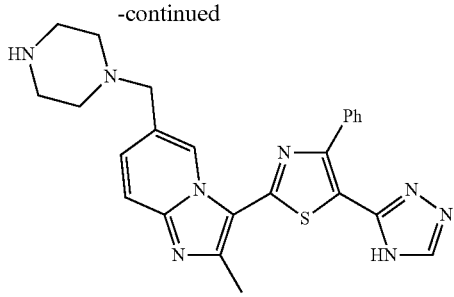

Step 1: Synthesis of 2-methyl-3-{4-phenyl-5-[1-(tetrahydro-2H-pyran-2-yl)-1H-1,2,4-triazol-3-yl]-1,3-thiazol-2-yl}-6-vinylimidazo[1,2-a]pyridine A mixture (suspension) of [A] 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (1.04 g, 2.00 mmol), Potassiumvinyltrifluoroborate (0.402 g, 3.00 mmol), [1,1'-Bis(diphenylphosphino)ferrocene]dichloropalladium (II), complex with dichloromethane (1:1) (0.163 g, 0.200 mmol) and Cesium Carbonate (1.95 g, 6.00 mmol) in 1,2-Dimethoxyethane (70 mL, 700 mmol) and Water (14 mL, 780 mmol) was heated to 95° C. under atmosphere of $N_2$ for 4 hours. The mixture was cooled to r.t., diluted with EtOAc (40 mL), filtered through Celite. The filtrate was diluted further with EtOAc (500 mL), washed with water, brine, dried over $Na_2SO_4$, filtered, rotavaped to give a crude product. Chromatograph in a 40 g ISCO column using MeOH/DCM (0/100 to 5/95) gave a solid product (0.747 g, 79.7% yield). LCMS: (FA) $ES^+$ 468. $^1H$ NMR (400 MHz, $d_r$-chloroform) δ 9.97 s, 1H), 8.29 (σ, 1H), 7.95-7.98 (m, 2H), 7.56-7.62 (m, 2H), 7.42-7.46 (m, 3H), 6.71-6.78 (dd, J=17.57, 10.79 Hz, 1H), 5.76-5.81 (d, J=17.57 Hz, 1H), 5.48-5.51 (dd, J=8.53, 3.26 Hz, 1H), 5.33-5.36 (d, J=11.04 Hz, 1H), 4.06-4.10 (m, 1H), 3.70-3.77 (m, 1H), 2.81 (s, 3H), 2.00-2.18 (m, 3H), 1.63-1.74 (m, 3H).

Step 2: Synthesis of 2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde and 1-(2-methyl-3-{4-phenyl-5-[1-(tetrahydro-2H-pyran-2-yl)-1H-1,2,4-triazol-3-yl]-1,3-thiazol-2-yl}imidazo[1,2-a]pyridin-6-yl)ethane-1,2-diol To the solution of 2-methyl-3-{4-phenyl-5-[1-(tetrahydro-2H-pyran-2-yl)-1H-1,2,4-triazol-3-yl]-1,3-thiazol-2-yl}-6-vinylimidazo[1,2-a]pyridine (0.747 g, 1.59 mmol) in Tetrahydrofuran (55 mL, 680 mmol) and Water (16 mL, 890 mmol) was added Sodium metaperiodate (0.852 g, 3.98 mmol), followed by 0.157 M of Osmium tetraoxide in Water (0.53 mL, 0.083 mmol). The solution was stirred at r.t, for 3 days. The mixture was diluted with ~100 mL of water, filtered to collect the solid product as the first crop of 2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde (0.255 g, 24% yield). LCMS: (FA) $ES^+$ 471. $^1H$ NMR (400 MHz, $d_1$-chloroform) δ 10.56 (σ, 1H), 10.00 (σ, 1H), 8.30 (σ, 1H), 7.94-7.97 (m, 2H), 7.82-7.85 (m, 1H), 7.69-7.71 (m, 1H), 7.46 (m, 3H), 5.48-5.51 (dd, J=8.78, 2.76 Hz, 1H), 4.06-4.09 (m, 1H), 3.73-3.77 (m, 1H), 2.85 (s, 3H), 2.02-2.15 (m, 3H), 1.59-1.69 (m, 3H). The filtrate was rotavaped to remove THF, extracted with 5% MeOH/DCM (4×60 mL). The combined DCM solution was dried over $Na_2SO_4$, filtered, rotavaped to give a crude material. Chromatograph in a 40 g ISCO column using MeOH/DCM (0/100 to 5/95) gave the second crop of 2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde (fast fraction, 0.104 g, 14% yield), and 1-(2-methyl-3-{4-phenyl-5-[1-(tetrahydro-2H-pyran-2-yl)-1H-1,2,4-triazol-3-yl]-1,3-thiazol-2-yl}imidazo[1,2-a]pyridin-6-yl)ethane-1,2-diol (slow fraction, 0.243 g, 30.3% yield). LCMS: (FA) $ES^+$ 503. $^1H$ NMR (400 MHz, $d_1$-chloroform & d4-methanol) δ 9.90 (σ, 1H), 8.28 (σ, 1H), 7.86-7.88 (m, 2H), 7.54-7.57 (d, J=9.29 Hz, 1H), 7.37-7.41 (m, 4H), 5.44-5.47 (m, 1H), 4.80-4.82 (m, 1H), 4.02-4.05 (m, 1H), 3.68-3.80 (m, 3H), 2.73 (s, 3H), 2.00-2.11 (m, 3H), 1.65-1.68 (m, 3H).

Step 3: Synthesis of tert-butyl 4-[(2-methyl-3-{4-phenyl-5-[1-(tetrahydro-2H-pyran-2-yl)-1H-1,2,4-triazol-3-yl}-1,3-thiazol-2-yl]imidazo[1,2-a]pyridin-6-yl)methyl]piperazine-1-carboxylate To the suspension of 2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde (0.0300 g, 0.0638 mmol), tert-Butyl 1-piperazinecarboxylate (20.8 mg, 0.112 mmol) and Acetic acid (11 mg, 0.18 mmol) in dry Methylene chloride (2.0 mL, 31 mmol) was added Sodium triacetoxyborohydride (27.0 mg, 0.128 mmol). The mixture was stirred at r.t. for 46 hours. The mixture was washed with water (2×2 mL) and brine, dried over $Na_2SO_4$, filtered and the filtrate was chromatographed in an 8 g AnaLogix column using MeOH/DCM (0/100 to 5/95) to give a solid product (0.0253 g, 61.9% yield). LCMS: (FA) $ES^+$ 641. $^1H$ NMR (400 MHz, d-chroloform) δ 9.91 (s, 1H), 8.28 (s, 1H), 7.94-7.97 (m, 2H), 7.58-7.60 (m, 1H), 7.34-7.46 (m, 4H), 5.47-5.51 (m, 1H), 4.05-4.13 (m, 1H), 3.70-3.76 (m, 1H), 3.58 (s, 2H), 3.42 (s, br, 4H), 2.81 (s, 3H), 2.45 (s, br, 4H), 2.00-2.17 (m, 3H), 1.65-1.72 (m, 3H), 1.46 (s, 9H).

Step 4: Synthesis of 2-methyl-3-[4-phenyl-5-(1H-1,2,4-triazol-3-yl)-1,3-thiazol-2-yl]-6-(piperazin-1-ylmethyl)imidazo[1,2-a]pyridine (159-B)

tert-Butyl 4-[(2-methyl-3-{4-phenyl-5-[1-(tetrahydro-2H-pyran-2-yl)-1H-1,2,4-triazol-3-yl]-1,3-thiazol-2-yl}imidazo[1,2-a]pyridin-6-yl)methyl]piperazine-1-carboxylate (0.025 g, 0.039 mmol) was treated with Trifluoroacetic Acid (2.0 mL, 26 mmol) in Methylene chloride (2.0 mL, 31 mmol) at r.t, for 18 hours. The mixture was rotavaped. The residue was triturated with hexane (3×5 mL). The solid residue was suspended in water and neutralized with saturated aqueous $NaHCO_3$ to pH ~9, extracted with 10% MeOH in DCM (3×10 mL). The combined organic layer was dried over $Na_2SO_4$, filtered, rotavaped and dried in hi-vac to give a solid product (0.0085 g, 45% yield). LCMS: (FA) $ES^+$ 457, $ES^-$ 455. $^1H$ NMR (400 MHz, d-chroloform & d4-methanol) δ 9.82 (σ, 1H), 8.14 (σ, 1H), 7.80-7.82 (m, 2H), 7.55-7.58 (m, 1H), 7.37-7.46 (m, 4H), 3.54 (s, 2H), 2.84 (m, 2H), 2.76 (s, 3H), 2.47 (s, br, 2H), 2.32 (m, 4H).

Compounds in the following table were prepared from the appropriate starting materials in a method analogous to that of Example 159-B:

| | |
|---|---|
| 127-B | LCMS: (FA) ES + 521. |
| 139-B | LCMS: (FA) ES + 457. |
| 161-B | LCMS: (FA) ES + 445. |
| 162-B | LCMS: (FA) ES + 431. |

Example 147-B

Synthesis of N-methyl-N-({2-methyl-3-[4-phenyl-5-(4H-1,2,4-triazol-3-yl)-1,3-thiazol-2-yl]imidazo[1,2-a]pyridin-6-yl}methyl)ethane-1,2-diamine

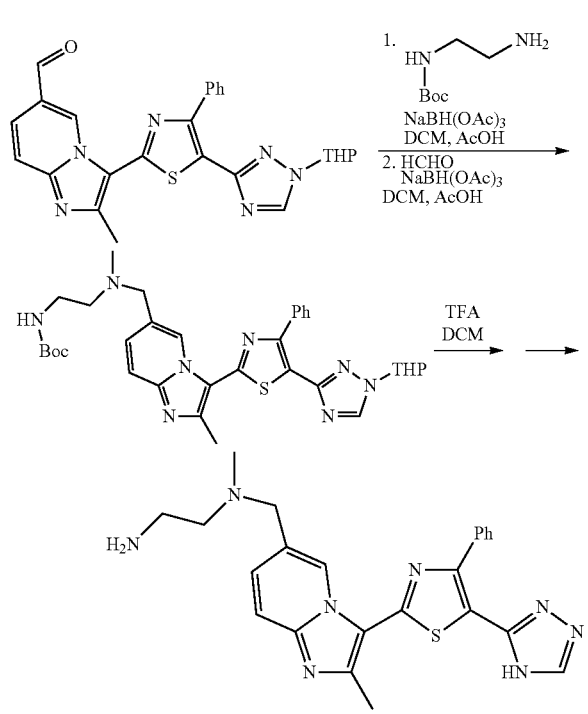

The mixture of 2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde (0.0300 g, 0.0638 mmol) and N-(2-aminoethyl)(tert-butoxy)carboxamide (15.3 mg, 0.0956 mmol) in dry Methylene chloride (2.0 mL, 31 mmol) and Acetic acid (50 mg, 0.8 mmol) was stirred at r.t. for 20 min, Sodium triacetoxyborohydride (23.3 mg, 0.110 mmol) was added and the mixture was stirred at r.t, for 21 hours. Paraformaldehyde (25 mg, 0.28 mmol) was added, followed by Acetic acid (100 mg, 2 mmol). The mixture was stirred at r.t. for 10 min. Sodium triacetoxyborohydride (172 mg, 0.812 mmol) was added and the mixture was stirred at r.t. for 17 hours. The mixture was quenched with saturated NaHCO$_3$, extracted with DCM. The DCM solution was washed with water, brine, dried over Na$_2$SO$_4$, filtered. The filtrate was chromatographed in a 24 g ISCO column using MeOH/DCM (0/100 to 5/95) to give a solid. LCMS: (FA) ES$^+$ 629. This solid was treated with Trifluoroacetic Acid (1.0 mL, 13 mmol) in Methylene chloride (1.0 mL, 16 mmol) at r.t. for 18 hours. The mixture was rotavaped, azeotroped with DCM. The residue was triturated with Et$_2$O and decanted to give a solid residue, dried in hi-vac to give 30 mg of crude product, HPLC purification gave a solid product (0.0040 g, 13.8% yield). LCMS: (FA) ES$^+$ 445, ES$^-$ 443. $^1$H NMR (400 MHz, d4-methanol) δ 9.88 (σ, 1H), 8.47 (σ, 1H), 7.78-7.81 (m, 2H), 7.61 (s, 2H), 7.41-7.43 (m, 3H), 3.68 (s, 2H), 3.00-3.03 (m, 2H), 2.75 (s, 3H), 2.66-2.69 (m, 2H), 2.32 (s, 3H).

Example 132-B

Synthesis of 2-methyl-3-[4-phenyl-5-(4H-1,2,4-triazol-3-yl)-1,3-thiazol-2-yl]imidazo[1,2-a]pyridine-6-carbaldehyde

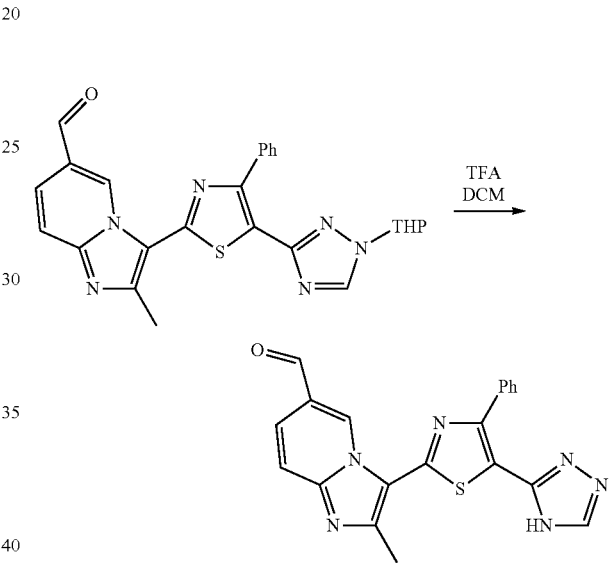

2-Methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde (0.0300 g, 0.0638 mmol) was treated with Trifluoroacetic Acid (0.30 mL, 3.9 mmol) in Methylene chloride (1.5 mL, 23 mmol) at r.t. for 16 hours. The solvent and TFA were removed by purging with N$_2$. The residue was treated with Potassium carbonate (82 mg, 0.59 mmol) in Methanol (2.0 mL, 49 mmol) at r.t. for 3 hours. The solvent was removed and the residue was suspended in 5% MeOH/DCM, filtered. The filtrate was purified by chromatograph in a 8 g AnaLogix column using MeOH/DCM (0/100 to 10/90) to afford a solid product (0.012 g, 48.7% yield). LCMS: (FA) ES$^+$ 387, ES$^-$ 385. $^1$H NMR (400 MHz, d$_6$-DMSO) δ 10.39 (σ, 1H), 10.03 (σ, 1H), 8.71 (σ, 1H), 7.99-8.01 (m, 2H), 7.82 (s, 1H), 7.43-7.50 (m, 4H), 2.75 (s, 3H).

Compound in the following table was prepared from the appropriate starting material in a method analogous to that of Example 132-B:

| | |
|---|---|
| 157-B | LCMS: (FA) ES+ 468. |

Example 138-B

Synthesis of 2-{2-methyl-3-[4-phenyl-5-(4H-1,2,4-triazol-3-yl)-1,3-thiazol-2-yl]imidazo[1,2-a]pyridin-6-yl}ethanamine

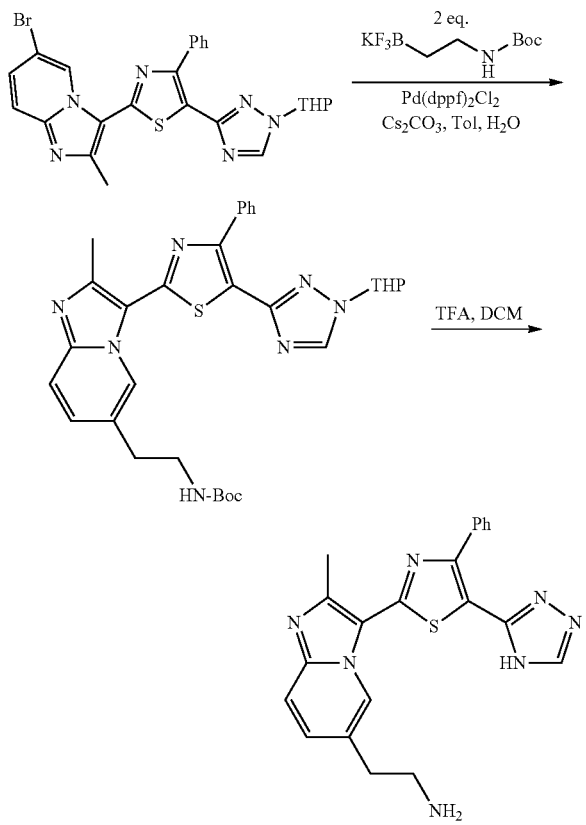

Example 128-B

Synthesis of 3-{2-methyl-3-[4-phenyl-5-(4H-1,2,4-triazol-3-yl)-1,3-thiazol-2-yl]imidazo[1,2-a]pyridin-6-yl}propan-1-amine

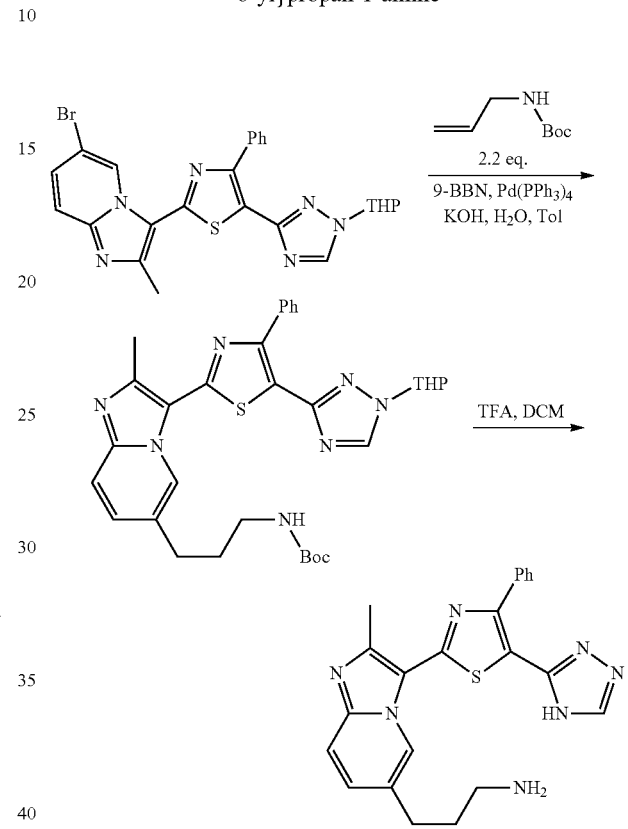

The mixture of [A] 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (0.0500 g, 0.0959 mmol), potassium [2-(tert-butoxycarbonylamino)ethyl]trifluoroborate (48.2 mg, 0.192 mmol), [1,1'-Bis(diphenylphosphino)ferrocene]dichloropalladium(II),complex with dichloromethane (1:1) (7.83 mg, 0.00959 mmol) and Cesium Carbonate (125 mg, 0.384 mmol) in Toluene (2.0 mL, 19 mmol) and Water (0.3 mL, 20 mmol) in a 4 mL vial was degassed with house vacuum and backfilled with $N_2$ back and forth for 6 times. The mixture was heated under $N_2$ atmosphere to 100° C. (heating block) for 3 hours. The mixture was partitioned between EtOAc/water (100 mL/50 mL). The organic layer was washed with water, brine, dried over $Na_2SO_4$, filtered, rotavaped to give solid crude. Chromatograph in a 24 g ISCO column using MeOH/DCM (0/100 to 5/95) gave 0.014 g of solid. This solid was treated with Trifluoroacetic Acid (1.0 mL, 13 mmol) in Methylene chloride (1.0 mL, 16 mmol) at r.t. for 3 hours. The mixture was rotavaped and the residue was dissolved in small amount of MeOH, diluted with $Et_2O$ (~10 mL) to form precipitate. After 10 min the $Et_2O$ was decanted out and the residue was dried with $N_2$ flow then in hi-vac to give a solid product (0.0098 g, 19.5% yield). LCMS: (FA) $ES^+$ 402, $ES^-$ 400. $^1$H NMR (400 MHz, $d_6$-DMSO) δ 9.65 (s), 8.67 (m), 7.93 (m, 1H), 7.71-7.78 (m, 2H), 7.43-7.51 (m, 4H), 3.11-3.17 (m, 2H), 2.94-2.97 (m, 2H), 2.72 (s, 3H).

A solution of 3-N-t-Butoxycarbonylamino-1-propene (33.2 mg, 0.211 mmol) in dry Toluene (1.0 mL, 9.4 mmol) was degassed by vacuum and backfill with $N_2$ for 4 times, cooled with ice bath. 0.5 M of 9-BBN in Tetrahydrofuran (0.460 mL, 0.230 mmol) was added and the mixture was stirred at r.t. for 20 hours. The solution was added to a mixture of 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (0.0500 g, 0.0959 mmol) and 1.0 M of Potassium hydroxide in Water (0.30 mL, 0.30 mmol) in Toluene (0.5 mL, 5 mmol). The mixture was degassed by vacuum and backfill with $N_2$ for 4 times. Tetrakis(triphenylphosphine)palladium(0) (5.54 mg, 0.00479 mmol) was added and the mixture was then heated under $N_2$ atmosphere to 80° C. for 22 hours. The mixture was cooled to Lt., diluted with EtOAc (50 mL), washed with water (2x), brine, dried over $Na_2SO_4$, filtered. The filtrate was rotavaped to give a crude product. Chromatograph in a 24 g AnaLogix column using MeOH/DCM (0/100 to 5/95) gave 0.0336 g of solid. This solid was treated with Trifluoroacetic Acid (1.0 mL, 13 mmol) in Methylene chloride (1.0 mL, 16 mmol) for 15 hours. The mixture was rotavaped. The residue was diluted with Et2O (10 mL) to give an off-white precipitate. The solvent was decanted. The precipitate was dissolved in water, washed with $Et_2O$, basified with $NaHCO_3$ solution to pH ~9, extracted with DCM for 4 times. The combined DCM solution was washed with brine, dried over Na₂SO₄, filtered, rotavaped and dried over hi-vac to give a solid product. The solid product was dissolved in small amount of DCM, acidified with 2 drops of TFA, rotavaped, diluted with Et₂O, decanted and triturated with Et₂O one more time to give a powder product as TFA salt (0.0102 g, 19% yield). LCMS: (FA) ES⁺ 416. ¹H NMR (400 MHz, d₄-Methanol) δ 9.90 (s, 1H), 8.54 (s, 1H), 7.79-7.84 (m, 4H), 7.43-7.45 (m, 3H), 3.00-3.04 (m, 2H), 2.88-2.93 (m, 2H), 2.85 (s, 3H), 2.04-2.10 (m, 2H).

Example 5-C

Synthesis of N-{4-[4-(2,4-Dichlorophenyl)-5-(1H-imidazol-2-yl)-1,3-thiazol-2-yl]pyridin-2-yl}acetamide

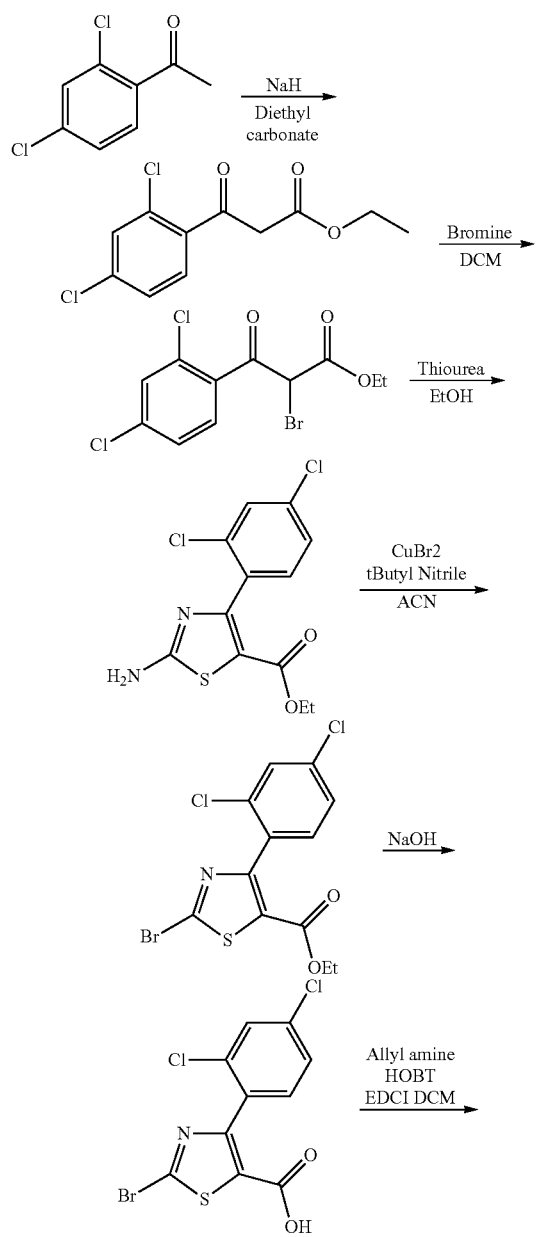

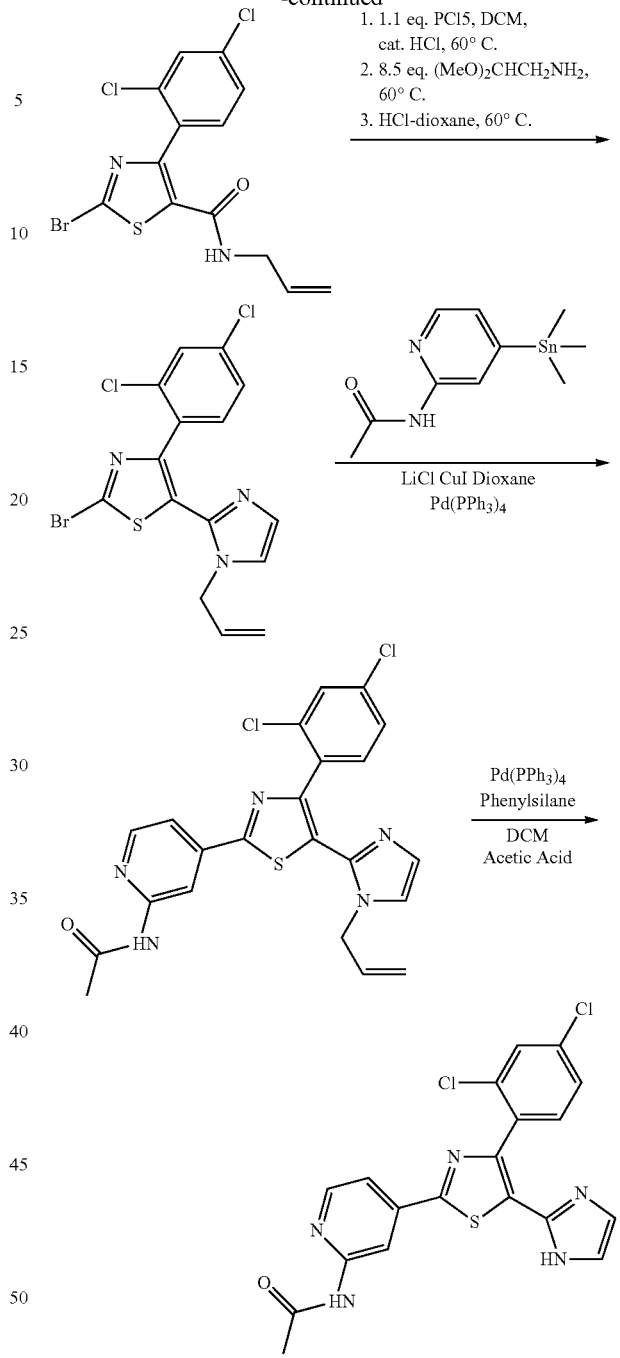

Step 1: Ethyl 3-(2,4-dichlorophenyl)-3-oxopropanoate

To a solution of 2',4'-Dichloroacetophenone (1.50 g, 7.93 mmol) in diethyl carbonate (24.0 mL, 198 mmol) at 0° C. was added slowly NaH (60% suspension in mineral oil, 0.657 g, 16.4 mmol). The mixture was then stirred at 80° C. for 90 minutes. The mixture was cooled to room temperature then poured into an ice cold solution of 2.0 mL acetic acid in 56 mL water. The layers were separated and the aqueous phase was extracted with ether 3 times. The organic extracts were washed with brine, dried over anhydrous sodium sulfate, filtered and concentrated in vacuo. Column chromatography was performed to yield the title compound (1.16 g, 56%). LCMS: (FA) ES+, 262. $^1$H NMR (400 MHz, $d_1$-chloroform) δ (2 sets of signals, keto and enol): 12.49 (s, 1H), 7.61-7.29 (m, 2 sets of 3H), 5.57 (s, 1H), 4.28 (q, J=7.28 Hz, 2H), 4.19 (q, J=7.28 Hz, 2H), 4.02 (s, 2H), 1.34 (t, J=7.03 Hz, 3H), 1.25 (t, J=7.03 Hz, 3H).

Step 2: Ethyl 2-bromo-3-(2,4-dichlorophenyl)-3-oxopropanoate

To a solution of ethyl 3-(2,4-dichlorophenyl)-3-oxopropanoate (3.95 g, 15.1 mmol) in dichloromethane (150 mL) was added a solution of bromine (0.935 mL, 18.2 mmol) in dichloromethane (20.0 mL) dropwise at 0° C. The solution was then stirred at room temperature for 1 hour. The reaction was quenched with 10% aqueous potassium carbonate solution, and then the layers were separated. The organic extracts were washed with brine, dried over anhydrous sodium sulfate, filtered and concentrated in vacuo. The crude oil was used directly in the next step (5.27 g, quantitative). LCMS: (AA) ES+, 341. $^1$H NMR (400 MHz, $d_1$-chloroform) δ (2 sets of signals, keto and enol): 12.78 (s, 1H), 7.73-7.28 (m, 2 sets of 3H), 5.73 (s, 1H), 4.37 (q, J=7.28 Hz, 2H), 4.29 (q, J=7.28 Hz, 2H), 1.41 (t, J=7.03 Hz, 3H), 1.29 (t, J=7.03 Hz, 3H).

Step 3: Ethyl 2-amino-4-(2,4-dichlorophenyl)-1,3-thiazole-5-carboxylate

To a solution of ethyl 2-bromo-3-(2,4-dichlorophenyl)-3-oxopropanoate (5.14 g, 15.1 mmol) in ethanol (90 mL) was added thiourea (1.26 g, 16.6 mmol) and the solution was stirred at reflux for 2 hours. The reaction was allowed to cool to room temperature, then the solvent was evaporated in vacuo. Column chromatography was performed to yield the title compound (4.79 g, 99%). LCMS: (AA) ES+, 319. $^1$H NMR (300 MHz, $d_1$-chloroform) δ: 8.11 (br s, 2H), 7.52-7.33 (m, 3H), 4.24-4.16 (m, 2H), 1.23-1.17 (m, 3H).

Step 4: Ethyl 2-bromo-4-(2,4-dichlorophenyl)-1,3-thiazole-5-carboxylate

To a suspension of ethyl 2-amino-4-(2,4-dichlorophenyl)-1,3-thiazole-5-carboxylate (4.89 g, 15.4 mmol) in acetonitrile (102 mL) at 0° C. was added copper (II) bromide (4.13 g, 18.5 mmol) and tert-butyl nitrite (2.80 mL, 23.6 mmol). The mixture was stirred at 0° C. 2 hours then concentrated in vacuo. Column chromatography was performed to yield the title compound (4.52 g, 77%). LCMS: (AA) ES+, 382. $^1$H NMR (400 MHz, $d_1$-chloroform) δ: 7.49-7.48 (m, 1H), 7.36-7.31 (m, 2H), 4.23 (q, J=7.03 Hz, 2H), 1.21 (t, J=7.03 Hz, 3H).

Step 5: 2-Bromo-4-(2,4-dichlorophenyl)-1,3-thiazole-5-carboxylic acid

To a solution of Ethyl 2-bromo-4-(2,4-dichlorophenyl)-1,3-thiazole-5-carboxylate (4.05 g, 10.6 mmol) in THF (50 mL) and water (20 mL) was added a solution of sodium hydroxide in water (1.0M, 31.9 mL, 31.9 mmol). The solution was stirred at room temperature for 16 hours. The reaction was quenched by the addition of aqueous HCl solution (1N, 38 mL), and then extracted five times with ethyl acetate. The organic extracts were washed with brine, dried over anhydrous sodium sulfate, filtered and concentrated in vacuo to give white solid which was dried overnight and then used directly in the next step (3.74 g, 99%). LCMS: (AA) ES+, 354. $^1$H NMR (400 MHz, $d_4$-Methanol) δ: 7.57-7.55 (m, 1H), 7.41-7.39 (m, 2H),

Step 6: N-Allyl-2-bromo-4-(2,4-dichlorophenyl)-1,3-thiazole-5-carboxamide

To a solution of 2-Bromo-4-(2,4-dichlorophenyl)-1,3-thiazole-5-carboxylic acid (3.42 g, 9.69 mmol) in dichloromethane (59 mL) was added HOBT.H$_2$O (1.48 g, 9.69 mmol) and N-(3-dimethylaminopropyl)-N'-ethylcarbodiimide hydrochloride (2.97 g, 15.5 mmol) followed by 2-propen-1-amine (2.91 mL, 38.8 mmol) and the solution was stirred at room temperature for 16 hours. The solution was then diluted with water and the layers were separated. The organic extracts were washed with brine, dried over anhydrous sodium sulfate, filtered and concentrated in vacuo. Column chromatography was performed to yield the title compound (3.11 g, 82%). LCMS: (AA) ES+, 393. $^1$H NMR (400 MHz, $d_1$-chloroform) δ: 7.57-7.56 (m, 1H), 7.46-7.39 (m, 2H), 5.75-5.65 (m, 1H), 5.43 (br s, 1H), 5.10-5.06 (m, 1H), 5.00-4.94 (m, 1H), 3.88-3.84 (m, 2H).

Step 7: 5-(1-Allyl-1H-imidazol-2-yl)-2-bromo-4-(2,4-dichlorophenyl)-1,3-thiazole To a solution of N-Allyl-2-bromo-4-(2,4-dichlorophenyl)-1,3-thiazole-5-carboxamide (8.40 g, 21.4 mmol) in dichloromethane (200 mL) was added phosphorus pentachloride (5.05 g, 24.2 mmol) and 4M hydrochloric acid in dioxane (0.833 mL, 3.26 mmol), and the reaction was heated to 60° C. for 90 minutes under an atmosphere on nitrogen. The reaction was allowed to cool to room temperature and then aminoacetaldehyde dimethyl acetal (25.7 mL, 236 mmol) was added slowly through the condenser. The mixture was heated to 60° C. for 2 hours under an atmosphere on nitrogen. The mixture was cooled to room temperature, and water was added (200 mL). The layers were separated and the organic phase was washed with water again (2×200 mL). The organic extracts were washed with brine, dried over anhydrous sodium sulfate, filtered and washed with dichloromethane (200 mL). To this dichloromethane solution of the intermediate was added 4M hydrochloric acid in dioxane (17 mL, 65 mmol) and the solution was stirred at 60° C. for 16 hours. The solution was decanted (leaving behind an oily black residue on the flask) and then evaporated and diluted with ethyl acetate and saturated sodium bicarbonate solution. The layers were separated and the aqueous phase was extracted 3 more times with ethyl acetate. The organic extracts were washed with brine, dried over anhydrous sodium sulfate, filtered and concentrated in vacuo. Column chromatography was performed to yield the title compound (5.93 g, 67%). LCMS: (FA) ES+, 416. $^1$H NMR (400 MHz, $d_1$-chloroform) δ: 7.45-7.42 (m, 1H), 7.25-7.19 (m, 2H), 7.16-7.14 (m, 1H), 6.93-6.90 (m, 1H), 5.55-5.44 (m, 1H), 5.13-5.08 (m, 1H), 5.95-4.88 (m, 1H), 4.19-4.15 (m, 2H).

Step 8: N-{4-[5-(1-Allyl-1H-imidazol-2-yl)-4-(2,4-dichlorophenyl)-1,3-thiazol-2-yl]pyridin-2-yl}acetamide To a solution of 5-(1-Allyl-1H-imidazol-2-yl)-2-bromo-4-(2,4-dichlorophenyl)-1,3-thiazole (0.133 g, 0.320 mmol) in 1,4-dioxane (8 mL) was added N-[4-(trimethylstannyl)pyridine-2-yl]acetamide (0.115 g, 0.384 mmol), lithium chloride (0.0407 g, 0.961 mmol), copper (I) iodide (0.0183 g, 0.0961 mmol) and tetrakis (triphenylphosphine)palladium(0) (0.0185 g, 0.0160 mmol). The flask was purged with argon and then the mixture was heated at 115° C. for 3 hours. The reaction was allowed to cool to room temperature, and then the solvent was evaporated in vacuo. Column chromatography was performed to yield the title compound (0.0650 g, 43%). LCMS: (FA) ES+, 472. ¹H NMR (400 MHz, d₄-Methanol) δ: 8.75-8.72 (m, 1H), 8.45-8.41 (m, 1H), 7.71-7.68 (m, 1H), 7.58-7.55 (m, 1H), 7.43-7.35 (m, 2H), 7.20 (d, 1H, J=1.51 Hz), 7.14 (d, J=1.51 Hz, 1H), 5.69-5.58 (m, 1H), 5.13-5.08 (m, 1H), 4.94-4.88 (m, 1H), 4.38-4.33 (m, 2H), 2.20 (s, 3H).

Step 9: N-{4-[4-(2,4-Dichlorophenyl)-5-(1H-imidazol-2-yl)-1,3-thiazol-2-yl]pyridin-2-yl}acetamide (5-C)

To a solution of N-{4-[5-(1-Allyl-1H-imidazol-2-yl)-4-(2,4-dichlorophenyl)-1,3-thiazol-2-yl]pyridin-2-yl}acetamide (0.0650 g, 0.138 mmol) in dichloromethane (1.0 mL) and acetic acid (0.34 mL) was added tetrakis(triphenylphosphine)palladium(0) (0.00798 g, 0.00691 mmol) followed by phenylsilane (0.0870 mL, 0.706 mmol). The solution was stirred at 40° C. for 90 minutes. The solution was cooled to room temperature then concentrated in vacuo and diluted with ethyl acetate and saturated sodium bicarbonate solution. The layers were separated and the aqueous phase was extracted 3 more times with ethyl acetate. The organic extracts were washed with brine, dried over anhydrous sodium sulfate, filtered and concentrated in vacuo. Column chromatography was performed to yield the title compound (0.0380 g, 64%). LCMS: (FA) ES+, 431. ¹H NMR (400 MHz, d₄-Methanol) δ: 8.75-8.70 (m, 1H), 8.44-8.39 (m, 1H), 7.70-7.44 (m, 4H), 7.13-7.07 (m, 2H), 2.20 (s, 3H).

Compounds in the following table were prepared from the appropriate starting materials in a method analogous to that of Example 5-C:

| | |
|---|---|
| 11-C | LCMS: (FA) ES+ 444, 446. |
| 15-C | LCMS: (FA) ES+ 446, 448. |
| 18-C | LCMS: (AA) ES+ 460, 462. |
| 31-C | LCMS: (FA) ES+ 456, 458. |
| 32-C | LCMS: (FA) ES+ 388, 390. |
| 30-C | LCMS: (FA) ES+ 410, 412. |
| 36-C | LCMS: (FA) ES+ 376. |
| 43-C | LCMS: (FA) ES+ 431, 433. |
| 66-C | LCMS: (FA) ES+ 444, 446. |
| 76-C | LCMS: (FA) ES+ 389, 391. |

Example 67-C

Synthesis of N-{4-[5-(1H-imidazol-2-yl)-4-phenyl-1,3-thiazol-2-yl]pyridin-2-yl}acetamide

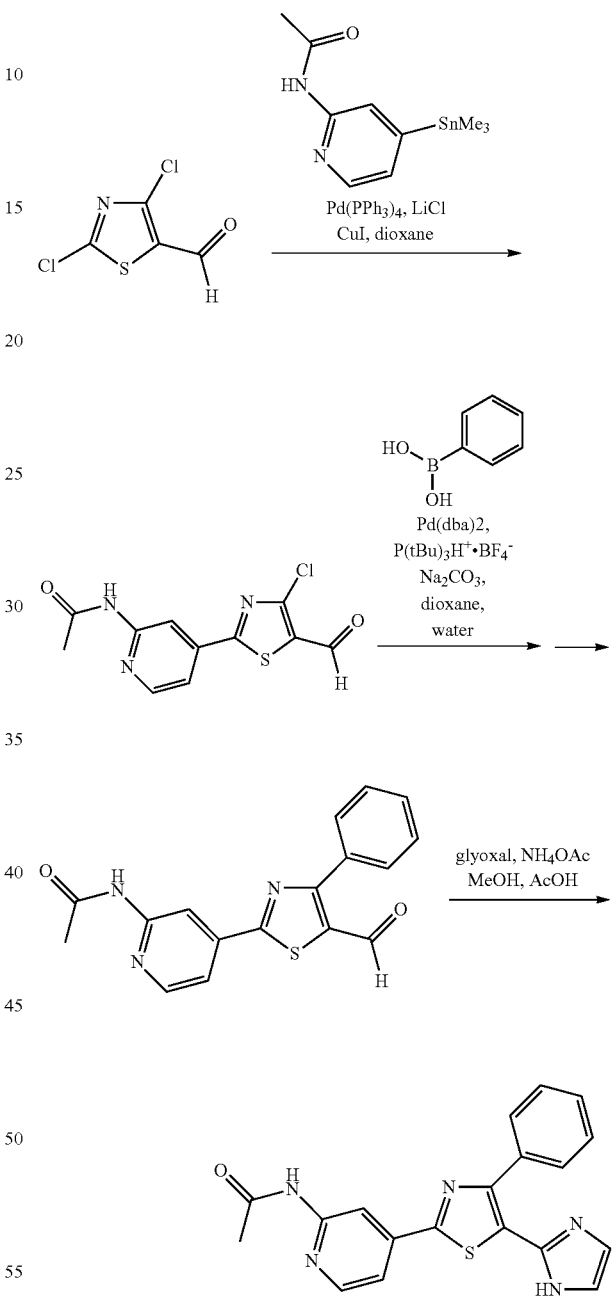

Step 1: Synthesis of N-[4-(4-chloro-5-formyl-1,3-thiazol-2-yl)pyridin-2-yl]acetamide 2,4-Dichloro-5-thiazolecarboxaldehyde (2.50 g, 0.0137 mol), N-[4-(trimethylstannyl)pyridin-2-yl]acetamide (4.93 g, 0.0165 mot), lithium chloride (1.75 g, 0.0412 mol), copper (I) iodide (0.785 g, 0.00412 mol), tetrakis(triphenylphosphine)palladium(0) (0.794 g, 0.000687 mol) were combined in dioxane (200 mL) under an atmosphere of Argon. The solution was heated at 110° C. for 2 hr. TLC indicated complete conversion. Mixture was cooled to rt and MeOH (100 mL) was added until almost all solids dissolved. Suspension was filtered through celite and the filtrate was evaporated. Water (100 mL) was added and the solids were collected by filtration, washed with water and hexane and dried in vacuum at 40° C. to give 1.76 g of amorphous solid (46%). LCMS: (FA) ES+ 282, 284. $^1$H NMR (400 MHz, $d_6$-DMSO) δ 10.83 (s, 1H), 10.02 (s, 1H), 8.70 (s, 1H), 8.51 (dd, J=5.20, 0.67 Hz, 1H), 7.68 (dd, J=5.20, 1.67 Hz, 1H), 2.13 (s, 3H).

Step 2: Synthesis of N-[4-(5-formyl-4-phenyl-1,3-thiazol-2-yl)pyridin-2-yl]acetamide Tris(dibenzylideneacetone)dipalladium(0) (0.0162 g, 0.0177 mmol) and tri-t-butylphosphonium tetrafluoroborate (0.0103 g, 0.0355 mmol) were weighed into a round bottom flask and dissolved in DME (3 mL). The mixture was sonicated for 15 min under atmosphere of Argon. After addition of water (1 mL), sodium carbonate (0.226 g, 2.13 mmol) was added to the dark purple solution followed by phenylboronic acid (0.173 g, 1.42 mmol) and N-[4-(4-chloro-5-formyl-1,3-thiazol-2-yl)pyridin-2-yl]acetamide (0.200 g, 0.710 mmol). The resulting mixture was stirred for 10 h at 80° C., cooled to room temperature, diluted with water and extracted with DCM (3×5 mL). The organics were washed with brine, dried over anhydrous sodium sulfate, filtered and concentrated. The result mixture was purified by ISCO column with 0-5% MeOH in DCM in 10 min. Fractions containing product were combined and solvent was removed under reduced pressure to give crude material (0.099 g, 43%), which was used in the next step without further purification. LCMS: (FA) ES+ 324.

Step 3: Synthesis of N-{4-[5-(1H-imidazol-2-yl)-4-phenyl-1,3-thiazol-2-yl]pyridin-2-yl}acetamide (67-C)

N-[4-(5-formyl-4-phenyl-1,3-thiazol-2-yl)pyridin-2-yl]acetamide (0.0900 g, 0.278 mmol was weighed into a round bottom flask and dissolved in methanol (5 mL). Acetic acid (0.158 mL, 2.78 mmol) and ammonium acetate (0.257 g, 3.34 mmol) were added followed by glyoxal trimer dihydrate (351 mg, 1.67 mmol). The mixture was stirred at room temperature overnight. At that time LCMS indicated formation of product. The mixture was evaporated to dryness and the residue was purified using preparative HPLC to give the 0.024 mg of the product (22%). LCMS: (FA) ES+ 362, $^1$H NMR (400 MHz, $d_6$-DMSO) δ 10.46 (s, 1H), 8.37 (s, 1H), 8.14 (d, J=5.16 Hz, 1H), 7.45 (s, 2H), 7.34 (dd, J=5.18, 1.60 Hz, 1H), 7.12-7.07 (m, 5H), 1.76 (s, 3H)

Compounds in the following table were prepared from the appropriate starting materials in a method analogous to that of Example 67-C:

| | |
|---|---|
| 7-C | LCMS: (FA) ES+ 396, 398. |
| 34-C | LCMS: (FA) ES+ 396, 398. |
| 42-C | LCMS: (FA) ES+ 458, 460. |
| 55-C | LCMS: (FA) ES+ 396, 398. |

Example 74-C

Synthesis of N-{4-[5-(1H-imidazol-2-yl)-4-phenyl-1,3-thiazol-2-yl]pyridin-2-yl}acetamide

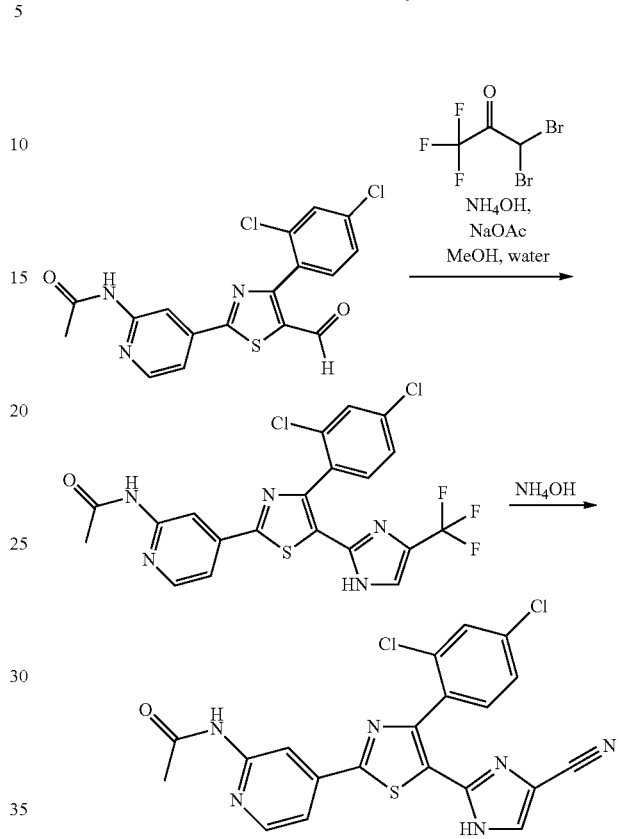

Step 1: Synthesis N-(4-{4-(2,4-dichlorophenyl)-5-[4-(trifluoromethyl)-1H-imidazol-2-yl]-1,3-thiazol-2-yl}pyridin-2-yl)acetamide To a solution of Sodium acetate (104.6 mg, 1.275 mmol) in water (400 uL, 20 mmol) was added 1,1-dibromo-3,3,3-trifluoroacetone (89.73 uL, 0.7648 mmol) and the mixture was stirred at 100° C. for 30 min. N-{4-[4-(2,4-dichlorophenyl)-5-formyl-1,3-thiazol-2-yl]pyridin-2-yl}acetamide (100 mg, 0.2 mmol; prepared as described in Example 2-C) in methanol (5 mL) was added to the above mixture followed by ammonium hydroxide (0.5956 mL, 15.30 mmol). The mixture was stirred at rt for 48 hours, at which time LCMS indicated formation of the product. Mixture was extracted with ethyl acetate (3×10 mL), washed with brine, dried with MgSO4, filtered and evaporated. The crude mixture was purified by ISCO chromatography, eluted with EtOAc in hexanes, 0-45% to give pure product 0.020 g of amorphous solid (20%), LCMS: (FA) ES+ 498, 500. $^1$H NMR (400 MHz, $d_1$-Methanol) δ 8.75 (s, 1H), 8.43 (d, J=5.24 Hz, 1H), 7.69 (dd, J=5.22, 1.57 Hz, 1H), 7.63-7.55 (m, 3H), 7.49 (dd, J=8.36, 2.01 Hz, 1H), 2.22 (s, 3H).

Step 2: Synthesis of N-{4-[5-(4-cyano-1H-imidazol-2-yl)-4-(2,4-dichlorophenyl)-1,3-thiazol-2-yl]pyridin-2-yl}acetamide (74-C)

N-(4-{4-(2,4-dichlorophenyl)-5-[4-(trifluoromethyl)-1H-imidazol-2-yl]-1,3-thiazol-2-yl}pyridin-2-yl)acetamide (20 mg, 0.04 mmol) was taken up in 1 M of Ammonium hydroxide in water (2 mL, 3 mmol) and the mixture was stirred at 60° C. for 6 h. At that time, LCMS indicated complete conversion. Reaction mixture was evaporated under reduced pressure and was purified using preparative HPLC to give 0.004 g of the title compound (20%). LCMS: (FA) ES+ 455, 457. $^1$H NMR (400 MHz, d$_6$-DMSO) δ 8.70 (s, 1H), 8.34 (dd, J=5.26, 0.71 Hz, 1H), 7.65 (dd, J=5.26, 1.60 Hz, 1H), 7.55-7.46 (m, 3H), 7.39 (dd, J=8.28, 2.06 Hz, 1H), 2.24 (s, 3H).

Example 49-C

Synthesis of N-{4-[4-(2,4-dichlorophenyl)-5-(4-methyl-1H-imidazol-2-yl)-1,3-thiazol-2-yl]pyridin-2-yl}acetamide

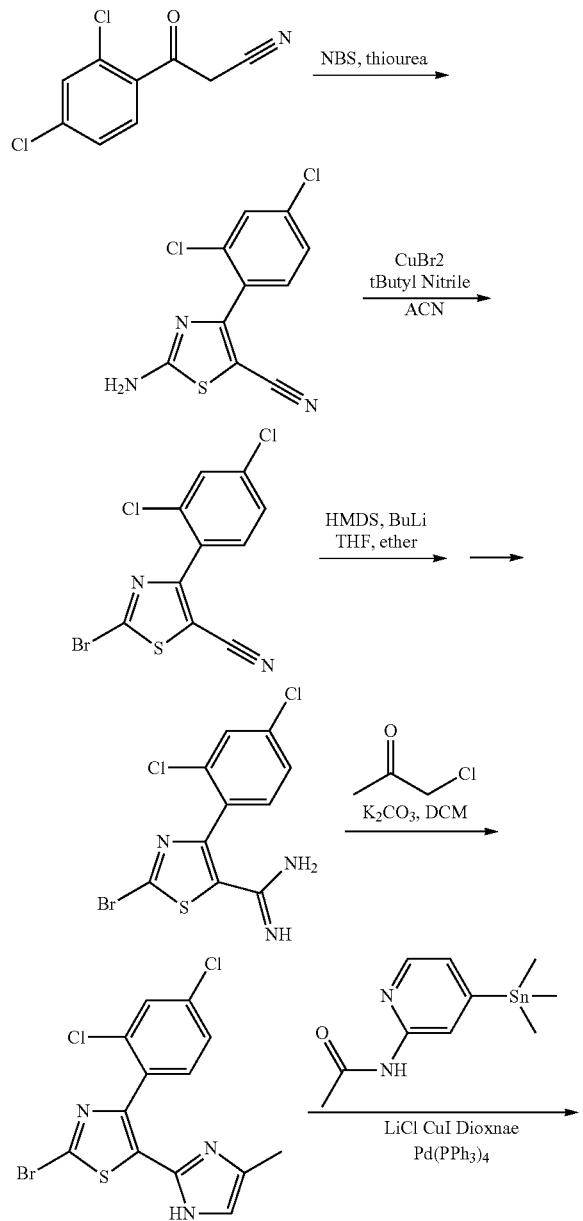

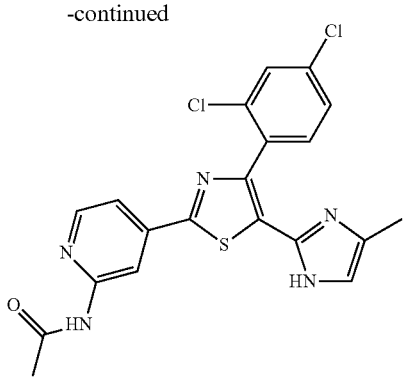

Step 1: 2-amino-4-(2,4-dichlorophenyl)-1,3-thiazole-5-carbonitrile beta-Cyclodextrin (4.29 g, 3.78 mmol) was dissolved in water (75 mL) at 50° C. and a solution of 3-(2,4-dichlorophenyl)-3-oxopropanenitrile (810 mg, 3.8 mmol) in Acetone (3.80 mL) was added dropwise, followed by NBS (0.808 g, 4.54 mmol) and thiourea (0.346 g, 4.54 mmol). Reaction mixture was stirred at 50° C. 1 hr. LCMS indicated complete conversion. Reaction mixture was cooled to rt, extracted with ethyl acetate (3×50 mL), dried with MgSO$_4$, filtered and concentrated under reduced pressure. The residue was purified by ISCO with 5-30% ethyl acetate in hexanes to give 0.43 g of the title compound (42%). LCMS; (FA) ES$^+$, 270, 272, $^1$H NMR (400 MHz, d$_1$-chloroform) δ 7.49 (d, J=1.84 Hz, 1H), 7.41 (d, J=8.30 Hz, 1H), 7.31 (dd, J=8.16, 1.74 Hz, 1H).

Step 2: 2-bromo-4-(2,4-dichlorophenyl)-1,3-thiazole-5-carbonitrile

To a suspension of 2-amino-4-(2,4-dichlorophenyl)-1,3-thiazole-5-carbonitrile (423 mg, 1.57 mmol) in acetonitrile (10 mL) at 0° C. was added copper (II) bromide (420 mg, 1.9 mmol) and tert-butyl nitrite (0.285 mL, 2.40 mmol). The mixture was stirred at 0° C. for 2 hours, then concentrated in vacuo. Column chromatography was performed to yield the title compound (0.400 g, 80%). LCMS: (FA) ES$^+$, 333, 335, 337. $^1$H NMR (400 MHz, d$_1$-chloroform) δ: 7.57 (t, J=2.07, 2.07 Hz, 1H), 7.49 (d, J=8.32 Hz, 1H), 7.39 (dd, J=8.33, 2.02 Hz, 1H)

Step 3: 2-bromo-4-(2,4-dichlorophenyl)-1,3-thiazole-5-carboximidamide 2.5 M n-Butyllithium in hexanes (1.20 mL, 2.99 mmol) was added dropwise to a solution of hexamethyldisilazane (0.61 mL, 2.9 mmol) in diethylether (5 mL) at 0° C. The mixture was stirred for 30 mins at 0° C. and 2-bromo-4-(2,4-dichlorophenyl)-1,3-thiazole-5-carbonitrile (400 mg, 1.0 mmol) in THF (50 mL) was added. After stirring at rt for 2 hours LCMS indicated complete conversion. The reaction mixture was poured to a cold 2N HCl (10 ml) and was extracted with diethylether (2×20 mL). The aqueous phase was adjusted to pH~10 with NH$_4$OH and was extracted with DCM (3×30 mL). Combined DCM extracts were dried over Na$_2$SO$_4$, filtered and evaporated under reduced pressure to afford the title compound which was used directly in the next step (0.360 g, 80%). LCMS: (FA) ES$^+$, 350, 352, 354.

Step 4: 2-bromo-4-(2,4-dichlorophenyl)-5-(4-methyl-1H-imidazol-2-yl)-1,3-thiazol To a solution of 2-bromo-4-(2,4-dichlorophenyl)-1,3-thiazole-5-carboximidamide (70 mg, 0.2 mmol) in DCM (4 mL) was added potassium carbonate (82.7 mg, 0.598 mmol) followed by solution of chloroacetone (50 uL, 0.6 mmol) in DCM (0.4 mL). The mixture was heated to reflux for 3 hours, at which time LCMS indicated ~50% conversion. Additional chloroacetone (11 ul) and $K_2CO_3$ (19 mg) were added and heating was continued for additional 4 hours. LCMS showed complete conversion. Solvent was removed under reduced pressure and the residue was purified using ISCO chromatography, 20%-60% ethyl acetate in hexane to afford the title compound (56 mg, 70%). LCMS: (FA) ES+, 388, 390, 392. $^1$H NMR (400 MHz, $d_1$-chloroform) δ: 7.60 (dd, J=5.37, 1.71 Hz, 1H), 7.45-7.40 (m, 3H), 2.23 (s, 3H).

Step 5: N-{4-[4-(2,4-dichlorophenyl)-5-(4-methyl-1H-imidazol-2-yl)-1,3-thiazol-2-yl]pyridin-2-yl}acetamide (49-C)

2-bromo-4-(2,4-dichlorophenyl)-5-(4-methyl-1H-imidazol-2-yl)-1,3-thiazole (55 mg, 0.141 mmol), N-[4-(trimethylstannyl)pyridin-2-yl]acetamide (64 mg, 0.214 mmol) were dissolved in 1,4-dioxane (3.4 mL). Lithium chloride (18.1 mg, 0.427 mmol), copper(I) iodide (8.14 mg, 0.0427 mmol) and tetrakis(triphenylphosphine)palladium(0) (8.23 mg, 0.00712 mmol) were added under atmosphere of argon. The reaction mixture was heated at 90° C. for 7 hours. LCMS indicated complete conversion. Solvent was evaporated and the residue was purified using preparative HPLC to afford 15 mg of the title compound (24%). LCMS; (AA) ES+ 444, 446. $^1$H NMR (400 MHz, $d_1$-chloroform) δ: 8.79-8.70 (m, 1H), 8.43 (s, 1H), 8.35-8.28 (m, 1H), 7.62-7.59 (m, 2H), 7.50 (d, J=8.25 Hz, 1H), 7.43 (dd, J=8.23, 2.01 Hz, 1H), 2.24 (s, 3H), 2.20 (s, 3H).

Example 6-C

Synthesis of N-(4-(4-(1-methyl-3-(trifluoromethyl)-1H-pyrazol-4-yl)-5-(1-((2-(trimethylsilyl)ethoxy)methyl)-1H-imidazol-2-yl)thiazol-2-yl)pyridin-2-yl)acetamide

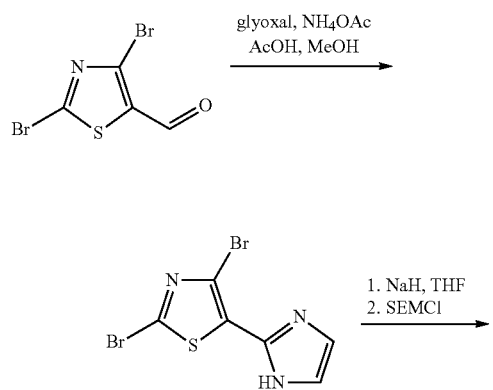

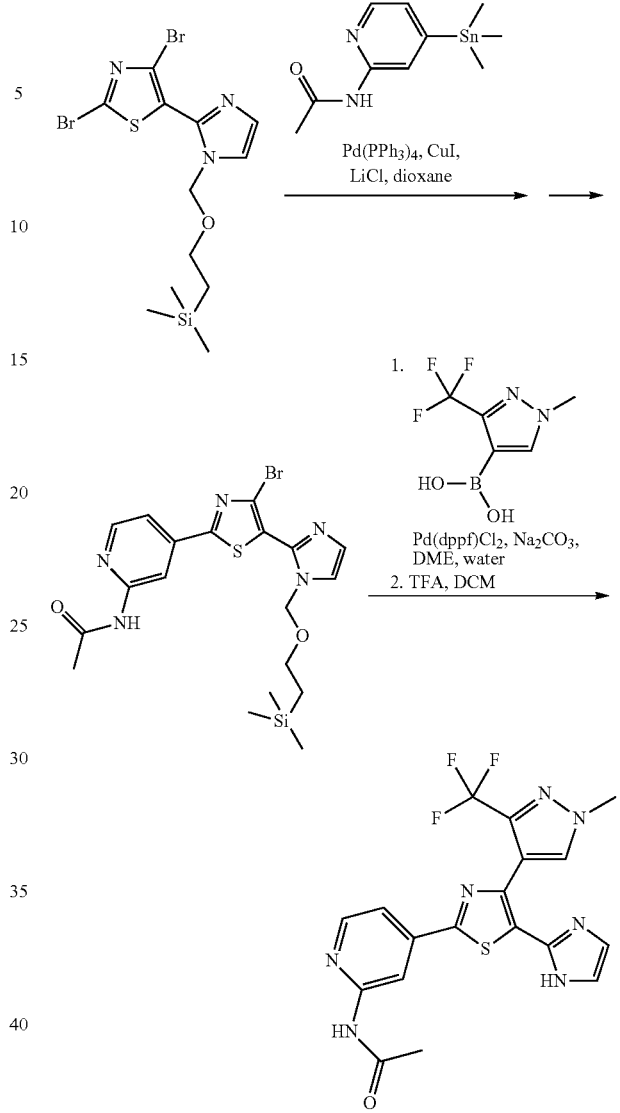

Step 1: 2,4-dibromo-5-(1H-imidazol-2-yl)thiazole

A mixture of 2,4-Dibromo-thiazole-5-carbaldehyde (14.8 g, 54.6 mmol), glyoxal trimer dihydrate (22.96 g, 109.2 mmol) and ammonium acetate (25.26 g, 327.8 mmol) in MeOH (450 mL) and AcOH (31.06 mL) was stirred at RT overnight. The reaction mixture was concentrated in vacuo to a thick liquid mixture. Remaining acetic acid was removed by azeotroping with toluene (3×100 mL) to afford a dark brown solid. The mixture was purified by ISCO chromatography, eluted with EtOAc in hexanes, 0-25% to give pure product (9.12 g, 54%). LCMS: (AA) ES+, 310, 312. $^1$H NMR (400 MHz, $d_6$-DMSO) δ: 12.50 (br, 1H) 7.21 (br, 2H).

Step 2: 2,4-dibromo-5-(1-((2-(trimethylsilyl)ethoxy)methyl)-1H-imidazol-2-yl)thiazole To a mixture of sodium hydride (2.89 g, 72.2 mmol) in THF (431 mL) was added 2,4-dibromo-5-(1H-imidazol-2-yl)thiazole (18.81 g, 60.88 mmol) in THF (60 mL) at 0° C. After stirring 30 min, [β-(Trimethylsilyl)ethoxy]methyl chloride (11.85 mL, 66.96 mmol) in THF (24 mL) was slowly added at 0° C. After 30 min at this temperature, the reaction was quenched by addition of MeOH (20 mL). The solvent was evaporated and the residue was purified by ISCO chromatography, eluted with EtOAc in hexanes, 0-25%. Product was obtained as colorless oil (21.84 g, 81.6%). LCMS: (AA) ES+, 440, 442. $^1$H NMR (300 MHz, $d_1$-chloroform) δ: 7.24 (dd, 2H) 5.27 (s, 2H) 3.39 (t, 2H) 0.85 (t, 2H) −0.03 (s, 9H).

Step 3: N-(4-(4-bromo-5-(1-((2-(trimethylsilyl)ethoxy)methyl)-1H-imidazol-2-yl)thiazol-2-yl)pyridin-2-yl)acetamide A mixture of 2,4-dibromo-5-(1-((2-(trimethylsilyl)ethoxy)methyl)-1H-imidazol-2-yl)thiazole (13.62 g, 31.01 mmol), N-[4-(trimethylstannyl)pyridin-2-yl]acetamide (11.1 g, 37.2 mmol), tetrakis(triphenylphosphine)palladium(0) (1.792 g, 1.550 mmol), copper(I) iodide (1.772 g, 9.302 mmol) and lithium chloride (3.944 g, 93.02 mmol) in 1,4-dioxane (569 mL) was degassed with argon. The mixture was sonicated for 20 min and then heated at 120° C. for 5 hrs. Solvent was evaporated and the crude reaction mixture was purified by ISCO chromatography, eluted with MeOH in DCM, 0-3%. Product was obtained as an orange solid (10.13 g, 66.0%). LCMS: (AA) ES+, 494, 496. $^1$H NMR (300 MHz, $d_1$-chloroform) δ: 8.65 (s, 1H) 8.44 (br, 1H) 8.34 (d, 1H) 7.60 (dd, 1H) 7.30 (d, 2H) 5.30 (s, 2H) 3.40 (t, 2H) 2.25 (s, 3H) 0.86 (t, 2H) −0.05 (s, 9H).

Step 4 and Step 5: N-(4-(4-(1-methyl-3-(trifluoromethyl)-1H-pyrazol-4-yl)-5-(1-((2-(trimethylsilyl)ethoxy)methyl)-1H-imidazol-2-yl)thiazol-2-yl)pyridin-2-yl)acetamide (6-C)

N-(4-(4-bromo-5-(1-((2-(trimethylsilyl)ethoxy)methyl)-1H-imidazol-2-yl)thiazol-2-yl)pyridin-2-yl)acetamide (70.0 mg, 0.120 mmol), 1-methyl-3-trifluoromethyl-1H-pyrazole-4-boronic acid pinacol ester (0.0708 g, 0.241 mmol), [1,1'-bis(diphenylphosphino)ferrocene]palladium(II)dichloride (4.95 mg, 0.00602 mmol) and sodium carbonate (38.3 mg, 0.361 mmol) in DME (1.2 mL) was degassed with argon. Water (0.5 mL) was added to the above mixture. The mixture was irradiated in microwave at 125° C. for 30 min. At that time, LCMS showed the desired product. Reaction mixture was filtered, the filtrate was evaporated to dryness, dissolved in DCM (1.20 mL) and treated with TFA (1.20 mL). This mixture was stirred at room temperature overnight. At that time, LCMS indicated formation of the desired product. The mixture was evaporated to dryness in vacuo, the residue was taken up by DMSO and purified using preparative HPLC to give product as yellow powder (16.3 mg, 31.2%). LCMS: (AA) ES+, 434, 435. $^1$H NMR (400 MHz, $d_4$-methanol) δ: 8.67 (br, 1H) 8.38 (dd, 1H) 7.87 (s, 1H) 7.63 (dd, 1H) 7.14 (d, 2H) 3.98 (s, 3H) 2.19 (s 3H).

Compounds in the following table were prepared from the appropriate starting materials in a method analogous to that of Example 6-C:

| | |
|---|---|
| 2-C | LCMS: (FA) ES+ 447 |
| 3-C | LCMS: (FA) ES+ 430 |
| 8-C | LCMS: (FA) ES+ 445 |
| 9-C | LCMS: (FA) ES+ 407 |
| 10-C | LCMS: (FA) ES+ 414 |
| 13-C | LCMS: (FA) ES+ 425, 427. |
| 14-C | LCMS: (FA) ES+ 429 |
| 16-C | LCMS: (FA) ES+ 423 |
| 17-C | LCMS: (FA) ES+ 430 |
| 19-C | LCMS: (FA) ES+ 475. |
| 21-C | LCMS: (FA) ES+ 393 |
| 22-C | LCMS: (FA) ES+ 431 |
| 23-C | LCMS: (FA) ES+ 426 |
| 24-C | LCMS: (FA) ES+ 378. |
| 25-C | LCMS: (FA) ES+ 407 |
| 26-C | LCMS: (FA) ES+ 430 |
| 27-C | LCMS: (FA) ES+ 363 |
| 28-C | LCMS: (FA) ES+ 366 |
| 29-C | LCMS: (FA) ES+ 393 |
| 33-C | LCMS: (FA) ES+ 379 |
| 35-C | LCMS: (FA) ES+ 393 |
| 38-C | LCMS: (FA) ES+ 376. |
| 39-C | LCMS: (FA) ES+ 431 |
| 40-C | LCMS: (FA) ES+ 426, 428. |
| 41-C | LCMS: (FA) ES+ 376 |
| 45-C | LCMS: (FA) ES+ 421 |
| 46-C | LCMS: (FA) ES+ 421 |
| 47-C | LCMS: (FA) ES+ 411 |
| 50-C | LCMS: (FA) ES+ 419 |
| 51-C | LCMS: (FA) ES+ 368 |
| 52-C | LCMS: (FA) ES+ 405 |
| 54-C | LCMS: (FA) ES+ 426 |
| 57-C | LCMS: (FA) ES+ 376 |
| 58-C | LCMS: (FA) ES+ 364, 366. |
| 60-C | LCMS: (FA) ES+ 455 |
| 61-C | LCMS: (FA) ES+ 420 |
| 62-C | LCMS: (FA) ES+ 394 |
| 63-C | LCMS: (FA) ES+ 398 |
| 68-C | LCMS: (FA) ES+ 406 |
| 69-C | LCMS: (FA) ES+ 478 |
| 72-C | LCMS: (FA) ES+ 420 |
| 73-C | LCMS: (FA) ES+ 378 |
| 75-C | LCMS: (FA) ES+ 419 |

Example 56-C

Synthesis of N-{4-[4-(2,6-dimethylphenyl)-5-(4H-1,2,4-triazol-3-yl)-1,3-thiazol-2-yl]pyridin-2-yl}acetamide

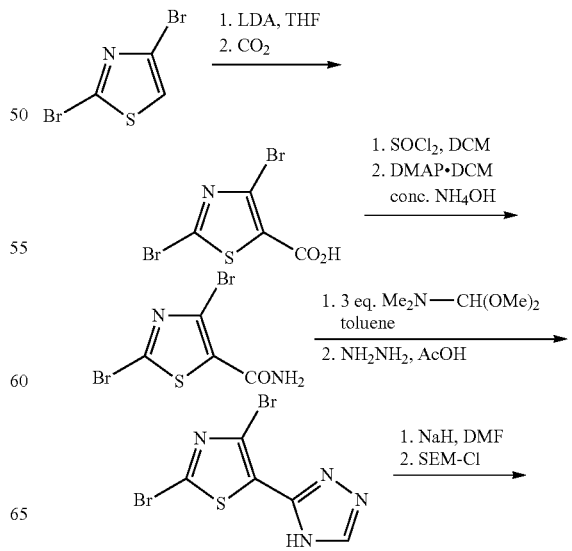

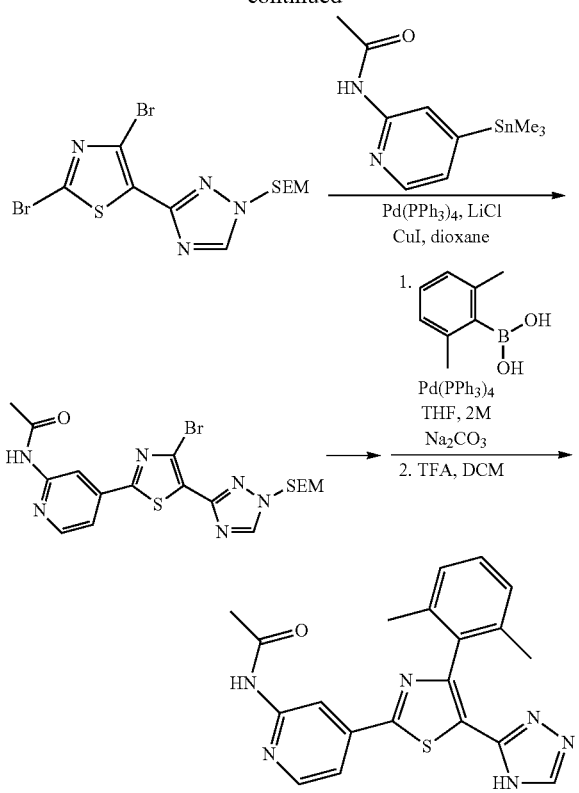

Step 1: Synthesis of 2,4-dibromo-1,3-thiazole-5-carboxylic acid

To a 500 mL 3-neck round bottom flask equipped with dropping funnel and internal temp monitor was added THF (200 mL) and N,N-Diisopropylamine (14.7 mL, 105 mmol) under atmosphere of Argon. After cooling at −75° C., 2.50 M of n-Butyllithium in Hexane (41.1 mL, 103 mmol) was added dropwise into the solution over 30 min. The internal temperature was kept below −70° C. and the resulting solution was stirred for 15 min at −75° C. To this LDA solution was added a solution of 2,4-dibromothiazole (25.0 g, 99.8 mmol) in THF (60 mL) via dropping funnel over 40 min and the internal temperature was kept below −70° C., then this solution was stirred for 20 min at −75° C. To this solution was added crushed dry ice at −75° C. and the mixture was stirred for 15 min. At that time, 10 mL water was added dropwise. Cooling bath was removed and the mixture was brought to r.t. over 1 hour with a water bath. The solvent was evaporated under reduced pressure to give a solid residue. The residue was suspended in 100 mL water, basified with 1.00 M of Sodium hydroxide in water (110 mL) and extracted with 100 mL ether. The ether layer was washed with 0.5 N NaOH (2×30 mL). The combined aqueous solution was acidified with conc. HCl with ice to pH~2, extracted with ether (5×100 mL, adjusting pH~2 each time after separation). The combined ether solution was washed with brine, dried over $Na_2SO_4$, filtered, evaporated to give a solid product (28.04 g, 98%). LCMS: (FA) ES+ 288, ES− 286.

Step 2: Synthesis of 2,4-dibromo-1,3-thiazole-5-carboxamide

A suspension of 2,4-dibromo-1,3-thiazole-5-carboxylic acid (16.33 g, 56.91 mmol) in dry DCM (250 mL) and DMF (0.400 mL) was cooled with ice bath. Thionyl chloride (40.0 mL, 548 mmol) was added dropwise. The cooling bath was removed and the suspension was stirred at r.t. for 2.5 hours, Toluene (80 mL, 800 mmol) was added and the suspension was heated to reflux for 1 hour. The mixture was cooled to room temperature, solvent was removed and the residue was azeotroped with toluene (2×100 mL) to give a crude intermediate. This material was suspended in DCM (230 mL) and cooled with ice bath. N,N-dimethylaminopyridine (0.70 g, 5.7 mmol) was added, followed by slow addition of 8.5 M of Ammonium hydroxide in Water (100.0 mL, 850.0 mmol). The mixture was stirred at room temperature overnight. The mixture was filtered, aqueous layer was separated and extracted with DCM (3×100 mL). The combined DCM layers were washed with water, brine, dried over $Na_2SO_4$, filtered, and evaporated to give a solid product (11.2 g, 69%). LCMS: (FA) ES+ 287 and ES− 285.

Step 3: Synthesis of 3-(2,4-dibromo-1,3-thiazol-5-yl)-4H-1,2,4-triazole

To the suspension of 2,4-dibromo-1,3-thiazole-5-carboxamide (0.110 g, 0.385 mmol) in dry Toluene (8.0 mL, 75 mmol) was added DMFDMA (0.204 mL, 1.54 mmol). The mixture was stirred at 60° C. under N2 atmosphere for 3 hours. The solvent was removed and to the intermediate was added acetic acid (2.0 mL, 35 mmol), followed by hydrazine (0.0604 mL, 1.92 mmol). The mixture was heated to 120° C. for 30 min. The mixture was cooled to room temperature, solvent was removed and the residual acetic acid was azeotroped with toluene (2×5 mL) to give an oily material, which was basified with saturated aqueous NaHCO3 to pH~8 and extracted with EtOAc (3×30 mL). The EtOAc layer was washed with water, brine, dried over $Na_2SO_4$, filtered, and evaporated to give a crude product. Chromatography on a silica column using EtOAc/hexane (0/100 to 50/50) gave a solid product (0.073 g, 61%). LCMS: (FA) ES+ 311 and ES− 309. $^1$H NMR (400 MHz, $d_4$-Methanol) δ 8.53 (s, 1H).

Step 4: Synthesis of 3-(2,4-dibromo-1,3-thiazol-5-yl)-1-{[2-(trimethylsilyl)ethoxy]methyl}-1H-1,2,4-triazole To the solution of 3-(2,4-dibromo-1,3-thiazol-5-yl)-4H-1,2,4-triazole (1.16 g, 3.74 mmol) in dry DMF (5.0 mL) at 0° C. was added portionwise sodium hydride (60%, 0.180 g, 4.49 mmol). The ice bath was removed, mixture was stirred for 5 min. at ambient temperature and cooled with ice bath. SEM chloride (0.795 mL, 4.49 mmol) in dry DMF (2.0 mL) was added dropwise and the mixture was stirred at room temperature for 2 hours. The mixture was quenched with ice-water, extracted with EtOAc, washed with brine, dried over $Na_2SO_4$, filtered, evaporated to give a crude oil. Chromatograph in a silica column using EtOAc/hexane (0/100 to 20/80) afforded white solid product (1.10 g, 67%). LCMS: (FA) ES+ 441. $^1$H NMR (400 MHz, d₁-chloroform) δ 8.29 (s, 1H), 5.54 (s, 2H), 3.71 (t, J=8.28 Hz, 2H), 0.95 (t, J=8.28 Hz, 2H), δ 0.00 (s, 9H).

Step 5: Synthesis of N-{-4-[4-bromo-5-(1-{[2-(trimethylsilyl)ethoxy]methyl}-1H-1,2,4-triazol-3-yl)-1,3-thiazol-2-yl]pyridin-2-yl}acetamide The mixture of 3-(2,4-dibromo-1,3-thiazol-5-yl)-1-{[2-(trimethylsilyl)ethoxy]methyl}-1H-1,2,4-triazole (1.10 g, 2.50 mmol), N-[4-(trimethylstannyl)pyridin-2-yl]acetamide (0.896 g, 3.00 mmol), tetrakis(triphenylphosphine)palladium (0) (0.155 g, 0.125 mmol), copper(I) iodide (0.143 g, 0.750 mmol) and lithium chloride (0.318 g, 7.50 mmol) in dry 1,4-Dioxane (100 mL) was sonicated for 2 min, degassed and backfilled with nitrogen for 5 times. The mixture was heated under nitrogen atmosphere to reflux for 90 min, cooled to room temperature, filtered thought celite and washed with dioxane/DCM. The filtrate was evaporated under reduced pressure to give a crude residue, which was purified using chromatography on a silica column using MeOH/DCM (0/100 to 5/95) to give a product, which was further purified on a silica column using MeOH/EtOAc/hexane (0/0/100 to 5/45/50) to give pure product (0.150 g, 13%). LCMS: (FA) ES+ 495, 497. ¹H NMR (400 MHz, d₁-chloroform) δ 8.72 (s, 1H), 8.37 (m, 1H), 8.33 (s, 1H), 8.26 (s, 1H), 7.68 (m, 1H), 5.57 (s, 2H), 3.73 (t, J=8.28 Hz, 2H), 2.25 (s, 3H), 0.97 (t, J=8.28 Hz, 2H), 0.00 (s, 9H).

Step 6: Synthesis of N-{4-[4-(2,6-dimethylphenyl)-5-(4H-1,2,4-triazol-3-yl)-1,3-thiazol-2-yl]pyridin-2-yl}acetamide (56-C)

The mixture of N-{-4-[4-bromo-5-(1-{[2-(trimethylsilyl)ethoxy]methyl}-1H-1,2,4-triazol-3-yl)-1,3-thiazol-2-yl]pyridin-2-yl}acetamide (0.0340 g, 0.0686 mmol), 2,6-dimethylphenylboronic acid (20.6 mg, 0.137 mmol), tetrakis(triphenylphosphine)palladium (0) (9.1 mg, 0.0073 mmol), and 2 M sodium carbonate in water (0.0850 mL, 0.170 mmol) in 1,4-dioxane (2.0 mL) in capped vial was heated to 140° C. for 19 hours. Additional tetrakis(triphenylphosphine)palladium(0) (7.1 mg, 0.0057 mmol) was added and the mixture was heated to 140° C. for 1 additional day. The mixture was filtered through celite/Na₂SO₄, washed with EtOAc, and evaporated under reduced pressure to give a crude intermediate. The material was treated with TFA (2.0 mL, 26 mmol) in dry DCM (2.0 mL) for 5 hours. The solvent was evaporated under reduced pressure and azeotroped with toluene to give a crude product. HPLC purification gave 0.002 g of pure product as a white powder (7.5%). LCMS: (FA) ES+ 391 and ES- 389. ¹H NMR (400 MHz, d₄-Methanol) δ 8.73 (s, 1H), 8.40 (d, J=5.84 Hz, 1H), 8.35 (s, 1H), 7.68 (d, J=5.84 Hz, 1H), 7.20 (m, 1H), 7.11 (s, 1H), 7.09 (d, J=7.35 Hz, 1H), 2.21 (s, 3H), 2.03 (s, 6H).

Compounds in the following table were prepared from the appropriate starting materials in a method analogous to that of Example 56-C:

| 53-C | LCMS: (FA) ES+ 431, 433. |
| 65-C | LCMS: (FA) ES+ 411, 413. |
| 70-C | LCMS: (FA) ES+ 394. |
| 71-C | LCMS: (FA) ES+ 432. |

Example 48-C

Synthesis of 2-[2-(acetylamino)pyridin-4-yl]-4-(2-chlorophenyl)-N-(2-hydroxyethyl)-1,3-thiazole-5-carboxamide

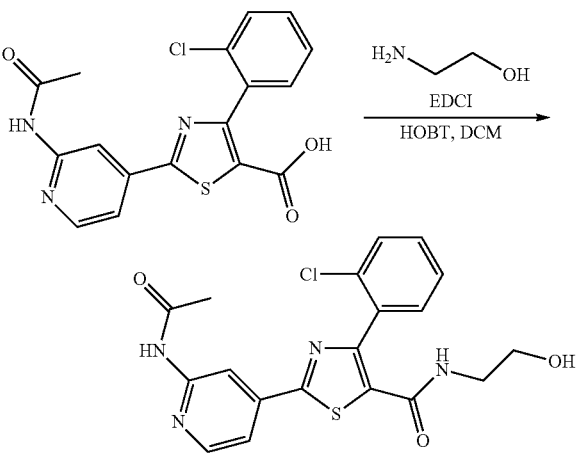

Step 1, Preparation of 2-[2-(acetylamino)pyridin-4-yl]-4-(2-chlorophenyl)-N-(2-hydroxyethyl)-1,3-thiazole-5-carboxamide (48-C)

To a stirred solution of 2-[2-(acetylamino)pyridin-4-yl]-4-(2-chlorophenyl)-1,3-thiazole-5-carboxylic acid (0.050 g, 0.130 mmol) in methylene chloride (3.00 mL, 46.80 mmol) was added N-(3-dimethylaminopropyl)-N'-ethylcarbodiimide hydrochloride (0.056 g, 0.294 mmol) followed by 1-hydroxybenzotriazole (0.040 g, 0.294 mmol) and the resulting solution was stirred for 1 h. Ethanolamine (0.081 mL, 1.340 mmol) was added and the reaction mixture was continued to stir for 18 h. The mixture was quenched by the addition of water (5.0 mL) and extracted with EtOAc (10.0 mL×3). The combined organic layers were dried over anhydrous Na₂SO₄, filtered, and concentrated in vacuo. The residue was purified by column chromatography (SiO₂, elution with 0-75% EtOAc in hexanes) to provide 0.0300 g of product as a clear colorless oil (54% 2 steps). LC/MS (AA) ES+ 417, 419. ¹H NMR (400 MHz, d₁ CDCl₃) δ: 8.06-7.98 (m, 1H), 7.72-7.54 (m, 3H), 7.49-7.44 (m, 2H), 7.02-6.96 (m, 1H), 6.28 (br s, 1H), 4.72 (br t, J=5.6 Hz, 1H), 4.66 (br t, J=5.4 Hz, 1H), 3.37 (q, J=6.0 Hz, 2H), 3.18 (q, J=6.4 Hz, 2H), 2.12 (s, 3H).

Compounds in the following table were prepared from the appropriate starting materials in a method analogous to that of Example 48-C:

| 4-C | LC/MS (AA) ES+ 431, 433. |
| 64-C | LCMS: (AA) ES+ 431, 433. |

Example 1-D

Synthesis of 5-[4-(2,4-dichlorophenyl)-5-(1H-imidazol-2-yl)-1,3-thiazol-2-yl]-3,4-dihydro-1,8-naphthyridin-2(1H)-one

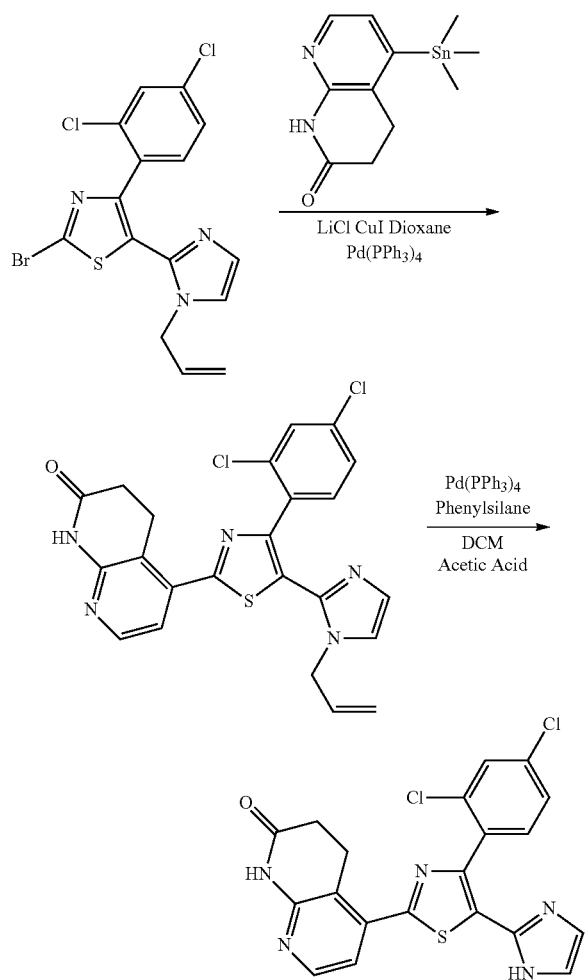

The title compound was prepared from 5-(1-Allyl-1H-imidazol-2-yl)-2-bromo-4-(2,4-dichlorophenyl)-1,3-thiazole and 5-(trimethylstannyl)-3,4-dihydro-1,8-naphthyridin-2(1H)-one using procedures analogous to those described in Example 1-C, Steps 8 and 9:LCMS: (FA) ES+ 442, 444. $^1$H NMR (300 MHz, d$_6$-DMSO) δ: 12.10-11.89 (bs, 1H), 10.64 (s, 1H), 8.25 (d, J=5.28 Hz, 1H), 7.74 (d, J=1.72 Hz, 1H), 7.60-7.46 (m, 2H), 739 (d, J=5.29 Hz, 1H), 7.23-6.94 (m, 2H), 4.11-4.06 (m, 1H), 3.38-3.30 (m, 1H), 3.16 (d, J=5.21 Hz, 2H).

Compounds in the following table were prepared from the appropriate starting materials in a method analogous to that of Example 1-D:

| 2-D | LCMS: (FA) ES+ 412, 414. |
| 3-D | LCMS: (FA) ES+ 440, 442. |

Biological Data:
PI3K Enzyme Assay
Expression and Purification of PI3K Enzyme

Active phosphatidylinositol 3' kinase (PI3K) enzyme is purified at Millennium Pharmaceuticals from SF9 insect cells (Invitrogen) co-infected with baculovirus containing aminoterminal His-tagged p110α and p85αexpression constructs.

PI3K Enzyme Homogenous Time Resolved Fluorescence (HTRF®) Assay

The PI3K enzyme HTRF® assay makes use of an energy transfer complex comprised of biotin-PI(3,4,5)P$_3$, Europhium labeled anti-GST monoclonal antibody, a OST-tagged GRP1 pleckstrin homology (PH) domain, and Streptavidin-APC (allophycocyanin). Excitation of the Europium in the complex results in a stable time-resolved fluorescence resonance energy transfer (FRET) signal. Phosphatidylinositol 3,4,5 triphosphate (PI(3,4,5)P$_3$, the product of PI3K, disrupts the energy transfer complex by competing with biotin-PI(3,4,5)P$_3$ for binding to the GRP1 PH domain, resulting in a decreased fluorescent signal. Inhibitors of PI3K in the reaction prevent a decrease in the fluorescent signal.

PI3K enzyme (325 pM) is incubated with di-C8 PI(4,5)P$_2$ substrate (3.5 μM, CellSignals, Inc.) in assay buffer (50 mM HEPES pH 7.0, 5 mM DTT, 150 mM NaCl, 10 mM (3-glycerophosphate, 5 mM MgCl$_2$, 0.25 mM sodium cholate, 0.001% CHAPS) containing 25 μM ATP and 0.5 μL of test compound (in 100% DMSO) at multiple concentrations in a final volume of 20.5 μL in 384 well plates for 30 min at 22-23° C. The reaction is terminated by adding 5 μL of detection buffer (50 mM HEPES pH7.0, 5 mM DTT, 1 mM NaCl, 10% Tween-20) containing EDTA (90 mM) and biotin-PI(3,4,5)P$_3$ (150 nM, Echelon Bioscience) to each well. 5 μL of detection buffer containing GST-fused GRP1 PH domain protein (210 nM, Millennium Pharmaceuticals), anti-GST-Europium tagged cryptate antibody (2.25 nM, CisBio), Streptavidin-XL (90 nM, CisBio) and potassium fluoride (240 mM) are then added to each well and incubated for 1 hour. Fluorescent signal for each well is then measured on an LJL_Analyst (Molecular Devices). Concentration response curves were generated by calculating the fluorescent signal in test compound-treated samples relative to DMSO-treated (0% inhibition) and EDTA-treated (100% inhibition) controls, and concentrations producing 50% inhibition (IC$_{50}$ values) are determined from those curves.

PI3K Cell Assays
Forkhead Redistribution Assay

Inhibition of PI3K in cells can be assessed using the Forkhead Redistribution Assay (BioImage). Foxo1A fused to EGFP (Foxo1A-EGFP) expressed in U2OS osteosarcoma cells localizes to the cytoplasm when the PI3K pathway is actively signaling. Inactivation of pathway signaling leads to a translocation of the protein from the cytoplasm to the nucleus. Therefore, pathway inhibition can be measured by quantifying the fluorescent intensity of Foxo1A-EGFP within the nucleus.

U2OS cells constitutively expressing Foxo1A-EGFP (6500 cells/well) are plated onto the inner 60 wells of 96 well dishes (BD Falcon OPTILUX black clear bottom) in 100 μL of cell culture media (DMEM (Invitrogen) containing 10% Fetal Bovine Serum (HyClone) and 1% Penicillin-Streptavidin (Invitrogen) and grown overnight in a humidified chamber at 37° C. The cell culture media is removed and the cells are rinsed with 100 μL of low serum media (DMEM containing 0.933% Fetal Bovine Serum and 1% Penicillin-Streptavadin) and incubated in 75 μL of low serum media for 1 hour in a humidified chamber at 37° C. Test compounds (25 μL) at multiple concentrations suspended in DMEM containing 1% Penicillin-Streptavadin are added to cells and incubated in a humidified chamber at 37° C. for 1 hour. The media is removed and the cells were fixed in 100 μL of 4% paraformaldehyde in phosphate buffered saline (PBS) for 10 min and then washed with 100 µL of PBS. DRAQ5 mix (100 µL, Alexis Biochemicals) diluted 1:5000 in PBS containing RNAase (1:10,000, Sigma) is added to cells for 30 minutes. The plates are then imaged (16 fields per well) using an Opera Imager (Evotec) and Foxo1A-EGFP fluorescent intensity within the nucleus (DRAQ5-positive) was quantified using Acapella Software (Evotec). Concentration response curves are generated by calculating the nuclear fluorescent intensity of Foxo-1A EGFP in test compound-treated samples and concentrations producing 50% inhibition ($IC_{50}$ values) relative to the positive control were determined from those curves.

Anti-Proliferation Assay

ATPlite Assay

The ATPLite™ (Perkin-Elmer) Assay measures cellular adenosine-triphosphate (ATP) through the generation of a luminescent signal formed from the ATP dependent enzyme firefly luciferase. The luminescent signal intensity can be used as a measure of cellular proliferation, and therefore the anti-proliferative effects of PI3K inhibitors.

Test compounds (4 µL in 100% DMSO) are diluted in 75 µL of Hanks Buffered Saline Solution (Invitrogen). The diluted test compounds (8 µL) are then added to 384-well TC-treated Black/Clear plates (Falcon). HCT-116 cells (American Type Culture Collection) maintained in McCoy's 5a modified media (Invitrogen) containing 10% Fetal Bovine Serum and 1% Penicillin-Streptavadin are added at 1000 cells per well. H460 cells (American Type Culture Collection) maintained in RPMI 1640 containing 10% Fetal Bovine Serum and 1% Penicillin-Streptavadin were added at 1500 cells per well. The cells were then incubated with compound in a humidified chamber at 37° C. for 72 hours. The plates are then removed from the cell culture chambers and allowed to equilibrate to room temperature for 30 min. All but 25 µL of cell culture media is removed from each well, and 25 p. 1 of ATPlite reagent (Perkin Elmer) is added to each well. Luminescence is measured within 5 minutes of adding the ATPlite reagent on a LEADSeeker Luminescence Counter (GE Healthcare Life Sciences). Concentration response curves are generated by calculating the luminescence decrease in test compound-treated samples relative to DMSO-treated controls, and growth inhibition ($IC_{50}$) values are determined from those curves.

Formulation Example I

Amount Per Tablet

| (1) Compound obtained in Example 1 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 1, 60.0 mg of lactose and 35.0 mg of corn starch is granulated through a 1 mm-mesh sieve using 0.03 ml of a 10% by weight aqueous solution of gelatin (3.0 mg of gelatin), after which the granules are dried at 40° C. and filtered again. The granules obtained are mixed with 2.0 mg of magnesium stearate and compressed. The core tablets obtained are coated with a sugar coat comprising a suspension of sucrose, titanium dioxide, talc and gum arabic and polished with beeswax to yield sugar-coated tablets.

Formulation Example 2

Dose Per Tablet

| (1) Compound obtained in Example 1 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 1 and 3.0 mg of magnesium stearate are granulated using 0.07 ml of an aqueous solution of soluble starch (7.0 mg of soluble starch), after which these granules are dried and mixed with 70.0 mg of lactose and 50.0 mg of corn starch. This mixture is compressed to yield tablets.

Gene Cloning hPIK3CA; p110alpha catalytic subunit (GenBank ACCESSION# NM_006218) and hPIK3R1; p85alpha regulatory subunit (GenBank ACCESSION# NM_181523) are cloned from human cDNA library (Clonetec).

Purification of Human PI3Kα Enzyme

Human p110alpha catalytic subunit gene and human p85alpha regulatory subunit gene are respectively inserted into pFASTBacHT (Invitrogen), and each gene was introduced into a baculovirus vector using a Bac-to-Bac system (Invitrogen). Both viruses are injected to insect cultured cells Sf21 to allow coexpression of proteins. p110alpha catalytic subunit and human p85alpha regulatory subunit complex (hPI3Kα) are purified from the cell extract using a Ni chelate column.

Human PI3Kα Enzyme Assay Method

L-alpha-Phosphatidyl-D-myo-inositol 4,5-Diphosphate (diC16) [PI(4,5)P2, Wako Pure Chemical Industries, Ltd.] is suspended in Phospholipid FlashPlate Coating Buffer (PerkinElmer) and applied onto Phospholipid FlashPlate PLUS. PI3K reaction buffer (50 mM Tris-HCl, pH 7.4, 5 mM $MgCl_2$, 1 mM DTT, 0.005% BSA) containing hPI3Kα, γ-[$^{33}$P] ATP (PerkinElmer) and cold 500 nM ATP is added to the wells on this plate and the mixture is reacted at room temperature for 1 hr. 50 mM EDTA solution is added to quench the reaction, and the wells are washed with PBS. The radioactivity remaining in the well is measured as enzyme activity by TopCount (PerkinElmer).

The obtained results are shown in Table 3. From the results, the compounds of the present invention were shown to strongly inhibit the activity of PI3Kα.

TABLE 3

| Example | Inhibitory rate at 1.0 µm (%) |
| --- | --- |
| 27-B | 100 |
| 32-B | 100 |
| 35-B | 101 |

Human mTOR Enzyme Assay Method mTOR reaction buffer (50 mM HEPES, pH 7.5, 5 mM $MgCl_2$, 5 mM $MnCl_2$, 1 mM EGTA, 1 mM DTT, 0.01% BRIJ-35, 0.01% $NaN_3$) containing human mTOR (Invitrogen), 10 µM ATP and 2 µM Z'-lyte 11Ser/Thr peptide (Invitrogen) is added to the well and the mixture is reacted at room temperature for 1 hr.

Development Buffer containing Development Reagent B (for Z'-lyte peptide, Invitrogen) was added, and the mixture is reacted at room temperature for 30 min. The fluorescence at 520 nm and fluorescence at 445 nm are measured with excitation at 400 nm using SpectraMax M5e (Molecular Device). The ratio of the obtained 445 nm fluorescence value/520 nm fluorescence value is calculated, and changes in the fluorescence resonance energy transfer (FRET) of Z'-lyte peptide are detected as the enzyme activity.

The obtained results are shown in Table 4. From the results, the compounds of the present invention are shown to strongly inhibit the activity of mTOR.

TABLE 4

| Example | Inhibitory rate at 1.0 µm (%) |
|---------|-------------------------------|
| 31-B    | 93                            |
| 33-B    | 91                            |

PI3K and VPS34 Enzyme Assays

Cloning, Expression, and Purification of PI3Ks and VPS34

The catalytic subunits of PI3Ks are cloned into either pDEST8 (p110 alpha) or pDEST10 (p110beta, p110delta, and p110gamma) as N-terminal His tagged fusion proteins using the Gateway system (Invitrogen, catalog#11804-010 for pDEST8 and 11806-015 for pDEST10). The sequences are verified before recombinant protein expression using the Baculovirus Expression System with Gateway® Technology. The accession numbers for the subunits are as follows:
p110 alpha (GB:U79143)
p110beta (GB:S67334)
p110delta (GB: U86453)
p110gamma (GB: X83368)
The regulatory subunits of PI3Ks are cloned into pDEST8 as un-tagged protein using the Gateway system (Catalog#11804-010). The sequences are verified before recombinant protein expression using the Baculovirus Expression System with Gateway® Technology. The accession numbers for the subunits are as following:
p85 alpha (GB: BC030815)
p101 (GB: AB028925)
VPS34 (accession number GB:BC033004) is cloned into pDEST20-Thombin as N-terminal GST tagged fusion proteins using the Gateway system (Invitrogen, catalog#11804-013). The sequences are verified before recombinant protein expression using the Baculovirus Expression System with Gateway® Technology.

For expression of the p110 complexes, the p85 (MOI of 4) is co-infected with p110 alpha, beta, and delta respectively (1MOI) in SF9 cells and harvested at 60 hours post co-infection. P110 gamma was infected at 1 MOI and harvested at 60 hours post infection.

VPS34 is infected at 1MOI in SF9 cells and harvested 72 hours post infection.

For purification, PI3Ks are purified by Ni-NTA Agarose (Qiagen #30250) followed by Mono Q 10/100 GL (Ge Healthcare #17-5167-01). VPS34 is purified by Glutathione Sepharose 4 Fast Flow (GE Healthcare #17-5132-03) followed by HiTrap Q (GE Healthcare #17-1153-01).

PI3K Assay Conditions

1) Human PI3Kα Enzyme Assay Method 0.5 uL compounds in DMSO are added to wells of a 384 well microtitre plate (Corning 3575). At room temperature: 10 ul PI3K reaction buffer (50 mM Hepes, 5 mM DTT, 150 mM NaCl, 10 mM beta-glycerophosphate, 10 mM $MgCl_2$, 0.25 mM sodium cholate and 0.001% CHAPS, pH 7.00) containing ATP (25 uM, Promega) is added followed immediately by 10 ul PI3K reaction buffer containing di-C8 PI(4,5)P2 (3.5 uM, CellSignals) and PI3Kalpha (0.4875 nM, Millennium Protein Sciences Group) and the mixture is incubated with shaking at room temperature for 30 minutes. Then 5 ul PI3K stop mix (50 mM Hepes, 5 mM DTT, 150 mM NaCl, 0.01% Tween-20, 15 mM EDTA and 25 nM biotin-PI (3,4,5)P3 (Echelon) is added to quench the reaction followed immediately by addition of 5 ul HTRF detection mix (50 mM Hepes, 5 mM DTT, 150 mM NaCl, 0.01% Tween-20, 40 mM KF, 10 nM GST:GRP-1 PH domain (Millennium Protein Sciences Group), 15 nM Streptavidin-XL (CisBio) and 0.375 nM anti-GST Eu++ antibody (CisBio) at pH 7.00). The plates are then incubated for 1 hour at room temperature with shaking and then read on a BMG PheraStar Plus reader.

2) Human PI3K beta, delta and gamma isoforms are tested using the procedure described for PI3K alpha above but with the following changes: PI3K beta (5.25 nM), PI3K delta (0.75 nM) and PI3K gamma (5 nM). All isoforms supplied by Millennium Protein Science Group.

3) VPS34 is assayed using Adapta™ Universal Kinase Assay Kit (Invitrogen).

Example 2

PI3K Cell Assays

Forkhead Redistribution Assay

Inhibition of PI3K in cells can be assessed using the Forkhead Redistribution Assay (BioImage). Foxo1A fused to EGFP (Foxo1A-EGFP) expressed in U2OS osteosarcoma cells localizes to the cytoplasm when the PI3K pathway is actively signaling. Inactivation of pathway signaling leads to a translocation of the protein from the cytoplasm to the nucleus. Therefore, pathway inhibition can be measured by quantifying the fluorescent intensity of Foxo1A-EGFP within the nucleus.

U2OS cells constitutively expressing Foxo1A-EGFP (6500 cells/well) are plated onto the inner 60 wells of 96 well dishes (BD Falcon OPTILUX black clear bottom) in 100 µL of cell culture media (DMEM (Invitrogen) containing 10% Fetal Bovine Serum (HyClone) and 1% Penicillin-Streptavidin (Invitrogen) and grown overnight in a humidified chamber at 37° C. The cell culture media is removed and the cells are rinsed with 100 µL of low serum media (DMEM containing 0.933% Fetal Bovine Serum and 1% Penicillin-Streptavadin) and incubated in 75 µL of low serum media for 1 hour in a humidified chamber at 37° C. Test compounds (25 µL) at multiple concentrations suspended in DMEM containing 1% Penicillin-Streptavadin are added to cells and incubated in a humidified chamber at 37° C. for 1 hour. The media is removed and the cells are fixed in 100 µL of 4% paraformaldehyde in phosphate buffered saline (PBS) for 10 min and then washed with 100 µL of PBS. DRAQ5 mix (100 µL, Alexis Biochemicals) diluted 1:5000 in PBS containing RNAase (1:10,000, Sigma) is added to cells for 30 minutes. The plates are then imaged (16 fields per well) using an Opera Imager (Evotec) and Foxo1A-EGFP fluorescent intensity within the nucleus (DRAQ5-positive) is quantified using Acapella Software (Evotec). Concentration response curves are generated by calculating the nuclear fluorescent intensity of Foxo-1A EGFP in test compound-treated samples and concentrations producing 50% inhibition ($IC_{50}$ values) relative to the positive control are determined from those curves.

Example 3

Anti-Proliferation Assay

ATPlite Assay

The ATPLite™ (Perkin-Elmer) Assay measures cellular adenosine-triphosphate (ATP) through the generation of a luminescent signal formed from the ATP dependent enzyme firefly luciferase. The luminescent signal intensity can be used as a measure of cellular proliferation, and therefore the anti-proliferative effects of PI3K inhibitors.

Test compounds (4 µL in 100% DMSO) are diluted in 75 µL of Hanks Buffered Saline Solution (Invitrogen). The diluted test compounds (8 pt) are then added to 384-well TC-treated Black/Clear plates (Falcon). HCT-116 cells (American Type Culture Collection) maintained in McCoy's 5a modified media (Invitrogen) containing 10% Fetal Bovine Serum and 1% Penicillin-Streptavadin are added at 1000 cells per well. H460 cells (American Type Culture Collection) maintained in RPMI 1640 containing 10% Fetal Bovine Serum and 1% Penicillin-Streptavadin are added at 1500 cells per well. The cells are then incubated with compound in a humidified chamber at 37° C. for 72 hours. The plates are then removed from the cell culture chambers and allowed to equilibrate to room temperature for 30 min. All but 25 µL of cell culture media is removed from each well, and 25 µl of ATPlite reagent (Perkin Elmer) is added to each well. Luminescence is measured within 5 minutes of adding the ATPlite reagent on a LEADSeeker Luminescence Counter (GE Healthcare Life Sciences). Concentration response curves are generated by calculating the luminescence decrease in test compound-treated samples relative to DMSO-treated controls, and growth inhibition ($IC_{50}$) values are determined from those curves.

As detailed above, compounds of the invention inhibit PI3K. In certain embodiments, compounds inhibit one or more isoforms of PI3K. In other embodiments, compounds of the invention inhibit PI3Kalpha and have an $IC_{50}>1.0$ µM. For example, these compounds include compounds 19-B, 41-B, 49-B, 50-B, 52-B, 54-B, 66-B, 67-B, 68-B, 71-B, 102-B, 4-C, 8-C, 14-C, 16-C, 18-C, 27-C, 30-C, 36-C, 46-C, 47-C, 48-C, 56-C, 57-C, 58-C, 60-C, 61-C, 62-C, 64-C, 65-C, 72-C, and 73-C. In other embodiments, compounds of the invention have an IC50<1.0 µM but >0.1 µM. For example, these compounds include compounds 2-B, 4-B, 5-B, 7-B, 9-B, 10-B, 12-B, 16-B, 37-B, 47-B, 48-B, 53-B, 55-B through 64-B, 69-B, 84-B, 105-B, 113-B, 115-B, 116-B, 119-B, 122-B, 123-B, 124-B, 126-B, 129-B, 140-B, 142-B, 148-B, 149-B, 150-B, 152-B through 155-B, 164-B, 2-C, 7-C, C, 9-C, 10-C, 13-C, 19-C, 21-C, 22-C, 24-C, 26-C, 29-C, 33-C, 34-C, 35-C, 41-C, 42-C, 45-C, 51-C, 52-C, 56-C, 58-C, 60-C, and 66-C through 71-C. In still other embodiments, compounds of the invention have an IC50<0.1 µM. For example, these compounds include compounds 1-B, 3-B, 6-B, 8-B, 11-B, 13-B, 14-B, 15-B, 17-B, 18-B, 20-B through 36-B, 38-B, 39-B, 42-B, 43-B, 44-B, 46-B, 51-B, 65-B, 70-B, 72-B through 79-B, 81-B, 82-B, 83-B, 85-B through 101-B, 103-B, 104-B, 106-B through 112-B, 114-B, 117-B, 118-B, 120-B, 121-B, 125-B, 127-B, 128-B, 130-B through 139-B, 141-B, 147-B, 151-B, 156-B through 163-B, 3-C, 5-C, 6-C, 11-C, 15-C, 17-C, 23-C, 25-C, 31-C, 32-C, 38-C, 39-C, 40-C, 43-C, 49-C, 50-C, 53-C, 54-C, 55-C, 57-C, 63-C, 1-D, 2-D, and 3-D.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

INDUSTRIAL APPLICABILITY

According to the present invention, thiazole derivatives and use of the derivatives are provided. These thiazole derivatives have a superior PI3K inhibitory activity and(or) a superior mTOR inhibitory activity, are low toxic, and are sufficiently satisfactory as pharmaceutical products.

The invention claimed is:

1. A compound of formula Ia:

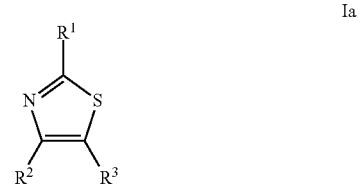

or a pharmaceutically acceptable salt thereof, wherein
$R^1$ is
(i) an optionally substituted group represented by

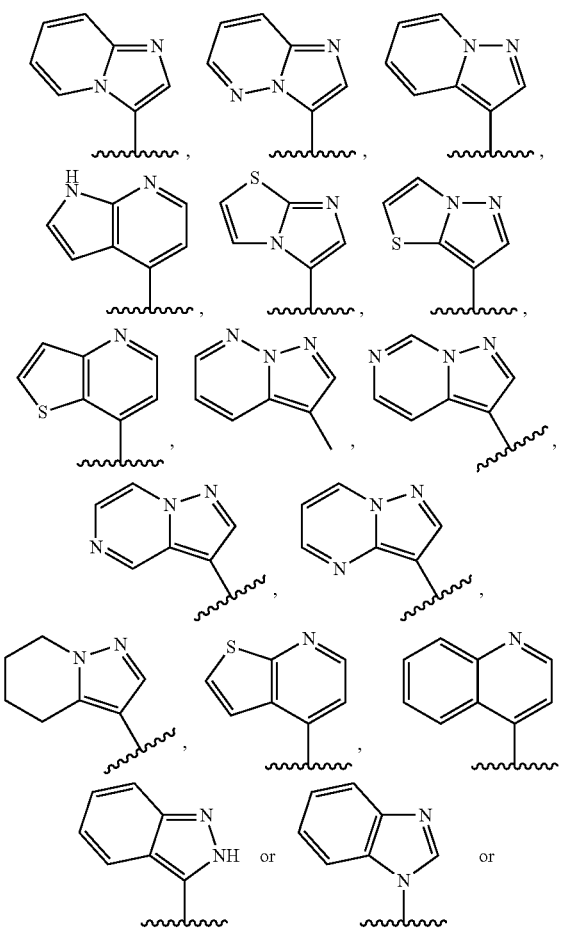

(ii) a group represented by:

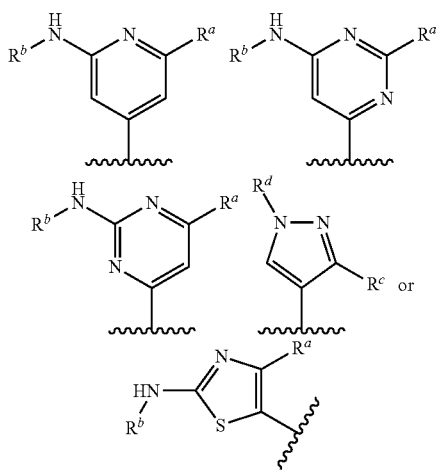

wherein
$R^a$ and $R^c$ are each hydrogen atom, an alkyl group or a halogen atom,
$R^b$ is (i) a hydrogen atom, (ii) an optionally substituted hydrocarbon-carbonyl group, (iii) an optionally substituted heterocyclyl-carbonyl group, (iv) an optionally substituted carbamoyl group, (v) an optionally substituted alkoxycarbonyl group, (vi) an optionally substituted hydrocarbon-sulfonyl group, (vii) an optionally substituted heterocyclyl-sulfonyl group, (viii) an optionally substituted sulfamoyl group, (ix) an optionally substituted hydrocarbon group or (x) an optionally substituted heterocyclic group, and
$R^d$ is (i) a hydrogen atom, (ii) an optionally substituted hydrocarbon group or (iii) an optionally substituted heterocyclic group;
$R^2$ is a halogen atom, or an optionally substituted group bonded via a carbon atom, a nitrogen atom, an oxygen atom or a sulfur atom, wherein
a) the optionally substituted group bonded via a carbon atom is selected from cyano, an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, and an optionally substituted carbamoyl group,
b) the optionally substituted group bonded via a nitrogen atom is selected from
i) amino;
ii) mono- or di-substituted amino, wherein the amino is substituted by an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, or an optionally substituted carbamoyl group, and
iii) an optionally substituted heterocyclic group bonded via a nitrogen atom;
c) the optionally substituted group bonded via an oxygen atom is selected from hydroxy optionally substituted by an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, and an optionally substituted carbamoyl group , and
d) the optionally substituted group bonded via a sulfur atom is selected from mercapto optionally substituted by: an optionally substituted alkyl group, an optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, and an optionally substituted carbamoyl group;
$R^3$ is (1) an optionally substituted 5-membered aromatic heterocyclic group containing 2 to 4 nitrogen atoms besides carbon atom, which is bonded via a carbon atom, or (2) an optionally substituted 5-membered aromatic heterocyclic group containing 1 to 3 nitrogen atoms besides carbon atom and further containing one oxygen atom or sulfur atom, which is bonded via a carbon atom.

2. The compound of claim 1, wherein $R^2$ is
(i) a halogen atom,
(ii) hydroxy optionally substituted by an optionally substituted alkyl group, an optionally substituted alkenyl group, an optionally substituted alkynyl group, an optionally substituted aryl group, an optionally substituted $C_{6-18}$ aryl-$C_{1-4}$ alkyl group, or an optionally substituted heterocyclic group bonded via a carbon atom;
(iii) an optionally substituted alkyl group, an optionally substituted alkenyl group, an optionally substituted alkynyl group, an optionally substituted $C_{3-8}$ cycloalkyl group, an optionally substituted aryl group, or an optionally substituted $C_{6-18}$ aryl-$C_{1-4}$ alkyl group;
(iv) an optionally substituted heterocyclic group bonded via a carbon atom, or an optionally substituted heterocyclic group bonded via a nitrogen atom;
(v) amino, or mono- or di-substituted amino, wherein the amino is substituted by an optionally substituted alkyl group, optionally substituted alkenyl group, an optionally substituted alkynyl group, an optionally substituted $C_{1-8}$ alkyl-carbonyl group, an optionally substituted $C_{3-8}$ cycloalkyl group, an optionally substituted aryl group, an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl- carbonyl group, an optionally substituted heterocyclic group bonded via a carbon atom, an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, or an optionally substituted carbamoyl group;
(vi) mercapto optionally substituted by an optionally substituted alkyl group, an optionally substituted alkenyl group, an optionally substituted alkynyl group, an optionally substituted aryl group, an optionally substituted $C_{6-18}$ aryl-$C_{1-4}$ alkyl group, or an optionally substituted heterocyclic group bonded via a carbon atom; or
(vii) an optionally substituted $C_{1-8}$ alkyl-carbonyl group, an optionally substituted $C_{6-18}$ aryl-carbonyl group, an optionally substituted $C_{6-18}$ aryl-$C_{1-4}$ alkyl-carbonyl group, an optionally substituted heterocyclyl-carbonyl group, an optionally substituted heterocyclyl-$C_{1-4}$ alkyl-carbonyl group.

3. The compound of claim 1, wherein $R^3$ is an optionally substituted Triazolyl group.

4. The compound of claim 1, wherein:
$R^2$ is selected from:
(i) a $C_{1-8}$ alkyl group,
(ii) a $C_{2-8}$ alkenyl group,
(iii) a $C_{3-8}$ cycloalkyl group,
(iv) a hydroxyl group optionally substituted by a $C_{1-8}$ alkyl, $C_{2-8}$ alkenyl or $C_{6-18}$ aryl-$C_{1-4}$ alkyl,
(v) a $C_{6-18}$ aryl group optionally substituted by a halogen atom, optionally halogenated $C_{1-8}$ alkyl or $C_{1-8}$ alkoxy,
(vi) a $C_{6-18}$ aryl-$C_{1-4}$ alkyl group,
(vii) a 4- to 7-membered aromatic monocyclic heterocyclic group containing, besides carbon atom, 1 to 3 heteroatoms selected from a nitrogen atom, an oxygen atom and a sulfur atom, and
(viii) a 4- to 7-membered non-aromatic heterocyclic group containing, besides carbon atom, 1 to 3 heteroatoms selected from a nitrogen atom, an oxygen atom and a sulfur atom; and
wherein $R^3$ is a 5-membered aromatic heterocyclic group containing 2 to 4 nitrogen atoms, which is bonded via a carbon atom and optionally substituted by $C_{1-8}$ alkyl.

5. A compound of formula Ib:

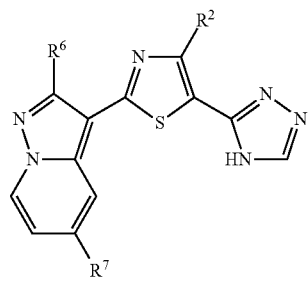

(Ib)

or a pharmaceutically acceptable salt, wherein
$R^2$ is (i) a halogen atom, (ii) an optionally substituted hydroxy group, (iii) an optionally substituted hydrocarbon group, (iv) an optionally substituted heterocyclic group, (v) an optionally substituted amino group, (vi) an optionally substituted thiol group or (vii) an acyl group $R^6$ is hydrogen or optionally substituted $C_{1-4}$ alkyl, and $R^7$ is H, hydroxyl optionally substituted by optionally halogenated $C_{1-6}$ alkyl, $C_{1-6}$ alkoxy optionally substituted by a group selected from hydroxy, $C_{1-6}$ alkyl-carbonylamino and amino-$C_{1-6}$ alkyl-carbonylamino, $C_{6-18}$ aryl-$C_{1-4}$ alkyl-oxy, 4- to 7-membered monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by $C_{1-6}$ alkyl optionally substituted by halogen and 4- to 7-membered monocyclic non-aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by a group selected from halogen, $C_{1-6}$ alkyl, $C_{1-6}$ alkyl-sulfonyloxy and $C_{1-6}$ alkyl-carbonyl optionally substituted by hydroxy.

6. The compound of claim 5, wherein $R^2$ is an optionally substituted phenyl group.

7. A composition comprising the compound of claim 1 or 5, or a pharmaceutically acceptable salt thereof, and a pharmaceutically acceptable carrier.

8. A method for inhibiting PI3K or mTor activity in a patient comprising administering a composition comprising an amount of a compound of claim 1 or 5, or a pharmaceutically acceptable salt thereof, effective to inhibit PI3K or mTor activity in the patient.

9. A compound selected from the group consisting of

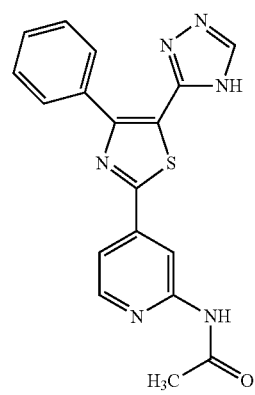

1-B

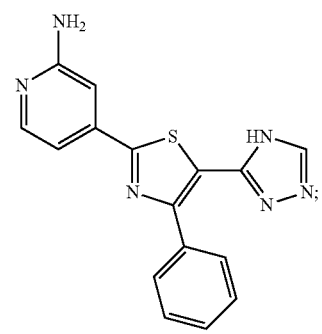

2-B

3-B
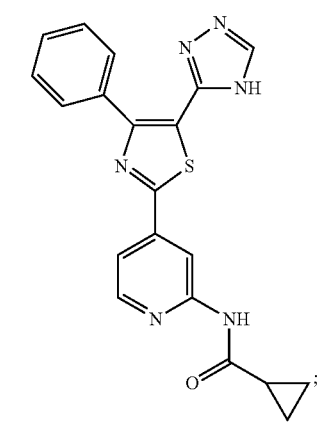
4-B
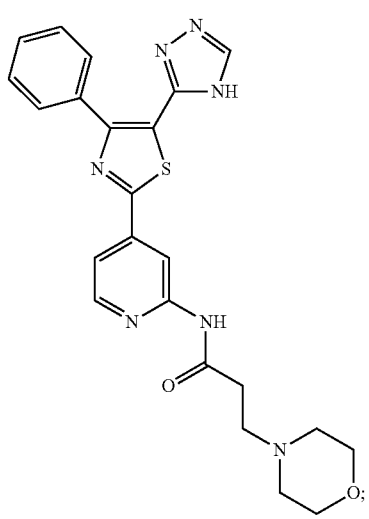
5-B
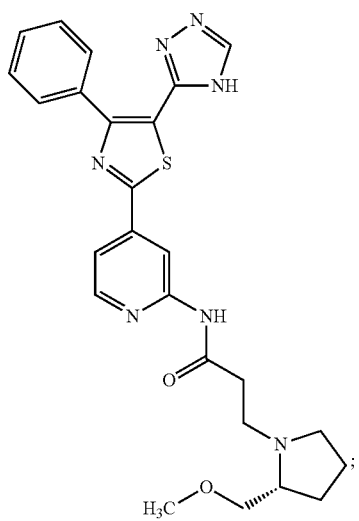
6-B
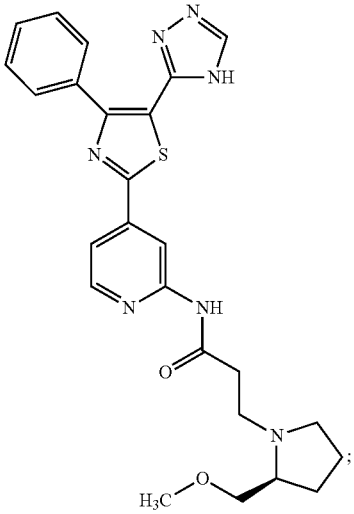
7-B
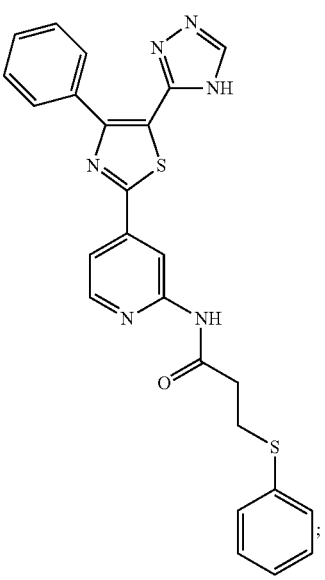
8-B
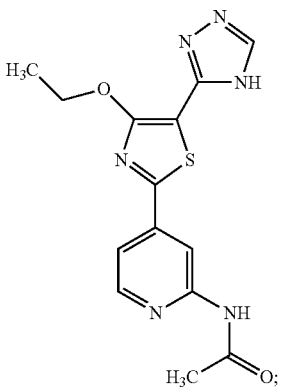

9-B
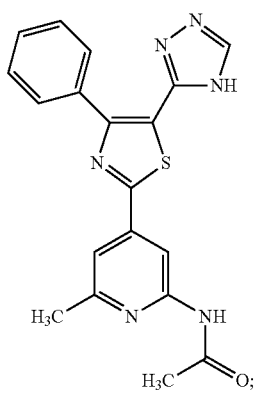
10-B
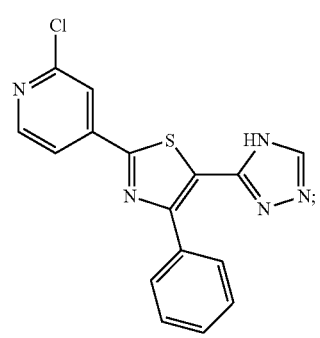
11-B
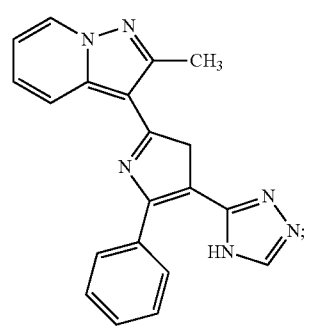
12-B
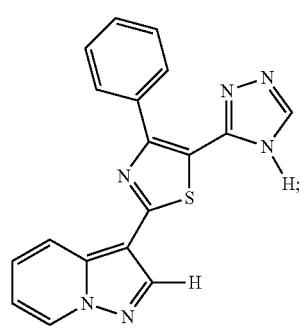
13-B
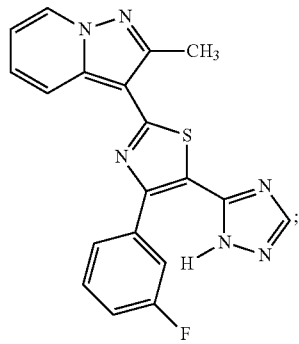
14-B
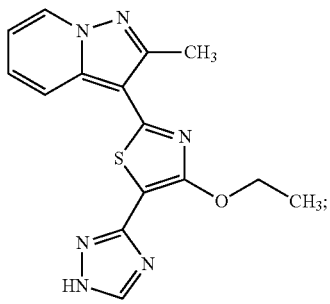
15-B
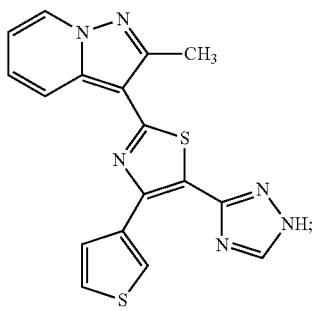
16-B
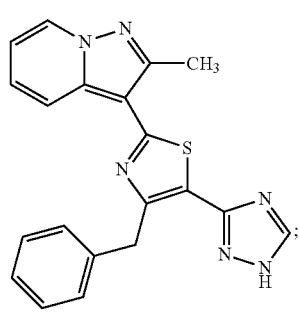
17-B
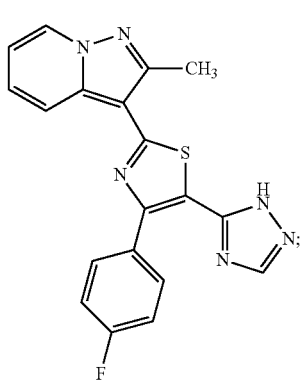

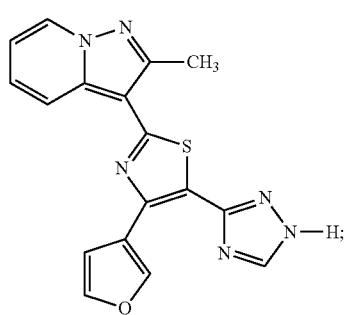
18-B
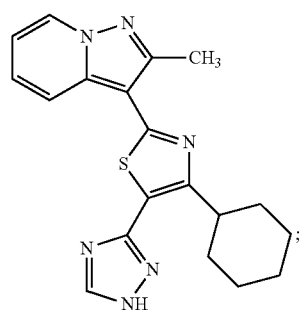
19-B
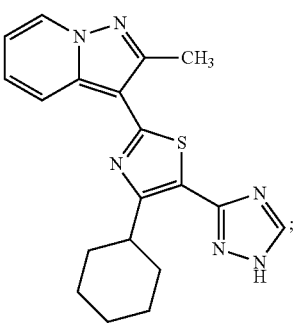
20-B
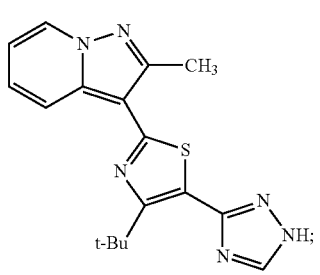
21-B
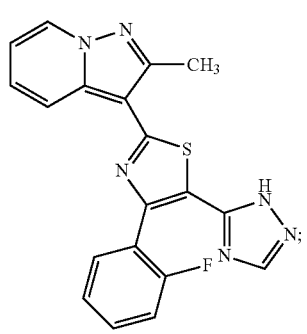
22-B
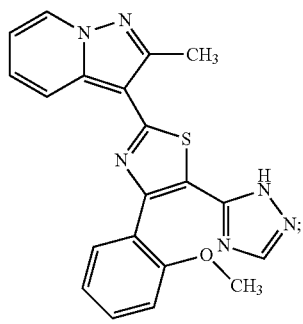
23-B
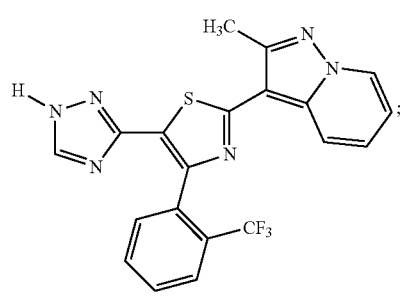
24-B
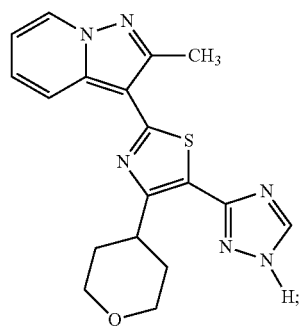
25-B
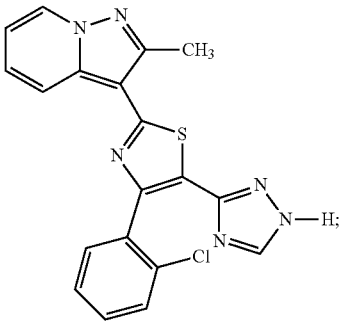
26-B
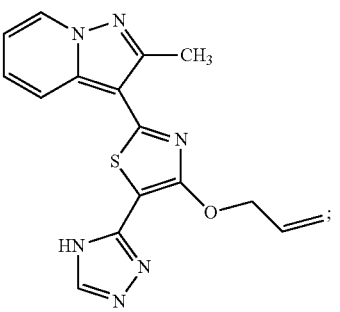
27-B

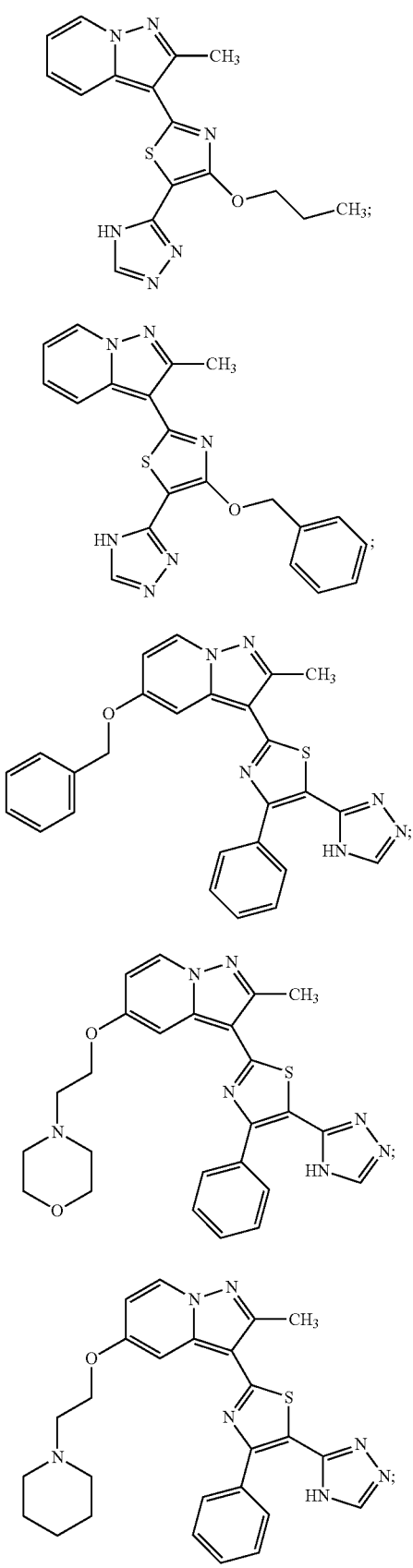

38-B
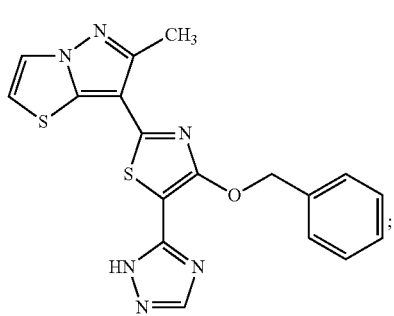
39-B
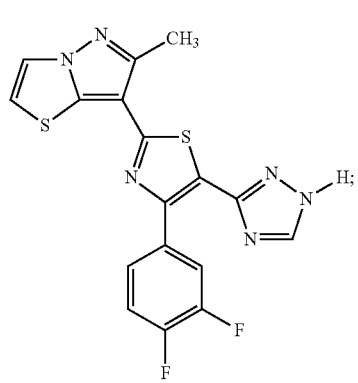
40-B
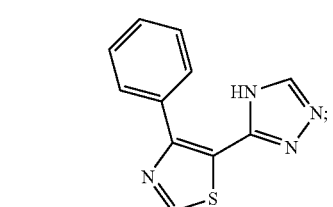
41-B
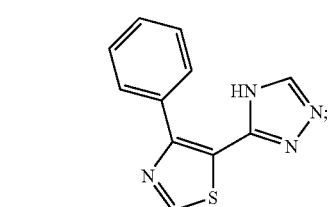
42-B
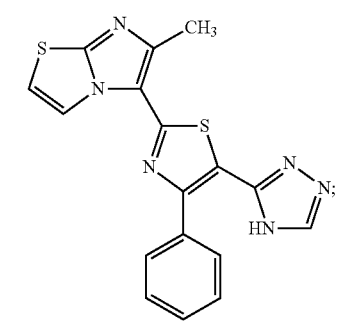
43-B
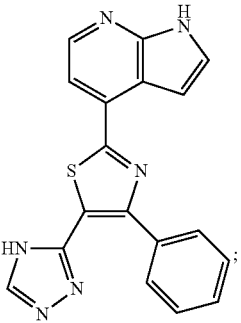
44-B
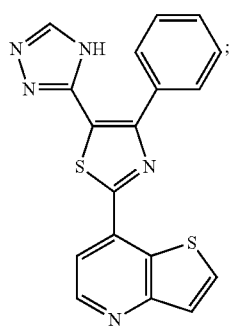
45-B
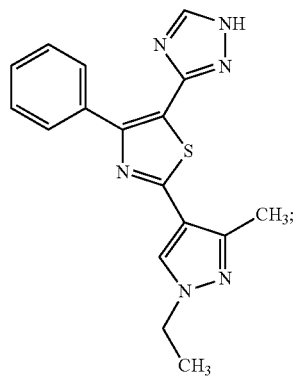
46-B
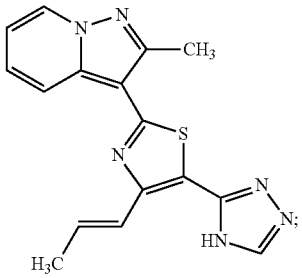

-continued
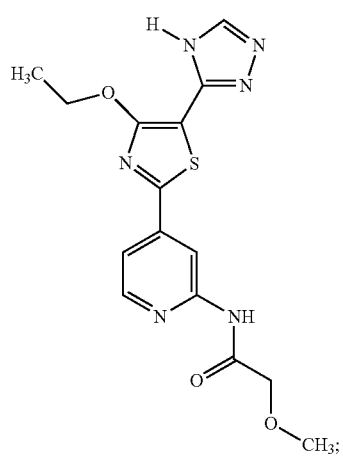
47-B
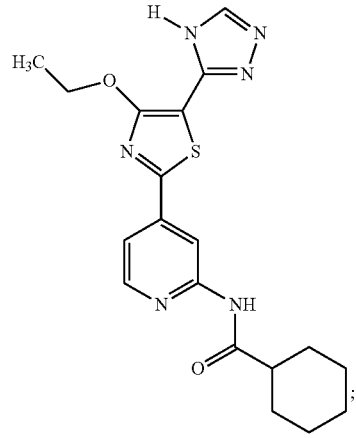
50-B
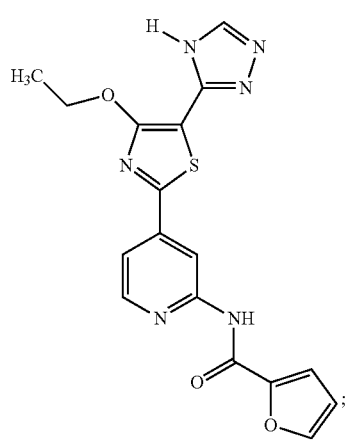
48-B
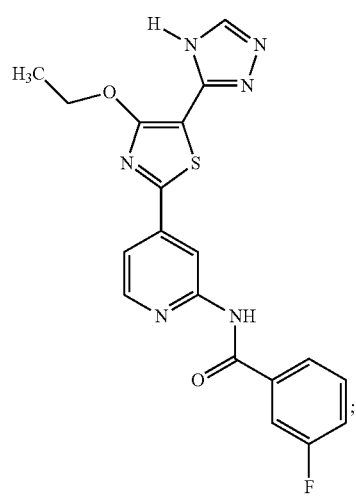
51-B
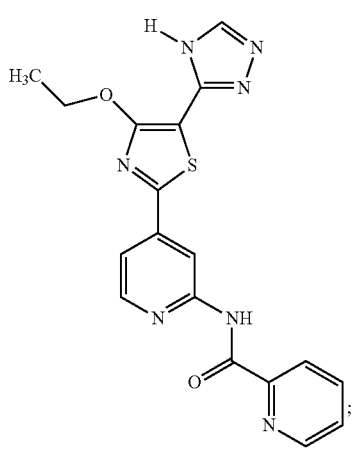
49-B
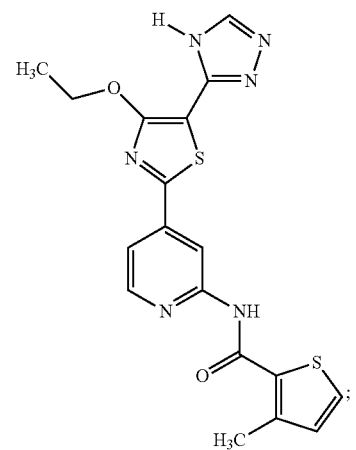
52-B

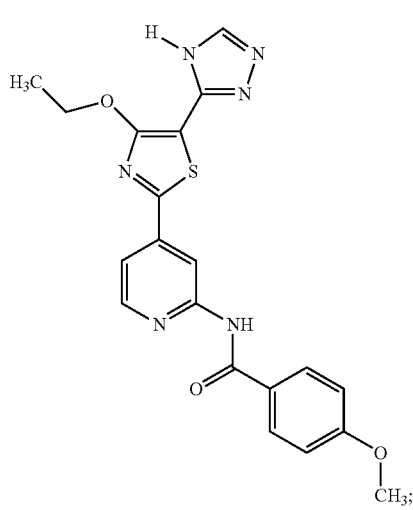
53-B
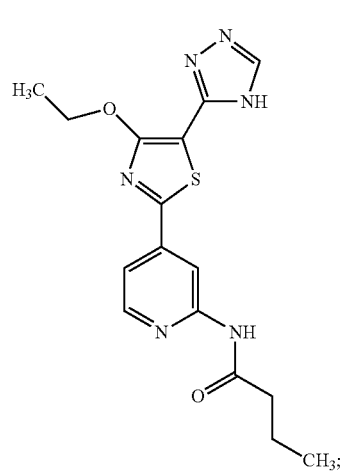
55-B
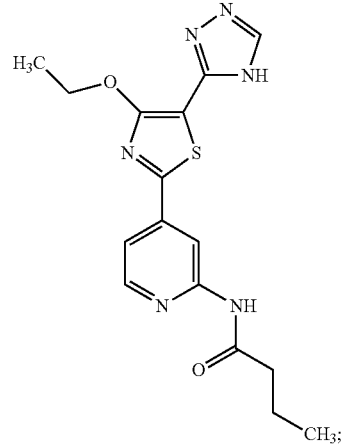
54-B
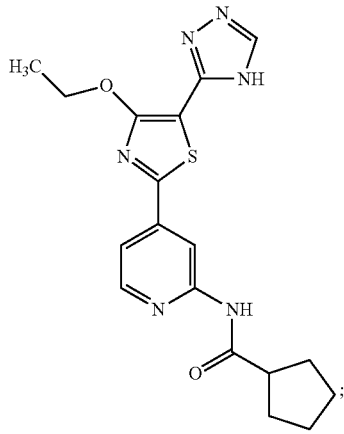
57-B
55-B
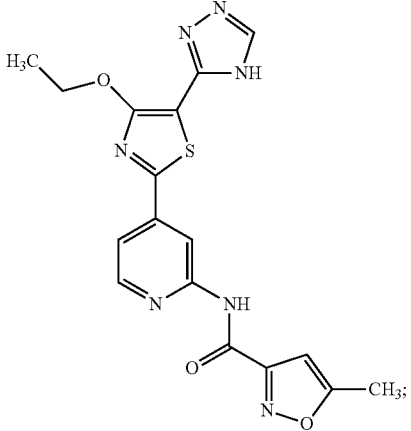
58-B -continued
59-B
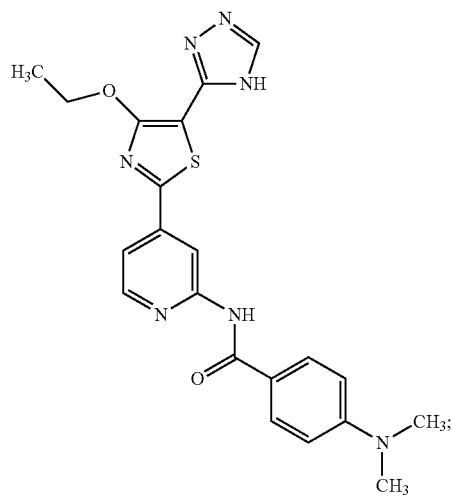
60-B
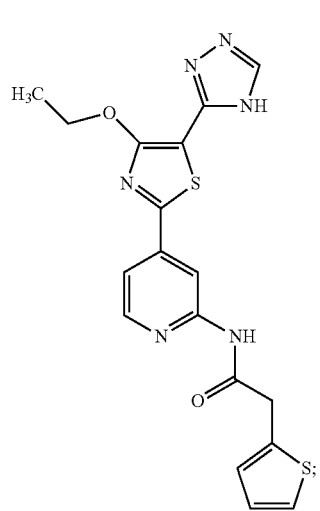
61-B
-continued
62-B
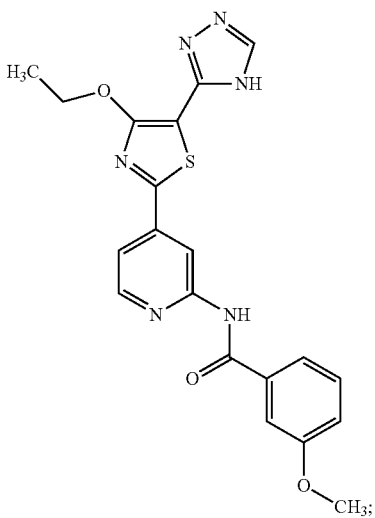
63-B
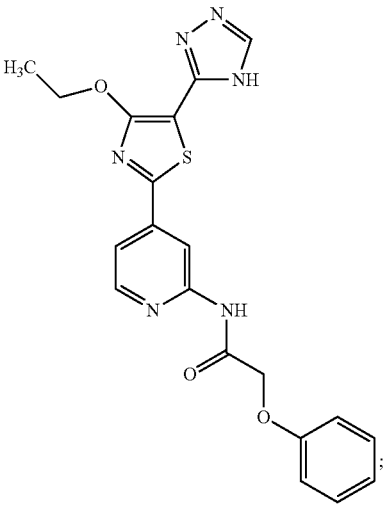
64-B
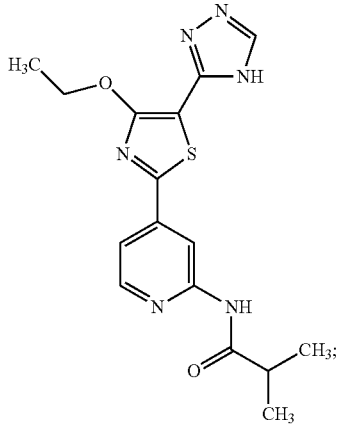

383
-continued
65-B
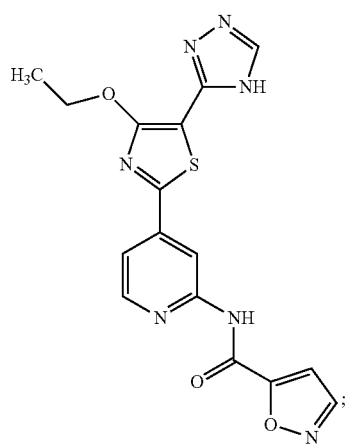
66-B
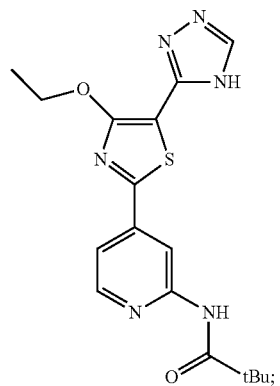
67-B
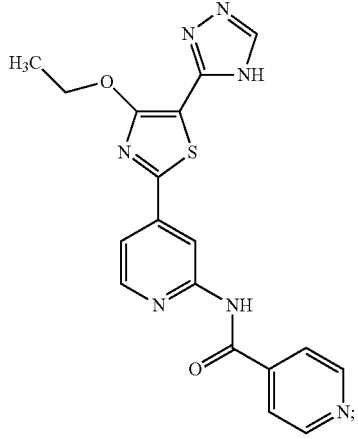
384
-continued
68-B
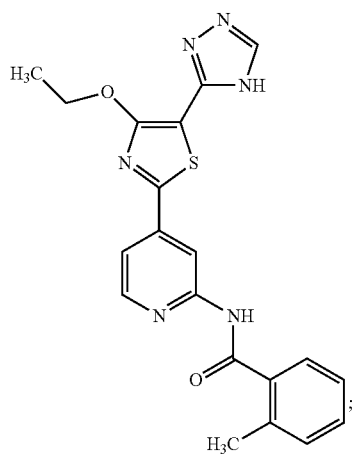
69-B
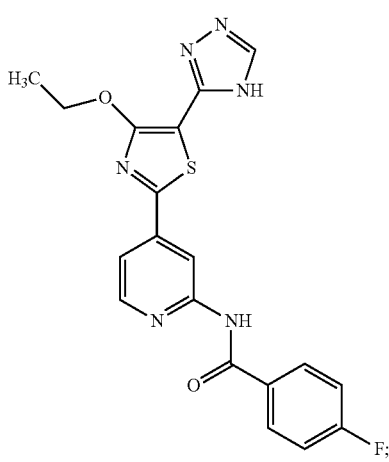
70-B
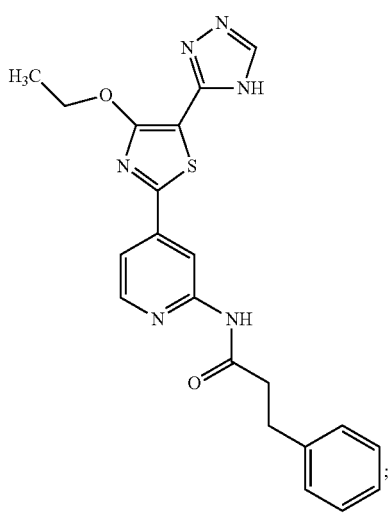

385
-continued
71-B
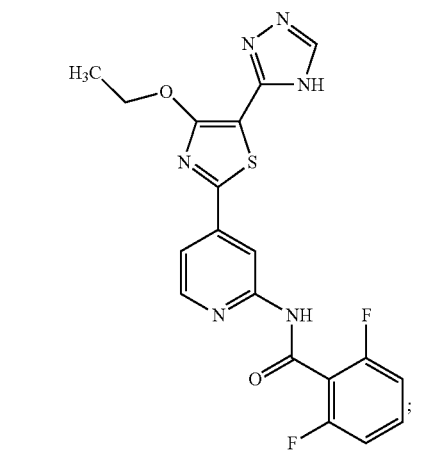
72-B
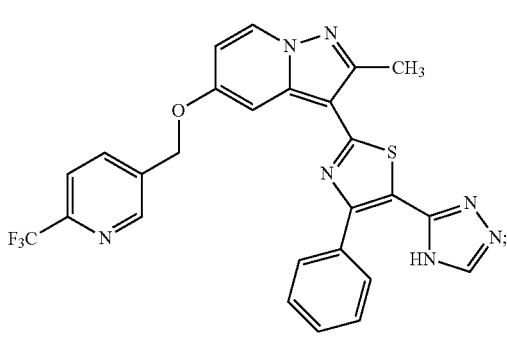
73-B
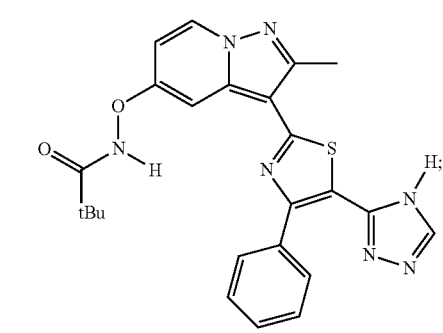
74-B
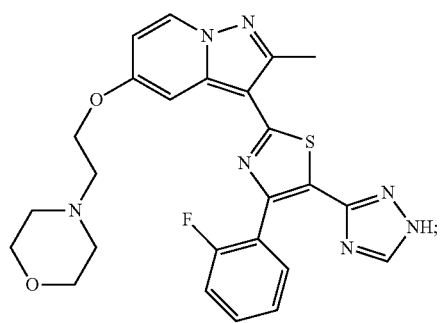
386
-continued
75-B
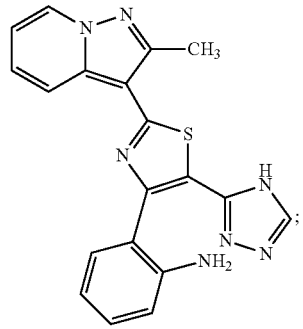
76-B
77-B
78-B
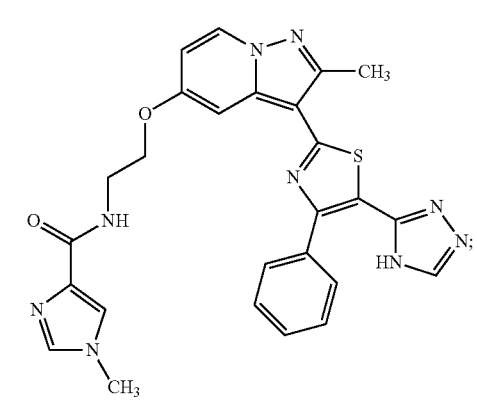

79-B
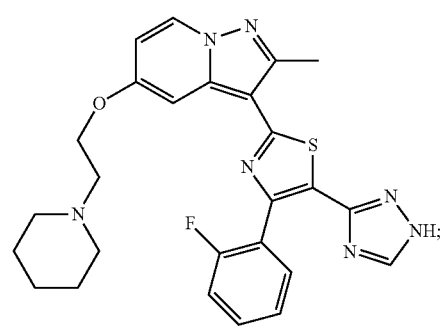
81-B
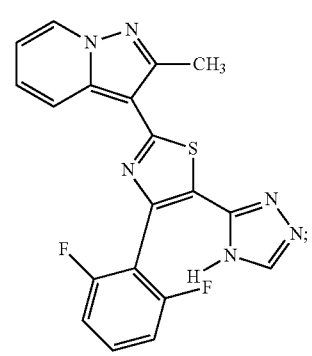
82-B
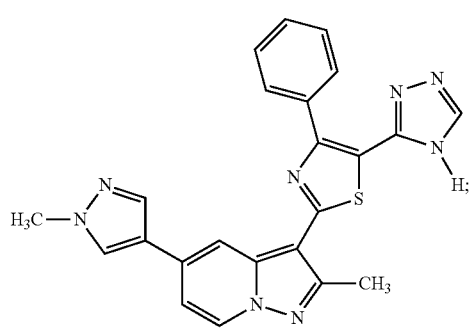
83-B
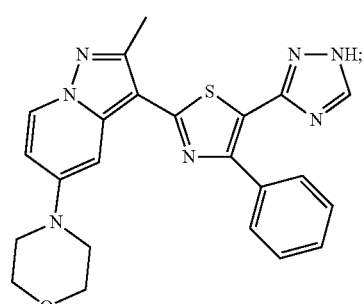
84-B
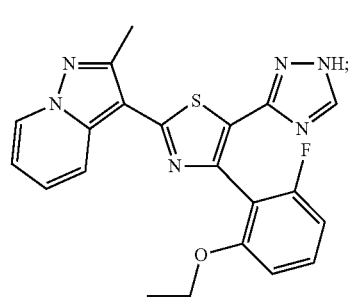
85-B
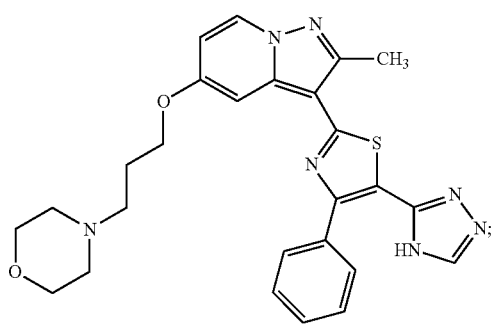
86-B
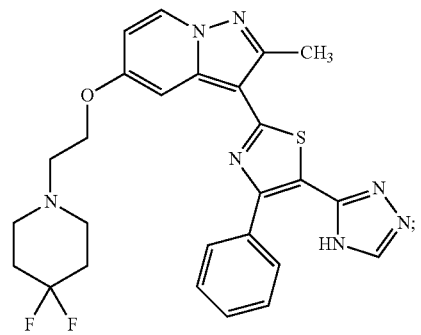
87-B
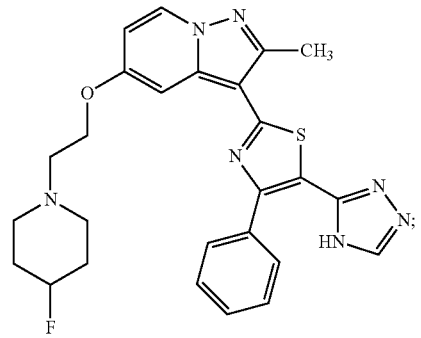
88-B
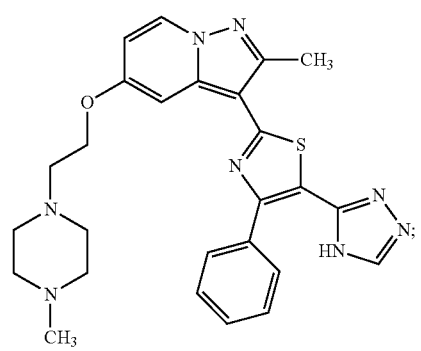

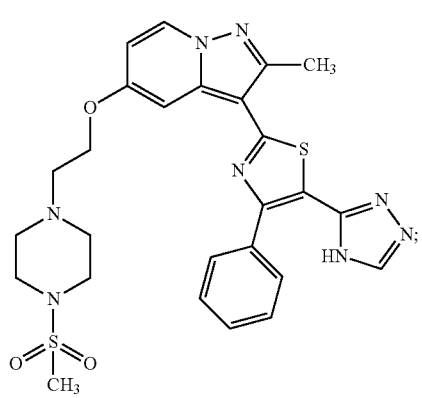
89-B
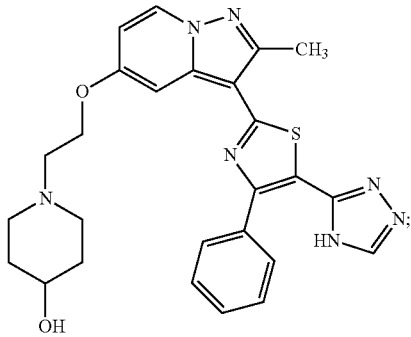
93-B
90-B
94-B
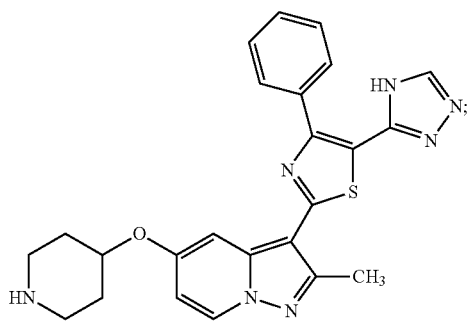
91-B
95-B
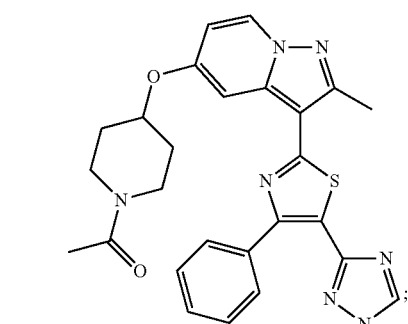
92-B
96-B
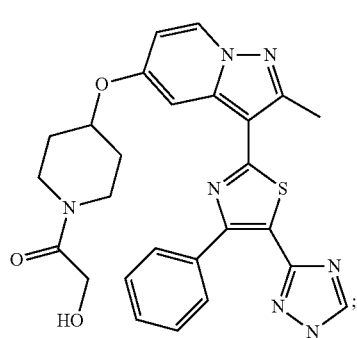

| | |
|---|---|
| 97-B 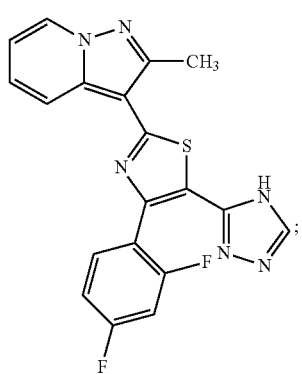 | 101-B 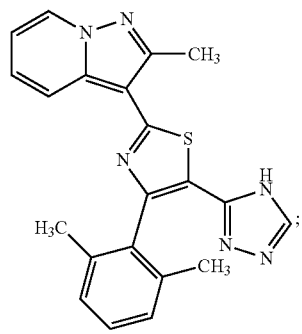 |
| 98-B 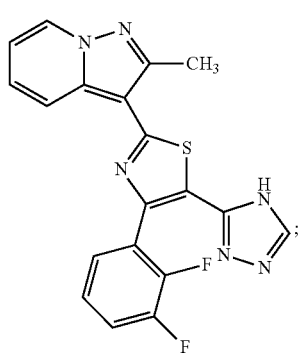 | 102-B 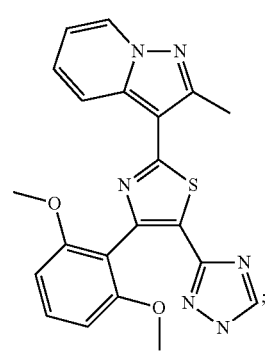 |
| 99-B 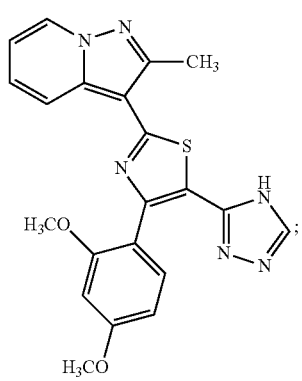 | 103-B 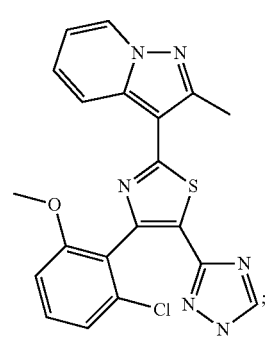 |
| 100-B 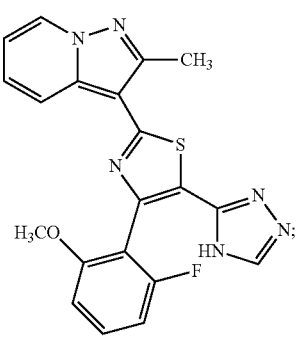 | 104-B 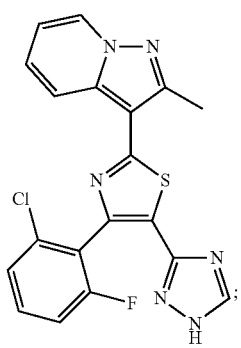 |

106-B 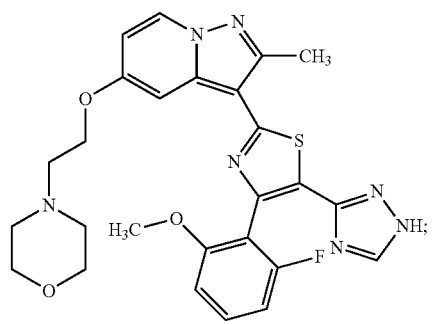
107-B 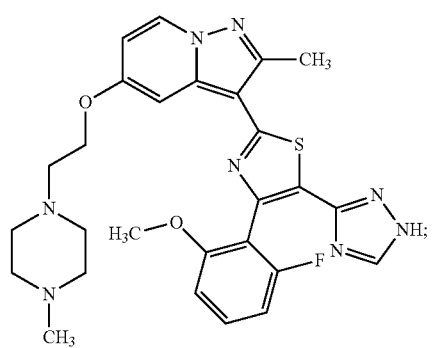
108-B 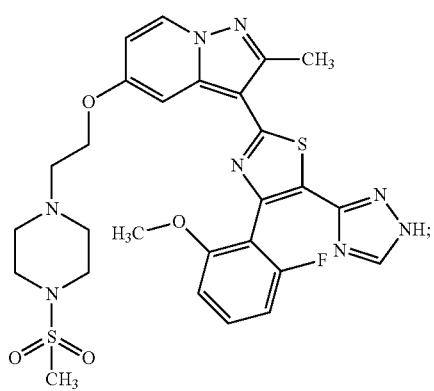
109-B 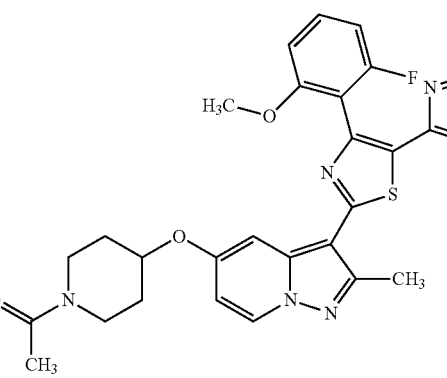
110-B 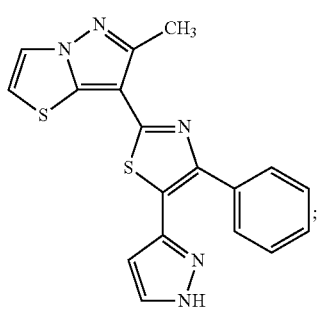
111-B 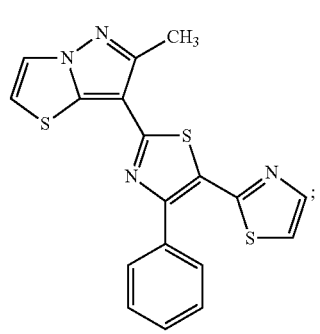
112-B 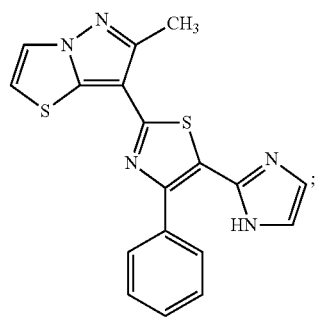
113-B 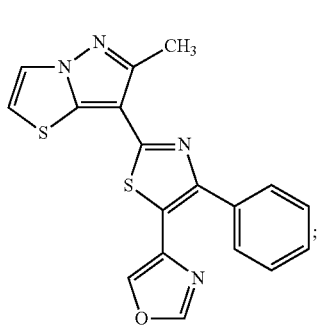
114-B 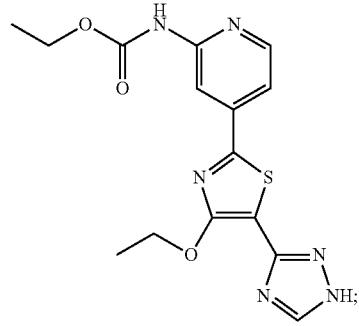

395
-continued
115-B
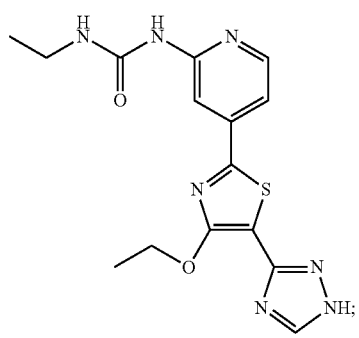
116-B
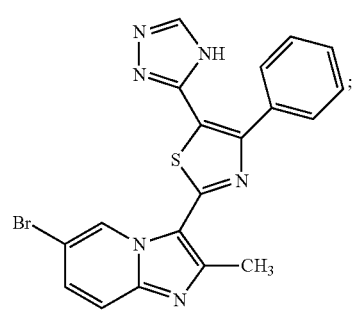
117-B
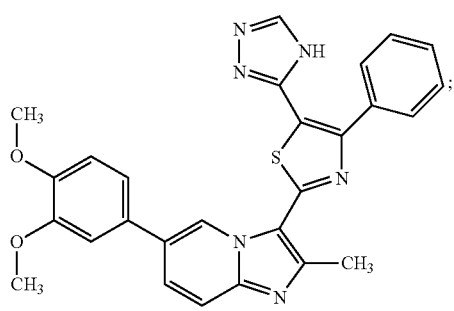
118-B
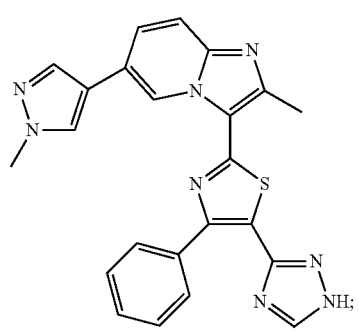
119-B
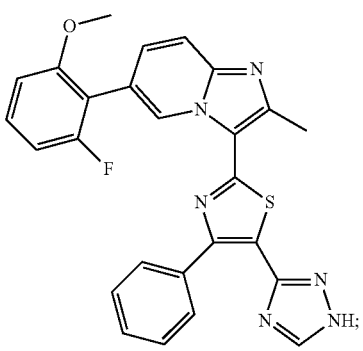
396
-continued
120-B
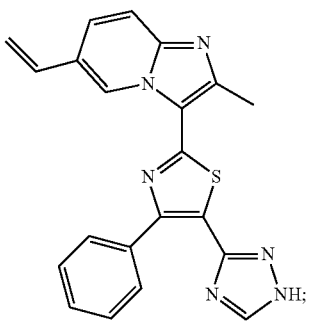
121-B
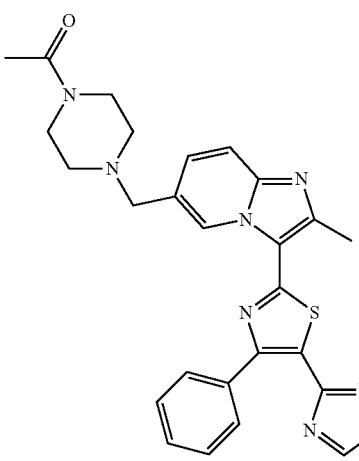
122-B
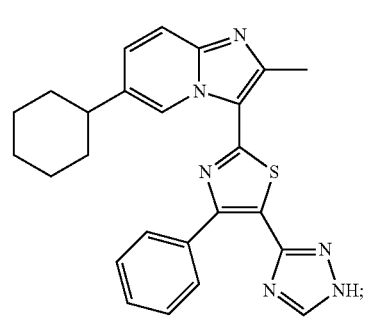
123-B
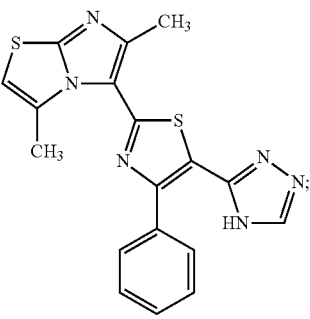

-continued
124-B
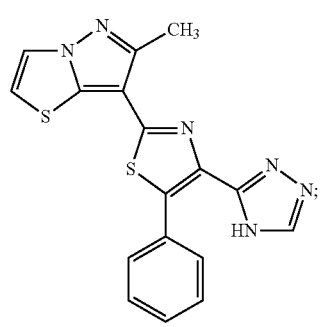
125-B
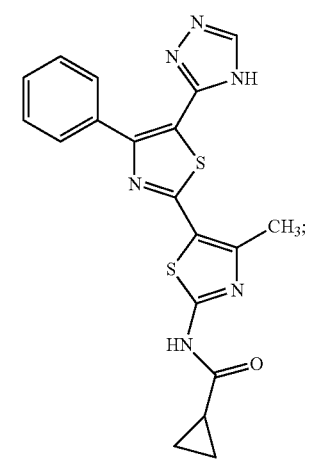
126-B
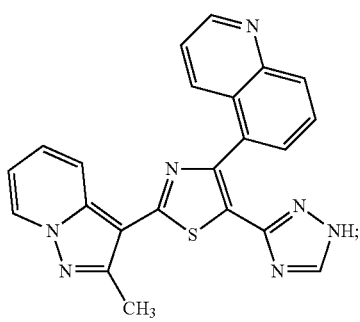
127-B
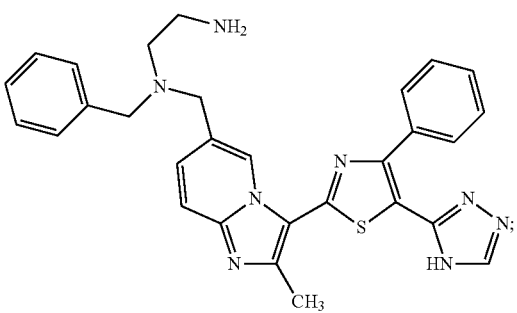
-continued
128-B
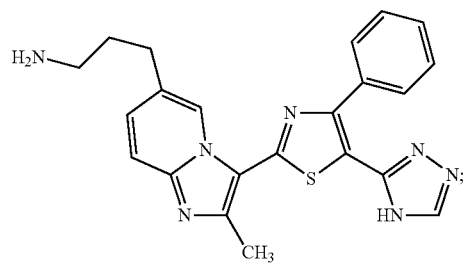
129-B
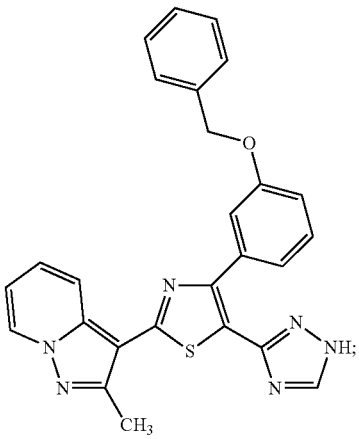
130-B
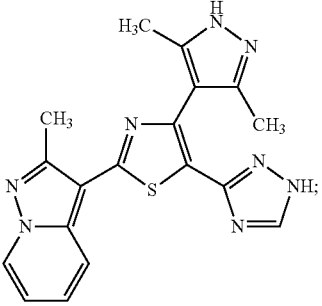
131-B
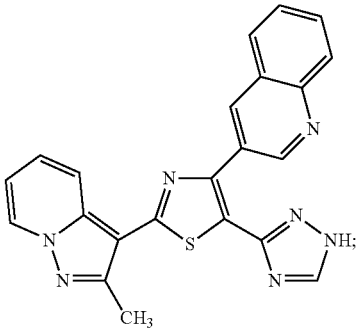
132-B
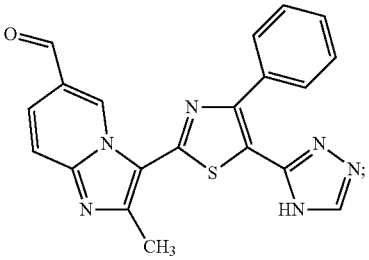

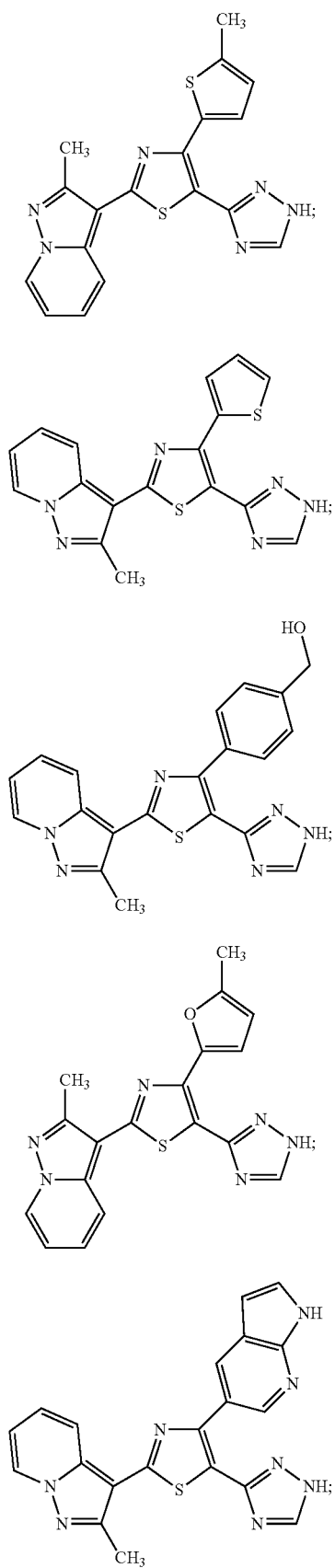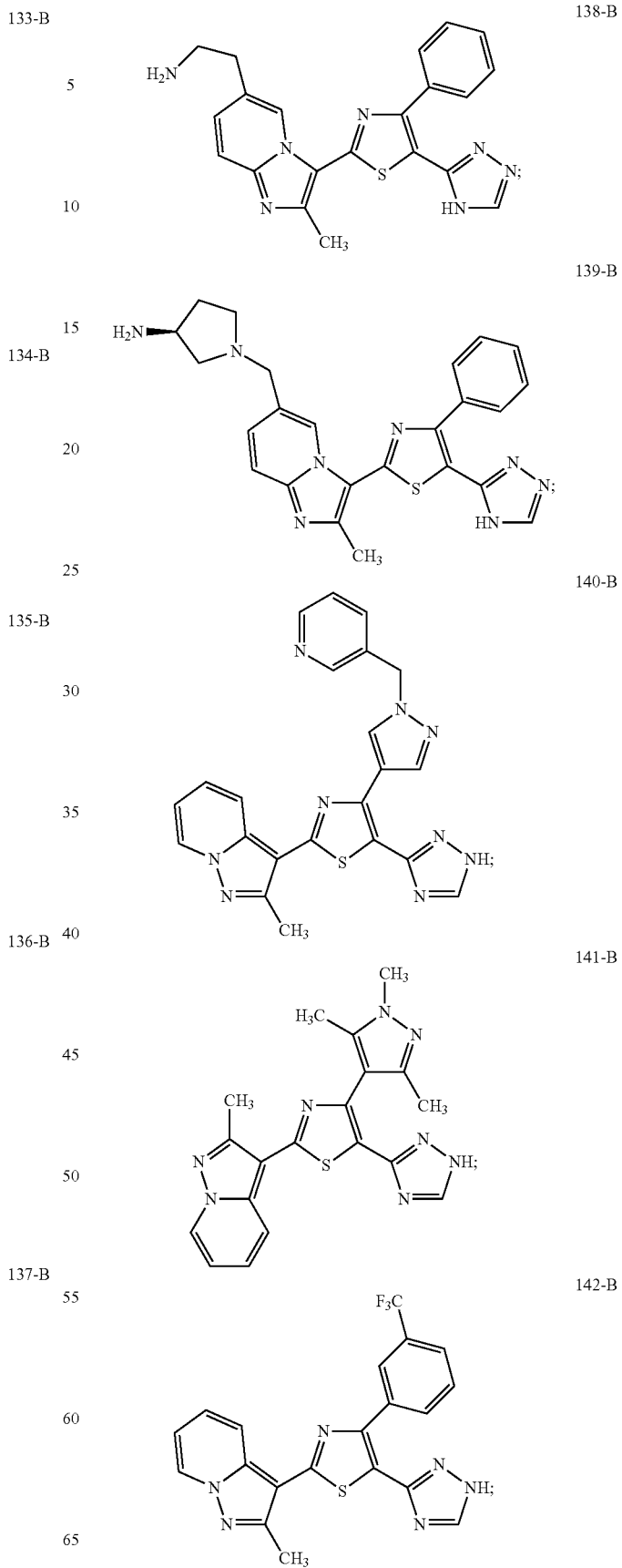

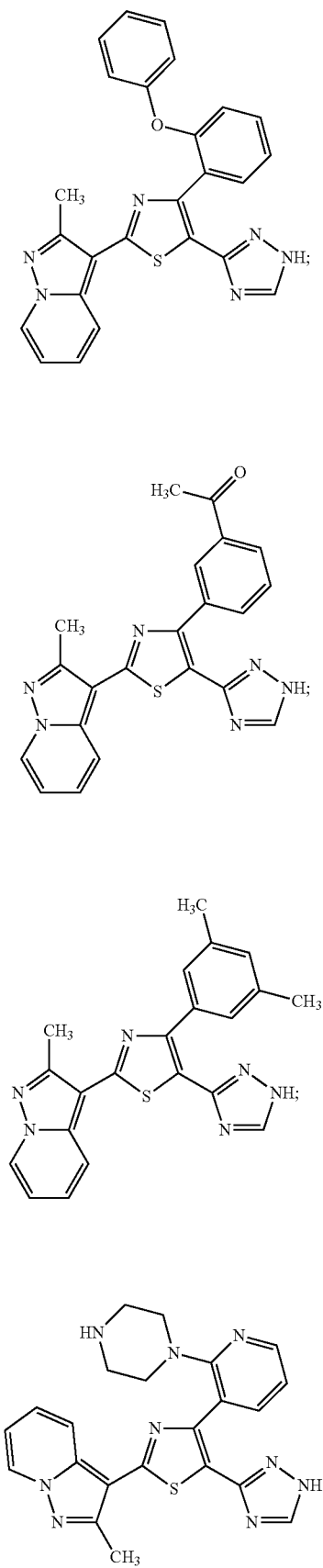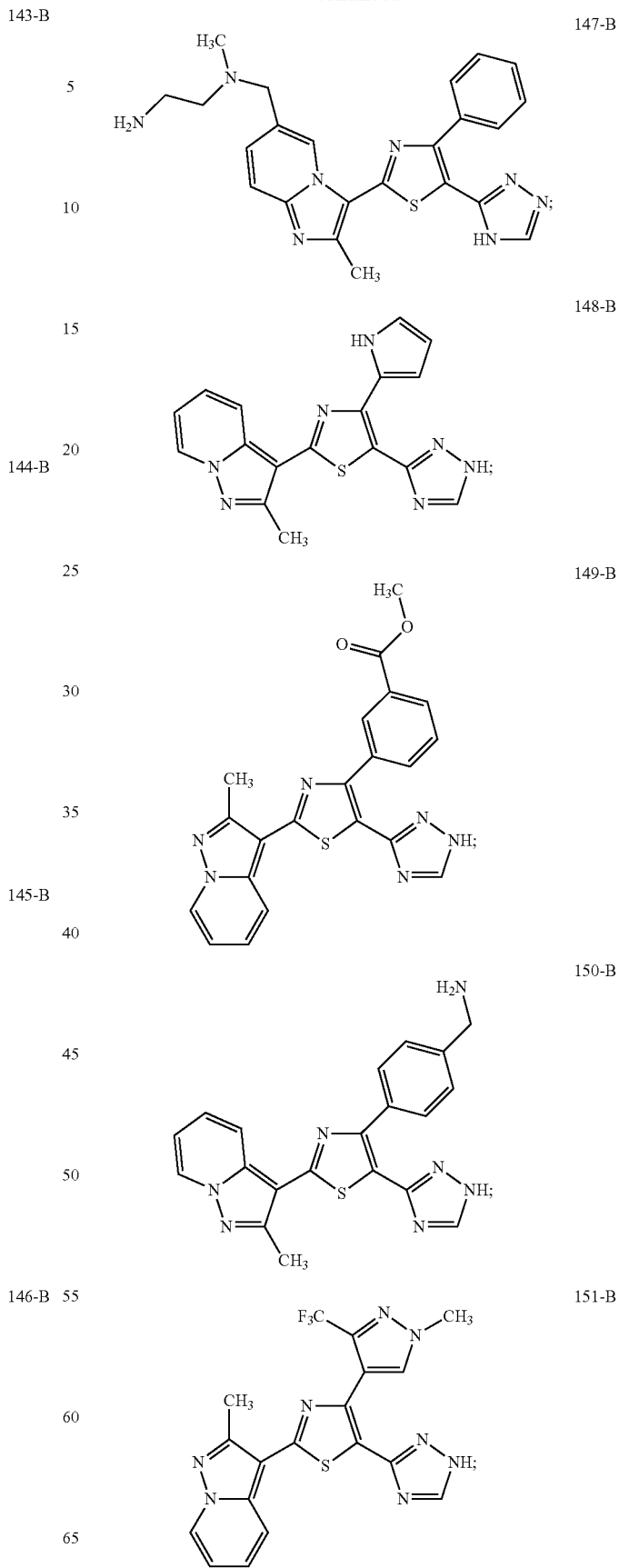

152-B
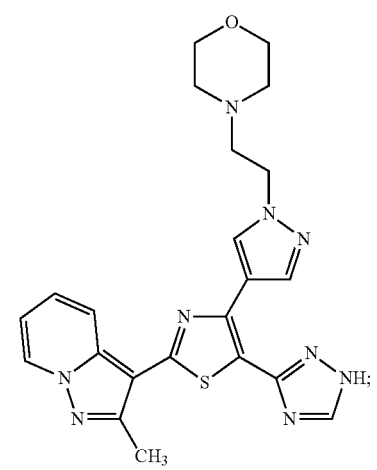
153-B
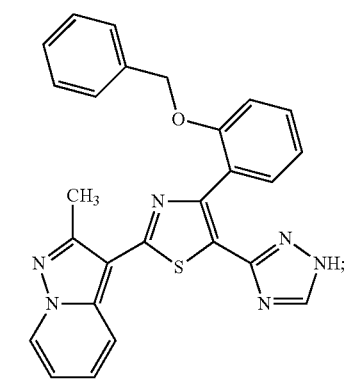
154-B
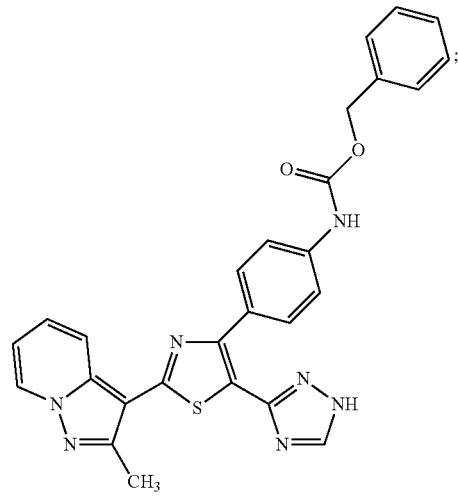
155-B
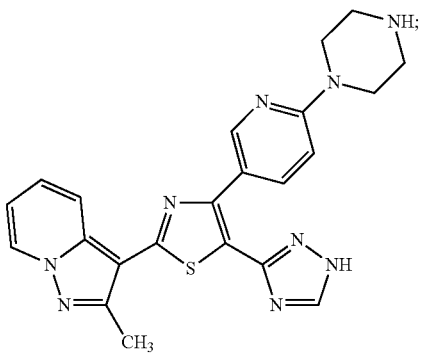
156-B
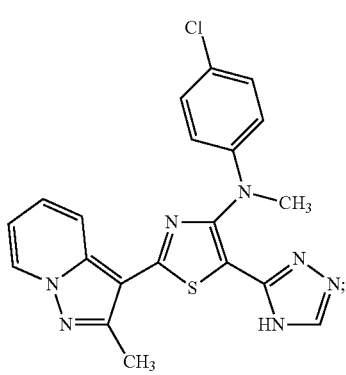
157-B
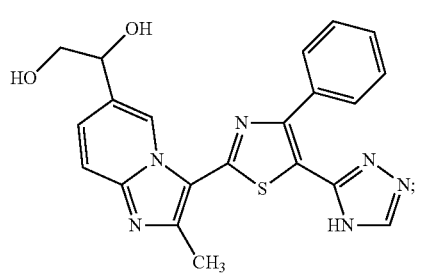
158-B
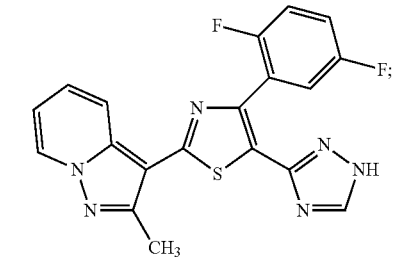
159-B
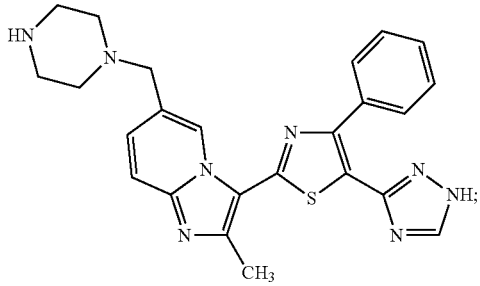

160-B 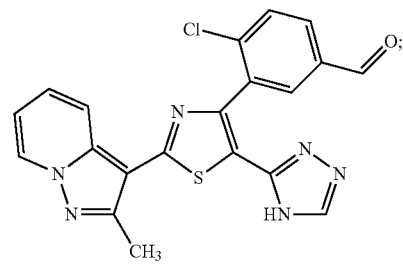
161-B 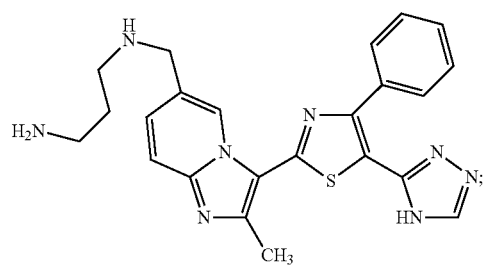
162-B 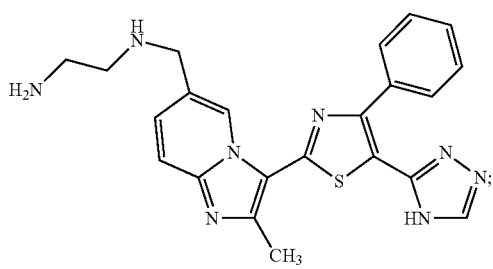
163-B 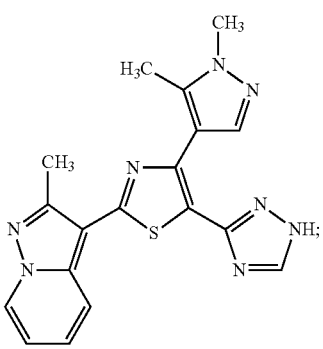
164-B 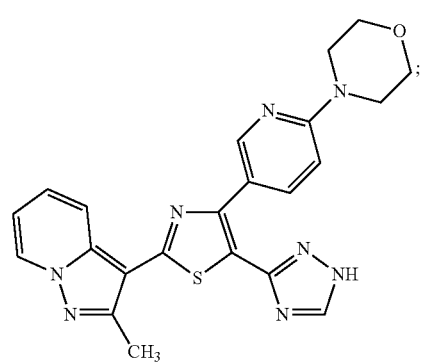
2-C 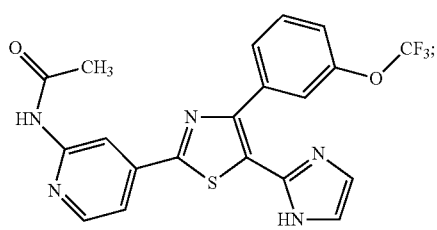
3-C 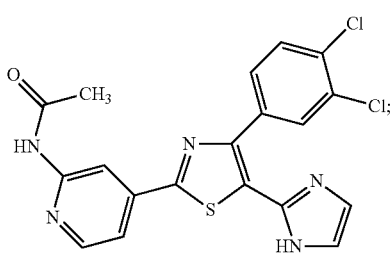
4-C 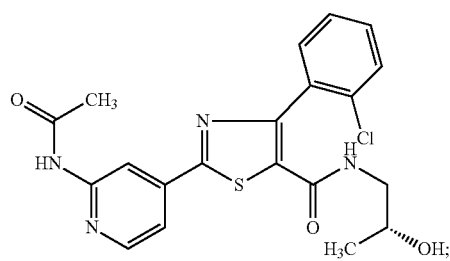
5-C 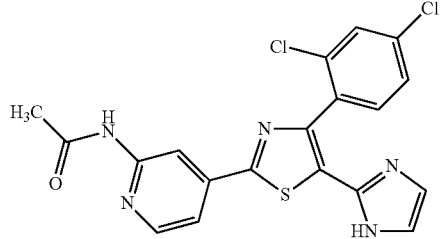
6-C 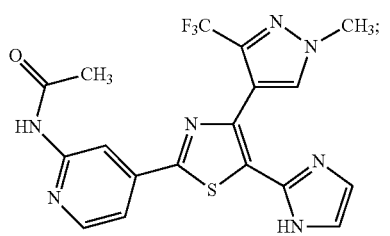
7-C 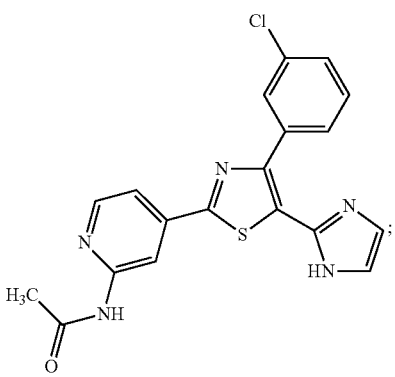

8-C
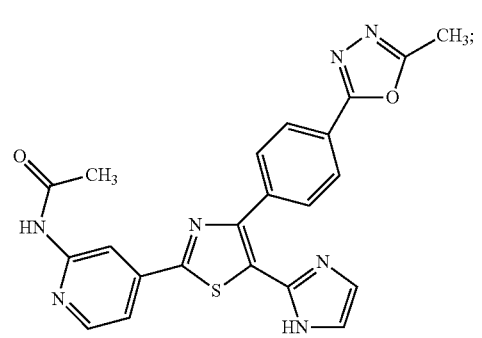
9-C
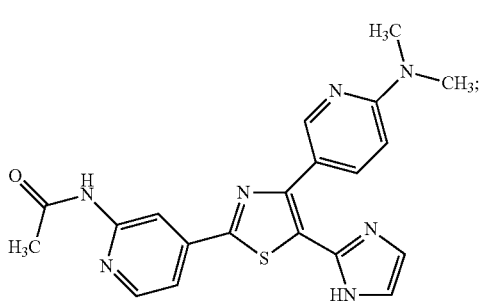
10-C
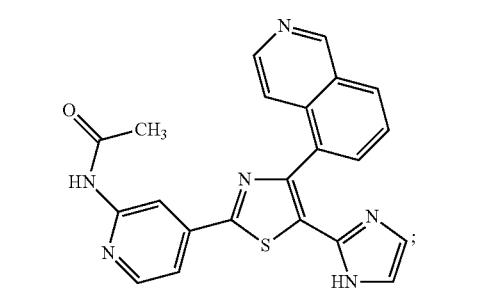
11-C
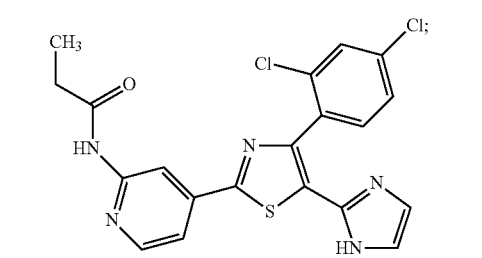
13-C
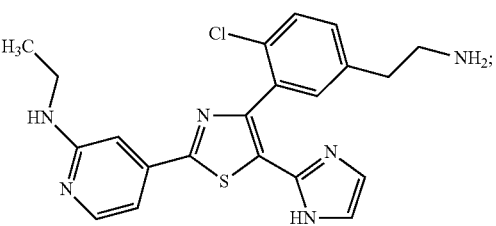
14-C
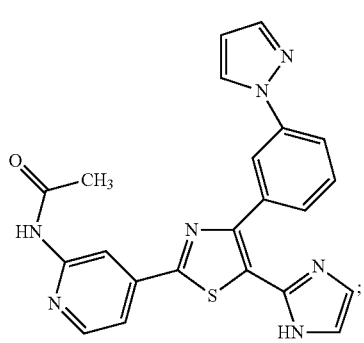
15-C
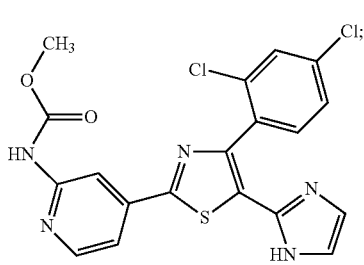
16-C
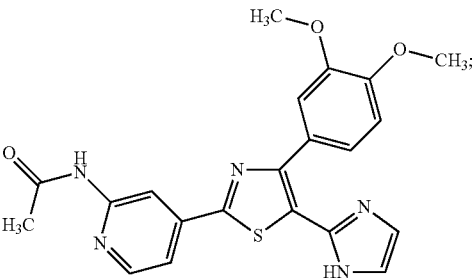
17-C
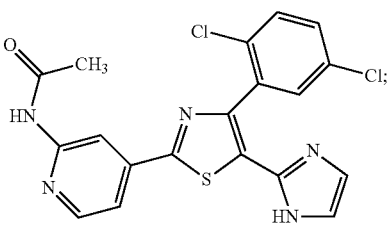
18-C
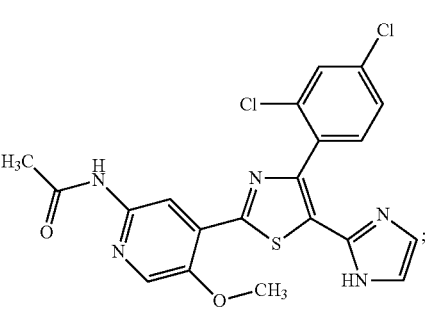

19-C
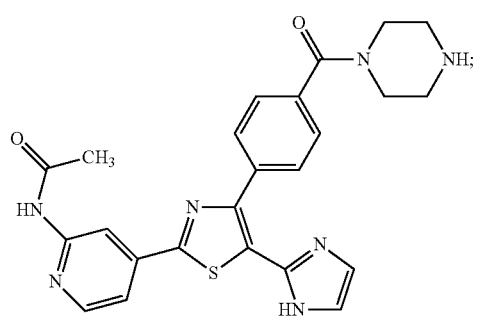
21-C
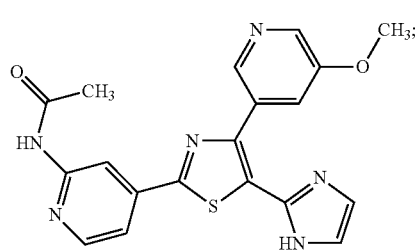
22-C
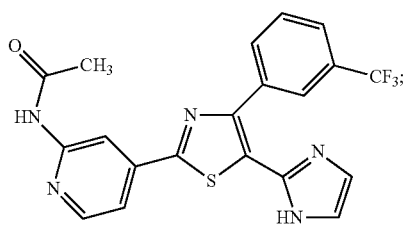
23-C
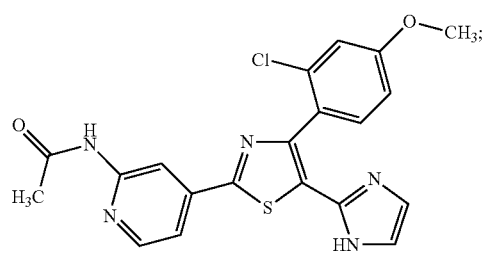
24-C
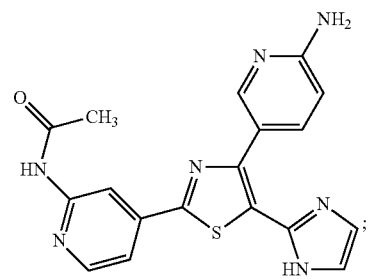
25-C
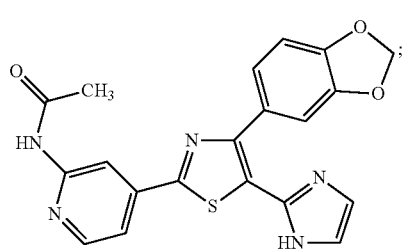
26-C
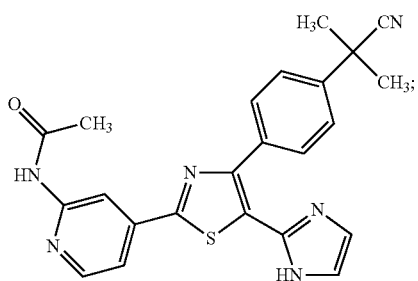
27-C
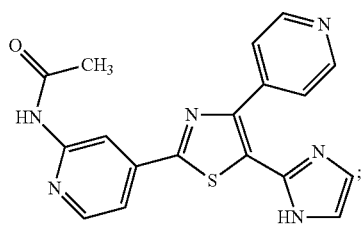
28-C
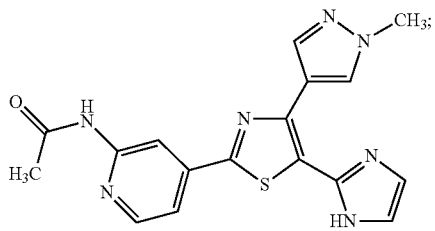
29-C
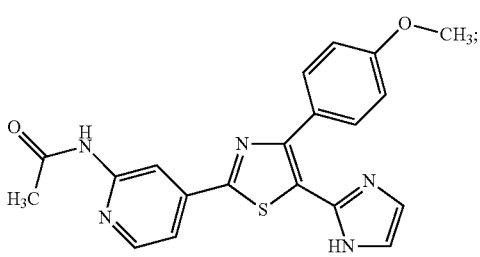
30-C
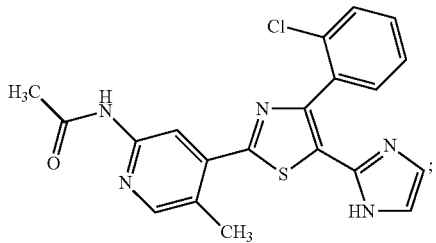
31-C
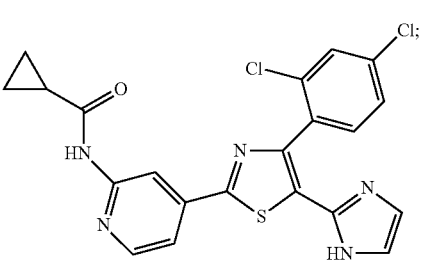

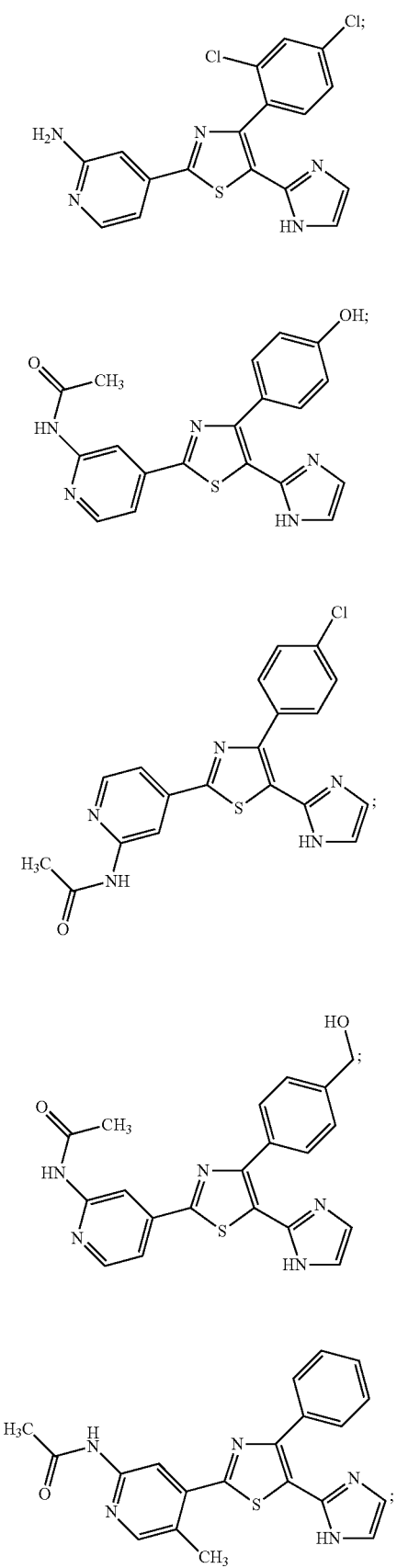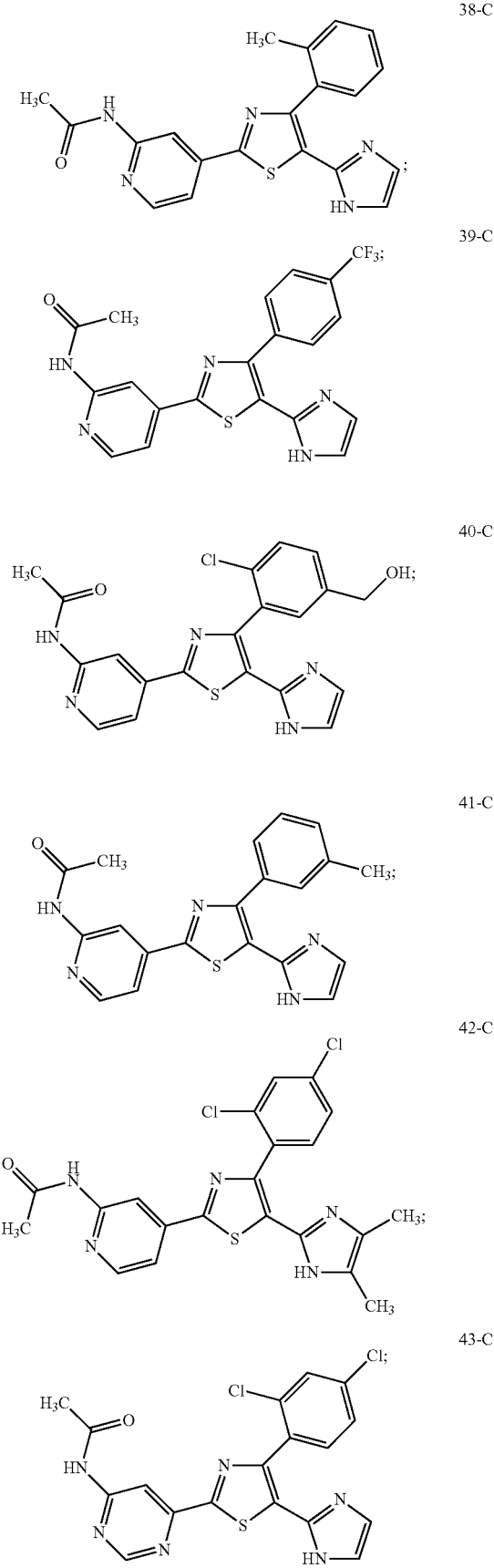

45-C
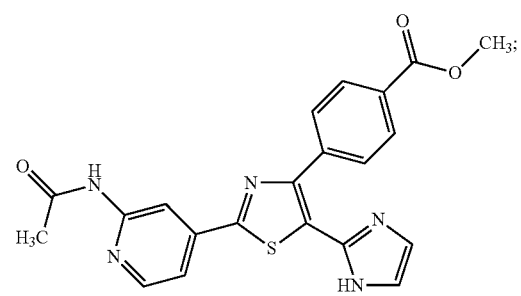
46-C
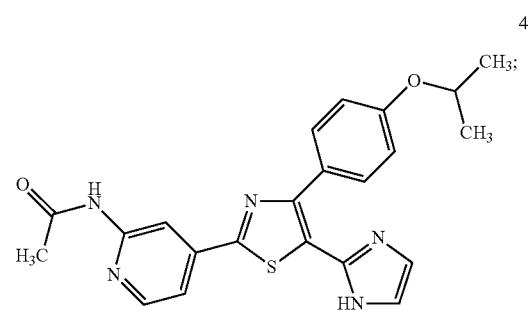
47-C
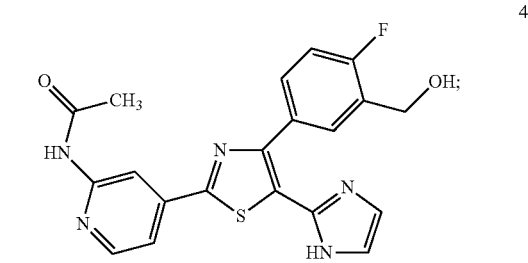
48-C
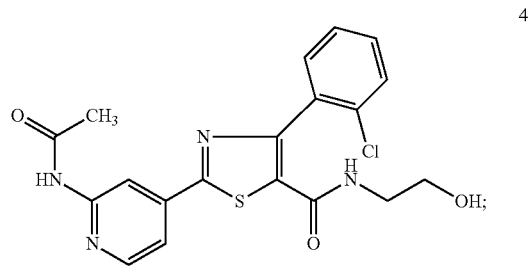
49-C
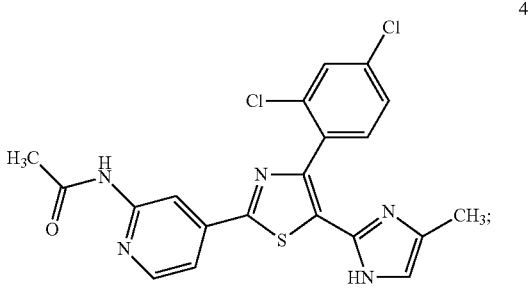
50-C
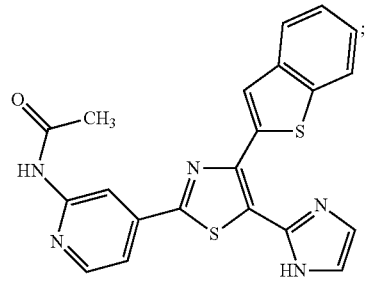
51-C
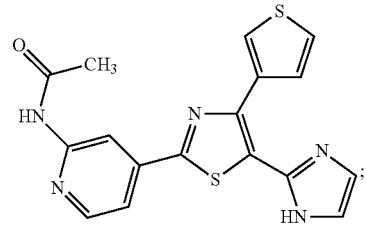
52-C
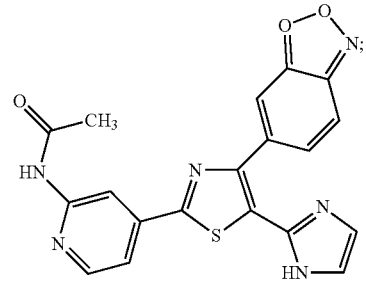
53-C
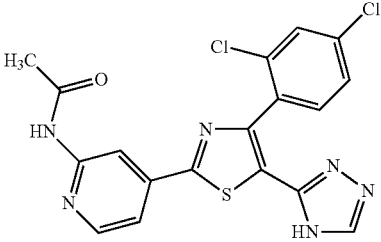
54-C
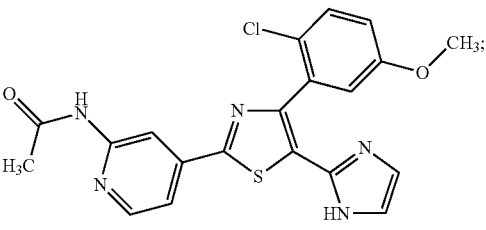
55-C
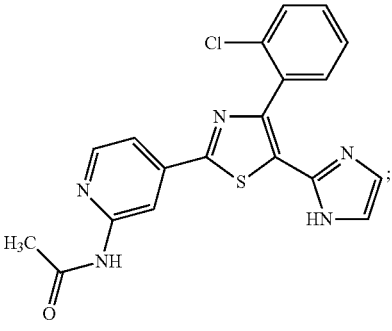

415
-continued
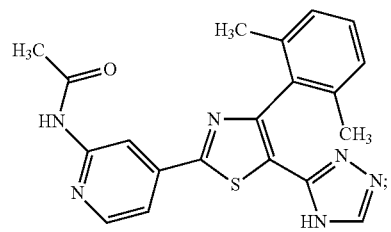
56-C
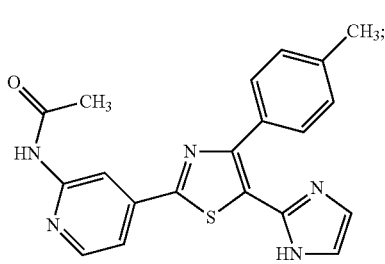
57-C
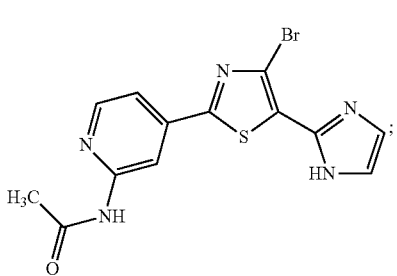
58-C
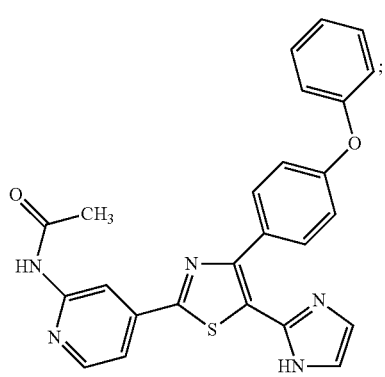
60-C
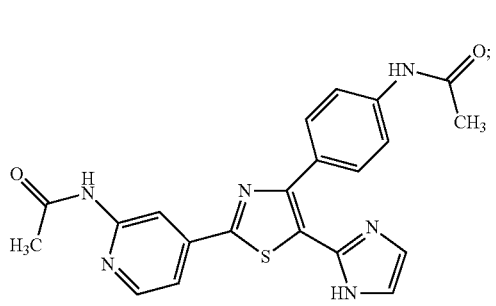
61-C
416
-continued
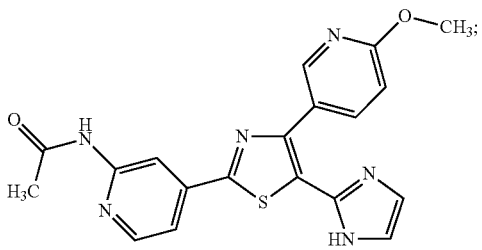
62-C
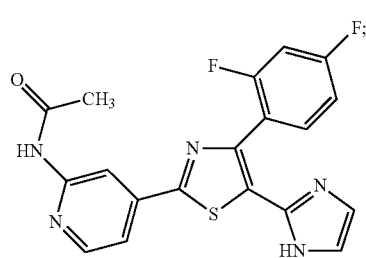
63-C
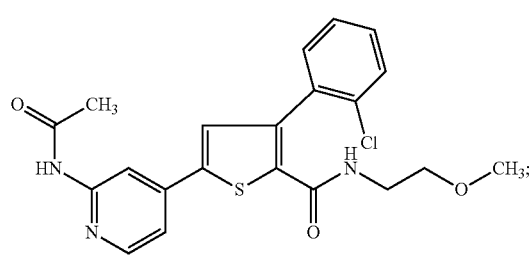
64-C
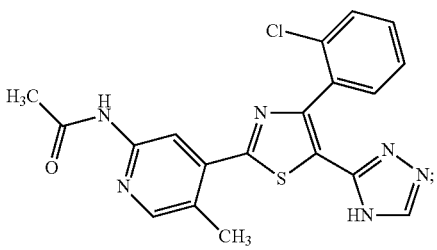
65-C
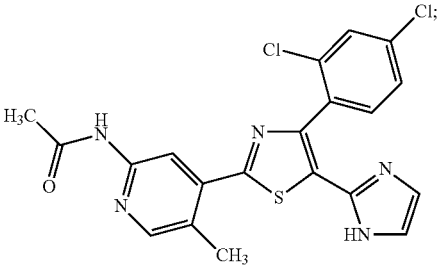
66-C
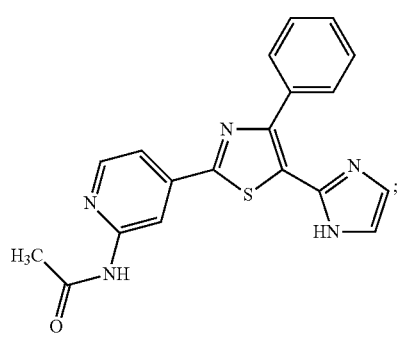
67-C 68-C 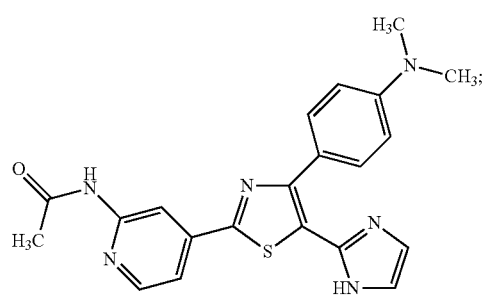
69-C 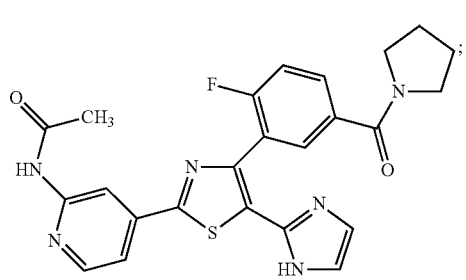
70-C 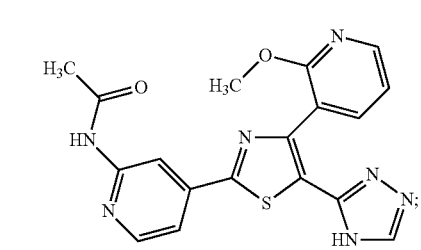
71-C 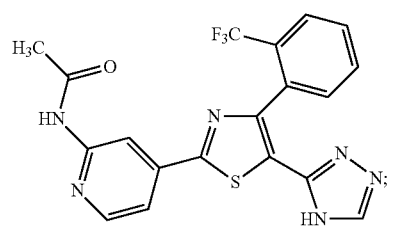
72-C 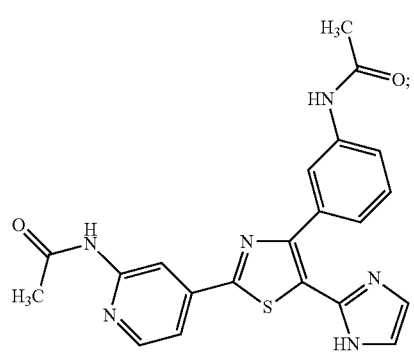
73-C 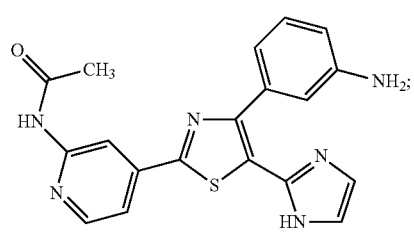
74-C 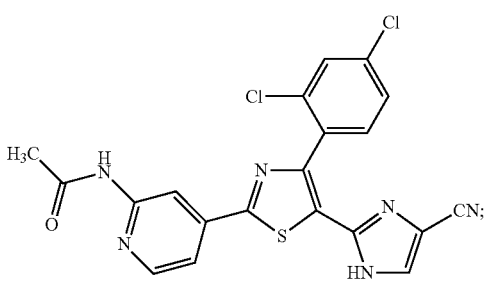
75-C 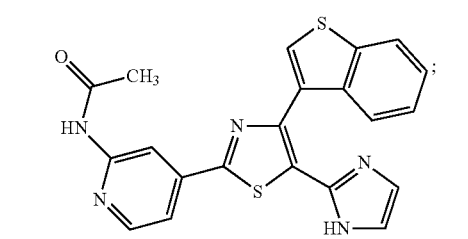
76-C 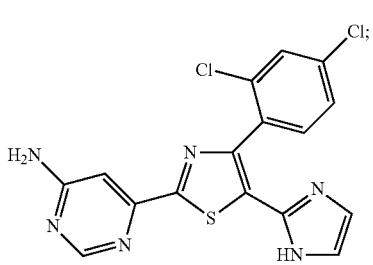
1-D 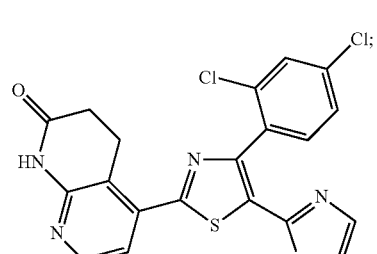
2-D and 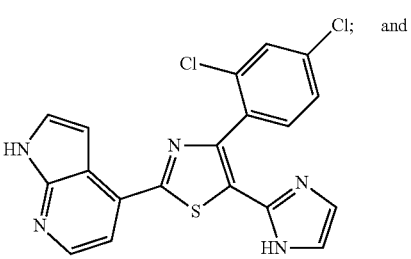
3-D 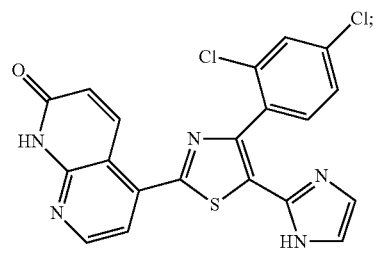
or a pharmaceutically acceptable salt thereof.

10. A composition comprising a compound of claim 9, or a pharmaceutically acceptable salt thereof, and a pharmaceutically acceptable carrier.

\* \* \* \* \*